United States Patent
Schunk et al.

(10) Patent No.: US 8,455,475 B2
(45) Date of Patent: Jun. 4, 2013

(54) SUBSTITUTED SPIRO-AMIDE COMPOUNDS

(75) Inventors: Stefan Schunk, Aachen (DE); Melanie Reich, Aachen (DE); Stefan Oberboersch, Aachen (DE); Michael Engels, Turnhout (DE); Tieno Germann, Aachen (DE); Ruth Jostock, Stolberg (DE); Christa Kneip, Aachen (DE)

(73) Assignee: Gruenenthal GmbH, Aachen (DE)

( * ) Notice: Subject to any disclaimer, the term of this patent is extended or adjusted under 35 U.S.C. 154(b) by 248 days.

(21) Appl. No.: 12/730,597

(22) Filed: Mar. 24, 2010

(65) Prior Publication Data
US 2010/0249095 A1    Sep. 30, 2010

Related U.S. Application Data

(60) Provisional application No. 61/163,116, filed on Mar. 25, 2009, provisional application No. 61/242,097, filed on Sep. 14, 2009.

(30) Foreign Application Priority Data

Mar. 25, 2009  (EP) .................................. 09004235
Sep. 14, 2009  (EP) .................................. 09011708

(51) Int. Cl.
*A61K 31/00*  (2006.01)
*A61K 31/495*  (2006.01)
*A61K 31/497*  (2006.01)
*A61K 31/505*  (2006.01)
*A61K 31/44*  (2006.01)

(52) U.S. Cl.
USPC ................... 514/210.18; 514/210.2; 514/249; 514/253.13; 514/275; 514/278

(58) Field of Classification Search
None
See application file for complete search history.

(56) References Cited

FOREIGN PATENT DOCUMENTS

| WO | WO 2005/087236 A1 | 9/2005 |
|---|---|---|
| WO | WO 2005/095387 A1 | 10/2005 |
| WO | WO 2007/011809 A1 | 1/2007 |
| WO | WO 2007/101007 A2 | 9/2007 |
| WO | WO 2007/140383 A2 | 12/2007 |
| WO | WO 2008/040492 A1 | 4/2008 |
| WO | WO 2008/046573 A1 | 4/2008 |

OTHER PUBLICATIONS

Anderson (Chem and Biol 10:787-797, 2003).*
Thiel (Nature Biotechnol 2:513-519, 2004).*
Biswas et al (J Med Chem 50:2200-2212, 2007).*
Su et al (J Med Chem 51:3946-3952, 2008).*
Von Siegfried Skraup et al., "Zum Oxydativen Abbau von Carbonsauren", Justus Liebigs Annalen der Chemie; Mar. 1928, pp. 135-158, vol. 462.

David C. Horwell et al., "The Design of Dipeptide Helical Mimetics, Part I: the Synthesis of 1,6-Disubstituted Indanes", Tetrahedron; 1995, p. 203-216, vol. 51, No. 1, Elsevier Science Ltd.
Antoni Stadnicki et al., "Immunolocalization and Expression of Kinin $B_1R$ and $B_2R$ Receptors in Human Inflammatory Bowel Disease", Am. J. Physiol. Gastrointest. Liver Physiol, Mar. 31, 2005, pp. G361-G366, vol. 289, American Physiological Society.
Dieter Hamprecht et al., "Isoindolone Derivatives, a New Class of $5\text{-}HT_{2c}$ Antagonists: Synthesis and Biological Evaluation", Bioorganic & Medicinal Chemistry Letters, 2007, pp. 428-433, vol. 17.
Dieter Hamprecht et al., "$5\text{-}HT_{2c}$ Antagonists Based on Fused Heterotricyclic Templates: Design, Synthesis and Biological Evaluation", Bioorganic & Medicinal Chemistry Letters, 2007, pp. 424-427, vol. 17.
A. Prat et al., "Bradykinin $B_1$ Receptor Expression and Function on T Lymphocytes in Active Multiple Sclerosis", Neurology, Dec. 10, 1999, pp. 2087-2092, vol. 53, No. 9, 1999 American Academy of Neurology, ISSN: 0028-3878.
Joao B. Pesquero et al., "Genetically Altered Animal Models in the Kallikrein-Kinin System", Biol. Chem., Feb. 2006, pp. 119-126, vol. 387.
Joao B. Pesquero et al., "Hypoalgesia and Altered Inflammatory Responses in Mice Lacking Kinin B1 Receptors", PNAS, Jul. 5, 2000, pp. 8140-8145, vol. 97, No. 14.
Giselle F. Passos et al., "Kinin $B_1$ Receptor Up-Regulation after Lipopolysaccharide Administration: Role of Proinflammatory Cytokines and Neutrophil Influx[1]", The Journal of Immunology, 2004, pp. 1839-1847, vol. 172, The American Association of Immunologists, Inc.
Hideki Takahashi et al., "Novel Rh Catalysis in Cross-Coupling Between Alkyl Halides and Arylzinc Compounds Possessing Ortho-COX (X=OR, $NMe_2$, or Ph) Groups", Organic Letters, 2006, pp. 3037-3040, vol. 8, No. 14.

(Continued)

*Primary Examiner* — Craig Ricci
(74) *Attorney, Agent, or Firm* — Crowell & Moring LLP

(57) ABSTRACT

Substituted spiro-amide compounds corresponding to formula I

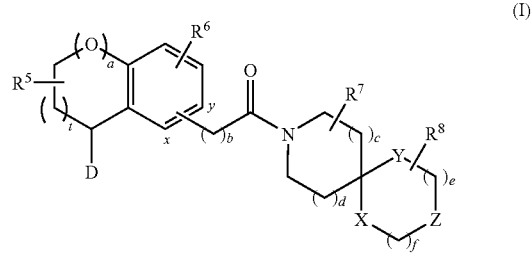

(I)

in which R5 through R8, D, X, Y and Z have defined meanings, processes for preparing such spiro-amide compounds, pharmaceutical compositions containing such compounds, and methods of using such spiro-amide compounds for treating and/or inhibiting disorders or disease states mediated at least in part by the bradykinin 1 receptor.

13 Claims, No Drawings

OTHER PUBLICATIONS

Nathan Moses, "Ueber p-Oyanbensylohlorid", Chemische Berichte; 1900, pp. 2623-2630, vol. 33.

L.M. Fredrik Leeb-Lundberg et al., "International Union of Pharmacology. XLV. Classification of the Kinin Receptor Family: from Molecular Mechanism to Pathophysiological Consequences", Pharmacological Reviews, 2005, pp. 27-77, vol. 57, No. 1, The American Society for Pharmacology and Experimental Therapeutics, USA.

Paulo Gomes et al., "Addition of Electrochemically Prepared Arylzine Species onto Activated Olefins via a Cobalt Catalysis", 2002, pp. 1673-1676, No. 10, ISSN: 0936-5214.

Roberto Pellicclari et al., "1-Aminoindan-1,5-dicarboxylic Acid: A Novel Antagonist at Phospholipase C-Linked Metabotropic Glutamate Receptors", Journal of Medicinal Chemistry, 1995, pp. 3717-3719, vol. 38, No. 19.

Yoshihiko Kotake et al., "Synthesis and Antitumor Activities of Novel 6-5 Fused Ring Heterocycle Antifolates: N-[4-[.omega.-2(2-Amino-4-substituted-6,7-dihydrocyclopenta[d]pyrimidin-5-yl)alkyl]benzoyl]-L-glutamic Acids", Journal of Medicinal Chemistry, 1994, pp. 1616-1624, vol. 37, No. 11, American Chemical Society.

Ryo Takeuchi, "Rhodium Complex-Catalyzed Desilylative Cyclocarbonylation of 1-aryl-2-(trimethylsilyl)acetylenes: A New Route to 2,3-dihydro-1H-inden-1-ones", Journal of Organic Chemistry, 1993, pp. 5385-5392, vol. 58, No. 20.

Hakaru Horiguchi et al., "Palladium/Phosphite-Catalyzed 1,4-Addition of Arylboronic Acids to Acrylic Acid Derivatives", Journal of Organic Chemistry, 2008, pp. 1590-1592, vol. 73, No. 4, American Chemical Society.

Muriel Amatore et al., "CoBr(Bpy): An Efficient Catalyst for the Direct Conjugate Addition of Aryl Halides or Triflates onto Activated Olefins", Journal of Organic Chemistry, 2006, pp. 6130-6134, vol. 71, No. 15.

J. Fred Hess et al., "Generation and Characterization of a Humanized Bradykinin B1 Receptor Mouse", Biol. Chem., Feb. 2006, pp. 195-201, vol. 387.

R. Hayashi et al., "Bradykinin Stimulates IL-6 and IL-8 Production by Human Lung Fibroblasts Through ERK- and p38 MAPK-dependent Mechanisms", European Respiratory Journal, 2000, pp. 452-458, vol. 16, ISSN: 0903-1936.

Bichoy H. Gabra et al., "The Kinin System Mediates Hyperalgesia through the Inducible Bradykinin B1 Receptor Subtype: Evidence in Various Experimental Animal Models of Type 1 and Type 2 Diabetic Neuropathy", Biol. Chem., Feb. 2006, pp. 127-143, vol. 387.

Joao B. Calixto et al., "Kinin $B_1$ Receptors: Key G-protein-coupled Receptors and their Role in Inflammatory and Painful Processes", British Journal of Pharmacology, 2004, pp. 803-818, vol. 143, 2004 Nature Publishing Group.

Sara H. Bengtson et al., "Kinin Receptor Expression During *Staphylococcus aureus* Infection", Blood, Sep. 15, 2006, pp. 2055-2063, vol. 108, No. 6, The American Society of Hematology.

European Search Report dated Jul. 16, 2009 with partial English translation (Five (5) pages).

\* cited by examiner

SUBSTITUTED SPIRO-AMIDE COMPOUNDS

CROSS REFERENCE TO RELATED APPLICATIONS

This application claims priority from U.S. provisional patent application Nos. 61/163,116, filed Mar. 25, 2009, and 61/242,097, filed Sep. 14, 2009. Priority is also claimed based upon European patent application nos. EP 09004235.9, filed Mar. 25, 2009, and EP 09011708.6, filed Sep. 14, 2009.

BACKGROUND OF THE INVENTION

The present invention relates to substituted spiro-amide compounds, processes for the preparation thereof, medicaments containing these compounds and the use of substituted spiro-amide compounds for the preparation of medicaments.

In contrast to the constitutive expression of the bradykinin 2 receptor (B2R), in most tissues the bradykinin 1 receptor (B1R) is not expressed or is expressed only weakly. Nevertheless, expression of B1R can be induced on various cells. For example, in the course of inflammation reactions a rapid and pronounced induction of B1R takes place on neuronal cells, but also various peripheral cells, such as fibroblasts, endothelial cells, granulocytes, macrophages and lymphocytes. In the course of inflammation reactions, a switch from a B2R to a B1R dominance thus occurs on the cells involved. The cytokines interleukin-1 (IL-1) and tumour necrosis factor alpha (TNFα) are involved to a considerable degree in this upwards regulation of B1R (Passos et al. J. Immunol. 2004, 172, 1839-1847). After activation with specific ligands, B1R-expressing cells then themselves can secrete inflammation-promoting cytokines such as IL-6 and IL-8 (Hayashi et al., Eur. Respir. J. 2000, 16, 452-458). This leads to inwards migration of further inflammation cells, e.g. neutrophilic granulocytes (Pesquero et al., PNAS 2000, 97, 8140-8145). The bradykinin B1R system can contribute towards chronification of diseases via these mechanisms. This is demonstrated by a large number of animal studies (overviews in Leeb-Lundberg et al., Pharmacol Rev. 2005, 57, 27-77 and Pesquero et al., Biol. Chem. 2006, 387, 119-126). On humans too, an enhanced expression of B1R, e.g. on enterocytes and macrophages in the affected tissue of patients with inflammatory intestinal diseases (Stadnicki et al., Am. J. Physiol. Gastrointest. Liver Physiol. 2005, 289, G361-366) or on T lymphocytes of patients with multiple sclerosis (Prat et al., Neurology. 1999; 53,2087-2092) or an activation of the bradykinin B2R-B1R system in the course of infections with *Staphyloccocus aureus* (Bengtson et al., Blood 2006, 108, 2055-2063) is found. Infections with *Staphyloccocus aureus* are responsible for syndromes such as superficial infections of the skin up to septic shock.

Based on the pathophysiological relationships described, there is a great therapeutic potential for the use of B1R antagonists on acute and, in particular, chronically inflammatory diseases. These include diseases of the respiratory tract (bronchial asthma, allergies, COPD/chronic obstructive pulmonary disease, cystic fibrosis etc.), inflammatory intestinal diseases (ulcerative colitis, CD/Crohn's disease etc.), neurological diseases (multiple sclerosis, neurodegeneration etc.), inflammations of the skin (atopic dermatitis, psoriasis, bacterial infections etc.) and mucous membranes (Behcet's disease, pelvitis, prostatitis etc.), rheumatic diseases (rheumatoid arthritis, osteoarthritis etc.), septic shock and reperfusion syndrome (following cardiac infarction, stroke).

The bradykinin (receptor) system is moreover also involved in regulation of angiogenesis (potential as an angiogenesis inhibitor in cancer cases and macular degeneration on the eye), and B1R knockout mice are protected from induction of obesity by a particularly fat-rich diet (Pesquero et al., Biol. Chem. 2006, 387, 119-126). B1R antagonists are therefore also suitable for treatment of obesity.

B1R antagonists are suitable in particular for treatment of pain, in particular inflammation pain and neuropathic pain (Calixto et al., Br. J. Pharmacol 2004, 1-16), and here in particular diabetic neuropathy (Gabra et al., Biol. Chem. 2006, 387, 127-143). They are furthermore suitable for treatment of migraine.

In the development of B1R modulators, however, there is the problem that the human and the rat B1 receptor differ so widely that many compounds which are good B1R modulators on the human receptor have only a poor or no affinity for the rat receptor. This makes pharmacological studies on animals considerably difficult, since many studies are usually conducted on the rat. However, if no activity exists on the rat receptor, neither the action nor side effects can be investigated on the rat. This has already led to transgenic animals with human B1 receptors being produced for pharmacological studies on animals (Hess et al., Biol. Chem 2006; 387(2):195-201). Working with transgenic animals, however, is more expensive than working with the unmodified animals.

International patent application nos. WO 2008/040492 and WO 2008/046573 describe compounds which, in in vitro assays, show an antagonistic action both on the human B1 receptor and on the B1 receptor of the rat.

International patent application nos. WO 2007/140383 and WO 2007/101007 describe compounds which have an antagonistic action on the macaque B1 receptor in in vitro assays. Experimental data on the activity on the human B1 receptor or the B1 receptor of the rat are not disclosed.

Despite the efforts of the prior art, there continues to be a need for novel B1R modulators, B1R modulators which bind both to the rat receptor and to the human receptor offering particular advantages.

SUMMARY OF THE INVENTION

An object of the present invention was therefore to provide novel compounds which are suitable in particular as pharmacologically active compounds in pharmaceutical compositions.

Another object was to provide novel pharmacologically active compounds which are useful for treating or inhibiting disorders or disease states which are at least partly mediated by B1R receptors.

These and other objects are achieved in accordance with the present invention by providing the substituted spiro-amide compounds described and claimed hereinafter.

The present invention therefore provides substituted spiro-amide compounds corresponding to formula (I)

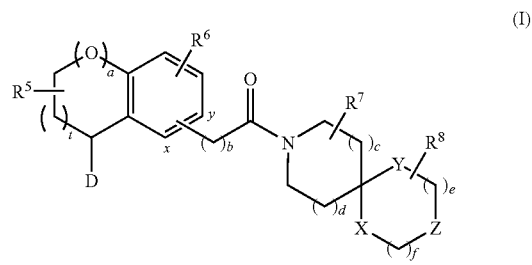

wherein
a represents 0 or 1;
t represents 1, 2 or 3;
b represents 0, 1 or 2;
c, d, e and f each independently represent 0, 1 or 2;
D represents one of the following groups D1 or D2

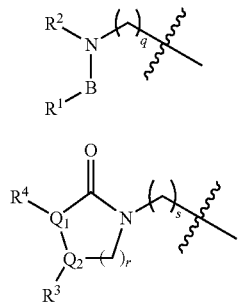

q represents 0 or 1;
s represents 0 or 1;
r represents 1, 2 or 3;
B represents C(=O), S(=O)$_2$ or the group —C(=O)—N(R$^9$), wherein the nitrogen atom thereof is bonded to R$^1$;
Q$_1$ and Q$_2$ each independently represent C, CH or N;
R$^1$ represents C$_{1-6}$-alkyl, aryl, heteroaryl, —CH(aryl)$_2$, C$_{3-8}$-cycloalkyl or an aryl, heteroaryl or C$_{3-8}$-cycloalkyl bonded via a C$_{1-6}$-alkylene group, C$_{2-6}$-alkenylene group or C$_{2-6}$-alkynylene group, or an aryl or heteroaryl group bonded via a C$_{3-6}$ cycloalkylene group;
R$^2$ represents H, C$_{1-6}$-alkyl, C$_{3-8}$-cycloalkyl, aryl, heteroaryl or a C$_{3-8}$-cycloalkyl, aryl or heteroaryl group bonded via a C$_{1-6}$-alkylene group;
R$^3$ and R$^4$ together with the group -Q$_1$-Q$_2$- joining them form a ring, which may be unsubstituted or substituted on one or more, for example 1, 2 or 3, of its carbon ring members by one or more, for example 1, 2, 3 or 4, substituents independently selected from the group consisting of F, Cl, Br, I, CF$_3$, C$_{1-6}$-alkyl, O—C$_{1-6}$-alkyl, OH, OCF$_3$, SH, SCF$_3$, aryl and heteroaryl and/or can be fused with at least one, for example 1 or 2, aryl or heteroaryl, wherein the ring is saturated, unsaturated one or more times, for example once or twice, or aromatic, is 4-, 5-, 6- or 7-membered, and can optionally contain one or more, for example 1, 2 or 3, hetero atoms or hetero atom groups independently selected from the group consisting of N, NR$^{50}$, O, S, S(=O) and S(=O)$_2$; wherein R$^{50}$ denotes H, C$_{1-6}$-alkyl, —C(=O)—R$^{51}$, C$_{3-8}$-cycloalkyl, aryl, heteroaryl or a C$_{3-8}$-cycloalkyl, aryl or heteroaryl group bonded via a C$_{1-3}$-alkylene group, and R$^{51}$ denotes C$_{1-6}$-alkyl, C$_{3-8}$-cycloalkyl, aryl, heteroaryl or a C$_{3-8}$-cycloalkyl, aryl or heteroaryl group bonded via a C$_{1-3}$-alkylene group;
R$^5$ represents 0, 1, 2, 3 or 4 substituents independently selected from the group consisting of F, Cl, CF$_3$, OCF$_3$, OH, C$_{1-6}$-alkyl and O—C$_{1-6}$-alkyl and/or two adjacent substituents R$^5$ form a fused-on aryl, heteroaryl or C$_{4-8}$-cycloalkyl and/or two substituents R$^5$ bonded to a carbon atom form a 3, 4 or 5 membered saturated carbocyclic ring, which may be unsubstituted or substituted on one or more, for example 1, 2 or 3, of its carbon ring members by one or more, for example 1, 2, 3 or 4, substituents independently selected from the group consisting of F, CF$_3$ and C$_{1-6}$-alkyl;

R$^6$ represents 0, 1, 2, 3 or 4 substituents independently selected from the group consisting of F, Cl, Br, CF$_3$, OCF$_3$, OH, C$_{1-6}$-alkyl, C$_{3-8}$-cycloalkyl, O—C$_{1-6}$-alkyl, NO$_2$, NH$_2$, N(H)(C$_{1-6}$-alkyl) and N(C$_{1-6}$-alkyl)$_2$ and/or two adjacent substituents R$^6$ form a fused-on aryl, heteroaryl or C$_{4-8}$-cycloalkyl;
R$^7$ and R$^8$ each independently represent 0, 1, 2, 3 or 4 substituents which in each case independently of one another are selected from the group consisting of F, Cl, OH, =O, C$_{1-6}$-alkyl, O—C$_{1-6}$-alkyl, C$_{3-8}$-cycloalkyl, aryl, heteroaryl and C$_{3-8}$-cycloalkyl, aryl or heteroaryl group bonded via a C$_{1-6}$-alkylene group and/or two adjacent substituents R$^7$ or R$^8$ form a fused-on aryl or heteroaryl;
R$^9$ represents H, C$_{1-6}$-alkyl, C$_{3-8}$-cycloalkyl, aryl, heteroaryl or a C$_{3-8}$-cycloalkyl, aryl or heteroaryl group bonded via a C$_{1-3}$-alkylene group;
X represents CR$^{10a}$R$^{10b}$, NR$^{11}$ or O;
Y represents CR$^{12a}$R$^{12b}$, NR$^{13}$ or O;
with the proviso that X does not denote NR$^{11}$ if Y denotes NR$^{13}$; and
with the proviso that X and Y do not simultaneously denote O;
wherein
R$^{10a}$, R$^{10b}$, R$^{12a}$ and R$^{12b}$ independently of one another each denote H, F, Cl, OH, C$_{1-6}$-alkyl, O—C$_{1-6}$-alkyl, C$_{3-8}$-cycloalkyl, aryl or heteroaryl, or represent a C$_{3-8}$-cycloalkyl, aryl or heteroaryl group bonded via a C$_{1-6}$-alkylene group, and/or
in each case R$^{10a}$ and R$^{10b}$ together can represent =O and/or in each case R$^{12a}$ and R$^{12b}$ together can represent =O;
R$^{11}$ and R$^{13}$ each independently represent H, C$_{1-6}$-alkyl, C$_{3-8}$-cycloalkyl, aryl or heteroaryl, or denote a C$_{3-8}$-cycloalkyl, aryl or heteroaryl group bonded via a C$_{1-6}$-alkylene group;
Z represents CR$^{14a}$R$^{14b}$, NR$^{15}$ or O;
R$^{14a}$ represents H, NR$^{16}$R$^{17}$, C$_{1-6}$-alkylene-NR$^{16}$R$^{17}$, O—C$_{1-6}$-alkylene-NR$^{16}$R$^{17}$, C(=O)—NR$^{16}$R$^{17}$, C(=O)—C$_{1-6}$-alkylene-NR$^{16}$R$^{17}$, OR$^{18}$, C$_{1-6}$-alkylene-OR$^{18}$, C$_{1-6}$-alkylene-O—C$_{1-6}$-alkylene-OR$^{18}$, C$_{1-6}$-alkyl, C$_{3-8}$-cycloalkyl, heterocyclyl, aryl or heteroaryl, or denotes a C$_{3-8}$-cycloalkyl, heterocyclyl, aryl or heteroaryl group bonded via a C$_{1-6}$-alkylene group,
R$^{14b}$ represents H, NR$^{16}$R$^{17}$, C$_{1-6}$-alkylene-NR$^{16}$R$^{17}$, O—C$_{1-6}$-alkylene-NR$^{16}$R$^{17}$, C(=O)—NR$^{16}$R$^{17}$, C(=O)—C$_{1-6}$-alkylene-NR$^{16}$R$^{17}$, OR$^{18}$, C$_{1-6}$-alkylene-OR$^{18}$, C$_{1-6}$-alkylene-O—C$_{1-6}$-alkylene-OR$^{18}$, C$_{1-6}$-alkyl, C$_{3-8}$-cycloalkyl, heterocyclyl, aryl or heteroaryl, or denotes a C$_{3-8}$-cycloalkyl, heterocyclyl, aryl or heteroaryl group bonded via a C$_{1-6}$-alkylene group;
R$^{15}$ represents H, —C(=O)—R$^{19}$, —S(=O)$_2$—R$^{19}$, —C(=O)—N(R$^{20}$)—R$^{19}$, CHR$^{25}$R$^{26}$, C$_{1-10}$-alkyl, C$_{3-8}$-cycloalkyl, heterocyclyl, aryl or heteroaryl or denotes a CHR$^{25}$R$^{26}$, C$_{3-8}$-cycloalkyl, heterocyclyl, aryl or heteroaryl group bonded via a C$_{1-6}$-alkylene group;
R$^{16}$ and R$^{17}$ each independently represent H, C$_{1-6}$-alkyl or C$_{3-8}$-cycloalkyl, or
R$^{16}$ and R$^{17}$ together with the nitrogen atom joining them form a heterocyclic ring, which may be unsubstituted or substituted on one or more, for example 1, 2 or 3, of its carbon ring members by one or more, for example 1, 2, 3 or 4, substituents independently selected from the group consisting of F, Cl, Br, I, CF$_3$, C$_{1-6}$-alkyl, O—C$_{1-6}$-alkyl, OH, OCF$_3$, SH, SCF$_3$, NR$^A$R$^B$, aryl and heteroaryl and/or can be fused with at least one, for example 1 or 2, aryl or heteroaryl, wherein the heterocyclic ring is saturated or unsaturated one or more times, for example once or twice, is 4-, 5-, 6- or 7-membered, and can optionally contain one or more, for example 1, 2 or 3, hetero atoms or hetero atom groups independently selected from the group consisting of N, $NR^{50a}$, O, S, S(=O) and S(=O)$_2$; wherein $R^{50a}$ denotes H, $C_{1-6}$-alkyl, —C(=O)—$R^{51a}$, $C_{3-8}$-cycloalkyl, aryl, heteroaryl or a $C_{3-8}$-cycloalkyl, aryl or heteroaryl group bonded via a $C_{1-3}$-alkylene group, and $R^{51}$ denotes $C_{1-6}$-alkyl, $C_{3-8}$-cycloalkyl, aryl, heteroaryl or a $C_{3-8}$-cycloalkyl, aryl or heteroaryl group bonded via a $C_{1-3}$-alkylene group;

$R^{18}$ represents H, $C_{1-6}$-alkyl, $C_{3-8}$-cycloalkyl, heterocyclyl, aryl, heteroaryl or $C_{2-6}$-alkylene-$NR^{16}R^{17}$ or denotes a heterocyclyl, $C_{3-8}$-cycloalkyl, aryl or heteroaryl group bonded via a $C_{1-6}$-alkylene group;

$R^{19}$ represents $C_{1-6}$-alkyl, aryl, heteroaryl, —CH(aryl)$_2$, $C_{3-8}$-cycloalkyl, heterocyclyl or an aryl, heteroaryl, $C_{3-8}$-cycloalkyl or heterocyclyl bonded via a $C_{1-6}$-alkylene group, $C_{2-6}$-alkenylene group or $C_{2-6}$-alkynylene group;

$R^{20}$ represents H, $C_{1-6}$-alkyl, $C_{3-8}$-cycloalkyl, aryl, heteroaryl or a $C_{3-8}$-cycloalkyl, aryl or heteroaryl group bonded via a $C_{1-3}$-alkylene group;

or if X represents O and f represents 0, then Z denotes —(C($R^{21}$)—C($R^{22}$))—, wherein
$R^{21}$ and $R^{22}$, together with the carbon atoms joining them, form a fused-on aryl or heteroaryl; or if X represents O and f represents 0, then Z denotes =(N(C$R^{23}$))—, wherein the N atom is bonded to the O atom via a single bond, and
$R^{23}$ represents H, $C_{1-6}$-alkyl, $C_{3-8}$-cycloalkyl, aryl or heteroaryl or denotes a $C_{3-8}$-cycloalkyl, aryl or heteroaryl group bonded via a $C_{1-6}$-alkylene group;

$R^{25}$ and $R^{26}$ each independently represent H, $C_{1-4}$-alkyl, $C_{3-8}$-cycloalkyl, aryl or heteroaryl, or $R^{25}$ and $R^{26}$ together with the CH grouping joining them form a ring, which may be unsubstituted or substituted on one or more, for example 1, 2 or 3, of its carbon ring members by one or more, for example 1, 2, 3 or 4, substituents independently selected from the group consisting of F, Cl, Br, I, CF$_3$, $C_{1-6}$-alkyl, O—$C_{1-6}$-alkyl, OH, OCF$_3$, SH, SCF$_3$, $NR^AR^B$, aryl and heteroaryl, wherein the ring is saturated or unsaturated one or more times, for example once or twice, but is not aromatic, is 4-, 5-, 6- or 7-membered, and can optionally contain one or more, for example 1, 2 or 3, hetero atoms or hetero atom groups independently selected from the group consisting of N, $NR^{50b}$, O, S, S(=O) and S(=O)$_2$; wherein $R^{50b}$ denotes H, $C_{1-6}$-alkyl, —C(=O)—$R^{51b}$, $C_{3-8}$-cycloalkyl, aryl, heteroaryl or a $C_{3-8}$-cycloalkyl, aryl or heteroaryl group bonded via a $C_{1-3}$-alkylene group, and $R^{51b}$ denotes $C_{1-6}$-alkyl, $C_{3-8}$-cycloalkyl, aryl, heteroaryl or a $C_{3-8}$-cycloalkyl, aryl or heteroaryl group bonded via a $C_{1-3}$-alkylene group;

$R^A$ and $R^B$ each independently represent H, $C_{1-6}$-alkyl or $C_{3-8}$-cycloalkyl, or $R^A$ and $R^B$ together with the nitrogen atom joining them form a heterocyclic ring, which may be unsubstituted or substituted on one or more, for example 1, 2 or 3, of its carbon ring members by one or more, for example 1, 2, 3 or 4, substituents independently selected from the group consisting of F, Cl, Br, I, CF$_3$, $C_{1-6}$-alkyl, O—$C_{1-6}$-alkyl, OH, OCF$_3$, SH, SCF$_3$, aryl and heteroaryl, wherein the heterocyclic ring is saturated or unsaturated one or more times, for example once or twice, but is not aromatic, is 4-, 5-, 6- or 7-membered, and can optionally contain one or more, for example 1, 2 or 3, hetero atoms or hetero atom groups independently selected from the group consisting of N, $NR^C$, O, S, S(=O) and S(=O)$_2$; wherein $R^C$ denotes H, $C_{1-6}$-alkyl, —C(=O)—$R^D$, $C_{3-8}$-cycloalkyl, aryl, heteroaryl or a $C_{3-8}$-cycloalkyl, aryl or heteroaryl group bonded via a $C_{1-3}$-alkylene group, and $R^D$ denotes $C_{1-6}$-alkyl, $C_{3-8}$-cycloalkyl, aryl, heteroaryl or a $C_{3-8}$-cycloalkyl, aryl or heteroaryl group bonded via a $C_{1-3}$-alkylene group; and wherein the partial structure

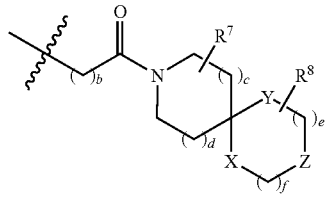

is preferably bonded to the base structure in position x or y, and wherein the abovementioned $C_{1-4}$-alkyl, $C_{1-6}$-alkyl, $C_{1-10}$-alkyl, $C_{1-3}$-alkylene, $C_{1-6}$-alkylene, $C_{2-6}$-alkylene, $C_{2-6}$-alkenylene, $C_{2-6}$-alkynylene, $C_{3-8}$-cycloalkyl, $C_{4-8}$-cycloalkyl, heterocyclyl, aryl and heteroaryl groups can in each case be unsubstituted or substituted one or more times by identical or different substituents and the abovementioned radicals $C_{1-4}$-alkyl, $C_{1-6}$-alkyl, $C_{1-10}$-alkyl, $C_{1-3}$-alkylene, $C_{1-6}$-alkylene, $C_{2-6}$-alkylene, $C_{2-6}$-alkenylene and $C_{2-6}$-alkynylene can in each case be branched or unbranched;

in the form of the free compounds; of the tautomers; of the N-oxides; of the racemate; of the enantiomers, diastereomers, mixtures of the enantiomers or diastereomers or of an individual enantiomer or diastereomer; or in the form of the salts of physiologically acceptable acids or bases.

In the context of the present invention, the term "halogen" preferably represents F, Cl, Br and I, in particular F and Cl.

In the context of this invention, the expression "$C_{1-10}$-alkyl", "$C_{1-6}$-alkyl" or "$C_{1-4}$-alkyl" includes acyclic saturated hydrocarbon groups having 1-10 C atoms, 1, 2, 3, 4, 5 or 6 C atoms or, respectively, 1, 2, 3 or 4 C atoms, which can be branched- or straight-chain (unbranched) and unsubstituted or substituted one or more times, for example 2, 3, 4 or 5 times, by identical or different substituents. The alkyl groups can preferably be selected from the group consisting of methyl, ethyl, n-propyl, iso-propyl, n-butyl, iso-butyl, sec-butyl, tert-butyl, n-pentyl, iso-pentyl, neo-pentyl and hexyl. Particularly preferred alkyl groups are selected from the group consisting of methyl, ethyl, n-propyl, iso-propyl, n-butyl, sec-butyl, iso-butyl and tert-butyl.

In the context of this invention, the expression "$C_{3-8}$-cycloalkyl", "$C_{4-8}$-cycloalkyl" or "$C_{3-6}$-cycloalkyl" denotes cyclic saturated hydrocarbons having 3, 4, 5, 6, 7 or 8, having 4, 5, 6, 7 or 8 or, respectively, having 3, 4, 5 or 6 carbon atoms, which can be unsubstituted or substituted once or more times, for example by 2, 3, 4 or 5 identical or different substituents, on one or more ring members. $C_{3-8}$-Cycloalkyl can preferably be selected from the group consisting of cyclopropyl, cyclobutyl, cyclopentyl, cyclohexyl, cycloheptyl and cyclooctyl.

The term "heterocyclyl" includes saturated or unsaturated (but not aromatic) cycloalkyls having three to seven ring members, in which one, two or three carbon atoms are replaced by a hetero atom in each case independently of one another chosen from the group S, N or O, wherein the ring members can be unsubstituted or substituted one or more times. The bonding of the heterocyclyl to the main general structure can be via any desired and possible ring member of the heterocyclyl radical. The heterocyclyl groups can also be condensed with further saturated, (partially) unsaturated or aromatic or heteroaromatic ring systems, which in turn can be unsubstituted or substituted one or more times. Heterocyclyl groups selected from the group consisting of azetidinyl, aziridinyl, azepanyl, dioxanyl, dioxolanyl, morpholinyl, pyranyl, pyrrolidinyl, piperazinyl, piperidinyl, pyrazolidinyl, pyrazolinonyl or thiomorpholinyl are preferred.

Cycloalkyl and heterocyclyl groups also may be bridged by $C_{1-6}$-alkylene, preferably by $C_{1-3}$-alkylene, as, for example, in

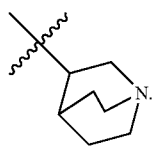

Where an aryl or heteroaryl group is bonded via a $C_{3-6}$ cycloalkylene group this bonding may be effected via the same or different carbon atoms of the cycloalkylene group, e.g

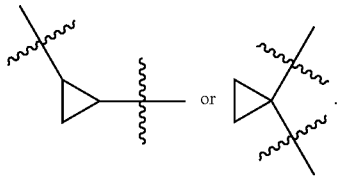 [SMILES: *C1CC1* ; *C1(*)CC1]

In the context of this invention, the expression "aryl" denotes aromatic hydrocarbons, in particular phenyls and naphthyls. The aryl groups can also be condensed with further saturated, (partially) unsaturated or aromatic ring systems. Each aryl group radical can be unsubstituted or substituted one or more times, for example 2, 3, 4 or 5 times, wherein the substituents on the aryl can be identical or different and can be in any desired and possible position of the aryl. Aryl can advantageously be selected from the group consisting of phenyl, 1-naphthyl and 2-naphthyl, which in each case can be unsubstituted or substituted one or more times, for example by 2, 3, 4 or 5 substituents.

In the context of the present invention, the expression "heteroaryl" represents a 5-, 6- or 7-membered cyclic aromatic group which contains at least 1, optionally also 2, 3, 4 or 5 hetero atoms, wherein the hetero atoms can be identical or different and the heteroaryl can be unsubstituted or substituted one or more times, for example 2, 3, 4 or 5 times, by identical or different substituents. The substituents can be bonded in any desired and possible position of the heteroaryl. The heterocyclic ring can also be part of a bi- or polycyclic, in particular a mono-, bi- or tricyclic system, which can then be more than 7-membered in total, preferably up to 14-membered. Preferred hetero atoms are independently selected from the group consisting of N, O and S. The heteroaryl group can be selected, for example, from the group consisting of isoxazolyl, [1,2,3]-thiadiazolyl, pyrrolyl, indolyl, furyl (furanyl), benzofuranyl, thienyl (thiophenyl), benzimidazolyl, benzothienyl, benzothiadiazolyl, benzothiazolyl, benzotriazolyl, benzodioxolanyl, benzodioxanyl, benzooxazolyl, benzooxadiazolyl, imidazothiazolyl, dibenzofuranyl, dibenzothienyl, phtalazinyl, pyrazolyl, imidazolyl, thiazolyl, oxazolyl, oxadiazolyl, triazinyl, triazole, tetrazole, isoxazoyl, pyridinyl (pyridyl), pyridazinyl, pyrimidinyl, pyrazinyl, pyranyl, indazolyl, purinyl, indolizinyl, quinolinyl, isoquinolinyl, quinazolinyl, quinoxalinyl, carbazolyl, phenazinyl, phenothiazinyl and oxadiazolyl, in particular from the group consisting of thienyl (thiophenyl), pyridinyl (pyridyl), pyrimidinyl, thiazolyl, triazolyl, imidazolyl, oxazolyl, oxadiazolyl, quinazolinyl, quinolinyl and isoquinolinyl, wherein bonding to the general structure (I) can be via any desired and possible ring member of the heteroaryl radical. The heteroaryl radical can preferably be selected from the group consisting of pyrrolyl, indolyl, furyl (furanyl), benzofuranyl, thienyl (thiophenyl), benzimidazolyl, benzothienyl, benzothiadiazolyl, benzothiazolyl, benzotriazolyl, benzodioxolanyl, benzodioxanyl, benzooxazolyl, benzooxadiazolyl, imidazothiazolyl, dibenzofuranyl, dibenzothienyl, phtalazinyl, pyrazolyl, imidazolyl, thiazolyl, oxazolyl, oxadiazolyl, triazinyl, triazole, tetrazole, isoxazoyl, pyridinyl (pyridyl), pyridazinyl, pyrimidinyl, pyrazinyl, pyranyl, indazolyl, purinyl, indolizinyl, quinolinyl, isoquinolinyl, quinazolinyl, quinoxalinyl, carbazolyl, phenazinyl, phenothiazinyl and oxadiazolyl, in particular from the group consisting of thienyl (thiophenyl), pyridinyl (pyridyl), pyrimidinyl, thiazolyl, triazolyl, imidazolyl, oxazolyl, oxadiazolyl, quinazolinyl, quinolinyl and isoquinolinyl, wherein bonding to the general structure (I) can be via any desired and possible ring member of the heteroaryl group.

The heteroaryl group can particularly preferably be selected from the group consisting of thienyl, imidazoyl, thiazolyl, triazolyl, pyridinyl and pyrimidinyl.

In the context of the present invention, the expression "$C_{1-3}$-alkylene group", "$C_{1-6}$-alkylene group" or "$C_{2-6}$-alkylene group" includes acyclic saturated hydrocarbon groups having 1, 2 or 3 C atoms, 1, 2, 3, 4, 5 or 6 C atoms or, respectively, 2, 3, 4, 5 or 6 C atoms, which can be branched- or straight-chain (unbranched) and unsubstituted or substituted one or more times, for example 2, 3, 4 or 5 times, by identical or different substituents and which link a corresponding radical to the main general structure. The alkylene groups can preferably be selected from the group consisting of —$CH_2$—, —$CH_2$—$CH_2$—, —$CH(CH_3)$—, —$CH_2$—$CH_2$—$CH_2$—, —$CH(CH_3)$—$CH_2$—, —$CH(CH_2CH_3)$—, —$CH_2$—$(CH_2)_2$—$CH_2$—, —$CH(CH_3)$—$CH_2$—$CH_2$—, —$CH_2$—$CH(CH_3)$—$CH_2$—, —$CH(CH_3)$—$CH(CH_3)$—, —$CH(CH_2CH_3)$—$CH_2$—, —$C(CH_3)_2$—$CH_2$—, —$CH(CH_2CH_2CH_3)$—, —$C(CH_3)(CH_2CH_3)$—, —$CH_2$—$(CH_2)_3$—$CH_2$—, —$CH(CH_3)$—$CH_2$—$CH_2$—$CH_2$—, —$CH_2$—$CH(CH_3)$—$CH_2$—$CH_2$—, —$CH(CH_3)$—$CH_2$—$CH(CH_3)$—, —$CH(CH_3)$—$CH(CH_3)$—$CH_2$—, —$C(CH_3)_2$—$CH_2$—$CH_2$—, —$CH_2$—$C(CH_3)_2$—$CH_2$—, —$CH(CH_2CH_3)$—$CH_2$—$CH_2$—, —$CH_2$—$CH(CH_2CH_3)$—$CH_2$—, —$C(CH_3)_2$ —$CH(CH_3)$—, —$CH(CH_2CH_3)$—$CH(CH_3)$—, —$C(CH_3)(CH_2CH_3)$—$CH_2$—, —$CH(CH_2CH_2CH_3)$—$CH_2$—, —$C(CH_2CH_2CH_3)$—$CH_2$—, —$CH(CH_2CH_2CH_2CH_3)$—, —$C(CH_3)(CH_2CH_2CH_3)$—, —$C(CH_2CH_3)_2$— and —$CH_2$—$(CH_2)_4$—$CH_2$—. The alkylene groups can particularly preferably be selected from the group consisting of —$CH_2$—, —$CH_2$—$CH_2$— and —$CH_2$—$CH_2$—$CH_2$—.

In the context of the present invention, the expression "$C_{2-6}$- alkenylene group" includes acyclic hydrocarbon radicals having 2, 3, 4, 5 or 6 C atoms which are unsaturated one or more times, for example 2, 3 or 4 times, and can be branched- or straight-chain (unbranched) and unsubstituted or substituted one or more times, for example 2, 3, 4 or 5 times, by identical or different substituents and which link a corresponding radical to the main general structure. In this context, the alkenylene groups contain at least one C═C double bond. The alkenylene groups can preferably be selected from the group consisting of —CH═CH—, —CH═CH—$CH_2$—, —$C(CH_3)$═$CH_2$—, —CH═CH—$CH_2$—$CH_2$—, —$CH_2$—CH═CH—$CH_2$—, —CH═CH—

CH=CH—, —C(CH$_3$)=CH—CH$_2$—, —CH=C(CH$_3$)—CH$_2$—, —C(CH$_3$)=C(CH$_3$)—, —C(CH$_2$CH$_3$)=CH—, —CH=CH—CH$_2$—CH$_2$—CH$_2$—, —CH$_2$—CH=CH$_2$—CH$_2$—CH$_2$—, —CH=CH—CH—CH$_2$—CH$_2$— and —CH=CH$_2$—CH=CH—CH$_2$—.

In the context of the invention, the expression "C$_{2-6}$-alkynylene group" includes acyclic hydrocarbon groups having 2, 3, 4, 5 or 6 C atoms which are unsaturated one or more times, for example 2, 3 or 4 times, and can be branched- or straight-chain (unbranched) and unsubstituted or substituted one or more times, for example 2, 3, 4 or 5 times, by identical or different substituents and which link a corresponding group to the main general structure. In this context, the alkynylene groups contain at least one C≡C triple bond. The alkynylene groups can preferably be selected from the group consisting of —C≡C—, —C≡C—CH$_2$—, —C≡C—CH$_2$—CH$_2$—, —C≡C—CH(CH$_3$)—, —CH$_2$—C≡C—CH$_2$—, —C≡C—C≡C—, —C≡C—C(CH$_3$)$_2$—, —C≡C—CH$_2$—CH$_2$—CH$_2$—, —CH$_2$—C≡C—CH$_2$—CH$_2$—, —C≡C—C≡C—CH$_2$— and —C≡C—CH$_2$—C≡C—.

In the context of the present invention, the expression "aryl or heteroaryl group bonded via a C$_{1-3}$-alkylene group, a C$_{1-6}$-alkylene group, "C$_{2-6}$-alkylene group", C$_{2-6}$-alkenylene group or C$_{2-6}$-alkynylene group" means that the C$_{1-3}$alkylene groups, C$_{1-6}$-alkylene groups, C$_{2-6}$-alkylene groups, C$_{2-6}$-alkenylene groups, C$_{2-6}$-alkynylene groups and aryl or heteroaryl have the meanings defined above and the aryl or heteroaryl is bonded to the main general structure via a C$_{1-3}$-alkylene group, C$_{1-6}$-alkylene group, C$_{2-6}$-alkylene group, C$_{2-6}$-alkenylene group or C$_{2-6}$-alkynylene group. Examples included benzyl, phenethyl and phenylpropyl groups.

In the context of the present invention, the expression "C$_{3-8}$- cycloalkyl and heterocyclyl bonded via a C$_{1-3}$-alkylene group, C$_{1-6}$-alkylene group, C$_{2-6}$-alkylene group, C$_{2-6}$-alkenylene group or C$_{2-6}$-alkynylene group" means that the C$_{1-3}$-alkylene group, C$_{1-6}$-alkylene group, C$_{2-6}$-alkylene group, C$_{2-6}$-alkenylene group, C$_{2-6}$-alkynylene group, C$_{3-8}$-cycloalkyl and heterocyclyl have the meanings defined above and C$_{3-8}$-cycloalkyl and heterocyclyl is bonded to the main general structure via a C$_{1-3}$-alkylene group, C$_{1-6}$-alkylene group, C$_{2-6}$-alkylene group, C$_{2-6}$-alkenylene group or C$_{2-6}$-alkynylene group.

In connection with "alkyl", "alkylene", alkenylene", "alkynylene", "cycloalkyl" and "heterocyclyl", in the context of this invention the term "substituted" is understood as meaning replacement of a hydrogen by F, Cl, Br, I, CF$_3$, OCF$_3$, CN, NH$_2$, NH—C$_{1-6}$-alkyl, NH—C$_{1-6}$-alkylene-OH, C$_{1-6}$-alkyl, N(C$_{1-6}$-alkyl)$_2$, N(C$_{1-6}$-alkylene-OH)$_2$, NO$_2$, SH, S—C$_{1-6}$-alkyl, C$_{1-6}$-alkyl, S-benzyl, O—C$_{1-6}$-alkyl, OH, O—C$_{1-6}$-alkylene-OH, =O, O-benzyl, C(=O)C$_{1-6}$-alkyl, CO$_2$H, CO$_2$—C$_{1-6}$-alkyl, phenyl, phenoxy, benzyl, naphthyl, furyl, thienyl and pyridinyl, wherein radicals substituted several times are to be understood as meaning those radicals which are substituted several times, for example two or three times, either on different or on the same atoms, for example three times on the same C atom, as in the case of CF$_3$ or CH$_2$CF$_3$, or at different places, as in the case of CH(Cl)—CH=CH—CHCl$_2$. Substitution several times can be by identical or different substituents, such as, for example, in the case of CH(OH)—CH=CH—CHCl$_2$. In particular, this is to be understood as meaning replacement of one or more hydrogens by F, Cl, NH$_2$, OH, phenyl, O—CF$_3$ or O—C$_{1-6}$-alkyl, in particular methoxy.

With respect to "aryl" and "heteroaryl", in the context of this invention "substituted" is understood as meaning replacement one or more times, for example 2, 3, 4 or 5 times, of one or more hydrogen atoms of the corresponding ring system by F, Cl, Br, I, CN, NH$_2$, NR$^A$R$^B$, C(=O)—NR$^A$R$^B$, NH—C$_{1-6}$-alkyl, NH—C$_{1-6}$-alkylene-OH, N(C$_{1-6}$-alkyl)$_2$, N(C$_{1-6}$-alkylene-OH)$_2$, NH-aryl$^1$, N(aryl$^1$)$_2$, N(C$_{1-6}$-alkyl)aryl$^1$, pyrrolinyl, piperazinyl, morpholinyl, azetidinyl, piperidinyl, thiazolinyl, azepanyl, diazepanyl, (C$_{1-3}$-alkylene)-azetidinyl, (C$_{1-3}$-alkylene)-pyrrolinyl, (C$_{1-3}$-alkylene)-piperidinyl, (C$_{1-3}$-alkylene)-morpholinyl, (C$_{1-3}$-alkylene)-piperazinyl, (C$_{1-3}$-alkylene)-thiazolinyl, (C$_{1-3}$-alkylene)-azepanyl, (C$_{1-3}$-alkylene)-diazepanyl, NO$_2$, SH, S—C$_{1-6}$-alkyl, OH, O—C$_{1-6}$-alkyl, O—C$_{1-6}$-alkyl-OH, C(=O)C$_{1-6}$-alkyl, NHSO$_2$C$_{1-6}$-alkyl, NHCOC$_{1-6}$-alkyl, CO$_2$H, CH$_2$SO$_2$-phenyl, CO$_2$—C$_{1-6}$-alkyl, OCF$_3$, CF$_3$, —O—CH$_2$—O—, —O—CH$_2$—CH$_2$—O—, —O—C(CH$_3$)$_2$—CH$_2$—, unsubstituted C$_{1-6}$-alkyl, C$_{3-6}$-cycloalkyl, O—C$_{3-6}$-cycloalkyl, pyrrolidinyl, imidazolyl, benzyloxy, phenoxy, phenyl, naphthyl, pyridinyl, pyrimidinyl, —C$_{1-3}$-alkylene-aryl', benzyl, thienyl, furyl, or OCF$_3$, OH, O—C$_{1-6}$-alkyl, SH, S—C$_{1-6}$-alkyl, C$_{3-6}$-cycloalkyl, O—C$_{3-6}$-cycloalkyl, NR$^A$R$^B$, C(=O)—NR$^A$R$^B$, phenyl, pyridyl or pyrimidyl bonded via a C$_{1-6}$-alkylene group, wherein aryl$^1$ represents phenyl, thiazolyl, thienyl or pyridinyl, on one or various atoms, wherein the abovementioned substituents—unless stated otherwise—can optionally be substituted in their turn by the substituents mentioned. Substitution of aryl and heteroaryl several times can be by identical or different substituents. Preferred substituents for aryl and heteroaryl can be selected from the group consisting of —O—C$_{1-3}$-alkyl, unsubstituted C$_{1-6}$-alkyl, F, Cl, Br, I, CN, CF$_3$, OCF$_3$, OH, SH, —CH$_2$-azetidinyl, —CH$_2$-pyrrolidinyl, —CH$_2$-piperidinyl, —CH$_2$-piperazinyl, —CH$_2$-morpholinyl, phenyl, naphthyl, thiazolyl, thienyl and pyridinyl, in particular from the group consisting of F, Cl, CN, CF$_3$, CH$_3$; OCH$_3$, OCF$_3$, and —CH$_2$-azetidinyl.

In the chemical structural formulae used here to describe the compounds according to the invention, the symbol

is also used to describe one or more substitution patterns, this group not being bonded to a particular atom within the chemical structural formula, in contrast to the representation of a bond to a particular atom (by way of example R$^a$ here represents a substituent R having a numbering represented by the variable "a"). For example—if the symbol is used in connection with a ring, the particular substituent can be bonded to any possible ring atom.

In the context of the present invention, the symbol

used in formulae designates a linking of a corresponding group to the particular main general structure.

Persons skilled in the art understand that identical atoms or groups that are used for definition of different substituents are in each case independent of one another, such as, for example, in the groupings NR$^{16}$R$^{17}$, C$_{1-6}$-alkylene-NR$^{16}$R$^{17}$, O—C$_{1-6}$-alkylene-NR$^{16}$R$^{17}$ and C(=O)—NR$^{16}$R$^{17}$.

In the context of this invention, the term "physiologically acceptable salt" is understood as meaning preferably salts of the compounds according to the invention with inorganic or organic acids, which are physiologically acceptable—in particular when used on humans and/or mammals. Examples of suitable acids are hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro1$\lambda^6$-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, hippuric acid, phosphoric acid and/or aspartic acid. The salts of hydrochloric acid (hydrochlorides) and of citric acid (citrates) are particularly preferred. This term is furthermore also understood as meaning those compounds which are obtained by quaternization of a nitrogen atom present in the structure (e.g. pyridyl, N-methylpiperidinyl). Such compounds can be obtained, for example, by alkylation with generation of the corresponding cation, with counterions such as, for example, Cl⁻ and F⁻.

In the context of the invention, the term isolated used with respect to a stereoisomer—e.g., an enantiomer or diastereomer—means substantially separated from the opposite stereoisomer, but not necessarily from other substances.

In preferred embodiments of the compounds according to the present invention $R^1$ represents $C_{1-6}$-alkyl, aryl, heteroaryl, —CH(aryl)$_2$, $C_{3-8}$-cycloalkyl or an aryl, heteroaryl or $C_{3-8}$-cycloalkyl bonded via a $C_{1-6}$-alkylene group, $C_{2-6}$-alkenylene group or $C_{2-6}$-alkynylene group and all the other substituents and indices have the meaning given above.

In preferred embodiments of the compounds according to the invention $R^{14a}$ represents H, $NR^{16}R^{17}$, $C_{1-6}$-alkylene-$NR^{16}R^{17}$, O—$C_{1-6}$-alkylene-$NR^{16}R^{17}$, C(=O)—$NR^{16}R^{17}$, $OR^{18}$, $C_{1-6}$-alkylene-$OR^{18}$, $C_{1-6}$-alkylene-O—$C_{1-6}$-alkylene-$OR^{18}$, $C_{1-6}$-alkyl, $C_{3-8}$-cycloalkyl, heterocyclyl, aryl or heteroaryl, or denotes a $C_{3-8}$-cycloalkyl, heterocyclyl, aryl or heteroaryl group bonded via a $C_{1-6}$-alkylene group, and $R^{14b}$ represents H, $NR^{16}R^{17}$, $C_{1-6}$-alkylene-$NR^{16}R^{17}$, O—$C_{1-6}$-alkylene-$NR^{16}R^{17}$, C(=O)—$NR^{16}R^{17}$, $OR^{18}$, $C_{1-6}$-alkylene-$OR^{18}$, $C_{1-6}$-alkylene-O—$C_{1-6}$-alkylene-$OR^{18}$, $C_{1-6}$-alkyl, $C_{3-8}$-cycloalkyl, heterocyclyl, aryl or heteroaryl, or denotes a $C_{3-8}$-cycloalkyl, heterocyclyl, aryl or heteroaryl group bonded via a $C_{1-6}$-alkylene group, and all the other substituents and indices have the meaning given above.

In preferred embodiments of the compounds according to the invention, q represents 0, so that D1 assumes the following form D1':

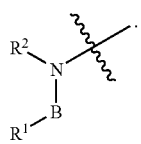

In embodiments of the compounds according to the invention which are likewise preferred, s represents 0, so that D2 assumes the following form D2':

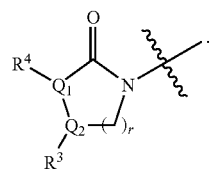

In embodiments of the compounds according to the invention which are furthermore preferred, the partial structure (Ac)

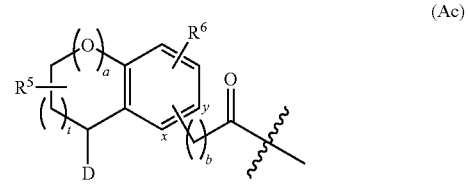

can represent a partial structure which is selected from the group consisting of:

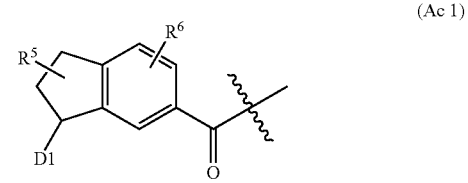

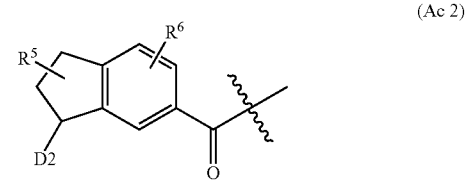

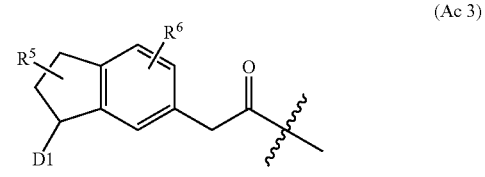

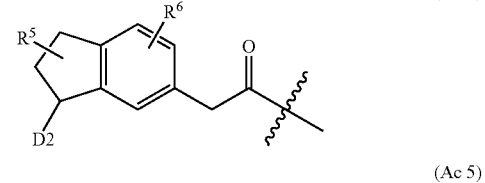

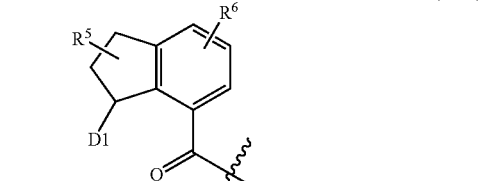

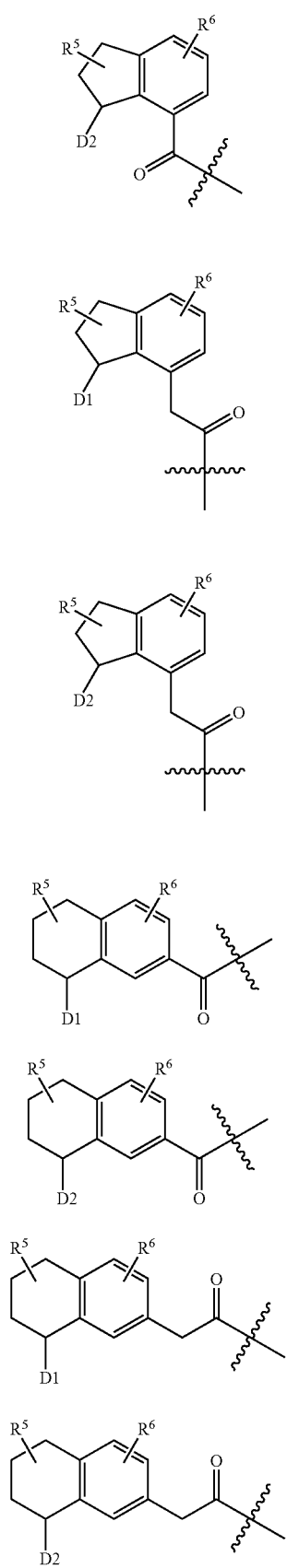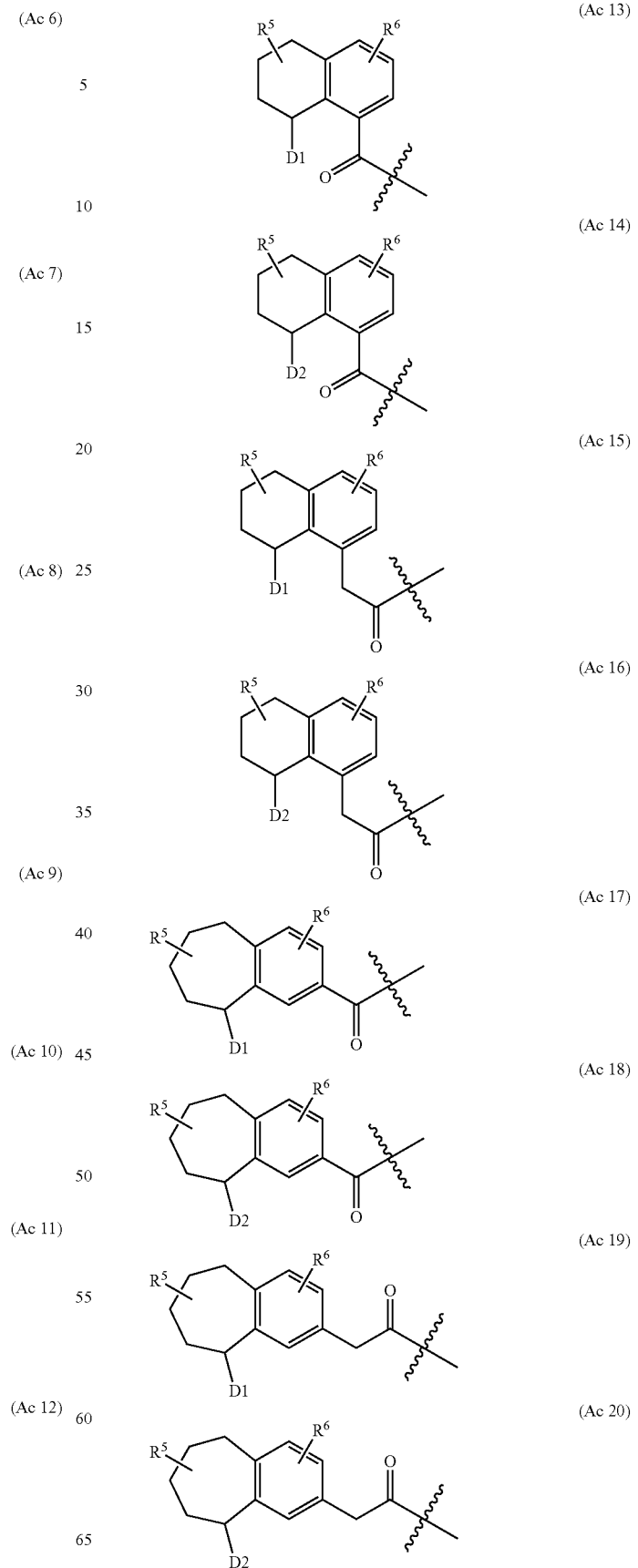

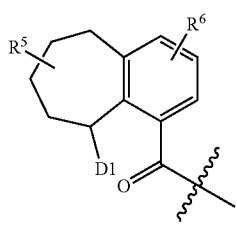 (Ac 21)
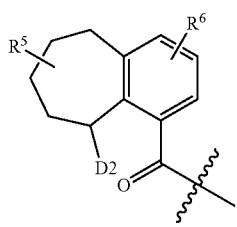 (Ac 22)
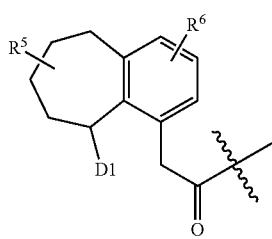 (Ac 23)
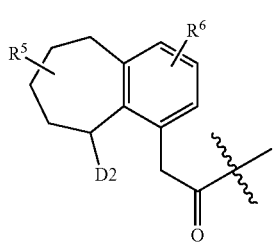 (Ac 24)
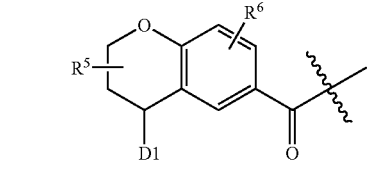 (Ac 25)
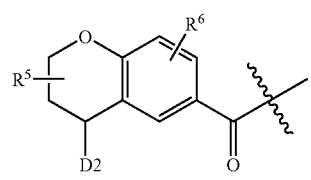 (Ac 26)
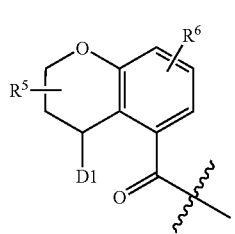 (Ac 27)
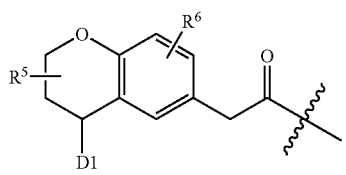 (Ac 28)
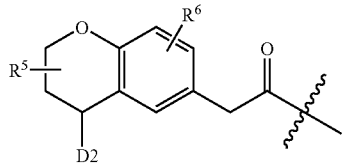 (Ac 29)
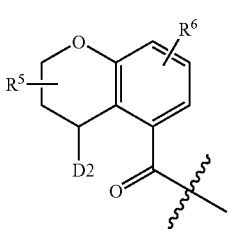 (Ac 30)
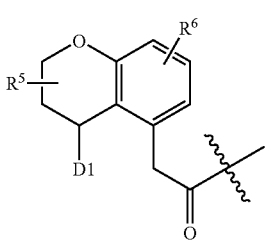 (Ac 31)
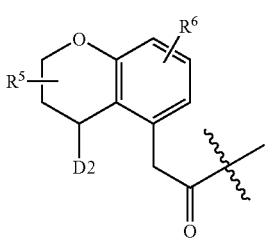 (Ac 32)
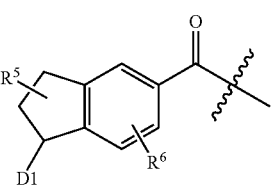 (Ac 33)
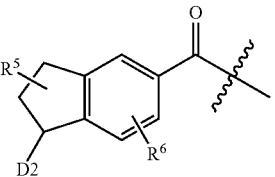 (Ac 34)
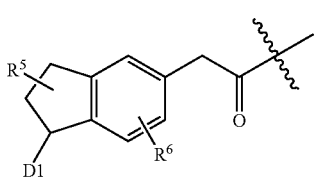 (Ac 35)

(Ac 36)
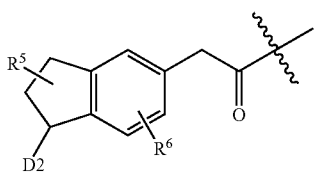

(Ac 37)
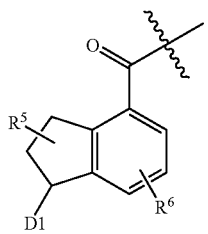

(Ac 38)
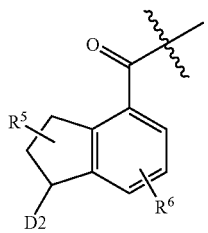

(Ac 39)
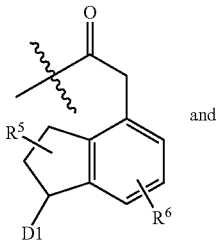

and (Ac 40)
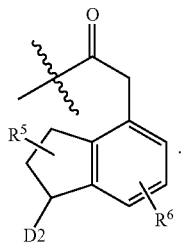

.

In other preferred embodiments of the compounds according to the present invention the partial structure (Ac) can represent a partial structure which is selected from the group consisting of Ac 1-Ac 32 as defined above.

In embodiments of the compounds according to the invention which are furthermore preferred, the partial structure D1 is selected from the group consisting of D1-1
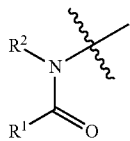

D1-2
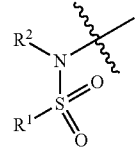

D1-3
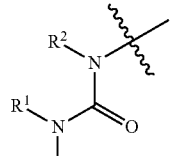

D1-4
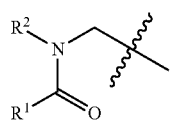

D1-5
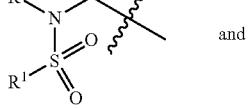

and

D1-6
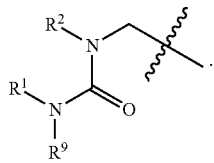

.

$R^1$ in the compounds according to the invention preferably represents $C_{1-6}$-alkyl, —CH(phenyl)$_2$, $C_{3-8}$-cycloalkyl, phenyl, naphthyl, chromanyl, indolyl, benzofuranyl, benzothiophenyl (benzothienyl), benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothiophenyl (dibenzothienyl) or a phenyl or naphthyl bonded via a $C_{1-3}$-alkylene group, a $C_{2-3}$-alkenylene group or a $C_{2-3}$-alkynylene group, particularly preferably $C_{1-4}$-alkyl, —CH(phenyl)$_2$, $C_{3-6}$-cycloalkyl, phenyl, naphthyl, chromanyl, benzothiophenyl (benzothienyl), benzooxadiazolyl, thienyl, pyridinyl, imidazothiazolyl, dibenzofuranyl or a phenyl bonded via a $C_{1-3}$-alkylene group or a $C_{2-3}$-alkenylene group, very particularly preferably $C_{1-4}$-alkyl, —CH(phenyl)$_2$, $C_{3-6}$-cycloalkyl, phenyl, naphthyl, chromanyl, benzothiophenyl (benzothienyl), pyridinyl, thienyl or a phenyl bonded via a $C_{1\ or\ 2}$-alkylene group or —CH=CH— group, wherein the abovementioned aryl or heteroaryl radicals are in each case unsubstituted or substituted one or more times by identical or different substituents, wherein the substituents independently of one another in particular are selected from the group consisting of —O—$C_{1-3}$-alkyl, $C_{1-6}$-alkyl, F, Cl, Br, I, $CF_3$, $OCF_3$, OH, SH, phenyl, phenoxy, naphthyl, furyl, thienyl and pyridinyl and wherein the abovementioned alkyl, alkylene, alkenylene and alkynylene groups in each case are unsubstituted or substituted one or more times by identical or different substituents, wherein the substituents independently of one another in particular are selected from the group consisting of —O—$C_{1-3}$-alkyl, F, Cl, Br, I, $CF_3$, $OCF_3$, OH, SH, phenyl, phenoxy, naphthyl, furyl, thienyl and pyridinyl.

In another embodiment $R^1$ in the compounds according to the invention preferably represents $C_{1-6}$-alkyl, —CH(phenyl)$_2$, $C_{3-8}$-cycloalkyl, phenyl, naphthyl, chromanyl, indolyl, benzofuranyl, benzothiophenyl (benzothienyl), benzooxazolyl, benzooxadiazolyl, pyrrolyl, furanyl, thienyl, pyridinyl, pyridazinyl, pyrimidinyl, pyrazolyl, isoxazolyl, [1,2,3]-thiadiazolyl, pyrazinyl, imidazothiazolyl, carbazolyl, quinoxalinyl, quinolinyl, imidazolyl, benzotriazolyl, dibenzofuranyl, dibenzothiophenyl (dibenzothienyl) or a phenyl or naphthyl bonded via a $C_{1-3}$-alkylene group, a $C_{2-3}$-alkenylene group or a $C_{2-3}$-alkynylene group, or a phenyl or naphthyl bonded via a cyclopropane, cyclobutane, cyclopentane or cyclohexane group; or a $C_{3-8}$-cycloalkyl group bonded via a $C_{1-3}$-alkylene group.

Particularly preferably $R^1$ is $C_{1-6}$-alkyl, —CH(phenyl)$_2$, $C_{3-6}$-cycloalkyl, phenyl, naphthyl, chromanyl, benzothiophenyl (benzothienyl), benzooxadiazolyl, thienyl, pyridinyl, imidazothiazolyl, dibenzofuranyl or a phenyl bonded via a $C_{1-3}$-alkylene group or a $C_{2-3}$-alkenylene group, or a phenyl or naphthyl bonded via a cyclopropane, cyclobutane, cyclopentane or cyclohexane group, or a $C_{3-6}$-cycloalkyl group bonded via a $C_{1-3}$-alkylene group.

Very particularly preferably $R^1$ is $C_{1-6}$-alkyl, —CH(phenyl)$_2$, $C_{3-6}$-cycloalkyl, phenyl, naphthyl, chromanyl, benzothiophenyl (benzothienyl), pyridinyl, thienyl or a phenyl bonded via a $C_{1\ or\ 2}$-alkylene group or —CH═CH— group, or a phenyl bonded via a cyclopropane group, or a $C_{3-6}$-cycloalkyl group bonded via a $C_{1-3}$-alkylene group;
wherein the abovementioned aryl or heteroaryl groups are in each case unsubstituted or substituted one or more times by identical or different substituents, wherein the substituents independently of one another in particular are selected from the group consisting of —O—$C_{1-3}$-alkyl, —S—$C_{1-3}$-alkyl, $C_{1-6}$-alkyl, F, Cl, Br, I, CN, CF$_3$, OCF$_3$, OH, SH, N(CH$_3$)$_2$, NH(CH$_3$), NH$_2$, phenyl, phenoxy, naphthyl, furyl, thienyl and pyridinyl, and
wherein the abovementioned alkyl, alkylene, alkenylene and alkynylene groups in each case are unsubstituted or substituted one or more times by identical or different substituents, wherein the substituents independently of one another in particular are selected from the group consisting of —O—$C_{1-3}$-alkyl, F, Cl, Br, I, CF$_3$, OCF$_3$, OH, SH, phenyl, phenoxy, naphthyl, furyl, thienyl and pyridinyl.

$R^1$ can represent in particular —CH(phenyl)$_2$, phenyl, naphthyl, pyridinyl or thienyl or a phenyl bonded via a $C_{1\ or\ 2}$-alkylene group or —CH═CH— group, wherein the phenyl, naphthyl, pyridinyl and thienyl is in each case unsubstituted or substituted one or more times, for example 2, 3, 4 or 5 times, by identical or different substituents chosen from methyl, methoxy, CF$_3$, OCF$_3$, F and Cl.

In embodiments of the compounds according to the invention which are likewise preferred, $R^1$ can be selected from the group consisting of pyridin-2-yl, pyridin-3-yl, pyridin-4-yl, 3-chloro-thien-2-yl, 5-chloro-thien-2-yl, 4-methoxy-2,3,6-trimethylphenyl, 4-methoxy-2,6-dimethylphenyl, 4-methoxy-2,3,5-trimethylphenyl, 2,4,6-trimethylphenyl, 2-chloro-6-methylphenyl, 2,4,6-trichlorophenyl, 1,3-dichloro-5-trifluoromethylphenyl, 2-chloro-6-(trifluoromethyl)phenyl, 2,6-dichloro-4-methoxyphenyl, 2,6-dichloro-4-trifluoromethyl, 2-methylnaphthyl, 2-chloronaphthyl, 2-fluoronaphthyl, 2-chloro-4-(trifluoromethoxy)phenyl, 4-chloro-2,5-dimethylphenyl, 2-chloro-6-methylphenyl, 2,3-dichlorophenyl, 3,4-dichlorophenyl, 2,4-dichlorophenyl, 2,4,5-trichlorophenyl, 2,4,6-trichlorophenyl, 2-(trifluoromethyl)phenyl, 3-(trifluoromethyl)phenyl, 4-(trifluoromethyl)phenyl, 1-naphthyl and 2-naphthyl. In particular, $R^1$ can represent 4-methoxy-2,6-dimethylphenyl or 2-chlorophenyl.

$R^2$ in the compounds according to the invention represents H, —CF$_3$, —CH$_2$—CF$_3$, methyl, ethyl, n-propyl, iso-propyl, n-butyl, iso-butyl, sec-butyl, tert-butyl, cyclopropyl, cyclobutyl, cyclopentyl or cyclohexyl, preferably H, methyl, ethyl or cyclopropyl. $R^2$ particularly preferably represents H.

Preferably, $R^2$ in the compounds according to the present invention represents H, —CF$_3$, —CH$_2$—CF$_3$, methyl, ethyl, n-propyl, iso-propyl, n-butyl, iso-butyl, sec-butyl, tert-butyl, cyclopropyl, cyclobutyl, cyclopentyl or cyclohexyl, preferably H, methyl, ethyl or cyclopropyl. $R^2$ particularly preferably represents H.

In preferred embodiments of the compounds according to the invention, $R^5$ and/or $R^6$ represent 0 substituents, i.e. are absent.

$R^9$ in the compounds according to the invention preferably represents H, methyl, ethyl, n-propyl, iso-propyl, n-butyl, iso-butyl, sec-butyl, tert-butyl, cyclopropyl, cyclobutyl, cyclopentyl, cyclohexyl, preferably H, methyl, ethyl or cyclopropyl. $R^9$ particularly preferably represents H.

Embodiments of the compounds according to the invention which are likewise preferred are those in which the partial structure D2 is selected from the group consisting of

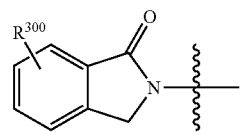

D2-1

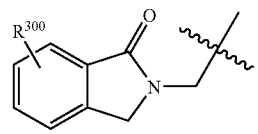

D2-2

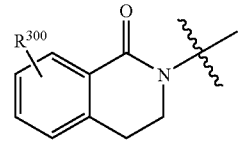

D2-3

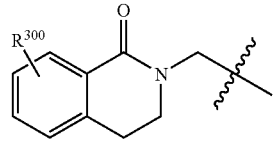

D2-4

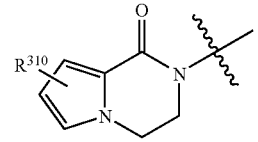

D2-5

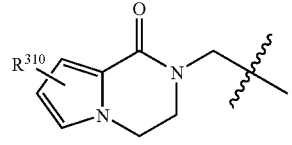

D2-6

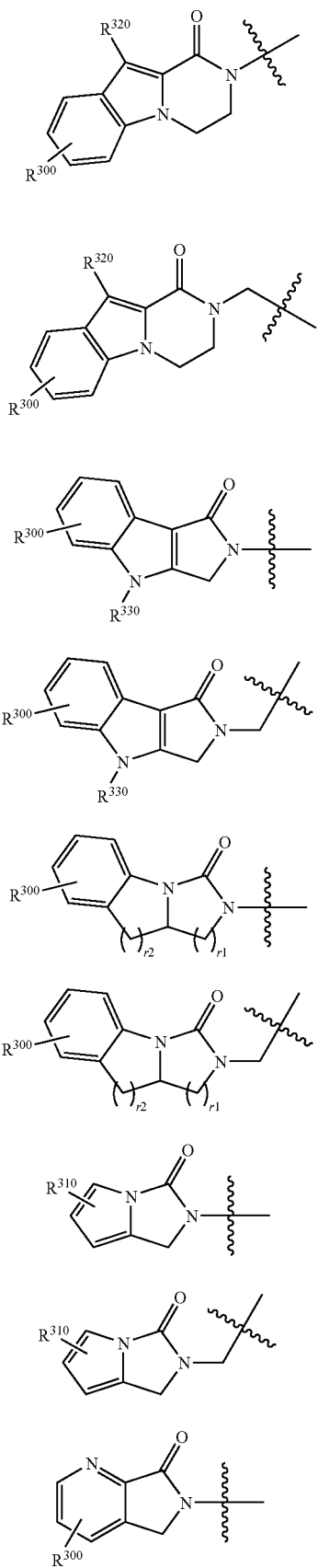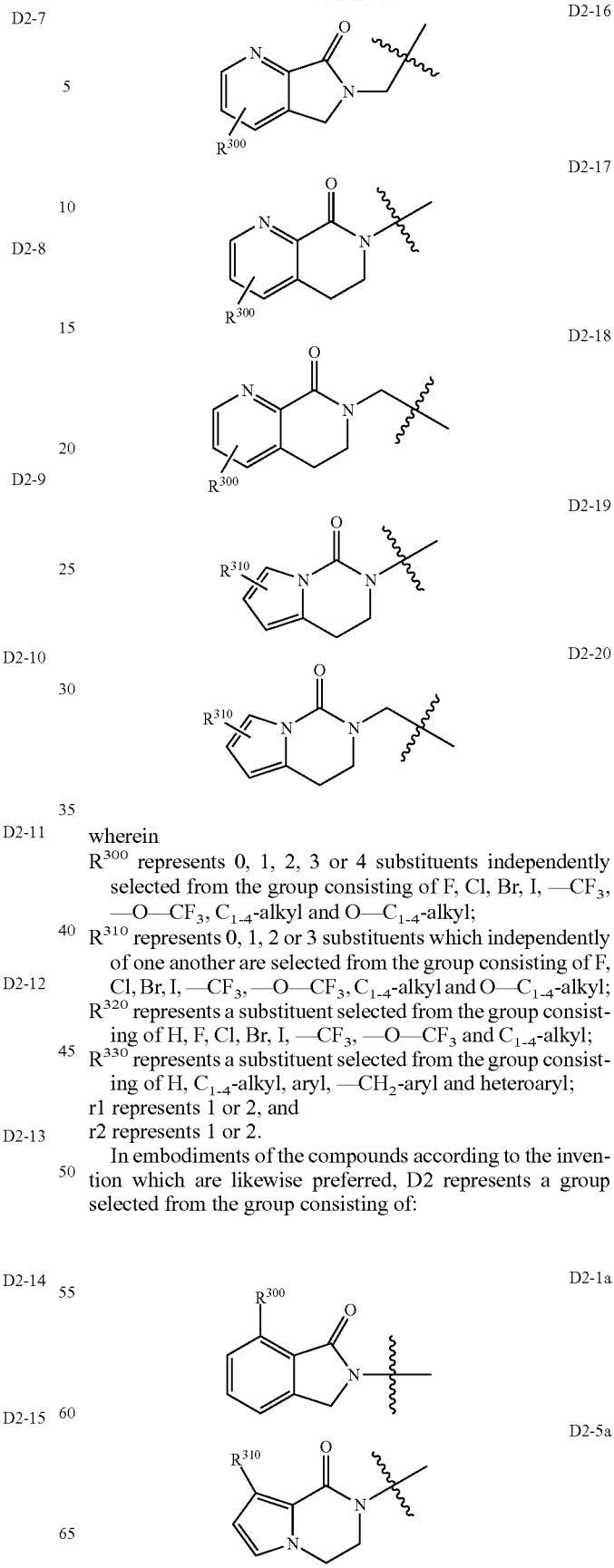

wherein
R³⁰⁰ represents 0, 1, 2, 3 or 4 substituents independently selected from the group consisting of F, Cl, Br, I, —CF₃, —O—CF₃, $C_{1-4}$-alkyl and O—$C_{1-4}$-alkyl;
R³¹⁰ represents 0, 1, 2 or 3 substituents which independently of one another are selected from the group consisting of F, Cl, Br, I, —CF₃, —O—CF₃, $C_{1-4}$-alkyl and O—$C_{1-4}$-alkyl;
R³²⁰ represents a substituent selected from the group consisting of H, F, Cl, Br, I, —CF₃, —O—CF₃ and $C_{1-4}$-alkyl;
R³³⁰ represents a substituent selected from the group consisting of H, $C_{1-4}$-alkyl, aryl, —CH₂-aryl and heteroaryl;
r1 represents 1 or 2, and
r2 represents 1 or 2.

In embodiments of the compounds according to the invention which are likewise preferred, D2 represents a group selected from the group consisting of:

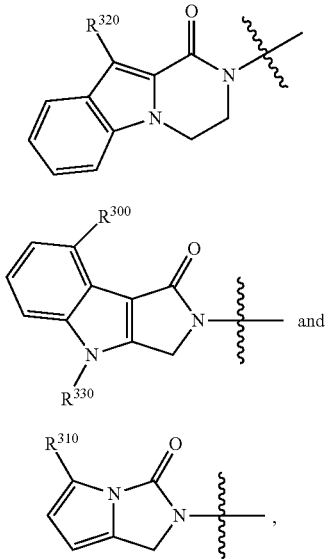

wherein
R³⁰⁰ represents a substituent selected from the group consisting of H, F, Cl, Br, I, —CF₃, —O—CF₃, $C_{1-4}$-alkyl and O—$C_{1-4}$-alkyl;
R³¹⁰ represents a substituent selected from the group consisting of H, F, Cl, Br, I, —CF₃, —O—CF₃, $C_{1-4}$-alkyl and O—$C_{1-4}$-alkyl;
R³²⁰ represents a substituent selected from the group consisting of H, F, Cl, Br, I, —CF₃, —O—CF₃ and $C_{1-4}$-alkyl, and
R³³⁰ represents a substituent selected from the group consisting of H, $C_{1-4}$-alkyl, aryl, —CH₂-aryl and heteroaryl.

In embodiments of the compounds according to the invention which are furthermore preferred, D2 represents a group selected from the group consisting of:

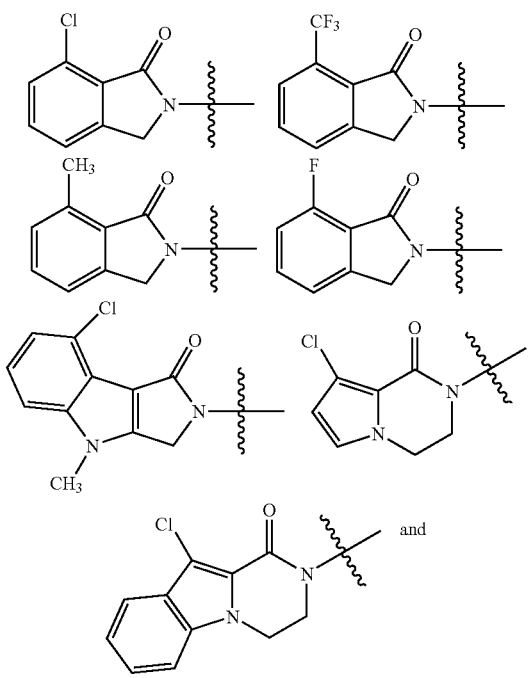

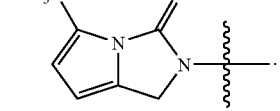

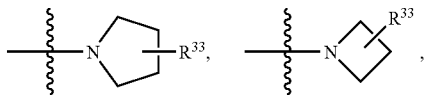

Embodiments of the substituted spiro-amides according to the invention which are likewise preferred are those in which
R¹⁴ᵃ represents H, aryl, heteroaryl, $C_{1-3}$-alkylene-aryl or $C_{1-3}$-alkylene-heteroaryl;
R¹⁴ᵇ represents aryl, heteroaryl, $C_{1-3}$-alkylene-aryl, $C_{1-3}$-alkylene-heteroaryl, NR¹⁶R¹⁷, $C_{1-3}$-alkylene-NR¹⁶R¹⁷, C(=O)—NR¹⁶R¹⁷, OR³⁵ or $C_{1-3}$-alkylene-OR³⁵;
R¹⁶ and R¹⁷ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or R¹⁶ and R¹⁷ together with the nitrogen atom to which they are bound form a structure selected from the group consisting of

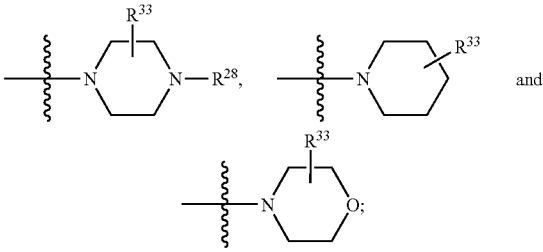

R²⁸ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;
R³³ represents 0, 1 or 2 substituents each independently selected from the group consisting of F, Cl, CF₃, OCF₃, $C_{1-6}$-alkyl, O—$C_{1-3}$-alkyl and NR³⁴ᵃR³⁴ᵇ;
R³⁴ᵃ and R³⁴ᵇ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or R³⁴ᵃ and R³⁴ᵇ together with the nitrogen atom joining them form a group selected from the group consisting of:

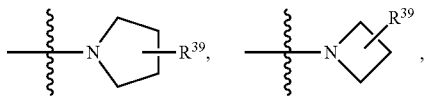

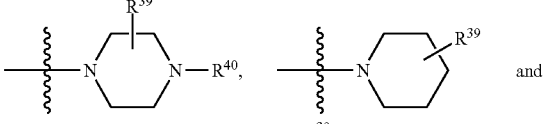

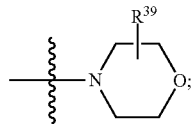

R³⁹ represents 0, 1 or 2 substituents each independently selected from the group consisting of F, Cl, CF₃, OCF₃, $C_{1-6}$-alkyl and O—$C_{1-3}$-alkyl;

$R^{40}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

$R^{35}$ represents H, $C_{3-6}$-cycloalkyl, aryl, heteroaryl, $C_{1-3}$-alkylene-$C_{3-6}$-cycloalkyl, $C_{1-3}$-alkylene-aryl, $C_{1-3}$-alkylene-heteroaryl or the group

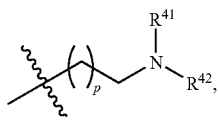

wherein p represents 1, 2 or 3, wherein $R^{41}$ and $R^{42}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{41}$ and $R^{42}$ together with the nitrogen atom joining them form a group selected from the group consisting of:

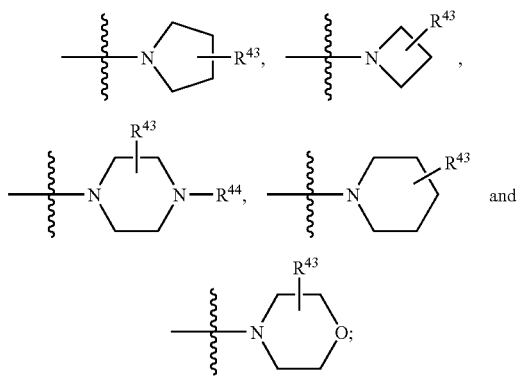

$R^{43}$ represents 0, 1 or 2 substituents each independently selected from the group consisting of F, Cl, $CF_3$, $OCF_3$, $C_{1-6}$-alkyl, O—$C_{1-3}$-alkyl and $NR^{45a}R^{45b}$;

$R^{44}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

$R^{45a}$ and $R^{45b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{45a}$ and $R^{45b}$ together with the nitrogen atom joining them form a group selected from the group consisting of:

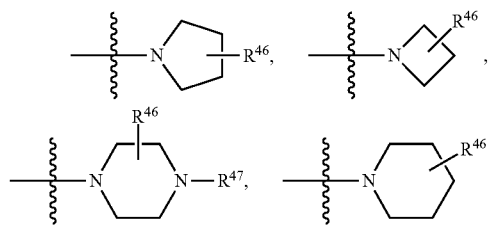

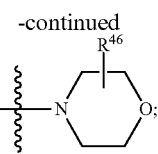

$R^{46}$ represents 0, 1 or 2 substituents each independently selected from the group consisting of F, Cl, $CF_3$, $OCF_3$, $C_{1-6}$-alkyl and O—$C_{1-3}$-alkyl; and $R^{47}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl.

Embodiments of the substituted spiro-amides according to the invention which are furthermore preferred are those compounds wherein $R^{15}$ represents H, $C_{1-6}$-alkyl, —$CHR^{25}R^{26}$, $C_{1-3}$-alkylene—$CHR^{25}R^{26}$, aryl, heteroaryl, $C_{1-3}$-alkylene-aryl, $C_{1-3}$-alkylene-heteroaryl, —C(=O)—$R^{19}$, —S(=O)$_2$—$R^{19}$ or the group —C(=O)—N($R^{20}$)—$R^{19}$;

$R^{25}$ and $R^{26}$ each independently represent H, $C_{1-4}$-alkyl, $C_{3-6}$-cycloalkyl, aryl or heteroaryl, or $R^{25}$ and $R^{26}$ together with the CH grouping to which they are bound form a structure selected from the group consisting of

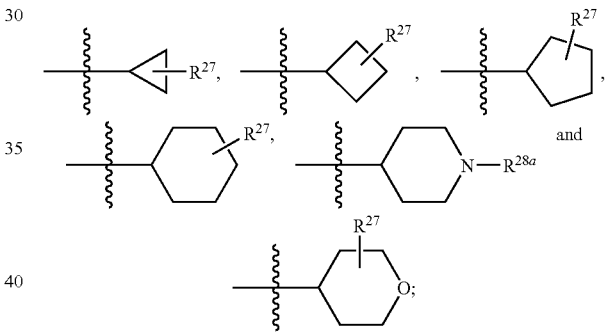

$R^{27}$ represents 0, 1 or 2 substituents each independently selected from the group consisting of F, Cl, $CF_3$, $OCF_3$, $C_{1-6}$-alkyl, O—$C_{1-3}$-alkyl and $NR^{48a}R^{48b}$;

$R^{28a}$ represents a substituent selected from the group consisting of H, methyl, ethyl, n-propyl, iso-propyl, n-butyl, iso-butyl, sec-butyl, tert-butyl, aryl and heteroaryl;

$R^{48a}$ and $R^{48b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, $R^{48a}$ and $R^{48b}$ together with the nitrogen atom to which they are bound form a structure selected from the group consisting of:

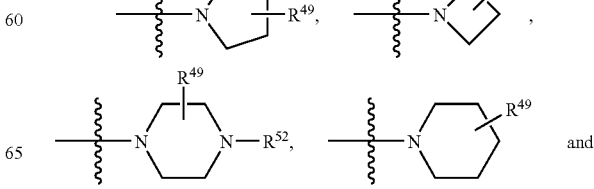

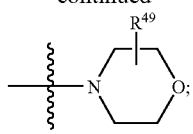

R⁴⁹ represents 0, 1 or 2 substituents each independently selected from the group consisting of F, Cl, $CF_3$, $OCF_3$, $C_{1-6}$-alkyl and O—$C_{1-3}$-alkyl;

R⁵² represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

R¹⁹ represents $C_{1-6}$-alkyl, aryl, heteroaryl, —CH(aryl)₂, $C_{3-8}$-cycloalkyl, heterocyclyl or an aryl, heteroaryl, $C_{3-8}$-cycloalkyl or heterocyclyl bonded via a $C_{1-6}$-alkylene group, $C_{2-6}$-alkenylene group or $C_{2-6}$-alkynylene group; and R²⁰ represents H, methyl, ethyl, n-propyl, iso-propyl, n-butyl, iso-butyl, sec-butyl, tert-butyl, cyclopropyl, cyclobutyl, cyclopentyl or cyclohexyl.

Further preferred embodiments of the compounds according to the invention are those compounds in which the following partial structure SP

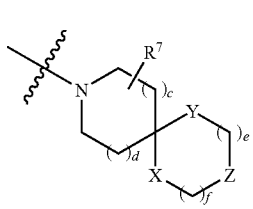

(SP)

is selected from the group consisting of

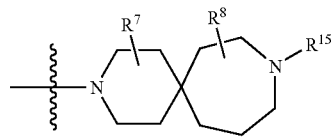
SP 1

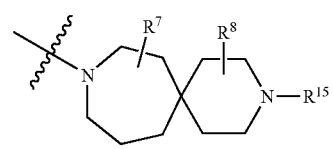
SP 2

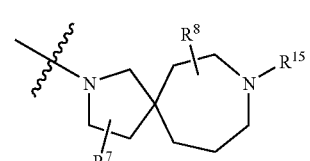
SP 3

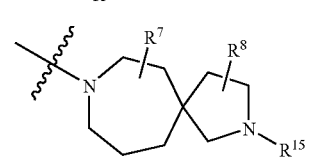
SP 4

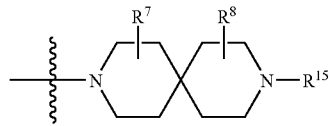
SP 5

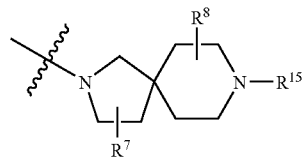
SP 6

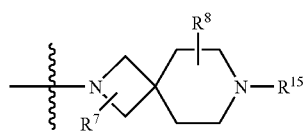
SP 7

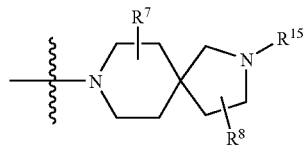
SP 8

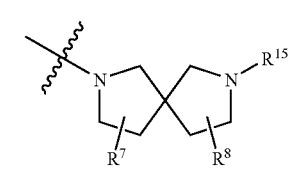
SP 9

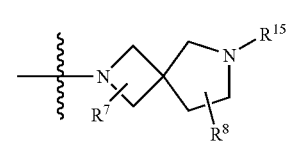
SP 10

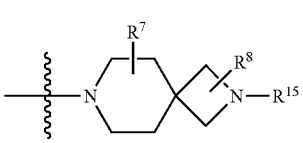
SP 11

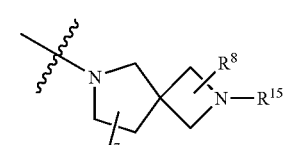
SP 12

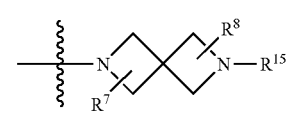
SP 13

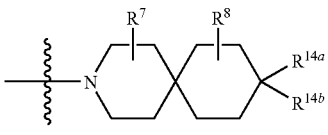
SP 14

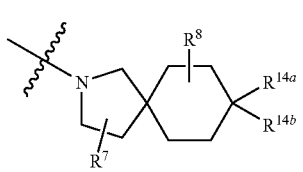
SP 15

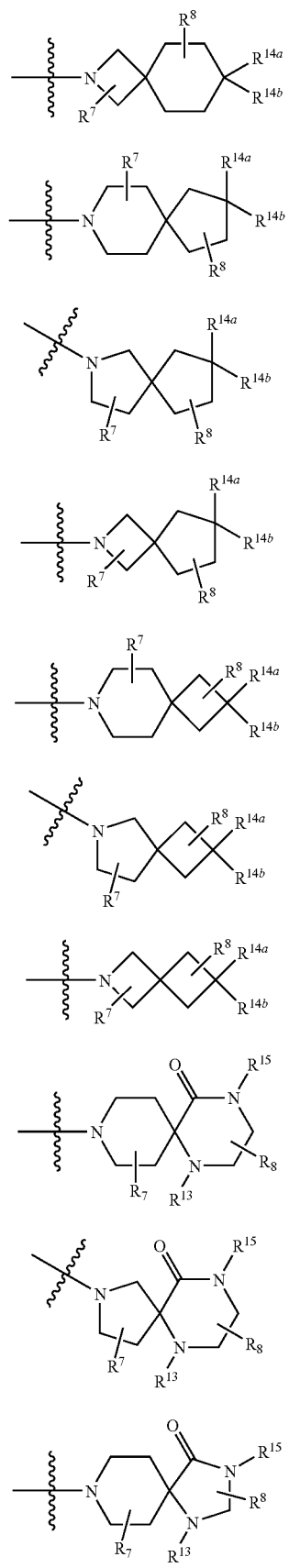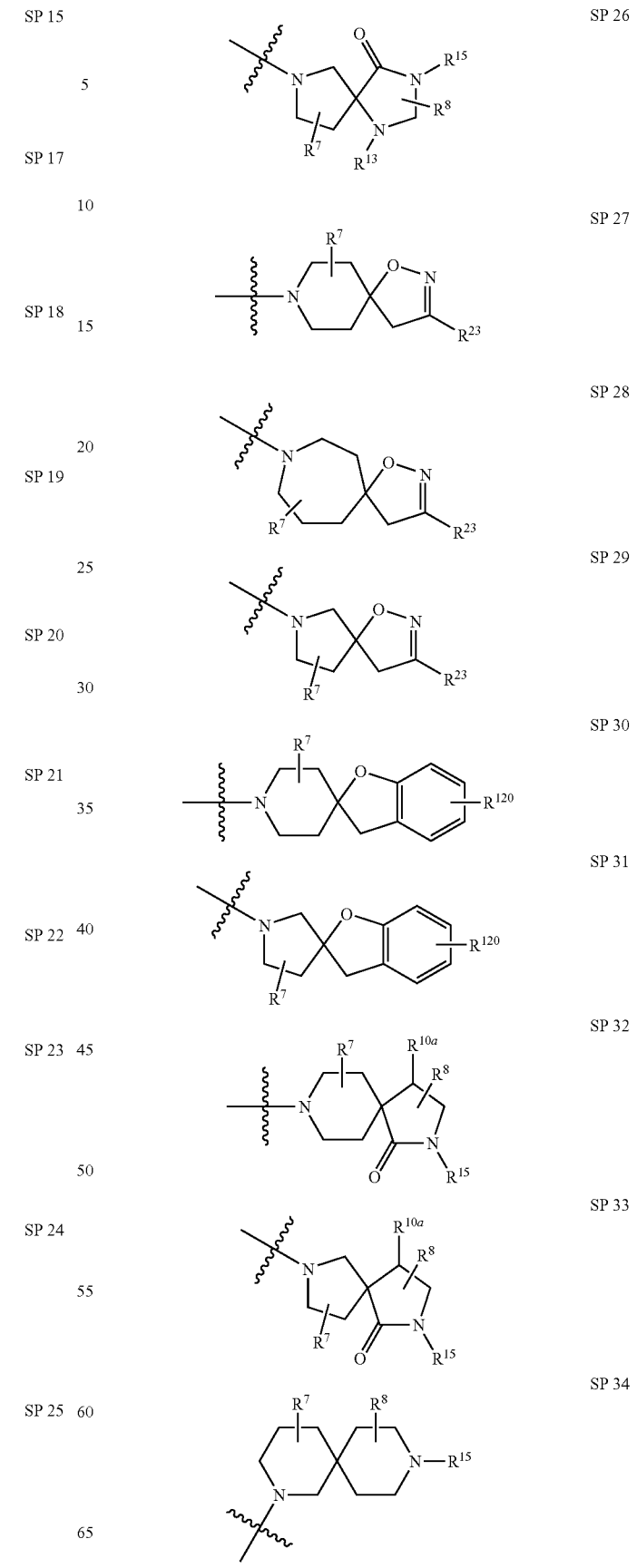

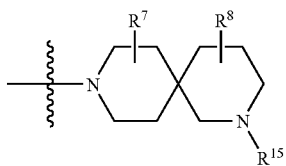
SP 35

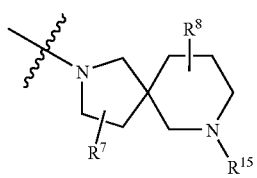
SP 36

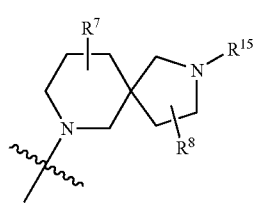
SP 37

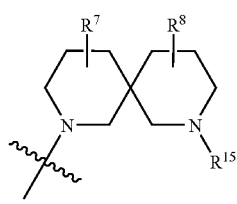
SP 38 wherein $R^8$, $R^{10a}$, $R^{13}$, $R^{14a}$, $R^{14b}$, $R^{15}$ and $R^{23}$ have the abovementioned meanings, and $R^{120}$ represents 0, 1, 2, 3 or 4 substituents independently selected from the group consisting of F, Cl, $OCF_3$, $CF_3$, CN, methyl and methoxy.

Further preferred embodiments of the compounds according to the invention are those compounds in which the abovementioned partial structure SP is selected from the group consisting of

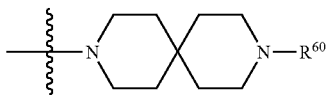

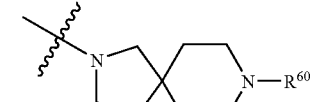

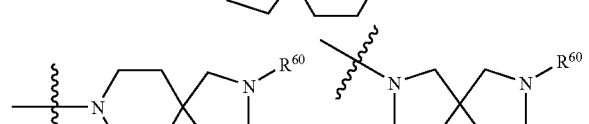

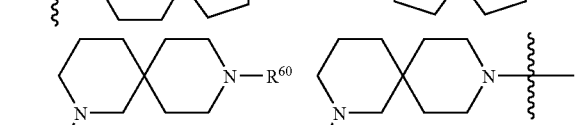

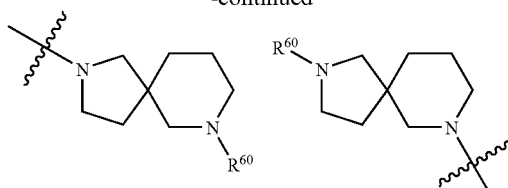

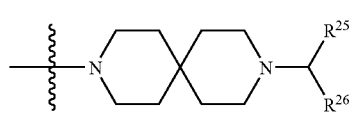

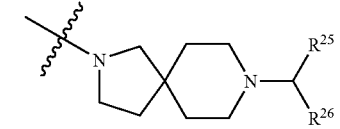

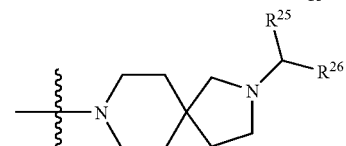

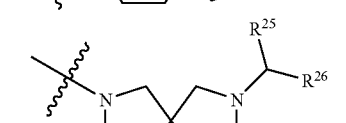

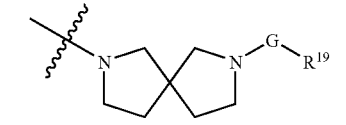

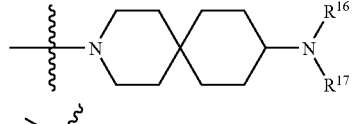

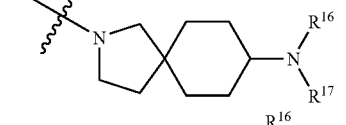

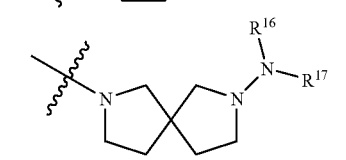

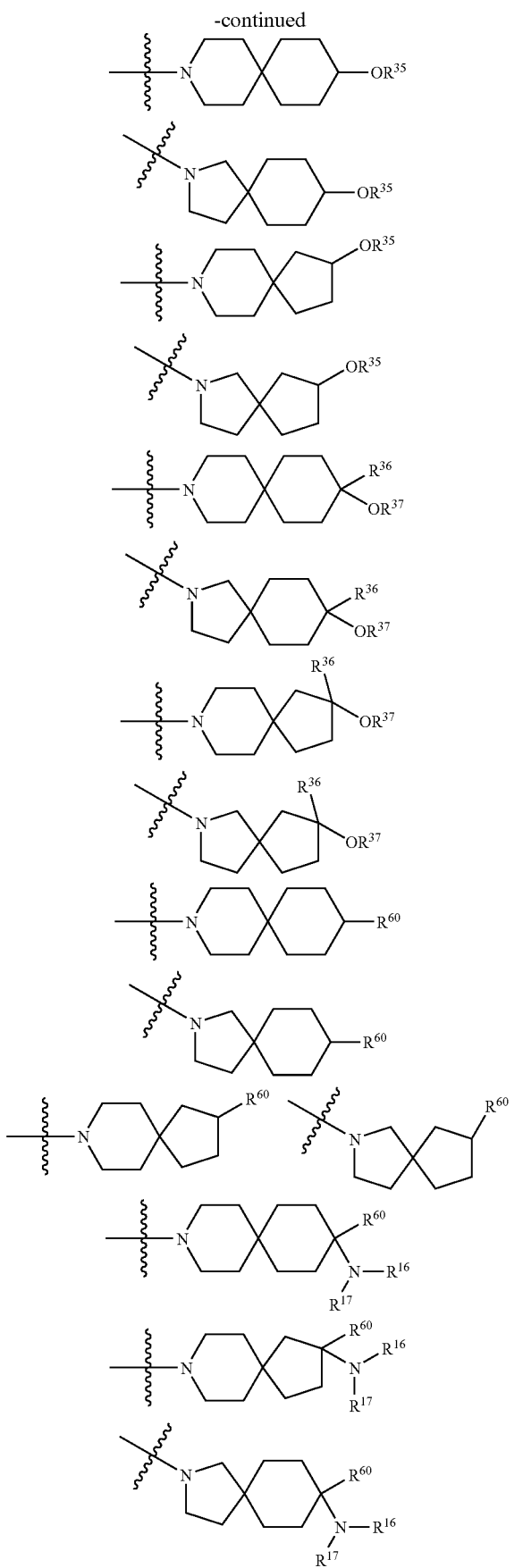
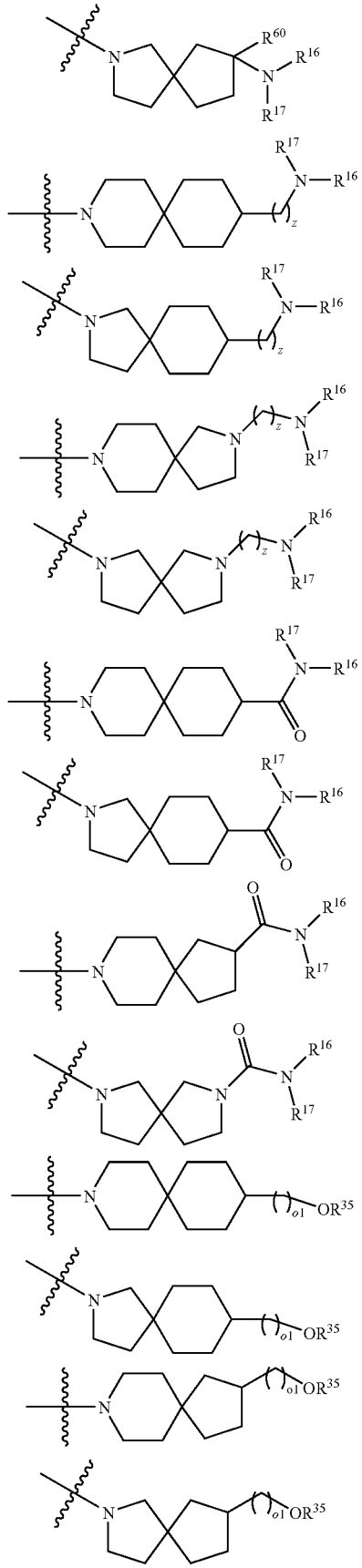

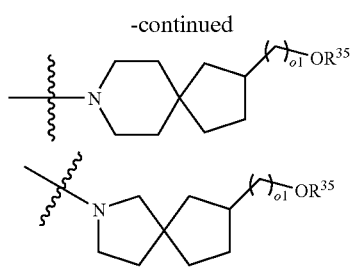

wherein z represents 1, 2 or 3;

o1 represents 1;

$R^{60}$ in each case represents (het)aryl or $C_{1-3}$-alkylene-(het)aryl;

$R^{25}$ and $R^{26}$ each independently represent H, $C_{1-6}$-alkyl, $C_{3-6}$-cycloalkyl or (het)aryl, or $R^{25}$ and $R^{26}$ together with the CH grouping to which they are bound form a structure selected from the group consisting of

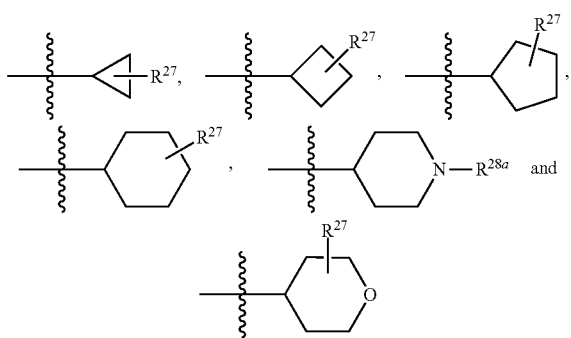

$R^{27}$ represents 0, 1 or 2 substituents each independently selected from the group consisting of F, Cl, $CF_3$, $OCF_3$, $C_{1-6}$-alkyl, O—$C_{1-3}$-alkyl and $NR^{48a}R^{48b}$;

$R^{28a}$ represents a substituent selected from the group consisting of H, methyl, ethyl, n-propyl, iso-propyl, n-butyl, iso-butyl, sec-butyl, tert-butyl and het(aryl);

$R^{48a}$ and $R^{48b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, $R^{48a}$ and $R^{48b}$ together with the nitrogen atom to which they are bound form a structure selected from the group consisting of:

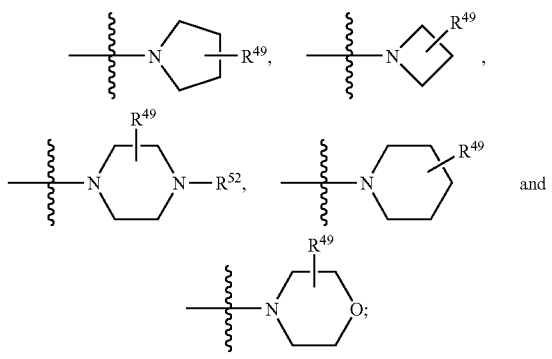

$R^{49}$ represents 0, 1 or 2 substituents each independently selected from the group consisting of F, Cl, $CF_3$, $OCF_3$, $C_{1-6}$-alkyl and O—$C_{1-3}$-alkyl;

$R^{52}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl and (het)aryl;

G represents C(=O), S(=O)$_2$ or the group —C(=O)—N($R^{20}$), wherein the nitrogen atom thereof is bonded to $R^{19}$, $R^{19}$ represents $C_{1-6}$-alkyl, (het)aryl, —CH(aryl)$_2$, $C_{3-8}$-cycloalkyl, heterocyclyl or a (het)aryl, $C_{3-8}$-cycloalkyl or heterocyclyl bonded via a $C_{1-6}$-alkylene group, $C_{2-6}$-alkenylene group or $C_{2-6}$-alkynylene group;

$R^{20}$ represents H, methyl, ethyl, n-propyl, iso-propyl, n-butyl, iso-butyl, sec-butyl, tert-butyl, cyclopropyl, cyclobutyl, cyclopentyl or cyclohexyl;

$R^{16}$ and $R^{17}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{16}$ and $R^{17}$ together with the nitrogen atom to which they are bound form a structure selected from the group consisting of

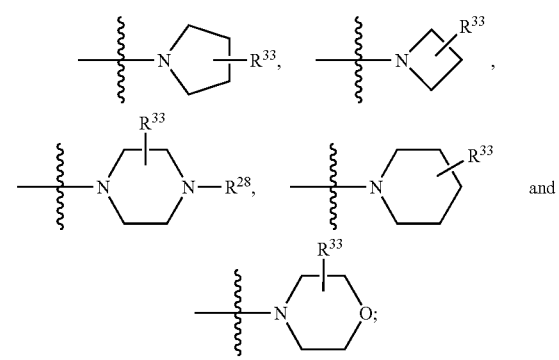

$R^{28}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl and (het)aryl;

$R^{33}$ represents 0, 1 or 2 substituents each independently selected from the group consisting of F, Cl, $CF_3$, $OCF_3$, $C_{1-6}$-alkyl, O—$C_{1-3}$-alkyl and $NR^{34a}R^{34b}$;

$R^{34a}$ and $R^{34b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{34a}$ and $R^{34b}$ together with the nitrogen atom to which they are bound form a structure selected from the group consisting of:

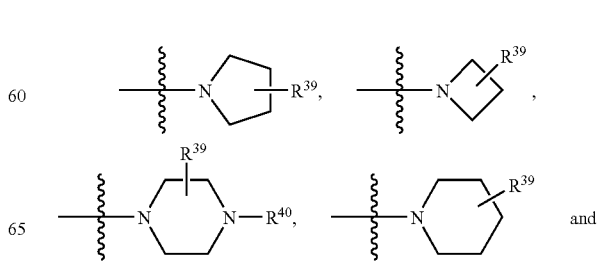

-continued

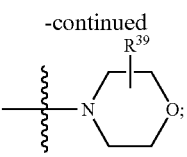

R$^{39}$ represents 0, 1 or 2 substituents each independently selected from the group consisting of F, Cl, CF$_3$, OCF$_3$, C$_{1-6}$-alkyl and O—C$_{1-3}$-alkyl;

R$^{40}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

R$^{35}$ represents H, C$_{1-6}$-alkyl, C$_{3-6}$-cycloalkyl, (het)aryl or a C$_{3-6}$-cycloalkyl or (het)aryl bonded via a C$_{1-3}$-alkylene group;

R$^{36}$ represents (het)aryl or C$_{1-3}$-alkylene-(het)aryl;

R$^{37}$ represents H, C$_{1-6}$-alkyl or for the group

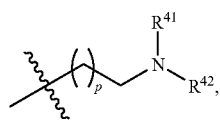

wherein p represents 1, 2 or 3, wherein

R$^{41}$ and R$^{42}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or R$^{41}$ and R$^{42}$ together with the nitrogen atom to which they are bound form a structure selected from the group consisting of:

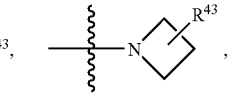
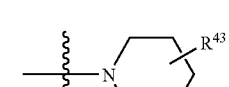
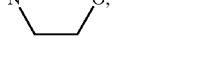

R$^{43}$ represents 0, 1 or 2 substituents each independently selected from the group consisting of F, Cl, CF$_3$, OCF$_3$, C$_{1-6}$-alkyl, O—C$_{1-3}$-alkyl and NR$^{45a}$R$^{45b}$;

R$^{44}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

R$^{45a}$ and R$^{45b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or R$^{45a}$ and R$^{45b}$ together with the nitrogen atom to which they are bound form a structure selected from the group consisting of:

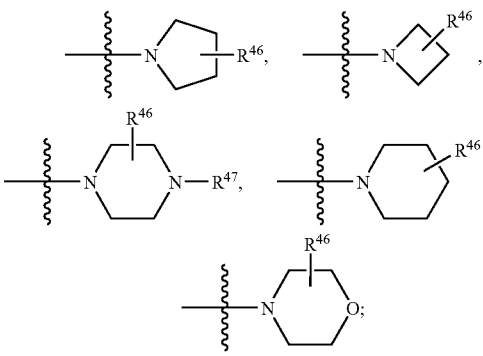

R$^{46}$ represents 0, 1 or 2 substituents each independently selected from the group consisting of F, Cl, CF$_3$, OCF$_3$, C$_{1-6}$-alkyl and O—C$_{1-3}$-alkyl;

R$^{47}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl, and het(aryl) in each case represents a structure selected from the group consisting of:

(1)
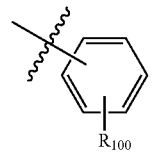

(2)
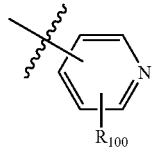

(3)
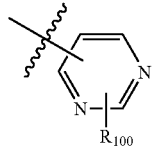

(4)
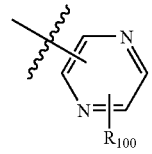

(5)
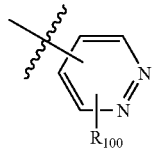

(6)
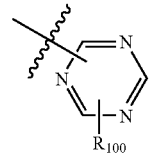

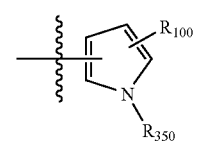 (7)
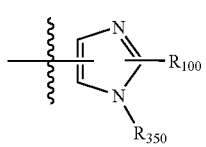 (8)
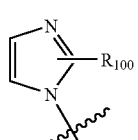 (9)
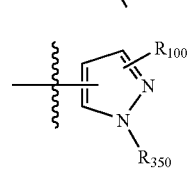 (10)
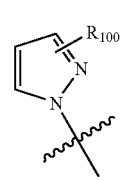 (11)
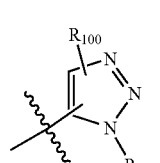 (12)
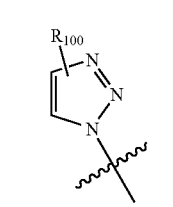 (13)
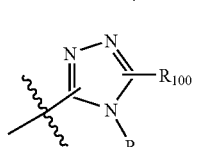 (14)
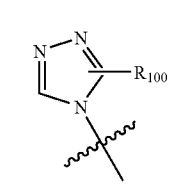 (15)
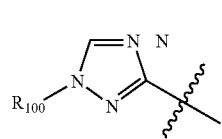 (16)
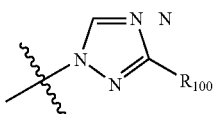 (17)
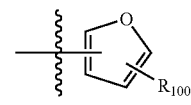 (18)
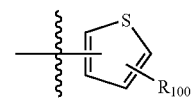 (19)
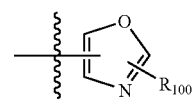 (20)
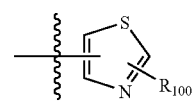 (21)
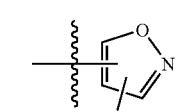 (22)
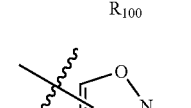 (23)
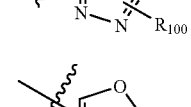 (24)
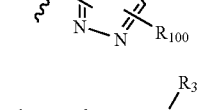 (25)
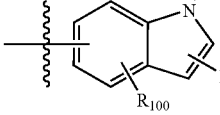 (26)
(27)
(28)

(29) 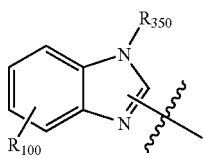

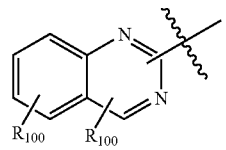
(38)

(30) 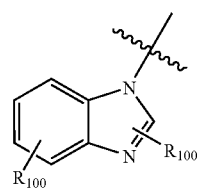

wherein
R$^{100}$ represents 0, 1, 2 or 3 substituents each independently selected from the group consisting of F, Cl, CF$_3$, OCF$_3$, OH, O—C$_{1-6}$-alkyl, SH, S—C$_{1-6}$-alkyl, C$_{1-6}$-alkyl, C$_{3-6}$-cycloalkyl, O—C$_{3-6}$-cycloalkyl, NR$^{61}$R$^{62}$, C(=O)—NR$^{61}$R$^{62}$, phenyl, pyridyl, pyrimidyl, or OCF$_3$, OH, O—C$_{1-6}$-alkyl, SH, S—C$_{1-6}$-alkyl, C$_{3-6}$-cycloalkyl, O—C$_{3-6}$-cycloalkyl, NR$^{61}$R$^{62}$, C(=O)—NR$^{61}$R$^{62}$, phenyl, pyridyl or pyrimidyl bonded via a C$_{1-6}$-alkylene group;

(31) R$^{61}$ and R$^{62}$ each independently represent H, C$_{1-6}$-alkyl or C$_{3-6}$-cycloalkyl, or R$^{61}$ and R$^{62}$ together with the nitrogen atom to which they are bound form a structure selected from the group consisting of:

(32) 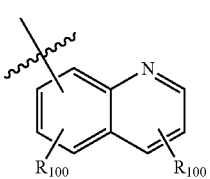

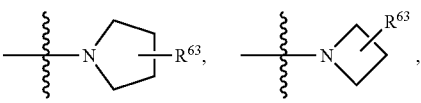

(33) 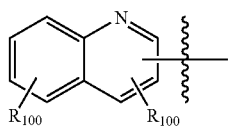

and

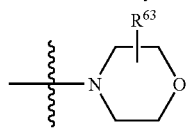

(34) 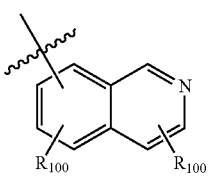

R$^{63}$ represents 0, 1 or 2 substituents each independently selected from the group consisting of F, Cl, CF$_3$, OCF$_3$, C$_{1-6}$-alkyl and O—C$_{1-3}$-alkyl;

R$^{64}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl and cyclohexyl; and

(35) 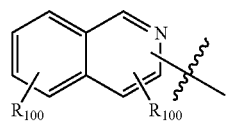

R$^{350}$ represents H, CF$_3$, phenyl, pyridyl, pyrimidyl or a phenyl, pyridyl or pyrimidyl bonded via a C$_{1-6}$-alkylene group.

In embodiments of the spiro-amides according to the invention which are also preferred, the abovementioned radical (SP) is selected from the group consisting of

(36) 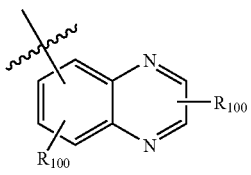

(1)

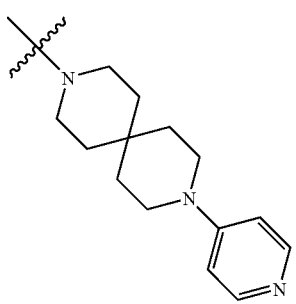

(37) 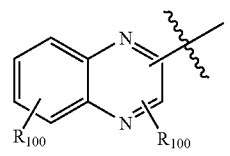

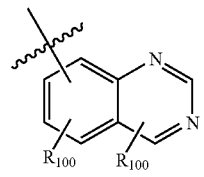

(2)
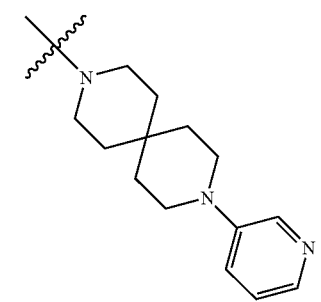
(3)
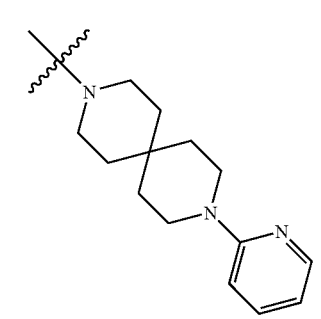
(4)
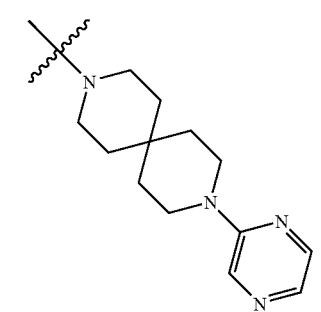
(5)
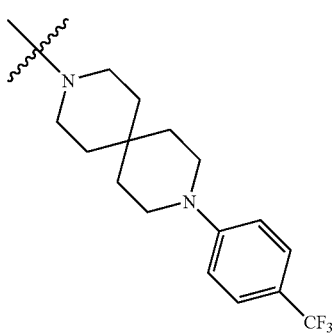
(6)
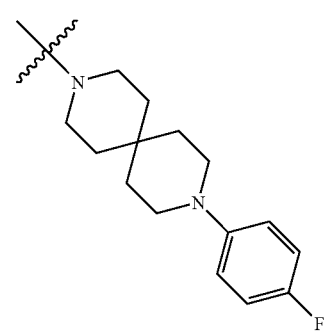
(7)
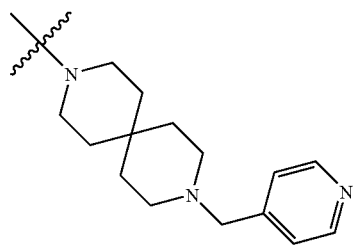
(8)
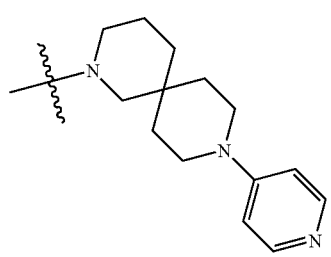
(9)
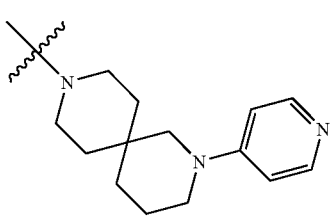
(10)
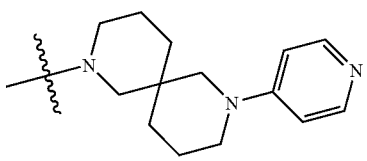
(11)
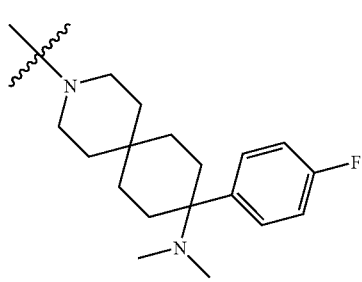
(12)
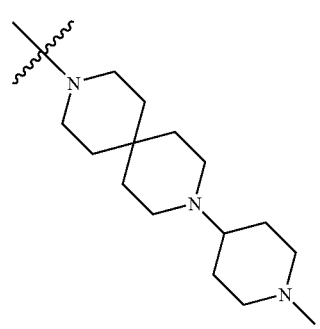

(13) 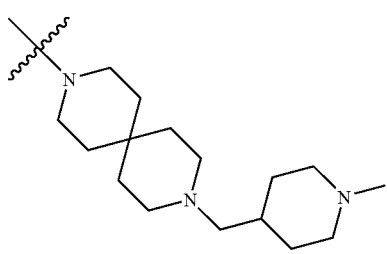
(14) 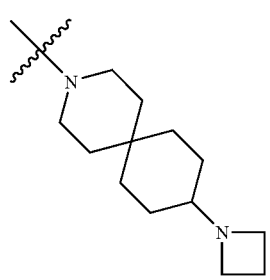
(15) 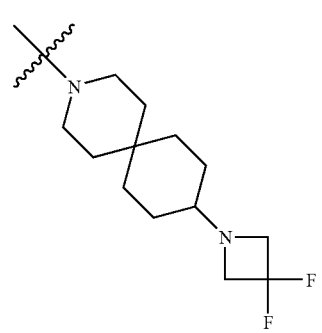
(16) 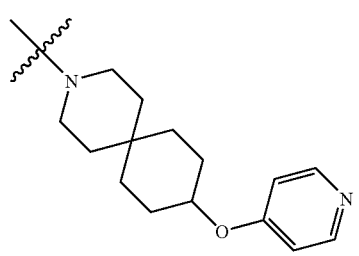
(17) 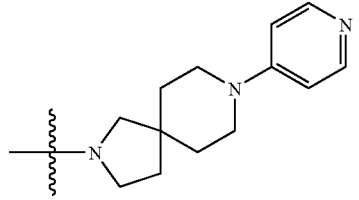
(18) 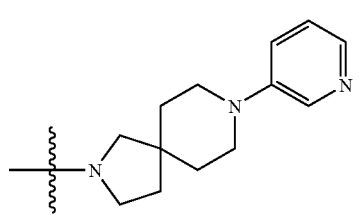
(19) 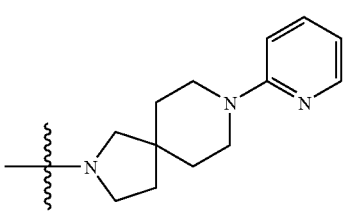
(20) 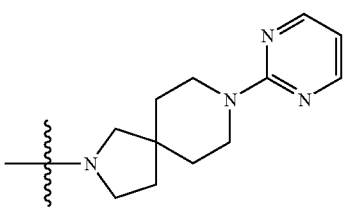
(21) 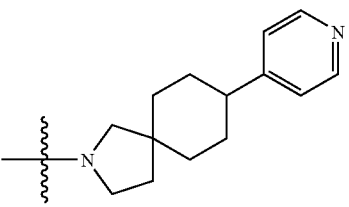
(22) 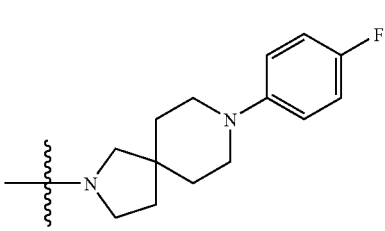
(23) 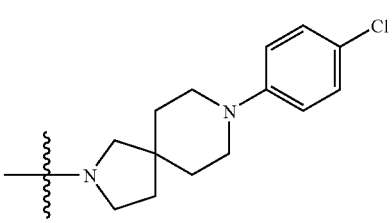
(24) 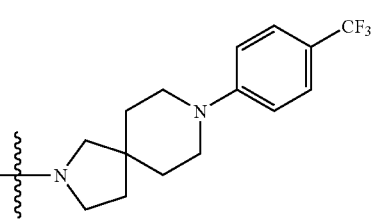
(25) 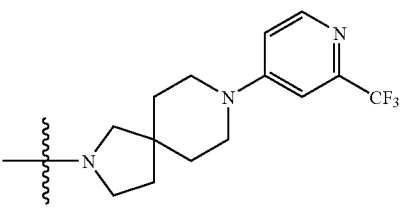

(26) 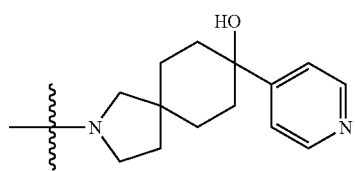
(27) 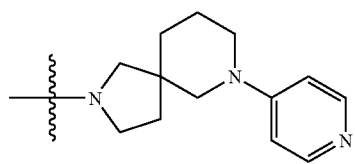
(28) 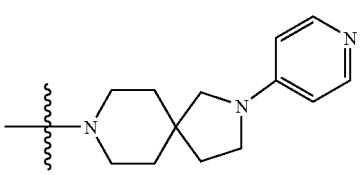
(29) 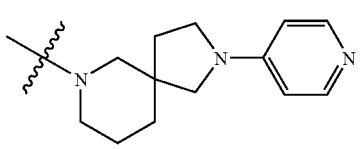
(30) 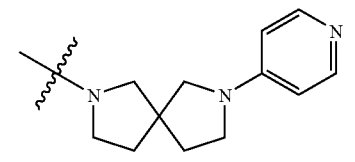
(31) 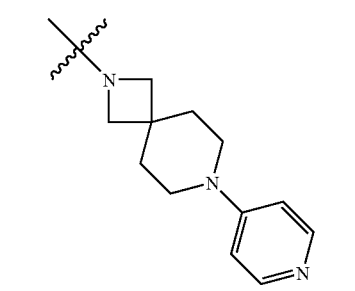
(32) 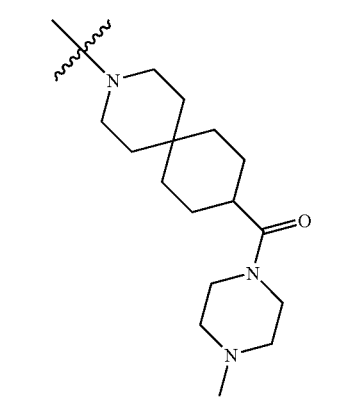
(33) 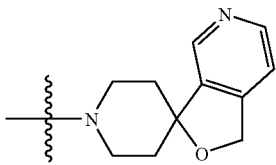
(34) 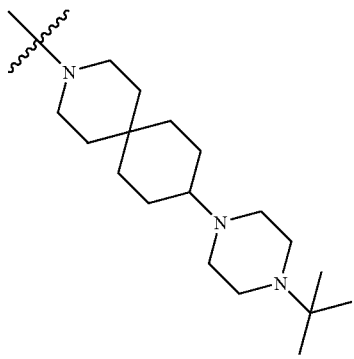
(35) 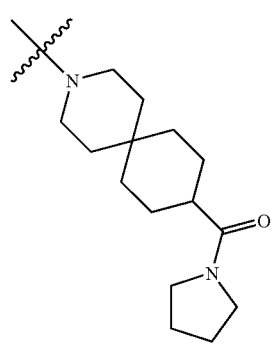
(36) 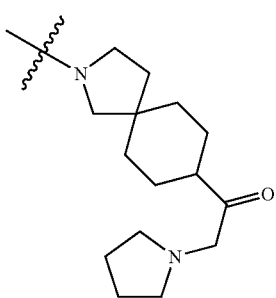
(37) 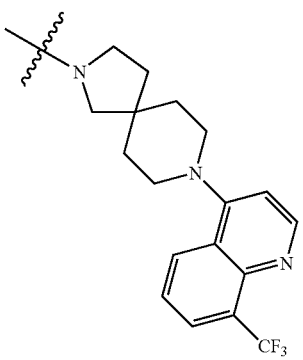

(38) 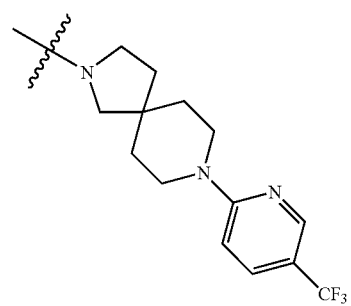
(39) 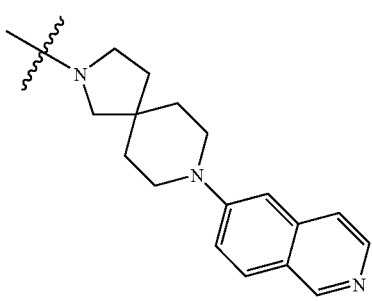
(40) 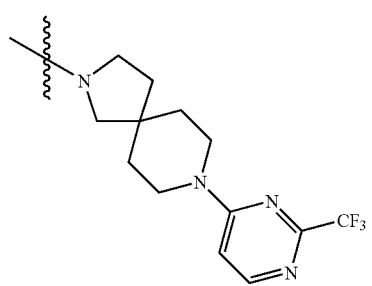
(41) 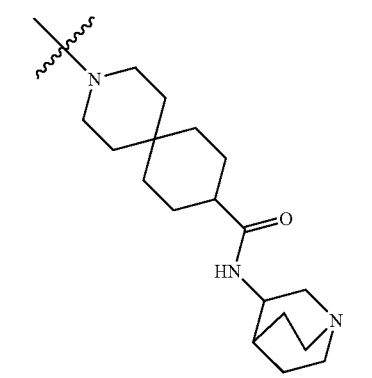
(42) 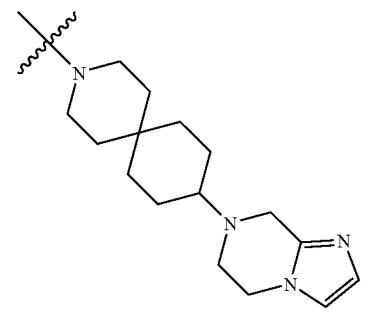
(43) 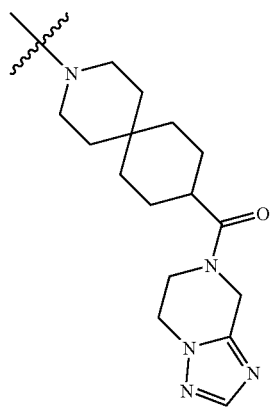
(44) 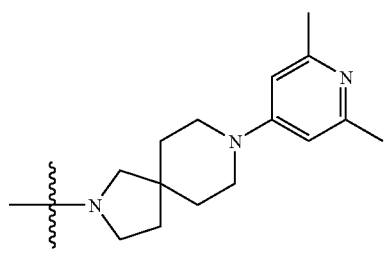
(45) 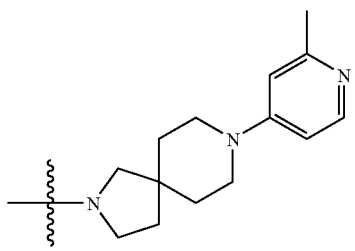
(46) 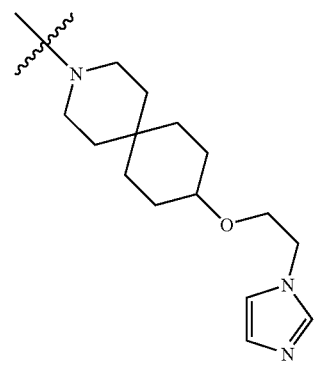
(47) 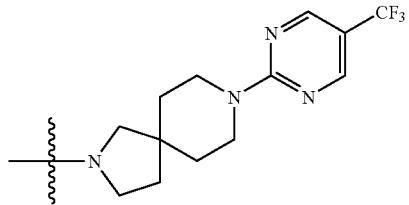

(48) 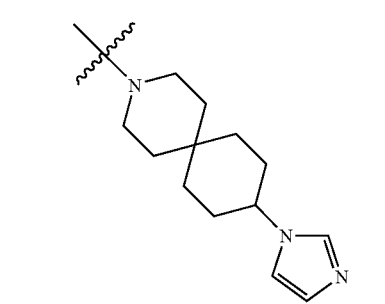
(49) 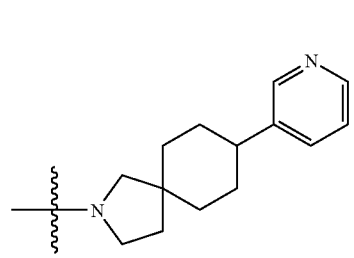
(50) 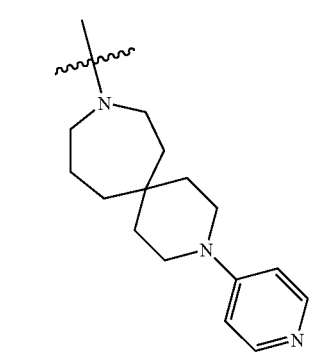
(51) 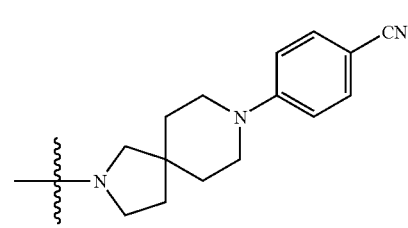
(52) 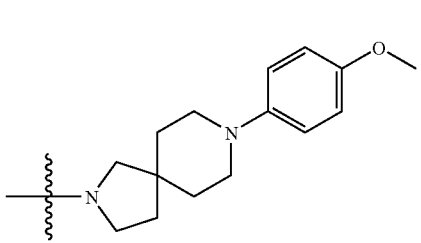
In embodiments of the spiro-amides according to the invention which are furthermore preferred, the abovementioned radical (SP) is selected from the group consisting of
(1) 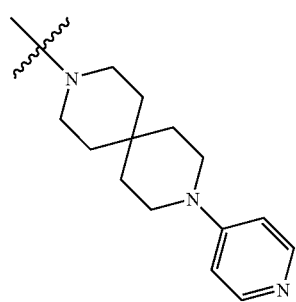
(2) 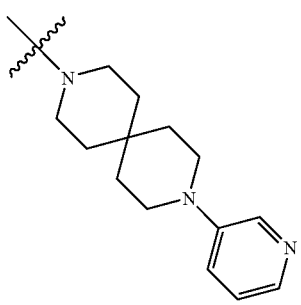
(3) 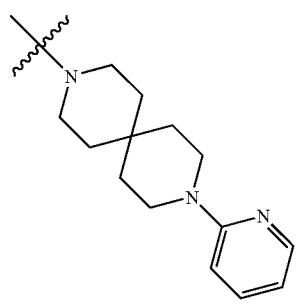
(4) 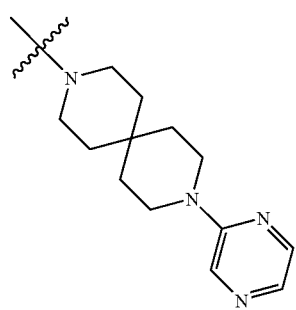
(5) 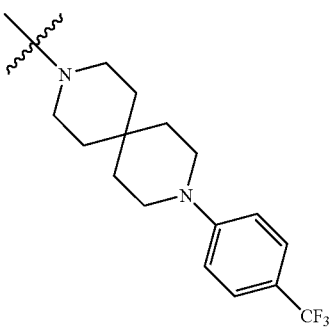

(6)
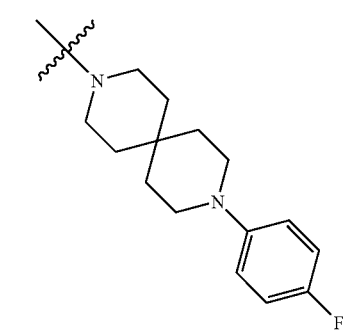
(7)
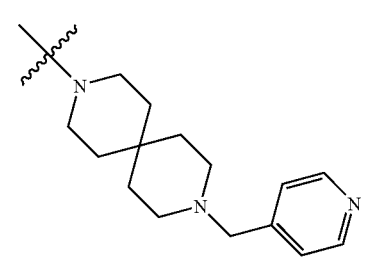
(8)
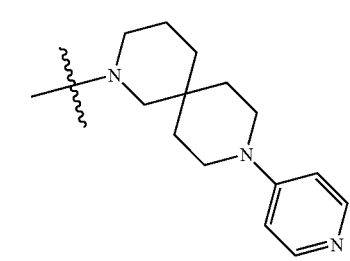
(9)
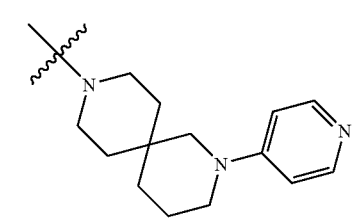
(10)
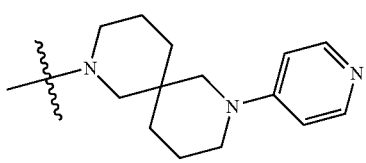
(11)
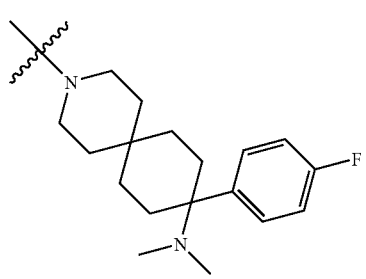
(12)
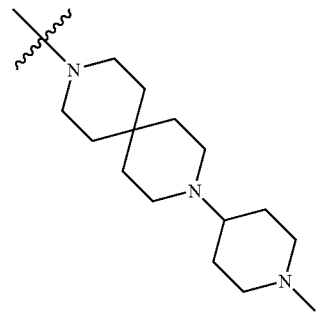
(13)
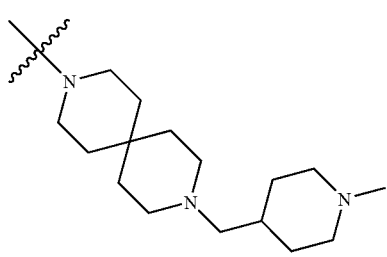
(14)
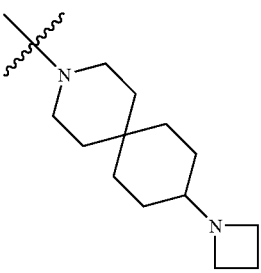
(15)
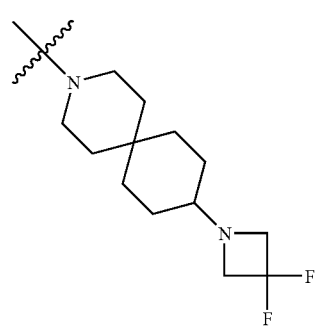
(16)
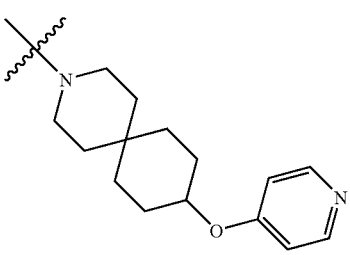
(17)
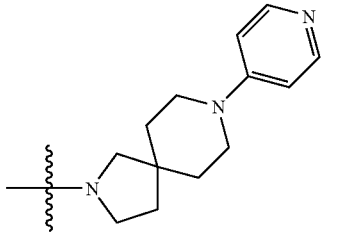

(18) 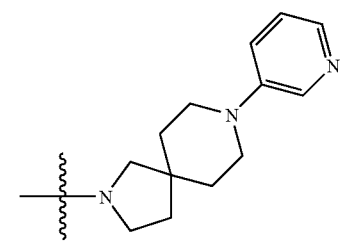
(19) 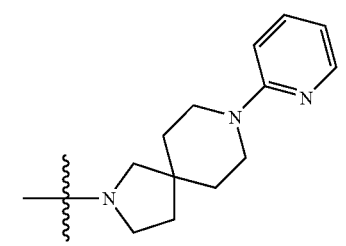
(20) 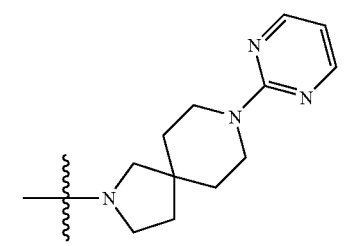
(21) 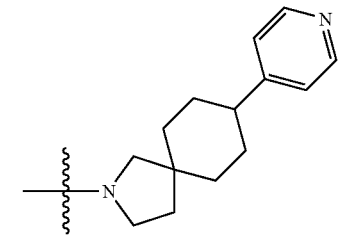
(22) 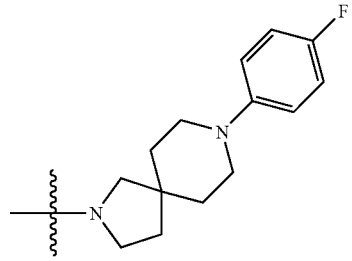
(23) 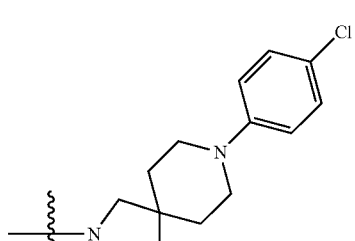
(24) 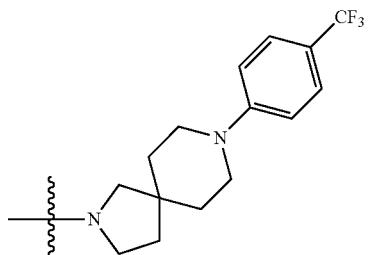
(25) 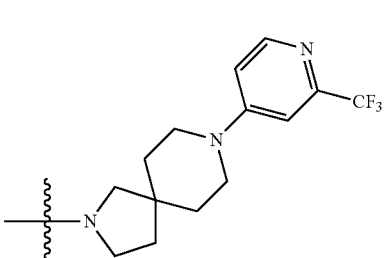
(26) 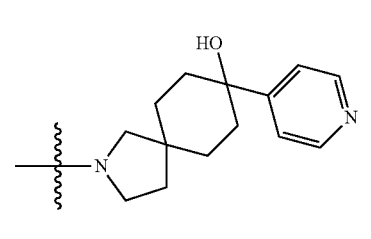
(27) 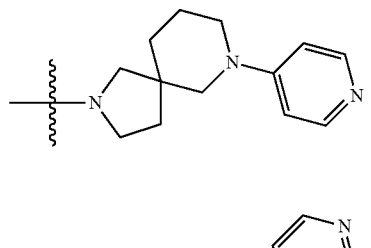
(28) 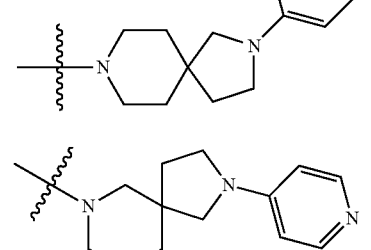
(29) 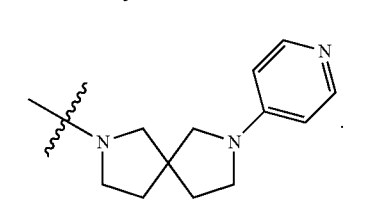
(30) 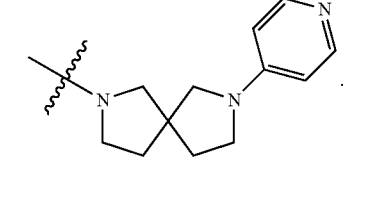
Further embodiments of the compounds according to the invention are those which are represented by the general formulae C1-C16 shown in the following:

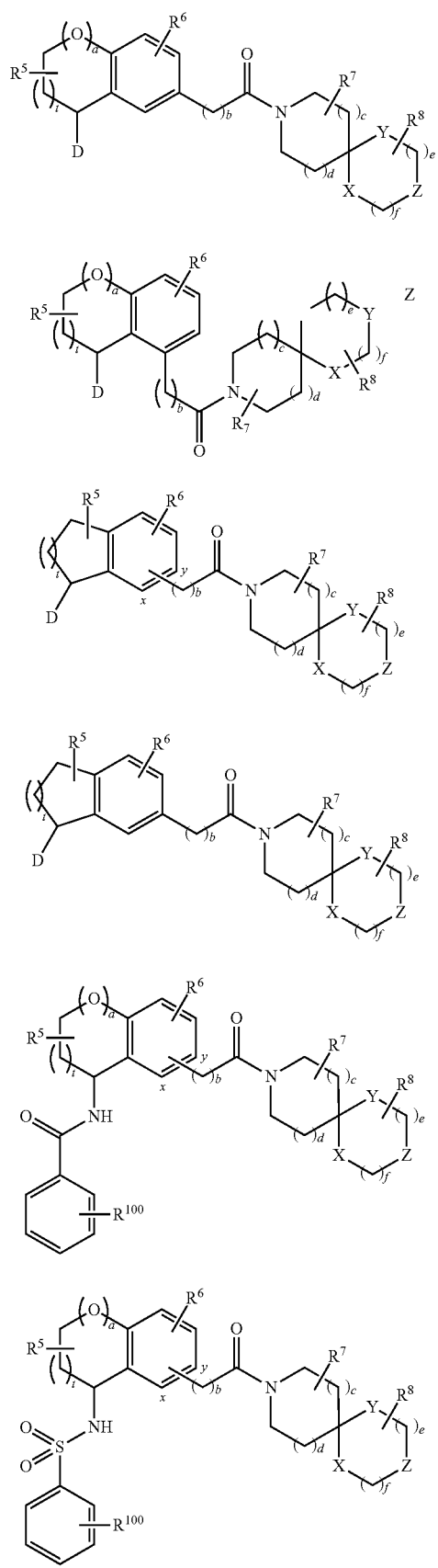
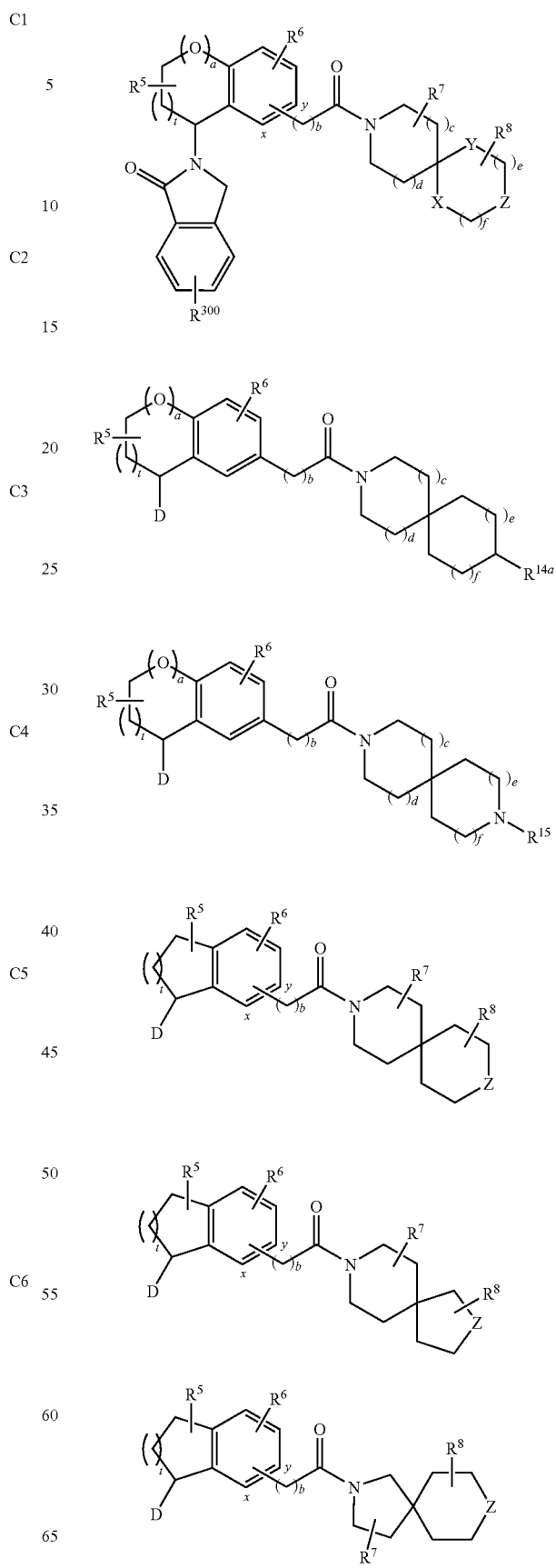

-continued

C13
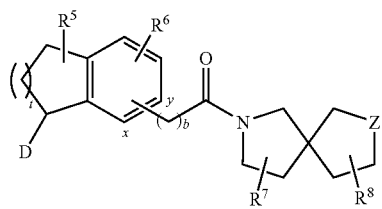

C14
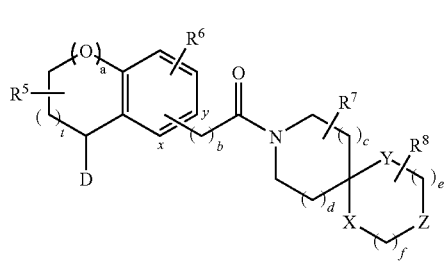

C15

C16 wherein the particular radicals, variables and indices have the meanings described herein in connection with the compounds according to the invention and preferred embodiments thereof.

Another preferred embodiment according to the present invention is a compounds corresponding to formula (IA)

(IA)

wherein the partial structure (Ac)

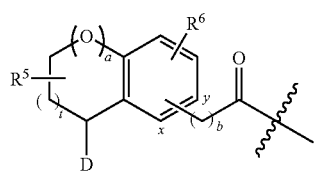
(Ac)

represents a partial structure selected from the group consisting of:

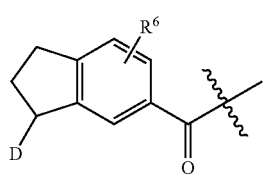
Ac a

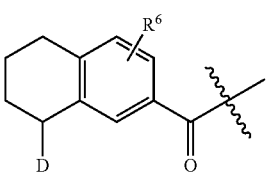
Ac b

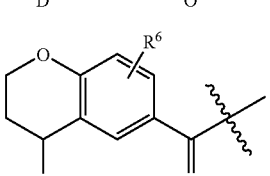
Ac c

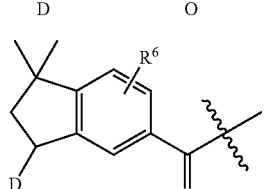
Ac d

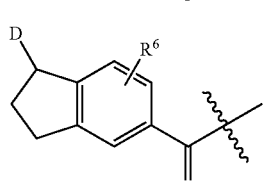
Ac e $R^6$ represents H or F;
D represents one of the following groups

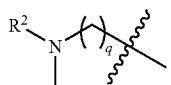 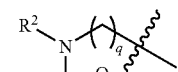

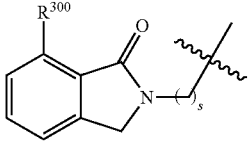 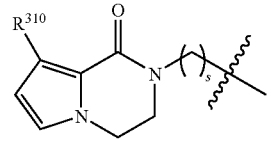

-continued

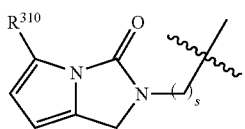

q represents 0 or 1, preferably 0;
s represents 0 or 1, preferably 0;
$R^{300}$ represents F, Cl, Methyl or $CF_3$,
$R^{310}$ represents F, Cl, Methyl or $CF_3$,
$R^1$ represents $C_{1-6}$-alkyl, $C_{3-8}$-cycloalkyl, phenyl, pyridinyl, benzyl, thienyl, pyrimidinyl, or phenyl bonded via a $C_{1-3}$-alkylene group; or phenyl bonded via a $C_{3-6}$-cycloalkylene group, wherein the above mentioned aryl or heteroaryl radicals are in each case unsubstituted or substituted one or more times, e.g. 1, 2, 3 or 4 times, by identical or different substituents, wherein the substituents independently of one another in particular are selected from the group consisting of Cl, $CF_3$, F, Methyl, $OCF_3$ and $OCH_3$;
$R^2$ represents H, $C_{1-6}$-alkyl, unsubstituted or substituted with 1, 2 or 3 F, $C_{3-8}$-cycloalkyl, preferably H, Cyclopropyl, Methyl, Isopropyl, tert-Butyl, —$CH_2$-iso-propyl, —$CH_2$-tert-Butyl or —$CH_2$—$CF_3$; and wherein the following partial structure (SP)

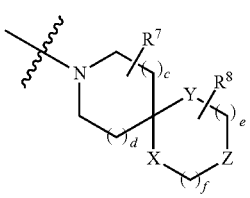

(SP)

is selected from the group

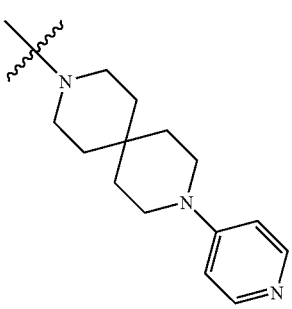

(1)

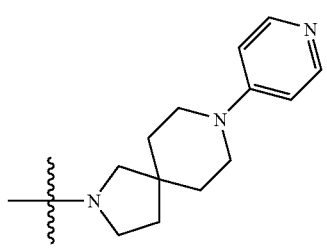

(17)

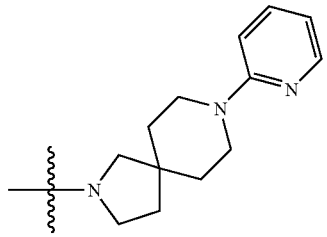

(19)

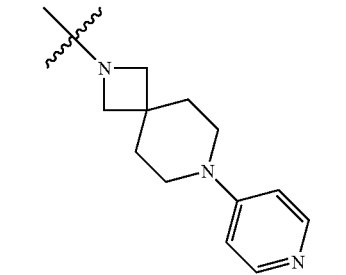

(28)

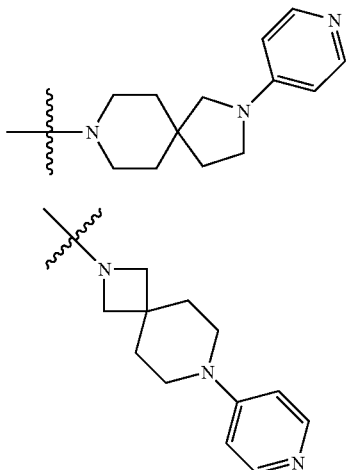

(31)

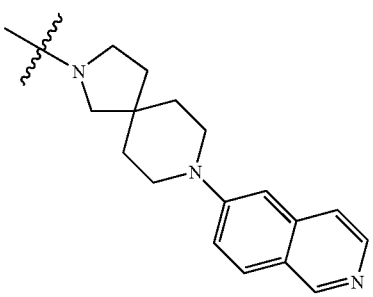

(39)

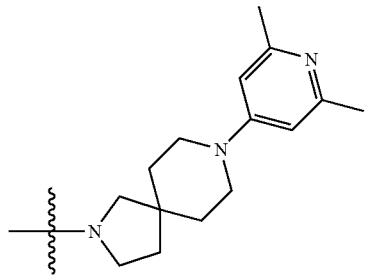

(44)

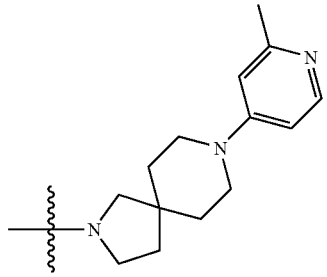

(45)

-continued (18)

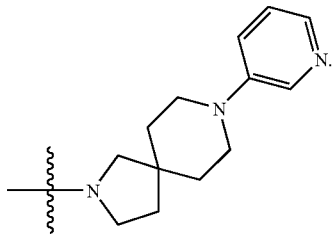

Preferably these aforementioned compounds of formula IA may be the R-Isomers.

Preferably the partial structure (SP) in the aforementioned compounds of formula IA may be selected from the group of (17), (44) and (45).

In the aforementioned compounds of formula IA, $R^1$ may preferably represent $C_{1-6}$-alkyl, $C_{3-8}$-cycloalkyl, phenyl, pyridinyl, benzyl, thienyl, pyrimidinyl, or phenyl bonded via a —C(H)(CH$_3$)— or —C(CH$_3$)$_2$— group, or phenyl bonded via

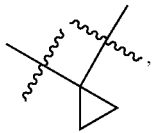

wherein the above mentioned aryl or heteroaryl groups may each be unsubstituted or substituted one or more times, e.g. 1, 2, 3 or 4 times, by identical or different substituents independently selected from the group consisting of Cl, CF$_3$, F, Methyl, OCF$_3$ and OCH$_3$.

In a further preferred embodiment of the present invention, the substituted compounds according to the invention can be selected from the group consisting of:

[H-01] 7-chloro-2-[6-(9-pyridin-4-yl-3,9-diazaspiro[5.5]undecane-3-carbonyl)-2,3-dihydro-1H-inden-1-yl]-2,3-dihydro-isoindol-1-one,

[H-02] 2-chloro-N-[6-(3-pyridin-4-yl-3,9-diazaspiro[5.5]undecane-9-carbonyl)-2,3-dihydro-1H-inden-1-yl]-benzamide,

[H-03] 4-methoxy-2,6-dimethyl-N-[6-(9-pyridin-4-yl-3,9-diazaspiro[5.5]undecane-3-carbonyl)-2,3-dihydro-1H-inden-1-yl]-benzenesulfonic acid amide,

[H-04] 2-chloro-N-[6-(8-pyridin-4-yl-3,8-diazaspiro[4.4]nonane-3-carbonyl)-2,3-dihydro-1H-inden-1-yl]-benzamide,

[H-05] 2-chloro-N-[6-(8-pyridin-4-yl-3,8-diazaspiro[4.5]decane-3-carbonyl)-2,3-dihydro-1H-inden-1-yl]-benzamide,

[H-06] N-[6-[9-(azetidin-1-yl)-3-azaspiro[5.5]undecane-3-carbonyl]-2,3-dihydro-1H-inden-1-yl]-2-chloro-benzamide,

[H-07] 2-chloro-N-[6-[9-(3,3-difluoro-azetidin-1-yl)-3-azaspiro[5.5]undecane-3-carbonyl]-2,3-dihydro-1H-inden-1-yl]-benzamide,

[H-08] 2-chloro-N-[6-(9-pyridin-4-yloxy-3-azaspiro[5.5]undecane-3-carbonyl)-2,3-dihydro-1H-inden-1-yl]-benzamide,

[H-09] 2-chloro-N-[(1R)-7-(9-pyridin-4-yl-3,9-diazaspiro[5.5]undecane-3-carbonyl)-1,2,3,4-tetrahydro-naphthalen-1-yl]-benzamide,

[H-10] 2-chloro-N-[(1S)-7-(9-pyridin-4-yl-3,9-diazaspiro[5.5]undecane-3-carbonyl)-1,2,3,4-tetrahydro-naphthalen-1-yl]-benzamide,

[H-11] 2-chloro-N-[(1R)-7-(8-pyridin-4-yl-3,8-diazaspiro[4.5]decane-3-carbonyl)-1,2,3,4-tetrahydro-naphthalen-1-yl]-benzamide,

[H-12] 2-chloro-N-[(1S)-7-(8-pyridin-4-yl-3,8-diazaspiro[4.5]decane-3-carbonyl)-1,2,3,4-tetrahydro-naphthalen-1-yl]-benzamide,

[H-13] 7-chloro-2-[(1R)-7-(8-pyridin-4-yl-3,8-diazaspiro[4.5]decane-3-carbonyl)-1,2,3,4-tetrahydro-naphthalen-1-yl]-2,3-dihydro-isoindol-1-one,

[H-14] 7-chloro-2-[(1R)-7-(9-pyridin-4-yl-3,9-diazaspiro[5.5]undecane-3-carbonyl)-1,2,3,4-tetrahydro-naphthalen-1-yl]-2,3-dihydro-isoindol-1-one,

[H-15] 7-chloro-2-[(1S)-7-(8-pyridin-4-yl-3,8-diazaspiro[4.5]decane-3-carbonyl)-1,2,3,4-tetrahydro-naphthalen-1-yl]-2,3-dihydro-isoindol-1-one,

[H-16] 4-methoxy-2,6-dimethyl-N-[(1R)-7-(8-pyridin-4-yl-3,8-diazaspiro[4.5]decane-3-carbonyl)-1,2,3,4-tetrahydro-naphthalen-1-yl]-benzenesulfonic acid amide,

[H-17]-methoxy-2,6-dimethyl-N-[(1R)-7-(9-pyridin-4-yl-3,9-diazaspiro[5.5]-undecane-3-carbonyl)-1,2,3,4-tetrahydro-naphthalen-1-yl]-benzenesulfonic acid amide,

[H-18] 4-methoxy-2,6-dimethyl-N-[(1S)-7-(8-pyridin-4-yl-3,8-diazaspiro[4.5]decane-3-carbonyl)-1,2,3,4-tetrahydro-naphthalen-1-yl]-benzenesulfonic acid amide,

[H-19] 4-methoxy-2,6-dimethyl-N-[(1S)-7-(9-pyridin-4-yl-3,9-diazaspiro[5.5]undecane-3-carbonyl)-1,2,3,4-tetrahydro-naphthalen-1-yl]-benzenesulfonic acid amide,

[H-20] 2-chloro-N-[(1S)-6-(8-pyridin-4-yl-3,8-diazaspiro[4.5]decane-3-carbonyl)-2,3-dihydro-1H-inden-1-yl]-benzamide,

[H-21] 2-chloro-N-[(1R)-6-(8-pyridin-4-yl-3,8-diazaspiro[4.5]decane-3-carbonyl)-2,3-dihydro-1H-inden-1-yl]-benzamide

[H-22] 2-chloro-N-[(1R)-7-(9-pyridin-4-yl-3,9-diazaspiro[5.5]undecane-3-carbonyl)-2,3-dihydro-1H-inden-1-yl]-benzamide,

[H-23] 2-chloro-N-[(1S)-7-(8-pyridin-4-yl-3,8-diazaspiro[4.5]decane-3-carbonyl)-2,3-dihydro-1H-inden-1-yl]-benzamide

[H-24] 2-chloro-N-[(1S)-7-(9-pyridin-4-yl-3,9-diazaspiro[5.5]undecane-3-carbonyl)-2,3-dihydro-1H-inden-1-yl]-benzamide,

[H-25] 2-chloro-N-[(1R)-7-(8-pyridin-4-yl-3,8-diazaspiro[4.5]decane-3-carbonyl)-2,3-dihydro-1H-inden-1-yl]-benzamide

[H-26] 2-chloro-N-[(1R)-6-(8-pyridin-4-yl-3,8-diazaspiro[5.5]undecane-3-carbonyl)-2,3-dihydro-1H-inden-1-yl]-benzamide,

[H-27] 2-chloro-N-[(1R)-6-(7-pyridin-4-yl-2,7-diazaspiro[3.5]nonane-2-carbonyl)-2,3-dihydro-1H-inden-1-yl]-benzamide,

[H-28] 2-chloro-N-[(1R)-6-[9-(1-methyl-piperidin-4-yl)-3,9-diazaspiro[5.5]undecane-3-carbonyl]-2,3-dihydro-1H-inden-1-yl]-benzamide,

[H-29] 2-chloro-N-[(1R)-6-[9-(4-methyl-piperazine-1-carbonyl)-3-azaspiro[5.5]undecane-3-carbonyl]-2,3-dihydro-1H-inden-1-yl]-benzamide,

[H-31] 2-chloro-N-[(1R)-6-[9-[(1-methyl-piperidin-4-yl)-methyl]-3,9-diazaspiro[5.5]undecane-3-carbonyl]-2,3-dihydro-1H-inden-1-yl]-benzamide,

[H-32] 2-chloro-N-[(1R)-6-(spiro[1H-furo[3,4-c]pyridine-3,4'-piperidine]-1'-carbonyl)-2,3-dihydro-1H-inden-1-yl]-benzamide,

[H-33] 2-chloro-N-[(1R)-6-(8-pyridin-4-yl-4,8-diazaspiro[5.5]undecane-4-carbonyl)-2,3-dihydro-1H-inden-1-yl]-benzamide,
[H-34] 2-chloro-N-[(1R)-6-(7-pyridin-4-yl-3,7-diazaspiro[4.5]decane-3-carbonyl)-2,3-dihydro-1H-inden-1-yl]-benzamide,
[H-35] 2-chloro-N-[(1R)-6-(2-pyridin-4-yl-2,9-diazaspiro[4.5]decane-9-carbonyl)-2,3-dihydro-1H-inden-1-yl]-benzamide,
[H-36] N-[(1R)-6-[9-(4-tert-butyl-piperazin-1-yl)-3-azaspiro[5.5]undecane-3-carbonyl]-2,3-dihydro-1H-inden-1-yl]-2-chloro-benzamide,
[H-37] 2-chloro-N-[(1R)-6-[9-(pyrrolidine-1-carbonyl)-3-azaspiro[5.5]undecane-3-carbonyl]-2,3-dihydro-1H-inden-1-yl]-benzamide,
[H-38] 2-chloro-N-[(1R)-6-[8-(2-pyrrolidin-1-yl-acetyl)-3,8-diazaspiro[4.5]decane-3-carbonyl]-2,3-dihydro-1H-inden-1-yl]-benzamide,
[H-39] 2-chloro-N-[6-(8-pyridin-2-yl-3,8-diazaspiro[4.5]decane-3-carbonyl)-2,3-dihydro-1H-inden-1-yl]-benzamide,
[H-40] 2-chloro-N-[6-[8-(4-chlorophenyl)-3,8-diazaspiro[4.5]decane-3-carbonyl]-2,3-dihydro-1H-inden-1-yl]-benzamide,
[H-41] 2-chloro-N-[6-[8-(4-fluorophenyl)-3,8-diazaspiro[4.5]decane-3-carbonyl]-2,3-dihydro-1H-inden-1-yl]-benzamide,
[H-42] 2-chloro-N-[6-[8-[4-(trifluoromethyl)-phenyl]-3,8-diazaspiro[4.5]decane-3-carbonyl]-2,3-dihydro-1H-inden-1-yl]-benzamide,
[H-43] 2-chloro-N-[6-(8-pyridin-3-yl-3,8-diazaspiro[4.5]decane-3-carbonyl)-2,3-dihydro-1H-inden-1-yl]-benzamide,
[H-44] 2-chloro-N-[6-(8-pyrimidin-2-yl-3,8-diazaspiro[4.5]decane-3-carbonyl)-2,3-dihydro-1H-inden-1-yl]-benzamide,
[H-45] 2-chloro-N-[6-[8-[2-(trifluoromethyl)-pyridin-4-yl]-3,8-diazaspiro[4.5]decane-3-carbonyl]-2,3-dihydro-1H-inden-1-yl]-benzamide,
[H-46] 2-chloro-N-[6-[8-[8-(trifluoromethyl)-quinolin-4-yl]-3,8-diazaspiro[4.5]decane-3-carbonyl]-2,3-dihydro-1H-inden-1-yl]-benzamide,
[H-47] 2-chloro-N-[2,2-dimethyl-6-(8-pyridin-4-yl-3,8-diazaspiro[4.5]decane-3-carbonyl)-1,3-dihydro-inden-1-yl]-benzamide,
[H-48] 2-chloro-N-[6-[8-[5-(trifluoromethyl)-pyridin-2-yl]-3,8-diazaspiro[4.5]decane-3-carbonyl]-2,3-dihydro-1H-inden-1-yl]-benzamide,
[H-49] 2-chloro-N-methyl-N-[6-(8-pyridin-4-yl-3,8-diazaspiro[4.5]decane-3-carbonyl)-2,3-dihydro-1H-inden-1-yl]-benzamide,
[H-50] 2-chloro-N-[6-(8-isoquinolin-6-yl-3,8-diazaspiro[4.5]decane-3-carbonyl)-2,3-dihydro-1H-inden-1-yl]-benzamide,
[H-51] 2-chloro-N-[6-[8-[2-(trifluoromethyl)-pyrimidin-4-yl]-3,8-diazaspiro[4.5]decane-3-carbonyl]-2,3-dihydro-1H-inden-1-yl]-benzamide,
[H-52] N-[(5R)-1-Azabicyclo[2.2.2]octan-5-yl]-3-[(3R)-3-[(2-chloro-benzoyl)amino]-2,3-dihydro-1H-indene-5-carbonyl]-3-azaspiro[5.5]undecane-9-carboxylic acid amide,
[H-53] 2-Methyl-N-[(1R)-6-(8-pyridin-4-yl-3,8-diazaspiro[4.5]decane-3-carbonyl)-2,3-dihydro-1H-inden-1-yl]-benzamide,
[H-54] 2-Chloro-N-[(1R)-6-(9-pyridin-4-yl-2,9-diazaspiro[5.5]undecane-2-carbonyl)-2,3-dihydro-1H-inden-1-yl]-benzamide,
[H-55] 2-Chloro-N-[(1R)-6-[9-(5,6,7,8-tetrahydro-[1,2,4]triazolo[1,5-a]pyrazin-7-yl)-3-azaspiro[5.5]undecane-3-carbonyl]-2,3-dihydro-1H-inden-1-yl]-benzamide,
[H-56] 6-Methoxy-N-[(1R)-6-(8-pyridin-4-yl-3,8-diazaspiro[4.5]decane-3-carbonyl)-2,3-dihydro-1H-inden-1-yl]-naphthalene-2-carboxylic acid amide,
[H-57] 2-Chloro-N-[(4R)-6-(3-pyridin-4-yl-3,8-diazaspiro[4.5]decane-8-carbonyl)-3,4-dihydro-2H-chromen-4-yl]-benzamide,
[H-58] 2-Chloro-N-[(4R)-6-(9-pyridin-4-yl-3,9-diazaspiro[5.5]undecane-3-carbonyl)-3,4-dihydro-2H-chromen-4-yl]-benzamide,
[H-59] 2-Chloro-N-[(1R)-5-methyl-6-(3-pyridin-4-yl-3,8-diazaspiro[4.5]decane-8-carbonyl)-2,3-dihydro-1H-inden-1-yl]-benzamide,
[H-60] 2-Chloro-4-methoxy-N-[(1R)-6-(3-pyridin-4-yl-3,8-diazaspiro[4.5]decane-8-carbonyl)-2,3-dihydro-1H-inden-1-yl]-benzamide,
[H-61] 4-Methoxy-2-methyl-N-[(1R)-6-(8-pyridin-4-yl-3,8-diazaspiro[4.5]decane-3-carbonyl)-2,3-dihydro-1H-inden-1-yl]-benzamide,
[H-62] N-[(5S)-1-Azabicyclo[2.2.2]octan-5-yl]-3-[(3R)-3-[(2-chloro-benzoyl)amino]-2,3-dihydro-1H-indene-5-carbonyl]-3-azaspiro[5.5]undecane-9-carboxylic acid amide,
[H-63] 2-Chloro-4-methoxy-N-[(1R)-6-(8-pyridin-4-yl-3,8-diazaspiro[4.5]decane-3-carbonyl)-2,3-dihydro-1H-inden-1-yl]-benzamide,
[H-64] 2-Chloro-N-[(1R)-5-fluoro-6-(8-pyridin-4-yl-3,8-diazaspiro[4.5]decane-3-carbonyl)-2,3-dihydro-1H-inden-1-yl]-benzamide hydrochloride,
[H-65] 2-Chloro-N-[(4R)-7-fluoro-6-(8-pyridin-4-yl-3,8-diazaspiro[4.5]decane-3-carbonyl)-3,4-dihydro-2H-chromen-4-yl]-benzamide,
[H-66] 2-Chloro-N-[(1R)-5-methyl-6-(9-pyridin-4-yl-3,9-diazaspiro[5.5]undecane-3-carbonyl)-2,3-dihydro-1H-inden-1-yl]-benzamide,
[H-67] 2-Chloro-N-[(4R)-6-(8-pyridin-4-yl-3,8-diazaspiro[4.5]decane-3-carbonyl)-3,4-dihydro-2H-chromen-4-yl]-benzamide,
[H-68] 6-Methoxy-N-[(1R)-6-(3-pyridin-4-yl-3,8-diazaspiro[4.5]decane-8-carbonyl)-2,3-dihydro-1H-inden-1-yl]-naphthalene-2-carboxylic acid amide,
[H-69] 2-Chloro-N-[(1R)-7-(8-pyridin-4-yl-4,8-diazaspiro[5.5]undecane-4-carbonyl)-1,2,3,4-tetrahydro-naphthalen-1-yl]-benzamide,
[H-70] 2-Chloro-N-[(1R)-7-(2-pyridin-4-yl-2,9-diazaspiro[4.5]decane-9-carbonyl)-1,2,3,4-tetrahydro-naphthalen-1-yl]-benzamide,
[H-71] 2-Chloro-N-[(1R)-7-(7-pyridin-4-yl-2,7-diazaspiro[3.5]nonane-2-carbonyl)-1,2,3,4-tetrahydro-naphthalen-1-yl]-benzamide,
[H-72] 2-Chloro-N-[(1R)-7-(3-pyridin-4-yl-3,8-diazaspiro[4.5]decane-8-carbonyl)-1,2,3,4-tetrahydro-naphthalen-1-yl]-benzamide,
[H-73] 2-Chloro-N-[(4R)-8-fluoro-6-(8-pyridin-4-yl-3,8-diazaspiro[4.5]decane-3-carbonyl)-3,4-dihydro-2H-chromen-4-yl]-benzamide,
[H-74] 2-Methyl-N-[(1R)-6-(8-pyridin-4-yl-3,8-diazaspiro[4.5]decane-3-carbonyl)-2,3-dihydro-1H-inden-1-yl]-4-(trifluoromethyloxy)-benzamide,
[H-75] 2-Methyl-N-[(1R)-6-(3-pyridin-4-yl-3,8-diazaspiro[4.5]decane-8-carbonyl)-2,3-dihydro-1H-inden-1-yl]-4-(trifluoromethyloxy)-benzamide,
[H-76] 2-Chloro-N-[(1R)-6-(8-pyridin-4-yl-3,8-diazaspiro[4.5]decane-3-carbonyl)-2,3-dihydro-1H-inden-1-yl]-6-(trifluoromethyl)-benzamide,

[H-77] 2-Chloro-N-[(4R)-8-fluoro-6-(3-pyridin-4-yl-3,8-diazaspiro[4.5]decane-8-carbonyl)-3,4-dihydro-2H-chromen-4-yl]-benzamide,

[H-78] 2-Chloro-N-[(4R)-8-fluoro-6-(9-pyridin-4-yl-3,9-diazaspiro[5.5]undecane-3-carbonyl)-3,4-dihydro-2H-chromen-4-yl]-benzamide,

[H-79] 2-Chloro-N-[(1R)-7-(8-pyridin-4-yl-3,8-diazaspiro[4.4]nonane-3-carbonyl)-1,2,3,4-tetrahydro-naphthalen-1-yl]-benzamide,

[H-80] 2-Chloro-N-[(1R)-7-(8-pyridin-4-yl-3,8-diazaspiro[5.5]undecane-3-carbonyl)-1,2,3,4-tetrahydro-naphthalen-1-yl]-benzamide,

[H-81] 2-Chloro-N-[(1R)-7-(7-pyridin-4-yl-3,7-diazaspiro[4.5]decane-3-carbonyl)-1,2,3,4-tetrahydro-naphthalen-1-yl]-benzamide,

[H-82] 2-Chloro-N-[(1R)-6-fluoro-7-(8-pyridin-4-yl-3,8-diazaspiro[4.5]decane-3-carbonyl)-1,2,3,4-tetrahydro-naphthalen-1-yl]-benzamide,

[H-83] 2-Chloro-N-[(1R)-6-(3-pyridin-4-yl-3,8-diazaspiro[4.5]decane-8-carbonyl)-2,3-dihydro-1H-inden-1-yl]-6-(trifluoromethyl)-benzamide,

[H-84] N-[(1R)-6-(8-Pyridin-4-yl-3,8-diazaspiro[4.5]decane-3-carbonyl)-2,3-dihydro-1H-inden-1-yl]-pyrimidine-5-carboxylic acid amide,

[H-85] 2-Chloro-N-[(1R)-6-(9-pyridin-4-yl-3,9-diazaspiro[5.5]undecane-3-carbonyl)-2,3-dihydro-1H-inden-1-yl]-6-(trifluoromethyl)-benzamide,

[H-86] N-[(1R)-6-(3-Pyridin-4-yl-3,8-diazaspiro[4.5]decane-8-carbonyl)-2,3-dihydro-1H-inden-1-yl]-pyrimidine-5-carboxylic acid amide,

[H-87] 2-Chloro-N-[(1R)-6-fluoro-7-(3-pyridin-4-yl-3,8-diazaspiro[4.5]decane-8-carbonyl)-1,2,3,4-tetrahydro-naphthalen-1-yl]-benzamide,

[H-88] 2-Chloro-N-[(1R)-6-fluoro-7-(9-pyridin-4-yl-3,9-diazaspiro[5.5]undecane-3-carbonyl)-1,2,3,4-tetrahydro-naphthalen-1-yl]-benzamide,

[H-89] 2-Chloro-N-[(1R)-5-fluoro-6-(3-pyridin-4-yl-3,8-diazaspiro[4.5]decane-8-carbonyl)-2,3-dihydro-1H-inden-1-yl]-benzamide,

[H-90] 2-Chloro-N-[(1R)-5-fluoro-6-(9-pyridin-4-yl-3,9-diazaspiro[5.5]undecane-3-carbonyl)-2,3-dihydro-1H-inden-1-yl]-benzamide,

[H-91] 2-Chloro-N-[(1R)-6-(3-pyridin-4-yl-3,8-diazaspiro[4.5]decane-8-carbonyl)-2,3-dihydro-1H-inden-1-yl]-benzamide,

[H-92] 2-Chloro-N-[(4R)-7-fluoro-6-(9-pyridin-4-yl-3,9-diazaspiro[5.5]undecane-3-carbonyl)-3,4-dihydro-2H-chromen-4-yl]-benzamide,

[H-93] 2-Chloro-N-[(1R)-5-methyl-6-(8-pyridin-4-yl-3,8-diazaspiro[4.5]decane-3-carbonyl)-2,3-dihydro-1H-inden-1-yl]-benzamide,

[H-94] 2,3-Dichloro-N-[(1R)-6-(8-pyridin-4-yl-3,8-diazaspiro[4.5]decane-3-carbonyl)-2,3-dihydro-1H-inden-1-yl]-benzamide,

[H-95] 2,3-Dichloro-N-[(1R)-6-(9-pyridin-4-yl-3,9-diazaspiro[5.5]undecane-3-carbonyl)-2,3-dihydro-1H-inden-1-yl]-benzamide,

[H-96] 7-Chloro-2-[(1R)-6-(8-pyridin-4-yl-3,8-diazaspiro[4.5]decane-3-carbonyl)-2,3-dihydro-1H-inden-1-yl]-2,3-dihydro-isoindol-1-one,

[H-97] 2-Chloro-N-[(1R)-6-[9-(5,6,7,8-tetrahydro-[1,2,4]triazolo[1,5-a]pyrazine-7-carbonyl)-3-azaspiro[5.5]undecane-3-carbonyl]-2,3-dihydro-1H-inden-1-yl]-benzamide,

[H-98] 2,5-Dichloro-N-[(1R)-6-(8-pyridin-4-yl-3,8-diazaspiro[4.5]decane-3-carbonyl)-2,3-dihydro-1H-inden-1-yl]-benzamide,

[H-99] 2,6-Dichloro-N-[(1R)-6-(8-pyridin-4-yl-3,8-diazaspiro[4.5]decane-3-carbonyl)-2,3-dihydro-1H-inden-1-yl]-benzamide,

[H-100] 2,6-Dichloro-N-[(1R)-6-(9-pyridin-4-yl-3,9-diazaspiro[5.5]undecane-3-carbonyl)-2,3-dihydro-1H-inden-1-yl]-benzamide,

[H-101] 2-Fluoro-N-[(1R)-6-(8-pyridin-4-yl-3,8-diazaspiro[4.5]decane-3-carbonyl)-2,3-dihydro-1H-inden-1-yl]-benzamide,

[H-102] 2-Fluoro-N-[(1R)-6-(9-pyridin-4-yl-3,9-diazaspiro[5.5]undecane-3-carbonyl)-2,3-dihydro-1H-inden-1-yl]-benzamide,

[H-103] 4-Methoxy-2,5-dimethyl-N-[(1R)-6-(8-pyridin-4-yl-3,8-diazaspiro[4.5]decane-3-carbonyl)-2,3-dihydro-1H-inden-1-yl]-benzamide,

[H-104] 2,6-Dimethyl-N-[(1R)-6-(8-pyridin-4-yl-3,8-diazaspiro[4.5]decane-3-carbonyl)-2,3-dihydro-1H-inden-1-yl]-benzamide,

[H-105] 2-Chloro-N-[(1R)-6-(8-pyridin-4-yl-3,8-diazaspiro[4.5]decane-3-carbonyl)-2,3-dihydro-1H-inden-1-yl]-benzenesulfonic acid amide,

[H-106] 2-Chloro-N-[(1R)-7-(8-pyridin-4-yl-3,8-diazaspiro[4.5]decane-3-carbonyl)-1,2,3,4-tetrahydro-naphthalen-1-yl]-benzenesulfonic acid amide,

[H-107] 2-Chloro-N-[(4R)-6-(8-pyridin-4-yl-3,8-diazaspiro[4.5]decane-3-carbonyl)-7-(trifluoromethyl)-3,4-dihydro-2H-chromen-4-yl]-benzamide,

[H-108] 2-Fluoro-4-methoxy-N-[(1R)-6-(8-pyridin-4-yl-3,8-diazaspiro[4.5]decane-3-carbonyl)-2,3-dihydro-1H-inden-1-yl]-benzamide,

[H-109] 2-Chloro-6-fluoro-N-[(1R)-6-(8-pyridin-4-yl-3,8-diazaspiro[4.5]decane-3-carbonyl)-2,3-dihydro-1H-inden-1-yl]-benzamide,

[H-110] 2-Fluoro-N-[(1R)-6-(8-pyridin-4-yl-3,8-diazaspiro[4.5]decane-3-carbonyl)-2,3-dihydro-1H-inden-1-yl]-6-(trifluoromethyl)-benzamide,

[H-111] 2-Chloro-N-[(1R)-6-[8-(2,6-dimethyl-pyridin-4-yl)-3,8-diazaspiro[4.5]decane-3-carbonyl]-2,3-dihydro-1H-inden-1-yl]-benzamide hydrochloride,

[H-112] 2-Chloro-N-[(1R)-6-[8-(2-methyl-pyridin-4-yl)-3,8-diazaspiro[4.5]decane-3-carbonyl]-2,3-dihydro-1H-inden-1-yl]-benzamide,

[H-113] 2,3-Dichloro-N-[(1R)-6-(8-pyridin-4-yl-3,8-diazaspiro[4.5]decane-3-carbonyl)-2,3-dihydro-1H-inden-1-yl]-benzenesulfonic acid amide,

[H-114] 2-Methyl-N-[(1R)-6-(8-pyridin-4-yl-3,8-diazaspiro[4.5]decane-3-carbonyl)-2,3-dihydro-1H-inden-1-yl]-pyridine-3-carboxylic acid amide,

[H-115] N-[(1R)-6-(8-Pyridin-4-yl-3,8-diazaspiro[4.5]decane-3-carbonyl)-2,3-dihydro-1H-inden-1-yl]-4-(trifluoromethyl)-pyridine-3-carboxylic acid amide,

[H-116] 2-Fluoro-N-[(1R)-6-(8-pyridin-4-yl-3,8-diazaspiro[4.5]decane-3-carbonyl)-2,3-dihydro-1H-inden-1-yl]-benzenesulfonic acid amide,

[H-117] 2-Methyl-N-[(1R)-6-(8-pyridin-4-yl-3,8-diazaspiro[4.5]decane-3-carbonyl)-2,3-dihydro-1H-inden-1-yl]-benzenesulfonic acid amide,

[H-118] N-[(1R)-6-(8-Pyridin-4-yl-3,8-diazaspiro[4.5]decane-3-carbonyl)-2,3-dihydro-1H-inden-1-yl]-2-(trifluoromethyl)-benzenesulfonic acid amide,

[H-119] 2,6-Dichloro-N-[(1R)-6-(8-pyridin-4-yl-3,8-diazaspiro[4.5]decane-3-carbonyl)-2,3-dihydro-1H-inden-1-yl]-benzenesulfonic acid amide,

[H-120] 2-Chloro-N-[6-[9-[2-(1H-imidazol-1-yl)-ethoxy]-3-azaspiro[5.5]undecane-3-carbonyl]-2,3-dihydro-1H-inden-1-yl]-benzamide,

[H-128] 2-Chloro-N-[6-(8-hydroxy-8-pyridin-4-yl-3-azaspiro[4.5]decane-3-carbonyl)-2,3-dihydro-1H-inden-1-yl]-benzamide,

[H-129] 2-Chloro-N-[6-[8-(1-oxido-pyridin-1-ium-4-yl)-3,8-diazaspiro[4.5]decane-3-carbonyl]-2,3-dihydro-1H-inden-1-yl]-benzamide,

[H-130] 2-Chloro-N-[6-[8-[5-(trifluoromethyl)-pyrimidin-2-yl]-3,8-diazaspiro[4.5]decane-3-carbonyl]-2,3-dihydro-1H-inden-1-yl]-benzamide,

[H-131] 2-Chloro-N-[6-[9-(1H-imidazol-1-yl)-3-azaspiro[5.5]undecane-3-carbonyl]-2,3-dihydro-1H-inden-1-yl]-benzamide,

[H-132] 2-Chloro-N-[3,3-dimethyl-6-(8-pyridin-4-yl-3,8-diazaspiro[4.5]decane-3-carbonyl)-1,2-dihydro-inden-1-yl]-benzamide,

[H-133] 2-Chloro-N-[6-(8-pyridin-4-yl-3-azaspiro[4.5]decane-3-carbonyl)-2,3-dihydro-1H-inden-1-yl]-benzamide,

[H-134] 5-Methyl-2-[(1R)-6-(8-pyridin-4-yl-3,8-diazaspiro[4.5]decane-3-carbonyl)-2,3-dihydro-1H-inden-1-yl]-1,2-dihydro-pyrrolo[2,1-e]imidazol-3-one,

[H-135] 2-Chloro-N-[(1R)-6-(8-pyridin-3-yl-3-azaspiro[4.5]decane-3-carbonyl)-2,3-dihydro-1H-inden-1-yl]-benzamide,

[H-136] 2-Chloro-N-methyl-N-[(1R)-6-(8-pyridin-4-yl-3,8-diazaspiro[4.5]decane-3-carbonyl)-2,3-dihydro-1H-inden-1-yl]-benzenesulfonic acid amide,

[H-137] 2-Chloro-N-[(1R)-6-(8-pyridin-4-yl-3,8-diazaspiro[4.5]decane-3-carbonyl)-2,3-dihydro-1H-inden-1-yl]-N-(2,2,2-trifluoro-ethyl)-benzamide,

[H-138] 2-Chloro-N-[6-(3-pyridin-4-yl-3,10-diazaspiro[5.6]dodecane-10-carbonyl)-2,3-dihydro-1H-inden-1-yl]-benzamide,

[H-139] 2-Chloro-N-[(1R)-6-[8-(4-methoxyphenyl)-3,8-diazaspiro[4.5]decane-3-carbonyl]-2,3-dihydro-1H-inden-1-yl]-benzamide,

[H-140] 2-Chloro-N-[(1R)-6-[8-(4-cyano-phenyl)-3,8-diazaspiro[4.5]decane-3-carbonyl]-2,3-dihydro-1H-inden-1-yl]-benzamide,

[H-141] 2-Chloro-5-fluoro-N-[(1R)-6-(8-pyridin-4-yl-3,8-diazaspiro[4.5]decane-3-carbonyl)-2,3-dihydro-1H-inden-1-yl]-benzamide,

[H-142] 2,5-Dichloro-N-[(1R)-6-(8-pyridin-4-yl-3,8-diazaspiro[4.5]decane-3-carbonyl)-2,3-dihydro-1H-inden-1-yl]-benzenesulfonic acid amide,

[H-143] 3-Methyl-N-[(1R)-6-(8-pyridin-4-yl-3,8-diazaspiro[4.5]decane-3-carbonyl)-2,3-dihydro-1H-inden-1-yl]-butyramide,

[H-144] 4-Methoxy-N-[(1R)-6-(8-pyridin-4-yl-3,8-diazaspiro[4.5]decane-3-carbonyl)-2,3-dihydro-1H-inden-1-yl]-2-(trifluoromethyl)-benzenesulfonic acid amide,

[H-145] 2-(2-Chlorophenyl)-N-[(1R)-6-(8-pyridin-4-yl-3,8-diazaspiro[4.5]decane-3-carbonyl)-2,3-dihydro-1H-inden-1-yl]-propionamide,

[H-146] 2-(2-Chlorophenyl)-2-methyl-N-[(1R)-6-(8-pyridin-4-yl-3,8-diazaspiro[4.5]decane-3-carbonyl)-2,3-dihydro-1H-inden-1-yl]-propionamide,

[H-147] 4-Methoxy-2-methyl-N-[(1R)-6-(8-pyridin-4-yl-3,8-diazaspiro[4.5]decane-3-carbonyl)-2,3-dihydro-1H-inden-1-yl]-benzenesulfonic acid amide,

[H-148] 1-(2-Chlorophenyl)-N-[(1R)-6-(8-pyridin-4-yl-3,8-diazaspiro[4.5]decane-3-carbonyl)-2,3-dihydro-1H-inden-1-yl]-cyclopropane-1-carboxylic acid amide,

[H-149] 2-Chloro-N-[(1R)-6-(8-pyridin-4-yl-3,8-diazaspiro[4.5]decane-3-carbonyl)-2,3-dihydro-1H-inden-1-yl]-6-(trifluoromethyl)-benzenesulfonic acid amide,

[H-150] 1-(2-Chlorophenyl)-N-[(1R)-6-(8-pyridin-4-yl-3,8-diazaspiro[4.5]decane-3-carbonyl)-2,3-dihydro-1H-inden-1-yl]-methanesulfonic acid amide,

[H-151] 2-(2-Chlorophenyl)-N-[(1R)-6-(8-pyridin-4-yl-3,8-diazaspiro[4.5]decane-3-carbonyl)-2,3-dihydro-1H-inden-1-yl]-acetamide,

[H-152] 2-(2-Fluorophenyl)-N-[(1R)-6-(8-pyridin-4-yl-3,8-diazaspiro[4.5]decane-3-carbonyl)-2,3-dihydro-1H-inden-1-yl]-acetamide,

[H-153] 2-Chloro-3-fluoro-N-[(1R)-6-(8-pyridin-4-yl-3,8-diazaspiro[4.5]decane-3-carbonyl)-2,3-dihydro-1H-inden-1-yl]-benzamide,

[H-154] 2-(o-Tolyl)-N-[(1R)-6-(8-pyridin-4-yl-3,8-diazaspiro[4.5]decane-3-carbonyl)-2,3-dihydro-1H-inden-1-yl]-acetamide,

[H-155] 2-Chloro-N-[(1S)-5-(8-pyridin-4-yl-3,8-diazaspiro[4.5]decane-3-carbonyl)-2,3-dihydro-1H-inden-1-yl]-benzamide,

[H-156] 2-Chloro-N-[(1S)-5-(9-pyridin-4-yl-3,9-diazaspiro[5.5]undecane-3-carbonyl)-2,3-dihydro-1H-inden-1-yl]-benzamide,

[H-157] 7-Chloro-2-[(1S)-5-(8-pyridin-4-yl-3,8-diazaspiro[4.5]decane-3-carbonyl)-2,3-dihydro-1H-inden-1-yl]-2,3-dihydro-isoindol-1-one,

[H-158] 7-Chloro-2-[(1S)-5-(9-pyridin-4-yl-3,9-diazaspiro[5.5]undecane-3-carbonyl)-2,3-dihydro-1H-inden-1-yl]-2,3-dihydro-isoindol-1-one,

[H-159] 7-Chloro-2-[(1R)-5-(9-pyridin-4-yl-3,9-diazaspiro[5.5]undecane-3-carbonyl)-2,3-dihydro-1H-inden-1-yl]-2,3-dihydro-isoindol-1-one,

[H-160] 7-Chloro-2-[(1R)-5-(8-pyridin-4-yl-3,8-diazaspiro[4.5]decane-3-carbonyl)-2,3-dihydro-1H-inden-1-yl]-2,3-dihydro-isoindol-1-one,

[H-161] 2-Chloro-N-[(1S)-4-(8-pyridin-4-yl-3,8-diazaspiro[4.5]decane-3-carbonyl)-2,3-dihydro-1H-inden-1-yl]-benzamide,

[H-162] 2-Chloro-N-[(1R)-4-(8-pyridin-4-yl-3,8-diazaspiro[4.5]decane-3-carbonyl)-2,3-dihydro-1H-inden-1-yl]-benzamide,

[H-163] 2-Chloro-N-[(1S)-4-(9-pyridin-4-yl-3,9-diazaspiro[5.5]undecane-3-carbonyl)-2,3-dihydro-1H-inden-1-yl]-benzamide,

[H-164] 2-Chloro-N-[(1R)-4-(9-pyridin-4-yl-3,9-diazaspiro[5.5]undecane-3-carbonyl)-2,3-dihydro-1H-inden-1-yl]-benzamide,

[H-165] 2-Chloro-N-[(1S)-4-(8-pyridin-4-yl-3,8-diazaspiro[4.5]decane-3-carbonyl)-2,3-dihydro-1H-inden-1-yl]-benzenesulfonic acid amide,

[H-166] 2-Chloro-N-[(1R)-4-(8-pyridin-4-yl-3,8-diazaspiro[4.5]decane-3-carbonyl)-2,3-dihydro-1H-inden-1-yl]-benzenesulfonic acid amide,

[H-167] 2-Chloro-N-[(1R)-4-(9-pyridin-4-yl-3,9-diazaspiro[5.5]undecane-3-carbonyl)-2,3-dihydro-1H-inden-1-yl]-benzenesulfonic acid amide,

[H-168] 7-Chloro-2-[(1S)-4-(8-pyridin-4-yl-3,8-diazaspiro[4.5]decane-3-carbonyl)-2,3-dihydro-1H-inden-1-yl]-2,3-dihydro-isoindol-1-one,

[H-169] 7-Chloro-2-[(1R)-4-(8-pyridin-4-yl-3,8-diazaspiro[4.5]decane-3-carbonyl)-2,3-dihydro-1H-inden-1-yl]-2,3-dihydro-isoindol-1-one,

[H-170] 7-Chloro-2-[(1R)-4-(9-pyridin-4-yl-3,9-diazaspiro[5.5]undecane-3-carbonyl)-2,3-dihydro-1H-inden-1-yl]-2,3-dihydro-isoindol-1-one,

[H-171] 2-Chloro-N-[(1R)-5-(8-pyridin-4-yl-3,8-diazaspiro[4.5]decane-3-carbonyl)-2,3-dihydro-1H-inden-1-yl]-benzamide,

[H-172] 2-Chloro-N-[(1R)-5-(9-pyridin-4-yl-3,9-diazaspiro[5.5]undecane-3-carbonyl)-2,3-dihydro-1H-inden-1-yl]-benzamide,

[H-173] 2-Chloro-N-[(1R)-5-(8-pyridin-4-yl-3,8-diazaspiro[4.5]decane-3-carbonyl)-2,3-dihydro-1H-inden-1-yl]-benzenesulfonic acid amide,

[Ind_CC-001] 4-methoxy-2,6-dimethyl-N-[6-(9-pyridin-4-yl-3,9-diazaspiro[5.5]undecane-3-carbonyl)-2,3-dihydro-1H-inden-1-yl]-benzenesulfonic acid amide,

[Ind_CC-002] N-[6-(9-pyridin-4-yl-3,9-diazaspiro[5.5]undecane-3-carbonyl)-2,3-dihydro-1H-inden-1-yl]-pyridine-2-carboxylic acid amide,

[Ind_CC-003] N-[6-(9-pyridin-4-yl-3,9-diazaspiro[5.5]undecane-3-carbonyl)-2,3-dihydro-1H-inden-1-yl]-2-(trifluoromethyl)-benzamide,

[Ind_CC-004] 3-chloro-N-[6-(9-pyridin-4-yl-3,9-diazaspiro[5.5]undecane-3-carbonyl)-2,3-dihydro-1H-inden-1-yl]-thiophene-2-carboxylic acid amide,

[Ind_CC-005] 5-chloro-N-[6-(9-pyridin-4-yl-3,9-diazaspiro[5.5]undecane-3-carbonyl)-2,3-dihydro-1H-inden-1-yl]-thiophene-2-carboxylic acid amide,

[Ind_CC-006] 2,4-dichloro-N-[6-(9-pyridin-4-yl-3,9-diazaspiro[5.5]undecane-3-carbonyl)-2,3-dihydro-1H-inden-1-yl]-benzamide,

[Ind_CC-007] 2-(2-chlorophenyl)-N-[6-(9-pyridin-4-yl-3,9-diazaspiro[5.5]undecane-3-carbonyl)-2,3-dihydro-1H-inden-1-yl]-acetamide,

[Ind_CC-008] (E)-3-(2-chlorophenyl)-N-[6-(9-pyridin-4-yl-3,9-diazaspiro[5.5]undecane-3-carbonyl)-2,3-dihydro-1H-inden-1-yl]-acrylamide,

[Ind_CC-009] 2-(2-chlorophenyl)-2-phenyl-N-[6-(9-pyridin-4-yl-3,9-diazaspiro[5.5]undecane-3-carbonyl)-2,3-dihydro-1H-inden-1-yl]-acetamide,

[Ind_CC-010] 2-chloro-N-[6-(9-pyridin-4-yl-3,9-diazaspiro[5.5]undecane-3-carbonyl)-2,3-dihydro-1H-inden-1-yl]-benzenesulfonic acid amide,

[Ind_CC-011] 1-(3,4-dichlorophenyl)-346-(9-pyridin-4-yl-3,9-diazaspiro[5.5]undecane-3-carbonyl)-2,3-dihydro-1H-inden-1-yl]-urea,

[Ind_CC-012] 1-[(2-chlorophenyl)-methyl]-3-[6-(9-pyridin-4-yl-3,9-diazaspiro[5.5]undecane-3-carbonyl)-2,3-dihydro-1H-inden-1-yl]-urea,

[Ind_CC-013] 4-methoxy-2,6-dimethyl-N-[6-(9-pyridin-4-yl-3,9-diazaspiro[5.5]undecane-3-carbonyl)-2,3-dihydro-1H-inden-1-yl]-benzamide,

[Ind_CC-014] N-methyl-N-[6-(9-pyridin-4-yl-3,9-diazaspiro[5.5]undecane-3-carbonyl)-2,3-dihydro-1H-inden-1-yl]-pyridine-2-carboxylic acid amide,

[Ind_CC-015] N-methyl-N-[6-(9-pyridin-4-yl-3,9-diazaspiro[5.5]undecane-3-carbonyl)-2,3-dihydro-1H-inden-1-yl]-2-(trifluoromethyl)-benzamide,

[Ind_CC-016] 3-chloro-N-methyl-N-[6-(9-pyridin-4-yl-3,9-diazaspiro[5.5]undecane-3-carbonyl)-2,3-dihydro-1H-inden-1-yl]-thiophene-2-carboxylic acid amide,

[Ind_CC-017] 5-chloro-N-methyl-N-[6-(9-pyridin-4-yl-3,9-diazaspiro[5.5]undecane-3-carbonyl)-2,3-dihydro-1H-inden-1-yl]-thiophene-2-carboxylic acid amide,

[Ind_CC-018] 2,4-dichloro-N-methyl-N-[6-(9-pyridin-4-yl-3,9-diazaspiro[5.5]undecane-3-carbonyl)-2,3-dihydro-1H-inden-1-yl]-benzamide,

[Ind_CC-019] 2-(2-chlorophenyl)-N-methyl-N-[6-(9-pyridin-4-yl-3,9-diazaspiro[5.5]undecane-3-carbonyl)-2,3-dihydro-1H-inden-1-yl]-acetamide,

[Ind_CC-020] (E)-3-(2-chlorophenyl)-N-methyl-N-[6-(9-pyridin-4-yl-3,9-diazaspiro[5.5]undecane-3-carbonyl)-2,3-dihydro-1H-inden-1-yl]-acrylamide,

[Ind_CC-021] 2-(2-chlorophenyl)-N-methyl-2-phenyl-N-[6-(9-pyridin-4-yl-3,9-diazaspiro[5.5]undecane-3-carbonyl)-2,3-dihydro-1H-inden-1-yl]-acetamide,

[Ind_CC-022] 3-(3,4-dichlorophenyl)-1-methyl-1-[6-(9-pyridin-4-yl-3,9-diazaspiro[5.5]undecane-3-carbonyl)-2,3-dihydro-1H-inden-1-yl]-urea,

[Ind_CC-023] 3-[(2-chlorophenyl)-methyl]-1-methyl-146-(9-pyridin-4-yl-3,9-diazaspiro[5.5]undecane-3-carbonyl)-2,3-dihydro-1H-inden-1-yl]-urea,

[Ind_CC-024] 2-chloro-N-methyl-N-[6-(9-pyridin-4-yl-3,9-diazaspiro[5.5]undecane-3-carbonyl)-2,3-dihydro-1H-inden-1-yl]-benzenesulfonic acid amide,

[Ind_CC-025] 4-methoxy-N,2,6-trimethyl-N-[6-(9-pyridin-4-yl-3,9-diazaspiro[5.5]undecane-3-carbonyl)-2,3-dihydro-1H-inden-1-yl]-benzenesulfonic acid amide,

[Ind_CC-026] 4-methoxy-N,2,6-trimethyl-N-[6-(9-pyridin-4-yl-3,9-diazaspiro[5.5]undecane-3-carbonyl)-2,3-dihydro-1H-inden-1-yl]-benzamide,

[Ind_CC-027] N-[6-[9-[4-(trifluoromethyl)-phenyl]-3,9-diazaspiro[5.5]undecane-3-carbonyl]-2,3-dihydro-1H-inden-1-yl]-pyridine-2-carboxylic acid amide,

[Ind_CC-028] 2-(trifluoromethyl)-N-[6-[9-[4-(trifluoromethyl)-phenyl]-3,9-diazaspiro[5.5]undecane-3-carbonyl]-2,3-dihydro-1H-inden-1-yl]-benzamide,

[Ind_CC-029] 3-chloro-N-[6-[9-[4-(trifluoromethyl)-phenyl]-3,9-diazaspiro[5.5]undecane-3-carbonyl]-2,3-dihydro-1H-inden-1-yl]-thiophene-2-carboxylic acid amide,

[Ind_CC-030] 5-chloro-N-[6-[9-[4-(trifluoromethyl)-phenyl]-3,9-diazaspiro[5.5]undecane-3-carbonyl]-2,3-dihydro-1H-inden-1-yl]-thiophene-2-carboxylic acid amide,

[Ind_CC-031] 2,4-dichloro-N-[6-[9-[4-(trifluoromethyl)-phenyl]-3,9-diazaspiro[5.5]undecane-3-carbonyl]-2,3-dihydro-1H-inden-1-yl]-benzamide,

[Ind_CC-032] 2-(2-chlorophenyl)-N-[6-[9-[4-(trifluoromethyl)-phenyl]-3,9-diazaspiro[5.5]undecane-3-carbonyl]-2,3-dihydro-1H-inden-1-yl]-acetamide,

[Ind_CC-033] (E)-3-(2-chlorophenyl)-N-[6-[9-[4-(trifluoromethyl)-phenyl]-3,9-diazaspiro[5.5]undecane-3-carbonyl]-2,3-dihydro-1H-inden-1-yl]-acrylamide,

[Ind_CC-034] 2-chloro-N-[6-[9-[4-(trifluoromethyl)-phenyl]-3,9-diazaspiro[5.5]undecane-3-carbonyl]-2,3-dihydro-1H-inden-1-yl]-benzenesulfonic acid amide,

[Ind_CC-035] 4-methoxy-2,6-dimethyl-N-[6-[9-[4-(trifluoromethyl)-phenyl]-3,9-diazaspiro[5.5]-undecane-3-carbonyl]-2,3-dihydro-1H-inden-1-yl]-benzenesulfonic acid amide,

[Ind_CC-036] 1-(3,4-dichlorophenyl)-3-[6-[9-[4-(trifluoromethyl)-phenyl]-3,9-diazaspiro[5.5]undecane-3-carbonyl]-2,3-dihydro-1H-inden-1-yl]-urea,

[Ind_CC-037] 1-[(2-chlorophenyl)-methyl]-3-[6-[9-[4-(trifluoromethyl)-phenyl]-3,9-diazaspiro[5.5]undecane-3-carbonyl]-2,3-dihydro-1H-inden-1-yl]-urea,

[Ind_CC-038] 2-(2-chlorophenyl)-2-phenyl-N-[6-[9-[4-(trifluoromethyl)-phenyl]-3,9-diazaspiro[5.5]undecane-3-carbonyl]-2,3-dihydro-1H-inden-1-yl]-acetamide,

[Ind_CC-039] 4-methoxy-2,6-dimethyl-N-[6-[9-[4-(trifluoromethyl)-phenyl]-3,9-diazaspiro[5.5]undecane-3-carbonyl]-2,3-dihydro-1H-inden-1-yl]-benzamide,

[Ind_CC-040] N-[6-(2-pyridin-4-yl-2,8-diazaspiro[4.5]decane-8-carbonyl)-2,3-dihydro-1H-inden-1-yl]-pyridine-2-carboxylic acid amide,

[Ind_CC-041] N-[6-(2-pyridin-4-yl-2,8-diazaspiro[4.5]decane-8-carbonyl)-2,3-dihydro-1H-inden-1-yl]-2-(trifluoromethyl)-benzamide,

[Ind_CC-042] 3-chloro-N-[6-(2-pyridin-4-yl-2,8-diazaspiro[4.5]decane-8-carbonyl)-2,3-dihydro-1H-inden-1-yl]-thiophene-2-carboxylic acid amide,

[Ind_CC-043] 5-chloro-N-[6-(2-pyridin-4-yl-2,8-diazaspiro[4.5]decane-8-carbonyl)-2,3-dihydro-1H-inden-1-yl]-thiophene-2-carboxylic acid amide,

[Ind_CC-044] 2,4-dichloro-N-[6-(2-pyridin-4-yl-2,8-diazaspiro[4.5]decane-8-carbonyl)-2,3-dihydro-1H-inden-1-yl]-benzamide,

[Ind_CC-045] 2-(2-chlorophenyl)-N-[6-(2-pyridin-4-yl-2,8-diazaspiro[4.5]decane-8-carbonyl)-2,3-dihydro-1H-inden-1-yl]-acetamide,

[Ind_CC-046] (E)-3-(2-chlorophenyl)-N-[6-(2-pyridin-4-yl-2,8-diazaspiro[4.5]decane-8-carbonyl)-2,3-dihydro-1H-inden-1-yl]-acrylamide,

[Ind_CC-047] 1-(3,4-dichlorophenyl)-346-(2-pyridin-4-yl-2,8-diazaspiro[4.5]decane-8-carbonyl)-2,3-dihydro-1H-inden-1-yl]-urea,

[Ind_CC-048] 1-[(2-chlorophenyl)-methyl]-3-[6-(2-pyridin-4-yl-2,8-diazaspiro[4.5]decane-8-carbonyl)-2,3-dihydro-1H-inden-1-yl]-urea,

[Ind_CC-049] 2-chloro-N-[6-(2-pyridin-4-yl-2,8-diazaspiro[4.5]decane-8-carbonyl)-2,3-dihydro-1H-inden-1-yl]-benzenesulfonic acid amide,

[Ind_CC-050] 4-methoxy-2,6-dimethyl-N-[6-(2-pyridin-4-yl-2,8-diazaspiro[4.5]decane-8-carbonyl)-2,3-dihydro-1H-inden-1-yl]-benzenesulfonic acid amide,

[Ind_CC-051] 2-(2-chlorophenyl)-2-phenyl-N-[6-(2-pyridin-4-yl-2,8-diazaspiro[4.5]decane-8-carbonyl)-2,3-dihydro-1H-inden-1-yl]-acetamide,

[Ind_CC-052] N-[3,3-dimethyl-6-(9-pyridin-4-yl-3,9-diazaspiro[5.5]undecane-3-carbonyl)-1,2-dihydro-inden-1-yl]-pyridine-2-carboxylic acid amide,

[Ind_CC-053] 2-(2-chlorophenyl)-N-[3,3-dimethyl-6-(9-pyridin-4-yl-3,9-diazaspiro[5.5]undecane-3-carbonyl)-1,2-dihydro-inden-1-yl]-acetamide,

[Ind_CC-054] 5-chloro-N-[3,3-dimethyl-6-(9-pyridin-4-yl-3,9-diazaspiro[5.5]undecane-3-carbonyl)-1,2-dihydro-inden-1-yl]-thiophene-2-carboxylic acid amide,

[Ind_CC-055] 3-chloro-N-[3,3-dimethyl-6-(9-pyridin-4-yl-3,9-diazaspiro[5.5]undecane-3-carbonyl)-1,2-dihydro-inden-1-yl]-thiophene-2-carboxylic acid amide,

[Ind_CC-056] 2-(2-chlorophenyl)-N-[3,3-dimethyl-6-(9-pyridin-4-yl-3,9-diazaspiro[5.5]-undecane-3-carbonyl)-1,2-dihydro-inden-1-yl]-2-phenyl-acetamide,

[Ind_CC-057] 1-(3,4-dichlorophenyl)-343,3-dimethyl-6-(9-pyridin-4-yl-3,9-diazaspiro[5.5]undecane-3-carbonyl)-1,2-dihydro-inden-1-yl]-urea,

[Ind_CC-058] N-[3,3-dimethyl-6-(9-pyridin-4-yl-3,9-diazaspiro[5.5]undecane-3-carbonyl)-1,2-dihydro-inden-1-yl]-2-(trifluoromethyl)-benzamide,

[Ind_CC-059] 2,4-dichloro-N-[3,3-dimethyl-6-(9-pyridin-4-yl-3,9-diazaspiro[5.5]undecane-3-carbonyl)-1,2-dihydro-inden-1-yl]-benzamide,

[Ind_CC-060] (E)-3-(2-chlorophenyl)-N-[3,3-dimethyl-6-(9-pyridin-4-yl-3,9-diazaspiro[5.5]undecane-3-carbonyl)-1,2-dihydro-inden-1-yl]-acrylamide,

[Ind_CC-061] 1-[(2-chlorophenyl)-methyl]-3-[3,3-dimethyl-6-(9-pyridin-4-yl-3,9-diazaspiro[5.5]undecane-3-carbonyl)-1,2-dihydro-inden-1-yl]-urea,

[Ind_CC-062] 2-chloro-N-[3,3-dimethyl-6-(9-pyridin-4-yl-3,9-diazaspiro[5.5]undecane-3-carbonyl)-1,2-dihydro-inden-1-yl]-benzenesulfonic acid amide,

[Ind_CC-063] N-[3,3-dimethyl-6-(9-pyridin-4-yl-3,9-diazaspiro[5.5]undecane-3-carbonyl)-1,2-dihydro-inden-1-yl]-4-methoxy-2,6-dimethyl-benzenesulfonic acid amide,

[Ind_CC-064] N-[2,2-dimethyl-6-(9-pyridin-4-yl-3,9-diazaspiro[5.5]undecane-3-carbonyl)-1,3-dihydro-inden-1-yl]-2-(trifluoromethyl)-benzamide,

[Ind_CC-065] 3-chloro-N-[2,2-dimethyl-6-(9-pyridin-4-yl-3,9-diazaspiro[5.5]undecane-3-carbonyl)-1,3-dihydro-inden-1-yl]-thiophene-2-carboxylic acid amide,

[Ind_CC-066] 5-chloro-N-[2,2-dimethyl-6-(9-pyridin-4-yl-3,9-diazaspiro[5.5]undecane-3-carbonyl)-1,3-dihydro-inden-1-yl]-thiophene-2-carboxylic acid amide,

[Ind_CC-067] 2,4-dichloro-N-[2,2-dimethyl-6-(9-pyridin-4-yl-3,9-diazaspiro[5.5]undecane-3-carbonyl)-1,3-dihydro-inden-1-yl]-benzamide,

[Ind_CC-068] N-[2,2-dimethyl-6-(9-pyridin-4-yl-3,9-diazaspiro[5.5]undecane-3-carbonyl)-1,3-dihydro-inden-1-yl]-4-methoxy-2,6-dimethyl-benzamide,

[Ind_CC-069] 2-(2-chlorophenyl)-N-[2,2-dimethyl-6-(9-pyridin-4-yl-3,9-diazaspiro[5.5]undecane-3-carbonyl)-1,3-dihydro-inden-1-yl]-acetamide,

[Ind_CC-070] (E)-3-(2-chlorophenyl)-N-[2,2-dimethyl-6-(9-pyridin-4-yl-3,9-diazaspiro[5.5]undecane-3-carbonyl)-1,3-dihydro-inden-1-yl]-acrylamide,

[Ind_CC-071] 1-(3,4-dichlorophenyl)-342,2-dimethyl-6-(9-pyridin-4-yl-3,9-diazaspiro[5.5]undecane-3-carbonyl)-1,3-dihydro-inden-1-yl]-urea,

[Ind_CC-072] 2-chloro-N-[2,2-dimethyl-6-(9-pyridin-4-yl-3,9-diazaspiro[5.5]undecane-3-carbonyl)-1,3-dihydro-inden-1-yl]-benzenesulfonic acid amide,

[Ind_CC-073] 1-[(2-chlorophenyl)-methyl]-3-[2,2-dimethyl-6-(9-pyridin-4-yl-3,9-diazaspiro[5.5]undecane-3-carbonyl)-1,3-dihydro-inden-1-yl]-urea,

[Ind_CC-074] N-[2,2-dimethyl-6-(9-pyridin-4-yl-3,9-diazaspiro[5.5]undecane-3-carbonyl)-1,3-dihydro-inden-1-yl]-pyridine-2-carboxylic acid amide,

[Ind_CC-075] 2-(2-chlorophenyl)-N-[2,2-dimethyl-6-(9-pyridin-4-yl-3,9-diazaspiro[5.5]-undecane-3-carbonyl)-1,3-dihydro-inden-1-yl]-2-phenyl-acetamide,

[Ind_CC-076] N-[2,2-dimethyl-6-(9-pyridin-4-yl-3,9-diazaspiro[5.5]undecane-3-carbonyl)-1,3-dihydro-inden-1-yl]-4-methoxy-2,6-dimethyl-benzenesulfonic acid amide,

[Ind_CC-077] 2-(2-chlorophenyl)-N-[6-(8-pyridin-4-yl-2,8-diazaspiro[4.5]decane-2-carbonyl)-2,3-dihydro-1H-inden-1-yl]-acetamide,

[Ind_CC-078] 2,4-dichloro-N-[6-(8-pyridin-4-yl-3,8-diazaspiro[4.5]decane-3-carbonyl)-2,3-dihydro-1H-inden-1-yl]-benzamide,

[Ind_CC-079] 5-chloro-N-[6-(8-pyridin-4-yl-3,8-diazaspiro[4.5]decane-3-carbonyl)-2,3-dihydro-1H-inden-1-yl]-thiophene-2-carboxylic acid amide,

[Ind_CC-080] 3-chloro-N-[6-(8-pyridin-4-yl-3,8-diazaspiro[4.5]decane-3-carbonyl)-2,3-dihydro-1H-inden-1-yl]-thiophene-2-carboxylic acid amide,

[Ind_CC-081] N-[6-(8-pyridin-4-yl-3,8-diazaspiro[4.5]decane-3-carbonyl)-2,3-dihydro-1H-inden-1-yl]-2-(trifluoromethyl)-benzamide,

[Ind_CC-082] 2-(2-chlorophenyl)-2-phenyl-N-[6-(8-pyridin-4-yl-3,8-diazaspiro[4.5]decane-3-carbonyl)-2,3-dihydro-1H-inden-1-yl]-acetamide,

[Ind_CC-083] (E)-3-(2-chlorophenyl)-N-[6-(8-pyridin-4-yl-2,8-diazaspiro[4.5]decane-2-carbonyl)-2,3-dihydro-1H-inden-1-yl]-acrylamide,

[Ind_CC-084] N-[6-(8-pyridin-4-yl-3,8-diazaspiro[4.5]decane-3-carbonyl)-2,3-dihydro-1H-inden-1-yl]-pyridine-2-carboxylic acid amide,

[Ind_CC-085] 1-(3,4-dichlorophenyl)-346-(8-pyridin-4-yl-2,8-diazaspiro[4.5]decane-2-carbonyl)-2,3-dihydro-1H-inden-1-yl]-urea,

[Ind_CC-086] 1-[(2-chlorophenyl)-methyl]-3-[6-(8-pyridin-4-yl-2,8-diazaspiro[4.5]decane-2-carbonyl)-2,3-dihydro-1H-inden-1-yl]-urea,

[Ind_CC-087] 4-methoxy-2,6-dimethyl-N-[6-(8-pyridin-4-yl-2,8-diazaspiro[4.5]decane-2-carbonyl)-2,3-dihydro-1H-inden-1-yl]-benzenesulfonic acid amide,

[Ind_CC-088] 4-methoxy-2,6-dimethyl-N-[6-(8-pyridin-4-yl-2,8-diazaspiro[4.5]decane-2-carbonyl)-2,3-dihydro-1H-inden-1-yl]-benzamide,

[Ind_CC-089] 2-chloro-N-[6-(8-pyridin-4-yl-3,8-diazaspiro[4.5]decane-3-carbonyl)-2,3-dihydro-1H-inden-1-yl]-benzenesulfonic acid amide,

[Ind_CC-090] 4-methoxy-2,6-dimethyl-N-[6-(9-pyridin-3-yl-3,9-diazaspiro[5.5]undecane-3-carbonyl)-2,3-dihydro-1H-inden-1-yl]-benzamide,

[Ind_CC-091] N-[6-[9-(4-fluorophenyl)-3,9-diazaspiro[5.5]undecane-3-carbonyl]-2,3-dihydro-1H-inden-1-yl]-4-methoxy-2,6-dimethyl-benzamide,

[Ind_CC-092] 4-methoxy-2,6-dimethyl-N-[6-[9-(pyridin-4-yl-methyl)-3,9-diazaspiro[5.5]undecane-3-carbonyl]-2,3-dihydro-1H-inden-1-yl]-benzamide,

[Ind_CC-093] N-[6-[9-dimethylamino-9-(4-fluorophenyl)-3-azaspiro[5.5]undecane-3-carbonyl]-2,3-dihydro-1H-inden-1-yl]-4-methoxy-2,6-dimethyl-benzamide,

[Ind_CC-094] 4-methoxy-2,6-dimethyl-N-[6-(2-pyridin-4-yl-2,8-diazaspiro[4.5]decane-8-carbonyl)-2,3-dihydro-1H-inden-1-yl]-benzamide,

[Ind_CC-095] 2-chloro-N-[6-(9-pyridin-4-yl-3,9-diazaspiro[5.5]undecane-3-carbonyl)-2,3-dihydro-1H-inden-1-yl]-benzamide,

[Ind_CC-096] 2-chloro-N-[6-(9-pyridin-3-yl-3,9-diazaspiro[5.5]undecane-3-carbonyl)-2,3-dihydro-1H-inden-1-yl]-benzamide,

[Ind_CC-097] 2-chloro-N-[6-[9-(4-fluorophenyl)-3,9-diazaspiro[5.5]undecane-3-carbonyl]-2,3-dihydro-1H-inden-1-yl]-benzamide,

[Ind_CC-098] 2-chloro-N-[6-[9-(pyridin-4-yl-methyl)-3,9-diazaspiro[5.5]undecane-3-carbonyl]-2,3-dihydro-1H-inden-1-yl]-benzamide,

[Ind_CC-099] 2-chloro-N-[6-[9-dimethylamino-9-(4-fluorophenyl)-3-azaspiro[5.5]undecane-3-carbonyl]-2,3-dihydro-1H-inden-1-yl]-benzamide,

[Ind_CC-100] 2-chloro-N-[6-(8-pyridin-4-yl-2,8-diazaspiro[4.5]decane-2-carbonyl)-2,3-dihydro-1H-inden-1-yl]-benzamide,

[Ind_CC-101] 2-chloro-N-[6-(2-pyridin-4-yl-2,8-diazaspiro[4.5]decane-8-carbonyl)-2,3-dihydro-1H-inden-1-yl]-benzamide,

[Ind_CC-102] 3-chloro-N-[6-(9-pyridin-3-yl-3,9-diazaspiro[5.5]undecane-3-carbonyl)-2,3-dihydro-1H-inden-1-yl]-thiophene-2-carboxylic acid amide,

[Ind_CC-103] 3-chloro-N-[6-[9-(4-fluorophenyl)-3,9-diazaspiro[5.5]undecane-3-carbonyl]-2,3-dihydro-1H-inden-1-yl]-thiophene-2-carboxylic acid amide,

[Ind_CC-104] 3-chloro-N-[6-[9-(pyridin-4-yl-methyl)-3,9-diazaspiro[5.5]undecane-3-carbonyl]-2,3-dihydro-1H-inden-1-yl]-thiophene-2-carboxylic acid amide,

[Ind_CC-105] 3-chloro-N-[6-[9-dimethylamino-9-(4-fluorophenyl)-3-azaspiro[5.5]undecane-3-carbonyl]-2,3-dihydro-1H-inden-1-yl]-thiophene-2-carboxylic acid amide,

[Ind_CC-106] 2-chloro-N-methyl-N-[6-(9-pyridin-4-yl-3,9-diazaspiro[5.5]undecane-3-carbonyl)-2,3-dihydro-1H-inden-1-yl]-benzamide,

[Ind_CC-107] 2-chloro-N-methyl-N-[6-(9-pyridin-3-yl-3,9-diazaspiro[5.5]undecane-3-carbonyl)-2,3-dihydro-1H-inden-1-yl]-benzamide,

[Ind_CC-108] 2-chloro-N-[6-[9-(4-fluorophenyl)-3,9-diazaspiro[5.5]undecane-3-carbonyl]-2,3-dihydro-1H-inden-1-yl]-N-methyl-benzamide,

[Ind_CC-109] 2-chloro-N-methyl-N-[6-[9-(pyridin-4-yl-methyl)-3,9-diazaspiro[5.5]undecane-3-carbonyl]-2,3-dihydro-1H-inden-1-yl]-benzamide,

[Ind_CC-110] 2-chloro-N-[6-[9-dimethylamino-9-(4-fluorophenyl)-3-azaspiro[5.5]undecane-3-carbonyl]-2,3-dihydro-1H-inden-1-yl]-N-methyl-benzamide,

[Ind_CC-111] 2-chloro-N-methyl-N-[6-(8-pyridin-4-yl-2,8-diazaspiro[4.5]decane-2-carbonyl)-2,3-dihydro-1H-inden-1-yl]-benzamide,

[Ind_CC-112] 2-chloro-N-methyl-N-[6-(2-pyridin-4-yl-2,8-diazaspiro[4.5]decane-8-carbonyl)-2,3-dihydro-1H-inden-1-yl]-benzamide,

[Ind_CC-113] 2-chloro-N-cyclopropyl-N-[6-(9-pyridin-4-yl-3,9-diazaspiro[5.5]undecane-3-carbonyl)-2,3-dihydro-1H-inden-1-yl]-benzamide,

[Ind_CC-114] 2-chloro-N-cyclopropyl-N-[6-(9-pyridin-3-yl-3,9-diazaspiro[5.5]undecane-3-carbonyl)-2,3-dihydro-1H-inden-1-yl]-benzamide,

[Ind_CC-115] 2-chloro-N-cyclopropyl-N-[6-[9-(4-fluorophenyl)-3,9-diazaspiro[5.5]undecane-3-carbonyl]-2,3-dihydro-1H-inden-1-yl]-benzamide,

[Ind_CC-116] 2-chloro-N-cyclopropyl-N-[6-[9-(pyridin-4-yl-methyl)-3,9-diazaspiro[5.5]undecane-3-carbonyl]-2,3-dihydro-1H-inden-1-yl]-benzamide,

[Ind_CC-117] 2-chloro-N-cyclopropyl-N-[6-[9-dimethylamino-9-(4-fluorophenyl)-3-azaspiro[5.5]undecane-3-carbonyl]-2,3-dihydro-1H-inden-1-yl]-benzamide,

[Ind_CC-118] 2-chloro-N-cyclopropyl-N-[6-(8-pyridin-4-yl-2,8-diazaspiro[4.5]decane-2-carbonyl)-2,3-dihydro-1H-inden-1-yl]-benzamide,

[Ind_CC-119] 2-chloro-N-cyclopropyl-N-[6-(2-pyridin-4-yl-2,8-diazaspiro[4.5]decane-8-carbonyl)-2,3-dihydro-1H-inden-1-yl]-benzamide,

[Ind_CC-120] 2-chloro-N-[3-(9-pyridin-4-yl-3,9-diazaspiro[5.5]undecane-3-carbonyl)-6,7,8,9-tetrahydro-5H-benzocyclohepten-5-yl]-benzamide,

[Ind_CC-121] 2-chloro-N-[3-(9-pyridin-3-yl-3,9-diazaspiro[5.5]undecane-3-carbonyl)-6,7,8,9-tetrahydro-5H-benzocyclohepten-5-yl]-benzamide,

[Ind_CC-122] 2-chloro-N-[3-[9-(4-fluorophenyl)-3,9-diazaspiro[5.5]undecane-3-carbonyl]-6,7,8,9-tetrahydro-5H-benzocyclohepten-5-yl]-benzamide,

[Ind_CC-123] 2-chloro-N-[3-[9-(pyridin-4-yl-methyl)-3,9-diazaspiro[5.5]undecane-3-carbonyl]-6,7,8,9-tetrahydro-5H-benzocyclohepten-5-yl]-benzamide

[Ind_CC-124] 2-chloro-N-[3-[9-dimethylamino-9-(4-fluorophenyl)-3-azaspiro[5.5]undecane-3-carbonyl]-6,7,8,9-tetrahydro-5H-benzocyclohepten-5-yl]-benzamide,

[Ind_CC-125] 2-chloro-N-[3-(8-pyridin-4-yl-2,8-diazaspiro[4.5]decane-2-carbonyl)-6,7,8,9-tetrahydro-5H-benzocyclohepten-5-yl]-benzamide,

[Ind_CC-126] 2-chloro-N-[3-(2-pyridin-4-yl-2,8-diazaspiro[4.5]decane-8-carbonyl)-6,7,8,9-tetrahydro-5H-benzocyclohepten-5-yl]-benzamide,

[Ind_CC-127] 2-chloro-N-[[6-(9-pyridin-4-yl-3,9-diazaspiro[5.5]undecane-3-carbonyl)-2,3-dihydro-1H-inden-1-yl]-methyl]-benzamide,

[Ind_CC-128] 2-chloro-N-[[6-(9-pyridin-3-yl-3,9-diazaspiro[5.5]undecane-3-carbonyl)-2,3-dihydro-1H-inden-1-yl]-methyl]-benzamide,

[Ind_CC-129] 2-chloro-N-[[6-[9-(4-fluorophenyl)-3,9-diazaspiro[5.5]undecane-3-carbonyl]-2,3-dihydro-1H-inden-1-yl]-methyl]-benzamide,

[Ind_CC-130] 2-chloro-N-[[6-[9-(pyridin-4-yl-methyl)-3,9-diazaspiro[5.5]undecane-3-carbonyl]-2,3-dihydro-1H-inden-1-yl]-methyl]-benzamide,

[Ind_CC-131] 2-chloro-N-[[6-[9-dimethylamino-9-(4-fluorophenyl)-3-azaspiro[5.5]-undecane-3-carbonyl]-2,3-dihydro-1H-inden-1-yl]-methyl]-benzamide,

[Ind_CC-132] 2-chloro-N-[[6-(8-pyridin-4-yl-2,8-diazaspiro[4.5]decane-2-carbonyl)-2,3-dihydro-1H-inden-1-yl]-methyl]-benzamide,

[Ind_CC-133] 2-chloro-N-[[6-(2-pyridin-4-yl-2,8-diazaspiro[4.5]decane-8-carbonyl)-2,3-dihydro-1H-inden-1-yl]-methyl]-benzamide,

[Ind_CC-134] 2-chloro-N-[6-[2-oxo-2-(9-pyridin-4-yl-3,9-diazaspiro[5.5]undecane-3-yl)-ethyl]-2,3-dihydro-1H-inden-1-yl]-benzamide,

[Ind_CC-135] 2-chloro-N-[6-[2-oxo-2-(9-pyridin-3-yl-3,9-diazaspiro[5.5]undecane-3-yl)-ethyl]-2,3-dihydro-1H-inden-1-yl]-benzamide,

[Ind_CC-136] 2-chloro-N-[6-[2-[9-(4-fluorophenyl)-3,9-diazaspiro[5.5]undecane-3-yl]-2-oxo-ethyl]-2,3-dihydro-1H-inden-1-yl]-benzamide,

[Ind_CC-137] 2-chloro-N-[6-[2-oxo-2-[9-(pyridin-4-yl-methyl)-3,9-diazaspiro[5.5]undecane-3-yl]-ethyl]-2,3-dihydro-1H-inden-1-yl]-benzamide,

[Ind_CC-138] 2-chloro-N-[6-[2-[9-dimethylamino-9-(4-fluorophenyl)-3-azaspiro[5.5]-undecane-3-yl]-2-oxo-ethyl]-2,3-dihydro-1H-inden-1-yl]-benzamide,

[Ind_CC-139] 2-chloro-N-[6-[2-oxo-2-(8-pyridin-4-yl-2,8-diazaspiro[4.5]decane-2-yl)-ethyl]-2,3-dihydro-1H-inden-1-yl]-benzamide,

[Ind_CC-140] 2-chloro-N-[6-[2-oxo-2-(2-pyridin-4-yl-2,8-diazaspiro[4.5]decane-8-yl)-ethyl]-2,3-dihydro-1H-inden-1-yl]-benzamide,

[Ind_CC-141] 8-chloro-2-[6-(9-pyridin-4-yl-3,9-diazaspiro[5.5]undecane-3-carbonyl)-2,3-dihydro-1H-inden-1-yl]-3,4-dihydro-2H-pyrrolo[1,2-a]pyrazin-1-one,

[Ind_CC-142] 8-chloro-2-[6-(9-pyridin-3-yl-3,9-diazaspiro[5.5]undecane-3-carbonyl)-2,3-dihydro-1H-inden-1-yl]-3,4-dihydro-2H-pyrrolo[1,2-a]pyrazin-1-one,

[Ind_CC-143] 8-chloro-2-[6-[9-(4-fluorophenyl)-3,9-diazaspiro[5.5]undecane-3-carbonyl]-2,3-dihydro-1H-inden-1-yl]-3,4-dihydro-2H-pyrrolo[1,2-a]pyrazin-1-one,

[Ind_CC-144] 8-chloro-2-[6-[9-(pyridin-4-yl-methyl)-3,9-diazaspiro[5.5]undecane-3-carbonyl]-2,3-dihydro-1H-inden-1-yl]-3,4-dihydro-2H-pyrrolo[1,2-a]pyrazin-1-one,

[Ind_CC-145] 8-chloro-2-[6-[9-dimethylamino-9-(4-fluorophenyl)-3-azaspiro[5.5]undecane-3-carbonyl]-2,3-dihydro-1H-inden-1-yl]-3,4-dihydro-2H-pyrrolo[1,2-a]pyrazin-1-one,

[Ind_CC-146] 8-chloro-2-[6-(8-pyridin-4-yl-2,8-diazaspiro[4.5]decane-2-carbonyl)-2,3-dihydro-1H-inden-1-yl]-3,4-dihydro-2H-pyrrolo[1,2-a]pyrazin-1-one,

[Ind_CC-147] 8-chloro-2-[6-(2-pyridin-4-yl-2,8-diazaspiro[4.5]decane-8-carbonyl)-2,3-dihydro-1H-inden-1-yl]-3,4-dihydro-2H-pyrrolo[1,2-a]pyrazin-1-one,

[Ind_CC-148] 8-chloro-4-methyl-2-[6-(9-pyridin-4-yl-3,9-diazaspiro[5.5]undecane-3-carbonyl)-2,3-dihydro-1H-inden-1-yl]-3,4-dihydro-2H-pyrrolo[3,4-b]indol-1-one,

[Ind_CC-149] 8-chloro-4-methyl-2-[6-(9-pyridin-3-yl-3,9-diazaspiro[5.5]undecane-3-carbonyl)-2,3-dihydro-1H-inden-1-yl]-3,4-dihydro-2H-pyrrolo[3,4-b]indol-1-one,

[Ind_CC-150] 8-chloro-2-[6-[9-(4-fluorophenyl)-3,9-diazaspiro[5.5]undecane-3-carbonyl]-2,3-dihydro-1H-inden-1-yl]-4-methyl-3,4-dihydro-2H-pyrrolo[3,4-b]indol-1-one,

[Ind_CC-151] 8-chloro-4-methyl-2-[6-[9-(pyridin-4-yl-methyl)-3,9-diazaspiro[5.5]undecane-3-carbonyl]-2,3-dihydro-1H-inden-1-yl]-3,4-dihydro-2H-pyrrolo[3,4-b]indol-1-one,

[Ind_CC-152] 8-chloro-2-[6-[9-dimethylamino-9-(4-fluorophenyl)-3-azaspiro[5.5]undecane-3-carbonyl]-2,3-dihydro-1H-inden-1-yl]-4-methyl-3,4-dihydro-2H-pyrrolo[3,4-b]indol-1-one,

[Ind_CC-153] 8-chloro-4-methyl-2-[6-(8-pyridin-4-yl-2,8-diazaspiro[4.5]decane-2-carbonyl)-2,3-dihydro-1H-inden-1-yl]-3,4-dihydro-2H-pyrrolo[3,4-b]indol-1-one and

[Ind_CC-154] 8-chloro-4-methyl-2-[6-(2-pyridin-4-yl-2,8-diazaspiro[4.5]decane-8-carbonyl)-2,3-dihydro-1H-inden-1-yl]-3,4-dihydro-2H-pyrrolo[3,4-b]indol-1-one

[IND_CC-200] 2,5-Dichloro-N-methyl-N-[6-(9-pyridin-4-yl-3,9-diazaspiro[5.5]undecane-3-carbonyl)-2,3-dihydro-1H-inden-1-yl]-benzamide

[IND_CC-201] 2-Chloro-4-methoxy-N-methyl-N-[6-(9-pyridin-4-yl-3,9-diazaspiro[5.5]undecane-3-carbonyl)-2,3-dihydro-1H-inden-1-yl]-benzamide

[IND_CC-202] 2-Chloro-N-methyl-N-[6-(9-pyridin-4-yl-3,9-diazaspiro[5.5]undecane-3-carbonyl)-2,3-dihydro-1H-inden-1-yl]-5-(trifluoromethyl)-benzamide

[IND_CC-203] 2-Chloro-5-fluoro-N-methyl-N-[6-(9-pyridin-4-yl-3,9-diazaspiro[5.5]undecane-3-carbonyl)-2,3-dihydro-1H-inden-1-yl]-benzamide

[IND_CC-204] 2-Chloro-N-[6-(9-pyridin-4-yl-3,9-diazaspiro[5.5]undecane-3-carbonyl)-2,3-dihydro-1H-inden-1-yl]-6-(trifluoromethyl)-benzamide

[IND_CC-205] 2-Chloro-N-[6-(2-pyridin-4-yl-2,8-diazaspiro[4.5]decane-8-carbonyl)-2,3-dihydro-1H-inden-1-yl]-6-(trifluoromethyl)-benzamide

[IND_CC-206] 2-Chloro-N-[2,2-dimethyl-6-(9-pyridin-4-yl-3,9-diazaspiro[5.5]undecane-3-carbonyl)-1,3-dihydro-inden-1-yl]-6-(trifluoromethyl)-benzamide

[IND_CC-207] 2,5-Dichloro-N-[6-(9-pyridin-4-yl-3,9-diazaspiro[5.5]undecane-3-carbonyl)-2,3-dihydro-1H-inden-1-yl]-benzamide

[IND_CC-208] 2,5-Dichloro-N-[6-(2-pyridin-4-yl-2,8-diazaspiro[4.5]decane-8-carbonyl)-2,3-dihydro-1H-inden-1-yl]-benzamide

[IND_CC-209] 2,5-Dichloro-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-210] 2,5-Dichloro-N-[2,2-dimethyl-6-(9-pyridin-4-yl-3,9-diazaspiro[5.5]undecane-3-carbonyl)-1,3-dihydro-inden-1-yl]-benzamide

[IND_CC-211] 2-Chloro-4-methoxy-N-[6-(9-pyridin-4-yl-3,9-diazaspiro[5.5]undecane-3-carbonyl)-2,3-dihydro-1H-inden-1-yl]-benzamide

[IND_CC-212] 2-Chloro-4-methoxy-N-[6-(2-pyridin-4-yl-2,8-diazaspiro[4.5]decane-8-carbonyl)-2,3-dihydro-1H-inden-1-yl]-benzamide

[IND_CC-213] 2-Chloro-4-methoxy-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-214] 2-Chloro-6-fluoro-3-methyl-N-[6-(9-pyridin-4-yl-3,9-diazaspiro[5.5]undecane-3-carbonyl)-2,3-dihydro-1H-inden-1-yl]-benzamide

[IND_CC-215] 2-Chloro-6-fluoro-3-methyl-N-[6-(2-pyridin-4-yl-2,8-diazaspiro[4.5]decane-8-carbonyl)-2,3-dihydro-1H-inden-1-yl]-benzamide

[IND_CC-216] 2-Chloro-N-[2,2-dimethyl-6-(9-pyridin-4-yl-3,9-diazaspiro[5.5]undecane-3-carbonyl)-1,3-dihydro-inden-1-yl]-6-fluoro-3-methyl-benzamide

[IND_CC-217] 2-Chloro-N-[6-(9-pyridin-4-yl-3,9-diazaspiro[5.5]undecane-3-carbonyl)-2,3-dihydro-1H-inden-1-yl]-5-(trifluoromethyl)-benzamide

[IND_CC-218] 2-Chloro-N-[6-(2-pyridin-4-yl-2,8-diazaspiro[4.5]decane-8-carbonyl)-2,3-dihydro-1H-inden-1-yl]-5-(trifluoromethyl)-benzamide

[IND_CC-219] 2-Chloro-N-[2,2-dimethyl-6-(9-pyridin-4-yl-3,9-diazaspiro[5.5]undecane-3-carbonyl)-1,3-dihydro-inden-1-yl]-5-(trifluoromethyl)-benzamide

[IND_CC-220] 2-Chloro-5-fluoro-N-[6-(9-pyridin-4-yl-3,9-diazaspiro[5.5]undecane-3-carbonyl)-2,3-dihydro-1H-inden-1-yl]-benzamide

[IND_CC-221] 2-Chloro-5-fluoro-N-[6-(2-pyridin-4-yl-2,8-diazaspiro[4.5]decane-8-carbonyl)-2,3-dihydro-1H-inden-1-yl]-benzamide

[IND_CC-222] 2-Chloro-5-fluoro-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-223] 2-Chloro-N-[2,2-dimethyl-6-(9-pyridin-4-yl-3,9-diazaspiro[5.5]undecane-3-carbonyl)-1,3-dihydro-inden-1-yl]-5-fluoro-benzamide

[IND_CC-224] 2-Chloro-4,5-difluoro-N-methyl-N-[6-(9-pyridin-4-yl-3,9-diazaspiro[5.5]undecane-3-carbonyl)-2,3-dihydro-1H-inden-1-yl]-benzamide

[IND_CC-225] 2-Chloro-N-methyl-N-[6-(9-pyridin-4-yl-3,9-diazaspiro[5.5]undecane-3-carbonyl)-2,3-dihydro-1H-inden-1-yl]-3-(trifluoromethyl)-benzamide

[IND_CC-226] N-Methyl-N-[6-(9-pyridin-4-yl-3,9-diazaspiro[5.5]undecane-3-carbonyl)-2,3-dihydro-1H-inden-1-yl]-1-[2-(trifluoromethyl)-phenyl]-methanesulfonic acid amide

[IND_CC-227] 2-Chloro-N,6-dimethyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-228] 2-Chloro-4,5-difluoro-N-[6-(9-pyridin-4-yl-3,9-diazaspiro[5.5]undecane-3-carbonyl)-2,3-dihydro-1H-inden-1-yl]-benzamide

[IND_CC-229] 2-Chloro-4,5-difluoro-N-[6-(2-pyridin-4-yl-2,8-diazaspiro[4.5]decane-8-carbonyl)-2,3-dihydro-1H-inden-1-yl]-benzamide

[IND_CC-230] 2-Chloro-4,5-difluoro-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-231] 2-Chloro-N-[2,2-dimethyl-6-(9-pyridin-4-yl-3,9-diazaspiro[5.5]undecane-3-carbonyl)-1,3-dihydro-inden-1-yl]-4,5-difluoro-benzamide

[IND_CC-232] 2-Chloro-N-[6-(9-pyridin-4-yl-3,9-diazaspiro[5.5]undecane-3-carbonyl)-2,3-dihydro-1H-inden-1-yl]-3-(trifluoromethyl)-benzamide

[IND_CC-233] 2-Chloro-N-[6-(2-pyridin-4-yl-2,8-diazaspiro[4.5]decane-8-carbonyl)-2,3-dihydro-1H-inden-1-yl]-3-(trifluoromethyl)-benzamide

[IND_CC-234] 2-Chloro-N-[2,2-dimethyl-6-(9-pyridin-4-yl-3,9-diazaspiro[5.5]undecane-3-carbonyl)-1,3-dihydro-inden-1-yl]-3-(trifluoromethyl)-benzamide

[IND_CC-235] 2-Cyano-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-236] N-[6-(9-Pyridin-4-yl-3,9-diazaspiro[5.5]undecane-3-carbonyl)-2,3-dihydro-1H-inden-1-yl]-1-[2-(trifluoromethyl)-phenyl]-methanesulfonic acid amide

[IND_CC-237] N-[6-(2-Pyridin-4-yl-2,8-diazaspiro[4.5]decane-8-carbonyl)-2,3-dihydro-1H-inden-1-yl]-1-[2-(trifluoromethyl)-phenyl]-methanesulfonic acid amide

[IND_CC-238] N-[2,2-Dimethyl-6-(9-pyridin-4-yl-3,9-diazaspiro[5.5]undecane-3-carbonyl)-1,3-dihydro-inden-1-yl]-1-[2-(trifluoromethyl)-phenyl]-methanesulfonic acid amide

[IND_CC-239] 2-Chloro-6-methyl-N-[6-[9-[4-(trifluoromethyl)-phenyl]-3,9-diazaspiro[5.5]undecane-3-carbonyl]-2,3-dihydro-1H-inden-1-yl]-benzenesulfonic acid amide

[IND_CC-240] 2-Chloro-N-[2,2-dimethyl-6-(9-pyridin-4-yl-3,9-diazaspiro[5.5]undecane-3-carbonyl)-1,3-dihydro-inden-1-yl]-6-methyl-benzenesulfonic acid amide

[IND_CC-241] 2-(2-Chlorophenyl)-N-[6-(9-pyridin-4-yl-3,9-diazaspiro[5.5]undecane-3-carbonyl)-2,3-dihydro-1H-inden-1-yl]-ethanesulfonic acid amide

[IND_CC-242] 2-(2-Chlorophenyl)-N-[2,2-dimethyl-6-(9-pyridin-4-yl-3,9-diazaspiro[5.5]-undecane-3-carbonyl)-1,3-dihydro-inden-1-yl]-ethanesulfonic acid amide

[IND_CC-243] 2-Chloro-N-[3,3-dimethyl-6-(3-pyridin-4-yl-3,9-diazaspiro[5.5]undecane-9-carbonyl)-1,2-dihydro-inden-1-yl]-6-(trifluoromethyl)-benzamide

[IND_CC-244] 2,5-Dichloro-N-[3,3-dimethyl-6-(3-pyridin-4-yl-3,9-diazaspiro[5.5]undecane-9-carbonyl)-1,2-dihydro-inden-1-yl]-benzamide

[IND_CC-245] 2,5-Dichloro-N-[6-(8-pyridin-4-yl-2,8-diazaspiro[4.5]decane-2-carbonyl)-2,3-dihydro-1H-inden-1-yl]-benzamide

[IND_CC-246] 2-Chloro-N-[3,3-dimethyl-6-(3-pyridin-4-yl-3,9-diazaspiro[5.5]undecane-9-carbonyl)-1,2-dihydro-inden-1-yl]-4-methoxy-benzamide

[IND_CC-247] 2-Chloro-4-methoxy-N-[6-(8-pyridin-4-yl-2,8-diazaspiro[4.5]decane-2-carbonyl)-2,3-dihydro-1H-inden-1-yl]-benzamide

[IND_CC-248] 2-Chloro-N-[3,3-dimethyl-6-(3-pyridin-4-yl-3,9-diazaspiro[5.5]undecane-9-carbonyl)-1,2-dihydro-inden-1-yl]-6-fluoro-3-methyl-benzamide

[IND_CC-249] 2-Chloro-6-fluoro-3-methyl-N-[6-(8-pyridin-4-yl-2,8-diazaspiro[4.5]decane-2-carbonyl)-2,3-dihydro-1H-inden-1-yl]-benzamide

[IND_CC-250] 2-Chloro-N-[3,3-dimethyl-6-(3-pyridin-4-yl-3,9-diazaspiro[5.5]undecane-9-carbonyl)-1,2-dihydro-inden-1-yl]-5-(trifluoromethyl)-benzamide

[IND_CC-251] 2-Chloro-N-[6-(8-pyridin-4-yl-2,8-diazaspiro[4.5]decane-2-carbonyl)-2,3-dihydro-1H-inden-1-yl]-5-(trifluoromethyl)-benzamide

[IND_CC-252] 2-Chloro-N-[3,3-dimethyl-6-(3-pyridin-4-yl-3,9-diazaspiro[5.5]undecane-9-carbonyl)-1,2-dihydro-inden-1-yl]-5-fluoro-benzamide

[IND_CC-253] 2-Chloro-5-fluoro-N-[6-(8-pyridin-4-yl-2,8-diazaspiro[4.5]decane-2-carbonyl)-2,3-dihydro-1H-inden-1-yl]-benzamide

[IND_CC-254] 2-Chloro-N-[3,3-dimethyl-6-(3-pyridin-4-yl-3,9-diazaspiro[5.5]undecane-9-carbonyl)-1,2-dihydro-inden-1-yl]-3-(trifluoromethyl)-benzamide

[IND_CC-255] 2-Chloro-N-[6-(8-pyridin-4-yl-2,8-diazaspiro[4.5]decane-2-carbonyl)-2,3-dihydro-1H-inden-1-yl]-3-(trifluoromethyl)-benzamide

[IND_CC-256] N-[3,3-Dimethyl-6-(3-pyridin-4-yl-3,9-diazaspiro[5.5]undecane-9-carbonyl)-1,2-dihydro-inden-1-yl]-1-[2-(trifluoromethyl)-phenyl]-methanesulfonic acid amide

[IND_CC-258] N-[6-(8-Pyridin-4-yl-2,8-diazaspiro[4.5]decane-2-carbonyl)-2,3-dihydro-1H-inden-1-yl]-1-[2-(trifluoromethyl)-phenyl]-methanesulfonic acid amide

[IND_CC-259] 2-Chloro-N-[3,3-dimethyl-6-(3-pyridin-4-yl-3,9-diazaspiro[5.5]undecane-9-carbonyl)-1,2-dihydro-inden-1-yl]-6-methyl-benzenesulfonic acid amide

[IND_CC-260] 2-(2-Chlorophenyl)-N-[3,3-dimethyl-6-(3-pyridin-4-yl-3,9-diazaspiro[5.5]-undecane-9-carbonyl)-1,2-dihydro-inden-1-yl]-ethanesulfonic acid amide

[IND_CC-261] 2-Chloro-4-fluoro-N-methyl-N-[6-(9-pyridin-4-yl-3,9-diazaspiro[5.5]undecane-3-carbonyl)-2,3-dihydro-1H-inden-1-yl]-benzamide

[IND_CC-262] 2-Chloro-4-fluoro-N-[6-(9-pyridin-4-yl-3,9-diazaspiro[5.5]undecane-3-carbonyl)-2,3-dihydro-1H-inden-1-yl]-benzamide

[IND_CC-263] 2-Chloro-4-fluoro-N-[6-(2-pyridin-4-yl-2,8-diazaspiro[4.5]decane-8-carbonyl)-2,3-dihydro-1H-inden-1-yl]-benzamide

[IND_CC-264] 2-Chloro-6-fluoro-N-[6-(2-pyridin-4-yl-2,8-diazaspiro[4.5]decane-8-carbonyl)-2,3-dihydro-1H-inden-1-yl]-benzamide

[IND_CC-265] 2,3-Dichloro-N-methyl-N-[6-(9-pyridin-4-yl-3,9-diazaspiro[5.5]undecane-3-carbonyl)-2,3-dihydro-1H-inden-1-yl]-benzamide

[IND_CC-266] 2,3-Dichloro-N-[6-(9-pyridin-4-yl-3,9-diazaspiro[5.5]undecane-3-carbonyl)-2,3-dihydro-1H-inden-1-yl]-benzamide

[IND_CC-267] 2,3-Dichloro-N-[6-(2-pyridin-4-yl-2,8-diazaspiro[4.5]decane-8-carbonyl)-2,3-dihydro-1H-inden-1-yl]-benzamide

[IND_CC-268] 2,6-Dichloro-N-methyl-N-[6-(9-pyridin-4-yl-3,9-diazaspiro[5.5]undecane-3-carbonyl)-2,3-dihydro-1H-inden-1-yl]-benzamide

[IND_CC-269] 2,6-Dichloro-N-[6-(9-pyridin-4-yl-3,9-diazaspiro[5.5]undecane-3-carbonyl)-2,3-dihydro-1H-inden-1-yl]-benzamide

[IND_CC-270] 2,6-Dichloro-N-[6-(2-pyridin-4-yl-2,8-diazaspiro[4.5]decane-8-carbonyl)-2,3-dihydro-1H-inden-1-yl]-benzamide

[IND_CC-271] 2-Chloro-N-[6-(2-pyridin-4-yl-2,8-diazaspiro[4.5]decane-8-carbonyl)-2,3-dihydro-1H-inden-1-yl]-benzamide

[IND_CC-272] 2-Chloro-N-methyl-N-[6-(9-pyridin-4-yl-3,9-diazaspiro[5.5]undecane-3-carbonyl)-2,3-dihydro-1H-inden-1-yl]-benzamide

[IND_CC-273] 2-Chloro-N-[6-(9-pyridin-4-yl-3,9-diazaspiro[5.5]undecane-3-carbonyl)-2,3-dihydro-1H-inden-1-yl]-benzamide

[IND_CC-274] 2-Chloro-4-fluoro-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-275] 2-Chloro-N-[2,2-dimethyl-6-(9-pyridin-4-yl-3,9-diazaspiro[5.5]undecane-3-carbonyl)-1,3-dihydro-inden-1-yl]-4-fluoro-benzamide

[IND_CC-276] 2-Chloro-N-[3,3-dimethyl-6-(3-pyridin-4-yl-3,9-diazaspiro[5.5]undecane-9-carbonyl)-1,2-dihydro-inden-1-yl]-4-fluoro-benzamide

[IND_CC-277] 2-Chloro-4-fluoro-N-[6-(8-pyridin-4-yl-2,8-diazaspiro[4.5]decane-2-carbonyl)-2,3-dihydro-1H-inden-1-yl]-benzamide

[IND_CC-278] 2-Chloro-6-fluoro-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-279] 2-Chloro-N-[3,3-dimethyl-6-(3-pyridin-4-yl-3,9-diazaspiro[5.5]undecane-9-carbonyl)-1,2-dihydro-inden-1-yl]-6-fluoro-benzamide

[IND_CC-280] 2-Chloro-6-fluoro-N-[6-(8-pyridin-4-yl-2,8-diazaspiro[4.5]decane-2-carbonyl)-2,3-dihydro-1H-inden-1-yl]-benzamide

[IND_CC-281] 2,3-Dichloro-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-282] 2,3-Dichloro-N-[2,2-dimethyl-6-(9-pyridin-4-yl-3,9-diazaspiro[5.5]undecane-3-carbonyl)-1,3-dihydro-inden-1-yl]-benzamide

[IND_CC-283] 2,3-Dichloro-N-[3,3-dimethyl-6-(3-pyridin-4-yl-3,9-diazaspiro[5.5]undecane-9-carbonyl)-1,2-dihydro-inden-1-yl]-benzamide

[IND_CC-284] 2,3-Dichloro-N-[6-(8-pyridin-4-yl-2,8-diazaspiro[4.5]decane-2-carbonyl)-2,3-dihydro-1H-inden-1-yl]-benzamide

[IND_CC-286] 2,6-Dichloro-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-287] 2,6-Dichloro-N-[2,2-dimethyl-6-(9-pyridin-4-yl-3,9-diazaspiro[5.5]undecane-3-carbonyl)-1,3-dihydro-inden-1-yl]-benzamide

[IND_CC-288] 2,6-Dichloro-N-[3,3-dimethyl-6-(3-pyridin-4-yl-3,9-diazaspiro[5.5]undecane-9-carbonyl)-1,2-dihydro-inden-1-yl]-benzamide

[IND_CC-289] 2,6-Dichloro-N-[6-(8-pyridin-4-yl-2,8-diazaspiro[4.5]decane-2-carbonyl)-2,3-dihydro-1H-inden-1-yl]-benzamide

[IND_CC-290] 2-Chloro-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-291] 2-Chloro-N-[2,2-dimethyl-6-(9-pyridin-4-yl-3,9-diazaspiro[5.5]undecane-3-carbonyl)-1,3-dihydro-inden-1-yl]-benzamide

[IND_CC-292] 2-Chloro-N-[3,3-dimethyl-6-(3-pyridin-4-yl-3,9-diazaspiro[5.5]undecane-9-carbonyl)-1,2-dihydro-inden-1-yl]-benzamide

[IND_CC-293] 2-Chloro-N-[6-(8-pyridin-4-yl-2,8-diazaspiro[4.5]decane-2-carbonyl)-2,3-dihydro-1H-inden-1-yl]-benzamide

[IND_CC-294] 2,6-Dimethyl-N-[6-(9-pyridin-4-yl-3,9-diazaspiro[5.5]undecane-3-carbonyl)-2,3-dihydro-1H-inden-1-yl]-benzamide

[IND_CC-295] 2,6-Dimethyl-N-[6-(2-pyridin-4-yl-2,8-diazaspiro[4.5]decane-8-carbonyl)-2,3-dihydro-1H-inden-1-yl]-benzamide

[IND_CC-296] 2-Fluoro-4-methoxy-N-methyl-N-[6-(9-pyridin-4-yl-3,9-diazaspiro[5.5]undecane-3-carbonyl)-2,3-dihydro-1H-inden-1-yl]-benzamide

[IND_CC-297] 2-Fluoro-4-methoxy-N-[6-(9-pyridin-4-yl-3,9-diazaspiro[5.5]undecane-3-carbonyl)-2,3-dihydro-1H-inden-1-yl]-benzamide

[IND_CC-298] 2-Fluoro-4-methoxy-N-[6-(2-pyridin-4-yl-2,8-diazaspiro[4.5]decane-8-carbonyl)-2,3-dihydro-1H-inden-1-yl]-benzamide

[IND_CC-299] N,2-Dimethyl-N-[6-(9-pyridin-4-yl-3,9-diazaspiro[5.5]undecane-3-carbonyl)-2,3-dihydro-1H-inden-1-yl]-4-(trifluoromethyloxy)-benzamide

[IND_CC-300] 2-Methyl-N-[6-(9-pyridin-4-yl-3,9-diazaspiro[5.5]undecane-3-carbonyl)-2,3-dihydro-1H-inden-1-yl]-4-(trifluoromethyloxy)-benzamide

[IND_CC-301] 5-Chloro-N-methyl-N-[6-(9-pyridin-4-yl-3,9-diazaspiro[5.5]undecane-3-carbonyl)-2,3-dihydro-1H-inden-1-yl]-2-(trifluoromethyl)-benzamide

[IND_CC-302] 5-Chloro-N-[6-(9-pyridin-4-yl-3,9-diazaspiro[5.5]undecane-3-carbonyl)-2,3-dihydro-1H-inden-1-yl]-2-(trifluoromethyl)-benzamide

[IND_CC-303] 5-Chloro-N-[6-(2-pyridin-4-yl-2,8-diazaspiro[4.5]decane-8-carbonyl)-2,3-dihydro-1H-inden-1-yl]-2-(trifluoromethyl)-benzamide

[IND_CC-304] 2-Fluoro-N,4-dimethyl-N-[6-(9-pyridin-4-yl-3,9-diazaspiro[5.5]undecane-3-carbonyl)-2,3-dihydro-1H-inden-1-yl]-benzamide

[IND_CC-305] 2-Fluoro-4-methyl-N-[6-(9-pyridin-4-yl-3,9-diazaspiro[5.5]undecane-3-carbonyl)-2,3-dihydro-1H-inden-1-yl]-benzamide

[IND_CC-306] 2-Fluoro-4-methyl-N-[6-(2-pyridin-4-yl-2,8-diazaspiro[4.5]decane-8-carbonyl)-2,3-dihydro-1H-inden-1-yl]-benzamide

[IND_CC-307] 2,6-Dimethyl-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-308] N-[2,2-Dimethyl-6-(9-pyridin-4-yl-3,9-diazaspiro[5.5]undecane-3-carbonyl)-1,3-dihydro-inden-1-yl]-2,6-dimethyl-benzamide

[IND_CC-309] N-[3,3-Dimethyl-6-(3-pyridin-4-yl-3,9-diazaspiro[5.5]undecane-9-carbonyl)-1,2-dihydro-inden-1-yl]-2,6-dimethyl-benzamide

[IND_CC-310] 2,6-Dimethyl-N-[6-(8-pyridin-4-yl-2,8-diazaspiro[4.5]decane-2-carbonyl)-2,3-dihydro-1H-inden-1-yl]-benzamide

[IND_CC-311] N-[2,2-Dimethyl-6-(9-pyridin-4-yl-3,9-diazaspiro[5.5]undecane-3-carbonyl)-1,3-dihydro-inden-1-yl]-2-fluoro-4-methoxy-benzamide

[IND_CC-312] N-[3,3-Dimethyl-6-(3-pyridin-4-yl-3,9-diazaspiro[5.5]undecane-9-carbonyl)-1,2-dihydro-inden-1-yl]-2-fluoro-4-methoxy-benzamide

[IND_CC-313] 2-Fluoro-4-methoxy-N-[6-(8-pyridin-4-yl-2,8-diazaspiro[4.5]decane-2-carbonyl)-2,3-dihydro-1H-inden-1-yl]-benzamide

[IND_CC-314] 5-Chloro-N-[2,2-dimethyl-6-(9-pyridin-4-yl-3,9-diazaspiro[5.5]undecane-3-carbonyl)-1,3-dihydro-inden-1-yl]-2-(trifluoromethyl)-benzamide

[IND_CC-315] 5-Chloro-N-[3,3-dimethyl-6-(3-pyridin-4-yl-3,9-diazaspiro[5.5]undecane-9-carbonyl)-1,2-dihydro-inden-1-yl]-2-(trifluoromethyl)-benzamide

[IND_CC-316] 5-Chloro-N-[6-(8-pyridin-4-yl-2,8-diazaspiro[4.5]decane-2-carbonyl)-2,3-dihydro-1H-inden-1-yl]-2-(trifluoromethyl)-benzamide

[IND_CC-317] N-[2,2-Dimethyl-6-(9-pyridin-4-yl-3,9-diazaspiro[5.5]undecane-3-carbonyl)-1,3-dihydro-inden-1-yl]-2-fluoro-4-methyl-benzamide

[IND_CC-318] N-[3,3-Dimethyl-6-(3-pyridin-4-yl-3,9-diazaspiro[5.5]undecane-9-carbonyl)-1,2-dihydro-inden-1-yl]-2-fluoro-4-methyl-benzamide

[IND_CC-319] 2-Fluoro-4-methyl-N-[6-(8-pyridin-4-yl-2,8-diazaspiro[4.5]decane-2-carbonyl)-2,3-dihydro-1H-inden-1-yl]-benzamide

[IND_CC-320] 2-Chloro-N-methyl-N-[6-(9-pyridin-4-yl-3,9-diazaspiro[5.5]undecane-3-carbonyl)-2,3-dihydro-1H-inden-1-yl]-4-(trifluoromethyl)-benzenesulfonic acid amide

[IND_CC-321] 2,6-Dichloro-N-methyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-322] 2,6-Dichloro-N-[6-(9-pyridin-4-yl-3,9-diazaspiro[5.5]undecane-3-carbonyl)-2,3-dihydro-1H-inden-1-yl]-benzenesulfonic acid amide

[IND_CC-323] 2,6-Dichloro-N-[6-(2-pyridin-4-yl-2,8-diazaspiro[4.5]decane-8-carbonyl)-2,3-dihydro-1H-inden-1-yl]-benzenesulfonic acid amide

[IND_CC-324] 2,4-Dichloro-N-methyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-325] 2-Chloro-N-methyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-326] 4-Fluoro-N,2-dimethyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-327] N-Methyl-N-[6-(9-pyridin-4-yl-3,9-diazaspiro[5.5]undecane-3-carbonyl)-2,3-dihydro-1H-inden-1-yl]-3-(trifluoromethyl)-benzenesulfonic acid amide

[IND_CC-328] N-[6-(9-Pyridin-4-yl-3,9-diazaspiro[5.5]undecane-3-carbonyl)-2,3-dihydro-1H-inden-1-yl]-3-(trifluoromethyl)-benzenesulfonic acid amide

[IND_CC-329] N-[6-(2-Pyridin-4-yl-2,8-diazaspiro[4.5]decane-8-carbonyl)-2,3-dihydro-1H-inden-1-yl]-3-(trifluoromethyl)-benzenesulfonic acid amide

[IND_CC-330] 2-Chloro-N-[2,2-dimethyl-6-(9-pyridin-4-yl-3,9-diazaspiro[5.5]undecane-3-carbonyl)-1,3-dihydro-inden-1-yl]-4-(trifluoromethyl)-benzenesulfonic acid amide

[IND_CC-331] 2-Chloro-N-[3,3-dimethyl-6-(3-pyridin-4-yl-3,9-diazaspiro[5.5]undecane-9-carbonyl)-1,2-dihydro-inden-1-yl]-4-(trifluoromethyl)-benzenesulfonic acid amide

[IND_CC-332] 2,6-Dichloro-N-[3,3-dimethyl-6-(3-pyridin-4-yl-3,9-diazaspiro[5.5]undecane-9-carbonyl)-1,2-dihydro-inden-1-yl]-benzenesulfonic acid amide

[IND_CC-333] 2,6-Dichloro-N-[6-(8-pyridin-4-yl-2,8-diazaspiro[4.5]decane-2-carbonyl)-2,3-dihydro-1H-inden-1-yl]-benzenesulfonic acid amide

[IND_CC-334] 2,4-Dichloro-N-[2,2-dimethyl-6-(9-pyridin-4-yl-3,9-diazaspiro[5.5]undecane-3-carbonyl)-1,3-dihydro-inden-1-yl]-benzenesulfonic acid amide

[IND_CC-335] 2,4-Dichloro-N-[3,3-dimethyl-6-(3-pyridin-4-yl-3,9-diazaspiro[5.5]undecane-9-carbonyl)-1,2-dihydro-inden-1-yl]-benzenesulfonic acid amide

[IND_CC-336] 2-Chloro-N-[2,2-dimethyl-6-(9-pyridin-4-yl-3,9-diazaspiro[5.5]undecane-3-carbonyl)-1,3-dihydro-inden-1-yl]-benzenesulfonic acid amide

[IND_CC-337] 2-Chloro-N-[3,3-dimethyl-6-(3-pyridin-4-yl-3,9-diazaspiro[5.5]undecane-9-carbonyl)-1,2-dihydro-inden-1-yl]-benzenesulfonic acid amide

[IND_CC-338] N-[2,2-Dimethyl-6-(9-pyridin-4-yl-3,9-diazaspiro[5.5]undecane-3-carbonyl)-1,3-dihydro-inden-1-yl]-4-fluoro-2-methyl-benzenesulfonic acid amide

[IND_CC-339] N-[3,3-Dimethyl-6-(3-pyridin-4-yl-3,9-diazaspiro[5.5]undecane-9-carbonyl)-1,2-dihydro-inden-1-yl]-4-fluoro-2-methyl-benzenesulfonic acid amide

[IND_CC-340] N-[3,3-Dimethyl-6-(3-pyridin-4-yl-3,9-diazaspiro[5.5]undecane-9-carbonyl)-1,2-dihydro-inden-1-yl]-3-(trifluoromethyl)-benzenesulfonic acid amide

[IND_CC-341] N-[2,2-Dimethyl-6-(9-pyridin-4-yl-3,9-diazaspiro[5.5]undecane-3-carbonyl)-1,3-dihydro-inden-1-yl]-3-(trifluoromethyl)-benzenesulfonic acid amide

[IND_CC-342] N-[6-(8-Pyridin-4-yl-2,8-diazaspiro[4.5]decane-2-carbonyl)-2,3-dihydro-1H-inden-1-yl]-3-(trifluoromethyl)-benzenesulfonic acid amide

[IND_CC-343] 2,3-Dichloro-N-methyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-344] 2,5-Dichloro-N-methyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-345] N,2-Dimethyl-N-[6-(9-pyridin-4-yl-3,9-diazaspiro[5.5]undecane-3-carbonyl)-2,3-dihydro-1H-inden-1-yl]-benzamide

[IND_CC-346] 2-Methyl-N-[6-(9-pyridin-4-yl-3,9-diazaspiro[5.5]undecane-3-carbonyl)-2,3-dihydro-1H-inden-1-yl]-benzamide

[IND_CC-347] 2-Methyl-N-[6-(2-pyridin-4-yl-2,8-diazaspiro[4.5]decane-8-carbonyl)-2,3-dihydro-1H-inden-1-yl]-benzamide

[IND_CC-348] 1-(2-Fluorophenyl)-N-methyl-N-[6-(9-pyridin-4-yl-3,9-diazaspiro[5.5]undecane-carbonyl)-2,3-dihydro-1H-inden-1-yl]-methanesulfonic acid amide

[IND_CC-349] 1-(2-Fluorophenyl)-N-[6-(9-pyridin-4-yl-3,9-diazaspiro[5.5]undecane-3-carbonyl)-2,3-dihydro-1H-inden-1-yl]-methanesulfonic acid amide

[IND_CC-350] 1-(2-Fluorophenyl)-N-[6-(2-pyridin-4-yl-2,8-diazaspiro[4.5]decane-8-carbonyl)-2,3-dihydro-1H-inden-1-yl]-methanesulfonic acid amide

[IND_CC-351] 1-(3-Chlorophenyl)-N-methyl-N-[6-(9-pyridin-4-yl-3,9-diazaspiro[5.5]undecane-3-carbonyl)-2,3-dihydro-1H-inden-1-yl]-methanesulfonic acid amide

[IND_CC-352] 1-(3-Chlorophenyl)-N-[6-(9-pyridin-4-yl-3,9-diazaspiro[5.5]undecane-3-carbonyl)-2,3-dihydro-1H-inden-1-yl]-methanesulfonic acid amide

[IND_CC-353] 1-(3-Chlorophenyl)-N-[6-(2-pyridin-4-yl-2,8-diazaspiro[4.5]decane-8-carbonyl)-2,3-dihydro-1H-inden-1-yl]-methanesulfonic acid amide

[IND_CC-354] 4-Fluoro-N,2,6-trimethyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-355] 4-Fluoro-2,6-dimethyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-356] 4-Fluoro-2,6-dimethyl-N-[6-(2-pyridin-4-yl-2,8-diazaspiro[4.5]decane-8-carbonyl)-2,3-dihydro-1H-inden-1-yl]-benzenesulfonic acid amide

[IND_CC-357] 2,5-Dichloro-N-[6-(8-pyridin-4-yl-2,8-diazaspiro[4.5]decane-2-carbonyl)-2,3-dihydro-1H-inden-1-yl]-benzenesulfonic acid amide

[IND_CC-358] 2-Methyl-N-[6-(8-pyridin-4-yl-2,8-diazaspiro[4.5]decane-2-carbonyl)-2,3-dihydro-1H-inden-1-yl]-benzamide

[IND_CC-359] 1-(2-Fluorophenyl)-N-[6-(8-pyridin-4-yl-2,8-diazaspiro[4.5]decane-2-carbonyl)-2,3-dihydro-1H-inden-1-yl]-methanesulfonic acid amide

[IND_CC-360] 1-(3-Chlorophenyl)-N-[6-(8-pyridin-4-yl-2,8-diazaspiro[4.5]decane-2-carbonyl)-2,3-dihydro-1H-inden-1-yl]-methanesulfonic acid amide

[IND_CC-361] 4-Fluoro-2,6-dimethyl-N-[6-(8-pyridin-4-yl-2,8-diazaspiro[4.5]decane-2-carbonyl)-2,3-dihydro-1H-inden-1-yl]-benzenesulfonic acid amide

[IND_CC-362] 2,4,5-Trichloro-N-methyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-363] 2,4,5-Trichloro-N-[6-(2-pyridin-4-yl-2,8-diazaspiro[4.5]decane-8-carbonyl)-2,3-dihydro-1H-inden-1-yl]-benzenesulfonic acid amide

[IND_CC-364] N-[6-(9-Pyridin-4-yl-3,9-diazaspiro[5.5]undecane-3-carbonyl)-2,3-dihydro-1H-inden-1-yl]-cyclohexanecarboxylic acid amide

[IND_CC-365] N-Methyl-N-[6-(9-pyridin-4-yl-3,9-diazaspiro[5.5]undecane-3-carbonyl)-2,3-dihydro-1H-inden-1-yl]-cyclohexanecarboxylic acid amide

[IND_CC-366] N-[6-(2-Pyridin-4-yl-2,8-diazaspiro[4.5]decane-8-carbonyl)-2,3-dihydro-1H-inden-1-yl]-cyclohexanecarboxylic acid amide

[IND_CC-367] N-[6-(8-Pyridin-4-yl-2,8-diazaspiro[4.5]decane-2-carbonyl)-2,3-dihydro-1H-inden-1-yl]-cyclohexanecarboxylic acid amide

[IND_CC-368] N-[6-(9-Pyridin-4-yl-3,9-diazaspiro[5.5]undecane-3-carbonyl)-2,3-dihydro-1H-inden-1-yl]-cyclopropanecarboxylic acid amide

[IND_CC-369] N-Methyl-N-[6-(9-pyridin-4-yl-3,9-diazaspiro[5.5]undecane-3-carbonyl)-2,3-dihydro-1H-inden-1-yl]-cyclopropanecarboxylic acid amide

[IND_CC-370] N-[6-(8-Pyridin-4-yl-2,8-diazaspiro[4.5]decane-2-carbonyl)-2,3-dihydro-1H-inden-1-yl]-cyclopropanecarboxylic acid amide

[IND_CC-371] 3,3-Dimethyl-N-[6-(9-pyridin-4-yl-3,9-diazaspiro[5.5]undecane-3-carbonyl)-2,3-dihydro-1H-inden-1-yl]-butyramide

[IND_CC-372] N,3,3-Trimethyl-N-[6-(9-pyridin-4-yl-3,9-diazaspiro[5.5]undecane-3-carbonyl)-2,3-dihydro-1H-inden-1-yl]-butyramide

[IND_CC-373] 3,3-Dimethyl-N-[6-(2-pyridin-4-yl-2,8-diazaspiro[4.5]decane-8-carbonyl)-2,3-dihydro-1H-inden-1-yl]-butyramide

[IND_CC-374] 3,3-Dimethyl-N-[6-(8-pyridin-4-yl-2,8-diazaspiro[4.5]decane-2-carbonyl)-2,3-dihydro-1H-inden-1-yl]-butyramide

[IND_CC-375] N-[6-(8-Pyridin-4-yl-2,8-diazaspiro[4.5]decane-2-carbonyl)-2,3-dihydro-1H-inden-1-yl]-acetamide

[IND_CC-376] 2-Fluoro-N-[6-(9-pyridin-4-yl-3,9-diazaspiro[5.5]undecane-3-carbonyl)-2,3-dihydro-1H-inden-1-yl]-6-(trifluoromethyl)-benzamide

[IND_CC-377] 2-Fluoro-N-[6-(2-pyridin-4-yl-2,8-diazaspiro[4.5]decane-8-carbonyl)-2,3-dihydro-1H-inden-1-yl]-6-(trifluoromethyl)-benzamide

[IND_CC-378] 2-Fluoro-N-[6-(8-pyridin-4-yl-2,8-diazaspiro[4.5]decane-2-carbonyl)-2,3-dihydro-1H-inden-1-yl]-6-(trifluoromethyl)-benzamide

[IND_CC-379] 4-Fluoro-N-[6-(9-pyridin-4-yl-3,9-diazaspiro[5.5]undecane-3-carbonyl)-2,3-dihydro-1H-inden-1-yl]-2-(trifluoromethyl)-benzamide

[IND_CC-380] 4-Fluoro-N-methyl-N-[6-(9-pyridin-4-yl-3,9-diazaspiro[5.5]undecane-3-carbonyl)-2,3-dihydro-1H-inden-1-yl]-2-(trifluoromethyl)-benzamide

[IND_CC-381] 4-Fluoro-N-[6-(2-pyridin-4-yl-2,8-diazaspiro[4.5]decane-8-carbonyl)-2,3-dihydro-1H-inden-1-yl]-2-(trifluoromethyl)-benzamide

[IND_CC-382] 4-Fluoro-N-[6-(8-pyridin-4-yl-2,8-diazaspiro[4.5]decane-2-carbonyl)-2,3-dihydro-1H-inden-1-yl]-2-(trifluoromethyl)-benzamide

[IND_CC-383] 2,6-Difluoro-N-[6-(9-pyridin-4-yl-3,9-diazaspiro[5.5]undecane-3-carbonyl)-2,3-dihydro-1H-inden-1-yl]-benzamide

[IND_CC-384] 2,6-Difluoro-N-methyl-N-[6-(9-pyridin-4-yl-3,9-diazaspiro[5.5]undecane-3-carbonyl)-2,3-dihydro-1H-inden-1-yl]-benzamide

[IND_CC-385] 2,6-Difluoro-N-[6-(2-pyridin-4-yl-2,8-diazaspiro[4.5]decane-8-carbonyl)-2,3-dihydro-1H-inden-1-yl]-benzamide

[IND_CC-386] 2,6-Difluoro-N-[6-(8-pyridin-4-yl-2,8-diazaspiro[4.5]decane-2-carbonyl)-2,3-dihydro-1H-inden-1-yl]-benzamide

[IND_CC-387] N,2,3-Trimethyl-N-[6-(9-pyridin-4-yl-3,9-diazaspiro[5.5]undecane-3-carbonyl)-2,3-dihydro-1H-inden-1-yl]-benzamide

[IND_CC-388] 2,3-Dimethyl-N-[6-(2-pyridin-4-yl-2,8-diazaspiro[4.5]decane-8-carbonyl)-2,3-dihydro-1H-inden-1-yl]-benzamide

[IND_CC-389] 2,3-Dimethyl-N-[6-(8-pyridin-4-yl-2,8-diazaspiro[4.5]decane-2-carbonyl)-2,3-dihydro-1H-inden-1-yl]-benzamide

[IND_CC-390] N-Methyl-N-[6-(9-pyridin-4-yl-3,9-diazaspiro[5.5]undecane-3-carbonyl)-2,3-dihydro-1H-inden-1-yl]-1-[3-(trifluoromethyl)phenyl]-methanesulfonic acid amide

[IND_CC-391] N-[6-(9-Pyridin-4-yl-3,9-diazaspiro[5.5]undecane-3-carbonyl)-2,3-dihydro-1H-inden-1-yl]-cyclopentanecarboxylic acid amide

[IND_CC-392] N-Methyl-N-[6-(9-pyridin-4-yl-3,9-diazaspiro[5.5]undecane-3-carbonyl)-2,3-dihydro-1H-inden-1-yl]-cyclopentanecarboxylic acid amide

[IND_CC-393] N-[6-(2-Pyridin-4-yl-2,8-diazaspiro[4.5]decane-8-carbonyl)-2,3-dihydro-1H-inden-1-yl]-cyclopentanecarboxylic acid amide

[IND_CC-394] N-[6-(8-Pyridin-4-yl-2,8-diazaspiro[4.5]decane-2-carbonyl)-2,3-dihydro-1H-inden-1-yl]-cyclopentanecarboxylic acid amide

[IND_CC-395] N-Methyl-N-[6-(9-pyridin-4-yl-3,9-diazaspiro[5.5]undecane-3-carbonyl)-2,3-dihydro-1H-inden-1-yl]-5-(trifluoromethyl)-pyridine-2-carboxylic acid amide

[IND_CC-396] N-[6-(8-Pyridin-4-yl-2,8-diazaspiro[4.5]decane-2-carbonyl)-2,3-dihydro-1H-inden-1-yl]-5-(trifluoromethyl)-pyridine-2-carboxylic acid amide

[IND_CC-397] N-[6-(9-Pyridin-4-yl-3,9-diazaspiro[5.5]undecane-3-carbonyl)-2,3-dihydro-1H-inden-1-yl]-pyrazine-2-carboxylic acid amide

[IND_CC-398] N-[6-(8-Pyridin-4-yl-2,8-diazaspiro[4.5]decane-2-carbonyl)-2,3-dihydro-1H-inden-1-yl]-pyrazine-2-carboxylic acid amide

[IND_CC-399] 2-Fluoro-N-[6-(9-pyridin-4-yl-3,9-diazaspiro[5.5]undecane-3-carbonyl)-2,3-dihydro-1H-inden-1-yl]-benzamide

[IND_CC-400] 2-Fluoro-N-methyl-N-[6-(9-pyridin-4-yl-3,9-diazaspiro[5.5]undecane-3-carbonyl)-2,3-dihydro-1H-inden-1-yl]-benzamide

[IND_CC-401] 2-Fluoro-N-[6-(2-pyridin-4-yl-2,8-diazaspiro[4.5]decane-8-carbonyl)-2,3-dihydro-1H-inden-1-yl]-benzamide

[IND_CC-402] 2-Fluoro-N-[6-(8-pyridin-4-yl-2,8-diazaspiro[4.5]decane-2-carbonyl)-2,3-dihydro-1H-inden-1-yl]-benzamide

[IND_CC-403] 2,6-Dichloro-N-methyl-N-[6-(9-pyridin-4-yl-3,9-diazaspiro[5.5]undecane-3-carbonyl)-2,3-dihydro-1H-inden-1-yl]-4-(trifluoromethyl)-benzenesulfonic acid amide

[IND_CC-404] 2,6-Dichloro-N-[6-(8-pyridin-4-yl-2,8-diazaspiro[4.5]decane-2-carbonyl)-2,3-dihydro-1H-inden-1-yl]-4-(trifluoromethyl)-benzenesulfonic acid amide

[IND_CC-405] 4-Bromo-2-chloro-N-methyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-406] 2,4,6-Trichloro-N-methyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-407] 2,4,6-Trichloro-N-[6-(8-pyridin-4-yl-2,8-diazaspiro[4.5]decane-2-carbonyl)-2,3-dihydro-1H-inden-1-yl]-benzenesulfonic acid amide

[IND_CC-408] N,3-Dimethyl-N-[6-(9-pyridin-4-yl-3,9-diazaspiro[5.5]undecane-3-carbonyl)-2,3-dihydro-1H-inden-1-yl]-butyramide

[IND_CC-409] 3-Methyl-N-[6-(8-pyridin-4-yl-2,8-diazaspiro[4.5]decane-2-carbonyl)-2,3-dihydro-1H-inden-1-yl]-butyramide

[IND_CC-410] N-Methyl-N-[6-(9-pyridin-4-yl-3,9-diazaspiro[5.5]undecane-3-carbonyl)-2,3-dihydro-1H-inden-1-yl]-butyramide

[IND_CC-411] N-[6-(8-Pyridin-4-yl-2,8-diazaspiro[4.5]decane-2-carbonyl)-2,3-dihydro-1H-inden-1-yl]-butyramide

[IND_CC-412] 3-Cyclopentyl-N-methyl-N-[6-(9-pyridin-4-yl-3,9-diazaspiro[5.5]undecane-3-carbonyl)-2,3-dihydro-1H-inden-1-yl]-propionamide

[IND_CC-413] 3-Cyclopentyl-N-[6-(8-pyridin-4-yl-2,8-diazaspiro[4.5]decane-2-carbonyl)-2,3-dihydro-1H-inden-1-yl]-propionamide

[IND_CC-414] N-Methyl-N-[6-(9-pyridin-4-yl-3,9-diazaspiro[5.5]undecane-3-carbonyl)-2,3-dihydro-1H-inden-1-yl]-cyclobutanecarboxylic acid amide

[IND_CC-415] N-[6-(8-Pyridin-4-yl-2,8-diazaspiro[4.5]decane-2-carbonyl)-2,3-dihydro-1H-inden-1-yl]-cyclobutanecarboxylic acid amide

[IND_CC-416] N,2-Dimethyl-N-[6-(9-pyridin-4-yl-3,9-diazaspiro[5.5]undecane-3-carbonyl)-2,3-dihydro-1H-inden-1-yl]-butyramide

[IND_CC-417] 2-Methyl-N-[6-(8-pyridin-4-yl-2,8-diazaspiro[4.5]decane-2-carbonyl)-2,3-dihydro-1H-inden-1-yl]-butyramide

[IND_CC-418] N,2-Dimethyl-N-[6-(9-pyridin-4-yl-3,9-diazaspiro[5.5]undecane-3-carbonyl)-2,3-dihydro-1H-inden-1-yl]-propionamide

[IND_CC-419] 2-Methyl-N-[6-(8-pyridin-4-yl-2,8-diazaspiro[4.5]decane-2-carbonyl)-2,3-dihydro-1H-inden-1-yl]-propionamide

[IND_CC-420] 2-Ethyl-N-[6-(8-pyridin-4-yl-2,8-diazaspiro[4.5]decane-2-carbonyl)-2,3-dihydro-1H-inden-1-yl]-butyramide

[IND_CC-500] 2-Chloro-N-[6-[8-[(2,4-difluoro-phenyl)sulfonyl]-2,8-diazaspiro[4.5]decane-2-carbonyl]-2,3-dihydro-1H-inden-1-yl]-benzamide

[IND_CC-501] 2-Chloro-N-[6-[8-[(2-cyano-phenyl)sulfonyl]-2,8-diazaspiro[4.5]decane-2-carbonyl]-2,3-dihydro-1H-inden-1-yl]-benzamide

[IND_CC-502] 2-[3-[(2-Chloro-benzoyl)amino]-2,3-dihydro-1H-indene-5-carbonyl]-N-(3-chloro-4-fluoro-phenyl)-2,8-diazaspiro[4.5]decane-8-carboxylic acid amide

[IND_CC-503] 2-[3-[(2-Chloro-benzoyl)amino]-2,3-dihydro-1H-indene-5-carbonyl]-N-(3-cyano-phenyl)-2,8-diazaspiro[4.5]decane-8-carboxylic acid amide

[IND_CC-504] 2-Chloro-N-[6-[8-[(2,6-difluoro-phenyl)-methyl]-2,8-diazaspiro[4.5]decane-2-carbonyl]-2,3-dihydro-1H-inden-1-yl]-benzamide

[IND_CC-505] 2-Chloro-N-[6-[8-[(2-cyano-phenyl)-methyl]-2,8-diazaspiro[4.5]decane-2-carbonyl]-2,3-dihydro-1H-inden-1-yl]-N-methyl-benzamide

[IND_CC-506] 2-Chloro-N-methyl-N-[6-[8-(quinoxalin-6-yl-methyl)-2,8-diazaspiro[4.5]decane-2-carbonyl]-2,3-dihydro-1H-inden-1-yl]-benzamide

[IND_CC-507] 2-Chloro-N-[6-[9-(1H-pyrrol-2-yl-methyl)-3,9-diazaspiro[5.5]undecane-3-carbonyl]-2,3-dihydro-1H-inden-1-yl]-benzamide

[IND_CC-508] 2-Chloro-N-[6-[9-(1H-imidazol-4-yl-methyl)-3,9-diazaspiro[5.5]undecane-3-carbonyl]-2,3-dihydro-1H-inden-1-yl]-benzamide

[IND_CC-509] 2-Chloro-N-[6-[9-(pyridin-2-yl-methyl)-3,9-diazaspiro[5.5]undecane-3-carbonyl]-2,3-dihydro-1H-inden-1-yl]-benzamide

[IND_CC-510] 2-Chloro-N-[6-[9-(pyridin-4-yl-methyl)-3,9-diazaspiro[5.5]undecane-3-carbonyl]-2,3-dihydro-1H-inden-1-yl]-benzamide

[IND_CC-511] 2-Chloro-N-[6-[9-(pyridin-3-yl-methyl)-3,9-diazaspiro[5.5]undecane-3-carbonyl]-2,3-dihydro-1H-inden-1-yl]-benzamide

[IND_CC-512] 2-Chloro-N-[6-[9-[(1-methyl-1H-pyrrol-2-yl)-methyl]-3,9-diazaspiro[5.5]undecane-3-carbonyl]-2,3-dihydro-1H-inden-1-yl]-benzamide

[IND_CC-513] 2-Chloro-N-[6-[9-[(2,6-difluoro-phenyl)-methyl]-3,9-diazaspiro[5.5]undecane-3-carbonyl]-2,3-dihydro-1H-inden-1-yl]-benzamide

[IND_CC-514] 2-Chloro-N-[6-[9-[(3,4-difluoro-phenyl)-methyl]-3,9-diazaspiro[5.5]undecane-3-carbonyl]-2,3-dihydro-1H-inden-1-yl]-benzamide

[IND_CC-515] 2-Chloro-N-[6-[9-[(2,5-difluoro-phenyl)-methyl]-3,9-diazaspiro[5.5]undecane-3-carbonyl]-2,3-dihydro-1H-inden-1-yl]-benzamide

[IND_CC-516] 2-Chloro-N-[6-[9-[(2,4-difluoro-phenyl)-methyl]-3,9-diazaspiro[5.5]undecane-3-carbonyl]-2,3-dihydro-1H-inden-1-yl]-benzamide

[IND_CC-517] 2-Chloro-N-[6-[9-[(2-fluoro-6-methoxy-phenyl)-methyl]-3,9-diazaspiro[5.5]undecane-3-carbonyl]-2,3-dihydro-1H-inden-1-yl]-benzamide

[IND_CC-518] 2-Chloro-N-cyclopropyl-N-[6-[8-(pyridin-3-yl-methyl)-2,8-diazaspiro[4.5]decane-2-carbonyl]-2,3-dihydro-1H-inden-1-yl]-benzamide
[IND_CC-519] 2-Chloro-N-cyclopropyl-N-[6-[8-[(1-methyl-1H-pyrrol-2-yl)-methyl]-2,8-diazaspiro[4.5]decane-2-carbonyl]-2,3-dihydro-1H-inden-1-yl]-benzamide
[IND_CC-520] 2-Chloro-N-cyclopropyl-N-[6-[8-[(2,6-difluoro-phenyl)-methyl]-2,8-diazaspiro[4.5]decane-2-carbonyl]-2,3-dihydro-1H-inden-1-yl]-benzamide
[IND_CC-521] 2-Chloro-N-cyclopropyl-N-[6-[8-[(3,4-difluoro-phenyl)-methyl]-2,8-diazaspiro[4.5]decane-2-carbonyl]-2,3-dihydro-1H-inden-1-yl]-benzamide
[IND_CC-522] 2-Chloro-N-cyclopropyl-N-[6-[8-[(2,5-difluoro-phenyl)-methyl]-2,8-diazaspiro[4.5]decane-2-carbonyl]-2,3-dihydro-1H-inden-1-yl]-benzamide
[IND_CC-523] 2-Chloro-N-cyclopropyl-N-[6-[8-[(2,4-difluoro-phenyl)-methyl]-2,8-diazaspiro[4.5]decane-2-carbonyl]-2,3-dihydro-1H-inden-1-yl]-benzamide
[IND_CC-524] 2-Chloro-N-cyclopropyl-N-[6-[8-[(3-fluoro-4-methoxy-phenyl)-methyl]-2,8-diazaspiro[4.5]decane-2-carbonyl]-2,3-dihydro-1H-inden-1-yl]-benzamide
[IND_CC-525] 2-Chloro-N-cyclopropyl-N-[6-[8-[(2-fluoro-6-methoxy-phenyl)-methyl]-2,8-diazaspiro[4.5]decane-2-carbonyl]-2,3-dihydro-1H-inden-1-yl]-benzamide
[IND_CC-526] 2-Chloro-N-[6-[9-[(3-methyl-3H-imidazol-4-yl)-methyl]-3,9-diazaspiro[5.5]undecane-3-carbonyl]-2,3-dihydro-1H-inden-1-yl]-benzamide
[IND_CC-527] 2-Chloro-N-[6-[9-[(5-methyl-3H-imidazol-4-yl)-methyl]-3,9-diazaspiro[5.5]undecane-3-carbonyl]-2,3-dihydro-1H-inden-1-yl]-benzamide
[IND_CC-528] 2-Chloro-N-[6-[9-[(2-methyl-1H-imidazol-4-yl)-methyl]-3,9-diazaspiro[5.5]undecane-3-carbonyl]-2,3-dihydro-1H-inden-1-yl]-benzamide
[IND_CC-529] 2-Chloro-N-[6-[9-[(2-chloro-4-fluoro-phenyl)-methyl]-3,9-diazaspiro[5.5]undecane-3-carbonyl]-2,3-dihydro-1H-inden-1-yl]-benzamide
[IND_CC-530] 2-Chloro-N-[6-[9-[(2-chloro-6-fluoro-phenyl)-methyl]-3,9-diazaspiro[5.5]undecane-3-carbonyl]-2,3-dihydro-1H-inden-1-yl]-benzamide
[IND_CC-531] 2-Chloro-N-[6-[9-[(1,5-dimethyl-1H-pyrazol-4-yl)-methyl]-3,9-diazaspiro[5.5]undecane-3-carbonyl]-2,3-dihydro-1H-inden-1-yl]-benzamide
[IND_CC-532] 2-Chloro-N-[6-[9-[(3,5-dimethyl-isoxazol-4-yl)-methyl]-3,9-diazaspiro[5.5]undecane-3-carbonyl]-2,3-dihydro-1H-inden-1-yl]-benzamide
[IND_CC-533] 2-Chloro-N-[6-[9-[(4-cyano-phenyl)-methyl]-3,9-diazaspiro[5.5]undecane-3-carbonyl]-2,3-dihydro-1H-inden-1-yl]-benzamide
[IND_CC-534] 2-Chloro-N-[6-[9-[(3-cyano-phenyl)-methyl]-3,9-diazaspiro[5.5]undecane-3-carbonyl]-2,3-dihydro-1H-inden-1-yl]-benzamide
[IND_CC-535] 2-Chloro-N-[6-[9-[(2-cyano-phenyl)-methyl]-3,9-diazaspiro[5.5]undecane-3-carbonyl]-2,3-dihydro-1H-inden-1-yl]-benzamide
[IND_CC-536] 2-Chloro-N-cyclopropyl-N-[6-[8-[(3-methyl-3H-imidazol-4-yl)-methyl]-2,8-diazaspiro[4.5]decane-2-carbonyl]-2,3-dihydro-1H-inden-1-yl]-benzamide
[IND_CC-537] 2-Chloro-N-[6-[8-[(2-chloro-4-fluoro-phenyl)-methyl]-2,8-diazaspiro[4.5]-decane-2-carbonyl]-2,3-dihydro-1H-inden-1-yl]-N-cyclopropyl-benzamide
[IND_CC-538] 2-Chloro-N-[6-[8-[(2-chloro-6-fluoro-phenyl)-methyl]-2,8-diazaspiro[4.5]-decane-2-carbonyl]-2,3-dihydro-1H-inden-1-yl]-N-cyclopropyl-benzamide
[IND_CC-539] 2-Chloro-N-[6-[8-[(4-cyano-phenyl)-methyl]-2,8-diazaspiro[4.5]decane-2-carbonyl]-2,3-dihydro-1H-inden-1-yl]-N-cyclopropyl-benzamide
[IND_CC-540] 2-Chloro-N-[6-[8-[(3-cyano-phenyl)-methyl]-2,8-diazaspiro[4.5]decane-2-carbonyl]-2,3-dihydro-1H-inden-1-yl]-N-cyclopropyl-benzamide
[IND_CC-541] 2-Chloro-N-[6-[8-[(2-cyano-phenyl)-methyl]-2,8-diazaspiro[4.5]decane-2-carbonyl]-2,3-dihydro-1H-inden-1-yl]-N-cyclopropyl-benzamide
[IND_CC-542] 2-Chloro-N-[6-[8-[(3,4-difluoro-phenyl)-methyl]-2,8-diazaspiro[4.5]decane-2-carbonyl]-2,3-dihydro-1H-inden-1-yl]-benzamide
[IND_CC-543] 2-Chloro-N-[6-[8-[(2,5-difluoro-phenyl)-methyl]-2,8-diazaspiro[4.5]decane-2-carbonyl]-2,3-dihydro-1H-inden-1-yl]-benzamide
[IND_CC-544] 2-Chloro-N-[6-[8-[(2,4-difluoro-phenyl)-methyl]-2,8-diazaspiro[4.5]decane-2-carbonyl]-2,3-dihydro-1H-inden-1-yl]-benzamide
[IND_CC-545] 2-Chloro-N-[6-[8-[(3-fluoro-4-methoxy-phenyl)-methyl]-2,8-diazaspiro[4.5]decane-2-carbonyl]-2,3-dihydro-1H-inden-1-yl]-benzamide
[IND_CC-546] 2-Chloro-N-[6-[8-[(2-fluoro-6-methoxy-phenyl)-methyl]-2,8-diazaspiro[4.5]decane-2-carbonyl]-2,3-dihydro-1H-inden-1-yl]-benzamide
[IND_CC-547] 3-Chloro-N-[6-[8-[(2,5-difluoro-phenyl)-methyl]-2,8-diazaspiro[4.5]decane-2-carbonyl]-2,3-dihydro-1H-inden-1-yl]-thiophene-2-carboxylic acid amide
[IND_CC-548] 3-Chloro-N-[6-[8-[(3-fluoro-4-methoxy-phenyl)-methyl]-2,8-diazaspiro[4.5]decane-2-carbonyl]-2,3-dihydro-1H-inden-1-yl]-thiophene-2-carboxylic acid amide
[IND_CC-549] 2-Chloro-N-[6-[8-[(3,4-difluoro-phenyl)-methyl]-2,8-diazaspiro[4.5]decane-2-carbonyl]-2,3-dihydro-1H-inden-1-yl]-N-methyl-benzamide
[IND_CC-550] 2-Chloro-N-[6-[8-[(2,5-difluoro-phenyl)-methyl]-2,8-diazaspiro[4.5]decane-2-carbonyl]-2,3-dihydro-1H-inden-1-yl]-N-methyl-benzamide
[IND_CC-551] 2-Chloro-N-[6-[8-[(2,4-difluoro-phenyl)-methyl]-2,8-diazaspiro[4.5]decane-2-carbonyl]-2,3-dihydro-1H-inden-1-yl]-N-methyl-benzamide
[IND_CC-552] 2-Chloro-N-[6-[8-[(3-fluoro-4-methoxy-phenyl)-methyl]-2,8-diazaspiro[4.5]-decane-2-carbonyl]-2,3-dihydro-1H-inden-1-yl]-N-methyl-benzamide
[IND_CC-553] 2-Chloro-N-[6-[8-[(5-methyl-3H-imidazol-4-yl)-methyl]-2,8-diazaspiro[4.5]decane-2-carbonyl]-2,3-dihydro-1H-inden-1-yl]-benzamide
[IND_CC-554] 2-Chloro-N-[6-[8-[(2-methyl-1H-imidazol-4-yl)-methyl]-2,8-diazaspiro[4.5]decane-2-carbonyl]-2,3-dihydro-1H-inden-1-yl]-benzamide
[IND_CC-555] 2-Chloro-N-[6-[8-([1,2,3]thiadiazol-4-yl-methyl)-2,8-diazaspiro[4.5]decane-2-carbonyl]-2,3-dihydro-1H-inden-1-yl]-benzamide
[IND_CC-556] 2-Chloro-N-[6-[8-[(2-chloro-4-fluoro-phenyl)-methyl]-2,8-diazaspiro[4.5]decane-2-carbonyl]-2,3-dihydro-1H-inden-1-yl]-benzamide
[IND_CC-557] 2-Chloro-N-[6-[8-[(2-chloro-6-fluoro-phenyl)-methyl]-2,8-diazaspiro[4.5]decane-2-carbonyl]-2,3-dihydro-1H-inden-1-yl]-benzamide
[IND_CC-558] 2-Chloro-N-[6-[8-[(2-chloro-6-fluoro-phenyl)-methyl]-2,8-diazaspiro[4.5]-decane-2-carbonyl]-2,3-dihydro-1H-inden-1-yl]-N-methyl-benzamide
[IND_CC-559] 2-Chloro-N-[6-[8-[(1,5-dimethyl-1H-pyrazol-4-yl)-methyl]-2,8-diazaspiro[4.5]decane-2-carbonyl]-2,3-dihydro-1H-inden-1-yl]-benzamide
[IND_CC-560] 2-Chloro-N-[6-[8-[(3,5-dimethyl-isoxazol-4-yl)-methyl]-2,8-diazaspiro[4.5]decane-2-carbonyl]-2,3-dihydro-1H-inden-1-yl]-benzamide
[IND_CC-561] 2-Chloro-N-[6-[8-[(4-cyano-phenyl)-methyl]-2,8-diazaspiro[4.5]decane-2-carbonyl]-2,3-dihydro-1H-inden-1-yl]-benzamide

[IND_CC-562] 2-Chloro-N-[6-[8-[(3-cyano-phenyl)-methyl]-2,8-diazaspiro[4.5]decane-2-carbonyl]-2,3-dihydro-1H-inden-1-yl]-benzamide
[IND_CC-563] 2-Chloro-N-[6-[8-[(2-cyano-phenyl)-methyl]-2,8-diazaspiro[4.5]decane-2-carbonyl]-2,3-dihydro-1H-inden-1-yl]-benzamide
[IND_CC-564] 2-Chloro-N-[6-[8-[(1,3,5-trimethyl-1H-pyrazol-4-yl)-methyl]-2,8-diazaspiro[4.5]decane-2-carbonyl]-2,3-dihydro-1H-inden-1-yl]-benzamide
[IND_CC-565] 2-Chloro-N-[6-[8-[(1-ethyl-3-methyl-1H-pyrazol-4-yl)-methyl]-2,8-diazaspiro[4.5]decane-2-carbonyl]-2,3-dihydro-1H-inden-1-yl]-benzamide
[IND_CC-566] 2-Chloro-N-[6-[8-[(2-dimethylamino-pyrimidin-5-yl)-methyl]-2,8-diazaspiro[4.5]decane-2-carbonyl]-2,3-dihydro-1H-inden-1-yl]-benzamide
[IND_CC-567] 2-Chloro-N-[6-[8-(quinolin-6-yl-methyl)-2,8-diazaspiro[4.5]decane-2-carbonyl]-2,3-dihydro-1H-inden-1-yl]-benzamide
[IND_CC-568] 2-Chloro-N-[6-[8-(quinoxalin-6-yl-methyl)-2,8-diazaspiro[4.5]decane-2-carbonyl]-2,3-dihydro-1H-inden-1-yl]-benzamide
[IND_CC-569] 3-Chloro-N-[6-[8-[(4-cyano-phenyl)-methyl]-2,8-diazaspiro[4.5]decane-2-carbonyl]-2,3-dihydro-1H-inden-1-yl]-thiophene-2-carboxylic acid amide
[IND_CC-570] 3-Chloro-N-[6-[8-(quinolin-6-yl-methyl)-2,8-diazaspiro[4.5]decane-2-carbonyl]-2,3-dihydro-1H-inden-1-yl]-thiophene-2-carboxylic acid amide
[IND_CC-571] 3-Chloro-N-[6-[8-(quinoxalin-6-yl-methyl)-2,8-diazaspiro[4.5]decane-2-carbonyl]-2,3-dihydro-1H-inden-1-yl]-thiophene-2-carboxylic acid amide
[IND_CC-572] 2-Chloro-N-[6-[8-[(3-cyano-phenyl)-methyl]-2,8-diazaspiro[4.5]decane-2-carbonyl]-2,3-dihydro-1H-inden-1-yl]-N-methyl-benzamide
[IND_CC-573] 2-Chloro-N-[6-[8-(cyclopropanecarbonyl)-2,8-diazaspiro[4.5]decane-2-carbonyl]-2,3-dihydro-1H-inden-1-yl]-benzamide
[IND_CC-574] 2-Chloro-N-[6-[8-(3,3-dimethyl-butanoyl)-2,8-diazaspiro[4.5]decane-2-carbonyl]-2,3-dihydro-1H-inden-1-yl]-benzamide
[IND_CC-575] 2-Chloro-N-[6-[8-(2-chloro-4-fluoro-benzoyl)-2,8-diazaspiro[4.5]decane-2-carbonyl]-2,3-dihydro-1H-inden-1-yl]-benzamide
[IND_CC-576] 2-Chloro-N-[6-[8-(2,4-difluoro-benzoyl)-2,8-diazaspiro[4.5]decane-2-carbonyl]-2,3-dihydro-1H-inden-1-yl]-benzamide
[IND_CC-577] 2-Chloro-N-[6-[8-[2-(4-chlorophenyl)-acetyl]-2,8-diazaspiro[4.5]decane-2-carbonyl]-2,3-dihydro-1H-inden-1-yl]-benzamide
[IND_CC-578] N-[6-[8-(5-tert-Butyl-2-methyl-2H-pyrazole-3-carbonyl)-2,8-diazaspiro-[4.5]decane-2-carbonyl]-2,3-dihydro-1H-inden-1-yl]-2-chloro-benzamide
[IND_CC-579] N-[6-[8-(2-tert-Butyl-5-methyl-2H-pyrazole-3-carbonyl)-2,8-diazaspiro-[4.5]decane-2-carbonyl]-2,3-dihydro-1H-inden-1-yl]-2-chloro-benzamide
[IND_CC-580] N-[6-[8-(5-tert-Butyl-2-methyl-2H-pyrazole-3-carbonyl)-2,8-diazaspiro[4.5]decane-2-carbonyl]-2,3-dihydro-1H-inden-1-yl]-4-methoxy-2,6-dimethyl-benzamide
[IND_CC-581] N-[6-[8-(2-tert-Butyl-5-methyl-2H-pyrazole-3-carbonyl)-2,8-diazaspiro[4.5]decane-2-carbonyl]-2,3-dihydro-1H-inden-1-yl]-4-methoxy-2,6-dimethyl-benzamide
[IND_CC-582] 3-Chloro-N-[6-[8-(cyclopropanecarbonyl)-2,8-diazaspiro[4.5]decane-2-carbonyl]-2,3-dihydro-1H-inden-1-yl]-thiophene-2-carboxylic acid amide
[IND_CC-583] 3-Chloro-N-[6-[8-(3,3-dimethyl-butanoyl)-2,8-diazaspiro[4.5]decane-2-carbonyl]-2,3-dihydro-1H-inden-1-yl]-thiophene-2-carboxylic acid amide
[IND_CC-584] 3-Chloro-N-[6-[8-(2-chloro-4-fluoro-benzoyl)-2,8-diazaspiro[4.5]decane-2-carbonyl]-2,3-dihydro-1H-inden-1-yl]-thiophene-2-carboxylic acid amide
[IND_CC-585] 3-Chloro-N-[6-[8-(2,4-difluoro-benzoyl)-2,8-diazaspiro[4.5]decane-2-carbonyl]-2,3-dihydro-1H-inden-1-yl]-thiophene-2-carboxylic acid amide
[IND_CC-586] 3-Chloro-N-[6-[8-[2-(4-chlorophenyl)-acetyl]-2,8-diazaspiro[4.5]decane-2-carbonyl]-2,3-dihydro-1H-inden-1-yl]-thiophene-2-carboxylic acid amide
[IND_CC-587] N-[6-[8-(5-tert-Butyl-2-methyl-2H-pyrazole-3-carbonyl)-2,8-diazaspiro[4.5]-decane-2-carbonyl]-2,3-dihydro-1H-inden-1-yl]-3-chloro-thiophene-2-carboxylic acid amide
[IND_CC-588] N-[6-[8-(2-tert-Butyl-5-methyl-2H-pyrazole-3-carbonyl)-2,8-diazaspiro[4.5]-decane-2-carbonyl]-2,3-dihydro-1H-inden-1-yl]-3-chloro-thiophene-2-carboxylic acid amide
[IND_CC-589] 2-Chloro-N-[6-[8-(cyclopropanecarbonyl)-2,8-diazaspiro[4.5]decane-2-carbonyl]-2,3-dihydro-1H-inden-1-yl]-N-methyl-benzamide
[IND_CC-590] 2-Chloro-N-[6-[8-(3,3-dimethyl-butanoyl)-2,8-diazaspiro[4.5]decane-2-carbonyl]-2,3-dihydro-1H-inden-1-yl]-N-methyl-benzamide
[IND_CC-591] 2-Chloro-N-[6-[8-(2-chloro-4-fluoro-benzoyl)-2,8-diazaspiro[4.5]decane-2-carbonyl]-2,3-dihydro-1H-inden-1-yl]-N-methyl-benzamide
[IND_CC-592] 2-Chloro-N-[6-[8-[2-(4-chlorophenyl)-acetyl]-2,8-diazaspiro[4.5]decane-2-carbonyl]-2,3-dihydro-1H-inden-1-yl]-N-methyl-benzamide
[IND_CC-593] N-[6-[8-(5-tert-Butyl-2-methyl-2H-pyrazole-3-carbonyl)-2,8-diazaspiro[4.5]-decane-2-carbonyl]-2,3-dihydro-1H-inden-1-yl]-2-chloro-N-methyl-benzamide
[IND_CC-594] 2-Chloro-N-[6-[9-(pyrazine-2-carbonyl)-3,9-diazaspiro[5.5]undecane-3-carbonyl]-2,3-dihydro-1H-inden-1-yl]-benzamide
[IND_CC-595] 2-Chloro-N-[6-[9-(2-methylsulfanyl-pyridine-3-carbonyl)-3,9-diazaspiro[5.5]undecane-3-carbonyl]-2,3-dihydro-1H-inden-1-yl]-benzamide
[IND_CC-596] 2-Chloro-N-[6-[9-(4-cyano-benzoyl)-3,9-diazaspiro[5.5]undecane-3-carbonyl]-2,3-dihydro-1H-inden-1-yl]-benzamide
[IND_CC-597] 2-Chloro-N-[6-[9-(cyclopropanecarbonyl)-3,9-diazaspiro[5.5]undecane-3-carbonyl]-2,3-dihydro-1H-inden-1-yl]-benzamide
[IND_CC-598] 2-Chloro-N-[6-[9-(3,3-dimethyl-butanoyl)-3,9-diazaspiro[5.5]undecane-3-carbonyl]-2,3-dihydro-1H-inden-1-yl]-benzamide
[IND_CC-599] 2-Chloro-N-[6-[9-(2-chloro-4-fluoro-benzoyl)-3,9-diazaspiro[5.5]undecane-3-carbonyl]-2,3-dihydro-1H-inden-1-yl]-benzamide
[IND_CC-600] 2-Chloro-N-[6-[9-(2,4-difluoro-benzoyl)-3,9-diazaspiro[5.5]undecane-3-carbonyl]-2,3-dihydro-1H-inden-1-yl]-benzamide
[IND_CC-601] N-[6-[9-(5-tert-Butyl-2-methyl-2H-pyrazole-3-carbonyl)-3,9-diazaspiro-[5.5]undecane-3-carbonyl]-2,3-dihydro-1H-inden-1-yl]-2-chloro-benzamide
[IND_CC-602] N-[6-[9-(2-tert-Butyl-5-methyl-2H-pyrazole-3-carbonyl)-3,9-diazaspiro-[5.5]undecane-3-carbonyl]-2,3-dihydro-1H-inden-1-yl]-2-chloro-benzamide
[IND_CC-603] 2-Chloro-N-[6-[8-(cyclopropanecarbonyl)-2,8-diazaspiro[4.5]decane-2-carbonyl]-2,3-dihydro-1H-inden-1-yl]-N-cyclopropyl-benzamide

[IND_CC-604] 2-Chloro-N-cyclopropyl-N-[6-[8-(3,3-dimethyl-butanoyl)-2,8-diazaspiro[4.5]decane-2-carbonyl]-2,3-dihydro-1H-inden-1-yl]-benzamide

[IND_CC-605] 2-Chloro-N-[6-[8-(2-chloro-4-fluoro-benzoyl)-2,8-diazaspiro[4.5]decane-2-carbonyl]-2,3-dihydro-1H-inden-1-yl]-N-cyclopropyl-benzamide

[IND_CC-606] 2-Chloro-N-cyclopropyl-N-[6-[8-(2,4-difluoro-benzoyl)-2,8-diazaspiro[4.5]decane-2-carbonyl]-2,3-dihydro-1H-inden-1-yl]-benzamide

[IND_CC-607] N-[6-[8-(5-tert-Butyl-2-methyl-2H-pyrazole-3-carbonyl)-2,8-diazaspiro[4.5]decane-2-carbonyl]-2,3-dihydro-1H-inden-1-yl]-2-chloro-N-cyclopropyl-benzamide

[IND_CC-608] 2-Chloro-N-[6-[9-[(5-chloro-thiophen-2-yl)sulfonyl]-3,9-diazaspiro[5.5]undecane-3-carbonyl]-2,3-dihydro-1H-inden-1-yl]-benzamide

[IND_CC-609] 2-Chloro-N-[6-[9-[(2,4-difluoro-phenyl)sulfonyl]-3,9-diazaspiro[5.5]undecane-3-carbonyl]-2,3-dihydro-1H-inden-1-yl]-benzamide

[IND_CC-610] 2-Chloro-N-[6-[9-[(3-cyano-4-fluoro-phenyl)sulfonyl]-3,9-diazaspiro[5.5]undecane-3-carbonyl]-2,3-dihydro-1H-inden-1-yl]-benzamide

[IND_CC-611] 2-Chloro-N-[6-[9-[(2-cyano-phenyl)sulfonyl]-3,9-diazaspiro[5.5]undecane-3-carbonyl]-2,3-dihydro-1H-inden-1-yl]-benzamide

[IND_CC-612] 2-Chloro-N-[6-[9-[(1-methyl-1H-indol-4-yl)sulfonyl]-3,9-diazaspiro[5.5]undecane-3-carbonyl]-2,3-dihydro-1H-inden-1-yl]-benzamide

[IND_CC-613] 2-Chloro-N-[6-[9-(isopropylsulfonyl)-3,9-diazaspiro[5.5]undecane-3-carbonyl]-2,3-dihydro-1H-inden-1-yl]-benzamide

[IND_CC-614] 2-Chloro-N-[6-[9-[(1-methyl-1H-indol-5-yl)sulfonyl]-3,9-diazaspiro[5.5]undecane-3-carbonyl]-2,3-dihydro-1H-inden-1-yl]-benzamide

[IND_CC-615] 2-Chloro-N-[6-[8-[(5-chloro-thiophen-2-yl)sulfonyl]-2,8-diazaspiro[4.5]-decane-2-carbonyl]-2,3-dihydro-1H-inden-1-yl]-N-cyclopropyl-benzamide

[IND_CC-616] 2-Chloro-N-cyclopropyl-N-[6-[8-[(2,4-difluoro-phenyl)sulfonyl]-2,8-diazaspiro[4.5]decane-2-carbonyl]-2,3-dihydro-1H-inden-1-yl]-benzamide

[IND_CC-617] 2-Chloro-N-[6-[8-[(3-cyano-4-fluoro-phenyl)sulfonyl]-2,8-diazaspiro[4.5]-decane-2-carbonyl]-2,3-dihydro-1H-inden-1-yl]-N-cyclopropyl-benzamide

[IND_CC-618] 2-Chloro-N-[6-[8-[(2-cyano-phenyl)sulfonyl]-2,8-diazaspiro[4.5]decane-2-carbonyl]-2,3-dihydro-1H-inden-1-yl]-N-cyclopropyl-benzamide

[IND_CC-619] 2-Chloro-N-cyclopropyl-N-[6-[8-[(1-methyl-1H-indol-5-yl)sulfonyl]-2,8-diazaspiro[4.5]decane-2-carbonyl]-2,3-dihydro-1H-inden-1-yl]-benzamide

[IND_CC-620] 5-Chloro-2-fluoro-N-[6-[8-(1H-pyrrol-2-yl-methyl)-2,8-diazaspiro[4.5]decane-2-carbonyl]-2,3-dihydro-1H-inden-1-yl]-benzamide

[IND_CC-621] 5-Chloro-N-[6-[8-[(3,4-difluoro-phenyl)-methyl]-2,8-diazaspiro[4.5]decane-2-carbonyl]-2,3-dihydro-1H-inden-1-yl]-2-fluoro-benzamide

[IND_CC-622] 5-Chloro-N-[6-[8-[(2,4-difluoro-phenyl)-methyl]-2,8-diazaspiro[4.5]decane-2-carbonyl]-2,3-dihydro-1H-inden-1-yl]-2-fluoro-benzamide

[IND_CC-623] 5-Chloro-2-fluoro-N-[6-[8-[(3-fluoro-4-methoxy-phenyl)-methyl]-2,8-diazaspiro[4.5]decane-2-carbonyl]-2,3-dihydro-1H-inden-1-yl]-benzamide

[IND_CC-624] 5-Chloro-2-fluoro-N-[6-[9-(1H-pyrrol-2-yl-methyl)-3,9-diazaspiro[5.5]undecane-3-carbonyl]-2,3-dihydro-1H-inden-1-yl]-benzamide

[IND_CC-625] 5-Chloro-2-fluoro-N-[6-[9-(1H-imidazol-4-yl-methyl)-3,9-diazaspiro[5.5]undecane-3-carbonyl]-2,3-dihydro-1H-inden-1-yl]-benzamide

[IND_CC-626] 5-Chloro-2-fluoro-N-[6-[9-(pyridin-2-yl-methyl)-3,9-diazaspiro[5.5]undecane-3-carbonyl]-2,3-dihydro-1H-inden-1-yl]-benzamide

[IND_CC-627] 5-Chloro-2-fluoro-N-[6-[9-(pyridin-4-yl-methyl)-3,9-diazaspiro[5.5]undecane-3-carbonyl]-2,3-dihydro-1H-inden-1-yl]-benzamide

[IND_CC-628] 5-Chloro-N-[6-[9-[(3,4-difluoro-phenyl)-methyl]-3,9-diazaspiro[5.5]undecane-3-carbonyl]-2,3-dihydro-1H-inden-1-yl]-2-fluoro-benzamide

[IND_CC-629] 5-Chloro-N-[6-[9-[(2,4-difluoro-phenyl)-methyl]-3,9-diazaspiro[5.5]undecane-3-carbonyl]-2,3-dihydro-1H-inden-1-yl]-2-fluoro-benzamide

[IND_CC-630] 5-Chloro-2-fluoro-N-[6-[9-[(3-fluoro-4-methoxy-phenyl)-methyl]-3,9-diazaspiro[5.5]undecane-3-carbonyl]-2,3-dihydro-1H-inden-1-yl]-benzamide

[IND_CC-631] 2-Chloro-N-[6-[8-(1H-imidazol-4-yl-methyl)-2,8-diazaspiro[4.5]decane-2-carbonyl]-2,3-dihydro-1H-inden-1-yl]-5-(trifluoromethyl)-benzamide

[IND_CC-632] 2-Chloro-N-[6-[8-[(2,6-difluoro-phenyl)-methyl]-2,8-diazaspiro[4.5]decane-2-carbonyl]-2,3-dihydro-1H-inden-1-yl]-5-(trifluoromethyl)-benzamide

[IND_CC-633] 2-Chloro-N-[6-[8-[(3,4-difluoro-phenyl)-methyl]-2,8-diazaspiro[4.5]decane-2-carbonyl]-2,3-dihydro-1H-inden-1-yl]-5-(trifluoromethyl)-benzamide

[IND_CC-634] 2-Chloro-N-[6-[8-[(2,5-difluoro-phenyl)-methyl]-2,8-diazaspiro[4.5]decane-2-carbonyl]-2,3-dihydro-1H-inden-1-yl]-5-(trifluoromethyl)-benzamide

[IND_CC-635] 2-Chloro-N-[6-[8-[(2,4-difluoro-phenyl)-methyl]-2,8-diazaspiro[4.5]decane-2-carbonyl]-2,3-dihydro-1H-inden-1-yl]-5-(trifluoromethyl)-benzamide

[IND_CC-636] 2-Chloro-N-[6-[8-[(3-fluoro-4-methoxy-phenyl)-methyl]-2,8-diazaspiro[4.5]-decane-2-carbonyl]-2,3-dihydro-1H-inden-1-yl]-5-(trifluoromethyl)-benzamide

[IND_CC-637] 2-Chloro-N-[6-[8-[(2-fluoro-6-methoxy-phenyl)-methyl]-2,8-diazaspiro[4.5]-decane-2-carbonyl]-2,3-dihydro-1H-inden-1-yl]-5-(trifluoromethyl)-benzamide

[IND_CC-638] 2-Chloro-N-[6-[9-(1H-pyrrol-2-yl-methyl)-3,9-diazaspiro[5.5]undecane-3-carbonyl]-2,3-dihydro-1H-inden-1-yl]-5-(trifluoromethyl)-benzamide

[IND_CC-639] 2-Chloro-N-[6-[9-(1H-imidazol-4-yl-methyl)-3,9-diazaspiro[5.5]undecane-3-carbonyl]-2,3-dihydro-1H-inden-1-yl]-5-(trifluoromethyl)-benzamide

[IND_CC-640] 2-Chloro-N-[6-[9-(pyridin-2-yl-methyl)-3,9-diazaspiro[5.5]undecane-3-carbonyl]-2,3-dihydro-1H-inden-1-yl]-5-(trifluoromethyl)-benzamide

[IND_CC-641] 2-Chloro-N-[6-[9-(pyridin-4-yl-methyl)-3,9-diazaspiro[5.5]undecane-3-carbonyl]-2,3-dihydro-1H-inden-1-yl]-5-(trifluoromethyl)-benzamide

[IND_CC-642] 2-Chloro-N-[6-[9-(pyridin-3-yl-methyl)-3,9-diazaspiro[5.5]undecane-3-carbonyl]-2,3-dihydro-1H-inden-1-yl]-5-(trifluoromethyl)-benzamide

[IND_CC-643] 2-Chloro-N-[6-[9-[(1-methyl-1H-pyrrol-2-yl)-methyl]-3,9-diazaspiro[5.5]-undecane-3-carbonyl]-2,3-dihydro-1H-inden-1-yl]-5-(trifluoromethyl)benzamide

[IND_CC-644] 2-Chloro-N-[6-[9-[(2,6-difluoro-phenyl)-methyl]-3,9-diazaspiro[5.5]undecane-3-carbonyl]-2,3-dihydro-1H-inden-1-yl]-5-(trifluoromethyl)-benzamide

[IND_CC-645] 2-Chloro-N-[6-[9-[(3,4-difluoro-phenyl)-methyl]-3,9-diazaspiro[5.5]undecane-3-carbonyl]-2,3-dihydro-1H-inden-1-yl]-5-(trifluoromethyl)-benzamide

[IND_CC-646] 2-Chloro-N-[6-[9-[(2,5-difluoro-phenyl)-methyl]-3,9-diazaspiro[5.5]undecane-3-carbonyl]-2,3-dihydro-1H-inden-1-yl]-5-(trifluoromethyl)-benzamide

[IND_CC-647] 2-Chloro-N-[6-[9-[(2,4-difluoro-phenyl)-methyl]-3,9-diazaspiro[5.5]undecane-3-carbonyl]-2,3-dihydro-1H-inden-1-yl]-5-(trifluoromethyl)-benzamide

[IND_CC-648] 2-Chloro-N-[6-[9-[(3-fluoro-4-methoxy-phenyl)-methyl]-3,9-diazaspiro[5.5]-undecane-3-carbonyl]-2,3-dihydro-1H-inden-1-yl]-5-(trifluoromethyl)benzamide

[IND_CC-649] 2-Chloro-N-[6-[9-[(2-fluoro-6-methoxy-phenyl)-methyl]-3,9-diazaspiro[5.5]-undecane-3-carbonyl]-2,3-dihydro-1H-inden-1-yl]-5-(trifluoromethyl)benzamide

[IND_CC-650] 5-Chloro-N-[6-[8-[(4-cyano-phenyl)-methyl]-2,8-diazaspiro[4.5]decane-2-carbonyl]-2,3-dihydro-1H-inden-1-yl]-2-fluoro-benzamide

[IND_CC-651] 5-Chloro-N-[6-[8-[(3-cyano-phenyl)-methyl]-2,8-diazaspiro[4.5]decane-2-carbonyl]-2,3-dihydro-1H-inden-1-yl]-2-fluoro-benzamide

[IND_CC-652] 5-Chloro-2-fluoro-N-[6-[9-([1,2,3]thiadiazol-4-yl-methyl)-3,9-diazaspiro[5.5]undecane-3-carbonyl]-2,3-dihydro-1H-inden-1-yl]-benzamide

[IND_CC-653] 5-Chloro-N-[6-[9-[(4-cyano-phenyl)-methyl]-3,9-diazaspiro[5.5]undecane-3-carbonyl]-2,3-dihydro-1H-inden-1-yl]-2-fluoro-benzamide

[IND_CC-654] 5-Chloro-N-[6-[9-[(3-cyano-phenyl)-methyl]-3,9-diazaspiro[5.5]undecane-3-carbonyl]-2,3-dihydro-1H-inden-1-yl]-2-fluoro-benzamide

[IND_CC-655] 2-Chloro-N-[6-[8-[(5-methyl-3H-imidazol-4-yl)-methyl]-2,8-diazaspiro[4.5]-decane-2-carbonyl]-2,3-dihydro-1H-inden-1-yl]-5-(trifluoromethyl)-benzamide

[IND_CC-656] 2-Chloro-N-[6-[8-([1,2,3]thiadiazol-4-yl-methyl)-2,8-diazaspiro[4.5]decane-2-carbonyl]-2,3-dihydro-1H-inden-1-yl]-5-(trifluoromethyl)-benzamide

[IND_CC-657] 2-Chloro-N-[6-[8-[(3,5-dimethyl-isoxazol-4-yl)-methyl]-2,8-diazaspiro[4.5]-decane-2-carbonyl]-2,3-dihydro-1H-inden-1-yl]-5-(trifluoromethyl)-benzamide

[IND_CC-658] 2-Chloro-N-[6-[8-[(4-cyano-phenyl)-methyl]-2,8-diazaspiro[4.5]decane-2-carbonyl]-2,3-dihydro-1H-inden-1-yl]-5-(trifluoromethyl)-benzamide

[IND_CC-659] 2-Chloro-N-[6-[8-[(3-cyano-phenyl)-methyl]-2,8-diazaspiro[4.5]decane-2-carbonyl]-2,3-dihydro-1H-inden-1-yl]-5-(trifluoromethyl)-benzamide

[IND_CC-660] 2-Chloro-N-[6-[8-[(2-cyano-phenyl)-methyl]-2,8-diazaspiro[4.5]decane-2-carbonyl]-2,3-dihydro-1H-inden-1-yl]-5-(trifluoromethyl)-benzamide

[IND_CC-661] 2-Chloro-N-[6-[9-[(5-methyl-3H-imidazol-4-yl)-methyl]-3,9-diazaspiro[5.5]-undecane-3-carbonyl]-2,3-dihydro-1H-inden-1-yl]-5-(trifluoromethyl)benzamide

[IND_CC-662] 2-Chloro-N-[6-[9-[(2-methyl-1H-imidazol-4-yl)-methyl]-3,9-diazaspiro[5.5]-undecane-3-carbonyl]-2,3-dihydro-1H-inden-1-yl]-5-(trifluoromethyl)benzamide

[IND_CC-663] 2-Chloro-N-[6-[9-([1,2,3]thiadiazol-4-yl-methyl)-3,9-diazaspiro[5.5]undecane-3-carbonyl]-2,3-dihydro-1H-inden-1-yl]-5-(trifluoromethyl)-benzamide

[IND_CC-664] 2-Chloro-N-[6-[9-[(1,5-dimethyl-1H-pyrazol-4-yl)-methyl]-3,9-diazaspiro[5.5]-undecane-3-carbonyl]-2,3-dihydro-1H-inden-1-yl]-5-(trifluoromethyl)benzamide

[IND_CC-665] 2-Chloro-N-[6-[9-[(3,5-dimethyl-isoxazol-4-yl)-methyl]-3,9-diazaspiro[5.5]-undecane-3-carbonyl]-2,3-dihydro-1H-inden-1-yl]-5-(trifluoromethyl)benzamide

[IND_CC-666] 2-Chloro-N-[6-[9-[(4-cyano-phenyl)-methyl]-3,9-diazaspiro[5.5]undecane-3-carbonyl]-2,3-dihydro-1H-inden-1-yl]-5-(trifluoromethyl)-benzamide

[IND_CC-667] 2-Chloro-N-[6-[9-[(3-cyano-phenyl)-methyl]-3,9-diazaspiro[5.5]undecane-3-carbonyl]-2,3-dihydro-1H-inden-1-yl]-5-(trifluoromethyl)-benzamide

[IND_CC-668] 2-Chloro-N-[6-[9-[(2-cyano-phenyl)-methyl]-3,9-diazaspiro[5.5]undecane-3-carbonyl]-2,3-dihydro-1H-inden-1-yl]-5-(trifluoromethyl)-benzamide

[IND_CC-669] 2-Chloro-N-[6-[9-[(2-chloro-4-fluoro-phenyl)-methyl]-3,9-diazaspiro[5.5]-undecane-3-carbonyl]-2,3-dihydro-1H-inden-1-yl]-5-(trifluoromethyl)benzamide

[IND_CC-670] 2-Chloro-N-[6-[9-[(2-chloro-6-fluoro-phenyl)-methyl]-3,9-diazaspiro[5.5]-undecane-3-carbonyl]-2,3-dihydro-1H-inden-1-yl]-5-(trifluoromethyl)benzamide

[IND_CC-671] 5-Chloro-2-fluoro-N-[6-[8-(quinolin-6-yl-methyl)-2,8-diazaspiro[4.5]decane-2-carbonyl]-2,3-dihydro-1H-inden-1-yl]-benzamide

[IND_CC-672] 5-Chloro-2-fluoro-N-[6-[8-(quinoxalin-6-yl-methyl)-2,8-diazaspiro[4.5]decane-2-carbonyl]-2,3-dihydro-1H-inden-1-yl]-benzamide

[IND_CC-673] 5-Chloro-2-fluoro-N-[6-[8-[(1-methyl-1H-benzotriazol-5-yl)-methyl]-2,8-diazaspiro[4.5]decane-2-carbonyl]-2,3-dihydro-1H-inden-1-yl]-benzamide

[IND_CC-674] 5-Chloro-2-fluoro-N-[6-[8-[3-(3-fluorophenyl)-propyl]-2,8-diazaspiro[4.5]decane-2-carbonyl]-2,3-dihydro-1H-inden-1-yl]-benzamide

[IND_CC-675] 5-Chloro-2-fluoro-N-[6-[8-[3-(4-fluorophenyl)-propyl]-2,8-diazaspiro[4.5]decane-2-carbonyl]-2,3-dihydro-1H-inden-1-yl]-benzamide

[IND_CC-676] 5-Chloro-N-[6-[9-[(2-dimethylamino-pyrimidin-5-yl)-methyl]-3,9-diazaspiro-[5.5]undecane-3-carbonyl]-2,3-dihydro-1H-inden-1-yl]-2-fluoro-benzamide

[IND_CC-677] 5-Chloro-2-fluoro-N-[6-[9-(quinolin-6-yl-methyl)-3,9-diazaspiro[5.5]undecane-3-carbonyl]-2,3-dihydro-1H-inden-1-yl]-benzamide

[IND_CC-678] 5-Chloro-2-fluoro-N-[6-[9-(quinoxalin-6-yl-methyl)-3,9-diazaspiro[5.5]undecane-3-carbonyl]-2,3-dihydro-1H-inden-1-yl]-benzamide

[IND_CC-679] 5-Chloro-2-fluoro-N-[6-[9-[(1-methyl-1H-benzotriazol-5-yl)-methyl]-3,9-diazaspiro[5.5]undecane-3-carbonyl]-2,3-dihydro-1H-inden-1-yl]-benzamide

[IND_CC-680] 5-Chloro-2-fluoro-N-[6-[9-(2-methyl-propyl)-3,9-diazaspiro[5.5]undecane-3-carbonyl]-2,3-dihydro-1H-inden-1-yl]-benzamide

[IND_CC-681] 5-Chloro-2-fluoro-N-[6-(9-phenethyl-3,9-diazaspiro[5.5]undecane-3-carbonyl)-2,3-dihydro-1H-inden-1-yl]-benzamide

[IND_CC-682] 2-Chloro-5-(trifluoromethyl)-N-[6-[8-[(1,3,5-trimethyl-1H-pyrazol-4-yl)-methyl]-2,8-diazaspiro[4.5]decane-2-carbonyl]-2,3-dihydro-1H-inden-1-yl]-benzamide

[IND_CC-683] 2-Chloro-N-[6-[8-[(2-dimethylamino-pyrimidin-5-yl)-methyl]-2,8-diazaspiro[4.5]-decane-2-carbonyl]-2,3-dihydro-1H-inden-1-yl]-5-(trifluoromethyl)-benzamide

[IND_CC-684] 2-Chloro-N-[6-[8-(quinolin-6-yl-methyl)-2,8-diazaspiro[4.5]decane-2-carbonyl]-2,3-dihydro-1H-inden-1-yl]-5-(trifluoromethyl)-benzamide

[IND_CC-685] 2-Chloro-N-[6-[8-(quinoxalin-6-yl-methyl)-2,8-diazaspiro[4.5]decane-2-carbonyl]-2,3-dihydro-1H-inden-1-yl]-5-(trifluoromethyl)-benzamide

[IND_CC-686] 2-Chloro-N-[6-[8-[(1-methyl-1H-benzotriazol-5-yl)-methyl]-2,8-diazaspiro[4.5]-decane-2-carbonyl]-2,3-dihydro-1H-inden-1-yl]-5-(trifluoromethyl)-benzamide

[IND_CC-687] 2-Chloro-N-[6-[8-(2-methyl-propyl)-2,8-diazaspiro[4.5]decane-2-carbonyl]-2,3-dihydro-1H-inden-1-yl]-5-(trifluoromethyl)-benzamide

[IND_CC-688] 2-Chloro-N-[6-[8-(2-ethyl-butyl)-2,8-diazaspiro[4.5]decane-2-carbonyl]-2,3-dihydro-1H-inden-1-yl]-5-(trifluoromethyl)-benzamide

[IND_CC-689] 2-Chloro-N-[6-[8-(cyclohexyl-methyl)-2,8-diazaspiro[4.5]decane-2-carbonyl]-2,3-dihydro-1H-inden-1-yl]-5-(trifluoromethyl)-benzamide

[IND_CC-690] 2-Chloro-N-[6-(8-phenethyl-2,8-diazaspiro[4.5]decane-2-carbonyl)-2,3-dihydro-1H-inden-1-yl]-5-(trifluoromethyl)-benzamide

[IND_CC-691] 2-Chloro-N-[6-[8-[3-(3-fluorophenyl)-propyl]-2,8-diazaspiro[4.5]decane-2-carbonyl]-2,3-dihydro-1H-inden-1-yl]-5-(trifluoromethyl)-benzamide

[IND_CC-692] 2-Chloro-N-[6-[8-[3-(4-fluorophenyl)-propyl]-2,8-diazaspiro[4.5]decane-2-carbonyl]-2,3-dihydro-1H-inden-1-yl]-5-(trifluoromethyl)-benzamide

[IND_CC-693] 2-Chloro-N-[6-[9-[(1-ethyl-3-methyl-1H-pyrazol-4-yl)-methyl]-3,9-diazaspiro[5.5]-undecane-3-carbonyl]-2,3-dihydro-1H-inden-1-yl]-5-(trifluoromethyl)-benzamide

[IND_CC-694] 2-Chloro-N-[6-[9-[(2-dimethylamino-pyrimidin-5-yl)-methyl]-3,9-diazaspiro[5.5]-undecane-3-carbonyl]-2,3-dihydro-1H-inden-1-yl]-5-(trifluoromethyl)-benzamide

[IND_CC-695] 2-Chloro-N-[6-[9-(quinolin-6-yl-methyl)-3,9-diazaspiro[5.5]undecane-3-carbonyl]-2,3-dihydro-1H-inden-1-yl]-5-(trifluoromethyl)-benzamide

[IND_CC-696] 2-Chloro-N-[6-[9-(quinoxalin-6-yl-methyl)-3,9-diazaspiro[5.5]undecane-3-carbonyl]-2,3-dihydro-1H-inden-1-yl]-5-(trifluoromethyl)-benzamide

[IND_CC-697] 2-Chloro-N-[6-[9-[(1-methyl-1H-benzotriazol-5-yl)-methyl]-3,9-diazaspiro[5.5]undecane-3-carbonyl]-2,3-dihydro-1H-inden-1-yl]-5-(trifluoromethyl)-benzamide

[IND_CC-698] 2-Chloro-N-[6-[9-(2-methyl-propyl)-3,9-diazaspiro[5.5]undecane-3-carbonyl]-2,3-dihydro-1H-inden-1-yl]-5-(trifluoromethyl)-benzamide

[IND_CC-699] 2-Chloro-N-[6-[9-(2-ethyl-butyl)-3,9-diazaspiro[5.5]undecane-3-carbonyl]-2,3-dihydro-1H-inden-1-yl]-5-(trifluoromethyl)-benzamide

[IND_CC-700] 2-Chloro-N-[6-[9-(cyclohexyl-methyl)-3,9-diazaspiro[5.5]undecane-3-carbonyl]-2,3-dihydro-1H-inden-1-yl]-5-(trifluoromethyl)-benzamide

[IND_CC-701] 2-Chloro-N-[6-(9-phenethyl-3,9-diazaspiro[5.5]undecane-3-carbonyl)-2,3-dihydro-1H-inden-1-yl]-5-(trifluoromethyl)-benzamide

[IND_CC-702] 2-Chloro-N-[6-[9-[3-(3-fluorophenyl)-propyl]-3,9-diazaspiro[5.5]undecane-3-carbonyl]-2,3-dihydro-1H-inden-1-yl]-5-(trifluoromethyl)-benzamide

[IND_CC-703] 2-Chloro-N-[6-[9-[3-(4-fluorophenyl)-propyl]-3,9-diazaspiro[5.5]undecane-3-carbonyl]-2,3-dihydro-1H-inden-1-yl]-5-(trifluoromethyl)-benzamide

[IND_CC-704] 3-[3-[(2-Chloro-benzoyl)amino]-2,3-dihydro-1H-indene-5-carbonyl]-N-propyl-3,9-diazaspiro[5.5]undecane-9-carboxylic acid amide

[IND_CC-705] 3-[3-[(2-Chloro-benzoyl)amino]-2,3-dihydro-1H-indene-5-carbonyl]-N-(3-cyano-phenyl)-3,9-diazaspiro[5.5]undecane-9-carboxylic acid amide

[IND_CC-706] N-Benzyl-3-[3-[(2-chloro-benzoyl)amino]-2,3-dihydro-1H-indene-5-carbonyl]-3,9-diazaspiro[5.5]undecane-9-carboxylic acid amide

[IND_CC-707] 3-[3-[(2-Chloro-benzoyl)amino]-2,3-dihydro-1H-indene-5-carbonyl]-N-(4-dimethylaminophenyl)-3,9-diazaspiro[5.5]undecane-9-carboxylic acid amide

[IND_CC-708] 3-[3-[(2-Chloro-benzoyl)amino]-2,3-dihydro-1H-indene-5-carbonyl]-N-cyclohexyl-3,9-diazaspiro[5.5]undecane-9-carboxylic acid amide

[IND_CC-709] 3-[3-[(2-Chloro-benzoyl)amino]-2,3-dihydro-1H-indene-5-carbonyl]-N-(2,6-dichloro-phenyl)-3,9-diazaspiro[5.5]undecane-9-carboxylic acid amide

[IND_CC-710] 3-[3-[(2-Chloro-benzoyl)amino]-2,3-dihydro-1H-indene-5-carbonyl]-N-(2,4-dichlorophenyl)-3,9-diazaspiro[5.5]undecane-9-carboxylic acid amide

[IND_CC-711] 3-[3-[(2-Chloro-benzoyl)amino]-2,3-dihydro-1H-indene-5-carbonyl]-N-(2,4-difluoro-phenyl)-3,9-diazaspiro[5.5]undecane-9-carboxylic acid amide

[IND_CC-712] 2-[3-[(2-Chloro-benzoyl)-cyclopropyl-amino]-2,3-dihydro-1H-indene-5-carbonyl]-N-propyl-2,8-diazaspiro[4.5]decane-8-carboxylic acid amide

[IND_CC-713] 2-[3-[(2-Chloro-benzoyl)-cyclopropyl-amino]-2,3-dihydro-1H-indene-5-carbonyl]-N-(3-chloro-4-fluoro-phenyl)-2,8-diazaspiro[4.5]decane-8-carboxylic acid amide

[IND_CC-714] 2-[3-[(2-Chloro-benzoyl)-cyclopropyl-amino]-2,3-dihydro-1H-indene-5-carbonyl]-N-[4-chloro-2-(trifluoromethyl)-phenyl]-2,8-diazaspiro[4.5]decane-8-carboxylic acid amide

[IND_CC-715] 2-[3-[(2-Chloro-benzoyl)-cyclopropyl-amino]-2,3-dihydro-1H-indene-5-carbonyl]-N-(3-cyano-phenyl)-2,8-diazaspiro[4.5]decane-8-carboxylic acid amide

[IND_CC-716] N-Benzyl-2-[3-[(2-chloro-benzoyl)-cyclopropyl-amino]-2,3-dihydro-1H-indene-5-carbonyl]-2,8-diazaspiro[4.5]decane-8-carboxylic acid amide

[IND_CC-717] 2-[3-[(2-Chloro-benzoyl)-cyclopropyl-amino]-2,3-dihydro-1H-indene-5-carbonyl]-N-cyclohexyl-2,8-diazaspiro[4.5]decane-8-carboxylic acid amide

[IND_CC-718] 2-[3-[(2-Chloro-benzoyl)-cyclopropyl-amino]-2,3-dihydro-1H-indene-5-carbonyl]-N-(2,6-dichloro-phenyl)-2,8-diazaspiro[4.5]decane-8-carboxylic acid amide

[IND_CC-719] 2-[3-[(2-Chloro-benzoyl)-cyclopropyl-amino]-2,3-dihydro-1H-indene-5-carbonyl]-N-(2,4-difluoro-phenyl)-2,8-diazaspiro[4.5]decane-8-carboxylic acid amide

[IND_CC-720] 2-[3-[(2-Chloro-benzoyl)-cyclopropyl-amino]-2,3-dihydro-1H-indene-5-carbonyl]-N-(3,5-difluoro-phenyl)-2,8-diazaspiro[4.5]decane-8-carboxylic acid amide

[IND_CC-721] 2-[3-[(2-Chloro-benzoyl)-cyclopropyl-amino]-2,3-dihydro-1H-indene-5-carbonyl]-N-[(3,4-dichlorophenyl)-methyl]-2,8-diazaspiro[4.5]decane-8-carboxylic acid amide

[IND_CC-722] 2,3-Dichloro-N-[6-[8-[(1,5-dimethyl-1H-pyrazol-4-yl)-methyl]-2,8-diazaspiro[4.5]decane-2-carbonyl]-2,3-dihydro-1H-inden-1-yl]-benzamide

[IND_CC-723] 2,3-Dichloro-N-[6-[8-[(3,5-dimethyl-isoxazol-4-yl)-methyl]-2,8-diazaspiro[4.5]decane-2-carbonyl]-2,3-dihydro-1H-inden-1-yl]-benzamide

[IND_CC-724] 2,3-Dichloro-N-[6-[8-[(2-cyano-phenyl)-methyl]-2,8-diazaspiro[4.5]decane-2-carbonyl]-2,3-dihydro-1H-inden-1-yl]-benzamide

[IND_CC-725] 2,3-Dichloro-N-[6-[8-[(2-chloro-6-fluoro-phenyl)-methyl]-2,8-diazaspiro[4.5]decane-2-carbonyl]-2,3-dihydro-1H-inden-1-yl]-benzamide

[IND_CC-726] 2,3-Dichloro-N-[6-[9-[(2-chloro-4-fluoro-phenyl)-methyl]-3,9-diazaspiro[5.5]undecane-3-carbonyl]-2,3-dihydro-1H-inden-1-yl]-benzamide

[IND_CC-727] 2,3-Dichloro-N-[6-[9-[(2-chloro-6-fluoro-phenyl)-methyl]-3,9-diazaspiro[5.5]undecane-3-carbonyl]-2,3-dihydro-1H-inden-1-yl]-benzamide

[IND_CC-728] 2-Chloro-6-methyl-N-[6-[8-[(2-methyl-1H-imidazol-4-yl)-methyl]-2,8-diazaspiro[4.5]decane-2-carbonyl]-2,3-dihydro-1H-inden-1-yl]-benzamide

[IND_CC-729] 2-Chloro-N-[6-[8-[(1,5-dimethyl-1H-pyrazol-4-yl)-methyl]-2,8-diazaspiro-[4.5]decane-2-carbonyl]-2,3-dihydro-1H-inden-1-yl]-6-methyl-benzamide

[IND_CC-730] 2-Chloro-N-[6-[8-[(3,5-dimethyl-isoxazol-4-yl)-methyl]-2,8-diazaspiro-[4.5]decane-2-carbonyl]-2,3-dihydro-1H-inden-1-yl]-6-methyl-benzamide

[IND_CC-731] 2-Chloro-N-[6-[8-[(4-cyano-phenyl)-methyl]-2,8-diazaspiro[4.5]decane-2-carbonyl]-2,3-dihydro-1H-inden-1-yl]-6-methyl-benzamide

[IND_CC-732] 2-Chloro-N-[6-[8-[(3-cyano-phenyl)-methyl]-2,8-diazaspiro[4.5]decane-2-carbonyl]-2,3-dihydro-1H-inden-1-yl]-6-methyl-benzamide

[IND_CC-733] 2-Chloro-N-[6-[8-[(2-cyano-phenyl)-methyl]-2,8-diazaspiro[4.5]decane-2-carbonyl]-2,3-dihydro-1H-inden-1-yl]-6-methyl-benzamide

[IND_CC-734] 2-Chloro-N-[6-[8-[(2-chloro-4-fluoro-phenyl)-methyl]-2,8-diazaspiro-[4.5]decane-2-carbonyl]-2,3-dihydro-1H-inden-1-yl]-6-methyl-benzamide

[IND_CC-735] 2-Chloro-N-[6-[8-[(2-chloro-6-fluoro-phenyl)-methyl]-2,8-diazaspiro-[4.5]decane-2-carbonyl]-2,3-dihydro-1H-inden-1-yl]-6-methyl-benzamide

[IND_CC-736] 2-Chloro-6-fluoro-N-[6-[8-[(2-methyl-1H-imidazol-4-yl)-methyl]-2,8-diazaspiro[4.5]decane-2-carbonyl]-2,3-dihydro-1H-inden-1-yl]-benzamide

[IND_CC-737] 2-Chloro-N-[6-[8-[(1,5-dimethyl-1H-pyrazol-4-yl)-methyl]-2,8-diazaspiro-[4.5]decane-2-carbonyl]-2,3-dihydro-1H-inden-1-yl]-6-fluoro-benzamide

[IND_CC-738] 2-Chloro-N-[6-[8-[(3,5-dimethyl-isoxazol-4-yl)-methyl]-2,8-diazaspiro-[4.5]decane-2-carbonyl]-2,3-dihydro-1H-inden-1-yl]-6-fluoro-benzamide

[IND_CC-739] 2-Chloro-N-[6-[8-[(4-cyano-phenyl)-methyl]-2,8-diazaspiro[4.5]decane-2-carbonyl]-2,3-dihydro-1H-inden-1-yl]-6-fluoro-benzamide

[IND_CC-740] 2-Chloro-N-[6-[8-[(2-cyano-phenyl)-methyl]-2,8-diazaspiro[4.5]decane-2-carbonyl]-2,3-dihydro-1H-inden-1-yl]-6-fluoro-benzamide

[IND_CC-741] 2-Chloro-N-[6-[8-[(2-chloro-4-fluoro-phenyl)-methyl]-2,8-diazaspiro-[4.5]decane-2-carbonyl]-2,3-dihydro-1H-inden-1-yl]-6-fluoro-benzamide

[IND_CC-742] 2,3-Dichloro-N-[6-[8-[(1-ethyl-3-methyl-1H-pyrazol-4-yl)-methyl]-2,8-diazaspiro[4.5]decane-2-carbonyl]-2,3-dihydro-1H-inden-1-yl]-benzamide

[IND_CC-743] 2,3-Dichloro-N-[6-[8-[(2-dimethylamino-pyrimidin-5-yl)-methyl]-2,8-diazaspiro[4.5]decane-2-carbonyl]-2,3-dihydro-1H-inden-1-yl]-benzamide

[IND_CC-744] 2,3-Dichloro-N-[6-[8-(quinolin-6-yl-methyl)-2,8-diazaspiro[4.5]decane-2-carbonyl]-2,3-dihydro-1H-inden-1-yl]-benzamide

[IND_CC-745] 2,3-Dichloro-N-[6-[8-(quinoxalin-6-yl-methyl)-2,8-diazaspiro[4.5]decane-2-carbonyl]-2,3-dihydro-1H-inden-1-yl]-benzamide

[IND_CC-746] 2,3-Dichloro-N-[6-[8-[(1-methyl-1H-benzotriazol-5-yl)-methyl]-2,8-diazaspiro[4.5]decane-2-carbonyl]-2,3-dihydro-1H-inden-1-yl]-benzamide

[IND_CC-747] 2,3-Dichloro-N-[6-[8-(2-methyl-propyl)-2,8-diazaspiro[4.5]decane-2-carbonyl]-2,3-dihydro-1H-inden-1-yl]-benzamide

[IND_CC-748] 2,3-Dichloro-N-[6-[8-(2-ethyl-butyl)-2,8-diazaspiro[4.5]decane-2-carbonyl]-2,3-dihydro-1H-inden-1-yl]-benzamide

[IND_CC-749] 2,3-Dichloro-N-[6-(8-phenethyl-2,8-diazaspiro[4.5]decane-2-carbonyl)-2,3-dihydro-1H-inden-1-yl]-benzamide

[IND_CC-750] 2,3-Dichloro-N-[6-[8-[3-(3-fluorophenyl)-propyl]-2,8-diazaspiro[4.5]decane-2-carbonyl]-2,3-dihydro-1H-inden-1-yl]-benzamide

[IND_CC-751] 2,3-Dichloro-N-[6-[8-[3-(4-fluorophenyl)-propyl]-2,8-diazaspiro[4.5]decane-2-carbonyl]-2,3-dihydro-1H-inden-1-yl]-benzamide

[IND_CC-752] 2,3-Dichloro-N-[6-[9-[(1-ethyl-3-methyl-1H-pyrazol-4-yl)-methyl]-3,9-diazaspiro[5.5]undecane-3-carbonyl]-2,3-dihydro-1H-inden-1-yl]-benzamide

[IND_CC-753] 2,3-Dichloro-N-[6-[9-[(2-dimethylamino-pyrimidin-5-yl)-methyl]-3,9-diazaspiro[5.5]undecane-3-carbonyl]-2,3-dihydro-1H-inden-1-yl]-benzamide

[IND_CC-754] 2,3-Dichloro-N-[6-[9-(quinolin-6-yl-methyl)-3,9-diazaspiro[5.5]undecane-3-carbonyl]-2,3-dihydro-1H-inden-1-yl]-benzamide

[IND_CC-755] 2,3-Dichloro-N-[6-[9-(quinoxalin-6-yl-methyl)-3,9-diazaspiro[5.5]undecane-3-carbonyl]-2,3-dihydro-1H-inden-1-yl]-benzamide

[IND_CC-756] 2,3-Dichloro-N-[6-[9-[(1-methyl-1H-benzotriazol-5-yl)-methyl]-3,9-diazaspiro[5.5]undecane-3-carbonyl]-2,3-dihydro-1H-inden-1-yl]-benzamide

[IND_CC-757] 2,3-Dichloro-N-[6-[9-(2-methyl-propyl)-3,9-diazaspiro[5.5]undecane-3-carbonyl]-2,3-dihydro-1H-inden-1-yl]-benzamide

[IND_CC-758] 2,3-Dichloro-N-[6-(9-phenethyl-3,9-diazaspiro[5.5]undecane-3-carbonyl)-2,3-dihydro-1H-inden-1-yl]-benzamide

[IND_CC-759] 2,3-Dichloro-N-[6-[9-[3-(3-fluorophenyl)-propyl]-3,9-diazaspiro[5.5]undecane-3-carbonyl]-2,3-dihydro-1H-inden-1-yl]-benzamide

[IND_CC-760] 2,3-Dichloro-N-[6-[9-[3-(4-fluorophenyl)-propyl]-3,9-diazaspiro[5.5]undecane-3-carbonyl]-2,3-dihydro-1H-inden-1-yl]-benzamide

[IND_CC-761] 2-Chloro-6-methyl-N-[6-[8-[(1,3,5-trimethyl-1H-pyrazol-4-yl)-methyl]-2,8-diazaspiro[4.5]decane-2-carbonyl]-2,3-dihydro-1H-inden-1-yl]-benzamide

[IND_CC-762] 2-Chloro-N-[6-[8-[(1-ethyl-3-methyl-1H-pyrazol-4-yl)-methyl]-2,8-diazaspiro-[4.5]decane-2-carbonyl]-2,3-dihydro-1H-inden-1-yl]-6-methyl-benzamide

[IND_CC-763] 2-Chloro-N-[6-[8-[(2-dimethylamino-pyrimidin-5-yl)-methyl]-2,8-diazaspiro[4.5]decane-2-carbonyl]-2,3-dihydro-1H-inden-1-yl]-6-methyl-benzamide

[IND_CC-764] 2-Chloro-6-methyl-N-[6-[8-(quinolin-6-yl-methyl)-2,8-diazaspiro[4.5]decane-2-carbonyl]-2,3-dihydro-1H-inden-1-yl]-benzamide

[IND_CC-765] 2-Chloro-6-methyl-N-[6-[8-(quinoxalin-6-yl-methyl)-2,8-diazaspiro[4.5]-decane-2-carbonyl]-2,3-dihydro-1H-inden-1-yl]-benzamide

[IND_CC-766] 2-Chloro-6-methyl-N-[6-[8-[(1-methyl-1H-benzotriazol-5-yl)-methyl]-2,8-diazaspiro[4.5]decane-2-carbonyl]-2,3-dihydro-1H-inden-1-yl]-benzamide

[IND_CC-767] 2-Chloro-6-methyl-N-[6-[8-(2-methyl-propyl)-2,8-diazaspiro[4.5]decane-2-carbonyl]-2,3-dihydro-1H-inden-1-yl]-benzamide

[IND_CC-768] 2-Chloro-N-[6-[8-(2-ethyl-butyl)-2,8-diazaspiro[4.5]decane-2-carbonyl]-2,3-dihydro-1H-inden-1-yl]-6-methyl-benzamide

[IND_CC-769] 2-Chloro-6-methyl-N-[6-(8-phenethyl-2,8-diazaspiro[4.5]decane-2-carbonyl)-2,3-dihydro-1H-inden-1-yl]-benzamide

[IND_CC-770] 2-Chloro-N-[6-[8-[3-(3-fluorophenyl)-propyl]-2,8-diazaspiro[4.5]decane-2-carbonyl]-2,3-dihydro-1H-inden-1-yl]-6-methyl-benzamide

[IND_CC-771] 2-Chloro-N-[6-[8-[3-(4-fluorophenyl)-propyl]-2,8-diazaspiro[4.5]decane-2-carbonyl]-2,3-dihydro-1H-inden-1-yl]-6-methyl-benzamide

[IND_CC-772] 2-Chloro-N-[6-[8-[(1-ethyl-3-methyl-1H-pyrazol-4-yl)-methyl]-2,8-diazaspiro-[4.5]decane-2-carbonyl]-2,3-dihydro-1H-inden-1-yl]-6-fluoro-benzamide

[IND_CC-773] 2-Chloro-N-[6-[8-[(2-dimethylamino-pyrimidin-5-yl)-methyl]-2,8-diazaspiro-[4.5]decane-2-carbonyl]-2,3-dihydro-1H-inden-1-yl]-6-fluoro-benzamide

[IND_CC-774] 2-Chloro-6-fluoro-N-[6-[8-(quinolin-6-yl-methyl)-2,8-diazaspiro[4.5]decane-2-carbonyl]-2,3-dihydro-1H-inden-1-yl]-benzamide

[IND_CC-775] 2-Chloro-6-fluoro-N-[6-[8-(quinoxalin-6-yl-methyl)-2,8-diazaspiro[4.5]decane-2-carbonyl]-2,3-dihydro-1H-inden-1-yl]-benzamide

[IND_CC-776] 2-Chloro-6-fluoro-N-[6-[8-[(1-methyl-1H-benzotriazol-5-yl)-methyl]-2,8-diazaspiro[4.5]decane-2-carbonyl]-2,3-dihydro-1H-inden-1-yl]-benzamide

[IND_CC-777] 2-Chloro-6-fluoro-N-[6-[8-(2-methyl-propyl)-2,8-diazaspiro[4.5]decane-2-carbonyl]-2,3-dihydro-1H-inden-1-yl]-benzamide

[IND_CC-778] 2-Chloro-N-[6-[8-(2-ethyl-butyl)-2,8-diazaspiro[4.5]decane-2-carbonyl]-2,3-dihydro-1H-inden-1-yl]-6-fluoro-benzamide

[IND_CC-779] 2-Chloro-N-[6-[8-(cyclohexyl-methyl)-2,8-diazaspiro[4.5]decane-2-carbonyl]-2,3-dihydro-1H-inden-1-yl]-6-fluoro-benzamide

[IND_CC-780] 2-Chloro-6-fluoro-N-[6-(8-phenethyl-2,8-diazaspiro[4.5]decane-2-carbonyl)-2,3-dihydro-1H-inden-1-yl]-benzamide

[IND_CC-781] 2-Chloro-6-fluoro-N-[6-[8-[3-(3-fluorophenyl)-propyl]-2,8-diazaspiro[4.5]decane-2-carbonyl]-2,3-dihydro-1H-inden-1-yl]-benzamide

[IND_CC-782] 2-Chloro-6-fluoro-N-[6-[8-[3-(4-fluorophenyl)-propyl]-2,8-diazaspiro[4.5]decane-2-carbonyl]-2,3-dihydro-1H-inden-1-yl]-benzamide

[IND_CC-783] 2-Chloro-6-fluoro-N-[6-[9-(1H-pyrrol-2-yl-methyl)-3,9-diazaspiro[5.5]undecane-3-carbonyl]-2,3-dihydro-1H-inden-1-yl]-benzamide

[IND_CC-784] 2-Chloro-6-fluoro-N-[6-[9-(pyridin-2-yl-methyl)-3,9-diazaspiro[5.5]undecane-3-carbonyl]-2,3-dihydro-1H-inden-1-yl]-benzamide

[IND_CC-785] 2-Chloro-6-fluoro-N-[6-[9-(pyridin-4-yl-methyl)-3,9-diazaspiro[5.5]undecane-3-carbonyl]-2,3-dihydro-1H-inden-1-yl]-benzamide

[IND_CC-786] 2-Chloro-6-fluoro-N-[6-[9-(pyridin-3-yl-methyl)-3,9-diazaspiro[5.5]undecane-3-carbonyl]-2,3-dihydro-1H-inden-1-yl]-benzamide

[IND_CC-787] 2-Chloro-6-fluoro-N-[6-[9-[(1-methyl-1H-pyrrol-2-yl)-methyl]-3,9-diazaspiro[5.5]undecane-3-carbonyl]-2,3-dihydro-1H-inden-1-yl]-benzamide

[IND_CC-788] 2-Chloro-N-[6-[9-[(2,6-difluoro-phenyl)-methyl]-3,9-diazaspiro[5.5]undecane-3-carbonyl]-2,3-dihydro-1H-inden-1-yl]-6-fluoro-benzamide

[IND_CC-789] 2-Chloro-N-[6-[9-[(3,4-difluoro-phenyl)-methyl]-3,9-diazaspiro[5.5]undecane-3-carbonyl]-2,3-dihydro-1H-inden-1-yl]-6-fluoro-benzamide

[IND_CC-790] 2-Chloro-N-[6-[9-[(2,5-difluoro-phenyl)-methyl]-3,9-diazaspiro[5.5]undecane-3-carbonyl]-2,3-dihydro-1H-inden-1-yl]-6-fluoro-benzamide

[IND_CC-791] 2-Chloro-N-[6-[9-[(2,4-difluoro-phenyl)-methyl]-3,9-diazaspiro[5.5]undecane-3-carbonyl]-2,3-dihydro-1H-inden-1-yl]-6-fluoro-benzamide

[IND_CC-792] 2-Chloro-6-fluoro-N-[6-[9-[(3-fluoro-4-methoxy-phenyl)-methyl]-3,9-diazaspiro[5.5]undecane-3-carbonyl]-2,3-dihydro-1H-inden-1-yl]-benzamide

[IND_CC-793] 2-Chloro-6-fluoro-N-[6-[9-[(2-fluoro-6-methoxy-phenyl)-methyl]-3,9-diazaspiro[5.5]undecane-3-carbonyl]-2,3-dihydro-1H-inden-1-yl]-benzamide

[IND_CC-794] 8-Chloro-2-[6-[8-[(3-fluoro-4-methoxy-phenyl)-methyl]-2,8-diazaspiro[4.5]-decane-2-carbonyl]-2,3-dihydro-1H-inden-1-yl]-4-methyl-3,4-dihydro-2H-pyrrolo[3,4-b]indol-1-one

[IND_CC-795] 8-Chloro-2-[6-[8-[(2-fluoro-6-methoxy-phenyl)-methyl]-2,8-diazaspiro[4.5]-decane-2-carbonyl]-2,3-dihydro-1H-inden-1-yl]-4-methyl-3,4-dihydro-2H-pyrrolo[3,4-b]indol-1-one

[IND_CC-796] 2-Chloro-6-fluoro-N-[6-[9-[(3-methyl-3H-imidazol-4-yl)-methyl]-3,9-diazaspiro[5.5]undecane-3-carbonyl]-2,3-dihydro-1H-inden-1-yl]-benzamide

[IND_CC-797] 2-Chloro-6-fluoro-N-[6-[9-([1,2,3]thiadiazol-4-yl-methyl)-3,9-diazaspiro[5.5]undecane-3-carbonyl]-2,3-dihydro-1H-inden-1-yl]-benzamide

[IND_CC-798] 2-Chloro-N-[6-[9-[(1,5-dimethyl-1H-pyrazol-4-yl)-methyl]-3,9-diazaspiro-[5.5]undecane-3-carbonyl]-2,3-dihydro-1H-inden-1-yl]-6-fluoro-benzamide

[IND_CC-799] 2-Chloro-N-[6-[9-[(3,5-dimethyl-isoxazol-4-yl)-methyl]-3,9-diazaspiro-[5.5]undecane-3-carbonyl]-2,3-dihydro-1H-inden-1-yl]-6-fluoro-benzamide

[IND_CC-800] 2-Chloro-N-[6-[9-[(3-cyano-phenyl)-methyl]-3,9-diazaspiro[5.5]undecane-3-carbonyl]-2,3-dihydro-1H-inden-1-yl]-6-fluoro-benzamide

[IND_CC-801] 2-Chloro-N-[6-[9-[(2-cyano-phenyl)-methyl]-3,9-diazaspiro[5.5]undecane-3-carbonyl]-2,3-dihydro-1H-inden-1-yl]-6-fluoro-benzamide

[IND_CC-802] 2-Chloro-N-[6-[9-[(2-chloro-4-fluoro-phenyl)-methyl]-3,9-diazaspiro-[5.5]undecane-3-carbonyl]-2,3-dihydro-1H-inden-1-yl]-6-fluoro-benzamide

[IND_CC-803] 2-Chloro-N-[6-[9-[(2-chloro-6-fluoro-phenyl)-methyl]-3,9-diazaspiro-[5.5]undecane-3-carbonyl]-2,3-dihydro-1H-inden-1-yl]-6-fluoro-benzamide

[IND_CC-804] 2-Chloro-N-[6-[2-oxo-2-[8-(quinolin-6-yl-methyl)-3,8-diazaspiro[4.5]decan-3-yl]-ethyl]-2,3-dihydro-1H-inden-1-yl]-benzamide

[IND_CC-805] 2-Chloro-N-[6-[2-oxo-2-[8-(quinoxalin-6-yl-methyl)-3,8-diazaspiro[4.5]decan-3-yl]-ethyl]-2,3-dihydro-1H-inden-1-yl]-benzamide

[IND_CC-806] 2-Chloro-N-[6-[2-[8-(2-ethyl-butyl)-3,8-diazaspiro[4.5]decan-3-yl]-2-oxo-ethyl]-2,3-dihydro-1H-inden-1-yl]-benzamide

[IND_CC-807] 2-Chloro-N-[6-[2-[8-(cyclohexyl-methyl)-3,8-diazaspiro[4.5]decan-3-yl]-2-oxo-ethyl]-2,3-dihydro-1H-inden-1-yl]-benzamide in the form of the free compounds; of the tautomers; of the N-oxides; of the racemate; of the enantiomers, diastereomers, mixtures of the enantiomers or diastereomers or of an individual enantiomer or diastereomer; or in the form of the salts of physiologically acceptable acids or bases.

The numbering of the individual embodiments of the compounds according to the invention used above is retained in the following explanations of the present invention, in particular in the description of the examples.

According to one aspect of the present invention, the compounds according to the invention preferably have an antagonistic action on the human B1R receptor or the B1R receptor of the rat. In a preferred embodiment of the invention, the compounds according to the invention have an antagonistic action both on the human B1R receptor (hB1R) and on the B1R receptor of the rat (rB1R).

In a preferred embodiment of the present invention, the compounds according to the invention show an inhibition of at least 15%, 25%, 50%, 70%, 80% or 90% on the human B1R receptor and/or on the B1R receptor of the rat in the FLIPR assay at a concentration of 10 µM. Compounds which show an inhibition on the human B1R receptor and on the B1R receptor of the rat of at least 70%, in particular of at least 80% and particularly preferably of at least 90% at a concentration of 10 µM are very particularly preferred.

The agonistic or antagonistic action of substances can be quantified on the bradykinin receptor 1 (B1R) of the human and rat species with ectopically expressing cell lines (CHO K1 cells) and with the aid of a $Ca^{2+}$-sensitive dyestuff (Fluo-4) in a fluorescent imaging plate reader (FLIPR). The figure in % activation is based on the $Ca^{2+}$ signal after addition of Lys-Des-$Arg^9$-bradykinin (0.5 nM) or Des-$Arg^9$-bradykinin (100 nM). Antagonists lead to a suppression of the $Ca^{2+}$ inflow after addition of the agonist. % inhibition compared with the maximum achievable inhibition is stated.

The substances according to the invention preferably act, for example, on the B1R relevant in connection with various diseases, so that they are suitable as a pharmaceutical active compound in medicaments.

The invention therefore also provides medicaments containing at least one compound according to the invention and optionally suitable additives and/or auxiliary substances and/or optionally further active compounds.

The medicaments according to the invention optionally contain, in addition to at least one compound according to the invention, suitable additives and/or auxiliary substances, that is to say also carrier materials, fillers, solvents, diluents, dyestuffs and/or binders, and can be administered as liquid medicament forms in the form of injection solutions, drops or juices or as semi-solid medicament forms in the form of granules, tablets, pellets, patches, capsules, plasters/spray-on plasters or aerosols. The choice of auxiliary substances etc. and the amounts thereof to be employed depend on whether the medicament is to be administered orally, perorally, parenterally, intravenously, intraperitoneally, intradermally, intramuscularly, nasally, buccally, rectally or topically, for example on the skin, the mucous membranes or into the eyes. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Substituted compounds according to the invention in a depot, in dissolved form or in a plaster, optionally with the addition of agents which promote penetration through the skin, are suitable formulations for percutaneous administration. Formulation forms which can be used orally or percutaneously can release the substituted compounds according to the invention in a delayed manner. The substituted compounds according to the invention can also be used in parenteral long-term depot forms, such as e.g. implants or implanted pumps. In principle, other further active compounds known to the person skilled in the art can be added to the medicaments according to the invention.

The amount of active compound to be administered to patients varies as a function of the weight of the patient, of the mode of administration, the indication and the severity of the disease. 0.00005 to 50 mg/kg, in particular 0.01 to 5 mg/kg of at least one compound according to the invention are conventionally administered.

In one form of the medicament, a substituted compound according to the invention contained therein is present as an isolated or pure diastereomer and/or enantiomer, as a racemate or as a non-equimolar or equimolar mixture of the diastereomers and/or enantiomers. Suitable methods for separation of stereoisomers are known to the person skilled in the art.

B1R is involved in particular in the pain event. The substituted compounds according to the invention can accordingly be used in particular for the preparation of a medicament for treatment of pain, in particular acute, visceral, neuropathic or chronic pain or inflammation pain.

The invention therefore also provides the use of at least one substituted compound according to the invention for the preparation of a medicament for treatment of pain, in particular acute, visceral, neuropathic or chronic pain. A particular embodiment of the present invention is the use of at least one of the substituted compounds according to the invention for the preparation of a medicament for treatment of inflammation pain.

The invention also provides the use of at least one substituted compound according to the invention for treatment of pain, in particular acute, visceral, neuropathic or chronic pain or inflammation pain.

The invention also provide the use of at least one substituted compound according to the invention for the preparation of a medicament for treatment of diabetes, diseases of the respiratory tract, for example bronchial asthma, allergies, COPD/chronic obstructive pulmonary disease or cystic fibrosis; inflammatory intestinal diseases, for example ulcerative colitis or CD/Crohn's disease; neurological diseases, for example multiple sclerosis, neurodegenerative diseases, fibrotic diseases, inflammations of the skin, for example atopic dermatitis, psoriasis or bacterial infections; rheumatic diseases, for example rheumatoid arthritis or osteoarthritis; septic shock; reperfusion syndrome, for example following cardiac infarction or stroke, obesity; and as an angiogenesis inhibitor.

The invention also provides the use of at least one substituted compound according to the invention for treatment of one of the abovementioned indications.

In this context, in one of the above uses it may be preferable for a substituted compound which is used to be present as an isolated or pure diastereomer and/or enantiomer, as a racemate or as a non-equimolar or equimolar mixture of the diastereomers and/or enantiomers.

The invention also provides a method for treatment, in particular in one of the abovementioned indications, of a non-human mammal or a human requiring treatment of the appropriate indication by administration of a therapeutically active dose of a substituted compound according to the invention or of a medicament according to the invention.

The invention also provides a method for treatment of pain, in particular one of the abovementioned forms of pain, in a non-human mammal or a human requiring treatment of pain, in particular of acute, visceral, neuropathic or chronic pain or inflammation pain, by administration of a therapeutically active dose of a substituted compound according to the invention, or of a medicament according to the invention.

The present invention also provides a process for the preparation of the substituted spiro-amide compounds according to the invention as described in the description and the examples.

In the following description of the process for preparing the compounds of the invention, references to the respective substituent R groups are intended to correspond to the groups $R^1$ to $R^{23}$ as defined above and/or to the subsequent, more preferred definitions of such substituent groups.

General Process for the Preparation of the Derivatives (IX)
Equation 1: General process for the preparation of substituted dihydroindenes (IX)
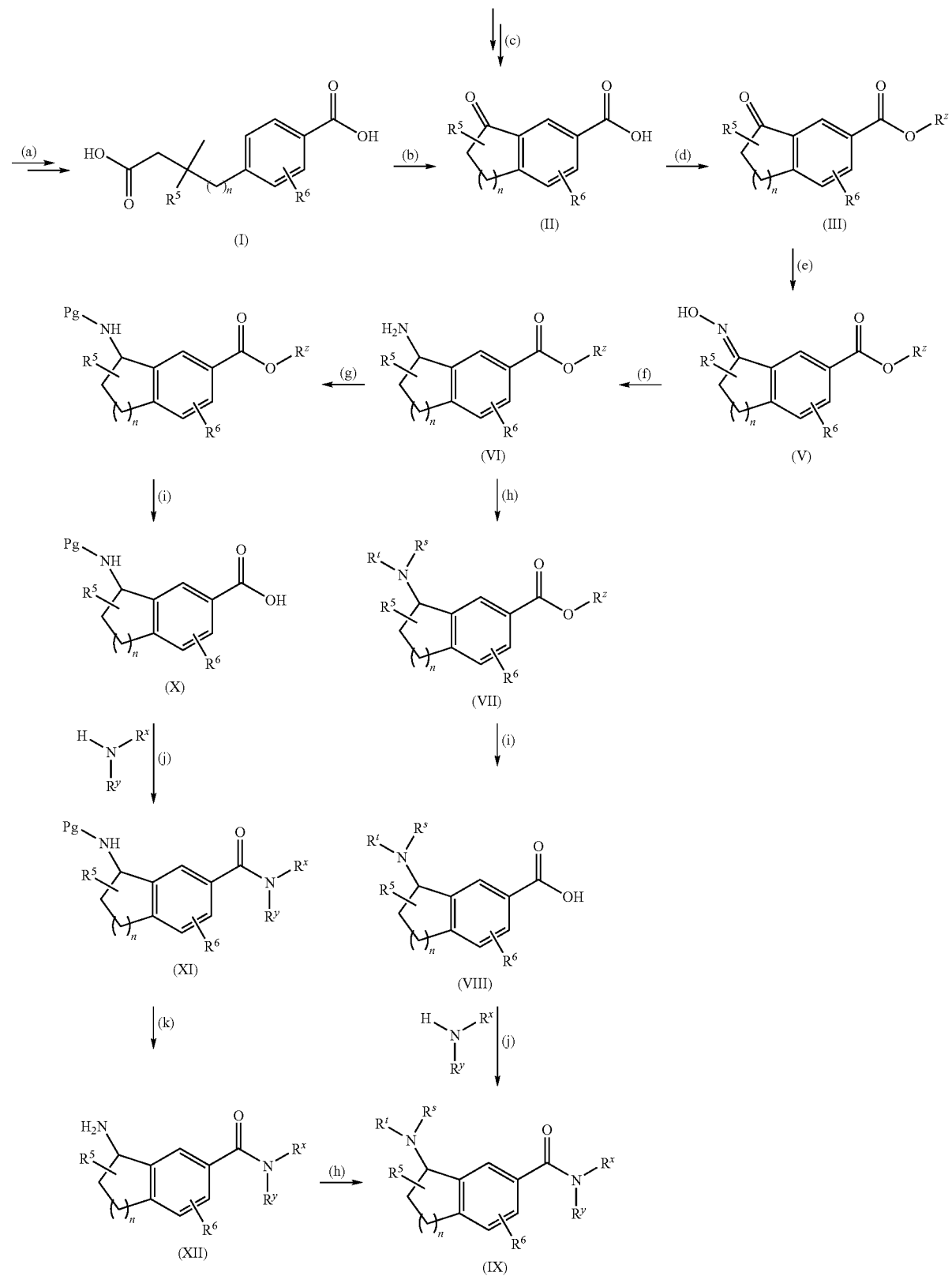

Step (a): Acids corresponding to formula (I) can be prepared by methods known from the literature, e.g. from methyl derivatives by oxidation, e.g. in accordance with: (lit. no. 1) Skraup; Schwamberger; Justus Liebigs Annalen der Chemie; vol. 462; (1928); p. 147, from nitriles by hydrolysis, e.g. in accordance with (lit. no. 2) Moses; Chemische Berichte; vol. 33; (1900); p. 2626, from aryl halides, e.g. in accordance with (lit. no. 3) Gomes, Paulo; Gosmini, Corinne; Perichon, Jacques; Synlett; vol. 10; (2002); p. 1673-1676. and (lit. no. 4) Amatore, Muriel; Gosmini, Corinne; Perichon, Jacques; Journal of Organic Chemistry; vol. 71; (2006); p. 6130-6134, from arylzinc compounds, e.g. in accordance with (lit. no. 5) Takahashi, Hideki; Inagaki, Shinya; Nishihara, Yasushi; Shibata, Takanori; Takagi, Kentaro; Organic Letters; vol. 8; (2006); p. 3037-3040, from aldehydes, e.g. in accordance with (lit. no. 6) Kotake, Yoshihiko; Iijima, Atsumi; Yoshimatsu, Kentaro; Tamai, Naoko; Ozawa, Yoichi; et al.; Journal of Medicinal Chemistry; vol. 37; (1994); p. 1616-1624, from arylboronic acids, e.g. in accordance with (lit. no. 7) Horiguchi, Hakaru; Tsurugi, Hayato; Satoh, Tetsuya; Miura, Masahiro; Journal of Organic Chemistry; vol. 73; (2008); p. 1590-1592. Ester derivatives of (I) are optionally obtained by these methods and are then converted into the acids (I) after step (j).

Step (b): Acids corresponding to formula (II) can be prepared from (I) by methods known from the literature, e.g. (lit. no. 8) Horwell, David C.; Howson, William; Nolan, William P. Ratcliffe, Giles S.; Rees, David C.; Willems, Henriette M. G.; Tetrahedron; vol. 51; (1995); p. 203-216. (lit. no. 9) or in accordance with WO2005/87236 (A1).

Step (c): Acids corresponding to formula (II) can be prepared by methods known from the literature, e.g. by oxidation (lit. no. 10) Matveeva, E. D.; Podrugina, T. A.; Zefirova, O. N.; Alekseev, A. S.; Bachurin, S. O.; Pellicciari, R.; Zefirov, N. S.; Russian Journal of Organic Chemistry; vol. 38; (2002); p. 1764-1768, by carbonyl insertion (lit. no. 11) WO2005/95387 (A1) and (lit. no. 12) Takeuchi, Ryo; Yasue, Hiroyuki; Journal of Organic Chemistry; vol. 58; (1993); p. 5386-5392, by oxidation:: (lit. no. 13) Pelliciari, Roberto; Luneia, Roberto; Costantino, Gabriele; Marinozzi, Maura; Natalini, Benedetto; et al.; Journal of Medicinal Chemistry; vol. 38; (1995); p. 3717-3719.

In step (d), acids corresponding to formula (II) are converted by a method known from the literature (cf. (a) Protecting Groups, Philip J. Kocienski, Thieme, Stuttgart; 3rd revised edition (14 Feb. 2005) (b) Protective Groups in Organic Synthesis, Theodora W. Greene and Peter G. M. Wuts, Wiley & Sons; 4th edition (30 Oct. 2006)) into an ester, preferably selected from the group consisting of the methyl, ethyl, isopropyl and tert-butyl ester, corresponding to formula (III).

In step (e), ketones corresponding to formula (III) are reacted in at least one solvent, preferably selected from the group consisting of water, methylene chloride, dimethylformamide, diethyl ether, dioxane, tetrahydrofuran, methanol, ethanol and isopropanol, with a reagent, preferably selected from the group consisting of hydroxylamine, hydroxylamine hydrochloride and N,O-bis(trimethylsilyl)hydroxylamine, optionally in the presence of at least one inorganic base, preferably selected from the group consisting of potassium hydride, potassium carbonate, sodium carbonate, cesium carbonate, sodium hydroxide, and sodium acetate, or an organic base, preferably selected from the group consisting of triethylamine, diisopropylethylamine and pyridine, at temperatures of from preferably −15° C. to 100° C. to give compounds with the general formula (IV).

In step (f), hydroxylamines corresponding to formula (IV) are reacted in at least one solvent, preferably selected from the group consisting of methylene chloride, chloroform, dimethylformamide, diethyl ether, dioxane, tetrahydrofuran, water, methanol, ethanol and isopropanol, with at least one reducing agent, preferably selected from the group consisting of lithium aluminum hydride, sodium borohydride, lithium borohydride, sodium, sodium amalgam and zinc, optionally in the presence of at least one acid or Lewis acid, preferably selected from the group consisting of hydrochloric acid, sulfuric acid, acetic acid and titanium tetrachloride, at temperatures of from preferably −15° C. to 100° C. to give compounds with the general formula (VI).

In step (f), hydroxylamines corresponding to formula (IV) can optionally also be reacted in at least one solvent, preferably selected from the group consisting of chloroform, ethyl acetate, dimethylformamide, diethyl ether, dioxane, tetrahydrofuran, methanol, ethanol and isopropanol, with hydrogen under pressure of from preferably 1 to 10 bar, in the presence of at least one catalyst, preferably selected from the group consisting of rhodium on charcoal, palladium on charcoal, palladium black, Raney nickel and platinum oxide, optionally in the presence of at least one acid, preferably selected from the group consisting of hydrochloric acid, sulfuric acid and acetic acid, at temperatures of from preferably 0° C. to 50° C. to give compounds with the general formula (VI).

In step (g), amines corresponding to formula (VI) are provided by a method known from the literature (cf. (a) Protecting Groups, Philip J. Kocienski, Thieme, Stuttgart; 3rd revised edition (14 Feb. 2005) (b) Protective Groups in Organic Synthesis, Theodora W. Greene and Peter G. M. Wuts, Wiley & Sons; 4th edition (30 Oct. 2006)) with suitable protective groups (Pg), preferably selected from the group consisting of tert-butyloxycarbonyl (Boc) and benzyl carbamate (Cbz).

In step (h), amines corresponding to formula (VI) or (XII) are reacted in at least one solvent, preferably selected from the group consisting of methylene chloride, acetonitrile, dimethylformamide, diethyl ether, dioxane, tetrahydrofuran, methanol, ethanol and isopropanol, with acid chlorides or sulfonyl chlorides, in the presence of at least one inorganic base, preferably selected from the group consisting of potassium carbonate and cesium carbonate, or an organic base, preferably selected from the group consisting of triethylamine, diisopropylethylamine and pyridine, and optionally with the addition of 4-(dimethylamino)pyridine or 1-hydroxybenzotriazole, at temperatures of from preferably −15° C. to 50° C. to give compounds with the general formula (VII) or (IX).

In step (h), instead of the carboxylic acid chlorides the corresponding carboxylic acids can also optionally be employed. These acids corresponding to formula $R^1OH$, wherein $R^1$ has the abovementioned meaning, are reacted in at least one solvent, preferably selected from the group consisting of methylene chloride, acetonitrile, dimethylformamide, diethyl ether, dioxane and tetrahydrofuran, with amines (VI) or (XII), with the addition of at least one coupling reagent, preferably selected from the group consisting of carbonyldiimidazole (CDI), 2-chloro-1-methylpyridinium iodide (Mukaiyama reagent), N-(3-dimethylaminopropyl)-N'-ethylcarbodiimide (EDCI), O-(benzotriazol-1-yl)-N,N,N',N'-tetramethyluronium tetrafluoroborate (TBTU), N,N'-dicyclohexylcarbodiimide (DCC) and 1-benzotriazolyloxy-tris-(dimethylamino)-phosphonium hexafluorophosphate (BOP), optionally in the presence of at least one inorganic base, preferably selected from the group consisting of potassium carbonate and cesium carbonate, or an organic base, preferably selected from the group consisting of triethylamine, diisopropylethylamine and pyridine, and optionally with the addition of 4-(dimethylamino)pyridine or 1-hydroxybenzotriazole, to give compounds with the general formula (VII) or (IX). Cyclic amidic systems are synthesized in step (h) analogously to instructions known from the literature, e.g. (lit. no. 14) Bioorganic & Medicinal Chemistry Letters 17 (2007) 428-433 and (lit. no. 15) Bioorganic & Medicinal Chemistry Letters 17 (2007) 424-427.

In step (i), compounds corresponding to formula (V) or (VII) are reacted in at least one solvent, preferably selected from the group consisting of water, methanol, ethanol, isopropanol, diethyl ether, tetrahydrofuran, toluene, acetonitrile, dimethylformamide, dioxane and dimethylsulfoxide, with an inorganic base, preferably selected from the group consisting of lithium hydroxide, sodium hydroxide, potassium hydroxide, potassium tert-butanolate, lithium propanethiolate and sodium phenylselenolate, optionally with the addition of HMPA or lithium chloride, or with a Lewis acid, preferably selected from the group consisting of trimethylsilyl chloride, boron tribromide and aluminum trichloride, optionally with the addition of thiolene, sodium iodide or lithium chloride, at temperatures of from preferably 0° C. to 100° C. to give compounds corresponding to formula (VIII) or (X).

In step (j), compounds corresponding to formula (X) or (VIII) are reacted in at least one solvent, preferably selected from the group consisting of methylene chloride, acetonitrile, dimethylformamide, diethyl ether, dioxane and tetrahydrofuran, with amines $HNR_4R_4'$, wherein $R_4$ and $R_4'$ have the abovementioned meaning, with the addition of at least one coupling reagent, preferably selected from the group consisting of carbonyldiimidazole (CDI), 2-chloro-1-methylpyridinium iodide (Mukaiyama reagent), N-(3-dimethylaminopropyl)-N'-ethylcarbodiimide (EDCI), O-(benzotriazol-1-yl)-N,N,N',N'-tetramethyluronium tetrafluoroborate (TBTU), N,N'-dicyclohexylcarbodiimide (DCC) and 1-benzotriazolyloxy-tris-(dimethylamino)-phosphonium hexafluorophosphate (BOP), optionally in the presence of at least one inorganic base, preferably selected from the group consisting of potassium carbonate and cesium carbonate, or an organic base, preferably selected from the group consisting of triethylamine, diisopropylethylamine and pyridine, and optionally with the addition of 4-(dimethylamino)pyridine or 1-hydroxybenzotriazole, to give compounds with the general formula (IX) or (XI).

In step (k), the amine-protecting group (Pg) is split off from molecules corresponding to formula (XI) by a method known from the literature (cf. (a) Protecting Groups, Philip J. Kocienski, Thieme, Stuttgart; 3rd revised edition (14 Feb. 2005) (b) Protective Groups in Organic Synthesis, Theodora W. Greene and Peter G. M. Wuts, Wiley & Sons; 4th edition (30 Oct. 2006)). In particular, for Pg=Boc: In step (k), the compounds corresponding to formula (XI) are reacted in at least one solvent, preferably selected from the group consisting of water, methanol, ethanol, isopropanol, diethyl ether, tetrahydrofuran, acetonitrile, dioxane, dimethylformamide and dimethylsulfoxide, with an acid, preferably selected from the group consisting of trifluoroacetic acid, sulfuric acid and hydrochloric acid, or acetyl chloride/methanol at temperatures of from preferably 0° C. to 80° C. to give compounds with the general formula (XII).

General Process for the Preparation of Spiro-Amines

Educts corresponding to formula (XIII), (XX) and (XXXIII) either are commercially obtainable or can be synthesized by conventional methods known to persons skilled in the art.

In step (o), the amine-protecting group (Pg) is split off from the corresponding compounds by a method known from the literature (cf. (a) Protecting Groups, Philip J. Kocienski, Thieme, Stuttgart; 3rd revised edition (14 Feb. 2005) (b) Protective Groups in Organic Synthesis, Theodora W. Greene and Peter G. M. Wuts, Wiley & Sons; 4th edition (30 Oct. 2006)). In particular, for Pg=Boc: In step (o), the corresponding compounds are reacted in at least one solvent, preferably selected from the group consisting of water, methanol, ethanol, isopropanol, diethyl ether, tetrahydrofuran, acetonitrile, dioxane, dimethylformamide and dimethylsulfoxide, with an acid, preferably selected from the group consisting of trifluoroacetic acid, sulfuric acid and hydrochloric acid, or acetyl chloride/methanol, at temperatures of from preferably 0° C. to 80° C. to give the corresponding deprotected compounds.

Part 1—General Process for the Preparation of the Amines (XV), (XVII) and (XIX)

Equation 2: Preparation of the amines (XV), (XVII) and (XIX)

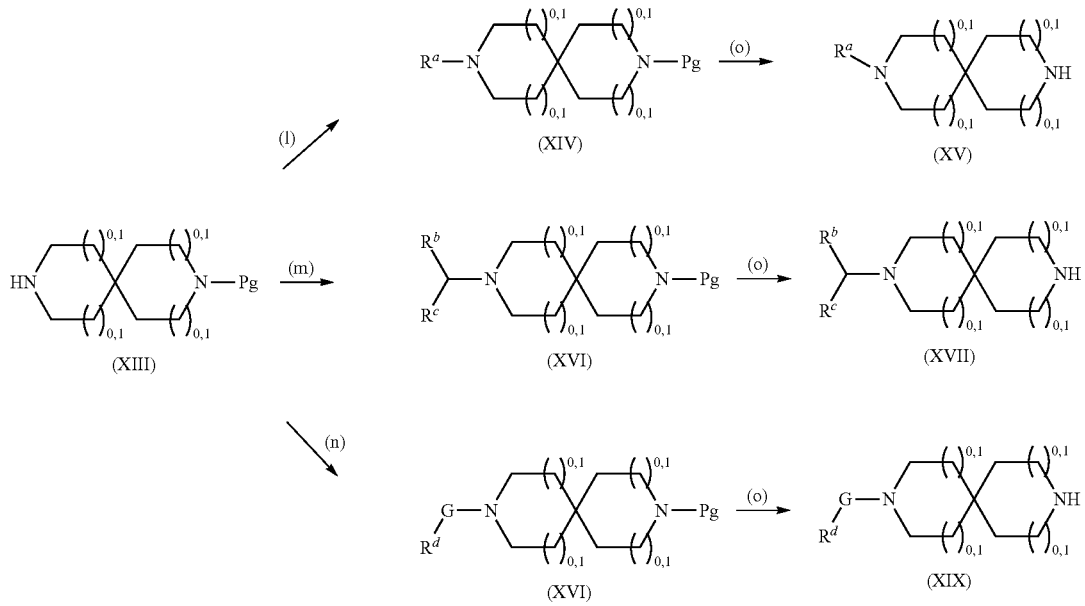

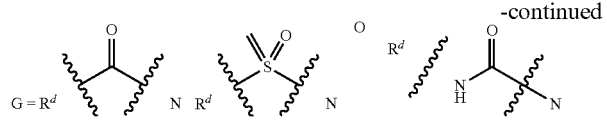

-continued

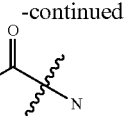

In step (l), compounds corresponding to formula (XIII) are reacted in at least one solvent, preferably selected from the group consisting of ethanol, methanol, n-butanol, iso-propanol, 2-butanone, DMSO, diethyl ether, water, benzene, toluene, THF, MC, acetonitrile, acetone, DMF and pentane, with boronic acids, iodide, bromide, chloride or mesylate compounds, optionally with the addition of at least one base, preferably selected from the group consisting of potassium hydroxide, sodium hydroxide, optionally in aqueous or alcoholic solution, potassium carbonate, potassium hexamethyldisilazane, sodium hydride, potassium hydride, sodium methanolate, sodium ethanolate, sodium tert-butylate and diisopropylethylamine, optionally with the addition of an auxiliary substance, preferably selected from the group consisting of 18-crown-6, 15-crown-5, terabutylammonium bromide or sulfate, benzyltriethylammonium chloride, 1-n-butyl-3-methylimidazolium tetrafluoroborate and DMAP, optionally using a catalyst, preferably selected from the group consisting of $Pd(Pcyclohexyl_3)_2Cl_2$, $Pd_2(dba)_3$, $Ni(OAc)_2$. $Cu(OAc)_2$, optionally using a ligand, preferably selected from the group consisting of $P(o\text{-tolyl})_3$, P(1,1'-bis(diphenylphosphino)ferrocene, 2,2'-bipyridine, $P(tri\text{-}o\text{-tolylphosphine})_3$, to give compounds corresponding to formula (XIV). Compounds corresponding to formula (XIV) are furthermore obtained by reaction of compounds corresponding to formula (XIII) with iodide, bromide, chloride or mesylate compounds under Buchwald-Hartwig conditions.

In step (m), compounds corresponding to formula (XIII) are reacted with aldehydes corresponding to formula $R^bCHO$ or ketones corresponding to formula $R^bCOR^c$, wherein $R^b$ and $R^c$ have the abovementioned meanings, in at least one solvent, preferably from the group consisting of diethyl ether, tetrahydrofuran, methanol, ethanol, dichloroethane, methylene chloride and toluene, with the addition of at least one reducing agent, preferably from the group consisting borane-pyridine complex, sodium borohydride, sodium triacetoxyborohydride, sodium cyanoborohydride and triethylsilane, optionally in the presence of at least one acid, preferably selected from the group consisting of formic acid, acetic acid, hydrochloric acid and trifluoroacetic acid, at temperatures of from preferably −70° C. to 100° C. to give compounds corresponding to formula (XVI).

In step (n), amines corresponding to formula (XIII) are reacted in at least one solvent, preferably selected from the group consisting of methylene chloride, acetonitrile, dimethylformamide, diethyl ether, dioxane, tetrahydrofuran, methanol, ethanol and isopropanol, with acid chlorides $R^dCOCl$ or sulfonyl chlorides $R^dSO_2Cl$ or isocyanates $R^dNCO$, wherein $R^d$ has the abovementioned meaning, in the presence of at least one inorganic base, preferably selected from the group consisting of potassium carbonate and cesium carbonate, or an organic base, preferably selected from the group consisting of triethylamine, diisopropylethylamine and pyridine, and optionally with the addition of 4-(dimethylamino)pyridine or 1-hydroxybenzotriazole, at temperatures of from preferably −15° C. to 50° C. to give compounds with the general formula (XVIII).

In step (n), instead of the carboxylic acid chlorides the corresponding carboxylic acids can optionally also be employed. These acids corresponding to formula $R^dCO_2H$, wherein $R^d$ has the abovementioned meaning, are reacted in at least one solvent, preferably selected from the group consisting of methylene chloride, acetonitrile, dimethylformamide, diethyl ether, dioxane and tetrahydrofuran, with amines (XIII), with the addition of at least one coupling reagent, preferably selected from the group consisting of carbonyldiimidazole (CDI), 2-chloro-1-methylpyridinium iodide (Mukaiyama reagent), N-(3-dimethylaminopropyl)-N'-ethylcarbodiimide (EDCI), O-(benzotriazol-1-yl)-N,N,N',N'-tetramethyluronium tetrafluoroborate (TBTU), N,N'-dicyclohexylcarbodiimide (DCC) and 1-benzotriazolyloxy-tris-(dimethylamino)-phosphonium hexafluorophosphate (BOP), optionally in the presence of at least one inorganic base, preferably selected from the group consisting of potassium carbonate and cesium carbonate, or an organic base, preferably selected from the group consisting of triethylamine, diisopropylethylamine and pyridine, and optionally with the addition of 4-(dimethylamino)pyridine or 1-hydroxybenzotriazole, to give compounds with the general formula (XVIII).

Step (o)—See above.

Part 2—General Process for the Preparation of the Amines (XXII), (XXV), (XXVIII), (XXXI) and (XXXII)

Equation 3: Preparation of the amines (XXII), (XXV), (XXVIII), (XXXI) and (XXXII)
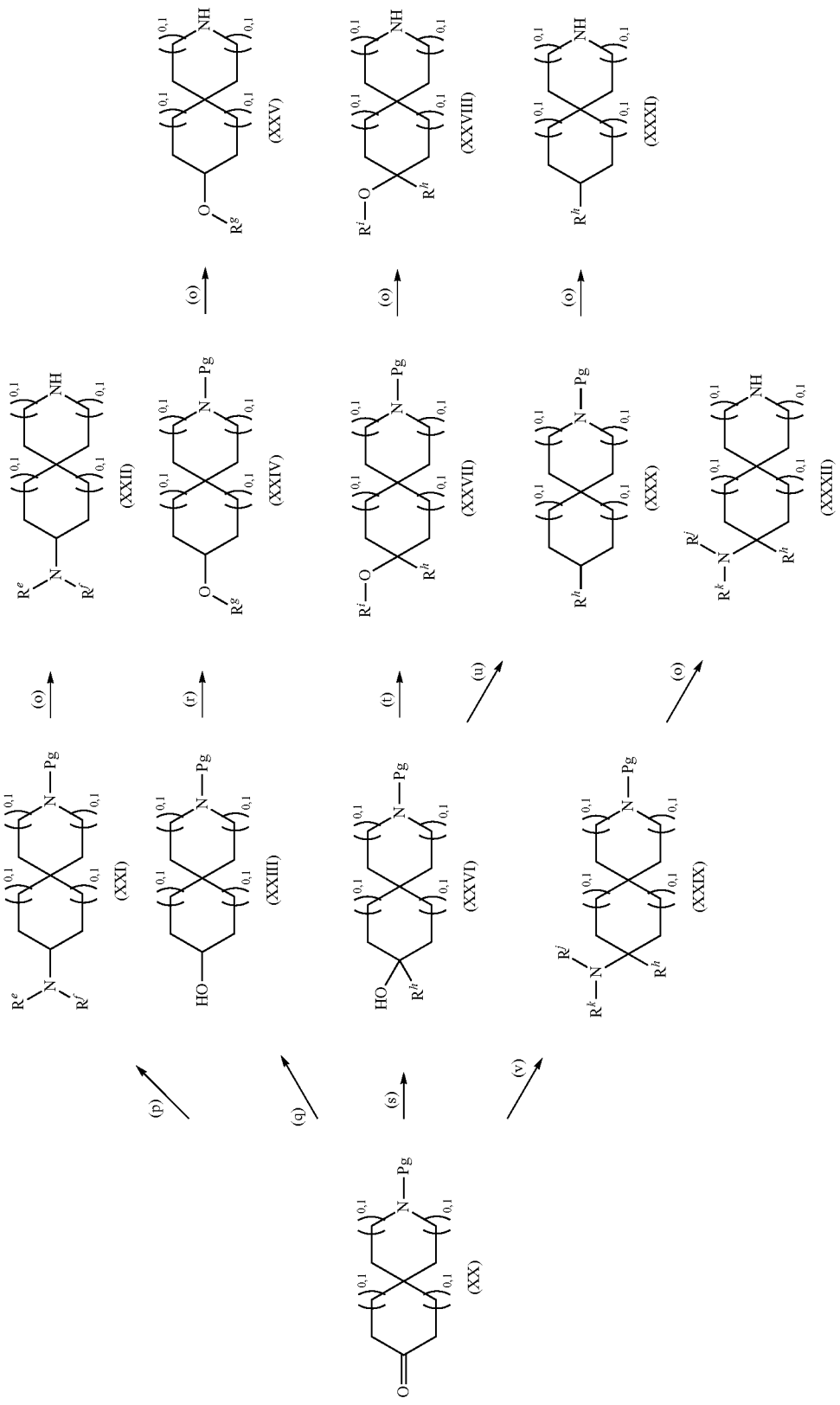

-continued
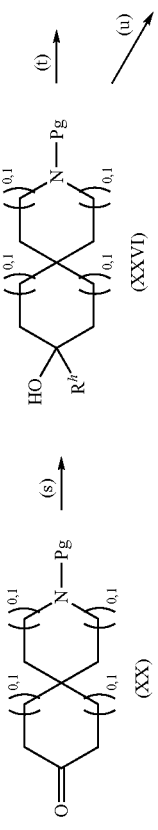
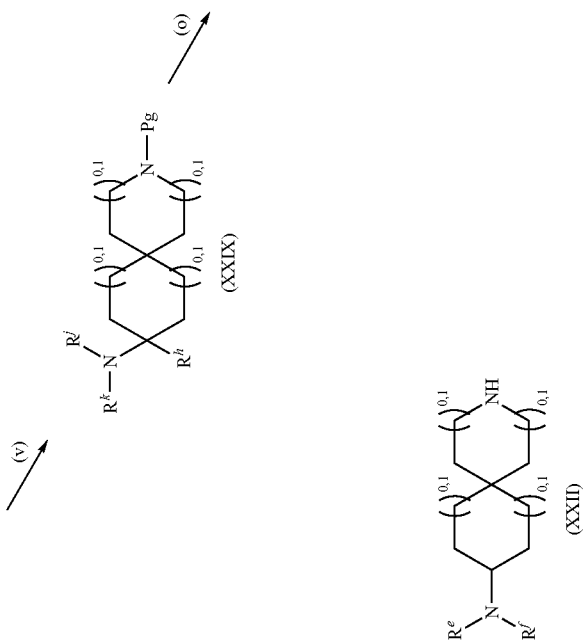

In step (p), compounds corresponding to formula (XX) are reacted with amines corresponding to formula $R^eNHR^f$, wherein $R^e$ and $R^f$ have the abovementioned meanings, in at least one solvent, preferably from the group consisting of diethyl ether, tetrahydrofuran, methanol, ethanol, dichloroethane, methylene chloride and toluene, with the addition of at least one reducing agent, preferably from the group consisting borane-pyridine complex, sodium borohydride, sodium triacetoxyborohydride, sodium cyanoborohydride and triethylsilane, optionally in the presence of at least one acid, preferably selected from the group consisting of formic acid, acetic acid, hydrochloric acid and trifluoroacetic acid, at temperatures of from preferably −70° C. to 100° C. to give compounds corresponding to formula (XXI).

In step (q), compounds corresponding to formula (XX) are reacted in at least one organic solvent, preferably from the group consisting of diethyl ether, tetrahydrofuran, methanol, ethanol, dichloroethane, methylene chloride and toluene, with the addition of at least one reducing agent, preferably from the group consisting of lithium aluminum hydride, RedAl® (sodium bis(2-methoxyethoxy)aluminum hydride), lithium tri-tert-butoxyaluminium hydride, sodium borohydride, sodium triacetoxyborohydride, sodium cyanoborohydride, diborane, Selectride$^e$ and triethylsilane, optionally in the presence of at least one acid, preferably selected from the group consisting of formic acid, acetic acid, hydrochloric acid and trifluoroacetic acid, at temperatures of from preferably −25° C. to 100° C. to give compounds corresponding to formula (XXIII).

In step (r), compounds corresponding to formula (XXIII) are converted, by introduction of a suitable leaving group, such as, for example, halogen or mesylate, and subsequent reaction with alcohols, into compounds corresponding to formula (XXIV). Compounds corresponding to formula (XXII) are converted in at least one solvent, preferably selected from the group consisting of methylene chloride, dioxane, diethyl ether, tetrahydrofuran, acetonitrile and dimethylformamide, with a sulfonyl chloride, preferably selected from the group consisting of methylsulfonyl chloride, trifluoromethylsulfonyl chloride, tolylsulfonyl chloride, and at least one base, preferably selected from the group consisting of cesium carbonate, calcium carbonate, potassium carbonate, triethylamine, diisopropylethylamine and pyridine, at temperatures of from preferably 0° C. to 80° C. into the corresponding mesylates. These are reacted in at least one solvent, preferably selected from the group consisting of methylene chloride, dioxane, diethyl ether, tetrahydrofuran, acetonitrile, toluene and dimethylformamide, with a suitable alcohol in the presence of an excess of a base, preferably selected from the group consisting of cesium carbonate, calcium carbonate, potassium carbonate, potassium bicarbonate, sodium bicarbonate, triethylamine, diisopropylethylamine and pyridine, at temperatures of from preferably 0° C. to 80° C. to give compounds corresponding to formula (XXIV). Alternatively, in step (r), compounds corresponding to formula (XXIV) can be prepared from compounds corresponding to formula (XXIV) in a Mitsunobu reaction. Step (r) can moreover be carried out analogously to step (t).

In step (s), the carbonyl compounds (XX) are reacted with metal organyls, typically Li or Mg organyls (Grignard), in solvents, such as, for example, toluene, benzene, hexane, pentane, THF or diethyl ether, optionally with the addition of, for example, $CeCl_3$, to give the tertiary alcohols (XXVI).

In step (t), in a substitution reaction alcohols corresponding to formula (XXVI) are dissolved in a suitable solvent, such as, for example, ethanol, methanol, n-butanol, iso-propanol, 2-butanone, DMSO, diethyl ether, water, benzene, toluene, THF, MC, acetonitrile, acetone, DMF or pentane or a mixture of these solvents, and a suitable base is added, such as, for example, potassium hydroxide, sodium hydroxide, optionally in aqueous or alcoholic solution, potassium carbonate, potassium hexamethyldisilazane, sodium hydride, potassium hydride, sodium methanolate, sodium ethanolate, sodium tert-butylate or diisopropylethylamine, optionally with the addition of an auxiliary substance, such as, for example, 18-crown-6, 15-crown-5, terabutylammonium bromide or sulfate, benzyltriethylammonium chloride, 1-n-butyl-3-methylimidazolium tetrafluoroborate or DMAP, and the reaction is carried out with an iodide, bromide, chloride or mesylate compound.

In step (u), compounds corresponding to formula (XXVI) are reacted in at least one solvent, preferably selected from the group consisting of methanol, ethanol, isopropanol, methylene chloride, dioxane, diethyl ether, dimethylsulfoxide, tetrahydrofuran, acetonitrile and dimethylformamide, in the presence of at least one acid, preferably selected from the group consisting of formic acid, acetic acid hydrochloric acid, sulfuric acid and trifluoroacetic acid, at temperatures of from preferably 0° C. to 100° C. The unsaturated systems formed by this procedure are reduced to the compounds corresponding to formula (XXX) by a method known to the person skilled in the art.

In step (v), compounds corresponding to formula (XXIX) are converted by method A or method B into compounds corresponding to formula (XXXII).

Method A: Compounds corresponding to formula (XXIX) are reacted in an aminal formation reaction by reaction with an amine and 1H-benzotriazole to give the benzotriazole aminal, it being known to the person skilled in the art that the bezotriazole aminal can exist in equilibrium both in the 1H and in the 2H form. Suitable solvents are, for example, benzene, toluene, ethanol, diethyl ether or THF. The use of a Dean-Stark water separator, a molecular sieve or other dehydrating means may be necessary. The reaction time can be between 1 and 20 h at a reaction temperature of from +20° C. to +110° C. The benzotriazole aminal obtained as the intermediate product is then reacted with metal organyls, such as magnesium, zinc or lithium organyls, in organic solvents, for example diethyl ether, dioxane or THF, to give compounds corresponding to formula (XXXII).

Method B: Compounds corresponding to formula (XXIX) are reacted by addition of an amine and a source of cyanide to give nitrile-amines. This reaction can be carried out in one or two steps. In the two-step variant, a nitrile-alcohol is first formed and isolated. The formation of the nitrile-alcohol can be carried out by reaction of compounds corresponding to formula (XXIX) with HCN, KCN or NaCN as the source of cyanide, if NaCN and KCN are used the required cyanide being liberated by the addition of, for example, sodium hydrogen sulfite, sulfuric acid, acetic acid or hydrochloric acid. Preferred solvents are water, methanol, ethanol, THF, piperidine, diethyl ether or a mixture of these solvents. Trimethylsilyl cyanide, for example, is likewise suitable as a source of cyanide; the cyanide can be liberated, for example, by boron trifluoride etherate, $InF_3$ or HCl. Preferred solvents are water or toluene. (Cyano-C)diethylaluminium, for example, is suitable as a further source of cyanide. THF, toluene or a mixture of the two solvents can be used as the solvent. The reaction temperature for all the variants is preferably between −78° C. and +25° C. Alcohols, such as methanol or ethanol, are particularly suitable as the solvent for the reaction of the nitrile alcohol with the amine to give nitrile-amines. The reaction temperature can be between 0° C. and +25° C. In the one-step variant, the nitrile alcohol primarily formed is formed in situ and reacted with the amine to give nitrile-amines. The nitrile-amine obtained as the intermediate product is then reacted with metal organyls, such as magnesium, zinc or lithium organyls, in organic solvents, for example diethyl ether, dioxane or THF, to give compounds corresponding to formula (XXXII).

Step (o)—See above.

Part 3—General Process for the Preparation of the Amines (XXXVI), (XXXVIII), (XLI) and (XLIV)

Equation 4: Preparation of the amines (XXXVI), (XXXVIII), (XLI) and (XLIV)
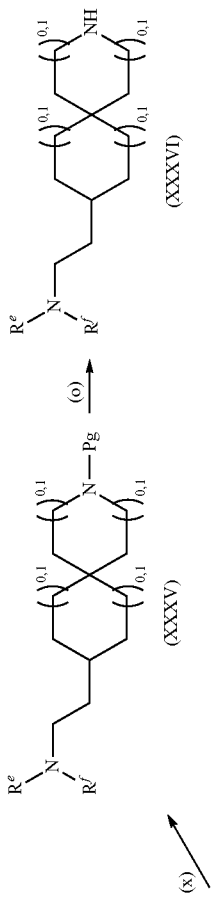
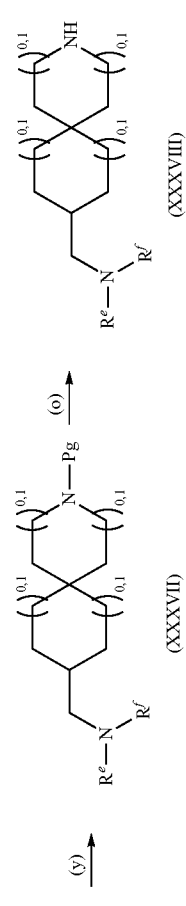
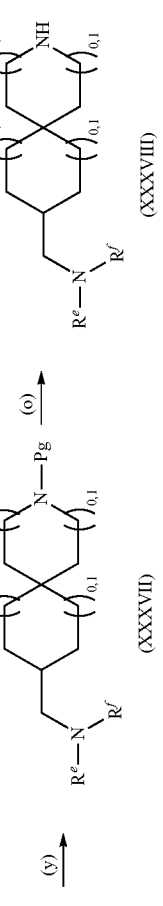
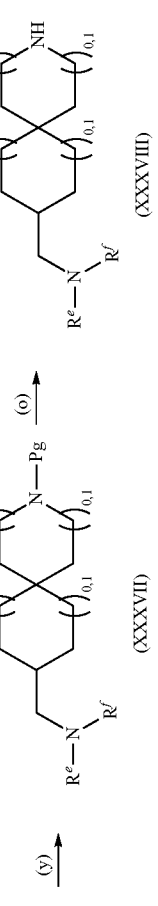
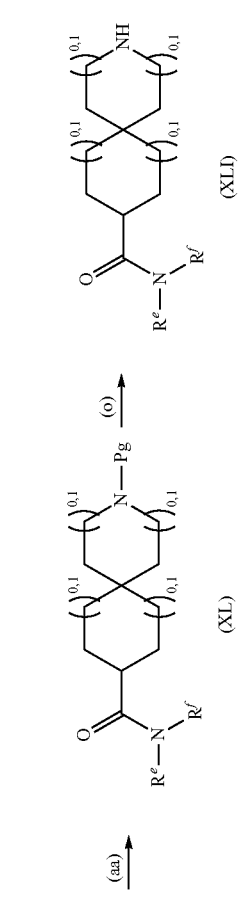
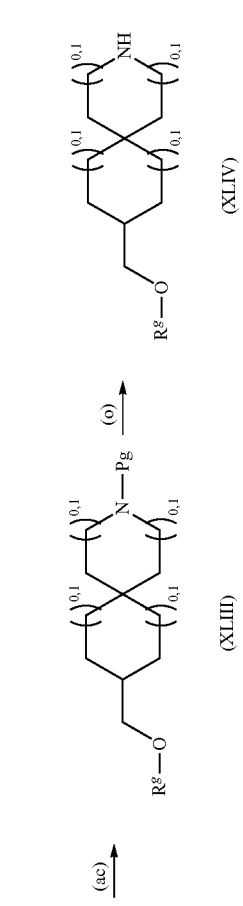

In step (w), the ester corresponding to formula (XXXIII) is reduced by a method known to the person skilled in the art to give the aldehyde corresponding to formula (XXXIV), or the corresponding alcohol is oxidized by a method known to the person skilled in the art to give the aldehyde corresponding to formula (XXXIV).

In step (x), aldehyde corresponding to formula (XXXIV) are reacted by methods known to the person skilled in the art in a Wittig reaction with (methoxymethyl)triphenyl-phosphonium chloride, and a strong base, for example potassium tert-butylate, n-butyllithium, s-butyllithium, phenyllithium, lithium diisopropylamide or lithium hexamethyldisilazide, in organic solvents, for example THF, diethyl ether, cyclohexane, toluene or corresponding mixtures. The aldehydes obtained in this way are then reacted with amines corresponding to formula $R^eNHR^f$ analogously to step (y) to give compounds corresponding to formula (XXXV).

In step (y), compounds corresponding to formula (XXXIV) are reacted with amines corresponding to formula $R^eNHR^f$, wherein $R^e$ and $R^f$ have the abovementioned meanings, in at least one solvent, preferably from the group consisting of diethyl ether, tetrahydrofuran, methanol, ethanol, dichloroethane, methylene chloride and toluene, with the addition of at least one reducing agent, preferably from the group consisting of borane-pyridine complex, sodium borohydride, sodium triacetoxyborohydride, sodium cyanoborohydride and triethylsilane, optionally in the presence of at least one acid, preferably selected from the group consisting of formic acid, acetic acid, hydrochloric acid and trifluoroacetic acid, at temperatures of from preferably −70° C. to 100° C. to give compounds corresponding to formula (XXXVII).

In step (z), compounds corresponding to formula (XXXIII) are reacted anologously to the methods described for step (i) to give compounds corresponding to formula (XXXIX).

In step (aa), compounds corresponding to formula (XXXIX) are reacted in at least one solvent, preferably selected from the group consisting of methylene chloride, acetonitrile, dimethylformamide, diethyl ether, dioxane and tetrahydrofuran, with amines corresponding to formula $R^eNHR^f$, wherein $R^e$ and $R^f$ have the abovementioned meanings, with the addition of at least one coupling reagent, preferably selected from the group consisting of carbonyldiimidazole (CDI), 2-chloro-1-methylpyridinium iodide (Mukaiyama reagent), N-(3-dimethylaminopropyl)-N'-ethylcarbodiimide (EDCI), O-(benzotriazol-1-yl)-N,N,AN',N'-tetramethyluronium tetrafluoroborate (TBTU), N,N'-dicyclohexylcarbodiimide (DCC) and 1-benzotriazolyloxy-tris-(dimethylamino)-phosphonium hexafluorophosphate (BOP), optionally in the presence of at least one inorganic base, preferably selected from the group consisting of potassium carbonate and cesium carbonate, or an organic base, preferably selected from the group consisting of triethylamine, diisopropylethylamine and pyridine, and optionally with the addition of 4-(dimethylamino)pyridine or 1-hydroxybenzotriazole, to give compounds with the general formula (XL).

In step (aa), compounds corresponding to formula (XXXIX) are optionally reacted in at least one solvent, preferably selected from the group consisting of methylene chloride, acetonitrile, dimethylformamide, diethyl ether, dioxane and tetrahydrofuran, using at least one coupling reagent, preferably selected from the group consisting of thienyl chloride, oxalyl chloride and phosphoryl chloride, in the presence of at least one inorganic base, preferably selected from the group consisting of potassium carbonate and cesium carbonate, or an organic base, preferably selected from the group consisting of triethylamine, diisopropylethylamine and pyridine, with amines corresponding to formula $R^eNHR^f$, wherein $R^e$ and $R^f$ have the abovementioned meanings, to give compounds with the general formula (XL).

In step (ab), carboxylic acid esters or carboxylic acids corresponding to formula (XXXIII) are reacted using suitable reducing agents, such as, for example, $LiBH_4$, $LiAlH_4$, Dibal-H, $BF_3$ etherate, $BH_3 \times DMS$ or $NaBH_4$, optionally with the addition of auxiliary reagents, such as, for example, boric acid esters, in an organic solvent, such as THF, MC, toluene, methanol, ethanol, DME, hexane, diethyl ether or mixtures of these solvents, at temperatures of from 0° C. to the reflux temperature, in a reduction the alcohols corresponding to formula (XLII).

In step (ac), compounds corresponding to formula (XXX-LII) are reacted anologously to the methods described for steps (r) and (t) to give compounds corresponding to formula (XXXLIII).

Step (o)—See above.

Pharmacological Methods

1. Functional Investigation on the Bradykinin Receptor 1 (B1R)

The agonistic or antagonistic action of substances can be determined on the bradykinin receptor 1 (B1R) of the human and rat species with the following assay. In accordance with this assay, the $Ca^{2+}$ inflow through the channel is quantified with the aid of a $Ca^{2+}$-sensitive dyestuff (type Fluo-4, Molecular Probes Europe BV, Leiden, Holland) in a fluorescent imaging plate reader (FLIPR, Molecular Devices, Sunnyvale, USA).

2. Method:

Chinese hamster ovary cells (CHO K1 cells) transfected stably with the human B1R gene (hB1R cells) or the B1R gene of the rat (rB1R cells) are used. For functional studies, these cells are plated out on black 96-well plates with a clear base (BD Biosciences, Heidelberg, Germany or Greiner, Frickenhausen, Germany) in a density of 20,000-35,000 cells/well. The cells are left overnight at 37° C. and 5% $CO_2$ in culture medium (hB1R cells: Nutrient Mixture Ham's F12, Gibco Invitrogen GmbH, Karlsruhe, Germany or DMEM, Sigma-Aldrich, Taufkirchen, Germany; rB1R cells: D-MEM/F12, Gibco Invitrogen GmbH, Karlsruhe, Germany) with 10 vol. % FBS (foetal bovine serum, Gibco Invitrogen GmbH, Karlsruhe, Germany or PAN Biotech GmbH, Aidenbach, Germany). On the following day, the cells are loaded for 60 min at 37° C. with 2.13 µM Fluo-4 (Molecular Probes Europe BV, Leiden Holland) in HBSS buffer (Hank's buffered saline solution, Gibco Invitrogen GmbH, Karlsruhe, Germany) with 2.5 mM probenecid (Sigma-Aldrich, Taufkirchen, Germany) and 10 mM HEPES (Sigma-Aldrich, Taufkirchen, Germany). The plates are then washed 2× with HBSS buffer, and HBSS buffer which additionally contains 0.1% BSA (bovine serum albumin; Sigma-Aldrich, Taufkirchen, Germany), 5.6 mM glucose and 0.05% gelatine (Merck KGaA, Darmstadt, Germany) is added. After a further incubation of 20 minutes at room temperature, the plates are inserted into the FLIPR for the $Ca^{2+}$ measurement. Alternatively, the plates are washed with buffer A (15 mM HEPES, 80 mM NaCl, 5 mM KCl, 1.2 mM $CaCl_2$, 0.7 mM $MgSO_4$, 2 g/l glucose, 2.5 mM probenecid), buffer A is added and the plates are loaded with 2.5 µM Fluo-4 and 0.025% Pluronic F127 (Sigma-Aldrich, Taufkirchen, Germany). Thereafter, the cells are washed 2× with buffer A and incubated for 30 minutes at room temperature with buffer A, which additionally contains 0.05% BSA and 0.05% gelatine, and thereafter inserted into the FLIPR for the $Ca^{2+}$ measurement. The $Ca^{2+}$-dependent fluorescence is measured here before and after addition of substances ($\lambda_{ex}$=488 nm, $\lambda_{em}$=540 nm). Quantification is by measurement of the highest fluorescence intensity (FC, fluorescence counts) over time.

3. FLIPR Assay:

The FLIPR protocol consists of 2 additions of substance. Test substances (10 µM) are first pipetted on to the cells and the $Ca^{2+}$ inflow is compared with the control (hB1R: Lys-Des-$Arg^9$-bradykinin>=50 nM; rB1R: Des-$Arg^9$-bradykinin 10 µM). This gives the result in % activation based on the $Ca^{2+}$ signal after addition of Lys-Des-$Arg^9$-bradykinin (>=50 nM) or Des-$Arg^9$-bradykinin (10 µM). After incubation for 10-20 minutes, Lys-Des-$Arg^9$-bradykinin (hB1R) or Des-$Arg^9$-bradykinin (rB1R) in the concentration of the $EC_{80}$ is applied and the inflow of $Ca^{2+}$ is likewise determined. Antagonists lead to a suppression of the $Ca^{2+}$ inflow. % inhibition compared with the maximum achievable inhibition is calculated.

For determination of the $IC_{50}$ value, the substances are added in various concentrations. Duplicate or triplicate determinations (n=2 or n=3) are carried out, and these are repeated in at least one further independent experiment (N>=2).

The compounds preferably have a B1R-antagonistic action on the human receptor and/or on the rat receptor.

The invention is explained in the following with the aid of examples, without limiting the general inventive idea.

EXAMPLES

List of Abbreviations

DIBAL-H=diisobutylaluminium hydride
eq. equiv.=equivalents
h=hours
d=days
min=minutes
Boc=tert-butoxycarbonyl
Cbz=benzyloxycarbonyl
DMSO=dimethylsulfoxide
THF=tetrahydrofuran
MC=methylene chloride
DMF=dimethylformamide
TFA=trifluoroacetic acid
wt. %=per cent by weight
conc.=concentrated
sat.=saturated
R.t.=retention time The chemicals and solvents employed were obtained commercially from the conventional suppliers (Acros, Aldrich, Fluke, Lancaster, Maybridge, TCI, Fluorochem, Tyger, ABCR, Fulcrum, FrontierScientific, Milestone etc.). The reactions were carried out in some cases under inert gas (nitrogen). The yields of the compounds prepared are not optimized. The mixing ratios of solvents are always stated in the volume/volume ratio. The equivalent amounts of reagents employed and the amounts of solvent and reaction temperatures and times can vary slightly between different reactions carried out by the same method. The working up and purification methods were adapted according to the characteristic properties of the compounds.

A. Synthesis of the Acid Units

1) Synthesis of the Amino Acid Esters (A)

Amino Acid Ester Overview:

| A no. | Structure | Amino acid ester (A) | Comments |
|---|---|---|---|
| A-01 | TFA, $H_2N$-indane-methyl ester | 3-amino-2,3-dihydro-1H-indene-5-carboxylic acid methyl ester (A-01) | see below |
| A-02 | (S)-$H_2N$-indane-methyl ester | (3S)-3-amino-2,3-dihydro-1H-indene-5-carboxylic acid methyl ester (A-02) | commercially obtainable from NetChem Company (order no. 517174) |
| A-03 | (R)-$H_2N$-indane-methyl ester | (3R)-3-amino-2,3-dihydro-1H-indene-5-carboxylic acid methyl ester (A-03) | commercially obtainable from NetChem Company (order no. 517173) synthesis see below: step 1 product of A-18 |
| A-04 | (S)-$H_2N$-indane-carboxylic acid | (3S)-3-amino-2,3-dihydro-1H-indene-4-carboxylic acid (A-04) | commercially obtainable from NetChem Company (order no. 517180) |

-continued

| A no. | Structure | Amino acid ester (A) | Comments |
|---|---|---|---|
| A-05 | 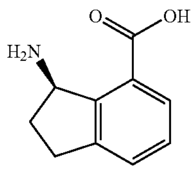 | (3R)-3-amino-2,3-dihydro-1H-indene-4-carboxylic acid (A-05) | commercially obtainable from NetChem Company (order no. 517179) |
| A-06 | 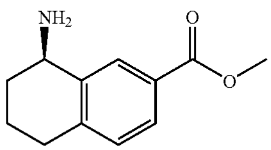 | (8R)-8-amino-5,6,7,8-tetrahydro-naphthalene-2-carboxylic acid methyl ester (A-06) | commercially obtainable from NetChem Company (order no. 517179) |
| A-07 | 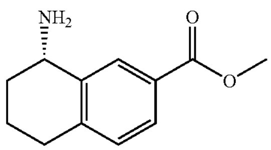 | (8S)-8-amino-5,6,7,8-tetrahydro-naphthalene-2-carboxylic acid methyl ester (A-07) | commercially obtainable from NetChem Company (order no. 517120) |
| A-08 | 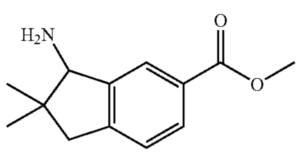 | methyl 3-amino-2,2-dimethyl-2,3-dihydro-1H-indene-5-carboxylate (A-08) | see below |
| A-09 | 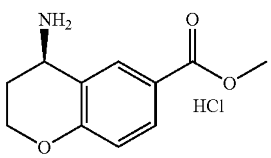 | (R)-methyl 4-aminochroman-6-carboxylate hydrochloride (A-09) | commercially obtainable from NetCham Company (order no. 517145) |
| A-11 | 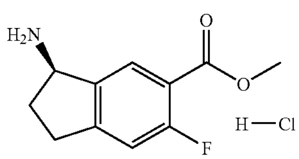 | (R)-methyl 3-amino-6-fluoro-2,3-dihydro-1H-indene-5-carboxylate hydrochloride (A-11) | Yield: 86% synthesis analogously to A-14 starting from (R)-3-amino-6-fluoro-2,3-dihydro-1H-indene-5-carboxylic acid hydrochloride (commercially obtainable from NetChem Company (order no. 573243)) |
| A-13 | 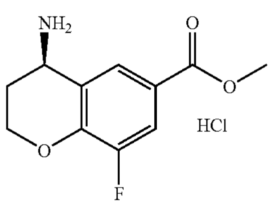 [SMILES: COC(=O)c1cc(F)c2c(c1)[C@H](N)CCO2 ; Cl] | (R)-methyl 4-amino-8-fluorochroman-6-carboxylate hydrochloride (A-13) | commercially obtainable from NetChem Company (order no. 572795) |
| A-14 | 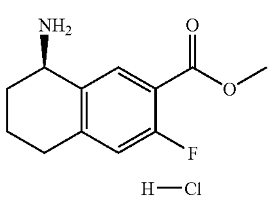 | (R)-methyl-8-amino-3-fluoro-5,6,7,8-tetrahydronaphthalene-2-carboxylate hydrochloride (A-14) | see below |
| A-15 | 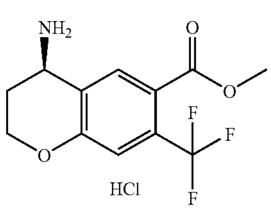 [SMILES: COC(=O)c1cc2c(cc1C(F)(F)F)OCC[C@H]2N ; Cl] | (R)-methyl-4-amino-7-(trifluoromethyl)chroman-6-carboxylate hydrochloride (A-15) | commercially obtainable from NetChem Company (order no. 572943) |

-continued

| A no. | Structure | Amino acid ester (A) | Comments |
|---|---|---|---|
| A-16 | 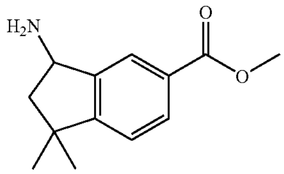 [SMILES: COC(=O)c1ccc2c(c1)C(N)CC2(C)C] | methyl 3-amino-1,1-dimethyl-2,3-dihydro-1H-indene-5-carboxylate (A-16) | see below |
| A-17 | 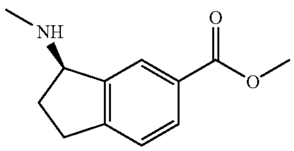 | (R)-methyl 3-(methylamino)-2,3-dihydro-1H-indene-5-carboxylate (A-17) | see below |
| A-18 | 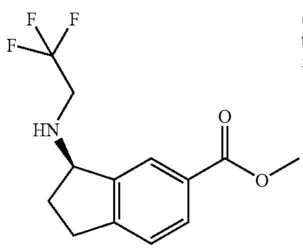 | (R)-methyl 3-(2,2,2-trifluroethylamino)-2,3-dihydro-1H-indene-5-carboxylate (A-18) | see below |
| A-19 | 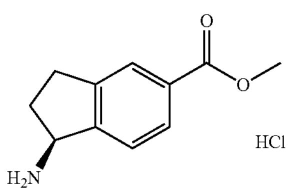 | (S)-methyl 1-amino-2,3-dihydro-1H-indene-5-carboxylate hydrochloride (A-19) | commercially obtainable from NetChem Company (order no. 517172) |
| A-20 | 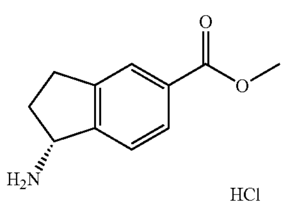 | (R)-methyl 1-amino-2,3-dihydro-1H-indene-5-carboxylate hydrochloride (A-20) | commercially obtainable from NetChem Company (order no. 517171) |
| A-21 | 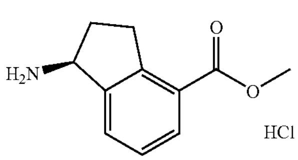 | (S)-methyl 1-amino-2,3-dihydro-1H-indene-4-carboxylate hydrochloride (A-21) | commercially obtainable from NetChem Company (order no. 517168) |
| A-22 | 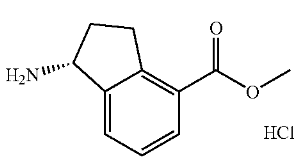 | (R)-methyl 1-amino-2,3-dihydro-1H-indene-4-carboxylate hydrochloride (A-22) | commercially obtainable from NetChem Company (order no. 517167) |

Note: The following amino acid esters were sometimes employed as as the corresponding HCl salts: A-02, A-03, A-04, A-05, A-06, A-07.

Synthesis of amino acid ester A-01

3-Amino-2,3-dihydro-1H-indene-5-carboxylic acid methyl ester (A-01)

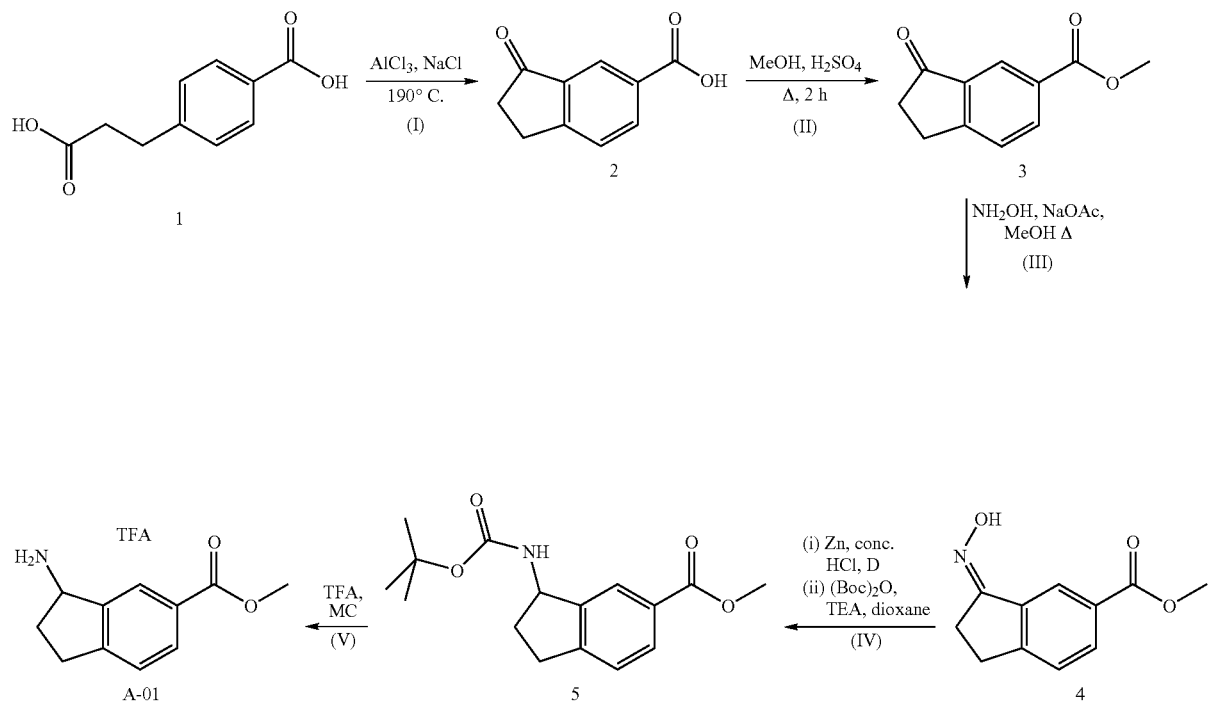

(I) A mixture of 4-(2-carboxyethyl)-benzoic acid (25.7 mmol), anhydrous aluminum trichloride (8 equiv.) and dry sodium chloride (10 wt. % of aluminium chloride) was heated slowly to 190° C. and this was maintained for 1 h. The reaction mixture was then poured on to an ice-water mixture and acidified with 6 N HCl. The aqueous phase was extracted with ethyl acetate and the organic phase was washed successively with water and sat. NaCL solution, dried over $Na_2SO_4$ and concentrated under reduced pressure to obtain the desired product (2). Yield: 88%

(II) One drop of conc. $H_2SO_4$ was added to a methanolic solution of the product just obtained in step (I) (0.5 mmol in 15 ml of methanol) and the mixture was heated under reflux for 3 h. The reaction mixture was then cooled to room temperature and concentrated and the residue was taken up in ethyl acetate. The ethyl acetate phase was washed with $NaHCO_3$ solution, water and sat. NaCl solution, dried over $Na_2SO_4$ and concentrated under reduced pressure to obtain the desired product (3). Yield: 81.7%

(III) Hydroxylamine hydrochloride (3 equiv.) and sodium acetate (6 equiv.) was added to a methanolic solution (15 ml) of the product just obtained in step (II) (2.8 mmol) and the mixture was heated under reflux under an $N_2$ atmosphere for 12 h. The reaction mixture was then cooled to room temperature and concentrated and the residue was taken up in ethyl acetate. The ethyl acetate phase was washed with water and sat. NaCl solution, dried over $Na_2SO_4$ and concentrated under reduced pressure to obtain the desired product (4). Yield: 95%

(IV) Zinc dust (1.2 equiv.) was added to an ethanolic solution (10 ml) of the product just obtained in step (III) (1.4 mmol), water (0.75 ml) and conc. HCl (1.5 ml) and the mixture was refluxed for 2 h. It was then cooled to room temperature, filtered over Celite and concentrated to obtain the desired amine. The crude amine was dissolved in 1,4 dioxane (15 ml) and triethylamine (3 equiv.), and $(BOC)_2O$ (1.5 equiv.) was added. This reaction mixture stirred at room temperature for 2 h and then concentrated and the residue taken up in ethyl acetate. The ethyl acetate phase was washed with water and sat. NaCl solution, dried over $Na_2SO_4$ and concentrated to obtain the desired product (5). Yield: 76%

(V) Trifluoroacetic acid (2 ml) was added to a solution of the product just obtained in step (IV) (0.4 mmol) in methylene chloride (15 ml) and the mixture was stirred at room temperature for 2 h. The reaction mixture was then concentrated and 2× chloroform was added to the residue and the mixture concentrated to obtain the desired 3-amino-2,3-dihydro-1H-indene-5-carboxylic acid methyl ester (A-01), which was employed in the subsequent reaction without further purification. Yield: 95% (crude)

Synthesis of amino acid ester A-08

Methyl 3-amino-2,2-dimethyl-2,3-dihydro-1H-indene-5-carboxylate (A-08)

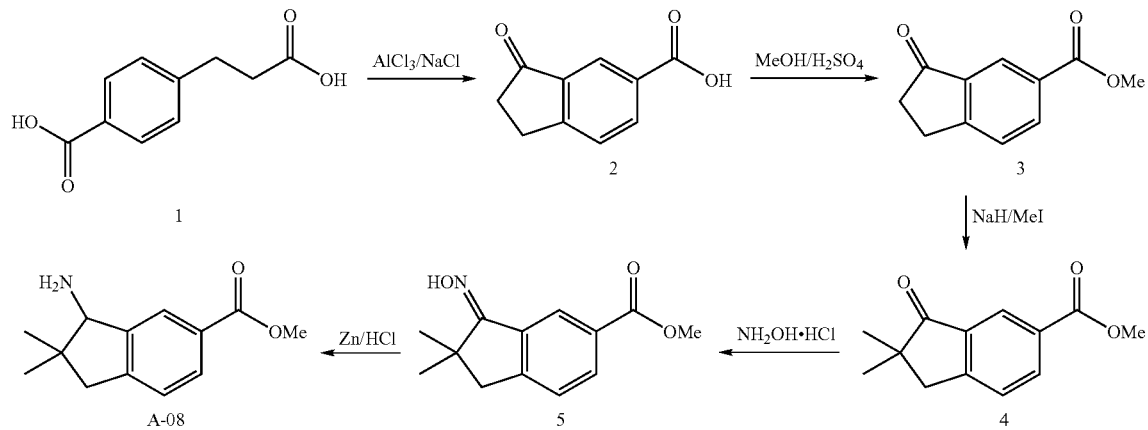

Step 1: A mixture of compound 1 (82.4 mmol, 1.0 eq.), AlCl₃ (593.8 mmol, 7.2 eq.) and NaCl (10% w/w of AlCl₃ used) was heated at 190° C. for 2 h. The reaction mixture was cooled to 25° C., the tacky mass was dissolved in ice-cold water and the solution was shaken with crushed ice in a 5 l glass beaker. A mixture of 600 ml of a 6 N HCl and 750 ml of ethyl acetate was added to the reaction mixture. The organic phase was separated off and the aqueous phase was extracted with ethyl acetate (3×650 ml). The combined organic phases were washed with 2 M HCl (100 ml), water (2×100 ml) and sat. NaCl solution (100 ml) and dried over sodium sulfate. The solvent was concentrated in vacuo in order to obtain the desired product 2. Yield: 90%

Step 2: H₂SO₄ (4 ml) was added to a solution of compound 2 (14 g, 79.5 mmol) in MeOH (100 ml) and the reaction mixture was heated under reflux for 3 h. The solvent was concentrated in vacuo, the residue was dissolved in water and the solution was rendered basic with sat. NaHCO₃ solution and extracted with ethyl acetate (2×600 ml). The combined organic phases were washed with water (2×150 ml) and sat. NaCl solution (2×50 ml) and dried over sodium sulfate. The solvent was concentrated in vacuo and the residue was purified by column chromatography (silica gel, 15% ethyl acetate in hexane) in order to obtain the desired ester 3. Yield: 66%

Step 3: A solution of compound 3 (36.38 mmol, 1.0 eq.) in abs. THF (50 ml) was added to a stirred suspension of NaH (2.2 eq.) in THF (50 ml) at 0° C. and the reaction mixture obtained was stirred at 25° C. for 30 min. The reaction mixture was cooled to 0° C., methyl iodide (254.66 mmol, 7.0 eq.) was added and the mixture was stirred at 25° C. for 2 h The reaction mixture was quenched with ice-water (50 ml and extracted with ethyl acetate (200 ml). The organic phase is washed with water (100 ml) and sat. NaCl solution (100 ml) and dried over sodium sulfate. The solvent was concentrated in vacuo in order to obtain the crude product, which was purified by column chromatography (silica gel, 15% ethyl acetate in hexane) in order to obtain the desired dimethylated product 4. Yield: 66%

Step 4: NH₂OH.HCl (60.54 mmol, 2.2 eq.) and CH₃COONa (121.08 mmol, 4.4 eq.) were added to a solution of compound 4 (27.52 mmol, 1.0 eq.) in methanol (50 ml) and the reaction mixture was heated under reflux for 6 h. When the reaction was complete (TLC control), the solvent was concentrated in vacuo, the residue was dissolved in ethyl acetate (300 l) and the solution was washed with water (2×100 ml) and sat. NaCl solution (2×100 ml). The organic phase was dried over sodium sulfate and the solvent was concentrated in vacuo in order to obtain the crude product, which was employed in the next step without further purification. Yield: 92%

Step 5: Conc. HCl (35 ml) was added to a solution of compound 5 (27.0 mmol, crude) in EtOH:H₂O (10:1, 220 ml). Zn dust (20 g) was added to the reaction mixture in portions and the mixture was heated under reflux for 2 h. The reaction mixture was filtered over Celite and the filtrate was concentrated in vacuo in order to obtain the crude product 6, which was employed in the next step without further purification. Yield: 40 g (crude)

Synthesis of amino acid ester A-14

(R)-Methyl 8-amino-3-fluoro-5,6,7,8-tetrahydronaphthalene-2-carboxylate hydrochloride (A-14)

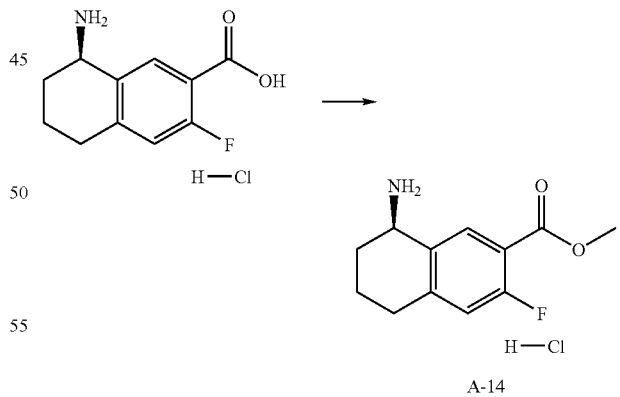

Step-1: (R)-8-Amino-3-fluoro-5,6,7,8-tetrahydronaphthalene-2-carboxylic acid hydrochloride (commercially obtainable from NetChem Company (order no. 573545)) (2.035 mmol, 1 eq.) was added to a solution of HCl in methanol (1.25 M, 15 eq.) and the resulting mixture was heated to reflux for 16 h. The solvent was concentrated in vacuo, and the residue was dissolved in acetone (5 ml) and diethyl ether (30 ml) was added. The white solid was collected by filtration, washed with diethyl ether and dried in vacuo. Yield: 95%

Synthesis of amino acid ester A-16

Methyl 3-amino-1,1-dimethyl-2,3-dihydro-1H-indene-5-carboxylate (A-16)

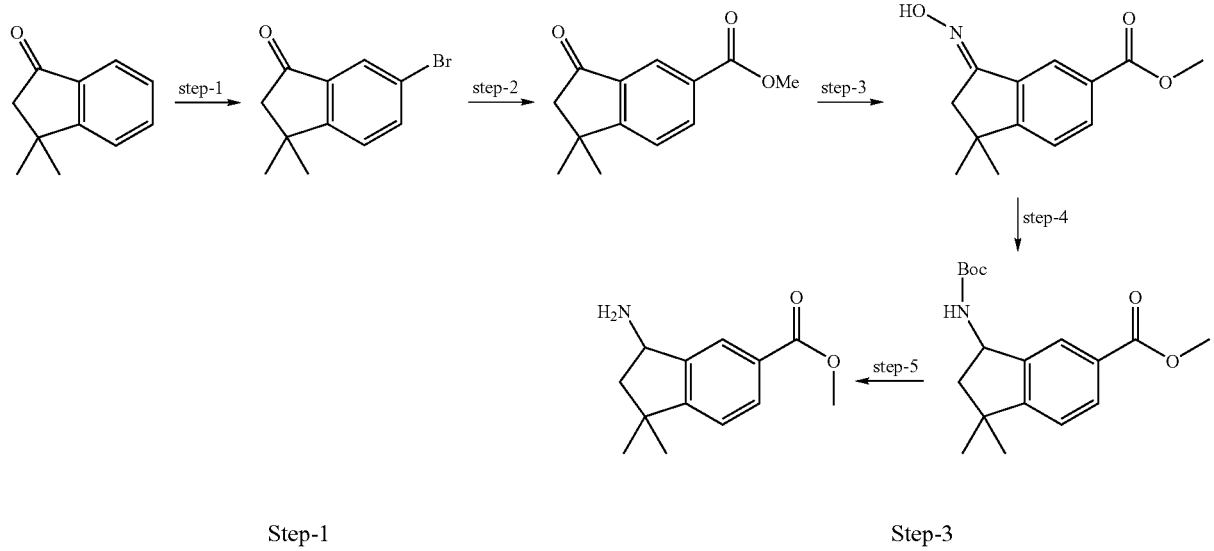

Step-1

6-Bromo-3,3-dimethyl-2,3-dihydro-1H-inden-1-one

Bromine (0.2 ml, 3.8 mmol, 1.2 eq.) was added to a mixture of $AlCl_3$ (1.04 g, 7.8 mmol, 2.5 eq.) and 3,3-dimethyl-indan-1-one (500 mg, 3.1 mmol) at 100° C. and the reaction mixture was heated at same temperature for 40-45 min. TLC (10% ethyl acetate/hexanes) showed the major product formation with little starting material and dibromo product. The reaction mass was quenched with crushed ice and extracted with ethyl acetate (3×50 ml). The organic part was separated, dried over $Na_2SO_4$ and evaporated under reduced pressure. The crude compound was purified by column chromatography (silica gel, 10% ethyl acetate/hexanes) to give the desired compound as a pale yellow solid. Yield: 27% (280 mg, 0.85 mmol).

Step-2

Methyl 1,1-dimethyl-3-oxo-2,3-dihydro-1H-indene-5-carboxylate

6-Bromo-3,3-dimethyl-2,3-dihydro-1H-inden-1-one (2 g, 8.36 mmol, 1.0 eq.) was taken up a mixture of DMSO (45 ml) and methanol (30 ml). The reaction mixture was degassed with argon for 15 min and then palladium acetate (80 mg, 0.35 mmol, 0.04 eq.) and dppp (1,3-bis-diphenylphosphino propane) (160 mg, 0.38 mmol, 0.04 eq.) was added and it was degassed with CO for 30 min. The reaction mixture was stirred at 65° C. under CO balloon pressure for 2 h. Methanol was evaporated under reduced pressure, the resulting solution was diluted with water (100 ml) and extracted with diethyl ether (3×25 ml). The organic layer was dried over sodium sulfate and the filtrate was concentrated to give the crude product which was purified by column chromatography (silica gel, 10% ethyl acetate/hexanes) to yield the desired product as a pale yellow solid. Yield: 45% (820 mg, 3.76 mmol).

Step-3

Methyl 3-(hydroxyimino)-1,1-dimethyl-2,3-dihydro-1H-indene-5-carboxylate

To a stirred solution of methyl 1,1-dimethyl-3-oxo-2,3-dihydro-1H-indene-5-carboxylate (430 mg, 1.97 mmol, 1.0 eq.) in methanol (7.5 ml) was added hydroxylamine hydrochloride (340 mg, 4.93 mmol, 2.5 eq.) followed by sodium acetate (807 mg, 9.85 mmol, 5.0 eq.) and the reaction mixture was heated at reflux for 2 h at 80° C. The reaction mixture was concentrated and then extracted with ethyl acetate (3×40 ml). The organic part was separated, washed with water (20 ml) and brine (20 ml) and dried over sodium sulfate. After concentrating the filtrate the crude product thus obtained was directly taken through to the next step without purification.

Step-4

Methyl 3-(tert-butoxycarbonylamino)-1,1-dimethyl-2,3-dihydro-1H-indene-5-carboxylate Conc. HCl (2 ml) and water (1 ml) were added to a stirred solution of methyl 3-(hydroxyimino)-1,1-dimethyl-2,3-dihydro-1H-indene-5-carboxylate (350 mg, 1.5 mmol, 1 eq.) in ethanol (3 ml) and the reaction mixture was stirred for 15 min. Zinc powder (640 mg, 100 mmol, 67 eq.) was added portion-wise and the reaction mixture was stirred until complete conversion had taken place. The mixture was filtered through a sintered funnel and the residue washed with ethanol. The filtrate was concentrated to give the crude amine (1 g; crude), which was dissolved, in dioxane (100 ml). The mixture was cooled to 5-10° C. and triethylamine (3.3 ml, 32.8 mmol) was added, followed by boc anhydride (500 mg, 2.3 mmol, 2 eq.), which was added slowly. The reaction mixture was stirred at room temperature for 12 h. The mixture was concentrated to dryness under reduced pressure and ethyl acetate (100 ml) and water (100 ml) were added. The organic part was separated, washed with water (20 ml) and brine (20 ml), and dried over sodium sulfate. The solvent was removed under reduced pressure to give the crude product which was purified by column chromatography (silica gel, 0-5% MeOH/MC) to yield the desired product as a colorless semisolid. Yield: 52% (250 mg, 0.78 mmol).

Step-5

Methyl 3-amino-1,1-dimethyl-2,3-dihydro-1H-indene-5-carboxylate

TFA (0.7 ml, 9 mmol, 13 eq.) was added to a stirred solution of methyl 3-(tert-butoxycarbonylamino)-1,1-dimethyl-2,3-dihydro-1H-indene-5-carboxylate (220 mg, 0.69 mmol, 1 eq.) in methylene chloride (10 ml) at 0° C. and the mixture was stirred at RT for 2 h. After complete deprotection (checked by TLC) the solvent was removed under reduced pressure. The residue was diluted with methylene chloride (50 ml) and washed with water (10 ml) and brine (10 ml). The organic part was evaporated under reduced pressure to give the crude product which was directly used for the next step without further purification.

Synthesis of amino acid ester A-17

(R)-Methyl 3-(methylamino)-2,3-dihydro-1H-indene-5-carboxylate (A-17)

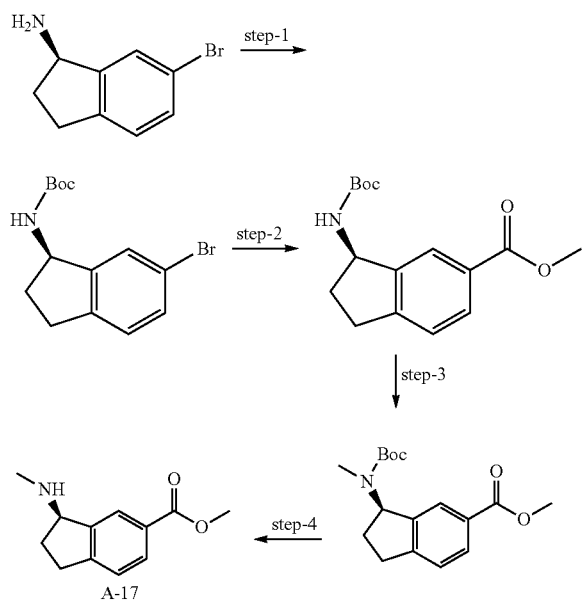

Step-1

(R)-tert-Butyl 6-bromo-2,3-dihydro-1H-inden-1-ylcarbamate

To a mixture of (R)-6-bromo-2,3-dihydro-1H-inden-1-amine (5.0 g, 20.16 mmol, 1.0 eq.) in methylene chloride (100 ml) and TEA (11.20 ml, 80.64 mmol, 4.0 eq.) was added dropwise boc-anhydride (6.47 ml, 30.24 mmol, 1.5 eq.) at 0° C. and the mixture was then stirred at RT for 16 h. After completion of the reaction (monitored by TLC) the mixture was diluted with methylene chloride (100 ml) and the organic layer was washed with water (100 ml) and brine (100 ml), and dried over anhydrous $Na_2SO_4$. The solvent was evaporated to afford the desired product as a brown solid which was used in the next step without further purification.

Step-2

(R)-Methyl 3-(tert-butoxycarbonylamino)-2,3-dihydro-1H-indene-5-carboxylate

A solution of (R)-tert-butyl 6-bromo-2,3-dihydro-1H-inden-1-ylcarbamate (15.0 g, 48.07 mmol, 1.0 eq.) in a mixture of MeOH (200 ml) and DMSO (30 ml) was degassed with argon for 30 min followed by addition of palladium acetate (0.53 g, 2.40 mmol, 0.05 eq.), 1,3-bis(diphenylphosphino) propane (0.99 g, 2.40 mmol, 0.05 eq.) and TEA (20 ml, 144.21 mmol, 3.0 eq.). The reaction mixture was then sealed in an autoclave using CO pressure (80 psi) and heated at 75° C. for 16 h. The mixture was evaporated to dryness, diluted with water (150 ml) and extracted with ethyl acetate (2×300 ml). The combined organic layers were washed with brine (100 ml), dried over anhydrous $Na_2SO_4$ and evaporated to give the crude product which was purified by column chromatography (silica gel; 5% ethyl acetate/hexanes) to yield the desired product as a white solid. Yield: 76% (10.6 g, 36.43 mmol).

Step-3

(R)-Methyl 3-(tert-butoxycarbonyl(methyl)amino)-2,3-dihydro-1H-indene-5-carboxylate A solution of (R)-methyl 3-(tert-butoxycarbonylamino)-2,3-dihydro-1H-indene-5-carboxylate (600 mg, 2.062 mmol, 1.0 eq.) in dry DMF (2 ml) was added to a stirred suspension of NaH (118 mg, 2.474 mmol, 1.2 eq., 50% in mineral oil) in DMF (3 ml) at 0° C. MeI (322 µl, 5.15 mmol, 2.5 eq.) was added to the reaction mixture at same temperature and it was stirred at RT for 2 h. After completion of the reaction (monitored by TLC), the reaction mixture diluted with ice-cold water (50 ml) and extracted with ethyl acetate (2×50 ml). The combined organic layers were washed with water (50 ml) and brine (50 ml), and dried over sodium sulfate. The solvent was evaporated under reduced pressure to give the crude product as a brown sticky solid which was used in the next step without further purification. Yield: 90% (566 mg, 1.855 mmol).

Step-4

(R)-Methyl 3-(methylamino)-2,3-dihydro-1H-indene-5-carboxylate (A-17)

TFA (2 ml) was added dropwise to a solution of (R)-methyl 3-(tert-butoxycarbonyl(methyl)-amino)-2,3-dihydro-1H-indene-5-carboxylate (760 mg, 2.49 mmol, 1.0 eq.) in methylene chloride (10 ml) at 0° C. The reaction mixture was then stirred at RT for 2 h. After completion of the reaction, the reaction mixture was concentrated to afford the desired product which was used in the next step without further purification.

Synthesis of amino acid ester A-18

(R)-Methyl 3-(2,2,2-trifluoroethylamino)-2,3-dihydro-1H-indene-5-carboxylate (A-18)

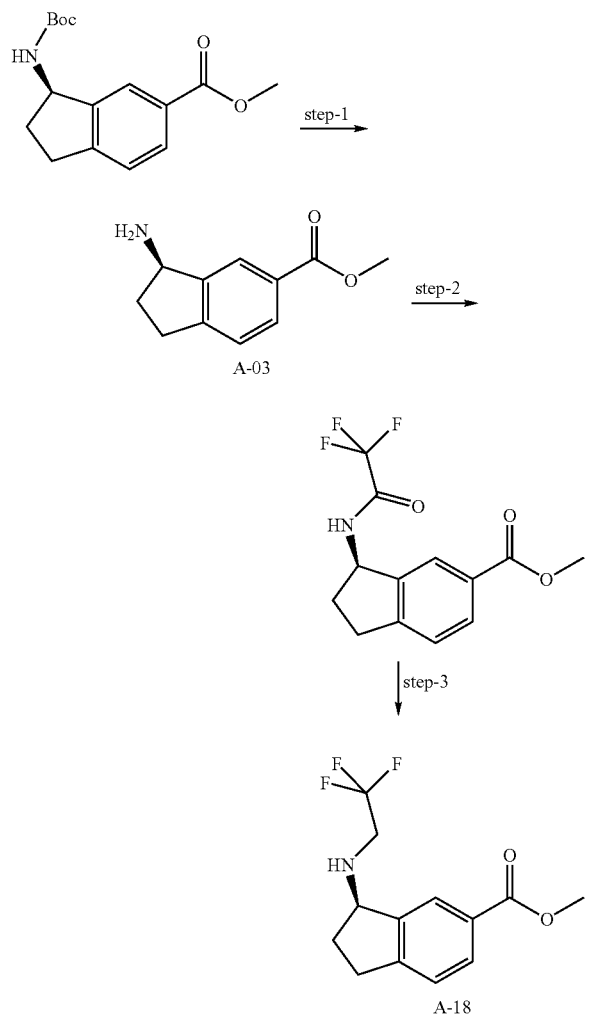

Step-1

(3R)-3-Amino-2,3-dihydro-1H-indene-5-carboxylic acid methyl ester (A-03)

TFA (10 ml) was added dropwise to a solution of (R)-methyl 3-(tert-butoxycarbonylamino)-2,3-dihydro-1H-indene-5-carboxylate (see step-2 product of A-17) (2.0 g, 6.87 mmol, 1.0 eq.) in methylene chloride (30 ml) at 0° C. The reaction mixture was then stirred at RT for 1 h. After completion (monitored by TLC), the reaction mixture was evaporated to afford the desired product as a colorless gummy solid which was used in the next step without further purification.

Step-2

(R)-Methyl 3-(2,2,2-trifluoroacetamido)-2,3-dihydro-1H-indene-5-carboxylate

To a solution of (3R)-3-amino-2,3-dihydro-1H-indene-5-carboxylic acid methyl ester (A-03) (2.09 g, 6.87 mmol, 1.0 eq.) in methylene chloride (30 ml) was added dropwise TEA (2.86 ml, 20.61 mmol, 3.0 eq.) at 0° C. and it was stirred for 15 min. Triflouroacetic anhydride (1.05 ml, 7.56 mmol, 1.1 eq.) was then added dropwise at 0° C. and the reaction mixture was stirred at RT for 12 h. After completion of the reaction (monitored by TLC), the mixture was diluted with methylene chloride (200 ml) and the organic layer was washed with water (50 ml) and brine (50 ml), and dried over anhydrous $Na_2SO_4$. The solvent was evaporated to afford the crude product which was purified by column chromatography (silica gel; 7% ethyl acetate/hexanes) to yield the desired compound as a white solid. Yield: 92% (1.8 g, 6.27 mmol).

Step-3

(R)-Methyl 3-(2,2,2-trifluoroethylamino)-2,3-dihydro-1H-indene-5-carboxylate (A-18)

To a cooled (0° C.) solution of (R)-methyl 3-(2,2,2-trifluoroacetamido)-2,3-dihydro-1H-indene-5-carboxylate (1.8 g, 6.27 mmol, 1.0 eq.) in THF (30 ml) is added $BH_3.Me_2S$ (0.9 ml, 9.4 mmol, 1.5 eq.) drop wise and the reaction mixture is heated at reflux for 2 h. The reaction mixture is then quenched with MeOH (0.5 ml) and then partitioned between water (30 ml) and ethyl acetate (100 ml). The organic layer is washed with brine (30 ml), dried over anhydrous $Na_2SO_4$ and evaporated to get the crude which is purified by column chromatography (silica gel; 4% ethyl acetate/hexanes) to yield the desired compound as a colourless oil. Yield: 43% (730 mg, 2.67 mmol).

2) Synthesis of the Acylated-& Sulfonylated Amino Acid Esters (B, C & D)

General Method for Synthesis of the Amino Acid Esters (B, C & D)

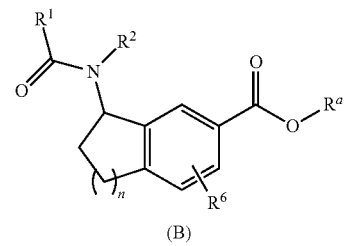

(B)

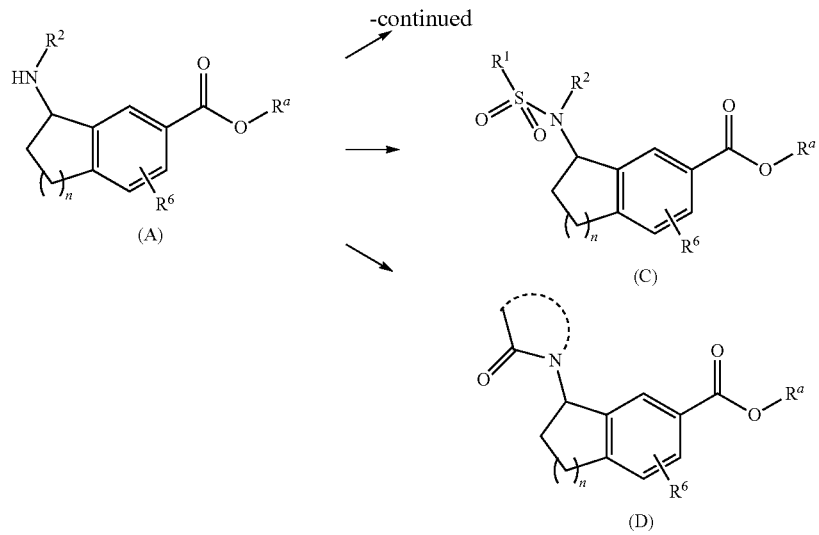

wherein

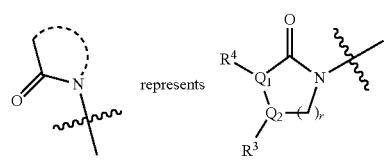

n = 1, 2 or 3

$R^a$ = $C_{1-4}$-alkyl

Synthesis of the Acylated-& Sulfonylated Amino Acid Esters (B, C & D)

Amino Acid Ester Overview:

| No. | Structure | Amino acid ester (B, C & D) | Comments |
|---|---|---|---|
| B-01 | 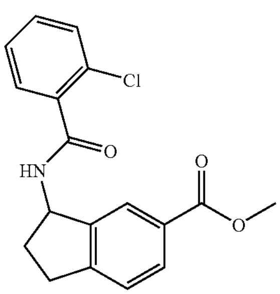 | 3-[(2-chloro-benzoyl)amino]-2,3-dihydro-1H-indene-5-carboxylic acid methyl ester (B-01) | see below |
| B-02 | 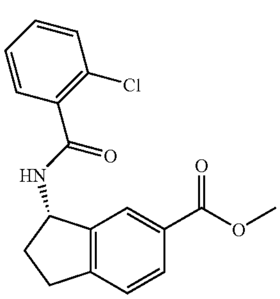 [SMILES: COC(=O)c1ccc2c(c1)[C@@H](NC(=O)c1ccccc1Cl)CC2] | (3S)-3-[(2-chloro-benzoyl)amino]-2,3-dihydro-1H-indene-5-carboxylic acid methyl ester (B-02) | Yield: 95.2% Synthesis was carried out analogously to B-01[a] (2 equiv. of NEt$_3$) starting from A-02 HCl |

-continued

| No. | Structure | Amino acid ester (B, C & D) | Comments |
|---|---|---|---|
| B-03 | 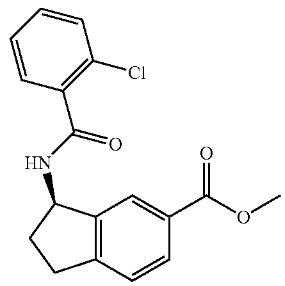 [SMILES: COC(=O)c1ccc2c(c1)[C@H](NC(=O)c1ccccc1Cl)CC2] | (3R)-3-[(2-chloro-benzoyl)amino]-2,3-dihydro-1H-indene-5-carboxylic acid methyl ester (B-03) | Yield: 93.1% Synthesis was carried out analogously to B-01[a] (2 equiv. of NEt₃) starting from A-03 HCl |
| B-06 | 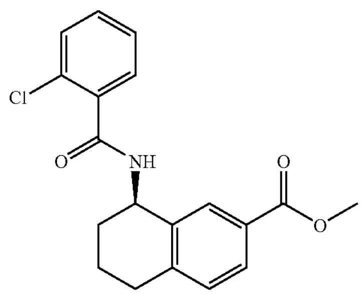 [SMILES: COC(=O)c1ccc2c(c1)[C@H](NC(=O)c1ccccc1Cl)CCC2] | (8R)-8-[(2-chloro-benzoyl)amino]-5,6,7,8-tetrahydro-naphthalene-2-carboxylic acid methyl ester (B-06) | Yield: 96.3% synthesis was carried out analogously to B-01 starting from A-06 HCl |
| B-07 | 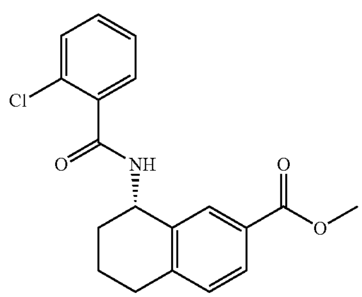 [SMILES: COC(=O)c1ccc2c(c1)[C@@H](NC(=O)c1ccccc1Cl)CCC2] | (8S)-8-[(2-chloro-benzoyl)amino]-5,6,7,8-tetrahydro-naphthalene-2-carboxylic acid methyl ester (B-07) | Yield: >100% synthesis was carried out analogously to B-01 starting from A-07 HCl |
| B-08 | 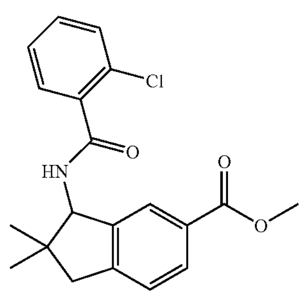 | methyl 3-(2-chlorobenzamido)-2,2-dimethyl-2,3-dihydro-1H-indene-5-carboxylate (B-08) | see below |
| B-09 | 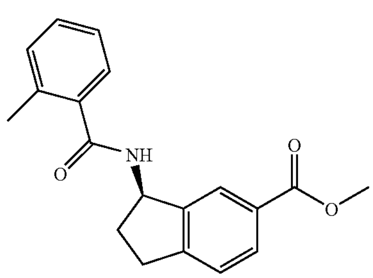 | (R)-methyl 3-(2-methylbenzamido)-2,3-dihydro-1H-indene-5-carboxylate (B-09) | see below |

| No. | Structure | Amino acid ester (B, C & D) | Comments |
|---|---|---|---|
| B-10 | 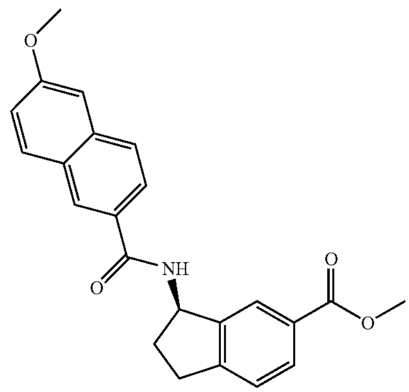 [SMILES: COC(=O)c1ccc2c(c1)[C@H](NC(=O)c1ccc3cc(OC)ccc3c1)CC2] | (R)-methyl 3-(6-methoxy-2-naphthamido)-2,3-dihydro-1H-indene-5-carboxylate (B-10) | see below |
| B-11 | 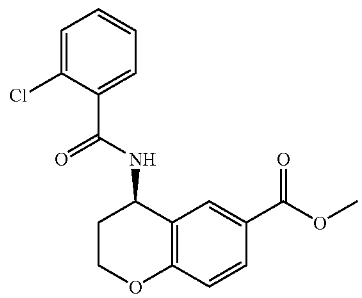 [SMILES: COC(=O)c1ccc2c(c1)[C@H](NC(=O)c1ccccc1Cl)CCO2] | (R)-methyl 4-(2-chlorobenzamido)chroman-6-carboxylate (B-11) | Yield: 92% synthesis was carried out analogously to B-09 (reaction times were adapted) Starting from A-09 |
| B-13 | 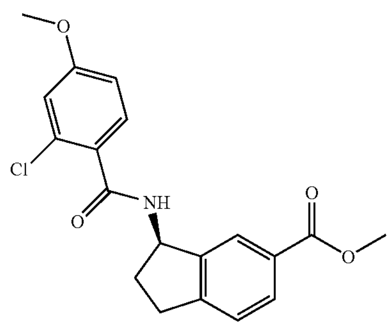 | (R)-methyl 3-(2-chloro-4-methoxybenzamide)-2,3-dihydro-1H-indene-5-carboxylate (B-14) | Yield: 80% synthesis was carried out analogously to B-10 starting from A-03 HCl |
| B-14 | 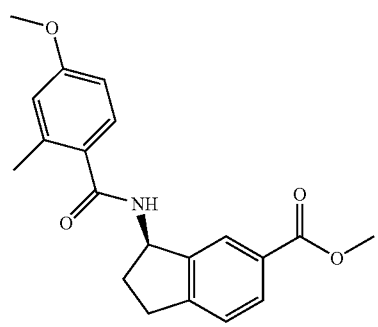 | (R)-methyl 3-(4-methoxy-2-methylbenzamido)-2,3-dihydro-1H-indene-5-carboxylate (B-14) | Yield: 75% synthesis was carried out analogously to B-10 starting from A-03 HCl |
| B-15 | 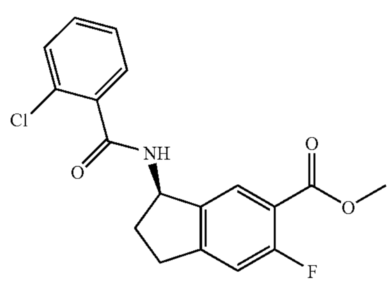 [SMILES: COC(=O)c1cc2c(cc1F)CC[C@H]2NC(=O)c1ccccc1Cl] | (R)-methyl 3-(2-chlorobenzamido)-6-fluoro-2,3-dihydro-1H-indene-5-carboxylate (B-15) | see below |

| No. | Structure | Amino acid ester (B, C & D) | Comments |
|---|---|---|---|
| B-17 | 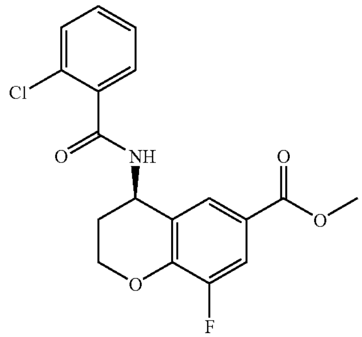 [SMILES: COC(=O)c1cc(F)c2c(c1)[C@H](NC(=O)c1ccccc1Cl)CCO2] | (R)-methyl 4-(2-chlorobenzamido)-8-fluorochroman-6-carboxylate (B-17) | Yield: 93% synthesis was carried out analogously to B-15 starting from A-13 |
| B-18 | 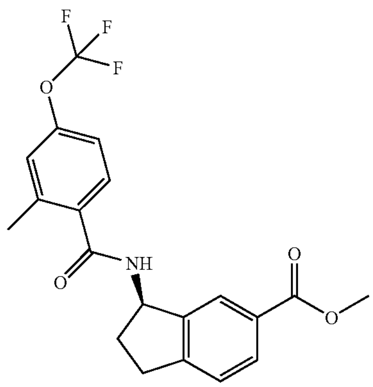 | (R)-methyl 3-(2-methyl-4-(trifluoromethoxy)benzamido)-2,3-dihydro-1H-indene-5-carboxylate (B-18) | Yield: 81% synthesis was carried out analogously to B-09 starting from A-03 HCl |
| B-19 | 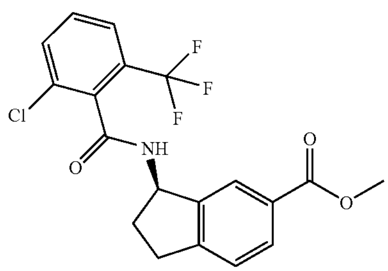 [SMILES: COC(=O)c1ccc2c(c1)[C@H](NC(=O)c1c(Cl)cccc1C(F)(F)F)CC2] | (R)-methyl 3-(2-chloro-6-(trifluoromethyl)benzamido)-2,3-dihydro-1H-indene-5-carboxylate (B-19) | Yield: >99% synthesis was carried out analogously to B-09 starting from A-03 HCl |
| B-20 | 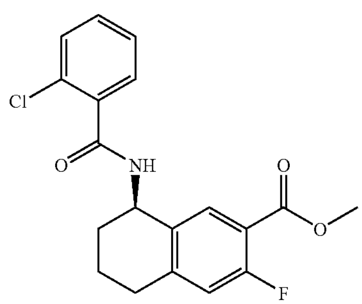 [SMILES: COC(=O)c1cc2c(cc1F)CCC[C@H]2NC(=O)c1ccccc1Cl] | (R)-methyl 8-(2-chlorobenzamido)-3-fluoro-5,6,7,8-tetrahydronaphthalene-2-carboxylate (B-20) | Yield: 94% synthesis was carried out analogously to B-15 starting from A-14 |
| B-21 | 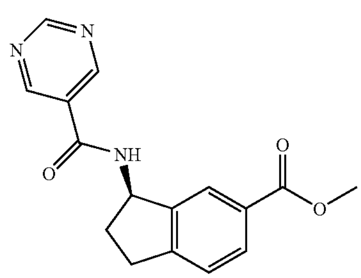 [SMILES: COC(=O)c1ccc2c(c1)[C@H](NC(=O)c1cncnc1)CC2] | (R)-methyl 3-(pyrimidine-5 carboxamido)-2,3-dihydro-1H-indene-5-carboxylate (B-21) | Yield: 73% synthesis was carried out analogously to B-10 (reaction times were adapted) stating from A-03 HCl |

| No. | Structure | Amino acid ester (B, C & D) | Comments |
|---|---|---|---|
| B-22 | 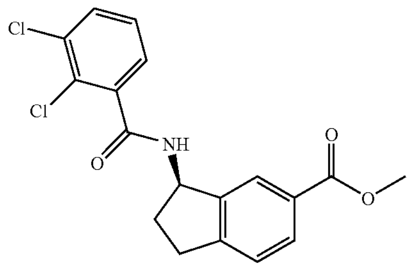 [SMILES: COC(=O)c1ccc2c(c1)[C@H](NC(=O)c1cccc(Cl)c1Cl)CC2] | (R)-methyl 3-(2,3-dichlorobenzamido)-2,3-dihydro-1H-indnee-5-carboxylate (B-22) | Yield: 94%<br>synthesis was carried out analogously to B-09 (reaction times were adapted)<br>starting from A-03 HCl |
| B-24 | 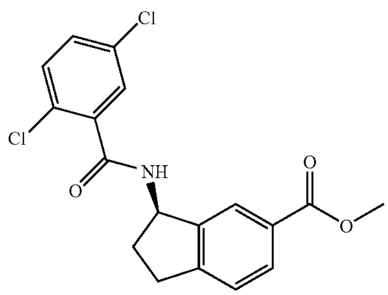 | (R)-methyl 3-(2,5-dichlorobenzamido)-2,3-dihydro-1H-indene-5-carboxylate (B-24) | Yield: 97%<br>synthesis was carried out analogously to B-09 (reaction times were adapted)<br>starting from A-03 HCl |
| B-25 | 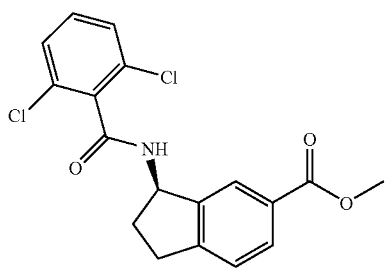 [SMILES: COC(=O)c1ccc2c(c1)[C@H](NC(=O)c1c(Cl)cccc1Cl)CC2] | (R)-methyl 3-(2,6-dichlorobenzamido)-2,3-dihydro-1H-indene-5-carboxylate (B-25) | Yield: 82%<br>synthesis was carried out analogously to B-09 (reaction times were adapted)<br>starting from A-03 HCl |
| B-26 | 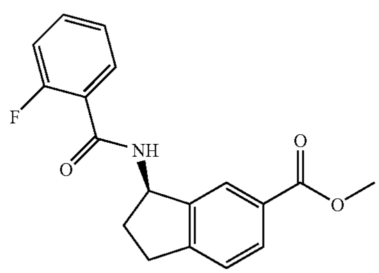 [SMILES: COC(=O)c1ccc2c(c1)[C@H](NC(=O)c1ccccc1F)CC2] | (R)-methyl 3-(2-fluorobenzamido)-2,3-dihydro-1H-indene-5-carboxylate (B-26) | Yield: 83%<br>synthesis was carried out analogously to B-09 (reaction times were adapted)<br>starting from A-03 HCl |
| B-27 | 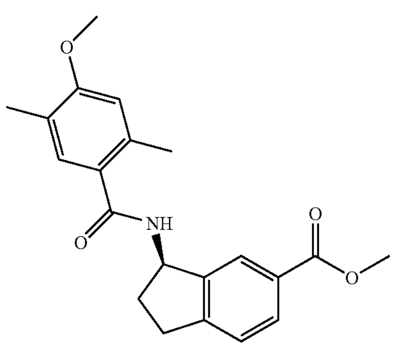 | (R)-methyl 3-(4-methoxy-2,5-dimethylbenzamido)-2,3-dihydro-1H-indene-5-carboxylate (B-27) | Yield: 82%<br>synthesis was carried out analogously to B-10 (reaction times were adapted)<br>starting from A-03 HCl |

-continued

| No. | Structure | Amino acid ester (B, C & D) | Comments |
|---|---|---|---|
| B-28 | 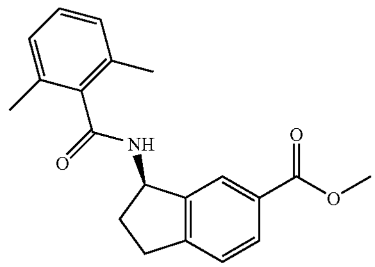 | (R)-methyl 3-(2,6-dimethylbenzamido)-2,3-dihydro-1H-indene-5-carboxylate (B-28) | Yield: >99% synthesis was carried out analogously to B-09 (reaction times were adapted) starting from A-03 HCl |
| B-29 | 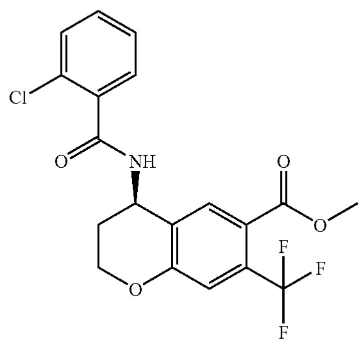 [SMILES: COC(=O)c1cc2c(cc1C(F)(F)F)OCC[C@H]2NC(=O)c1ccccc1Cl] | (R)-methyl 4-(2-chlorobenzamido)-7-(trifluoromethyl)chroman-6-carboxylate (B-29) | Yield: 50% synthesis was carried out analogously to B-15 (reaction times were adapted) starting from A-15 |
| B-30 | 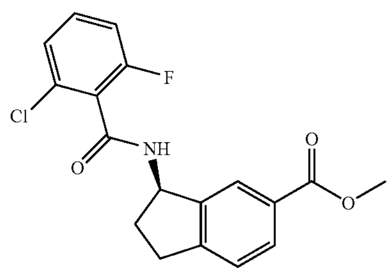 [SMILES: COC(=O)c1ccc2c(c1)[C@H](NC(=O)c1c(F)cccc1Cl)CC2] | (R)-methyl 3-(2-chloro-6-fluorobenzamido)-2,3-dihydro-1H-indene-5-carboxylate (B-30) | Yield: 96% synthesis was carried out analogously to B-09 reaction times were adapted) starting from A-03 HCl |
| B-31 | 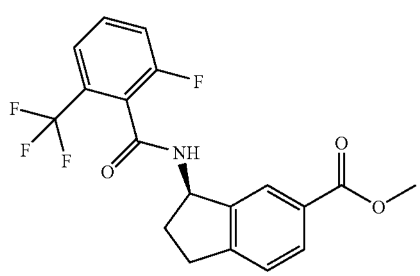 [SMILES: COC(=O)c1ccc2c(c1)[C@H](NC(=O)c1c(F)cccc1C(F)(F)F)CC2] | (R)-methyl 3-(2-fluoro-6-(trifluoromethyl)benzamido)-2,3-dihydro-1H-indene-5-carboxylate (B-31) | Yield: 88% synthesis was carried out analogously to B-09 (reaction times were adapted) starting from A-03 HCl |
| B-32 | 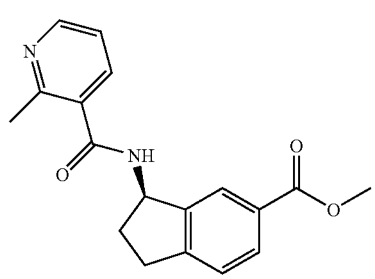 | (R)-methyl 3-(2-methylnicotinamido)-2,3-dihydro-1H-indene-5-carboxylate (B-32) | Yield: 82% synthesis was carried out analogously to B-10 (reaction times were adapted) starting from A-03 HCl |

| No. | Structure | Amino acid ester (B, C & D) | Comments |
|---|---|---|---|
| B-33 | 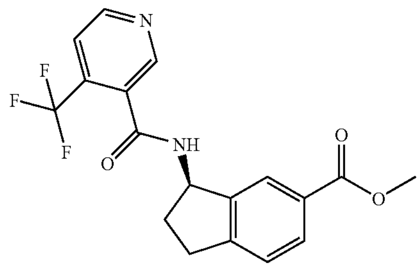 [SMILES: COC(=O)c1ccc2c(c1)[C@H](NC(=O)c1cnccc1C(F)(F)F)CC2] | (R)-methyl 3-(4-(trifluoromethyl)nicotinamido)-2,3-dihydro-1H-indene-5-carboxylate (B-33) | Yield: 79%<br>synthesis was carried out analogously to B-10 (reaction times were adapted)<br>starting from A-03 HCl |
| B-39 | 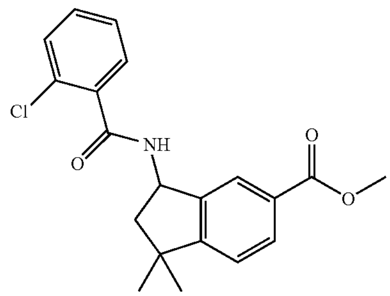 [SMILES: COC(=O)c1ccc2c(c1)C(NC(=O)c1ccccc1Cl)CC2(C)C] | methyl 3-(2-chlorobenzamido)-1,1-dimethyl-2,3-dihydro-1H-indene-5-carboxylate (B-39) | 26%<br>(reaction times were adapted) |
| B-41 | 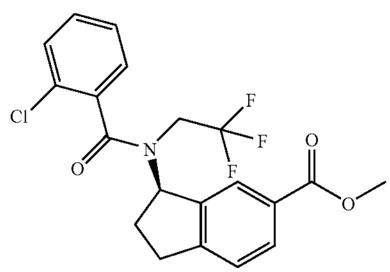 [SMILES: COC(=O)c1ccc2c(c1)[C@H](N(CC(F)(F)F)C(=O)c1ccccc1Cl)CC2] | (R)-methyl 3-(2-chloro-N-(2,2,2-trifluoroethyl)benzamido)-2,3-dihydro-1H-indene-5-carboxylate (B-41) | see below |
| B-42 | 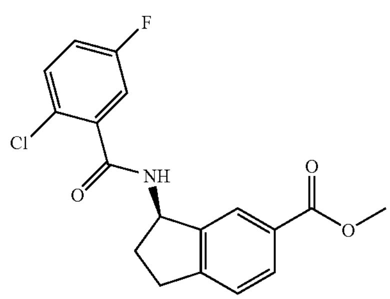 [SMILES: COC(=O)c1ccc2c(c1)[C@H](NC(=O)c1cc(F)ccc1Cl)CC2] | (R)-methyl 3-(2-chloro-5-fluorobenzamido)-2,3-dihydro-1H-indene-5-carboxylate (B-42) | Yield: 88%<br>synthesis was carried out analogously to B-15 (reaction times were adapted)<br>starting from A-03 HCl |
| B-43 | 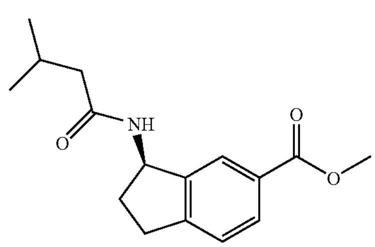 [SMILES: COC(=O)c1ccc2c(c1)[C@H](NC(=O)CC(C)C)CC2] | (R)-methyl 3-(3-methylbutanamido)-2,3-dihydro-1H-indene-5-carboxylate (B-43) | Yield: 76%<br>synthesis was carried out analogously to B-15 (reaction times were adapted)<br>starting from A-03 HCl |

-continued

| No. | Structure | Amino acid ester (B, C & D) | Comments |
|---|---|---|---|
| B-44 | 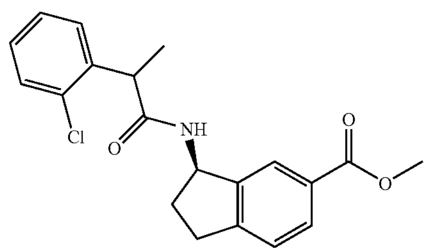 [SMILES: COC(=O)c1ccc2c(c1)[C@H](NC(=O)C(C)c1ccccc1Cl)CC2] | (3R)-methyl 3-(2-(2-chlorophenyl)propanamido)-2,3-dihydro-1H-indene-5-carobxylate (B-44) | Yield: 92% synthesis was carried out analogously to B-10 starting from A-03 HCl |
| B-45 | 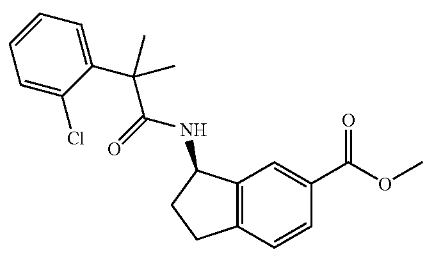 [SMILES: COC(=O)c1ccc2c(c1)[C@H](NC(=O)C(C)(C)c1ccccc1Cl)CC2] | (R)-methyl 3-(2-(2-chlorophenyl)-2-methylpropanamid)-2,3-dihydro-1H-indene-5-carboxylate (B-45) | Yield: 42% synthesis was carried out analogously to B-10 starting from A-03 HCl |
| B-46 | 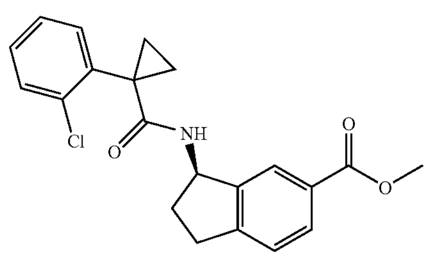 [SMILES: COC(=O)c1ccc2c(c1)[C@H](NC(=O)C1(c3ccccc3Cl)CC1)CC2] | (R)-methyl 3-(1-(2-chlorophenyl)cyclopropanecarobxamido)-2,3-dihydro-1H-indene-5-carboxylate (B-46) | Yield: 76% synthesis was carried out analogously to B-10 (reaction times were adapted) starting from A-03 HCl |
| B-47 | 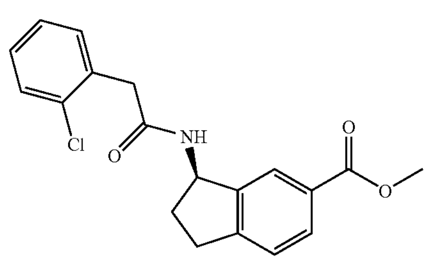 [SMILES: COC(=O)c1ccc2c(c1)[C@H](NC(=O)Cc1ccccc1Cl)CC2] | (R)-methyl 3-(2-(2-chlorophenyl)acetamido)-2,3-dihydro-1H-indene-5-carboxylate (B-47) | Yield: 80% synthesis was carried out analogously to B-10 (reaction times were adapted) starting from A-03 HCl |
| B-48 | 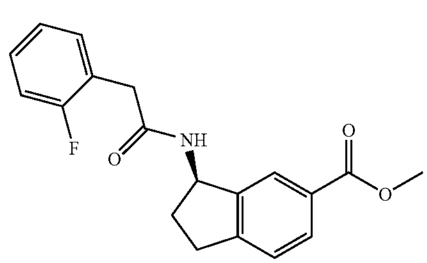 [SMILES: COC(=O)c1ccc2c(c1)[C@H](NC(=O)Cc1ccccc1F)CC2] | (R)-methyl 3-(2-(2-fluorophenyl)acetamido)-2,3-dihydro-1H-indene-5-carboxylate (B-50) | Yield: 74% synthesis was carried out analogously to B-10 (reaction times were adapted) starting from A-03 HCl |
| B-49 | 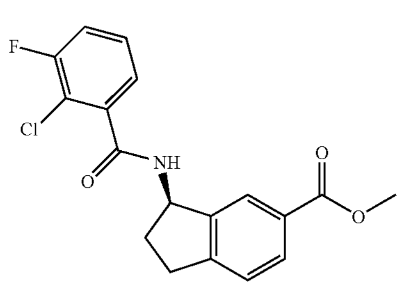 [SMILES: COC(=O)c1ccc2c(c1)[C@H](NC(=O)c1cccc(F)c1Cl)CC2] | (R)-methyl 3-(2-chloro-3-fluorobenzamido)-2,3-dihydro-1H-indene-5-carobxylate (B-49) | Yield: 92% synthesis was carried out analogously to B-15 (reaction times were adapted) starting from A-03 HCl |

-continued

| No. | Structure | Amino acid ester (B, C & D) | Comments |
|---|---|---|---|
| B-50 | 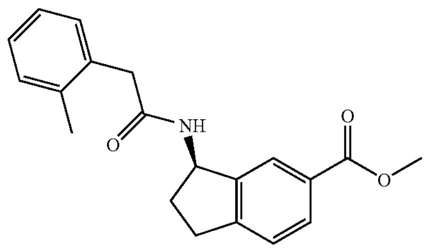 [SMILES: COC(=O)c1ccc2c(c1)[C@H](NC(=O)Cc1ccccc1C)CC2] | (R)-methyl 3-(2-o-tolylacetamido)-2,3-dihydro-1H-indene-5-carboxylate (B-50) | Yield: 99%<br>synthesis was carried out analogously to B-10 starting from A-03 HCl |
| B-51 | 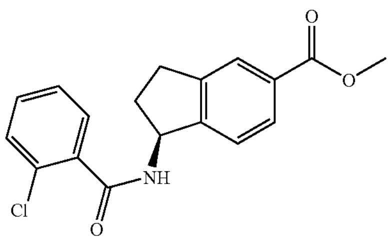 [SMILES: COC(=O)c1ccc2c(c1)CC[C@@H]2NC(=O)c1ccccc1Cl] | (S)-methyl 1-(2-chlorobenzamido)-2,3-dihydro-1H-indene-5-carboxylate (B-51) | Yield: 49%<br>synthesis was carried out analogously to B-15 starting from A-19 |
| B-52 | 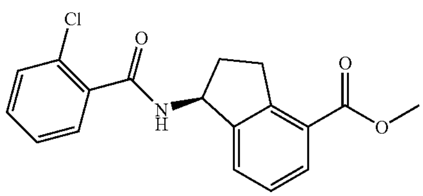 [SMILES: COC(=O)c1cccc2c1CC[C@@H]2NC(=O)c1ccccc1Cl] | (S)-methyl 1-(2-chlorobenzamido)-2,3-dihydro-1H-indene-4-carboxylate (B-52) | Yield: 93%<br>synthesis was carried out analogously to B-15 starting from A-21 |
| B-53 | 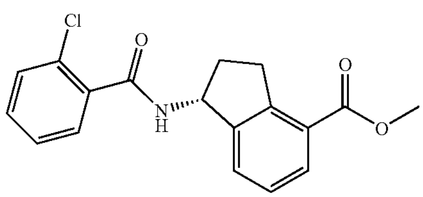 [SMILES: COC(=O)c1cccc2c1CC[C@H]2NC(=O)c1ccccc1Cl] | (R)-methyl 1-(2-chlorobenzamido)-2,3-dihydro-1H-indene-4-carboxylate (B-53) | Yield: 90%<br>synthesis was carried out analogously to B-15 starting from A-22 |
| B-54 | 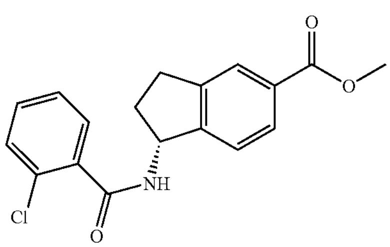 [SMILES: COC(=O)c1ccc2c(c1)CC[C@H]2NC(=O)c1ccccc1Cl] | (R)-methyl 1-(2-chlorobenzamido)-2,3-dihydro-1H-indene-5-carboxylate (B-54) | Yield: 83%<br>synthesis was carried out analogously to B-15 starting from A-20 |
| C-01 | 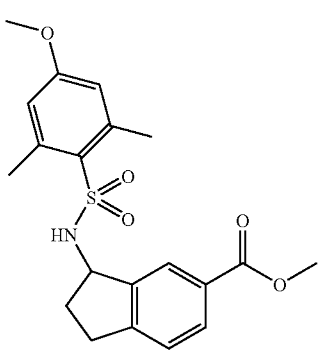 | 3-[[(4-methoxy-2,6-dimethyl-phenyl)sulfonyl]amino]-2,3-dihydro-1H-indene-5-carboxylic acid methyl ester (C-01) | see below |

| No. | Structure | Amino acid ester (B, C & D) | Comments |
|---|---|---|---|
| C-02 | 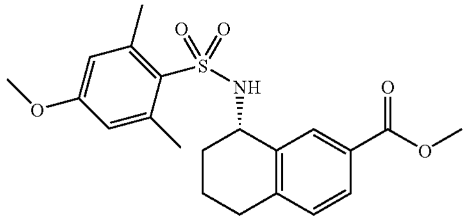 | (S)-methyl 8-(4-methoxy-2,6-dimethylphenylsulfonamido)-5,6,7,8-tetrahydronaphthalene-2-carboxylate (C-02) | Yield: 77%<br>Synthesis was carried out analogously to C-01[a]<br>(2 equiv. of NEt₃)<br>starting from A-07 |
| C-03 | 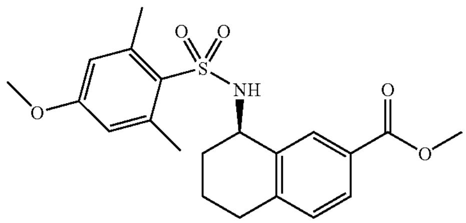 | (R)-methyl 8-(4-methoxy-2,6-dimethylphenylsulfonamido)-5,6,7,8-tetrahydronaphthalene-2-carboxylate (C-03) | Yield: 95.6%<br>Synthesis was carried out analogously to C-01[a]<br>(2 equiv. of NEt₃)<br>starting from A-06 |
| C-04 | 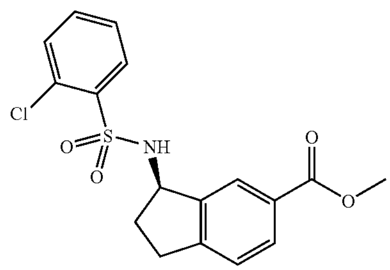 [SMILES: COC(=O)c1ccc2c(c1)[C@H](NS(=O)(=O)c1ccccc1Cl)CC2] | (R)-methyl 3-(2-chlorophenylsulfonamido)-2,3-dihydro-1H-indene-5-carboxylate (C-04) | see below |
| C-05 | 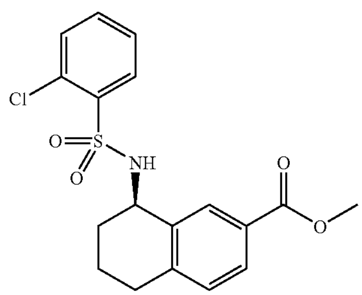 [SMILES: COC(=O)c1ccc2c(c1)[C@H](NS(=O)(=O)c1ccccc1Cl)CCC2] | (R)-methyl 8-(2-chlorophenylsulfonamido)-5,6,7,8-tetrahydronaphthalene-2-carboxylate (C-05) | Yield: 86%<br>synthesis was carried out analogously to C-04<br>starting from A-06 HCl |
| C-06 | 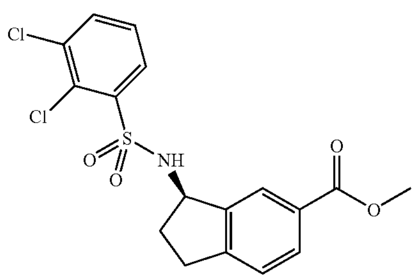 [SMILES: COC(=O)c1ccc2c(c1)[C@H](NS(=O)(=O)c1cccc(Cl)c1Cl)CC2] | (R)-methyl 3-(2,3-dichlorophenylsulfonamido)-2,3-dihydro-1H-indene-5-carboxylate (C-06) | see below |
| C-07 | 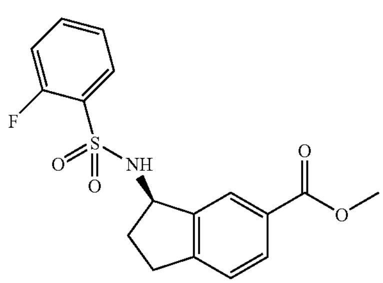 [SMILES: COC(=O)c1ccc2c(c1)[C@H](NS(=O)(=O)c1ccccc1F)CC2] | (R)-methyl 3-(2-fluorophenylsulfonamido)-2,3-dihydro-1H-indene-5-carboxylate (C-07) | Yield: 96%<br>synthesis was carried out analogously to C-06<br>(reaction times were adapted)<br>starting from A-03 HCl |

| No. | Structure | Amino acid ester (B, C & D) | Comments |
|---|---|---|---|
| C-08 | 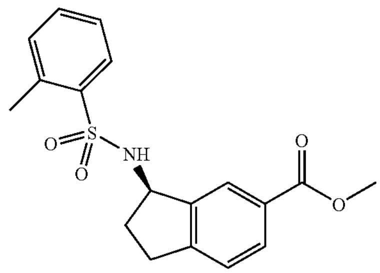 | (R)-methyl 3-(2-methylphenylsulfonamido)-2,3-dihydro-1H-indene-5-carboxylate (C-08) | Yield: 97%<br>synthesis was carried out analogously to C-06 (reaction times were adapted)<br>starting from A-03 HCl |
| C-09 | 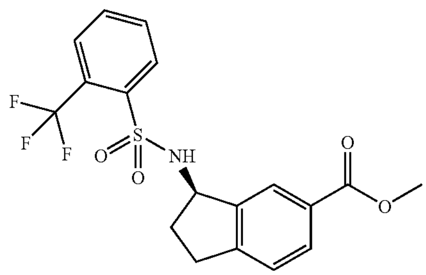 [SMILES: COC(=O)c1ccc2c(c1)[C@H](NS(=O)(=O)c1ccccc1C(F)(F)F)CC2] | (R)-methyl 3-(2-(trifluoromethyl)phenylsulfonamido)-2,3-dihydro-1H-indene-5-carboxylate (C-09) | Yield: 68%<br>synthesis was carried analogously to C-06 (reaction times were adapted)<br>starting from A-03 HCl |
| C-10 | 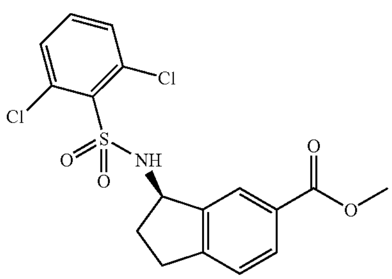 [SMILES: COC(=O)c1ccc2c(c1)[C@H](NS(=O)(=O)c1c(Cl)cccc1Cl)CC2] | (R)-methyl 3-(2,6-dichlorophenylsulfonamido)-2,3-dihydro-1H-indeme-5-carboxylate (C-10) | Yield: 99%<br>synthesis was carried out analogously to C-06 (reaction times were adapted)<br>starting from A-03 HCl |
| C-11 | 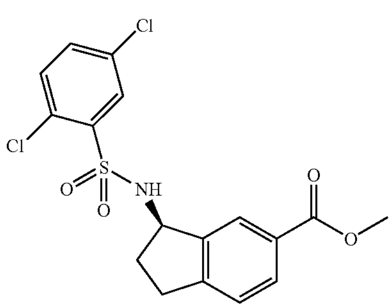 [SMILES: COC(=O)c1ccc2c(c1)[C@H](NS(=O)(=O)c1cc(Cl)ccc1Cl)CC2] | (R)-methyl 3-(2,5-dichlorophenylsulfonamido)-2,3-dihydro-1H-indene-5-carboxylate (C-11) | Yield: >99%<br>synthesis was carried out analogously to C-06 (reaction times were adapted)<br>starting from A-03 HCl |
| C-12 | 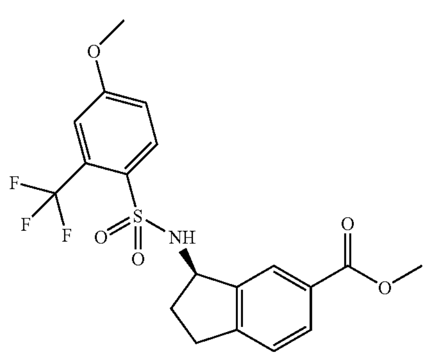 [SMILES: COC(=O)c1ccc2c(c1)[C@H](NS(=O)(=O)c1ccc(OC)cc1C(F)(F)F)CC2] | (R)-methyl 3-(4-methoxy-2-(trifluoromethyl)phenylsulfonamido)-2,3-dihydro-1H-indene-5-carboxylate (C-12) | Yield: 81%<br>synthesis was carried out analogously to C-06 (reaction times were adapted)<br>starting from A-03 HCl |

-continued

| No. | Structure | Amino acid ester (B, C & D) | Comments |
|---|---|---|---|
| C-13 | 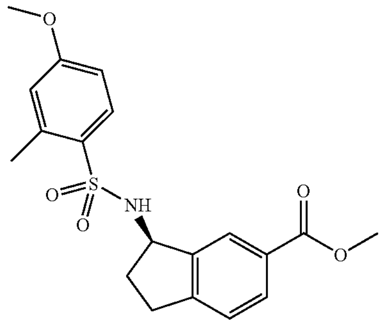 | (R)-methyl 3-(4-methoxy-2-methylphenylsulfonamido)-2,3-dihydro-1H-indene-5-carboxylate (C-13) | Yield: 93%<br>synthesis was carried out analogously to C-06<br>starting from A-03 HCl |
| C-14 | 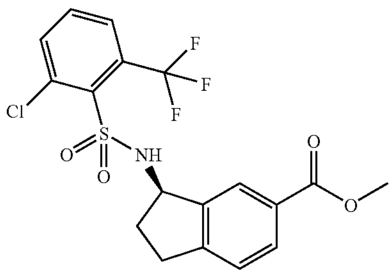 [SMILES: COC(=O)c1ccc2c(c1)[C@H](NS(=O)(=O)c1c(Cl)cccc1C(F)(F)F)CC2] | (R)-methyl 3-(2-chloro-6-(trifluoromethylphenylsulfonamido)-2,3-dihydro-1H-indene-5-carboxylate (C-14) | Yield: >99%<br>synthesis was carried out analogously to C-06 (reaction times were adapted)<br>starting from A-03 HCl |
| C-15 | 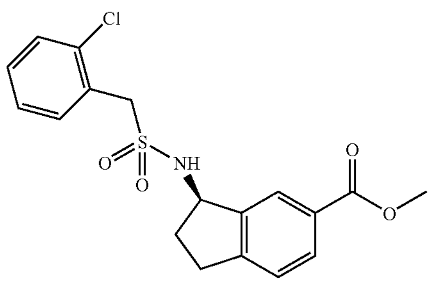 [SMILES: COC(=O)c1ccc2c(c1)[C@H](NS(=O)(=O)Cc1ccccc1Cl)CC2] | (R)-methyl 3-((2-chlorophenyl)methylsulfonamido)-2,3-dihydro-1H-indene-5-carboxylate (C-15) | Yield: 88%<br>synthesis was carried out analogously to C-06<br>starting from A-03 HCl |
| C-16 | 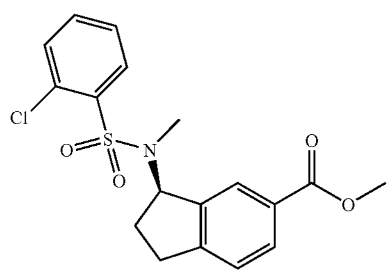 [SMILES: COC(=O)c1ccc2c(c1)[C@H](N(C)S(=O)(=O)c1ccccc1Cl)CC2] | (R)-methyl 3-(2-chloro-N-methylphenylsulfonamido)-2,3-dihydro-1H-indene-5-carboxylate (C-16) | see below |
| C-17 | 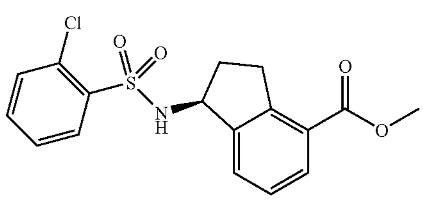 [SMILES: COC(=O)c1cccc2c1CC[C@@H]2NS(=O)(=O)c1ccccc1Cl] | (S)-methyl 1-(2-chlorophenylsulfonamido)-2,3-dihydro-1H-indene-4-carboxylate (C-17) | Yield: 62%<br>synthesis was carried out analgously to C-06<br>starting from A-21 |
| C-18 | 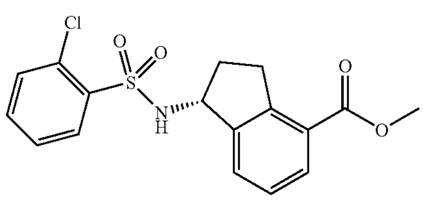 [SMILES: COC(=O)c1cccc2c1CC[C@H]2NS(=O)(=O)c1ccccc1Cl] | (R)-methyl 1-(2-chlorophenylsulfonamido)-2,3-dihydro-1H-indene-4-carboxylate (C-18) | Yield: 68%<br>synthesis was carried out analogously to C-06<br>starting from A-22 |

-continued

| No. | Structure | Amino acid ester (B, C & D) | Comments |
|---|---|---|---|
| C-19 | 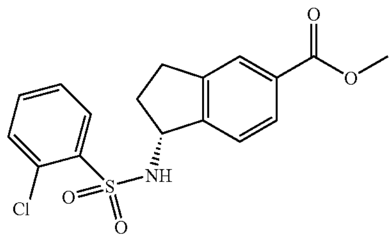 [SMILES: COC(=O)c1ccc2c(c1)CC[C@H]2NS(=O)(=O)c1ccccc1Cl] | (R)-methyl 1-(2-chlorophenylsulfonamido)-2,3-dihydro-1H-indene-5-carboxylate (C-19) | Yield: 87% synthesis was carried out analogously to C-06 starting from A-20 |
| D-01 | 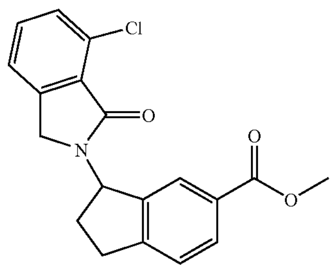 [SMILES: COC(=O)c1ccc2c(c1)C(N1Cc3cccc(Cl)c3C1=O)CC2] | 3-(4-chloro-3-oxo-1,2-dihydro-isoindol-2-yl)-2,3-dihydro-1H-indene-5-carboxylic acid methyl ester (D-01) | see below |
| D-02 | 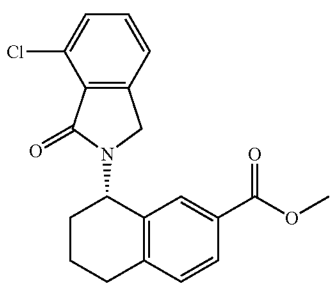 [SMILES: COC(=O)c1ccc2c(c1)[C@@H](N1Cc3cccc(Cl)c3C1=O)CCC2] | (S)-methyl 8-(7-chloro-1-oxoisoindolin-2-yl)-5,6,7,8-tetrahydronaphthalene-2-carboxylate (D-02) | see below |
| D-03 | 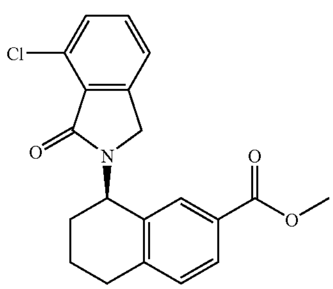 [SMILES: COC(=O)c1ccc2c(c1)[C@H](N1Cc3cccc(Cl)c3C1=O)CCC2] | ®-methyl 8-(7-chloro-1-oxoisoindolin-2-yl)-5,6,7,8-tetrahydronaphthalene-2-carboxylate (D-03) | Yield: 64.5% Synthesis was carried out analogously to D-02 starting from A-06 |
| D-07 | 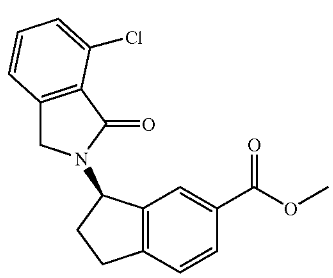 [SMILES: COC(=O)c1ccc2c(c1)[C@H](N1Cc3cccc(Cl)c3C1=O)CC2] | (R)-methyl 3-(7-chloro-1-oxoisoindolin-2-yl)-2,3-dihydro-1H-indene-5-carboxylate (G-07) | see below |

-continued

| No. | Structure | Amino acid ester (B, C & D) | Comments |
|---|---|---|---|
| D-08 | 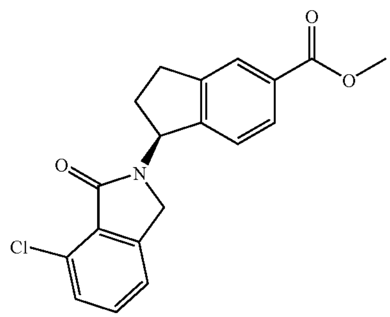 [SMILES: COC(=O)c1ccc2c(c1)CC[C@@H]2N1Cc2cccc(Cl)c2C1=O] | (S)-methyl 1-(7-chloro-1-oxoisoindolin-2-yl)-2,3-dihydro-1H-indene-5-carboxylate (D-08) | Yield: 48% synthesis was carried out analogously to D-07 starting from A-19 |
| D-09 | 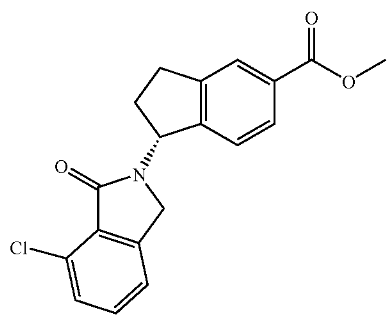 [SMILES: COC(=O)c1ccc2c(c1)CC[C@H]2N1Cc2cccc(Cl)c2C1=O] | (R)-methyl 1-(7-chloro-1-oxoisoindolin-2-yl)-2,3-dihydro-1H-indene-5-carboxylate (D-09) | Yield: 89% synthesis was carried out analogously to D-07 starting from A-20 |
| D-10 | 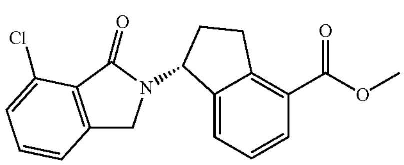 [SMILES: COC(=O)c1cccc2c1CC[C@H]2N1Cc2cccc(Cl)c2C1=O] | (R)-methyl 1-(7-chloro-1-oxoisoindolin-2-yl)-2,3-dihydro-1H-indene-4-carboxylate (D-10) | Yield: 76% synthesis was carried out analogously to D-07 starting from A-22 |
| D-22 | 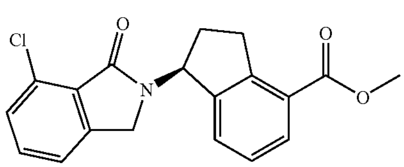 [SMILES: COC(=O)c1cccc2c1CC[C@@H]2N1Cc2cccc(Cl)c2C1=O] | (S)-methyl 1-(7-chloro-1-oxoisoindolin-2-yl)-2,3-dihydro-1H-indene-4-carboxylate (D-11) | Yield: 56% synthesis was carried out analogously to D-07 starting from A-21 |

Notes:
[a]Modified working up: The reaction mixture was finally diluted with methylene chloride, and sat. NaHCO₃ solution was added. The phases were separated and the aqueous phase was extracted 3× with methylene chloride. The organic phase was dried over Na₂SO₄ and concentrated. Concentration of the filtrate gave the crude product, which was purified by column chromatography over silica gel (hexane/ethyl acetate).
General note: For reactions which were carried out in analogy to a described method, it may have been necessary to adapt the reaction conditions slightly, especially regarding the no. of equivalents of reagents employed, the interchangability of Et₃N and DIPEA, the reaction times (which were adjusted according to tlc results), the drying agent (magnesium sulfate or sodium sulfate) and the need for purification by column chromatography being required.

Synthesis of Amino Acid Ester B-01

3-[(2-Chloro-benzoyl)amino]-2,3-dihydro-1H-indene-5-carboxylic acid methyl ester (B-01)

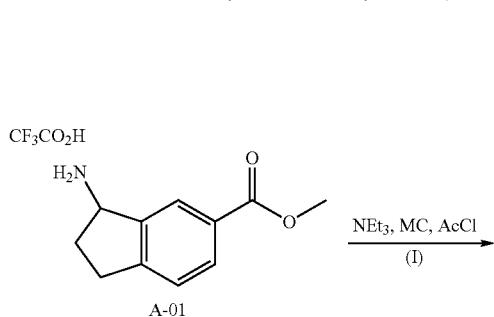

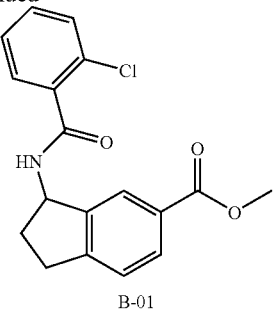

Triethylamine (5.1 mmol) and 2-chloro-benzoyl chloride (1.2 equiv.) were added to an ice-cold solution of A-01 (1.71 mmol) in methylene chloride at 0° C. and under an inert atmosphere and the mixture was then stirred at room temperature for 1 h. The reaction mixture was finally diluted with methylene chloride and the organic phase was washed with water and sat. NaCl solution, dried over Na₂SO₄ and concentrated to obtain 3-[(2-chloro-benzoyl)amino]-2,3-dihydro-1H-indene-5-carboxylic acid methyl ester (B-01). Yield: 93.5%

Synthesis of amino acid ester B-08

Methyl 3-(2-chlorobenzamido)-2,2-dimethyl-2,3-dihydro-1H-indene-5-carboxylate (B-08)

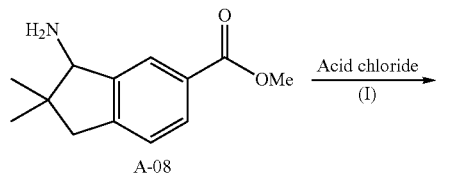

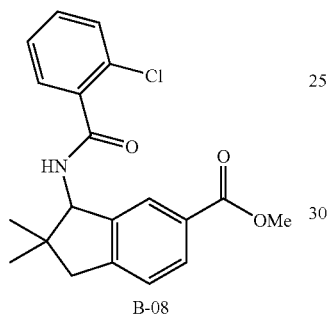

(I) Et₃N (1.6 ml) was added to a solution of methyl 3-amino-2,2-dimethyl-2,3-dihydro-1H-indene-5-carboxylate (A-08) (6 g, crude) in abs. CH₂Cl₂ (20 ml) at 0° C. and the mixture was stirred for 10 min. 2-Chlorobenzoyl chloride (1.2 ml) was then added dropwise to the reaction mixture at the same temperature and the mixture was stirred for 3 h. The reaction mixture was diluted with CH₂Cl₂ (100 ml), washed with water (2×50 ml) and sat. NaCl solution (2×50 ml) and dried over sodium sulfate. The solvent was removed in vacuo and the crude material was purified by column chromatography (silica gel, 8% ethyl acetate in hexane) in order to obtain the desired product. Yield: 38% (after two steps)

Synthesis of amino acid ester B-09

(R)-Methyl 3-(2-methylbenzamido)-2,3-dihydro-1H-indene-5-carboxylate (B-09)

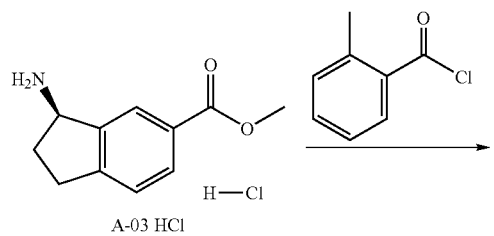

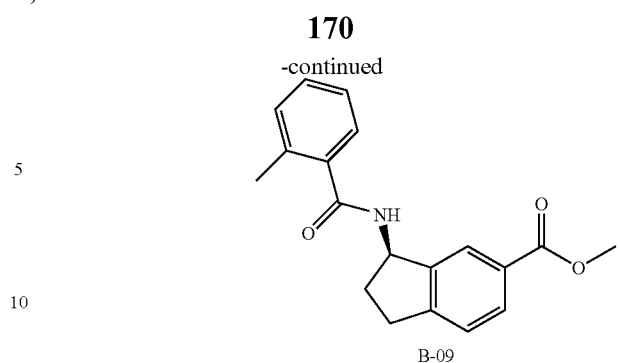

N-Ethyl-diisopropylamine (2.5 eq.) and 2-methylbenzoyl chloride (1.2 equiv.) were added to an ice-cold solution of (3R)-3-amino-2,3-dihydro-1H-indene-5-carboxylic acid methyl ester hydrochloride (A-03 HCl) (0.88 mmol, 1 equiv.) in methylene chloride at 0° C. under an inert atmosphere and the mixture was then stirred at room temperature for 2 d. The reaction mixture was diluted with ethyl acetate and the organic phase was washed with 10% NH₄Cl solution, sat. NaHCO₃ solution and sat. NaCl solution. The organic phase was dried over Na₂SO₄ and concentrated to obtain the crude product, which was purified by column chromatography (silica, cyclohexane/ethyl acetate 4:1). Yield: 70%

Synthesis of amino acid ester B-10

(R)-Methyl 3-(6-methoxy-2-naphthamido)-2,3-dihydro-1H-indene-5-carboxylate (B-10)

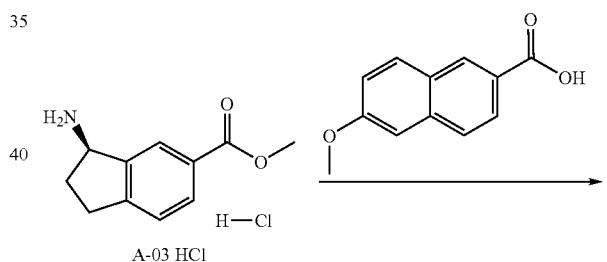

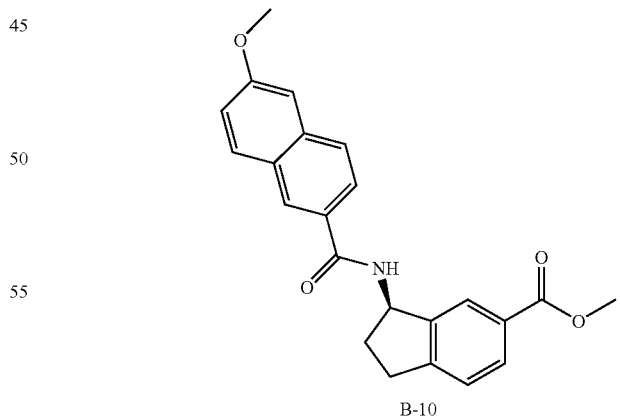

N-Ethyl-diisopropylamine (3 eq.) was added to an ice-cold solution of 6-methoxy-2-naphthoic acid (1 eq.) in methylene chloride. The reaction mixture was cooled to 0° C. and N-ethyl-N'-3-(dimethylamino)-propyl-carbodiimide hydrochloride (1.2 eq.) and 1-hydroxybenzotriazole hydrate (0.2 eq.) were then added. The mixture was stirred at this temperature for 15 min, before (3R)-3-amino-2,3-dihydro-1H-indene-5-carboxylic acid methyl ester hydrochloride (A-03 HCl) (0.989 mmol, 1 eq.) was added. The reaction mixture was then stirred at room temperature overnight. The mixture was diluted with ethyl acetate and the organic phase was washed with 10% $NH_4Cl$ solution, sat. $NaHCO_3$ solution and sat. NaCl solution. The organic phase was dried over sodium sulfate, filtered and concentrated in vacuo. The crude product was purified by column chromatography (silica, cyclohexane/ethyl acetate 2:1) to obtain the desired compound (B-10). Yield: 83%

Synthesis of amino acid ester B-15

(R)-Methyl 3-(2-chlorobenzamido)-6-fluoro-2,3-dihydro-1H-indene-5-carboxylate (B-15)

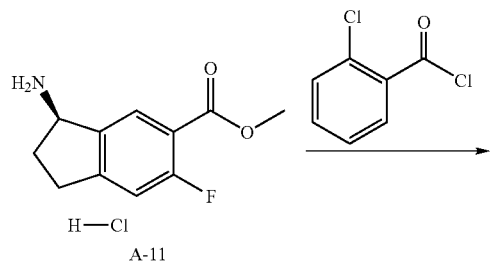

A-11

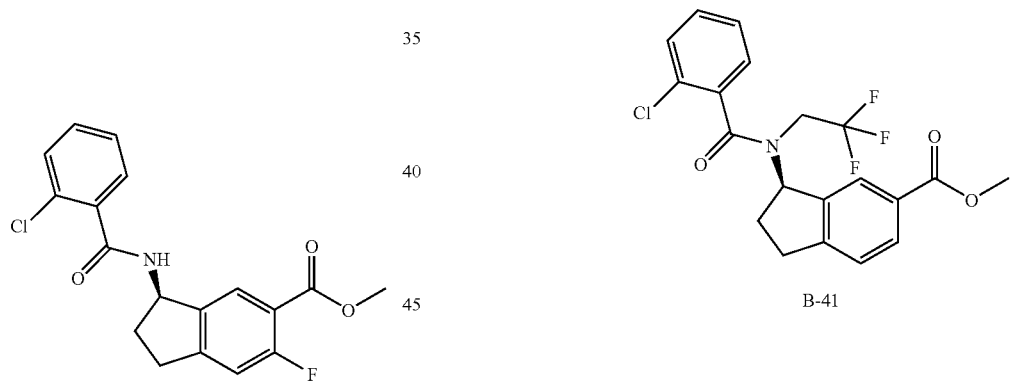

B-15

Triethylamine (2.5 eq.) was added to a solution of (R)-methyl 3-amino-6-fluoro-2,3-dihydro-1H-indene-5-carboxylate hydrochloride (A-11) (0.773 mmol, 1 eq.) in methylene chloride (6 ml) at 0° C. and the mixture was stirred for 10 min. 2-Chlorobenzoyl chloride (1.2 eq.) was added dropwise to the reaction mixture at the same temperature and the mixture was stirred for 16 h at room temperature. The reaction mixture was diluted with methylene chloride (50 ml) and was then washed with $NH_4Cl$ solution (20 ml) and sat. NaCl solution (20 ml). The organic phase was dried over magnesium sulfate and the solvent was removed in vacuo. The crude material was purified by column chromatography (silica gel, ethyl acetate/cyclohexane 2:1) to yield the desired product (B-15). Yield: 97%

Synthesis of amino acid ester B-41

(R)-methyl 3-(2-chloro-N-(2,2,2-trifluoroethyl)benzamido)-2,3-dihydro-1H-indene-5-carboxylate (B-41)

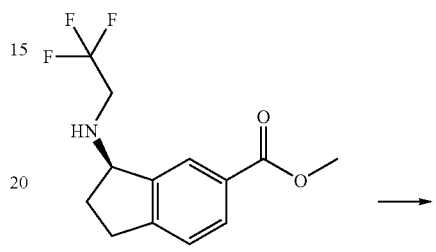

A-18

B-41

To a cooled (0° C.) solution of (R)-methyl 3-(2,2,2-trifluoroethylamino)-2,3-dihydro-1H-indene-5-carboxylate (A-18) (870 mg, 3.18 mmol, 1.0 eq.) in methylene chloride (12 ml) was added TEA (1.1 ml, 7.95 mmol, 2.5 eq.) and the reaction mixture was allowed to stir for 15 min. 2-Chlorobenzoyl chloride (0.44 ml, 3.50 mmol, 1.1 eq) was added to the reaction mixture and it was stirred at RT for 1 h. After completion of the reaction (monitored by TLC), the mixture was diluted with methylene chloride (50 ml) and the organic layer was washed with water (20 ml) and brine (20 ml), and dried over anhydrous $Na_2SO_4$. The solvent was evaporated to afford the crude product which was purified by column chromatography (silica gel; 7% ethyl acetate/hexanes) to yield the desired compounds as a colourless gummy solid. Yield: 85% (1.1 g, 2.67 mmol).

Synthesis of Amino Acid Ester C-01

3-[[(4-Methoxy-2,6-dimethyl-phenyl)sulfonyl]amino]-2,3-dihydro-1H-indene-5-carboxylic acid methyl ester (C-01)

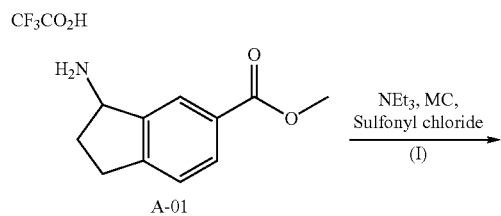

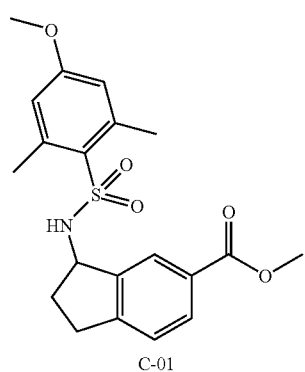

(I) Triethylamine (5.1 mmol) and 4-methoxy-2,6-dimethyl-benzenesulfonyl chloride (1.2 equiv.) were added to an ice-cold solution of A-01 (3.39 mmol) in methylene chloride at 0° C. and under an inert atmosphere and the mixture was then stirred at room temperature for 1 h. The reaction mixture was finally diluted with methylene chloride and the organic phase was washed with water and sat. NaCl solution, dried over $Na_2SO_4$ and concentrated to obtain 3-[[(4-methoxy-2,6-dimethyl-phenyl)sulfonyl]amino]-2,3-dihydro-1H-indene-5-carboxylic acid methyl ester (C-01). Yield: 50%

Synthesis of amino acid ester C-04

(R)-Methyl 3-(2-chlorophenylsulfonamido)-2,3-dihydro-1H-indene-5-carboxylate

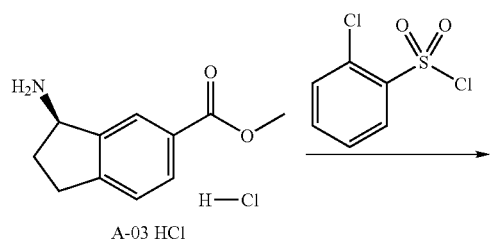

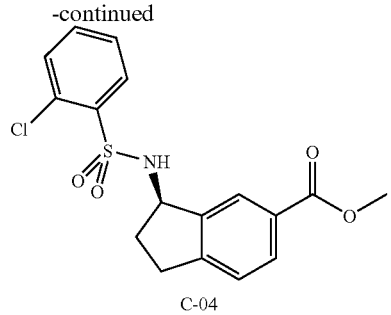

Triethylamin (2.195 mmol, 2,5 eq.) and 2-chlorobenzene-1-sulfonyl chloride (0,878 mmol, 1 eq.) were added to an ice-cold solution of (3R)-3-amino-2,3-dihydro-1H-indene-5-carboxylic acid methyl ester hydrochloride (A-03 HCl) (0.878 mmol, 1 eq.) in methylene chloride under an inert atmosphere. The mixture was then stirred at room temperature for 2 h. The reaction mixture was diluted with ethyl acetate (50 ml) and the organic phase was washed with 10% $NH_4Cl$ solution (20 ml), sat. $NaHCO_3$ solution (20 ml) and sat. NaCl solution (20 ml). The organic phase was dried over $MgSO_4$ and concentrated in vacuo. The crude product was purified by column chromatography over silica gel (cyclohexane/ethyl acetate, 2:1) to obtain the desired product. Yield: >99%

Synthesis of amino acid ester C-06

(R)-Methyl 3-(2,3-dichlorophenylsulfonamido)-2,3-dihydro-1H-indene-5-carboxylate (C-06)

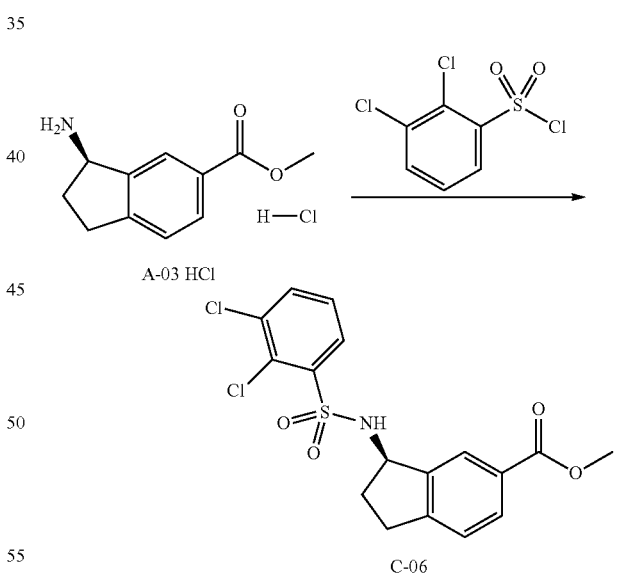

N-Ethyl-diisopropylamine (2.5 eq.) and 2,3-dichlorobenzene-1-sulfonyl chloride (1.2 eq.) were added to an ice-cold solution of (3R)-3-amino-2,3-dihydro-1H-indene-5-carboxylic acid methyl ester hydrochloride (A-03 HCl) (0.88 mmol, 1 eq.) in methylene chloride at 0° C. under an inert atmosphere. The mixture was then stirred at room temperature for 3 h. The reaction mixture was diluted with ethyl acetate and the organic phase was washed with 10% $NH_4Cl$ solution, sat. $NaHCO_3$ solution and sat. NaCl solution. The organic phase was dried over $Na_2SO_4$, filtered and concentrated. The crude product was purified by column chromatography (silica, cyclohexane/ethyl acetate, 2:1) to yield the desired compound (C-06). Yield: 97%

Synthesis of amino acid ester C-16

(R)-Methyl 3-(2-chloro-N-methylphenylsulfonamido)-2,3-dihydro-1H-indene-5-carboxylate (C-16)

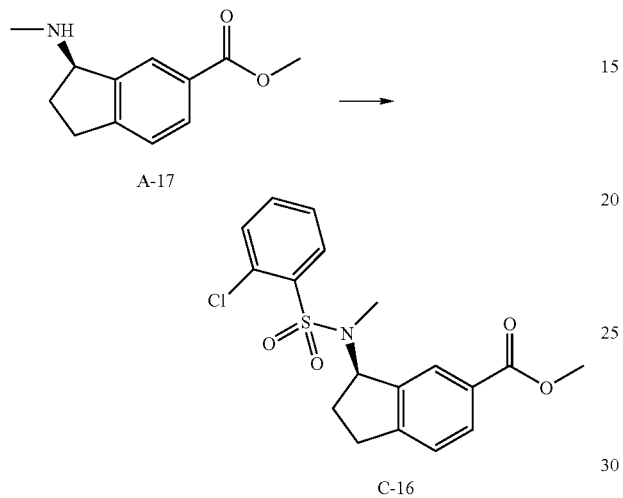

TEA (864 µl, 6.23 mmol, 2.5 eq.) was added to a cooled (0° C.) solution of (R)-methyl 3-(methylamino)-2,3-dihydro-1H-indene-5-carboxylate (A-17) (2.49 mmol, 1.0 eq.) in methylene chloride (10 ml) and the reaction mixture was allowed to stir for 15 min. A solution of 2-chlorobenzene-1-sulfonyl chloride (407 µl, 2.99 mmol, 1.2 eq.) in methylene chloride (5 ml) was then added and the reaction mixture was stirred at RT for 4 h. After completion of the reaction (monitored by TLC), the reaction mixture was diluted with methylene chloride (100 ml) and the organic layer was washed with water (50 ml) and brine (50 ml), and dried over anhydrous $Na_2SO_4$. The solvent was evaporated to afford the crude product which was purified by column chromatography (silica gel; 20% ethyl acetate/hexanes) to yield the desired compound as a white solid. Yield: 89% (840 mg, 2.216 mmol).

Synthesis of Amino Acid Ester D-01

3-(4-Chloro-3-oxo-1,2-dihydro-isoindol-2-yl)-2,3-dihydro-1H-indene-5-carboxylic acid methyl ester (D-01)

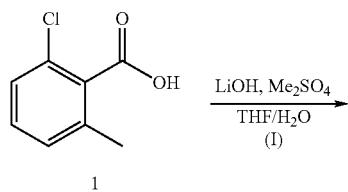

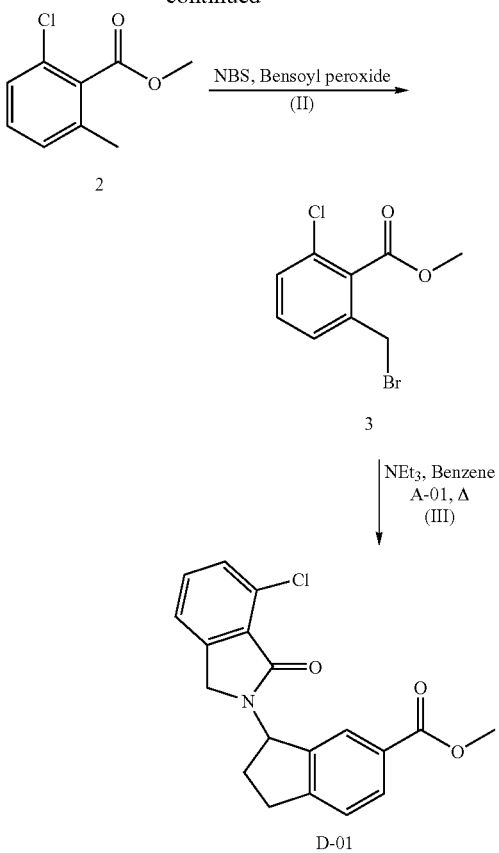

(I) LiOH (50 mmol) was added to a solution of 2-chloro-6-methyl benzoic acid (1) (50 mmol) in THF (75 ml), the reaction mixture was stirred at 25° C. for 1 h, dimethyl sulfate (1.1 equiv.) was added and the mixture was heated under reflux for 16 h. The reaction mixture was then cooled to 0° C., 50 ml of an aqueous $NH_4OH$ solution were added and the mixture was extracted with ethyl acetate. The organic phase was washed successively with water and sat. NaCl solution and dried over $Na_2SO_4$. Concentration of the organic phase gave the crude product (2), which was employed in the next step without further purification. Yield: 87%

(II) NBS (1.2 equiv.) and benzoyl peroxide (0.02 equiv.) were added to a suspension of 2-chloro-6-methyl benzoic acid methyl ester (2) (40 mmol) in $CCl_4$ and the mixture was heated under reflux for 16 h. The reaction mixture was cooled to room temperature and the solvent was concentrated under reduced pressure. The residue was taken up in chloroform and the mixture was filtered to remove the insoluble solid. Concentration of the filtrate gave the crude product (3), which was purified by column chromatography over aluminum oxide (hexane). Yield: 30%

Step 3: Triethylamine (1.2 equiv.) was added to a solution of 2-bromomethyl-6-chloro-benzoic acid methyl ester (3) (30 mmol) and 3-amino-2,3-dihydro-1H-indene-5-carboxylic acid methyl ester (A-01) (1 equiv.) in benzene (60 ml) and the reaction mixture obtained was heated under reflux for 25 h. The solvent was distilled off completely, the residue was taken up in methylene chloride and the mixture was washed successively with water and sat. NaCl solution and finally dried over $Na_2SO_4$. Concentration of the organic phase gave the crude product (D-01), which was purified by column chromatography (3:7 ethyl acetate in hexane). Yield: 50%

Synthesis of amino acid ester D-02

(S)-Methyl 8-(7-chloro-1-oxoisoindolin-2-yl)-5,6,7,8-tetrahydronaphthalene-2-carboxylate (D-02)

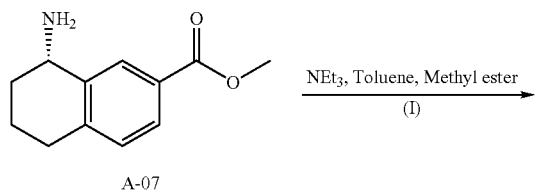

(I) (S)-Methyl 8-(7-chloro-1-oxoisoindolin-2-yl)-5,6,7,8-tetrahydronaphthalene-2-carboxylate (A-07) (1 equiv.) was added to a solution of 2-bromomethyl-6-chlorobenzoic acid methyl ester (3) (0.83 mmol) in toluene (4.5 ml) and triethylamine (2.1 equiv.) and the reaction mixture obtained was heated under reflux for 16 h. Water and methylene chloride were added to the reaction mixture and the phases were separated. The aqueous phase was extracted 2× with methylene chloride. The organic phase was washed with sat. NaCl solution and finally dried over MgSO₄. Concentration of the organic phase gave the crude product (D-02), which was purified by column chromatography (ethyl acetate/hexane, 4:1). Yield: 67%

Synthesis of amino acid ester D-07

(R)-Methyl 3-(7-chloro-1-oxoisoindolin-2-yl)-2,3-dihydro-1H-indene-5-carboxylate (D-07)

(3R)-3-Amino-2,3-dihydro-1H-indene-5-carboxylic acid methyl ester hydrochloride (A-03 HCl) (1.757 mmol, 1 equiv.) was added to a solution of 2-bromomethyl-6-chlorobenzoic acid methyl ester (1 equiv.) in toluene (5.4 ml) and triethylamine (2.1 equiv.). The resulting reaction mixture was heated at reflux for 16 h. Sat. NaHCO₃ solution (20 ml) and ethyl acetate (50 ml) were added to the mixture and the phases were separated. The organic phase was extracted with 0.05N HCl solution and sat. NaCl solution and was then dried over MgSO₄.

Concentration of the organic phase gave the crude product, which was purified by column chromatography (ethyl acetate/cyclohexane, 3:1) to yield the desired product (D-07). Yield: 72%

3) Synthesis of the Acylated-& Sulfonylated amino acids (E, F & G)

General Method for Synthesis of the amino acid esters (E, F & G)

-continued

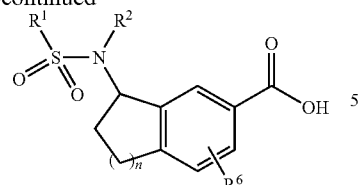

(F)

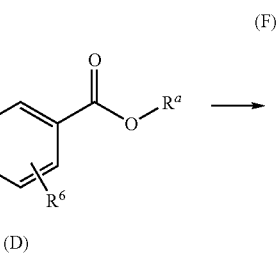

(D)

-continued

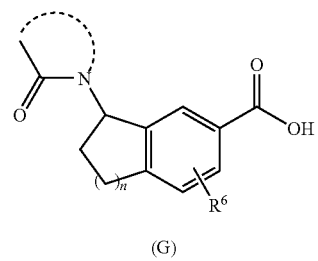

(G)

Synthesis of the Acylated-& Sulfonylated amino acid esters (E, F & G)

Amino acid Overview:

| No. | Structure | Amino acid ester (E, F & G) | Comments |
|---|---|---|---|
| E-01 | 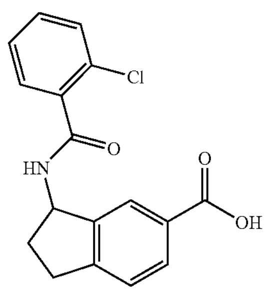 [SMILES: O=C(O)c1ccc2c(c1)C(NC(=O)c1ccccc1Cl)CC2] | 3-[(2-chloro-benzoyl)amino]-2,3-dihydro-1H-indene-5-carboxylic acid (E-01) | see below |
| E-02 | 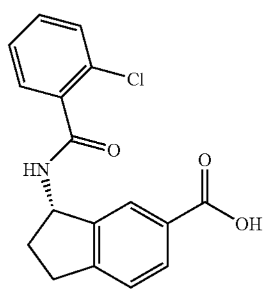 | (3S)-3-[(2-chloro-benzoyl)amino]-2,3-dihydro-1H-indene-5-carboxylic acid (E-02) | Yield: 86.2%<br>Synthesis was carried out analogously to E-07[b] (reaction times were adapted)<br>starting from B-02 |
| E-03 | 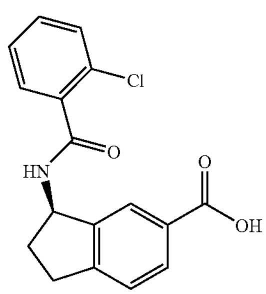 [SMILES: O=C(O)c1ccc2c(c1)[C@H](NC(=O)c1ccccc1Cl)CC2] | (3R)-3-[(2-chloro-benzoyl)amino]-2,3-dihydro-1H-indene-5-carboxylic acid (E-03) | Yield: 93.2%<br>Synthesis was carried out analogously to E-07 (reaction times were adapted)<br>starting from B-03 |
| E-04 | 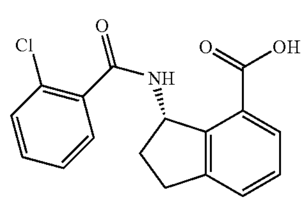 [SMILES: O=C(N[C@H]1CCc2cccc(C(=O)O)c21)c1ccccc1Cl] | (3S)-3-[(2-chloro-benzoyl)amino]-2,3-dihydro-1H-indene-4-carboxylic acid (E 04) | see below<br>[from A-04] |

-continued

| No. | Structure | Amino acid ester (E, F & G) | Comments |
|---|---|---|---|
| E-05 | 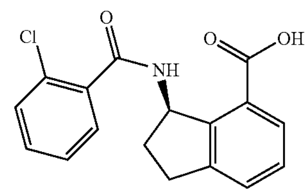 [SMILES: O=C(N[C@@H]1CCc2cccc(C(=O)O)c21)c1ccccc1Cl] | (3R)-3-[(2-chloro-benzoyl)amino]-2,3-dihydro-1H-indene-4-carboxylic acid (E 05) | [from A-05]<br>Yield: 54%<br>Synthesis was carried out analogously to E-04 |
| E-06 | 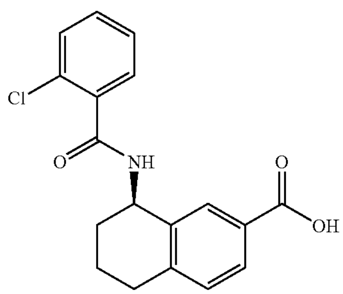 [SMILES: O=C(O)c1ccc2c(c1)[C@H](NC(=O)c1ccccc1Cl)CCC2] | (8R)-8-[(2-chloro-benzoyl)amino]-5,6,7,8-tetrahydro-naphthalene-2-carboxylic acid (E-06) | see below |
| E-07 | 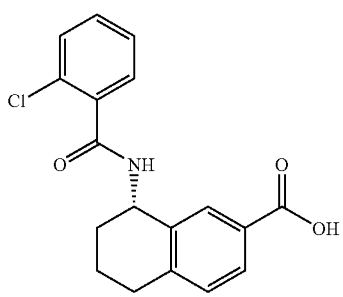 [SMILES: O=C(O)c1ccc2c(c1)[C@@H](NC(=O)c1ccccc1Cl)CCC2] | (8S)-8-[(2-chloro-benzoyl)amino]-5,6,7,8-tetrahydro-naphthelen-2-carboxylic acid (E-07) | see below |
| E-08 | 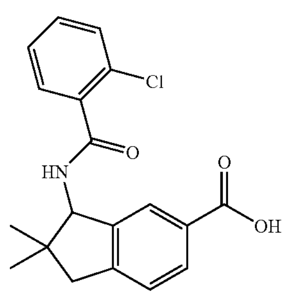 [SMILES: CC1(C)Cc2ccc(C(=O)O)cc2C1NC(=O)c1ccccc1Cl] | 3-(2-chlorobenzamido)-2,2-dimethyl-2,3-dihydro-1H-indene-5-carboxylic acid (E-08) | see below |
| E-09 | 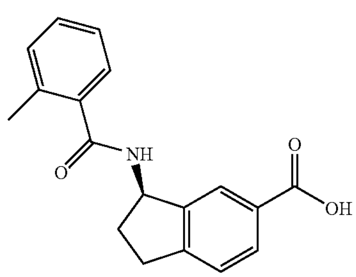 [SMILES: Cc1ccccc1C(=O)N[C@@H]1CCc2ccc(C(=O)O)cc21] | (R)-3-(2-methylbenzamido)-2,3-dihydro-1H-indene-5-carboxylic acid (E-09) | see below |

-continued

| No. | Structure | Amino acid ester (E, F & G) | Comments |
|---|---|---|---|
| E-10 | 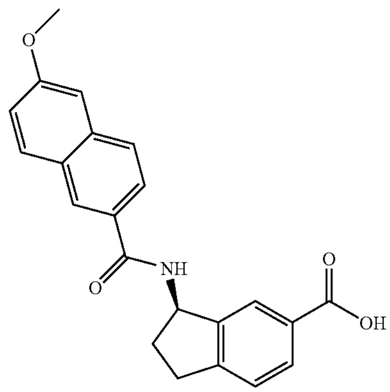 [SMILES: COc1ccc2cc(C(=O)N[C@@H]3CCc4ccc(C(=O)O)cc43)ccc2c1] | (R)-3-(6-methoxy-2-naphthamido)-2,3-dihydro-1H-indene-5-carboxylic acid (E-10) | Yield: 80%<br>Synthesis was carried out analogously to E-09 starting from B-10 |
| E-11 | 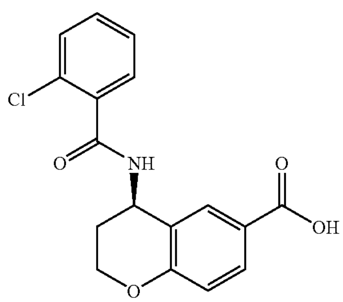 [SMILES: O=C(O)c1ccc2c(c1)[C@H](NC(=O)c1ccccc1Cl)CCO2] | (R)-4-(2-chlorobenzamido)chroman-6-carboxylic acid (E-11) | see below |
| E-12 | 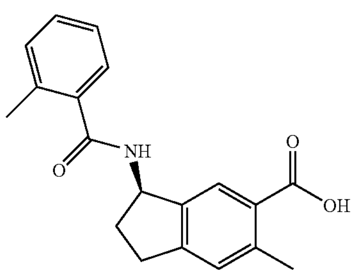 [SMILES: Cc1cc2c(cc1C(=O)O)[C@H](NC(=O)c1ccccc1C)CC2] | (R)-3-(2-chlorobenzamido)-6-methyl-2,3-dihydro-1H-indene-5-carboxylic acid (E-12) | see below |
| E-13 | 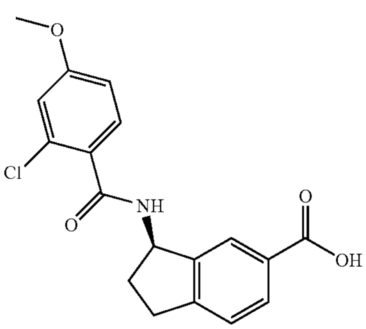 [SMILES: COc1ccc(C(=O)N[C@@H]2CCc3ccc(C(=O)O)cc32)c(Cl)c1] | (R)-3-(2-chloro-4-methoxybenzamido)-2,3-dihydro-1H-indene-5-carboxylic acid (E-13) | Yield: 97%<br>Synthesis was carried out analogously to E-09 starting from B-13 |
| E-14 | 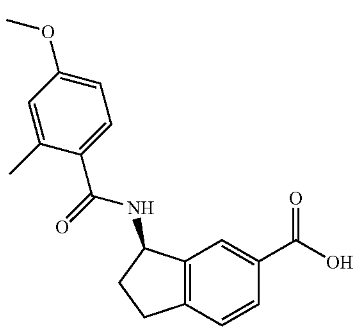 [SMILES: COc1ccc(C(=O)N[C@@H]2CCc3ccc(C(=O)O)cc32)c(C)c1] | (R)-3-(4-methoxy-2-methylbenzamido)-2,3-dihydro-1H-indene-5-carboxylic acid (E-14) | Yield: 86%<br>Synthesis was carried out analogously to E-09 starting from B-14 |

-continued

| No. | Structure | Amino acid ester (E, F & G) | Comments |
|---|---|---|---|
| E-15 | 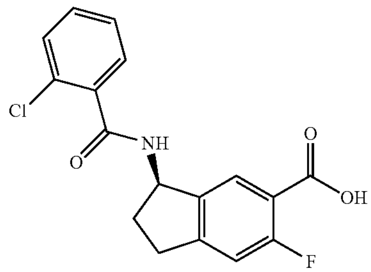 [SMILES: O=C(O)c1cc2c(cc1F)CC[C@H]2NC(=O)c1ccccc1Cl] | (R)-3-(2-chlorobenzamido)-6-fluoro-2,3-dihydro-1H-indene-5-carboxylic acid (E-15) | Yield: >99%<br>Synthesis was carried out analogously to E-11 starting from B-15 |
| E-16 | 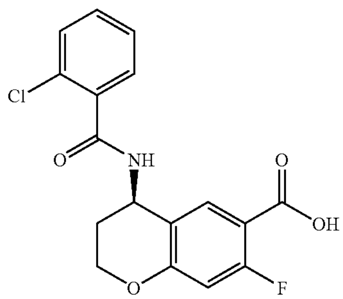 [SMILES: O=C(O)c1cc2c(cc1F)OCC[C@H]2NC(=O)c1ccccc1Cl] | (R)-4-(2-chlorobenzamido)-7-fluorochroman-6-carboxylic acid (E-16) | Yield: 63%<br>Synthesis was carried out analogously to E-12<br>Starting material available from NetChem. |
| E-17 | 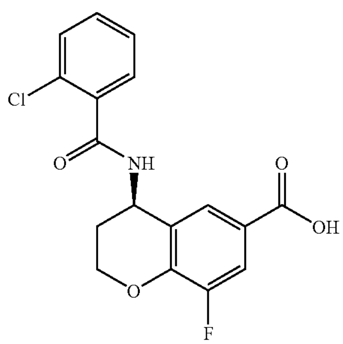 [SMILES: O=C(O)c1cc(F)c2c(c1)[C@H](NC(=O)c1ccccc1Cl)CCO2] | (R)-4-(2-chlorobenzamido)-8-fluorochroman-6-carboxylic acid (E-17) | Yield: 80%<br>Synthesis was carried out analogously to E-11 startng from B-17 |
| E-18 | 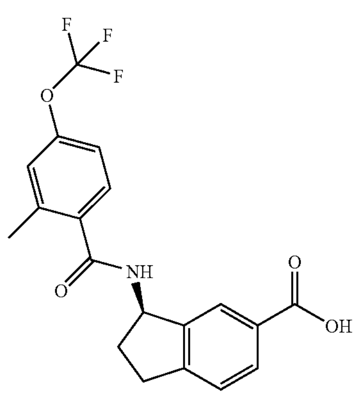 [SMILES: Cc1cc(OC(F)(F)F)ccc1C(=O)N[C@@H]1CCc2ccc(C(=O)O)cc21] | (R)-3-(2-methyl-4-(trifluoromethoxy)benzamido)-2,3-dihydro-1H-indene-5-carboxylic acid (E-18) | Yield: 95%<br>Synthesis was carried out analogously to E-09 starting from B-18 |
| E-19 | 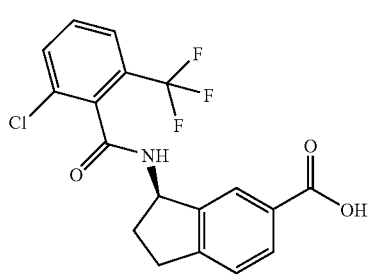 [SMILES: O=C(O)c1ccc2c(c1)[C@H](NC(=O)c1c(Cl)cccc1C(F)(F)F)CC2] | (R)-3-(2-chloro-6-(trifluoromethyl)benzamido)-2,3-dihydro-1H-indene-5-carboxylic acid (E-19) | Yield: 83%<br>Synthesis was carried out analogously to E-09 starting from B-19 |

-continued

| No. | Structure | Amino acid ester (E, F & G) | Comments |
|---|---|---|---|
| E-20 | 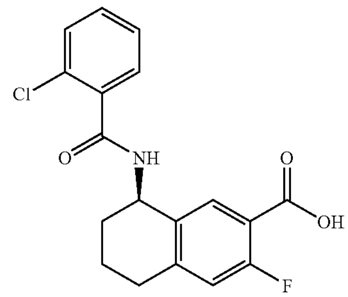 | (R)-8-(2-chlorobenzamido)-3-fluoro-5,6,7,8-tetrahydronaphthalene-2-carboxylic acid (E-20) | Yield: 55%<br>Synthesis was carried out analogously to E-11 starting from B-20 |
| E-21 | 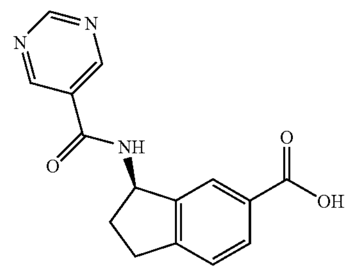 [SMILES: O=C(O)c1ccc2c(c1)[C@H](NC(=O)c1cncnc1)CC2] | (R)-3-(pyrimidine-5-carboxamido)-2,3-dihydro-1H-indene-5-carboxylic acid (E-21) | Yield: 79%<br>Synthesis was carried out analogously to E-09 starting from B-21 |
| E-22 | 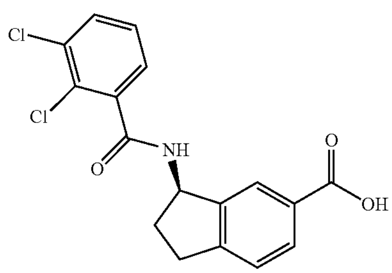 [SMILES: O=C(O)c1ccc2c(c1)[C@H](NC(=O)c1cccc(Cl)c1Cl)CC2] | (R)-3-(2,3-dichlorobenzamido)-2,3-dihydro-1H-indene-5-carboxylic acid (E-22) | Yield: 88%<br>Synthesis was carried out analogously to E-09 starting from B-22 |
| E-24 | 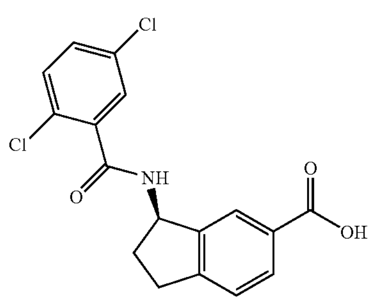 [SMILES: O=C(O)c1ccc2c(c1)[C@H](NC(=O)c1cc(Cl)ccc1Cl)CC2] | (R)-3-(2,5-dichlorobenzamido)-2,3-dihydro-1H-indene-5-carboxylic acid (E-24) | Yield: 47%<br>Synthessis was carried out analogously to E-09 starting from B-24 |
| E-25 | 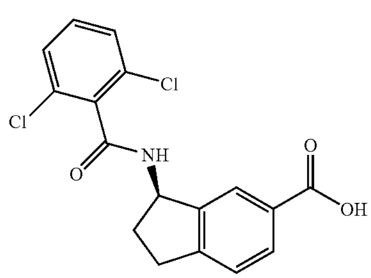 [SMILES: O=C(O)c1ccc2c(c1)[C@H](NC(=O)c1c(Cl)cccc1Cl)CC2] | (R)-3-(2,6-dichlorobenzamido)-2,3-dihydro-1H-indene-5-carboxylic acid (E-25) | Yield: 90%<br>Synthesis was carried out analogously to E-09 starting from B-25 |

-continued

| No. | Structure | Amino acid ester (E, F & G) | Comments |
|---|---|---|---|
| E-26 | 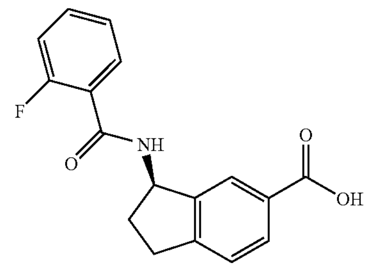 [SMILES: O=C(O)c1ccc2c(c1)[C@H](NC(=O)c1ccccc1F)CC2] | (R)-3-(2-fluorobenzamido)-2,3-dihydro-1H-indene-5-carboxylic acid (E-26) | Yield: 92%<br>Synthesis was carried out analogously to E-09 starting form B-26 |
| E-27 | 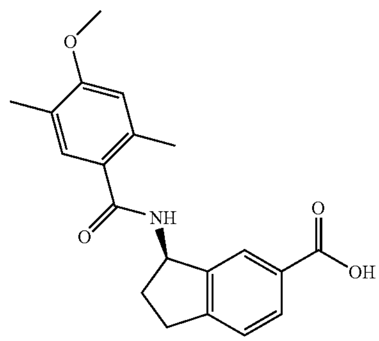 [SMILES: COc1cc(C)c(C(=O)N[C@@H]2CCc3ccc(C(=O)O)cc32)cc1C] | (R)-3-(4-methoxy-2,5-dimethylbenzamido)-2,3-dihydro-1H-indene-5-carboxylic acid (E-27) | Yield: 35%<br>Synthesis was carried out analogously to E-09 starting from B-27 |
| E-28 | 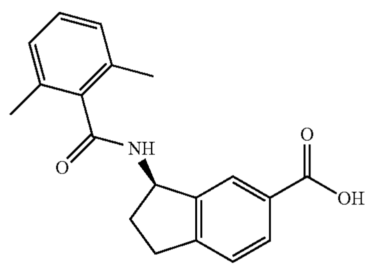 [SMILES: Cc1cccc(C)c1C(=O)N[C@@H]1CCc2ccc(C(=O)O)cc21] | (R)-3-(2,6-dimethylbenzamido)-2,3-dihydro-1H-indene-5-carboxylic acid (E-28) | Yield: 90%<br>Synthesis was carried out analogously to E-09 starting from B-28 |
| E-29 | 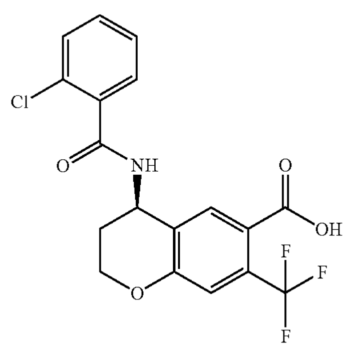 [SMILES: O=C(N[C@@H]1CCOc2cc(C(F)(F)F)c(C(=O)O)cc21)c1ccccc1Cl] | (R)-4-(2-chlorobenzamido)-7-(trifluoromethyl)chroman-6-carboxylic acid (E-29) | Yield: 46%<br>Synthesis was carried out analogously to E-09 starting from B-29 |
| E-30 | 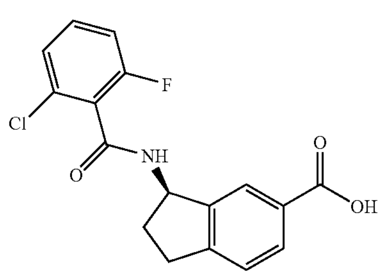 [SMILES: O=C(O)c1ccc2c(c1)[C@H](NC(=O)c1c(F)cccc1Cl)CC2] | (R)-3-(2-chloro-6-fluorobenzamido)-2,3-dihydro-1H-indene-5-carboxylic acid (E-30) | Yield: 84%<br>Synthesis was carried out analogously to E-09 starting from B-30 |

-continued

| No. | Structure | Amino acid ester (E, F & G) | Comments |
|---|---|---|---|
| E-31 | 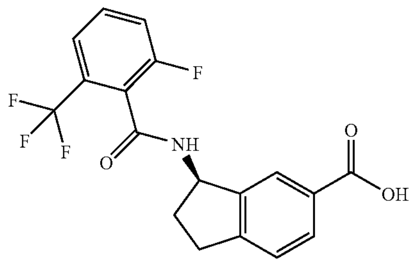 [SMILES: O=C(O)c1ccc2c(c1)[C@H](NC(=O)c1c(F)cccc1C(F)(F)F)CC2] | (R)-3-(2-fluoro-6-(trifluoromethyl)benzamido)-2,3-dihydro-1H-indene-5-carboxylic acid (E-31) | Yield: 79%<br>Synthesis was carried out analogously to E-09 starting from B-31 |
| E-32 | 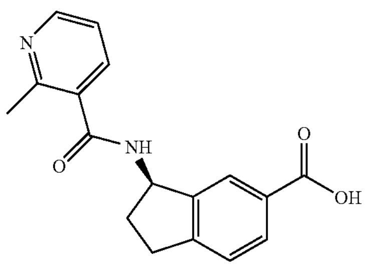 [SMILES: Cc1ncccc1C(=O)N[C@@H]1CCc2ccc(C(=O)O)cc21] | (R)-3-(2-methylnicotinamido)-2,3-dihydro-1H-indene-5-carboxylic acid (E-32) | Yield: 82%<br>Synthesis was carried out analogously to E-09 starting from B-32 |
| E-33 | 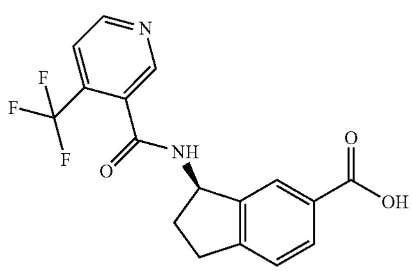 [SMILES: O=C(O)c1ccc2c(c1)[C@H](NC(=O)c1cnccc1C(F)(F)F)CC2] | (R)-3-(4-(trifluoromethyl)nicotinamido)-2,3-dihydro-1H-indene-5-carboxylic acid (E-33) | Yield: 35%<br>Synthesis was carried out analogously to E-09 starting from B-33 |
| E-39 | 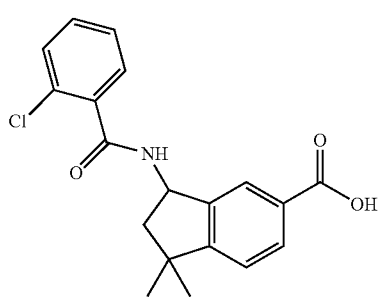 [SMILES: CC1(C)CC(NC(=O)c2ccccc2Cl)c2cc(C(=O)O)ccc21] | 3-(2-chlorobenzamido)-1,1-dimethyl-2,3-dihydro-1H-indene-5-carboxylic acid (E-39) | see below |
| E-41 | 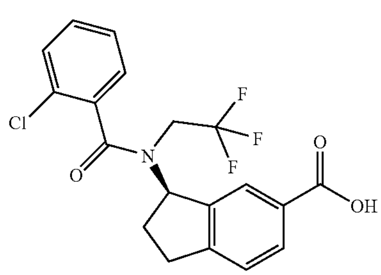 [SMILES: O=C(O)c1ccc2c(c1)[C@H](N(CC(F)(F)F)C(=O)c1ccccc1Cl)CC2] | (R)-3-(2-chloro-N-(2,2,2,-trifluoroethyl)benzamido)-2,3-dihydro-1H-indene-5-carboxylic acid (E-41) | see below |

-continued

| No. | Structure | Amino acid ester (E, F & G) | Comments |
|---|---|---|---|
| E-42 | 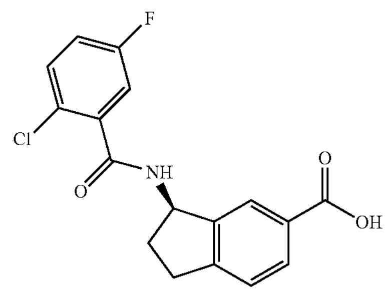 [SMILES: O=C(O)c1ccc2c(c1)[C@H](NC(=O)c1cc(F)ccc1Cl)CC2] | (R)-3-(2-chloro-5-fluorobenzamido)-2,3-dihydro-1H-indene-5-carboxylic acid (E-42) | Yield: 84%<br>Synthesis was carried out analogously to E-09 starting from B-42 |
| E-43 | 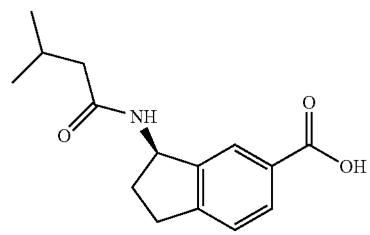 [SMILES: CC(C)CC(=O)N[C@@H]1CCc2ccc(C(=O)O)cc21] | (R)-3-(3-methylbutanamido)-2,3-dihydro-1H-indene-5-carboxylic acid (E-43) | Yield: >99%<br>Synthesis was carried out analogously to E-09 starting from B-43 |
| E-44 | 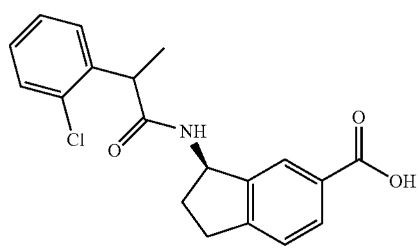 [SMILES: CC(C(=O)N[C@@H]1CCc2ccc(C(=O)O)cc21)c1ccccc1Cl] | (3R)-3-(2-(2-chlorophenyl)propanamido)-2,3-dihydro-1H-indene-5-carboxylic acid (E-44) | Yield: 74%<br>Synthesis was carried out analogously to E-09 starting from B-44 |
| E-45 | 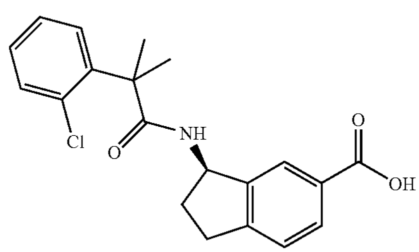 [SMILES: CC(C)(C(=O)N[C@@H]1CCc2ccc(C(=O)O)cc21)c1ccccc1Cl] | (R)-3-(2-(2-chlorophenyl)-2-methylpropanamido)-2,3-dihydro-1H-indene-5-carboxylic acid (E-45) | Yield: 78%<br>Synthesis was carried out analogously to E-09 starting from B-45 |
| E-46 | 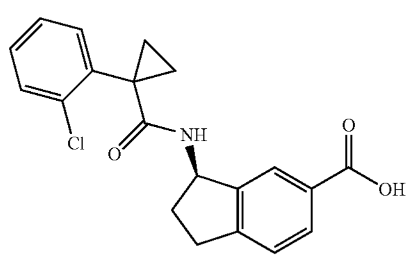 [SMILES: O=C(O)c1ccc2c(c1)[C@H](NC(=O)C1(c3ccccc3Cl)CC1)CC2] | (R)-3-(1-(2-chlorophenyl)cyclopropanecarboxamido)-2,3-dihydro-1H-indene-5-carboxylic acid (E-46) | Yield: 66%<br>Synthesis was carried out analogously to E-09 starting from B-46 |
| E-47 | 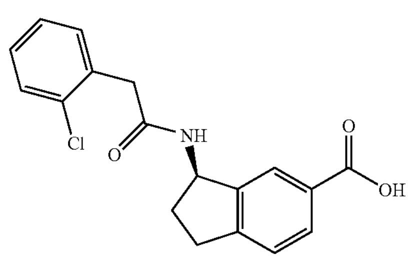 [SMILES: O=C(Cc1ccccc1Cl)N[C@@H]1CCc2ccc(C(=O)O)cc21] | (R)-3-(2-(2-chlorophenyl)acetamido)-2,3-dihydro-1H-indene-5-carboxylic acid (E-47) | Yield: 67%<br>Synthesis was carried out analogously to E-09 starting from B-47 |

-continued

| No. | Structure | Amino acid ester (E, F & G) | Comments |
|---|---|---|---|
| E-48 | 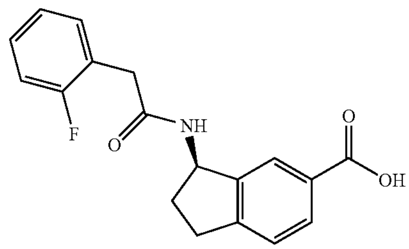 [SMILES: O=C(Cc1ccccc1F)N[C@@H]1CCc2ccc(C(=O)O)cc21] | (R)-3-(2-(2-fluorophenyl)acetamido)-2,3-dihydro-1H-indene-5-carboxylic acid (E-48) | Yield: 91%<br>Synthesis was carried out analogously to E-09 starting from B-48 |
| E-49 | 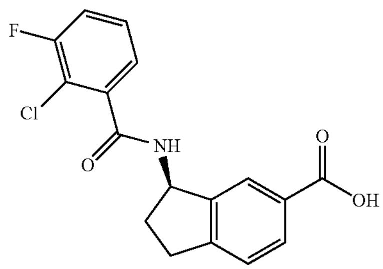 [SMILES: O=C(O)c1ccc2c(c1)[C@H](NC(=O)c1cccc(F)c1Cl)CC2] | (R)-3-(2-chloro-3-fluorobenzamido)-2,3-dihydro-1H-indene-5-carboxylic acid (E-49) | Yield: 92%<br>Synthesis was carried out analogously to E-09 starting from B-49 |
| E-50 | 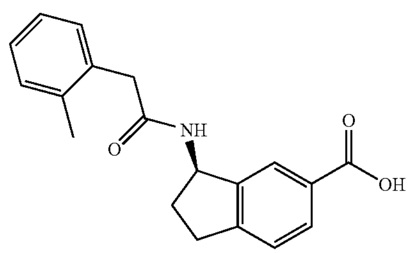 [SMILES: Cc1ccccc1CC(=O)N[C@@H]1CCc2ccc(C(=O)O)cc21] | (R)-3-(2-o-tolylacetamido)-2,3-dihydro-1H-indene-5-carboxylic acid (E-50) | Yield: 79%<br>Synthesis was carried out analogously to E-09 starting from B-50 |
| E-51 | 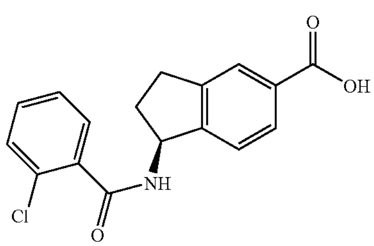 [SMILES: O=C(O)c1ccc2c(c1)CC[C@@H]2NC(=O)c1ccccc1Cl] | (S)-1-(2-chlorobenzamido)-2,3-dihydro-1H-indene-5-carboxylic acid (E-51) | Yield: 96%<br>Synthesis was carried out analogously to E-09 starting from B-51 |
| E-52 | 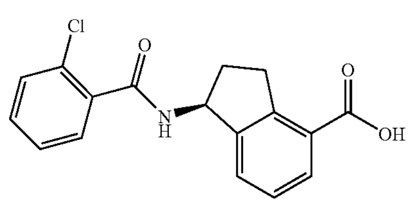 [SMILES: O=C(N[C@H]1CCc2c(C(=O)O)cccc21)c1ccccc1Cl] | (S)-1-(2-chlorobenzamido)-2,3-dihydro-1H-indene-4-carboxylic acid (E-52) | Yield: 84%<br>Synthesis was carried out analogously to E-09 starting from B-52 |
| E-53 | 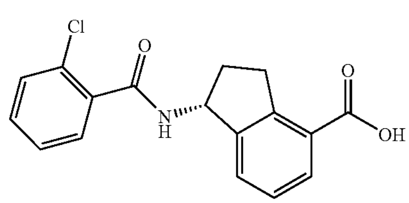 [SMILES: O=C(N[C@@H]1CCc2c(C(=O)O)cccc21)c1ccccc1Cl] | (R)-1-(2-chlorobenzamido)-2,3-dihydro-1H-indene-4-carboxylic acid (E-53) | Yield: 84%<br>Synthesis was carried out analogously to E-09 starting from B-53 |

-continued

| No. | Structure | Amino acid ester (E, F & G) | Comments |
|---|---|---|---|
| E-54 | 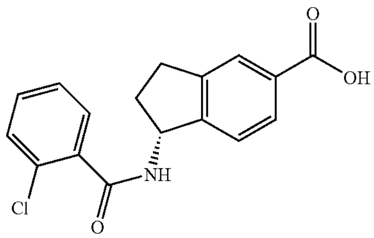 [SMILES: O=C(O)c1ccc2c(c1)CC[C@H]2NC(=O)c1ccccc1Cl] | (R)-1-(2-chlorobenzamido)-2,3-dihydro-1H-indene-5-carboxylic acid (E-54) | Yield: 58%<br>Synthesis was carried out analogously to E-09 starting from B-54 |
| F-01 | 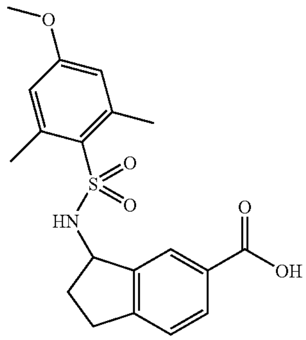 [SMILES: COc1cc(C)c(S(=O)(=O)NC2CCc3ccc(C(=O)O)cc32)c(C)c1] | 3-[[(4-methoxy-2,6-dimethyl-phenyl)sulfonyl]amino]-2,3-dihydro-1H-indene-5-carboxylic acid (F-01) | see below |
| F-02 | 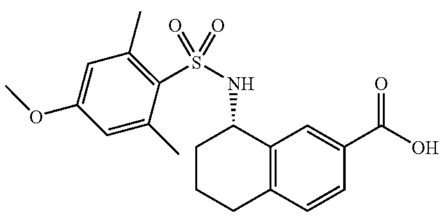 [SMILES: COc1cc(C)c(S(=O)(=O)N[C@H]2CCCc3ccc(C(=O)O)cc32)c(C)c1] | (S)-8-(4-methoxy-2,6-dimethylphenylsulfonamido)-5,6,7,8-tetrahydronaphthalene-2-carboxylic acid (F-02) | Yield: 77.7%<br>Synthesis was carried out analogously to F-01 starting from C-02 |
| F-03 | 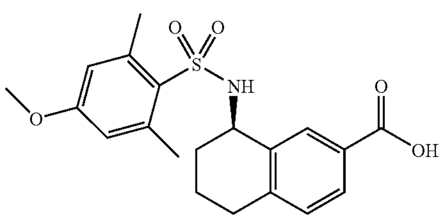 [SMILES: COc1cc(C)c(S(=O)(=O)N[C@@H]2CCCc3ccc(C(=O)O)cc32)c(C)c1] | (R)-8-(4-methoxy-2,6-dimethylphenylsulfonamido)-5,6,7,8-tetrahydronaphthalene-2-carboxylic acid (F-03) | see below |
| F-04 | 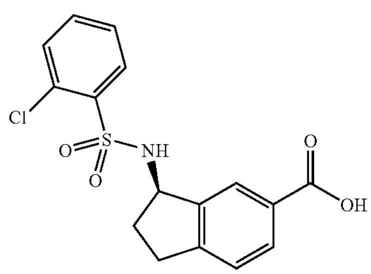 [SMILES: O=C(O)c1ccc2c(c1)[C@H](NS(=O)(=O)c1ccccc1Cl)CC2] | (R)-3-(2-chlorophenylsulfonamido)-2,3-dihydro-1H-indene-5-carboxylic acid (F-04) | Yield: 81%<br>Synthesis was carried out analogously to E-09 starting from C-04 |
| F-05 | 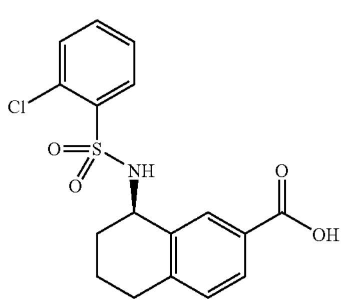 [SMILES: O=C(O)c1ccc2c(c1)[C@H](NS(=O)(=O)c1ccccc1Cl)CCC2] | (R)-8-(2-chlorophenylsulfonamido)-5,6,7,8-tetrahydronaphthalene-2-carboxylic acid (F-05) | Yield: 60%<br>Synthesis was carried out analogously to E-09 starting from C-05 |

-continued

| No. | Structure | Amino acid ester (E, F & G) | Comments |
|---|---|---|---|
| F-06 | 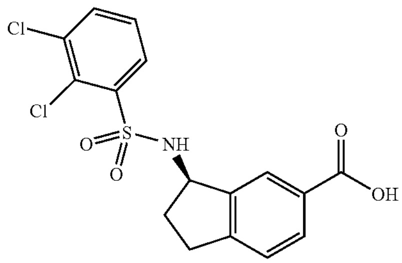 [SMILES: O=C(O)c1ccc2c(c1)[C@H](NS(=O)(=O)c1cccc(Cl)c1Cl)CC2] | (R)-3-(2,3-dichlorophenylsulfonamido)-2,3-dihydro-1H-indene-5-carboxylic acid (F-06) | see below |
| F-07 | 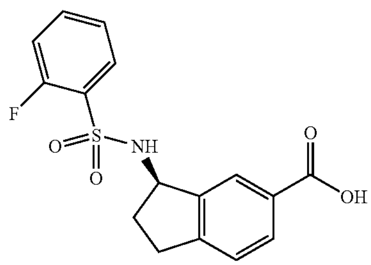 [SMILES: O=C(O)c1ccc2c(c1)[C@H](NS(=O)(=O)c1ccccc1F)CC2] | (R)-3-(2-fluorophenylsulfonamido)-2,3-dihydro-1H-indene-5-carboxylic acid (F-07) | Yield: 62%<br>Synthesis was carried out analogously to F-06 starting from C-07 |
| F-08 | 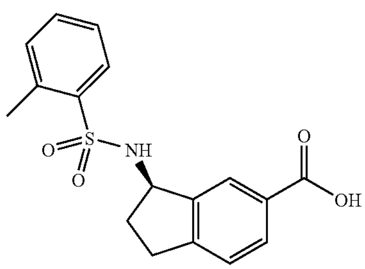 [SMILES: Cc1ccccc1S(=O)(=O)N[C@@H]1CCc2ccc(C(=O)O)cc21] | (R)-3-(2-methylphenylsulfonamido)-2,3-dihydro-1H-indene-5-carboxylic acid (F-08) | Yield: 85%<br>Synthesis was carried out analogously to F-06 starting from C-08 |
| F-09 | 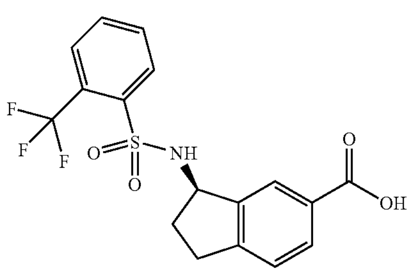 [SMILES: O=C(O)c1ccc2c(c1)[C@H](NS(=O)(=O)c1ccccc1C(F)(F)F)CC2] | (R)-3-(2-(trifluoromethyl)phenylsulfonamido)-2,3-dihydro-1H-indene-5-carboxylic acid (F-09) | Yield: 69%<br>Synthesis was carried out analogously to F-06 starting from C-09 |
| F-10 | 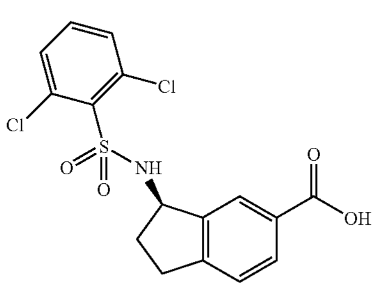 [SMILES: O=C(O)c1ccc2c(c1)[C@H](NS(=O)(=O)c1c(Cl)cccc1Cl)CC2] | (R)-3-(2,6-dichlorophenylsulfonamido)-2,3-dihydro-1H-indene-5-carboxylic acid (F-10) | Yield: 68%<br>Synthesis was carried out analogously to F-06 starting from C-10 |

-continued

| No. | Structure | Amino acid ester (E, F & G) | Comments |
|---|---|---|---|
| F-11 | (structure) | (R)-3-(2,5-dichlorophenylsulfonamido)-2,3-dihydro-1H-indene-5-carboxylic acid (F-11) | Yield: 71%<br>Synthesis was carried out analogously to F-06<br>(4 eq KOH)<br>starting from C-11 |
| F-12 | (structure) | (R)-3-(4-methoxy-2-(trifluoromethyl)phenylsulfonamido)-2,3-dihydro-1H-indene-5-carboxylic acid (F-12) | Yield: 80%<br>Synthesis was carried out analogously to F-06<br>starting from C-12 |
| F-13 | (structure) | (R)-3-(4-methoxy-2-methylphenylsulfonamido)-2,3-dihydro-1H-indene-5-carboxylic acid (F-13) | Yield: 77%<br>Synthesis was carried out analogously to F-06<br>starting from C-13 |
| F-14 | (structure) | (R)-3-(2-chloro-6-(trifluoromethyl)phenylsulfonamido)-2,3-dihydro-1H-indene-5-carboxylic acid (F-14) | Yield: 34%<br>Synthesis was carried out analogously to F-06<br>starting from C-14 |
| F-15 | (structure) | (R)-3-((2-chlorophenyl)methylsulfonamido)-2,3-dihydro-1H-indene-5-carboxylic acid (F-15) | Yield: 64%<br>Synthesis was carried out analogously to F-06<br>starting from C-15 |

-continued

| No. | Structure | Amino acid ester (E, F & G) | Comments |
|---|---|---|---|
| F-16 | 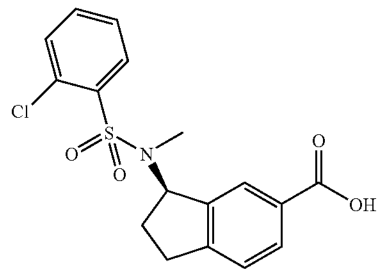 [SMILES: CN([C@@H]1CCc2ccc(C(=O)O)cc21)S(=O)(=O)c1ccccc1Cl] | (R)-3-(2-chloro-N-methylphenylsulfonamido)-2,3-dihydro-1H-indene-5-carboxylic acid (F-16) | see below |
| F-17 | 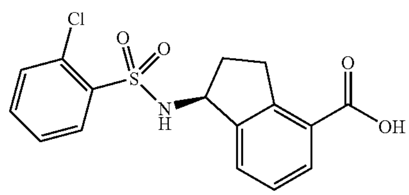 [SMILES: O=C(O)c1cccc2c1CC[C@@H]2NS(=O)(=O)c1ccccc1Cl] | (S)-1-(2-chlorophenylsulfonamido)-2,3-dihydro-1H-indene-4-carboxylic acid (F-17) | Yield: 73% Synthesis was carried out analogously to F-06 starting from C-17 |
| F-18 | 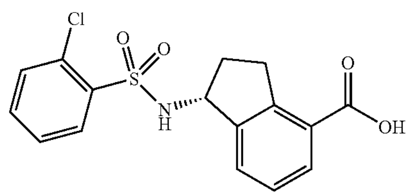 [SMILES: O=C(O)c1cccc2c1CC[C@H]2NS(=O)(=O)c1ccccc1Cl] | (R)-1-(2-chlorophenylsulfonamido)-2,3-dihydro-1H-indene-4-carboxylic acid (F-18) | Yield: 76% Synthesis was carried out analogously to F-06 starting from C-18 |
| F-19 | 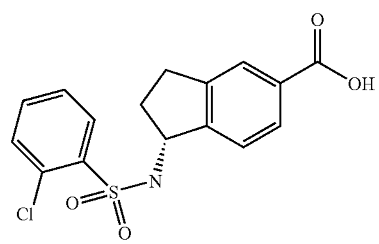 [SMILES: O=C(O)c1ccc2c(c1)CC[C@H]2NS(=O)(=O)c1ccccc1Cl] | (R)-1-(2-chlorophenylsulfonamido)-2,3-dihydro-1H-indene-5-carboxylic acid (F-19) | Yield: 62% Synthesis was carried out analogously to F-06 starting from C-19 |
| G-01 | 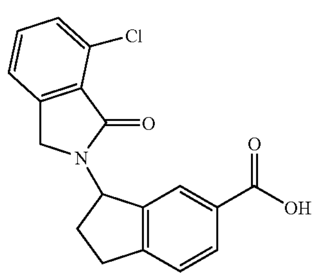 [SMILES: O=C(O)c1ccc2c(c1)C(N1Cc3cccc(Cl)c3C1=O)CC2] | 3-(4-chloro-3-oxo-1,2-dihydro-isoindol-2-yl)-2,3-dihydro-1H-indene-5-carboxylic acid (G-01) | see below |
| G-02 | 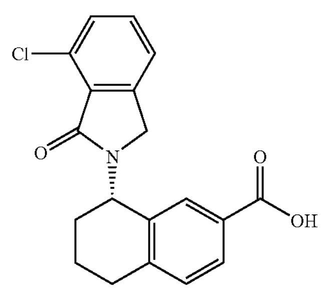 [SMILES: O=C(O)c1ccc2c(c1)[C@@H](N1Cc3cccc(Cl)c3C1=O)CCC2] | (S)-8-(7-chloro-1-oxoisoindolin-2-yl)-5,6,7,8-tetrahydronaphthalene-2-carboxylic acid (G-02) | Yield: 93.7% Synthesis was carried out analogously to G-01 starting from D-02 |

-continued

| No. | Structure | Amino acid ester (E, F & G) | Comments |
|---|---|---|---|
| G-03 | 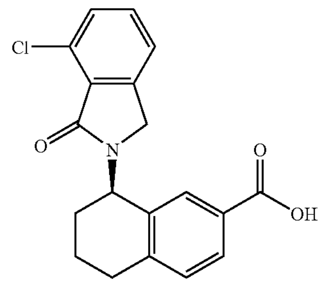 [SMILES: O=C(O)c1ccc2c(c1)[C@H](N1Cc3cccc(Cl)c3C1=O)CCC2] | (R)-8-(7-chloro-1-oxoisoindolin-2-yl)-5,6,7,8-tetrahydronaphthalene-2-carboxylic acid (G-03) | Yield: 95.9%<br>Synthesis was carried out analogously to G-01[c] starting from D-03 |
| G-06 | 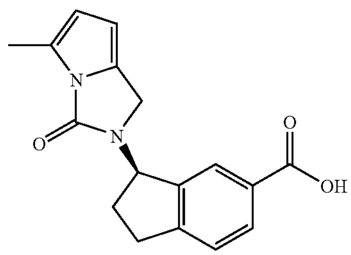 [SMILES: Cc1ccc2n1C(=O)N([C@@H]1CCc3ccc(C(=O)O)cc31)C2] | (R)-3-(5-methyl-3-oxo-1H-pyrrolo[1,2-c]imidazol-2(3H)-yl)-2,3-dihydro-1H-indene-5-carboxylic acid (G-06) | see below |
| G-07 | 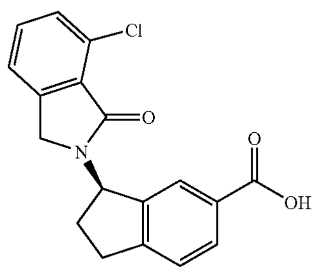 [SMILES: O=C(O)c1ccc2c(c1)[C@H](N1Cc3cccc(Cl)c3C1=O)CC2] | (R)-3-(7-chloro-1-oxoisoindolin-2-yl)-2,3-dihydro-1H-indene-5-carboxylic acid (G-07) | Yield: 82%<br>Synthesis was carried out analogously to E-09 starting from D-07 |
| G-08 | 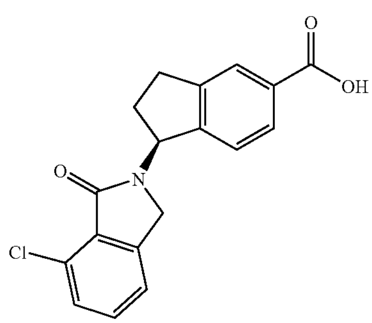 [SMILES: O=C(O)c1ccc2c(c1)CC[C@@H]2N1Cc2cccc(Cl)c2C1=O] | (S)-1-(7-chloro-1-oxoisoindolin-2-yl)-2,3-dihydro-1H-indene-5-carboxylic acid (G-08) | Yield: 87%<br>Synthesis was carried out analogously to E-09 starting from D-08 |
| G-09 | 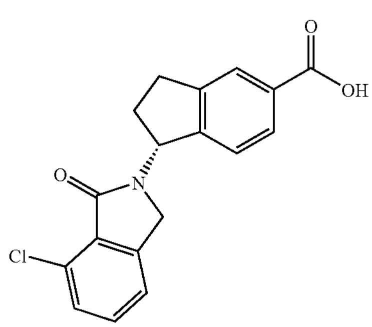 [SMILES: O=C(O)c1ccc2c(c1)CC[C@H]2N1Cc2cccc(Cl)c2C1=O] | (R)-1-(7-chloro-1-oxoisoindolin-2-yl)-2,3-dihydro-1H-indene-5-carboxylic acid (G-09) | Yield: 91%<br>Synthesis was carried out analogously to E-09 starting from D-09 |

| No. | Structure | Amino acid ester (E, F & G) | Comments |
|---|---|---|---|
| G-10 | 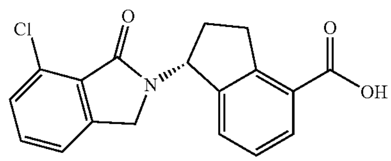 [SMILES: O=C(O)c1cccc2c1CC[C@H]2N1Cc2cccc(Cl)c2C1=O] | (R)-1-(7-chloro-1-oxoisoindolin-2-yl)-2,3-dihydro-1H-indene-4-carboxylic acid (G-10) | Yield: 86%<br>Synthesis was carried out analogously to E-09 starting from D-10 |
| G-11 | 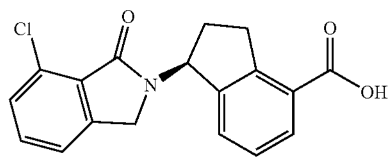 [SMILES: O=C(O)c1cccc2c1CC[C@@H]2N1Cc2cccc(Cl)c2C1=O] | (S)-1-(7-chloro-1-oxoisoindolin-2-yl)-2,3-dihydro-1H-indene-4-carboxylic acid (G-11) | Yield: 38%<br>Synthesis was carried out analogously to E-09 starting from D-11 |

[b] Modified working up: Methanol was distilled off and the aqueous residue was diluted with diethyl ether and dist. water. The phases were separated and the aqueous phase was acidified with 1N HCl, during which a white solid precipitated out. This was filtered out with suction, washed with water and concentrated.

[c] Modified working up: Methanol and THF were distilled off and the aqueous residue was diluted with diethyl ether and dist. water. The phases were separated and the aqueous phase was acidified with 1N HCl. Finally, the aqueous phase was extracted 4× with ethyl acetate (spot test) and the combined organic phases were dried over sodium sulfate and concentrated.

General note: For reactions which were carried out in analogy to a described method, it may have been necessary to adapt the reaction conditions slightly, especially regarding the no. of equivalents of reagents employed, the interchangability of Et$_3$N and DIPEA, the reaction times (which were adjusted according to tlc results), the drying agent (magnesium sulfate or sodium sulfate) and the need for purification by column chromatography being required.

Synthesis of amino acid E-01

3-[(2-Chloro-benzoyl)amino]-2,3-dihydro-1H-indene-5-carboxylic acid (E-01)

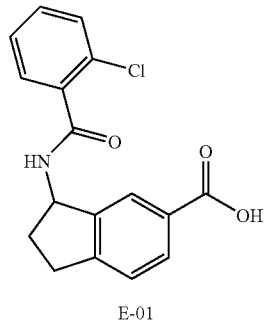

E-01

(I) LiOH (5 equiv.) was added to a suspension of 3-[(2-chloro-benzoyl)amino]-2,3-dihydro-1H-indene-5-carboxylic acid methyl ester (B-01) (11.75 mmol) in methanol (40 ml), tetrahydrofuran (40 ml) and water (30 ml) and the reaction mixture was stirred at 25° C. overnight. Methanol and THF were distilled off, the aqueous residue was acidified with 1N HCl and the mixture was filtered. The white solid obtained was taken up in a mixture of 350 ml of acetone and 50 ml of methanol and the mixture was stirred for 1 h. After filtration, the white solid was dried in vacuo to obtain 3-[(2-chloro-benzoyl)amino]-2,3-dihydro-1H-indene-5-carboxylic acid (E-01). Yield: 75%

Synthesis of amino acid E-04

(S)-3-(2-Chlorobenzamido)-2,3-dihydro-1H-indene-4-carboxylic acid (E-04)

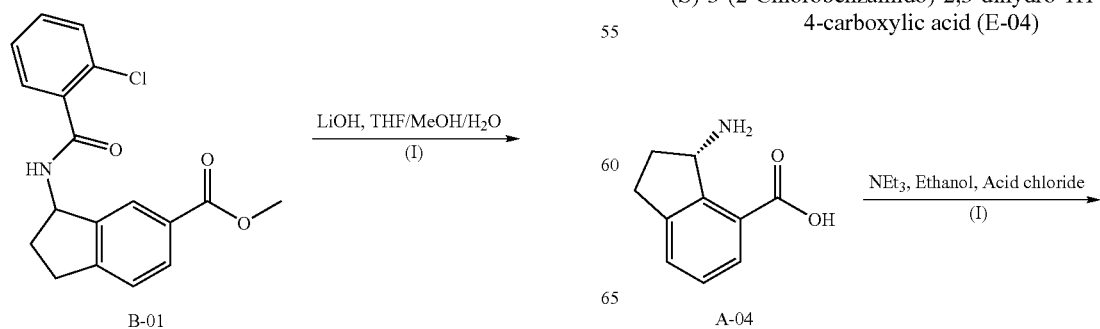

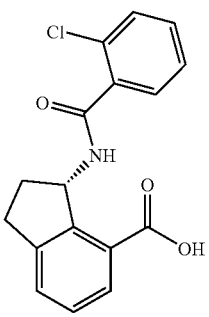

E-04

(I) N-Ethyl-diisopropylamine (2.5 mmol) and 2-chloro-benzoyl chloride (1.5 equiv.) were added to an ice-cold solution of A-04 (as corresponding HCl salt) (1.17 mmol) in ethanol at 0° C. and under an inert atmosphere and the mixture was then stirred at room temperature for 2 h. The ethanol was removed in vacuo and the residue was taken up in diethyl ether and water. The mixture was adjusted to pH 8-9 with dil. NaOH soln., the phases were separated and the aqueous phase was extracted 1× with diethyl ether. The aqueous phase was then adjusted to pH 2 with 1N HCl and the phases were separated. The aqueous phase was extracted 2× with methylene chloride and the combined organic phases were dried over $NaSO_4$ and concentrated to obtain the amino acid (E-04). Yield: 92%

Synthesis of amino acid E-06

(8R)-8-[(2-Chloro-benzoyl)amino]-5,6,7,8-tetrahydro-naphthalene-2-carboxylic acid (E-06)

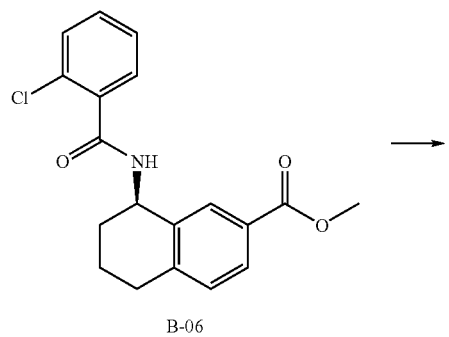

B-06

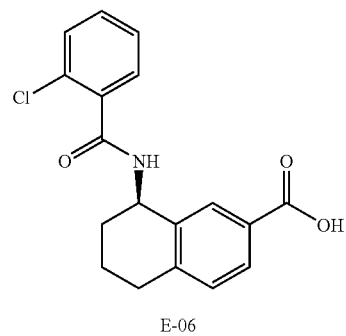

E-06

LiOH (4 equiv.) was added to a suspension of (8R)-8-[(2-chloro-benzoyl)amino]-5,6,7,8-tetrahydro-naphthalene-2-carboxylic acid methyl ester (B-06) in methanol and water and the reaction mixture was stirred at 25° C. for 2.5 hours. (According to TLC control: educt still present) The reaction mixture was topped up with 2 equiv. of LiOH and stirred at 25° C. overnight. Methanol was distilled off and the aqueous residue was diluted with ether and dist. water. The phases were separated and the aqueous phase was acidified with 1N HCl. Finally, the aqueous phase was extracted 4× with ethyl acetate (spot test) and the extract was dried over sodium sulfate and concentrated. Yield: 81.4%.

Synthesis of amino acid E-07

(8S)-8-[(2-Chloro-benzoyl)amino]-5,6,7,8-tetrahydro-naphthalene-2-carboxylic acid (E-07)

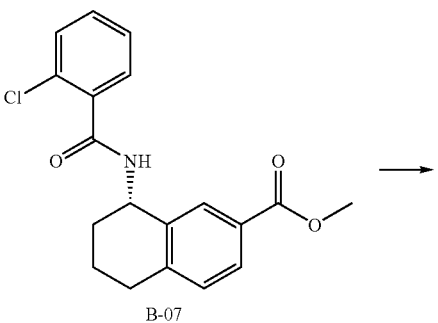

B-07

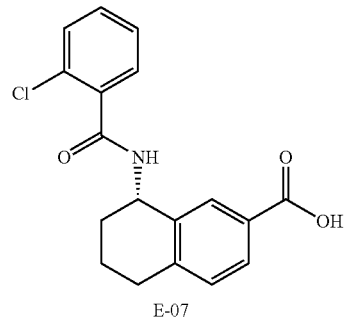

E-07

LiOH (6 equiv.) was added to a suspension of (8S)-8-[(2-chloro-benzoyl)amino]-5,6,7,8-tetrahydro-naphthalene-2-carboxylic acid methyl ester (B-07) in methanol and water and the reaction mixture was stirred at 25° C. for 4 hours. (According to TLC control: educt still present). The reaction mixture was topped up with 1 equiv. of LiOH and stirred at 25° C. for 1 hour. Methanol was distilled off and the aqueous residue was diluted with ether and dist. water. The phases were separated and the aqueous phase was acidified with 1N HCl. Finally, the aqueous phase was extracted 4× with ethyl acetate (spot test) and the extract was dried over sodium sulfate and concentrated. Yield: 84.8%

Synthesis of amino acid E-08

3-(2-Chlorobenzamido)-2,2-dimethyl-2,3-dihydro-1H-indene-5-carboxylic acid (E-08)

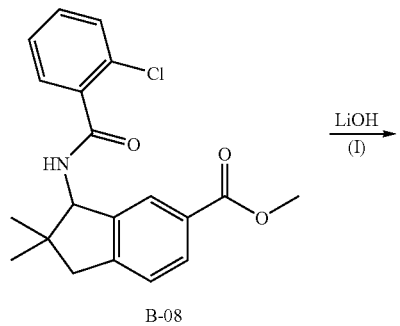

B-08

$\xrightarrow{\text{LiOH}}$ (I)

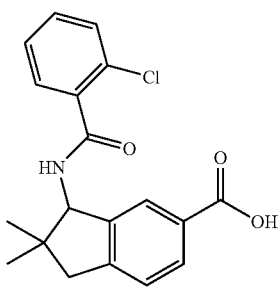

E-08

(I) A solution of LiOH.H₂O (4.0 eq.) in water (10 ml) was added to a solution of methyl 3-(2-chlorobenzamido)-2,2-dimethyl-2,3-dihydro-1H-indene-5-carboxylate (B-08) (1.54 mmol, 1.0 eq.) in methanol (20 ml) and the mixture was then stirred at 25° C. for 5 h. When the reaction was complete (TLC control), the methanol was evaporated off in vacuo and the residual aqueous phase was diluted with water (50 ml) and washed with ethyl acetate (2×25 ml). The aqueous phase was acidified to pH=2-3 with 1 (N) HCl and the solid was filtered out. 2× toluene was added to the solid and the mixture concentrated again, in order to obtain the desired product solid. Yield: 90%

Synthesis of amino acid E-09

(R)-3-(2-Methylbenzamido)-2,3-dihydro-1H-indene-5-carboxylic acid (E-09)

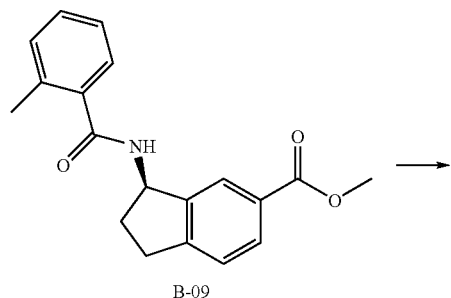

B-09

→

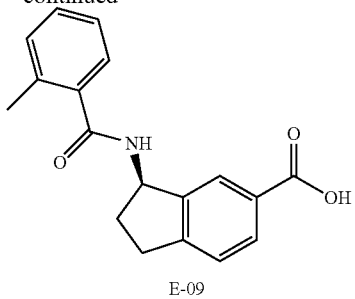

E-09

KOH (1 mol/l aq) (2 eq.) was added to a suspension of (R)-methyl 3-(2-methylbenzamido)-2,3-dihydro-1H-indene-5-carboxylate (B-09) (0.61 mmol, 1 eq.) in a mixture of ethanol (3.6 ml) and water (0.8 ml). The reaction mixture was stirred at room temperature overnight. Ethanol was removed in vacuo and the aqueous residue was diluted with diethyl ether and dist. water. The phases were separated and the aqueous phase was acidified with 1N HCl to pH 3 and then extracted 4× with ethyl acetate. The combined organics were dried over sodium sulfate and concentrated in vacuo to yield the desired product (E-09). Yield: 88%

Synthesis of amino acid E-11

4-(2-Chlorobenzamido)-chroman-6-carboxylic acid (E-11)

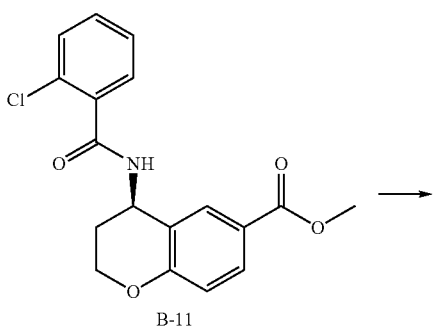

B-11

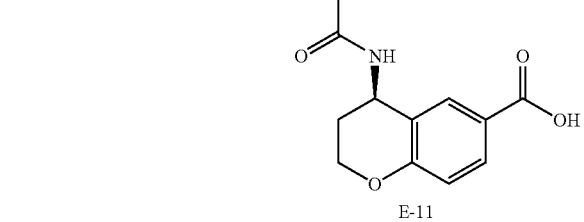

E-11

KOH (1 mol/1 aq) (2 eq.) was added to a suspension of methyl 4-(2-chlorobenzamido)chroman-6-carboxylate (B-11) (2.227 mmol, 1 eq.) in a mixture of ethanol (13 ml) and water (4.5 ml). The reaction mixture was stirred at room temperature for 16 h. Ethanol was removed in vacuo and the aqueous residue was diluted with diethyl ether (20 ml) and water (20 ml). The phases were separated and the aqueous phase was acidified with 1N HCl to pH 3. The white precipitate was filtered out, washed with aqueous HCl solution and diethyl ether and finally dried in vacuo to obtain the desired product (E-11). Yield: 85%

Synthesis of amino acid E-12

(R)-3-(2-Chlorobenzamido)-6-methyl-2,3-dihydro-1H-indene-5-carboxylic acid (E-12)

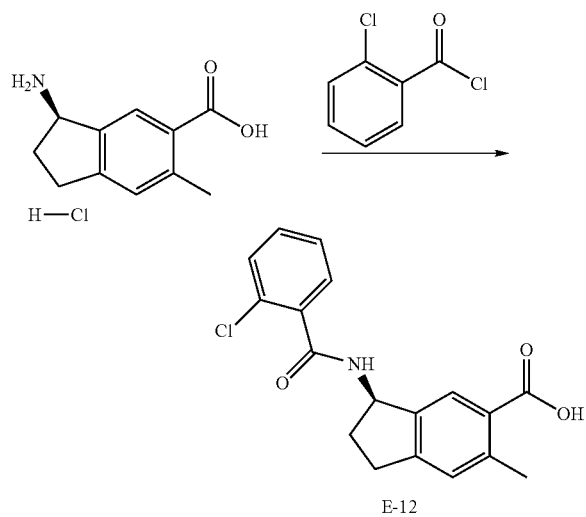

Triethylamine (4.707 mmol, 1.5 eq.) was added to a solution of (R)-3-amino-6-methyl-2,3-dihydro-1H-indene-5-carboxylic acid hydrochloride (commercially available from NetChem) (1 eq., 3.138 mmol) in methylene chloride (16 ml) at 0° C. 2-Chlorobenzoyl chloride (1.2 eq.) was added dropwise to the reaction mixture at the same temperature and the mixture was stirred for 16 h at room temperature. The reaction mixture was diluted with methylene chloride (50 ml), and washed with NH₄Cl solution (20 ml) and sat. NaCl solution (20 ml). The organic phase was dried over magnesium sulfate and the solvent was removed in vacuo. The crude material was purified by column chromatography (silica, ethyl acetate/cyclohexane 3:2) to yield the desired product (E-12). Yield: 43%

Synthesis of amino acid E-39

3-(2-Chlorobenzamido)-1,1-dimethyl-2,3-dihydro-1H-indene-5-carboxylic acid (E-39)

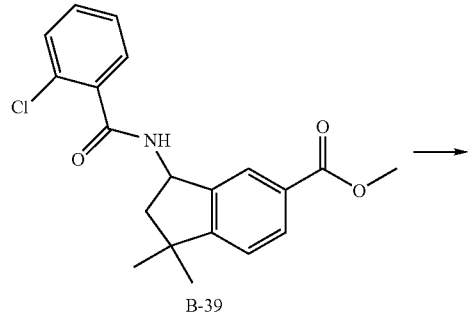

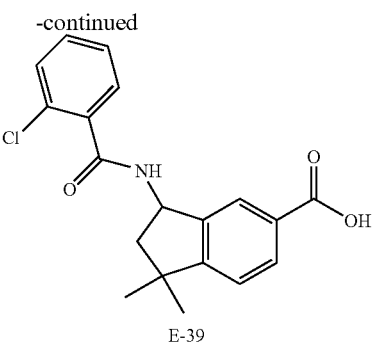

Methyl 3-(2-chlorobenzamido)-1,1-dimethyl-2,3-dihydro-1H-indene-5-carboxylate (B-39) (120 mg, 0.34 mmol, 1 eq.) was dissolved in a mixture of solvents THF:MeOH:H₂O (5:3:1, 5 ml) and LiOH (70 mg, 1.67 mmol, 5 eq.) was added portionwise at 0° C. The reaction mixture was stirred for 4 h and then the solvent was evaporated under reduced pressure. Water (4 ml) was added to the reaction to get a clear solution and it was then acidified with citric acid. This was followed by extraction with EtOAc (2×50 ml). The organic part was washed with brine (20 ml), dried over Na₂SO₄, filtered and evaporated under reduced pressure to yield the crude product which was purified by column chromatography (silica gel, 5% MeOH/MC) to yield the desired product as a white solid. Yield: 98% (115 mg, 0.34 mmol).

Synthesis of amino acid E-41

(R)-3-(2-chloro-N-(2,2,2-trifluoroethyl)benzamido)-2,3-dihydro-1H-indene-5-carboxylic acid (E-41)

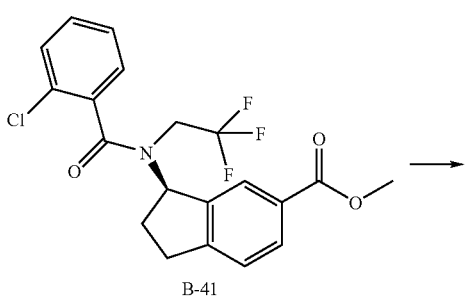

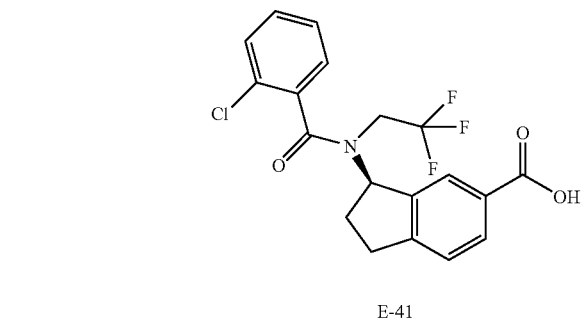

A solution of LiOH (153 mg, 3.64 mmol, 1.5 eq.) in water (8 ml) was added to a cooled (0° C.) solution of (R)-methyl 3-(2-chloro-N-(2,2,2-trifluoroethyl)benzamido)-2,3-dihydro-1H-indene-5-carboxylate (B-41) (1.0 g, 2.43 mmol, 1.0 eq.) in MeOH:THF (1:1, 16 ml) and the reaction mixture was then stirred at RT for 5 h. After completion of the reaction (monitored by TLC), the mixture was evaporated to dryness and diluted with water (15 ml). The aqueous layer was acidified to pH ~3 using 1N HCl and then extracted with ethyl acetate (2×30 ml). The organic layer was washed with brine (20 ml), dried over anhydrous $Na_2SO_4$ and evaporated to afford the desired product as a white solid. Yield: 88% (850 mg, 2.14 mmol).

Synthesis of amino acid F-01

3-[[(4-Methoxy-2,6-dimethyl-phenyl)sulfonyl]amino]-2,3-dihydro-1H-indene-5-carboxylic acid methyl ester (F-01)

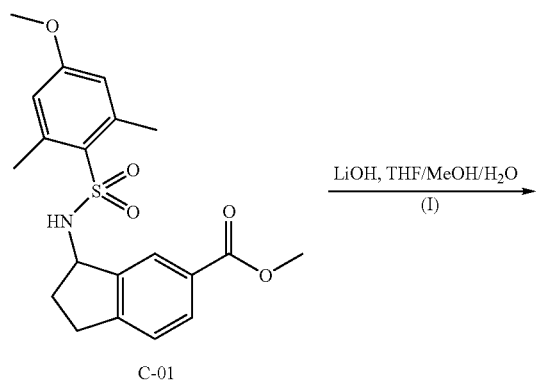

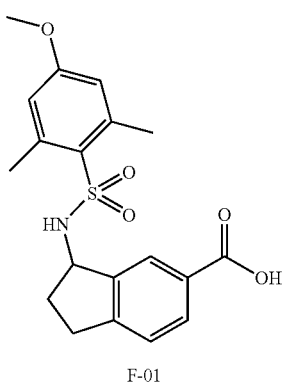

(I) LiOH (5 equiv.) was added to a suspension of 3-[[(4-methoxy-2,6-dimethyl-phenyl)sulfonyl]amino]-2,3-dihydro-1H-indene-5-carboxylic acid methyl ester (C-01) (11.75 mmol) in methanol (40 ml), tetrahydrofuran (40 ml) and water (30 ml) and the reaction mixture was stirred at 25° C. overnight. Methanol and THF were distilled off, the aqueous residue was acidified with 1N HCl and the mixture was filtered. The white solid obtained was taken up in a mixture of 350 ml of acetone and 50 ml of methanol and the mixture was stirred for 1 h. After filtration, the white solid was dried in vacuo to obtain 3-[[(4-methoxy-2,6-dimethyl-phenyl))sulfonyl]amino]-2,3-dihydro-1H-indene-5-carboxylic acid (F-01). Yield: 90%

Synthesis of amino acid F-03

(R)-8-(4-Methoxy-2,6-dimethylphenyl sulfonamido)-5,6,7,8-tetrahydronaphthalene-2-carboxylic acid (F-03)

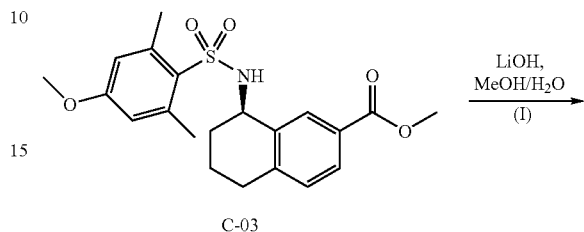

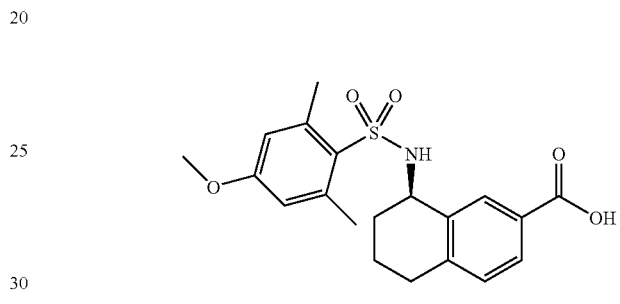

(I) LiOH (6 equiv.) was added to a suspension of (R)-methyl 8-(4-methoxy-2,6-dimethylphenylsulfonamido)5,6,7,8-tetrahydronaphthalene-2-carboxylate (C-03) (1.115 mmol) in methanol and water and the reaction mixture was stirred at 25° C. overnight. The reaction mixture was topped up with 2 equiv. of LiOH and stirred at 25° C. for 1 h. The methanol was distilled off and the aqueous residue was diluted with diethyl ether and dist. water. The phases were separated and the aqueous phase was acidified with 1N HCl. Finally, the aqueous phase was extracted 4× with ethyl acetate and the combined organic phases were dried over sodium sulfate and concentrated. Yield: 76%

Synthesis of amino acid F-06

(R)-3-(2,3-Dichlorophenylsulfonamido)-2,3-dihydro-1H-indene-5-carboxylic acid (F-06)

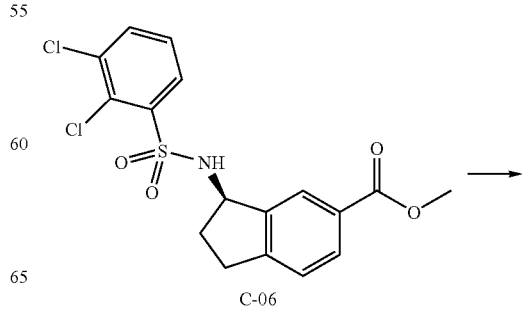

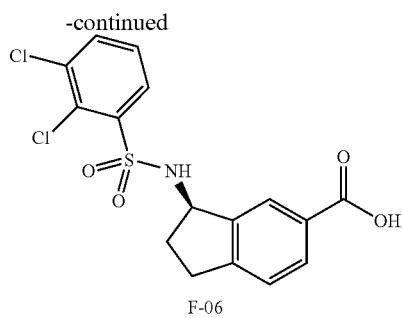

F-06

KOH (1 mol/l aq) (2 eq.) was added to a suspension of (R)-methyl 3-(2,3-dichlorophenyl-sulfonamido)-2,3-dihydro-1H-indene-5-carboxylate (C-06) (0.85 mmol, 1 eq.) in a mixture of ethanol (4.9 ml) and water (1.1 ml). The reaction mixture was stirred at room temperature overnight. Ethanol was removed in vacuo and the aqueous residue was diluted with diethyl ether and dist. water. The phases were separated and the aqueous phase was acidified to pH 3 with 1N HCl and extracted 4× with ethyl acetate. The combined organics were dried over sodium sulfate and concentrated to obtain the desired product (F-06). Yield: 61%

Synthesis of amino acid F-16

(R)-3-(2-Chloro-N-methylphenylsulfonamido)-2,3-dihydro-1H-indene-5-carboxylic acid (F-16)

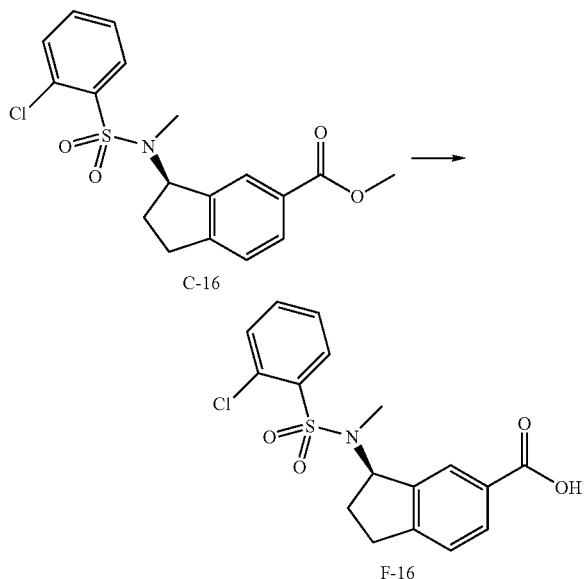

To a cooled (0° C.) solution of (R)-methyl 3-(2-chloro-N-methylphenylsulfonamido)-2,3-dihydro-1H-indene-5-carboxylate (C-16) (840 mg, 2.216 mmol, 1.0 eq.) in MeOH: THF (1:1, 20 ml) was added dropwise a solution of LiOH.H₂O (185 mg, 4.433 mmol, 2.0 eq.) in water (10 ml) and the reaction mixture was stirred at RT for 3 h. After completion of the reaction (monitored by TLC), the reaction mixture was concentrated to dryness and diluted with water (20 ml) and washed with ethyl acetate (20 ml). The aqueous layer was acidified to pH≈3 using 1N HCl and then extracted with methylene chloride (2×50 ml). The combined organic layers were dried over anhydrous Na₂SO₄ and concentrated to afford the desired product as an off-white solid. Yield: 58% (470 mg, 1.2876 mmol).

Synthesis of amino acid G-01

3-(4-Chloro-3-oxo-1,2-dihydro-isoindol-2-yl)-2,3-dihydro-1H-indene-5-carboxylic acid (G-01)

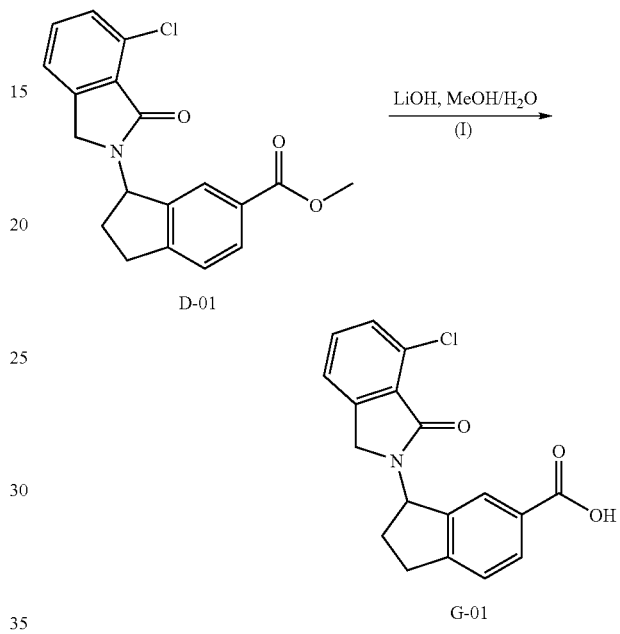

(I) LiOH (5 equiv.) was added to a suspension of 3-(4-chloro-3-oxo-1,2-dihydro-isoindol-2-yl)-2,3-dihydro-1H-indene-5-carboxylic acid methyl ester (D-01) (11.75 mmol) in methanol (90 ml) and water (30 ml) and the reaction mixture was stirred at 25° C. for 72 h. Methanol was distilled off, the aqueous residue was acidified with 1N HCl and the mixture was filtered. The white solid obtained was taken up in a mixture of 350 ml of acetone and 50 ml of methanol and the mixture was stirred for 1 h. After filtration, the white solid was dried in vacuo to obtain 3-(4-chloro-3-oxo-1,2-dihydro-isoindol-2-yl)-2,3-dihydro-1H-indene-5-carboxylic acid (G-01). Yield: 66%

Synthesis of amino acid G-06

(R)-3-(5-Methyl-3-oxo-1H-pyrrolo[1,2-c]imidazol-2(3H)-yl)-2,3-dihydro-1H-indene-5-carboxylic acid (G-06)

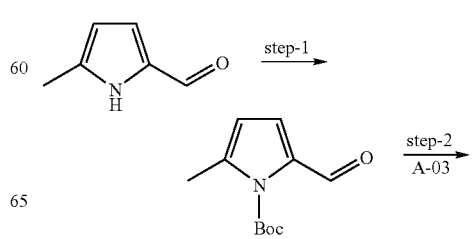

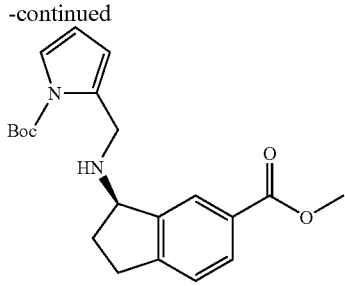

↓ step-3

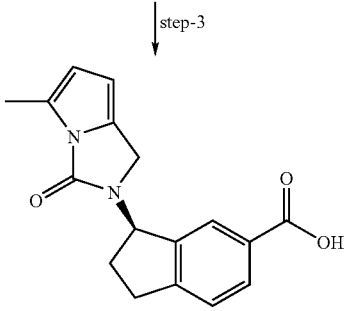

G-06

Step-1 tert-Butyl 2-formyl-5-methyl-1H-pyrrole-1-carboxylate

To a solution of 5-methyl-1H-pyrrole-2-carbaldehyde (500 mg, 4.58 mmol, 1 eq.) in acetonitrile (10 ml) were added DMAP (46 mg, 0.36 mmol, 1 eq.) and (Boc)₂O (1.19 g, 5.5 mmol, 1.2 eq.) and the mixture was stirred at RT for 2 h. The solvent was evaporated under reduced pressure and the crude product was purified by column chromatography (silica gel; 5% EtOAc/hexanes) to afford the desired product as a light yellow oil. Yield: 83% (800 mg, 3.8 mmol).

Step-2

(R)-tert-Butyl 2((6-(methoxycarbonyl)-2,3-dihydro-1H-inden-1-ylamino)methyl)-1H-pyrrole-1-carboxylate A solution of (3R)-3-amino-2,3-dihydro-1H-indene-5-carboxylic acid methyl ester (A-03) (361 mg, 1.88 mmol, 1 eq.) in methylene chloride (3 ml) was added to a solution of tert-butyl 2-formyl-5-methyl-1H-pyrrole-1-carboxylate (434 mg, 2.08 mmol, 1.1 eq.) in dry methylene chloride (17 ml) at 0° C. and the resulting reaction mixture was stirred at 25° C. for 2 h. The reaction mixture was cooled to 0° C. and then Na(OAc)₃BH (1.2 g, 5.66 mmol, 3 eq.) was added portionwise and it was stirred at 25° C. for 14 h. The reaction mixture was diluted with methylene chloride (200 ml) and washed with saturated sodium bicarbonate (50 ml), water (2×50 ml) and brine (50 ml), and dried over sodium sulfate. The solvent was evaporated under reduced pressure and the residue was purified by column chromatography (silica gel; 5% EtOAc/hexanes) to give the desired product as a light yellow oil. Yield: 82% (600 mg, 1.56 mmol).

Step-3

(R)-3-(5-Methyl-3-oxo-1H-pyrrolo[1,2-c]imidazol-2(3H)-yl)-2,3-dihydro-1H-indene-5-carboxylic acid A solution of (R)-tert-butyl 2-((6-(methoxycarbonyl)-2,3-dihydro-1H-inden-1-ylamino)methyl)-1H-pyrrole-1-carboxylate (500 mg, 1.3 mmol, 1.0 eq.) in THF (5 ml) was added to a stirred suspension of NaH (104 mg, 2.6 mmol, 2.0 eq., 60% in mineral oil) in THF (15 ml) at 0° C. and the resulting reaction mixture was stirred at 25° C. for 14 h. The reaction mixture was quenched with water (50 ml) and washed with ethyl acetate (50 ml). The aqueous layer was acidified with 2 N HCl (5 ml) and extracted with ethyl acetate (2×100 ml). The combined organic fractions were washed with brine (50 ml), dried over sodium sulfate and the solvent evaporated under reduced pressure. The residue obtained was used for the next step without further purification. Yield: 26% (100 mg, 0.34 mmol).

Synthesis of the Amine Units
Overview: Amine Units

| AMN unit no. | Structure | AMN name |
|---|---|---|
| AMN-01 | 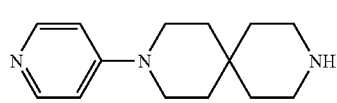 | 9-pyridin-4-Yl-3,9-diazaspiro[5.5]undecane dihydrochloride (AMN-01) |
| AMN-02 | 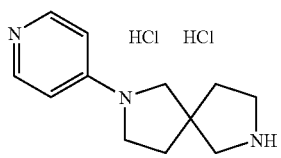 [SMILES: c1cc(N2CCC3(CCNC3)C2)ccn1 ; Cl ; Cl] | 8-pyridin-4-Yl-3,8-diazaspiro[4.4]nonane dihydrochloride (AMN-02) |
| AMN-03 | 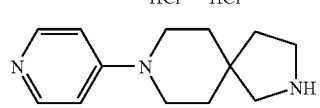 | 8-pyridin-4-Yl-3,8-diazaspiro[4.5]decane dihydrochloride (AMN-03) |

-continued

| AMN unit no. | Structure | AMN name |
|---|---|---|
| AMN-04 | 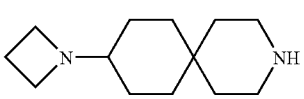 | 9-(azetidin-1-Yl)-3-azaspiro[5.5]undecane dihydrochloride (AMN-04) |
| AMN-05 | 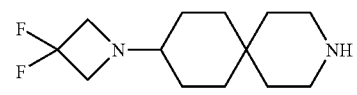 | 9-(3,3-difluoro-azetidin-1-yl)-3-azaspiro[5.5]undecane dihydrochloride (AMN-05) |
| AMN-06 | 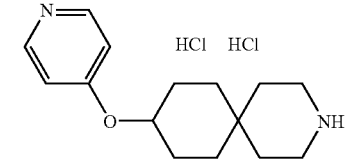 [SMILES: c1cc(OC2CCC3(CCNCC3)CC2)ccn1 ; Cl ; Cl] | 9-pyridin-4-Yloxy-3-azaspiro[5.5]undecane dihydrochloride (AMN-06) |
| AMN-07 | 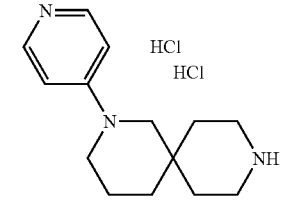 [SMILES: c1cc(N2CCCC3(CCNCC3)C2)ccn1 ; Cl ; Cl] | 2-(pyridin-4-yl)-2,9-diazaspiro[5.5]undecane dihydrochloride (AMN-07) |
| AMN-08 | 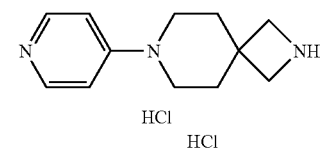 | 7-(pyridin-4-yl)-2,7-diazaspiro[3.5]nonane dihydrochloride (AMN-08) |
| AMN-09 | 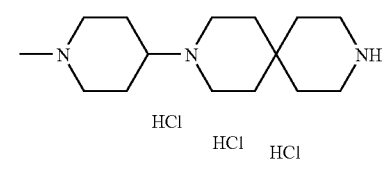 [SMILES: CN1CCC(N2CCC3(CCNCC3)CC2)CC1 ; Cl ; Cl ; Cl] | 3-(1-methylpiperidin-4-yl)-3,9-diazaspiro[5.5]undecane Trihydrochlorid (AMN-09) |
| AMN-10 | 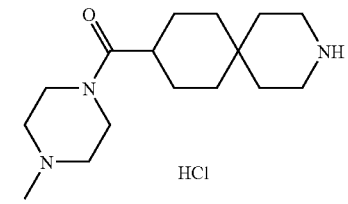 [SMILES: CN1CCN(C(=O)C2CCC3(CCNCC3)CC2)CC1 ; Cl] | (4-methylpiperazin-1-yl)(3-azaspiro[5.5]undecan-9-yl)methanone hydrochloride (AMN-10) |
| AMN-12 | 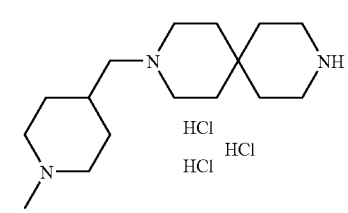 [SMILES: CN1CCC(CN2CCC3(CCNCC3)CC2)CC1 ; Cl ; Cl ; Cl] | 3-((1-methylpiperidin-4-yl)methyl)-3,9-diazaspiro[5.5]undecane trihydrochloride (AMN-12) |
| AMN-13 | 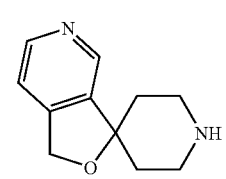 [SMILES: c1cc2c(cn1)C1(CCNCC1)OC2] | 1H-spiro[furo[3,4-c]pyridine-3,4'-piperidine] (AMN-13) |

US 8,455,475 B2

-continued

| AMN unit no. | Structure | AMN name |
|---|---|---|
| AMN-14 | 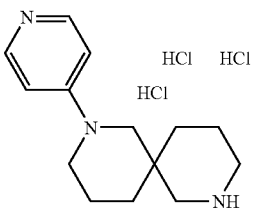 [SMILES: c1cc(N2CCCC3(CCCNC3)C2)ccn1 ; Cl ; Cl ; Cl] | 2-(pyridin-4-yl)-2,8-diazaspiro[5.5]undecane trifhydrochloride (AMN-14) |
| AMN-15 | 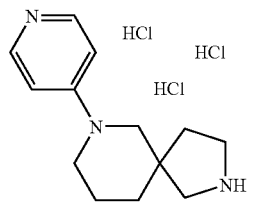 [SMILES: c1cc(N2CCCC3(CCNC3)C2)ccn1 ; Cl ; Cl ; Cl] | 7-(pyridin-4-yl)-2,7-diazaspiro[4.5]decane trihydrochloride (AMN-15) |
| AMN-16 | 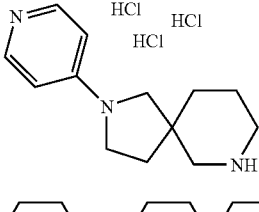 | 2-(pyridin-4-yl)-2,7-diazaspiro[4.5]decane trihydrochloride (AMN-16) |
| AMN-17 | 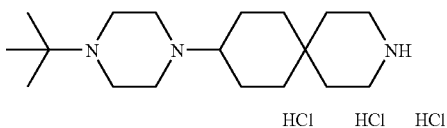 | 9-(4-tert-butylpiperazin-1-yl)-3-azaspiro[5.5]undecane trihydrochloride (AMN-17) |
| AMN-18 | 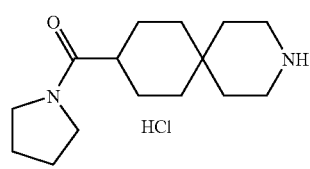 [SMILES: O=C(C1CCC2(CCNCC2)CC1)N1CCCC1 ; Cl] | pyrrolidin-1-yl(3-azaspiro[5.5]undecan-9-yl)methanone hydrochloride (AMN-18) |
| AMN-19 | 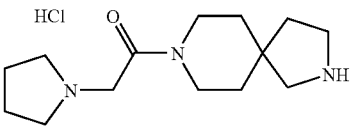 [SMILES: Cl ; O=C(CN1CCCC1)N1CCC2(CCNC2)CC1] | 2-(pyrrolidin-1-yl)-1-(2,8-diazaspiro[4.5]decan-8-yl)ethanone hydrochloride (AMN-19) |
| AMN-20 | 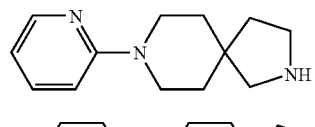 | 8-(pyridin-2-yl)-2,8-diazaspiro[4.5]decane (AMN-20) |
| AMN-21 | 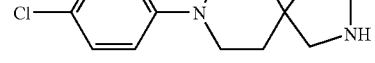 | 8-(4-chlorophenyl)-2,8-diazaspiro[4.5]decane (AMN-21) |
| AMN-22 | 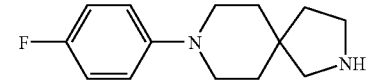 [SMILES: Fc1ccc(N2CCC3(CCNC3)CC2)cc1] | 8-(4-chlorophenyl)-2,8-diazaspiro[4.5]decane (AMN-22) |
| AMN-23 | 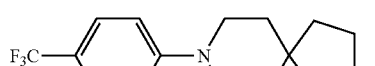 | 8-(4-(trifluoromethyl)phenyl)-2,8-diazaspiro[4.5]decane (AMN-23) |
| AMN-24 | 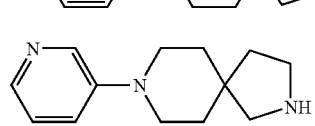 | 8-(pyridin-3-yl)-2,8-diazaspiro[4.5]decane (AMN-24) |

| AMN unit no. | Structure | AMN name |
| --- | --- | --- |
| AMN-25 | 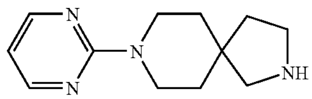 [SMILES: c1cnc(N2CCC3(CCNC3)CC2)nc1] | 8-(pyrimidin-2-yl)-2,8-diazaspiro[4.5]decane (AMN-25) |
| AMN-26 | 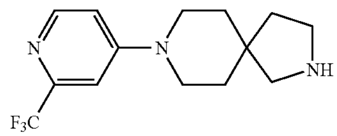 | 8-(2-(trifluoromethyl)pyridin-4-yl)-2,8-diazaspiro[4.5]decane (AMN-26) |
| AMN-27 | 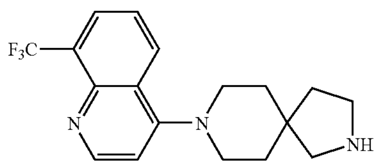 [SMILES: FC(F)(F)c1cccc2c(N3CCC4(CCNC4)CC3)ccnc12] | 4-(2,8-diazaspiro[4.5]decan-8-yl)-8-(trifluoromethyl)quinoline (AMN-27) |
| AMN-28 | 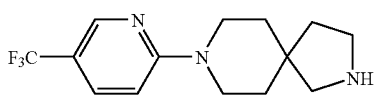 [SMILES: FC(F)(F)c1ccc(N2CCC3(CCNC3)CC2)nc1] | 8-(5-(trifluoromethyl)pyridin-2-yl)-2,8-diazaspiro[4.5]decane (AMN-28) |
| AMN-29 | 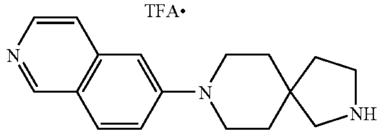 [SMILES: c1cc2cc(N3CCC4(CCNC4)CC3)ccc2cn1] | 6-(2,8-diazaspiro[4.5]decan-8-yl)isoquinoline trifluoroacetate (AMN-29) |
| AMN-30 | 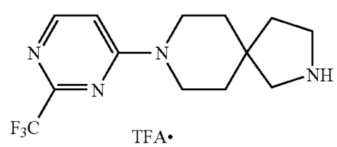 [SMILES: FC(F)(F)c1nccc(N2CCC3(CCNC3)CC2)n1] | 8-(2-(trifluoromethyl)pyrimidin-4-yl)-2,8-diazaspiro[4.5]decane trifluoroacetate (AMN-30) |
| AMN-31 | 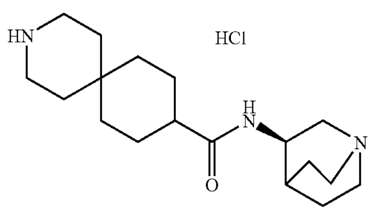 [SMILES: O=C(N[C@H]1CN2CCC1CC2)C1CCC2(CCNCC2)CC1 ; Cl] | N-((R)-quinuclidin-3-yl)-3-azaspiro[5.5]undecane-9-carboxamide hydrochloride (AMN-31) |
| AMN-32 | 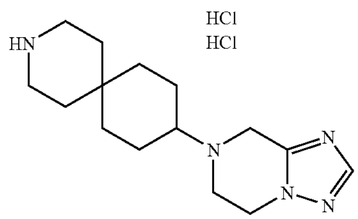 [SMILES: Cl ; c1nc2n(n1)CCN(C1CCC3(CCNCC3)CC1)C2 ; Cl] | 7-(3-azaspiro[5.5]undecan-9-yl)-5,6,7,8-tetrahydro-[1,2,4]triazolo[1,5-a]pyrazine dihydrochloride (AMN-32) |
| AMN-33 | 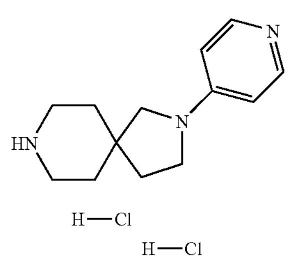 | 2-(pyridin-4-yl)-2,8-diazaspiro[4,5]decane dihydrochloride (AMN-33) |

| AMN unit no. | Structure | AMN name |
|---|---|---|
| AMN-34 | 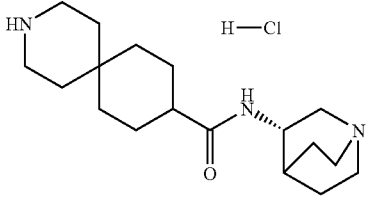 [SMILES: O=C(N[C@@H]1CN2CCC1CC2)C1CCC2(CCNCC2)CC1 ; Cl] | N-((S)-quinuclidin-3-yl)-3-azaspiro[5.5]undecane-9-carboxamide hydrochloride (AMN-34) |
| AMN-35 | 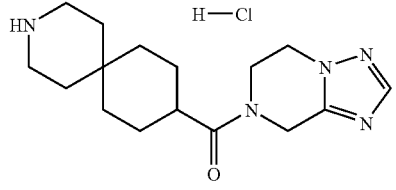 | (5,6-dihydro-[1,2,4]triazolo[1,5-a]pyrazin-7(8H)-yl)(3-azaspiro[5.5]undecan-9-yl)methanone hydrochloride (AMN-35) |
| AMN-36 | 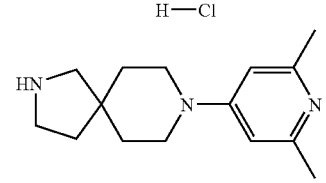 | 8-(2,6-dimethylpyridin-4-yl)-2,8-diazaspiro[4.5]decane hydrochloride (AMN-36) |
| AMN-37 | 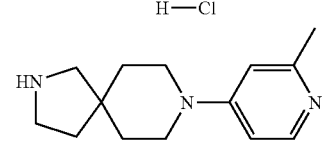 | 8-(2-methylpyridin-4-yl)-2,8-diazaspiro[4.5]decane dihydrochloride (AMN-37) |
| AMN-38 | 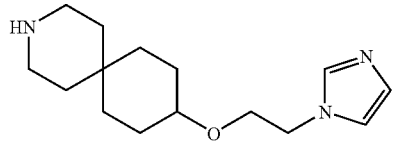 [SMILES: c1cn(CCOC2CCC3(CCNCC3)CC2)cn1] | 9-(2-(1H-imidazol-1-yl)ethoxy)-3-azaspiro[5.5]undecane (AMN-38) |
| AMN-39 | 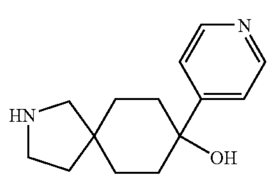 [SMILES: OC1(c2ccncc2)CCC2(CCNC2)CC1] | 8-(pyridin-4-yl)-2-azaspiro[4.5]decan-8-ol (AMN-39) |
| AMN-41 | 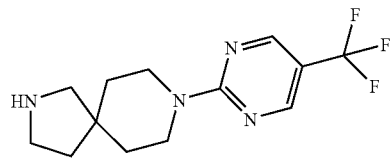 [SMILES: FC(F)(F)c1cnc(N2CCC3(CCNC3)CC2)nc1] | 8-(5-(trifluoromethyl)pyrimidin-2-yl)-2,8-diazaspiro[4.5]decane (AMN-41) |
| AMN-42 | 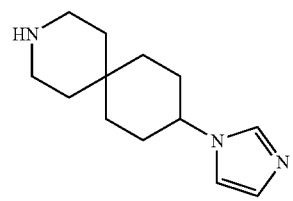 [SMILES: c1cn(C2CCC3(CCNCC3)CC2)cn1] | 9-(1H-imidazol-1-yl)-3-azaspiro[5.5]undecane (AMN-42) |

-continued

| AMN unit no. | Structure | AMN name |
|---|---|---|
| AMN-43 | 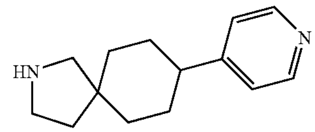 [SMILES: c1cc(C2CCC3(CCNC3)CC2)ccn1] | 8-(pyridin-4-yl)-2-azaspiro[4.5]decane (AMN-43) |
| AMN-44 | 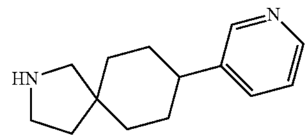 [SMILES: c1cncc(C2CCC3(CCNC3)CC2)c1] | 8-(pyridin-3-yl)-2-azaspiro[4.5]decane (AMN-44) |
| AMN-45 | 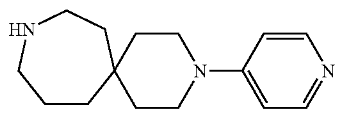 | 3-(pyridin-4-yl)-3,9-diazaspiro[5.6]dodecane (AMN-45) |
| AMN-46 | 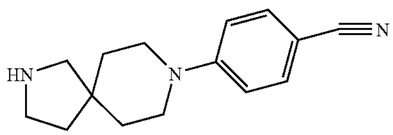 [SMILES: N#Cc1ccc(N2CCC3(CCNC3)CC2)cc1] | 4-(2,8-diazaspiro[4.5]decan-8-yl)benzonitrile (AMN-46) |
| AMN-47 | 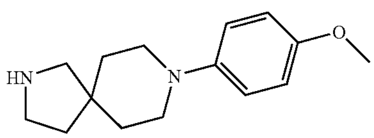 [SMILES: COc1ccc(N2CCC3(CCNC3)CC2)cc1] | 8-(4-methoxyphenyl)-2,8-diazaspiro[4.5]decane (AMN-47) |

Synthesis of the Amine Unit AMN-01

9-Pyridin-4-yl-3,9-diazaspiro[5.5]undecane dihydrochloride (AMN-01)

(i): tert-Butyl 3,9-diazaspiro[5.5]undecane-3-carboxylate (1 g, 3.931 mmol), 4-chloropyridinium chloride (1.765 g, 11.794 mmol) and triethylamine (2.2 ml, 15.725 mmol) were refluxed in 1-butanol (50 ml) for 15 h. Saturated sodium bicarbonate solution (30 ml) and ethyl acetate (80 ml) were added, the phases were separated and the aqueous phase was extracted with ethyl acetate (2×80 ml). The combined organic phases were dried over magnesium sulfate and concentrated in vacuo. The crude product was purified by column chromatography (silica gel) with ethyl acetate/hexane/methanol/ammonia (25% aq.) 400/40/40/1. Yield: 0.52 g, 39%

(ii): Hydrogen chloride in methanol (1.25 mol/l, 6.3 ml) was added to tert-butyl 9-(pyridin-4-yl)-3,9-diazaspiro[5.5] undecane-3-carboxylate (0.52 g, 1.569 mmol) and the mixture was refluxed for 1 h. The solvent was removed in vacuo, the residue was taken up in ethanol (3 ml) and the mixture was cooled. Acetone (80 ml) was added and the mixture was stirred in an ice bath for 30 min. The precipitate was filtered out with suction, washed with diethyl ether and dried in vacuo. Yield: 0.4 g, 83%

Synthesis of the Amine Unit AMN-02

8-Pyridin-4-Yl-3,8-diazaspiro[4.4]nonane dihydrochloride (AMN-02)

The synthesis was carried out analogously to the synthesis of amine AMN-01.

For this, in step (i) tert-butyl 2,7-diazaspiro[4.4]nonane-2-carboxylate was reacted with 4-chloropyridinium chloride (yield: 50%). The Boc protective group was then split off in step (ii). When the reaction had ended and the methanol had been removed in vacuo, the residue was taken up in ethanol, the mixture was cooled and acetone was added. The resulting suspension was stirred in an ice bath for 30 min and the precipitate was filtered out with suction, washed with acetone and dried in vacuo. Yield (AMN-02): 73%

Synthesis of the Amine Unit AMN-03

8-Pyridin-4-Yl-3,8-diazaspiro[4.5]decane dihydrochloride (AMN-03)

The synthesis was carried out analogously to the synthesis of amine AMN-01.

For this, in step (i) tert-butyl 2,8-diazaspiro[4.5]decane-2-carboxylate was reacted with 4-chloropyridinium chloride (yield: 22%). The Boc protective group was then split off in step (ii). When the reaction had ended and the methanol had been removed in vacuo, the residue taken up in ethanol, the mixture cooled and acetone added. The resulting suspension was stirred in an ice bath for 30 min and the precipitate was filtered out with suction, washed with acetone and dried in vacuo. Yield (AMN-03): 92%.

Synthesis of the Amine Unit AMN-04

9-(Azetidin-1-Yl)-3-azaspiro[5.5]undecane dihydrochloride (AMN-04)

Step (i): tert-Butyl 9-(azetidin-1-yl)-3-azaspiro[5.5] undecane-3-carboxylate tert-Butyl 9-oxo-3-azaspiro[5.5]undecane-3-carboxylate (step (iv) AMN-06) (1 g, 3.74 mmol) and azetidine (0.25 ml, 3.74 mmol) were initially introduced into 1,2-dichloroethane (15 ml), and sodium triacetoxyborohydride (1.1 g, 5.23 mmol) was added. The reaction mixture was stirred at room temperature for 3 d and saturated sodium bicarbonate solution was then added. After separation of the phases, the aqueous phase was extracted with methylene chloride (2×). The combined organic phases were washed with saturated sodium chloride solution (1×), dried over magnesium sulfate and concentrated in vacuo. The crude product was purified by column chromatography (silica gel, ethyl acetate/methanol/ammonia (25% aq.) 100:10:1). Yield: 1 g (89%)

Step (ii): 9-(Azetidin-1-Y1)-3-azaspiro[5.5]undecane dihydrochloride

Hydrogen chloride in methanol (1.25 mol/l, 15.5 ml) was added to tent-butyl 9-(azetidin-1-yl)-3-azaspiro[5.5]undecane-3-carboxylate (1 g, 3.24 mmol) and the mixture was refluxed for 45 min. The solvent was removed in vacuo and the residue was dissolved in a small amount of ethanol. A solid was then precipitated out by addition of acetone, and finally diethyl ether was added and the precipitate formed was filtered out with suction. Yield: 0.87 g (95%)

Synthesis of the Amine Unit AMN-05

9-(3,3-Difluoro-azetidin-1-yl)-3-azaspiro[5.5]undecane dihydrochloride (AMN-05)

Step (i)

tert-Butyl 9-(3,3-difluoroazetidin-1-yl)-3-azaspiro[5.5]undecane-3-carboxylate tert-Butyl 9-oxo-3-azaspiro[5.5]undecane-3-carboxylate (step (iv) AMN-06) (1 g, 3.74 mmol) was added to 3,3-difluoroazetidine hydrochloride (0.484 g, 3.74 mmol) and triethylamine (0.52 ml, 3.74 mmol) in 1,2-dichloroethane (15 ml). The mixture was stirred for 5 min and sodium triacetoxyborohydride (1.1 g, 5.23 mmol) was then added and the mixture was stirred at room temperature for 3 d. Saturated sodium bicarbonate solution was added and closely separation of the phases the aqueous phase was extracted with methylene chloride (2×). The combined organic phases were washed with saturated sodium chloride solution (1×), dried over magnesium sulfate and concentrated in vacuo. Yield: 1.26 g (98%)

Step (ii)

9-(3,3-Difluoro-azetidin-1-yl)-3-azaspiro[5.5]undecane dihydrochloride tert-Butyl 9-(3,3-difluoroazetidin-1-yl)-3-azaspiro[5.5]undecane-3-carboxylate (1.26 g, 3.66 mmol) was dissolved in hydrogen chloride in methanol (1.25 mol/l, 29 ml) and the solution was refluxed for 45 min. The solvent was removed in vacuo and the residue was dissolved in a small amount of ethanol. A solid was then precipitated out by addition of acetone. The mixture was stirred at room temperature for 10 min, diethyl ether was then added and the mixture was stirred at room temperature for a further 30 min. The precipitate formed was filtered out with suction, washed with diethyl ether and dried in vacuo. Yield: 1.1 g (95%)

Synthesis of the Amine Unit AMN-06

9-Pyridin-4-yloxy)-3-azaspiro[5.5]undecane dihydrochloride (AMN-06)

Step (i)

1-(Benzyloxycarbonyl)piperidine-4-carboxylic acid

Water (75 ml) was added to piperidine-4-carboxylic acid (25 g) in THF (75 ml), followed by sodium bicarbonate (30.8 g). The mixture was cooled to 0° C. and Cbz chloride (38.9 ml) was added dropwise. The reaction mixture was then stirred at room temperature for 5 h (TLC control) When the reaction was complete, the organic solvent was distilled off and the residue was taken up in water (200 ml), and the mixture was washed with ethyl acetate (2×150 ml). The aqueous phase was acidified with dilute aqueous HCl solution and extracted with ethyl acetate. The organic phase was dried ($Na_2SO_4$) and concentrated in vacuo. Yield: 48.5 g (96%)

Step (ii)

1-Benzyl 4-methyl piperidine-1,4-dicarboxylate 1-(Benzyloxycarbonyl)piperidine-4-carboxylic acid (48.5 g) in methanol (485 ml) was cooled to 0° C. and thionyl chloride (13.34 ml) was added dropwise. The mixture was then refluxed for 20 min (TLC control). When the reaction was complete, the methanol was distilled off, the residue was taken up in water (15 ml) and with ethyl acetate (2×150 ml). The combined organic phases were extracted with water and sat. sodium chloride solution and the extract was dried ($Na_2SO_4$) and concentrated in vacuo. Yield: 38 g (67%)

Step (iii)

Benzyl 4-formylpiperidine-1-carboxylate

A solution of 1-benzyl 4-methyl piperidine-1,4-dicarboxylate (10 g) in toluene (100 ml) under nitrogen was cooled to −78° C. DIBAL-H (60.9 ml) was then added dropwise at −78° C. and the mixture was stirred at this temperature for 1 h (TLC control). Because the reaction was incomplete, a further 0.2 eq. of DIBAL-H was added and the mixture was stirred for a further 30 min (TLC control: some educt and the corresponding alcohol were to be detected). Methanol (40 ml), followed by sat. sodium chloride solution (40 ml) were added slowly to the reaction mixture at −78° C. The mixture was filtered over Celite and the solvent was removed in vacuo. The residue was extracted with ethyl acetate (3×75 ml) and the extract was dried ($Na_2SO_4$) and concentrated in vacuo. The crude product obtained in this way was purified by column chromatography (silica gel, 20% ethyl acetate/hexane). Yield: 4.3 g (49%)

Step (iv)

Benzyl 9-oxo-3-azaspiro[5.5]undec-7-ene-3-carboxylate

Methyl vinyl ketone (1.64 ml), ethanol (5 ml) and water (5 ml) were added to benzyl 4-formylpiperidine-1-carboxylate (5 g). The mixture was then added to a boiling solution of potassium hydroxide (0.22 g) in ethanol (10 ml) and the resulting reaction mixture was refluxed for 1 h (TLC control). When the reaction was complete, the mixture was added to water (25 ml) and extracted with ethyl acetate (2×50 ml). The combined organic phases were dried (Na$_2$SO$_4$) and concentrated in vacuo. The crude product obtained in this way was purified by column chromatography (silica gel, 25% ethyl acetate/hexane). Yield: 2.8 g (46%)

Step (v)

tert-Butyl 9-oxo-3-azaspiro[5.5]undecane-3-carboxylate

Boc anhydride (9.4 ml) and potassium carbonate (7.56 g) were added to benzyl 9-oxo-3-azaspiro[5.5]undec-7-ene-3-carboxylate (8.2 g) in EtOH/water (9:1) (200 ml). Pd/C (1 g) was then added and hydrogenolysis was carried out under 80 psi for 4 h (TLC control). When the reaction was complete, the mixture was filtered over Celite and the residue was rinsed with ethanol and ethyl acetate. The filtrate was dried (Na$_2$SO$_4$) and concentrated in vacuo. The residue was taken up in ethyl acetate and water and the aqueous phase was extracted with ethyl acetate. The combined organic phases were dried (Na$_2$SO$_4$) and concentrated in vacuo. The crude product obtained in this way was purified by column chromatography (silica gel, 20% ethyl acetate/hexane). Yield: 2.92 g, 40%

Step (vi)

tert-Butyl 9-hydroxy-3-azaspiro[5.5]undecane-3-carboxylate tert-Butyl 9-oxo-3-azaspiro[5.5]undecane-3-carboxylate (1.5 g) was dissolved in THF (7.5 ml) and the solution was cooled to −5° C. NaBH$_4$ (0.212 g) was then added and the mixture was stirred at room temperature for 1 h (TLC control). When the reaction was complete, acetic acid was added to the mixture and the methanol was then distilled off. The residue was taken up in water (50 ml) and the mixture was extracted with ethyl acetate (2×50 ml). The combined organic phases were dried (Na$_2$SO$_4$) and concentrated in vacuo. The crude product obtained in this way was purified by column chromatography (silica gel, 30% ethyl acetate/hexane). Yield: 1.2 g (80%)

Step (vii)

tert-Butyl 9-(pyridin-4-yloxy)-3-azaspiro[5.5]undecane-3-carboxylate

4-Chloropyridine hydrochloride (1.3 g) was added to sodium hydride (0.89 g) in DMSO (20 ml) and the mixture was stirred for 10 min. tert-Butyl 9-hydroxy-3-azaspiro[5.5]undecane-3-carboxylate (2.0 g) in DMSO (20 ml) was then added slowly and the mixture was stirred overnight (TLC control: conversion approx. 30-35%). A catalytic amount of sodium iodide was added and the reaction mixture was stirred at 80° C. for 8 h (TLC control). Methanol and NaHCO$_3$ solution was added to the reaction mixture and the mixture was stirred for 20 min. It was then extracted with ethyl acetate and the extract was washed again with NaHCO$_3$ solution and cold water. The organic phase was dried (Na$_2$SO$_4$) and concentrated in vacuo. The crude product obtained in this way was purified by column chromatography (silica gel, 70% ethyl acetate/hexane). Yield: 1.0 g (40%)

Step (viii)

9-Pyridin-4-yloxy-3-azaspiro[5.5]undecane dihydrochloride tert-Butyl 9-(pyridin-4-yloxy)-3-azaspiro[5.5]undecane-3-carboxylate (1 g, 2.886 mmol) was dissolved in methanol (2 ml), hydrogen chloride in methanol (1.25 mol/l, 11.5 ml) was added and the mixture was refluxed for 30 min. The solvent was removed in vacuo and the residue was dissolved in a small amount of ethanol. Acetone (approx. 25 ml) was subsequently added, the mixture was stirred at 0° C. for 30 min and the solid formed was finally filtered out with suction. Yield: 0.96 g (>99%)

Synthesis of the Amine Unit AMN-07

2-(Pyridin-4-yl)-2,9-diazaspiro[5.5]undecane dihydrochloride (AMN-07)

Step (i)

tert-Butyl 2-(pyridin-4-yl)-2,9-diazaspiro[5.5]undecane-9-carboxylate tert-Butyl 2,9-diazaspiro[5.5]undecane-9-carboxylate (1 g, 3.931 mmol), 4-chloropyridinium chloride (1.765 g, 11.794 mmol) and N-ethyl-diisopropylamine (2.7 ml, 15.724 mmol) were refluxed in 2-propanol (8 ml) for 15 h, saturated NaHCO$_3$ solution (20 ml) and ethyl acetate (8 ml) were added, the phases were separated and the aqueous phase was extracted with ethyl acetate (2×80 ml). The combined organic phases were dried over sodium sulfate and concentrated in vacuo. The crude product was purified by column chromatography (silica; ethyl acetate/methanol/ammonia (25 aq.) 100:10:0.25). Yield: 0.67 g (51.4%)

Step (ii)

2-(Pyridin-4-yl)-2,9-diazaspiro[5.5]undecane dihydrochloride

Hydrogen chloride in methanol (1.25 mol/l, 15.9 ml) was added to tert-butyl 2-(pyridin-4-yl)-2,9-diazaspiro[5.5]undecane-9-carboxylate (0.66 g, 1.991 mmol) and the mixture was refluxed for 2 h. The solvent was removed in vacuo, the residue was taken up in ethanol (5 ml) and the mixture was cooled. Acetone (20 ml) was added and the mixture was stirred at 0° C. for 30 min. Diethyl ether (50 ml) was added and the precipitate was filtered out with suction, washed with diethyl ether and dried in vacuo. Yield: 0.42 g (69%)

Synthesis of the Amine Unit AMN-08

7-(Pyridin-4-yl)-2,7-diazaspiro[3.5]nonane dihydrochloride (AMN-08)

The synthesis was carried out analogously to the synthesis of amine AMN-07. For this, in step (i) tert-butyl 2,7-diazaspiro[3.5]nonane-2-carboxylate was reacted with 4-chloropyridinium chloride and in step (ii) the Boc protective group was split off in order to obtain the amine AMN-08.

Synthesis of the Amine Unit AMN-09

3-(1-Methylpiperidin-4-yl)-3,9-diazaspiro[5.5]undecane trihydrochloride (AMN-09)

The synthesis was carried out analogously to the synthesis of amine AMN-04. For this, in step (i) tert-butyl 3,9-diazaspiro[5.5]undecane-3-carboxylate was reacted with 1-methylpiperidin-4-one and in step (ii) the Boc protective group was split off in order to obtain the amine AMN-08.

Synthesis of the Amine Unit AMN-10

(4-Methylpiperazin-1-yl)(3-azaspiro[5.5]undecan-9-yl)methanone hydrochloride (AMN-10)

Step (i)

tert-Butyl 9-(4-methylpiperazine-1-carbonyl)-3-azaspiro[5.5]undecane-3-carboxylate O-(1H-Benzotriazol-1-yl)-N,N,N',N'-tetramethyluronium tetrafluoroborate (0.32 g, 1 eq.) and 1-hydroxybenzotriazole hydrate (0.14 g, 1 eq.) were added to a solution of 3-(tert-butoxycarbonyl)-3-azaspiro[5.5]undecane-9-carboxylic acid (commercially obtainable from Anthem, Order No. A1106) (0.3 g, 1 eq.) in tetrahydrofuran (20 ml) and the reaction mixture was stirred at room temperature for 0.5 h. 1-Methylpiperazine (0.11 ml, 1 eq.) and N-ethyl-diisopropylamine (0.17 ml, 1 eq.) were then added and the mixture was stirred at room temperature overnight. For working up, the reaction mixture was concentrated, methylene chloride and sat. NaHCO$_3$ solution were added to the residue and the aqueous phase was extracted with methylene chloride a further 2×. The combined organic phases were washed 1× with sat. NaCl solution, dried over sodium sulfate, filtered and concentrated. The crude product was purified by column chromatography (silica; ethyl acetate/ethanol/ammonia (25% aq.) 10:1:0.05) in order to obtain the desired product (AMN-10). Yield: 0.22 g (101%)

Step (ii)

(4-Methylpiperazin-1-yl)(3-azaspiro[5.5]undecan-9-yl)methanone hydrochloride

Ethanol (3 ml) and acetyl chloride (0.24 ml, 3.43 mmol) were added to tert-butyl 9-(4-methylpiperazine-1-carbonyl)-3-azaspiro[5.5]undecane-3-carboxylate (0.26 g, 0.685 mmol) and the mixture was stirred at room temperature for 12 h. When the reaction was complete, the solvent was removed in vacuo. Yield: 0.22 g (101%)

Synthesis of the Amine Unit AMN-12

3-((1-Methylpiperidin-4-yl)methyl)-3,9-diazaspiro[5.5]undecane trihydrochloride (AMN-12)

The synthesis was carried out analogously to the synthesis of amine AMN-05. For this, in step (i) tert-butyl 3,9-diazaspiro[5.5]undecane-3-carboxylate was reacted with 1-methylpiperidine-4-carbaldehyde and in step (ii) the Boc protective group was split off in order to obtain the amine AMN-12.

Amine Unit AMN-13

1H-Spiro[furo[3,4-c]pyridine-3,4'-piperidine] (AMN-13)

The amine AMN-13 is commercially obtainable from Shanghai AOK Chem group (Order No. A3031).

Synthesis of the Amine Unit AMN-14

2-(Pyridin-4-yl)-2,8-diazaspiro[5.5]undecane trihydrochloride (AMN-14)

The synthesis was carried out analogously to the synthesis of amine AMN-07. For this, in step (i) tert-butyl 2,8-diazaspiro[5.5]undecane-2-carboxylate was reacted with 4-chloropyridinium chloride (yield: 66%). The Boc protective group was then split off. In step (ii), ethanol (8 ml) and acetyl chloride (0.45 ml, 6.335 mmol) were added to tert-butyl 8-(pyridin-4-yl)-2,8-diazaspiro[5.5]undecane-2-carboxylate (0.42 g, 1.267 mmol) and the mixture was stirred at room temperature for 12 h. When the reaction was complete, the solvent was removed in vacuo. Yield: 0.39 g (90%)

Synthesis of the Amine Unit AMN-15

7-(Pyridin-4-yl)-2,7-diazaspiro[4.5]decane trihydrochloride (AMN-15)

The synthesis was carried out analogously to the synthesis of amine AMN-07. For this, in step (i) tert-butyl 2,7-diazaspiro[4.5]decane-2-carboxylate was reacted with 4-chloropyridinium chloride (yield: 53%). The Boc protective group was then split off. In step (ii), ethanol (8 ml) and acetyl chloride (0.37 ml, 5.355 mmol) were added to tert-butyl 7-(pyridin-4-yl)-2,7-diazaspiro[4.5]decane-2-carboxylate (0.34 g, 1.071 mmol) and the mixture was stirred at room temperature for 12 h. When the reaction was complete, the solvent was removed in vacuo. Yield: 0.28 g (80%)

Synthesis of the Amine Unit AMN-16

2-(Pyridin-4-yl)-2,7-diazaspiro[4.5]decane trihydrochloride (AMN-16)

The synthesis was carried out analogously to the synthesis of amine AMN-07. For this, in step (i) tert-butyl 2,7-diazaspiro[4.5]decane-7-carboxylate was reacted with 4-chloropyridinium chloride (yield: 41%). The Boc protective group was then split off. In step (ii), ethanol (6 ml) and acetyl chloride (0.27 ml, 3.94 mmol) were added to tert-butyl 2-(pyridin-4-yl)-2,7-diazaspiro[4.5]decane-7-carboxylate (0.25 g, 0.788 mmol) and the mixture was stirred at room temperature for 12 h. When the reaction was complete, the solvent was removed in vacuo. Yield: 0.23 g (89%).

Synthesis of the Amine Unit AMN-17

9-(4-tert-Butylpiperazin-1-yl)-3-azaspiro[5.5]undecane trihydrochloride (AMN-17)

Step (i)

tert-Butyl 9-(4-tert-butylpiperazin-1-yl)-3-azaspiro[5.5]undecane-3-carboxylate 1-tert-Butylpiperazine (0.21 g, 1.49 mmol) was added to tert-butyl 9-oxo-3-azaspiro[5.5]undecane-3-carboxylate (see product of step (v) of the synthesis of amine AMN-06) (0.4 g, 1.49 mmol) and triethylamine (0.52 ml, 3.74 mmol) in methylene chloride (9.6 ml). The mixture was stirred for 5 min and sodium triacetoxyborohydride (0.44 g, 2.09 mmol) was then added and the mixture was stirred at room temperature overnight. Sat. NaHCO$_3$ solution was added and, after separation of the phases, the organic phase was washed with sat. NaCl solution (2×), dried over sodium sulfate and concentrated in vacuo. Yield: 0.27 g (45%)

Step (ii)

9-(4-tert-Butylpiperazin-1-yl)-3-azaspiro[5.5]undecane trihydrochloride

Hydrogen chloride in methanol (1.25 mol/l, 5.3 ml) was added to tert-butyl 9-(4-tert-butylpiperazin-1-yl)-3-azaspiro[5.5]undecane-3-carboxylate (0.26 g, 0.661 mmol) and the mixture was refluxed for 1 h. The solvent was removed in vacuo, the residue was taken up in ethanol (10 ml) and the mixture was stirred for 15 min. Diethyl ether (50 ml) was added and the mixture was then stirred at room temperature. The precipitate was filtered out with suction, washed with diethyl ether and dried in vacuo. Yield: 0.23 g (86%)

Synthesis of the Amine Unit AMN-18

Pyrrolidin-1-yl(3-azaspiro[5.5]undecan-9-yl)methanone hydrochloride (AMN-18)

Step (i)

tert-Butyl 9-(pyrrolidine-1-carbonyl)-3-azaspiro[5.5]undecane-3-carboxylate

N-Ethyl-diisopropylamine (4 eq.) was added to a solution of 3-(tert-butoxycarbonyl)-3-azaspiro[5.5]undecane-9-carboxylic acid (commercially obtainable from Anthem, Order No. A1106) (0.35 g, 1.18 mmol, 1 eq.) in methylene chloride. The reaction mixture was cooled to 0° C. and N-ethyl-N'-3-(dimethylamino)-propyl-carbodiimide hydrochloride (1.2 eq.) and 1-hydroxybenzotriazole hydrate (0.2 eq.) were then added. The mixture was stirred at this temperature for 15 min, before the amine (1.1 eq.) was finally added. The reaction mixture was then stirred at room temperature overnight. For working up, the reaction mixture was washed in each case 1× with 10% strength $NH_4Cl$ solution, sat. $NaHCO_3$ solution and sat. NaCl solution. The organic phase was dried over sodium sulfate, filtered and concentrated. The crude product was purified by column chromatography (silica; ethyl acetate/ethanol) in order to obtain the desired product. Yield: 0.23 g (56%)

Step (ii)

Pyrrolidin-1-yl(3-azaspiro[5.5]undecan-9-yl)methanone hydrochloride

Ethanol (4 ml) and acetyl chloride (0.23 ml, 0.66 mmol) were added to tert-butyl 9-(pyrrolidine-1-carbonyl)-3-azaspiro[5.5]undecane-3-carboxylate (0.25 g, 0.788 mmol) and the mixture was stirred at room temperature for 12 h. When the reaction was complete, the solvent was removed in vacuo. Yield: 0.18 g (96%)

Synthesis of the Amine Unit AMN-19

2-(Pyrrolidin-1-yl)-1-(2,8-diazaspiro[4.5]decan-8-yl)ethanone hydrochloride (AMN-19)

The synthesis was carried out analogously to the synthesis of amine AMN-18. For this, in step (i) tert-butyl 2,8-diazaspiro[4.5]decane-2-carboxylate was reacted with 2-(pyrrolidin-1-yl)acetic acid and in step (ii) the Boc protective group was split off in order to obtain the amine AMN-19.

Synthesis of the Amine Unit AMN-20

8-(Pyridin-2-yl)-2,8-diazaspiro[4.5]decane (AMN-20)

Step 1 tert-Butyl 8-(pyridin-2-yl)-2,8-diazaspiro[4.5]decane-2-carboxylate

Sodium t-butylate (5.4 mmol, 3.0 eq.) was added to a stirred mixture of tert-butyl 2,8-diazaspiro[4.5]decane-2-carboxylate (1.8 mmol, 1.0 eq.) and 2-bromopyridine (1.8 mmol, 1.0 eq.) in toluene (30 ml) and the reaction mixture was degassed with $N_2$ for 15-20 min. BINAP (0.108 mmol, 0.06 eq.) and $Pd(OAc)_2$ (0.036 mmol, 0.02 eq.) were added and the reaction mixture obtained is heated at 120° C. for 12 h. The reaction mixture was filtered over Celite and the filtrate was concentrated in vacuo in order to obtain the crude product, which was purified by column chromatography (silica gel, 30% ethyl acetate in hexane). Yield: 69%

Step 2

8-(Pyridin-2-yl)-2,8-diazaspiro[4.5]decane

TFA (1 ml) was added to a solution of tert-butyl 8-(pyridin-2-yl)-2,8-diazaspiro[4.5]decane-2-carboxylate (0.47 mmol, 1.0 eq.) in methylene chloride (3 ml) at 0° C. and the reaction mixture was stirred at 25° C. for 1 h. When the reaction was complete (TLC), the solvent was removed in vacuo in order to obtain the desired amine (AMN-20).

Synthesis of the Amine Unit AMN-21

8-(4-Chlorophenyl)-2,8-diazaspiro[4.5]decane (AMN-21)

Step 1 tert-Butyl 8-(4-chlorophenyl)-2,8-diazaspiro[4.5]decane-2-carboxylate

Sodium t-butylate (4.99 mmol, 3.0 eq.) was added to a stirred solution of tert-butyl 2,8-diazaspiro[4.5]decane-2-carboxylate (1.66 mmol, 1.0 eq.) and 1-chloro-4-iodobenzene (1.66 mmol, 1.0 eq.) in toluene (12 ml) and the reaction mixture was degassed with $N_2$. BINAP (0.099 mmol, 0.06 eq.) and $Pd(OAc)_2$ (0.03 mmol, 0.02 eq.) were added and the reaction mixture obtained was heated at 120° C. for 12 h. The reaction mixture was filtered over Celite and the filtrate was concentrated in vacuo in order to obtain the crude product, which was purified by column chromatography (silica gel, 10% ethyl acetate in hexane), so that the desired product was achieved. Yield: 50%

Step 2 tert-Butyl 8-(4-chlorophenyl)-2,8-diazaspiro[4.5]decane-2-carboxylate

TFA (1 ml) was added to a solution of tert-butyl 8-(4-chlorophenyl)-2,8-diazaspiro[4.5]decane-2-carboxylate (0.47 mmol, 1.0 eq.) in methylene chloride (3 ml) at 0° C. and the reaction mixture was stirred at 25° C. for 1 h. When the reaction was complete, the solvent was removed in vacuo in order to obtain the desired amine (AMN-21).

Synthesis of the Amine Unit AMN-22

8-(4-Fluorophenyl)-2,8-diazaspiro[4.5]decane (AMN-22)

Step 1 tert-Butyl 8-(4-fluorophenyl)-2,8-diazaspiro[4.5] decane-2-carboxylate

Sodium t-butylate (6.24 mmol, 3.0 eq.) was added to a stirred solution of tert-butyl 2,8-diazaspiro[4.5]decane-2-carboxylate (2.08 mmol, 1.0 eq.) and 1-bromo-4-fluorobenzene (2.08 mmol, 1.0 eq.) in toluene (15 ml) and the reaction mixture was degassed with $N_2$. BINAP (0.12 mmol, 0.06 eq.) and Pd(OAc)$_2$ (0.04 mmol, 0.02 eq.) were added and the reaction mixture obtained was heated at 120° C. for 12 h. The reaction mixture was filtered over Celite and the filtrate was concentrated in vacuo in order to obtain the crude product, which was purified by column chromatography (silica gel, 12% ethyl acetate in hexane), so that the desired product was achieved. Yield: 28%

Step 2

8-(4-Fluorophenyl)-2,8-diazaspiro[4.5]decane

TFA (0.6 ml) was added to a cooled (0° C.) solution of tert-butyl 8-(4-fluorophenyl)-2,8-diazaspiro[4.5]decane-2-carboxylate (0.31 mmol, 1.0 eq.) in methylene chloride (2 ml) and the reaction mixture was stirred at 25° C. for 1 h. When the reaction was complete, the solvent was removed in vacuo in order to obtain the desired amine (AMN-22).

Synthesis of the Amine Unit AMN-23

8-(4-(Trifluoromethyl)phenyl)-2,8-diazaspiro[4.5] decane (AMN-23)

Step 1 tert-Butyl 8-(4-(trifluoromethyl)phenyl)-2,8-diazaspiro[4.5]decane-2-carboxylate Sodium t-butylate (6.24 mmol, 3.0 eq.) was added to a stirred mixture of tert-butyl 2,8-diazaspiro[4.5]decane-2-carboxylate (2.08 mmol, 1.0 eq.) and 1-bromo-4-(trifluoromethyl)benzene (2.08 mmol, 1.0 eq.) in toluene (15 ml) and the reaction mixture was degassed with $N_2$. BINAP (0.12 mmol, 0.06 eq.) and Pd(OAc)$_2$ (0.04 mmol, 0.02 eq.) were added and the reaction mixture obtained was heated at 120° C. for 12 h. The reaction mixture was filtered over Celite and the filtrate was concentrated in vacuo in order to obtain the crude product, which was purified by column chromatography (silica gel, 10% ethyl acetate in hexane), so that the desired product was achieved. Yield: 37%

Step 2

8-(4-(Trifluoromethyl)phenyl)-2,8-diazaspiro[4.5] decane

TFA (1 ml) was added to a cooled (0° C.) solution of tert-butyl 8-(4-(trifluoromethyl)phenyl)-2,8-diazaspiro[4.5] decane-2-carboxylate (0.47 mmol, 1.0 eq.) in methylene chloride (3 ml) and the reaction mixture was stirred at 25° C. for 1 h. When the reaction was complete, the solvent was removed in vacuo in order to obtain the desired amine (AMN-23).

Synthesis of the Amine Unit AMN-24

8-(Pyridin-3-yl)-2,8-diazaspiro[4.5]decane (AMN-24)

Step 1 tert-Butyl 8-(pyridin-3-yl)-2,8-diazaspiro[4.5]decane-2-carboxylate

Sodium t-butylate (5.4 mmol, 3.0 eq.) was added to a stirred solution of tert-butyl 2,8-diazaspiro[4.5]decane-2-carboxylate (1.8 mmol, 1.0 eq.) and 3-bromopyridine (1.8 mmol, 1.0 eq.) in toluene (30 ml) and the reaction mixture was degassed with $N_2$. BINAP (0.108 mmol, 0.06 eq.) and Pd(OAc)$_2$ (0.036 mmol, 0.02 eq.) were added and the reaction mixture obtained was heated at 120° C. for 12 h. The reaction mixture was filtered over Celite and the filtrate was concentrated in vacuo. The crude product was purified by column chromatography (silica gel, 30% ethyl acetate in hexane) in order to obtain the desired product. Yield: 69%

Step 2

8-(Pyridin-3-yl)-2,8-diazaspiro[4.5]decane

TFA (2 ml) was added to a solution of tert-butyl 8-(pyridine-3-yl)-2,8-diazaspiro[4.5]decane-2-carboxylate (1.14 mmol, 1.0 eq.) in methylene chloride (6 ml) at 0° C. and the reaction mixture was stirred at 25° C. for 2 h. When the reaction was complete, the solvent was concentrated in vacuo in order to obtain the desired amine (AMN-24).

Synthesis of the Amine Unit AMN-25

8-(Pyrimidin-2-yl)-2,8-diazaspiro[4.5]decane (AMN-25)

Step 1 tert-Butyl 8-(pyrimidin-2-yl)-2,8-diazaspiro[4.5] decane-2-carboxylate

A stirred mixture of tert-butyl 2,8-diazaspiro[4.5]decane-2-carboxylate (0.2 mmol, 1 eq.), 2-chloropyrimidine (0.4 mmol, 2 eq.), DIPEA (2 eq.), DMA (2 eq.) in 1,4-dioxane (0.5 ml) was subjected to microwave radiation in a 10 ml pressure tube at 120° C. for 30 min. After concentration, the crude product was purified by column chromatography (silica gel, 20% ethyl acetate in hexane) in order to obtain the desired product. Yield: 51%

Step 2

8-(Pyrimidin-2-yl)-2,8-diazaspiro[4.5]decane

TFA (1 ml) is added to a solution of tert-butyl 8-(pyrimidin-2-yl)-2,8-diazaspiro[4.5]decane-2-carboxylate (0.53 mmol, 1.0 eq.) in methylene chloride (5 ml) at 0° C. and the reaction mixture is stirred at 25° C. for 1 h. When the reaction was complete, the solvent was removed in vacuo in order to obtain the desired amine (AMN-25).

Synthesis of the Amine Unit AMN-26

8-(2-(Trifluoromethyl)pyridin-4-yl)-2,8-diazaspiro[4.5]decane (AMN-26)

Step 1 tert-Butyl 8-(2-(trifluoromethyl)pyridin-4-yl)-2,8-diazaspiro[4.5]decane-2-carboxylate Sodium t-Butylate (6.24 mmol, 3.0 eq.) was added to a stirred solution of tert-butyl 2,8-diazaspiro[4.5]decane-2-carboxylate (2.08 mmol, 1.0 eq.) and 4-bromo-2-(trifluoromethyl)pyridine (2.08 mmol, 1.0 eq.) in toluene (15 ml) and the reaction mixture was then degassed with $N_2$. BINAP (0.12 mmol, 0.06 eq.) and Pd(OAc)$_2$ (0.04 mmol, 0.02 eq.) were added and the reaction mixture obtained was heated at 120° C. for 12 h. The reaction mixture was filtered over Celite and the filtrate was concentrated in vacuo in order to obtain the crude product, which was purified by column chromatography (silica gel, 2% methanol in methylene chloride), in order to obtain the desired product. Yield: 62%

Step 2

8-(2-(Trifluoromethyl)pyridin-4-yl)-2,8-diazaspiro[4.5]decane

TFA (1.5 ml) is added to a solution of tert-butyl 8-(2-(trifluoromethyl)pyridin-4-yl)-2,8-diazaspiro[4.5]decane-2-carboxylate (0.64 mmol, 1.0 eq.) in methylene chloride (5 ml) at 0° C. and the reaction mixture is stirred at 25° C. for 1 h. When the reaction was complete, the solvent was removed in vacuo in order to obtain the desired amine (AMN-26).

Synthesis of the Amine Unit AMN-27

4-(2,8-Diazaspiro[4.5]decan-8-yl)-8-(trifluoromethyl)quinoline (AMN-27)

Step 1 tert-Butyl 8-(8-(trifluoromethyl)quinolin-4-yl)-2,8-diazaspiro[4.5]decane-2-carboxylate A mixture of tert-butyl 2,8-diazaspiro[4.5]decane-2-carboxylate (2.5 mmol, 1.0 eq.) and 4-bromo-8-(trifluoromethyl)quinoline (2.5 mmol, 1.0 eq.) and $^t$BuONa (7.5 mmol, 3.0 eq.) in toluene (12 ml) was degassed with argon for 10 min. BINAP (0.15 mmol, 0.06 eq.) and Pd(OAc)$_2$ (0.05 mmol, 0.02 eq.) were added and the reaction mixture obtained was heated under reflux for 14 h. The reaction mixture was filtered over Celite and the filtrate was concentrated in vacuo in order to obtain the crude product, which was purified by column chromatography (silica gel, 22-25% ethyl acetate in hexane), in order to obtain the desired product. Yield: 40%

Step 2

4-(2,8-Diazaspiro[4.5]decan-8-yl)-8-(trifluoromethyl)quinoline

TFA (1 ml) was added to a cooled (0° C.) solution of tert-butyl 8-(8-(trifluoromethyl)quinolin-4-yl)-2,8-diazaspiro[4.5]decane-2-carboxylate (0.69 mmol, 1.0 eq.) in methylene chloride (4 ml) and the reaction mixture was stirred at 25° C. for 2 h. When the reaction was complete, the solvent was removed in vacuo in order to obtain the desired amine (AMN-27).

Synthesis of the Amine Unit AMN-28

8-(5-(Trifluoromethyl)pyridin-2-yl)-2,8-diazaspiro[4.5]decane (A-28)

Step 1 tert-Butyl 8-(5-(trifluoromethyl)pyridin-2-yl)-2,8-diazaspiro[4.5]decane-2-carboxylate A mixture of tert-butyl 2,8-diazaspiro[4.5]decane-2-carboxylate (2.5 mmol, 1.0 eq.) and 2-bromo-5-(trifluoromethyl)pyridine (2.5 mmol, 1.0 eq.) and $^t$BuONa (7.5 mmol, 3.0 eq.) in toluene (12 ml) was degassed with argon for 10 min. BINAP (0.15 mmol, 0.06 eq.) and Pd(OAc)$_2$ (0.05 mmol, 0.02 eq.) were added and the reaction mixture obtained was heated under reflux for 14 h. The reaction mixture was filtered over Celite and the filtrate was concentrated in vacuo in order to obtain the crude product, which was purified by column chromatography (silica gel, 22-25% ethyl acetate in hexane), in order to obtain the desired product. Yield: 40%

Step 2

8-(5-(Trifluoromethyl)pyridin-2-yl)-2,8-diazaspiro[4.5]decane

TFA (1 ml) was added to a cooled (0° C.) solution of tert-butyl 8-(5-(trifluoromethyl)pyridin-4-yl)-2,8-diazaspiro[4.5]decane-2-carboxylate (0.69 mmol, 1.0 eq.) in methylene chloride (4 ml) and the reaction mixture was stirred at 25° C. for 2 h. When the reaction was complete, the solvent was concentrated in vacuo in order to obtain the desired amine (AMN-28) solid.

Synthesis of the Amine Unit AMN-29

6-(2,8-Diazaspiro[4.5]decan-8-yl)isoquinoline trifluoroacetate (A-29)

Step 1 tert-Butyl 8-(isoquinolin-6-yl)-2,8-diazaspiro[4.5]decane-2-carboxylate

Sodium t-butylate (6.24 mmol, 3.0 eq.) was added to a solution of tert-butyl 2,8-diazaspiro[4.5]decane-2-carboxylate (2.08 mmol, 1.0 eq.) and 6-bromoisoquinoline (2.08 mmol, 1.0 eq.) in toluene (10 ml) and the reaction mixture was degassed with $N_2$. BINAP (0.124 mmol, 0.06 eq.) and Pd acetate (0.04 mmol, 0.02 eq.) were added and the mixture was heated at 120° C. for 12 h. The reaction mixture was filtered over Celite and the filtrate was concentrated on a rotary evaporator. The crude product was purified by means of column chromatography (silica gel, 5% methanol in methylene chloride) in order to obtain the desired product. Yield: 52%

Step 2

6-(2,8-Diazaspiro[4.5]decan-8-yl)isoquinoline trifluoroacetate

TFA (2 ml) was added to a cooled (0° C.) solution of tert-butyl 8-(isoquinolin-6-yl)-2,8-diazaspiro[4.5]decane-2- carboxylate (0.544 mmol, 1.0 eq.) in methylene chloride (10 ml) and the reaction mixture was stirred at room temperature for 1 h. When the reaction was complete, the solvent was removed on a rotary evaporator. The crude product was employed directly in the next step.

Synthesis of the Amine Unit AMN-30

8-(2-(Trifluoromethyl)pyrimidin-4-yl)-2,8-diazaspiro[4.5]decane trifluoroacetate (A-30)

Step 1

4-Chloro-2-(trifluoromethyl)pyrimidine

N,N-Dimethylaniline (6.06 mmol. 2.3 eq.) was added dropwise to a stirring solution of 2-(trifluoromethyl)pyrimidin-4-ol (2.72 mmol, 1 eq.) in POCl₃ (4 ml) and the reaction mixture was stirred at 110° C. for 2 h. The reaction mixture was concentrated and the brown liquid was diluted with cold water (50 ml) and rendered basic with saturated sodium carbonate solution (50 ml). The mixture was extracted with methylene chloride (3×100 ml) and the combined organic phases were washed with water (2×50 ml) and sat. NaCl solution (50 ml) and dried over sodium sulfate. After concentration on a rotary evaporator, a blue liquid remained, which was employed in the next step without purification.

Step 2 tert-Butyl 8-(2-(trifluoromethyl)pyrimidin-4-yl)-2,8-diazaspiro[4.5]decane-2-carboxylate 4-Chloro-2-(trifluoromethyl)pyrimidine (2.72 mmol, 1 eq.) and isopropanol (4 ml) were introduced into a microwave vessel. tert-Butyl 2,8-diazaspiro[4.5]decane-2-carboxylate (2.72 mmol, 1 eq.) and DIPEA (0.6 ml, 6.8 mmol), 2.5 eq.) were added in succession and the reaction mixture was introduced into a microwave oven at 75° C. for 45 min. After TLC control, the reaction mixture was concentrated on a rotary evaporator. A reddish liquid remained and was diluted with methylene chloride (200 ml). The organic phase was washed with water (2×100 ml) and sat. NaCl solution (50 ml), dried over sodium sulfate and concentrated. The brown liquid residue was purified by column chromatography (silica gel, ethyl acetate). Yield: 47%

Step 3

8-(2-(Trifluoromethyl)pyridimin-4-yl)-2,8-diazaspiro[4.5]decane trifluoroacetate TFA (3.19 ml, 41.45 mmol) was added to a cooled (0° C.) solution of tert-butyl 8-(2-(trifluoromethyl)pyrimidin-4-yl)-2,8-diazaspiro[4.5]decane-2-carboxylate (400 mg, 1.03 mmol, 1.0 eq.) in methylene chloride (15 ml) and the reaction mixture was stirred at room temperature for 1 h. When the reaction was complete, the solvent was removed on a rotary evaporator. The crude product was employed directly in the next step. Crude weight: 570 mg Synthesis of the Amine Unit AMN-31

N—((R)-Quinuclidin-3-yl)-3-azaspiro[5.5]undecane-9-carboxamide hydrochloride (AMN-31)

Step 1 tert-Butyl 9-((R)-quinuclidin-3-ylcarbamoyl)-3-azaspiro[5.5]undecane-3-carboxylate N-Ethyl-diisopropylamine (4 eq.) was added to an ice-cold solution of 3-(tert-butoxycarbonyl)-3-azospiro[5.5]undecane-9-carboxylic acid (1.009 mmol, 1 eq.) in methylene chloride. The reaction mixture was cooled to 0° C. and N-ethyl-N'-3-(dimethylamino)-propyl-carbodiimide hydrochloride (1.2 eq.) and 1-hydroxybenzotriazole hydrate (0.2 eq.) were then added. The mixture was stirred at this temperature for 15 min, before (R)-quinuclidin-3-amine dihydrochloride (1.1 eq.) was finally added. The reaction mixture was stirred at room temperature overnight. The mixture was diluted with ethyl acetate and the organic phase was washed with 10% NH₄Cl solution, sat. NaHCO₃ solution and sat. NaCl solution. The organic phase was dried over sodium sulfate, filtered and concentrated. The crude product was purified by column chromatography (silica, ethyl acetate/ethanol/ammonia (25% aq) 100:10:1) to obtain the desired product. Yield: 27%

Step 2

N—((R)-Quinuclidin-3-yl)-3-azaspiro[5.5]undecane-9-carboxamide hydrochloride (AMN-31)

Acetyl chloride (5 eq.) was added to an ice-cold solution of 9-((R)-quinuclidin-3-ylcarbamoyl)-3-azaspiro[5.5]undecane-3-carboxylate (0.271 mmol, 1 eq.) in ethanol. The reaction mixture was stirred at room temperature overnight. The solvent was removed in vacuo and the residue dissolved in acetone/ethanol (1:3, 3 ml) and diethyl ether (20 ml) was added. The white solid was filtered out, washed with diethyl ether and dried in vacuo. Yield: 86%

Synthesis of the Amine Unit AMN-32

7-(3-Azaspiro[5.5]undecan-9-yl)-5,6,7,8-tetrahydro-[1,2,4]triazolo[1,5-a]pyrazine dihydrochloride (AMN-32)

Step 1 tert-Butyl 9-(5,6-dihydro-[1,2,4]triazolo[1,5-a]pyrazin-7(8H)-yl)-3-azaspiro[5.5]undecane-3-carboxylate Acetic acid (2.34 eq.) was added to a solution of tert-butyl 9-oxo-3-azaspiro[5.5]undecane-3-carboxylate (1.122 mmol, 1 eq.) and 5,6,7,8-tetrahydro-[1,2,4]triazolo[1,5-a]pyrazine (1.14 eq.) in methylene chloride (7 ml). Sodium triacetoxyborhydride (1.4 eq) was then added and the mixture was stirred at room temperature overnight. The reaction mixture was diluted with methylene chloride and sat. NaHCO₃ solution. The aqueous phase was washed with methylene chloride (2×20 ml), and the combined organic phases were dried over Na₂SO₄ and concentrated in vacuo. The crude product was purified by column chromatography (silica, ethyl acetate/ethanol 10:1) to obtain the desired product. Yield: 62%

Step 2

7-(3-Azaspiro[5.5]undecan-9-yl)-5,6,7,8-tetrahydro-[1,2,4]triazolo[1,5-a]pyrazine dihydrochloride (AMN-32)

Acetyl chloride (5 eq.) was added to an ice-cold solution of tert-butyl 9-(5,6-dihydro-[1,2,4]triazolo[1,5-a]pyrazin-7(8H)-yl)-3-azaspiro[5.5]undecane-3-carboxylate (0.666 mmol, 1 eq.) in ethanol (5 ml). The reaction mixture was stirred at room temperature for overnight. The white solid was filtered out, washed with diethyl ether and dried in vacuo. Yield: 91%

Synthesis of the Amine Unit AMN-33

2-(Pyridin-4-yl)-2,8-diazaspiro[4.5]decane dihydrochloride (AMN-33)

Step 1: tert-Butyl 2-(pyridin-4-yl)-2,8-diazaspiro[4.5]decane-8-carboxylate

A mixture of tert-butyl 2,8-diazaspiro[4.5]decane-8-carboxylate (10.402 mmol, 1.0 eq.), N-ethyl-diisopropylamine (4.0 eq.) and 4-chloropyridine hydrochloride (3.0 eq.) in 2-propanol (20 ml) was stirred at 90° C. overnight. Ethyl acetate and sat. NaHCO₃ solution were added and the aqueous phase was extracted with ethyl acetate a further 4×. The combined organic phases were washed 1× with sat. NaCl solution, dried over magnesium sulfate, filtered and concentrated in vacuo. The crude product was purified by column chromatography (silica, ethyl acetate/ethanol/ammonia (25% aq) 500:100:2). Yield: 45%

Step 2

2-(Pyridin-4-yl)-2,8-diazaspiro[4.5]decane dihydrochloride (AMN-33)

Acetyl chloride (5 eq.) was added to an ice-cold solution of tert-butyl 2-(pyridin-4-yl)-2,8-diazaspiro[4.5]decane-8-carboxylate (3.78 mmol, 1 eq.) in ethanol (14 ml). The reaction mixture was stirred at room temperature overnight. The solvent was concentrated in vacuo and the residue was dissolved in ethanol/acetone (2:1, 30 ml). The white solid which precipitated was filtered out, washed with diethyl ether and dried in vacuo. Yield: 98%

Synthesis of the Amine Unit AMN-34

N—((S)-Quinuclidin-3-yl)-3-azaspiro[5.5]undecane-9-carboxamide hydrochloride (AMN-34)

Synthesis of this amine was carried out in analogy to Amine AMN-31 employing (S)-quinuclidin-3-amine dihydrochloride as the amine starting material. Step 1—yield: 54%; Step 2-yield: 81%

Synthesis of the Amine Unit AMN-35

(5,6-Dihydro-[1,2,4]triazolo[1,5-a]pyrazin-7(8H)-yl)(3-azaspiro[5.5]undecan-9-yl)methanone hydrochloride (AMN-35)

Synthesis of this amine was carried out in analogy to Amine AMN-31 employing 5,6,7,8-tetrahydro-[1,2,4]triazolo[1,5-a]pyrazine as the amine starting material. Step 1—yield: 69%; Step 2—yield: 93%

Synthesis of the Amine Unit AMN-36

8-(2,6-Dimethylpyridin-4-yl)-2,8-diazaspiro[4.5]decane hydrochloride (AMN-36)

Synthesis of this amine was carried out in analogy to Amine AMN-33 employing tert-butyl 2,8-diazaspiro[4.5]decane-2-carboxylate (1 eq.) and 4-chloro-2-methylpyridine (3 eq.) as starting materials. In step 1 the number of equivalents of N-ethyl-diisopropylamine was adjusted to 3. Step 1—yield: 50%; Step 2—yield: 68%

Synthesis of the Amine Unit AMN-37

8-(2-Methylpyridin-4-yl)-2,8-diazaspiro[4.5]decane dihydrochloride (AMN-37)

Synthesis of this amine was carried out in analogy to Amine AMN-33 employing tert-butyl 2,8-diazaspiro[4.5]decane-2-carboxylate (1 eq.) and 4-chloro-2-methylpyridine (5 eq.) as starting materials. In step 1 the number of equivalents of N-ethyl-diisopropylamine was adjusted to 5 and the reaction mixture was stirred at 90° C. for 48 h. Step 1—yield: 87%; Step 2—yield: >99%

Synthesis of the Amine Unit AMN-38

9-(2-(1H-Imidazol-1-yl)ethoxy)-3-azaspiro[5.5]undecane (AMN-38)

Step 1

1-tert-Butyl 4-ethyl piperidine-1,4-dicarboxylate

Di-tert-butyldicarbonate (95.39 mmol, 1.5 eq.) was added to a stirred solution of ethyl piperidine-4-carboxylate (63.7 mmol, 1.0 eq.) and Et₃N (127.40 mmol, 2.0 eq.) in MC (200 ml) at 0° C. The mixture was then stirred at 25° C. for 16 h. It was diluted with MC (100 ml) and washed with water (100 ml) and brine (100 ml). The organic layer was dried over sodium sulfate and concentrated under reduced pressure to give the desired product which was employed in the next step without further purification. Yield: 93%

Step-2 tert-Butyl 4-(hydroxymethyl)piperidine-1-carboxylate

A solution of 1-tert-butyl 4-ethyl piperidine-1,4-dicarboxylate (60.0 mmol, 1.0 eq.) in dry THF (80 ml) was added dropwise to a suspension of LAH (90.0 mmol, 1.5 eq.) in THF (120 ml) at 0° C. After addition of the reagent was completed the reaction mixture was stirred at 25° C. for 1 h. The reaction mixture was quenched by very slow addition of a mixture of THF-water (9:1, 36 ml) and 10% NaOH solution (7.2 ml). The mixture was then filtered through celite and filtrate was concentrated to yield the desired product as a white solid which was used in the next step without further purification. Yield: 77%

Step-3 tert-Butyl 4-formylpiperidine-1-carboxylate

A mixture of dry DMSO (223.26 mmol, 4.0 eq.) and dry methylene chlloride (100 ml) was added dropwise to a solution of oxalyl chloride (111.63 mmol, 2.0 eq.) in dry methylene chloride (100 ml) at −78° C. A solution of tert-butyl 4-(hydroxymethyl)piperidine-1-carboxylate (55.81 mmol, 1.0 eq.) in dry methylene chloride (100 ml) was added dropwise to the reaction mixture at same temperature and it was then stirred for 30 min. $Et_3N$ (279.07 mmol, 5.0 eq.) was added at −78° C. and the reaction mixture allowed to slowly warm to 25° C. and stir for another 30 min. The reaction mixture was quenched with saturated ammonium chloride solution (200 ml), diluted with methylene chloride (100 ml) and the layers were separated. The organic layer was washed with brine (200 ml) and dried over sodium sulfate. The solvent was evaporated under reduced pressure to give the crude desired product as light orange oil which is used in the next step without purification. Yield: 95%

Step-4 tert-Butyl 9-oxo-3-azaspiro[5.5]undec-7-ene-3-carboxylate

3 N KOH in ethanol (7.5 ml) was added to mixture of tert-butyl 4-formylpiperidine-1-carboxylate (60.0 mmol, 1.0 eq.) and methyl vinyl ketone (70.0 mmol, 1.3 eq.) in THF (100 ml) at 0° C. and the mixture was then stirred at 25° C. for 16 h. The solvent was evaporated under reduced pressure and the residue diluted with water (100 ml) and $KHSO_4$ solution at 0° C. The aqueous layer was extracted with MC (2×150 ml). The combined organic layers were washed with brine (100 ml) and dried over sodium sulfate. The solvent was evaporated under reduced pressure and the crude product was purified by silica gel column chromatography eluting with 10-12% ethyl acetate in hexanes to give the desired product as a light brown sticky solid. Yield: 25%

Step-5 tert-Butyl 9-oxo-3-azaspiro[5.5]undecane-3-carboxylate

A solution of tert-butyl 9-oxo-3-azaspiro[5.5]undec-7-ene-3-carboxylate (15.09 mmol, 1.0 eq.) in MeOH (40 ml) was degassed with argon for 15 min and then Pd—C (1.0 g) was added. The reaction mixture was stirred under $H_2$ balloon pressure at 25° C. for 16 h. The mixture was filtered through celite and filtrate concentrated to give the desired product as a light yellow sticky solid. Yield: >99%

Step-6 tert-Butyl 9-hydroxy-3-azaspiro[5.5]undecane-3-carboxylate $NaBH_4$ (56.18 mmol, 3.0 eq.) was added portionwise to a stirred solution of tert-butyl 9-oxo-3-azaspiro[5.5]undecane-3-carboxylate (18.72 mmol, 1.0 eq.) in MeOH (40 ml) at 0° C. and the resulting reaction mixture was stirred at 25° C. for 1 h. The solvent was evaporated under reduced pressure. The residue was dissolved in MC (100 ml) and washed with water (50 ml) and brine (50 ml). The organic layer was dried over sodium sulfate and concentrated under reduced pressure to give the crude product which was used in the next step without further purification. Yield: 95%

Step-7 tert-Butyl 9-(allyloxy)-3-azaspiro[5.5]undecane-3-carboxylate

KOH (257.46 mmol, 21.0 eq.), allyl bromide (36.8 mmol, 3.0 eq.) and 18-crown-6 (4.9 mmol, 0.4 eq.) were added to a solution of tert-butyl 9-hydroxy-3-azaspiro[5.5]undecane-3-carboxylate (12.26 mmol, 1.0 eq.) in toluene (65 ml) at 0° C. and then reaction mixture was heated at reflux for 1 h. Then the reaction mixture was diluted with ethyl acetate (150 ml) and washed with water (150 ml) and brine (150 ml). The organic layer was dried over sodium sulfate and concentrated under reduced pressure to yield the crude product which was purified by silica gel column chromatography eluting with 10% ethyl acetate in hexanes to afford the desired product as a yellow oil. Yield: 92%

Step-8 tert-Butyl 9-(2-oxoethoxy)-3-azaspiro[5.5]undecane-3-carboxylate $O_3$ gas was passed through a stirred solution of tert-butyl 9-(allyloxy)-3-azaspiro[5.5]undecane-3-carboxylate (6.47 mmol, 1.0 eq.) in MeOH (40 ml) for 45 min at −78° C. Dimethylsulfide (77.64 mmol, 12.0 eq.) was added dropwise to the reaction mixture at 0° C. and it was stirred for 30 min at 25° C. The reaction mixture was concentrated under reduced pressure to yield the crude product as a light yellow oil which was used in next step without further purification. Yield: 99%

Step-9 tert-Butyl 9-(2-hydroxyethoxy)-3-azaspiro[5.5]undecane-3-carboxylate $NaBH_4$ (13.46 mmol, 2.0 eq.) was added portion wise to a stirred solution of tert-butyl 9-(2-oxoethoxy)-3-azaspiro[5.5] undecane-3-carboxylate (6.73 mmol, 1.0 eq.) in MeOH (65 ml) at 0° C. and the resulting reaction mixture was stirred at 25° C. for 16 h. The solvent was evaporated under reduced pressure. The residue was dissolved in ethyl acetate (300 ml) and washed with water (200 ml) and brine (200 ml). The organic layer was dried over sodium sulfate and concentrated under reduced pressure to give the crude product. The crude product was purified by silica gel column chromatography eluting with 20% ethyl acetate in hexanes to give the desired product as a yellow sticky solid. Yield: 40%

Step-10 tert-Butyl 9-(2-(methylsulfonyloxy)ethoxy)-3-azaspiro[5.5]undecane-3-carboxylate Methanesulfonyl chloride (5.43 mmol, 2.0 eq.) was added dropwise to a stirred solution of tert-butyl 9-(2-hydroxyethoxy)-3-azaspiro[5.5]undecane-3-carboxylate (2.71 mmol, 1.0 eq.) and $Et_3N$ (9.485 mmol, 3.5 eq.) in MC (30 ml) at 0° C. and the resulting reaction mixture was stirred at 25° C. for 3 h. The reaction mixture was diluted with MC (150 ml), washed with water (100 ml) and brine (100 ml) and dried over sodium sulfate. The solvent was evaporated under reduce pressure to give the crude product as a yellow sticky solid which was used in the next step reaction without further purification. Yield: 99%

Step-11 tert-butyl 9-(2-(1H-imidazol-1-yl)ethoxy)-3-azaspiro[5.5]undecane-3-carboxylate A solution of tert-butyl 9-(2-(methylsulfonyloxy)ethoxy)-3-azaspiro[5.5]undecane-3-carboxylate (2.68 mmol, 1.0 eq.) in DMF (10 ml) was added dropwise to a stirred mixture of NaH (8.04 mmol, 3.0 eq.) and imidazole (5.36 mmol, 2.0 eq.) in DMF (15 ml) at 0° C. and the resulting mixture was stirred at 25° C. for 16 h. The reaction mixture was diluted with ethyl acetate (300 ml) and washed with water (200 ml) and brine (200 ml). The organic layer was dried over sodium sulfate and concentrated under reduce pressure to give the crude product which was purified by silica gel column chromatography eluting with 2% MeOH in MC to afford the desired product as a yellow oil. Yield: 84%

Step-12

9-(2-(1H-Imidazol-1-yl)ethoxy)-3-azaspiro[5.5]undecane (AMN-38)

TFA (6.25 ml) was added to a solution of tert-butyl 9-(2-(1H-imidazol-1-yl)ethoxy)-3-azaspiro[5.5]undecane-3-carboxylate (2.28 mmol, 1.0 eq.) in MC (25 ml) at 0° C. and the mixture was stirred at 25° C. for 2 h. The reaction mixture was concentrated under reduced pressure and the residue was azeotroped with MC to give the crude product which was used in the next step without further purification.

Synthesis of the Amine Unit AMN-39

8-(Pyridin-4-yl)-2-azaspiro[4.5]decan-8-ol (AMN-39)

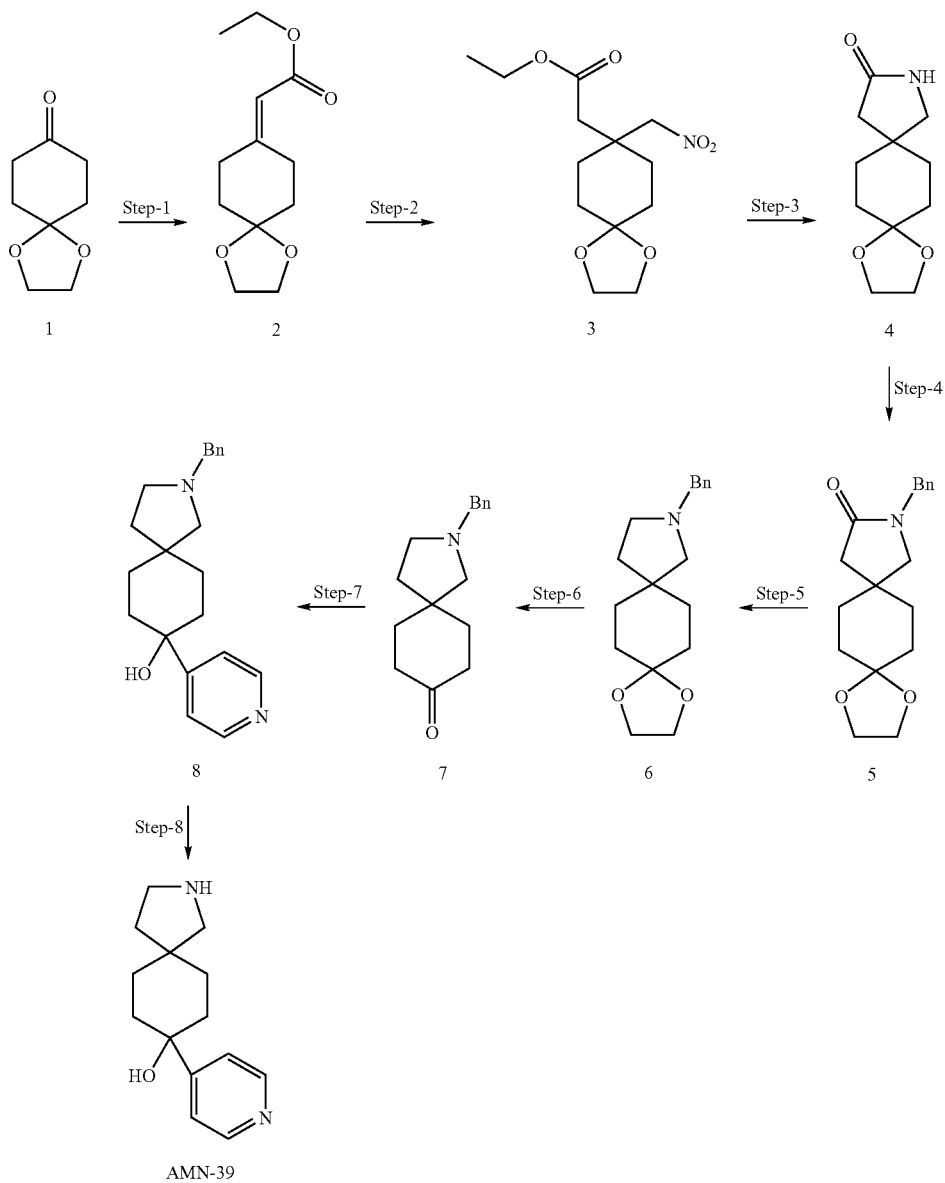

AMN-39

Step-1

Ethyl 2-(1,4-dioxaspiro[4.5]decan-8-ylidene)acetate

A solution of compound 1 (10.05 g, 64.04 mmol, 1.0 eq.) in THF (30 ml) was added dropwise to a suspension NaH (1.84 g, 76.85 mmol, 1.2 eq.) in THF (90 ml) at 0° C. and the mixture was stirred at same temperature for 1 h. Triethyl phosphonoacetate (16.5 ml, 83.25 mmol, 1.3 eq.) was added to the reaction mixture at −20° C. and the reaction mixture was allowed to warm to RT and stir for 2 h. The reaction mixture was diluted with ethyl acetate (100 ml), washed with water (2×100 ml) and the organic layer dried over sodium sulfate. The solvent was evaporated under reduced pressure to obtain the crude product which was purified by column chromatography (silica gel; 5% ethyl acetate/hexanes) to yield compound 2. Yield: 94% (17.28 g, 60.2 mmol).

Step-2

Ethyl 2-(8-(nitromethyl)-1,4-dioxaspiro[4.5]decan-8-yl)acetate

Nitromethane (5.665 g, 98.81 mmol, 1.5 eq.) was added to a solution of compound 2 (14.0 g, 61.87 mmol, 1.0 eq.) in dry THF (68 ml) at RT followed by addition of a 1M solution of TBAF (68 ml, 68.07 mmol, 1.1 eq.) in THF, which was added dropwise at the same temperature. The reaction mixture was heated to reflux for 20 h. After completion of the reaction (monitored by TLC), the reaction mixture was diluted with water (100 ml) and extracted with diethyl ether (3×100 ml). The combined organic layers were washed with sat. $KHSO_4$ solution (2×100 ml) and dried over sodium sulfate. The solvent was evaporated under reduced pressure to obtain the crude product which was purified by column chromatography (silica gel; 5-15% ethyl acetate/hexanes) to yield compound 3. Yield: 65% (11.5 g, 40.07 mmol).

Step-3

1,4-Dioxa-10-azadispiro[4.2.4^{8}.2^{5}]tetradecan-11-one

A solution of compound 3 (11.5 g, 40.07 mmol, 1.0 eq.) in EtOH (200 ml) was degassed with argon for 20 min followed by addition of Raney nickel (10.0 g). The reaction mixture was stirred under $H_2$ balloon pressure for 2 d. After completion of the reaction (monitored by TLC), the mixture was filtered through celite and the filtrate was concentrated to give the crude product which was purified by column chromatography (silica gel; 30% ethyl acetate/hexanes) to yield compound 4. Yield: 70% (5.9 g, 27.96 mmol).

Step-4

10-Benzyl-1,4-dioxa-10-azadispiro[4.2.4^{8}.2^{5}]tetradecan-11-one

NaH 60% in mineral oil (1.67 g, 41.63 mmol, 1.2 eq.) was added portionwise to a stirred solution of compound 4 (7.37 g, 34.88 mmol, 1.0 eq.) in THF (150 ml) at 0° C. and the reaction mixture was stirred at RT for 30 min. Benzyl bromide (7.16 g, 41.86 mmol, 1.2 eq.) was then added dropwise to the reaction mixture at 0° C. and the mixture was stirred at RT for 18 h. The reaction mixture was diluted with water (100 ml) and ethyl acetate (200 ml) and the layers were separated. The organic layer was washed with brine (2×100 ml) and dried over sodium sulfate. The solvent was evaporated under reduced pressure to give the crude product which was purified by column chromatography (silica gel; 10-15% ethyl acetate/hexanes) to yield compound 5. Yield: 76% (8.0 g, 26.58 mmol).

Step-5

10-Benzyl-1,4-dioxa-10-azadispiro[4.2.4^{8}.2^{5}]tetradecane

A solution of compound 5 (12.0 g, 39.8 mmol, 1.0 eq.) in dry THF (200 ml) was added dropwise to a stirred suspension of LAH (2.27 g, 59.8 mmol, 1.5 eq.) in THF (200 ml) at 0° C. and reaction mixture is stirred at RT for 5 h. The reaction mixture was quenched with THF: $H_2O$ (9:1, 30 ml) and 15% NaOH (2.5 ml) with cooling and stirred at RT for 1 h. Reaction mixture is filtered through celite and filtrate is concentrated under reduced pressure to get desired compound 6 which was used in the next step without further purification. Yield: 91% (10.40 g, 36.24 mmol).

Step-6

2-Benzyl-2-azaspiro[4.5]decan-8-one

2N HCl (15 ml) was added to a solution of compound 6 (10.4 g, 36.24 mmol, 1.0) in MeOH (350 ml) and the mixture was stirred at RT for 24 h. After completion of the reaction (monitored by LCMS), the solvent was evaporated under reduced pressure. The residue was dissolved in water (200 ml), basified with sat. $NaHCO_3$ solution and extracted with ethyl acetate (2×500 ml). The organic layer was dried over sodium sulfate and evaporated to give the crude product which was purified by column chromatography (silica gel; 2% MeOH/MC) to yield compound 7. Yield: 85% (7.48 g, 30.78 mmol).

Step-7

2-Benzyl-8-(pyridin-4-yl)-2-azaspiro[4.5]decan-8-ol

A solution of 4-bromopyridine.HCl (1.8 g, 9.25 mmol, 1.25 eq.) in dry THF (20 ml) was added dropwise to a solution of n-BuLi (7.4 ml, 14.8 mmol, 2.0 eq., 2M solution in hexane) in THF (10 ml) at −78° C. and the reaction mixture was stirred at same temperature for 1 h. A solution of compound 7 (1.8 g, 7.4 mmol, 1.0 eq.) in THF (20 ml) was added dropwise at −78° C. and the reaction mixture was allowed to warm to RT in 2 h. After completion of the reaction (monitored by TLC), the reaction mixture was quenched with water (60 ml) while cooling and extracted with ethyl acetate (2×50 ml). The combined organic layers were dried over sodium sulfate and concentrated under reduced pressure to give the crude product which was purified by column chromatography (neutral alumina; 0.5% MeOH/MC) to yield compound 8 as a light yellow semisolid. Yield: 46% (1.1 g, 3.42 mmol).

Step-8

8-(Pyridin-4-yl)-2-azaspiro[4.5]decan-8-ol (AMN-39)

A solution of compound 8 (500 mg, 1.55 mmol, 1.0 eq.) in MeOH (15 ml) was degassed with argon for 15 min followed by addition of $Pd(OH)_2$ (250 mg). The reaction mixture was stirred under $H_2$ balloon pressure for 4 h. After completion of the reaction (monitored by TLC), the reaction mixture was filtered through celite and the filtrate was concentrated under reduced pressure to yield AMN-39 as a white solid which was used in the next step without further purification. Yield: 88% (320 mg, 1.38 mmol).

Synthesis of the Amine Unit AMN-41

8-(5-(Trifluoromethyl)pyrimidin-2-yl)-2,8-diazaspiro[4.5]decane (AMN-41)

Step-1 tert-Butyl 8-(5-(trifluoromethyl)pyrimidin-2-yl)-2,8-diazaspiro[4.5]decane-2-carboxylate Sodium t-butoxide (625 mg, 6.51 mmol, 3.0 eq.) was added to a stirred solution of tert-butyl 2,8-diazaspiro[4.5]decane-2-carboxylate (600 mg, 2.17 mmol, 1.0 eq.) and 2-chloro-5-(trifluoromethyl)pyrimidine (391 mg, 2.17 mmol, 1.0 eq.) in toluene (15 ml) and the reaction mixture was degassed with nitrogen. BINAP (80 mg, 0.13 mmol, 0.06 eq.) and Pd(OAc)$_2$ (10 mg, 0.04 mmol, 0.02 eq.) were added and the resulting mixture was heated at 120° C. for 16 h. The reaction mixture was filtered through celite and the filtrate was evaporated under reduced pressure to afford the crude product which was purified by column chromatography (silica gel; 0-1% MeOH/MC) to yield the pure desired product as a white solid. Yield: 41% (350 mg, 1.2 mmol).

Step-2

8-(5-(Trifluoromethyl)pyrimidin-2-yl)-2,8-diazaspiro[4.5]decane (AMN-41)

TFA (1.5 ml) was added to a solution of tert-butyl 8-(5-(trifluoromethyl)pyrimidin-2-yl)-2,8-diazaspiro[4.5]decane-2-carboxylate (300 mg, 0.78 mmol, 1.0 eq.) in methylene chloride (6 ml) at 0° C. and the reaction mixture was stirred at 25° C. for 1 h. After completion of the reaction, the solvent was evaporated under reduced pressure to give the desired product as a yellow sticky solid which was directly used in the next step.

Synthesis of the Amine Unit AMN-42

9-(1H-Imidazol-1-yl)-3-azaspiro[5.5]undecane (AMN-42)

Step-1 tert-Butyl 9-(methylsulfonyloxy)-3-azaspiro[5.5]undecane-3-carboxylate

Methanesulfonyl chloride (0.98 ml, 12.27 mmol, 1.5 eq.) was added to a solution of tert-butyl 9-hydroxy-3-azaspiro[5.5]undecane-3-carboxylate (2.20 g, 8.18 mmol, 1.0 eq.) (see step-6 product of AMN-38) and Et$_3$N (2.84 ml, 20.45 mmol, 2.5 eq.) in MC (20 ml) at 0° C. and the resulting reaction mixture was stirred at RT for 14 h. The reaction mixture was diluted with MC (50 ml) and washed with sat. NH$_4$Cl solution (2×25 ml) and brine (2×25 ml) and then dried over sodium sulfate. The solvent was removed under reduced pressure and the crude product was purified by column chromatography (silica gel; 10% ethyl acetate/hexanes) to give the desired compound as a light orange solid. Yield: 88% (2.84 g, 8.18 mmol).

Step-2 tert-Butyl 9-(1H-imidazol-1-yl)-3-azaspiro[5.5]undecane-3-carboxylate

Imidazole (1.17 g, 17.3 mmol, 3.0 eq.) was added to a stirred suspension of NaH (20.16 mmol, 3.5 eq.) in DMF (10 ml) at 0° C. and the reaction mixture was allowed to stir at the same temperature for 20 min. A solution of tert-butyl 9-(methylsulfonyloxy)-3-azaspiro[5.5]undecane-3-carboxylate (2.0 g, 5.76 mmol, 1.0 eq.) in DMF (5 ml) was added to the reaction mixture at 0° C. and it was stirred at RT for 16 h. The reaction mixture was diluted with water (50 ml) and extracted with ethyl acetate (3×50 ml). The combined organic layers were washed with brine (60 ml) and dried over sodium sulfate. The solvent was evaporated under reduced pressure to obtain the crude product which was purified by column chromatography (silica gel; 3% MeOH/MC) to yield the desired product as a colorless oil. Yield: 59% (1.10 g, 3.45 mmol).

Step-3

9-(1H-Imidazol-1-yl)-3-azaspiro[5.5]undecane (AMN-42)

TFA (2 ml) was added to a solution of tert-butyl 9-(1H-imidazol-1-yl)-3-azaspiro[5.5]undecane-3-carboxylate (1.10 g, 3.45 mmol, 1.0 eq.) in MC (10 ml) at 0° C. and the resulting reaction mixture was stirred at 25° C. for 2 h. The solvent was evaporated under reduced pressure and the residue was azeotroped twice with MC to get the desired product.

Synthesis of the Amine Unit AMN-43

8-(Pyridin-4-yl)-2-azaspiro[4.5]decane (AMN-43)

Step-1

2-Benzyl-8-(pyridin-4-yl)-2-azaspiro[4.5]dec-7-ene

To a solution of 2-benzyl-8-(pyridin-4-yl)-2-azaspiro[4.5]decan-8-ol (500 mg, 1.55 mmol, 1.0 eq.) (see step-7 product AMN-39) in pyridine (5 ml) was added dropwise SOCl$_2$ (1 ml) at −10° C. and the reaction mixture was stirred at the same temperature for 10 min. After completion of the reaction (monitored by TLC), the reaction mixture was poured onto (50 g) and sat. NaHCO$_3$ solution (10 ml) was added. The mixture was extracted with methylene chloride (50 ml). The organic layer was washed with brine (30 ml) and dried over sodium sulfate. The solvent was evaporated under reduced pressure to give the crude product which was purified by column chromatography (silica gel; 2% MeOH/DCM) to yield the desired compound as a yellow semisold. Yield: 63% (300 mg, 0.987 mmol).

Step-2

8-(Pyridin-4-yl)-2-azaspiro[4.5]decane (AMN-43)

A solution of benzyl-8-(pyridin-4-yl)-2-azaspiro[4.5]dec-7-ene (300 mg, 0.987 mmol, 1.0 eq.) in MeOH (10 ml) was degassed with argon for 15 min followed by addition of Pd(OH)$_2$ (150 mg). The reaction mixture was stirred under H$_2$ balloon pressure for 4 h. After completion of the reaction (monitored by LCMS), the reaction mixture was filtered through celite and the filtrate was concentrated under reduced pressure to yield the desired compound as an off-white solid which was used in the next step without further purification. Yield: 80% (170 mg, 0.787 mmol).

Synthesis of the Amine Unit AMN-44

8-(Pyridin-3-yl)-2-azaspiro[4.5]decane (AMN-44)

Step-1

2-Benzyl-8-(pyridin-3-yl)-2-azaspiro[4.5]decan-8-ol

A solution of 3-bromopyridine (290 µl, 2.96 mmol, 1.20 eq.) in dry THF (9 ml) was added dropwise to a solution of n-BuLi (2.47 ml, 4.94 mmol, 2.0 eq., 2M solution in hexane) in THF (9 ml) at −78° C. and the reaction mixture was stirred at same temperature for 1 h. A solution of 2-benzyl-2-azaspiro[4.5]decan-8-one (600 mg, 2.47 mmol, 1.0 eq.) (see step-6 product AMN-39) in THF (10 ml) was added dropwise at −78° C. and the reaction mixture was stirred at the same temperature for 1 h. After completion of the reaction (monitored by TLC), the reaction mixture was quenched with water (15 ml) while cooling and extracted with ethyl acetate (2×30 ml). The combined organic layers were washed with water (20 ml) and brine (20 ml), and dried over sodium sulfate. The solvent was evaporated under reduced pressure to give the crude product which was purified by column chromatography (silica gel; 10% MeOH/MC) to yield the desired compound as a light brown semi-solid. Yield: 44% (350 mg, 1.08 mmol).

Step-2

2-Benzyl-8-(pyridin-3-yl)-2-azaspiro[4.5]dec-7-ene $SOCl_2$ (1 ml) was added dropwise to a solution of 2-benzyl-8-(pyridin-3-yl)-2-azaspiro[4.5]decan-8-ol (450 mg, 1.39 mmol, 1.0 eq.) in pyridine (5 ml) at −10° C. and the reaction mixture was stirred at the same temperature for 15 min. After completion of the reaction (monitored by TLC), the reaction mixture was poured onto crushed ice and the mixture was then neutralized with sat. $NaHCO_3$ solution (15 ml). It was extracted with methylene chloride (2×30 ml) and the combined organic layers were washed with water (20 ml) and brine (20 ml), and dried over sodium sulfate. The solvent was evaporated under reduced pressure to give the crude product which was purified by column chromatography (silica gel; 10% MeOH/DCM) to yield the desired compound as a reddish sticky solid. Yield: 71% (300 mg, 0.99 mmol).

Step-3

8-(Pyridin-3-yl)-2-azaspiro[4.5]decane

A solution of 2-benzyl-8-(pyridin-3-yl)-2-azaspiro[4.5]dec-7-ene (250 mg, 0.822 mmol, 1.0 eq.) in MeOH (15 ml) was degassed with argon for 15 min, followed by addition of $Pd(OH)_2$ (125 mg, 50% by wt.). The reaction mixture was stirred under $H_2$ balloon pressure for 4.5 h at RT. After completion of the reaction (monitored by LCMS), the reaction mixture was filtered through celite and the filtrate was concentrated under reduced pressure to yield the desired compound as an off-white solid which was used in the next step without further purification. Yield: 93% (165 mg, 0.76 mmol).

Synthesis of the Amine Unit AMN-45

3-(Pyridin-4-yl)-3,9-diazaspiro[5.6]dodecane (AMN-45)

Step-1

1-Benzylazepan-4-one

To a suspension of azepan-4-one (8.0 g, 53.47 mmol, 1.0 eq.) in methylene chloride (100 ml) was added TEA followed by benzaldehyde and reaction mixture was stirred at RT for 30 min. $Na(OAc)_3BH$ was added portionwise to the reaction mixture and it was then stirred at RT for another 4 h. The reaction mixture was quenched with NaOH (2 M, 80 ml) and extracted with methylene chloride (3×100 ml). The organic layer was dried over $Na_2SO_4$ and solvent was evaporated under reduced pressure to afford the crude product which was purified by column chromatography (silica gel, 20% EtOAc/hexanes) to yield the desired product as an oil. Yield: 78% (8.5 g, 41.87 mmol).

Step-2

9-Benzyl-2,4-dioxo-3,9-diazaspiro[5.6]dodecane-1,5-dicarbonitrile

To a mixture of 1-benzylazepan-4-one (10.0 g, 49.2 mmol, 1.0 eq.) and ethyl cyanoacetate (12.2 g, 108.3 mmol, 2.2 eq.) was added $EtOH-NH_3$ (50 ml) at −10° C. and it was stirred for 30 min. Then the reaction flask was sealed and kept inside a deep refrigerator (−5 to −10° C.) for 7 d. The solvent was removed under reduced pressure and the crude solid material was washed with ether (3×100 ml) to afford the desired solid product which was used in the next step without further purification.

Step-3

2,2'-(1-Benzylazepane-4,4-diyl)diacetic acid

65% $H_2SO_4$ (17.5 ml) was added to a solid powder of 9-benzyl-2,4-dioxo-3,9-diazaspiro[5.6]dodecane-1,5-dicarbonitrile (3.5 g, 10.4 mmol) and the reaction mixture was heated at reflux for 2 h. Then the reaction mixture was cooled to RT, water (6.1 ml) was added and it was again heated at reflux for 20 h. After cooling to 0° C., the reaction mixture was first basified to pH ~10-12 using 40% NaOH solution and then acidified to pH ~2-3 using 2 N HCl solution. The solvent was removed under reduced pressure and the residue was dried by azeotropic distillation with benzene. Residual benzene was removed under reduced pressure to afford the dry solid product which was used in the next step without further purification.

Step-4

Diethyl 2,2'-(1-benzylazepane-4,4-diyl)diacetate

A mixture of 2,2'-(1-benzylazepane-4,4-diyl)diacetic acid (3.5 g, 10.4 mmol), EtOH (100 ml) and $H_2SO_4$ (5 ml) was heated at reflux for 16 h. The solvent was removed under reduced pressure and the solid material was dissolved in water (100 ml) and basified with sat $Na_2CO_3$ solution to pH ~10. The desired compound was then extracted from the mixture with ethyl acetate (3×100 ml), dried over $Na_2SO_4$ and evaporated under reduced pressure. The crude material was purified through column chromatography (silica gel, 1.5% MeOH/MC) to yield the desired product as a brown oil. Yield: 26% (1.0 g, 2.78 mmol).

Step-5

2,2'-(1-Benzylazepane-4,4-diyl)diethanol

Diethyl 2,2'-(1-benzylazepane-4,4-diyl)diacetate (1.0 g, 2.77 mmol, 1.0 eq.) in THF (10 ml) was added to a suspension of LAH (315 mg, 8.3 mmol, 3.0 eq.) in THF (40 ml) at 0° C. and the mixture was stirred at RT for 20 h. The reaction mixture was then quenched with a mixture of $H_2O$-THF (1:10, 4 ml), stirred for 15 min and filtered through celite. The filtrate was concentrated under reduced pressure and the crude product thus obtained was used in the next step without further purification.

Step-6 tert-Butyl 4,4-bis(2-hydroxyethyl)azepane-1-carboxylate

A mixture of 2,2'-(1-benzylazepane-4,4-diyl)diethanol (1.5 g, 5.4 mmol, 1.0 eq.) in methanol (30 ml) and Boc-anhydride (1.2 ml, 6.47 mmol, 1.2 eq.) was degassed with nitrogen for 30 mins. Then Pd—C (1 g) was added to the mixture and it was stirred at RT under $H_2$ balloon pressure for 16 h. After completion of the reaction (monitored by TLC) the mixture was filtered through celite and the residue washed with methanol (100 ml). The filtrate and washings were then concentrated to afford the desired compound as a brown sticky compound. Yield: 52% (800 mg, 2.78 mmol).

Step-7 tert-Butyl 4,4-bis(2-(methylsulfonyloxy)ethyl) azepane-1-carboxylate

TEA (1.1 ml, 8.36 mmol, 3.0 eq.) was added to a cooled solution of tert-butyl 4,4-bis(2-hydroxyethyl)azepane-1-carboxylate (800 mg, 2.78 mmol, 1.0 eq.) in methylene chloride (10 ml) at 0° C. and then mesylchloride (0.47 ml, 6.13 mmol, 2.2 eq.) was added to the reaction mixture and it was stirred at RT for 2 h. After completion (monitored by TLC), the reaction mixture was diluted with water (20 ml) and methylene chloride (100 ml). The organic part was separated and the water layer was extracted with methylene chloride (2×20 ml). The combined organic layers were washed with brine (20 ml), dried over $Na_2SO_4$ and concentrated under reduced pressure to give the crude product which was used in the next step without further purification.

Step-8 tert-Butyl 3,9-diazaspiro[5.6]dodecane-9-carboxylate

A mixture of tert-butyl 4,4-bis(2-(methylsulfonyloxy) ethyl)azepane-1-carboxylate (500 mg, 1.12 mmol), MeOH (2 ml) and $NH_3$ solution (1.5 ml) was heated at 50° C. in a sealed tube for 16 h. The reaction mixture was concentrated under reduced pressure and the crude material was washed with hexanes and dried to afford the desired compound as a yellowish semi-solid which was used in the next step without further purification.

Step-9 tert-Btyl 3-(pyridin-4-yl)-3,9-diazaspiro[5.6]dodecane-9-carboxylate

A mixture of tert-butyl 3,9-diazaspiro[5.6]dodecane-9-carboxylate (300 mg, 1.1 mmol, 1.0 eq.), 4-bromo pyridine (260 mg, 1.34 mmol, 1.2 eq.) and DIPEA (0.2 ml, 1.49 mmol, 2.0 eq.) in n-butanol (4 ml) was heated at reflux for 48 h. After completion (monitored by LCMS) the reaction mixture was concentrated and the crude product was purified by column chromatography (alumina, 5% MeOH/MC) to yield the pure product as an off-white solid. Yield: 52% (200 mg, 0.579 mmol).

Step-10

3-(Pyridin-4-yl)-3,9-diazaspiro[5.6]dodecane (AMN-45)

TFA (1.0 ml) was added to a solution of tert-butyl 3-(pyridin-4-yl)-3,9-diazaspiro[5.6]dodecane-9-carboxylate (250 mg, 0.724 mmol) in methylene chloride (3 ml) at 0° C. and the resulting reaction mixture was stirred at RT for 2 h. The solvent was evaporated under reduced pressure and the residue was azeotroped with toluene to give the desired product which was used in the next step without further purification.

Synthesis of the Amine Unit AMN-46

4-(2,8-Diazaspiro[4.5]decan-8-yl)benzonitrile (AMN-46)

Step-I tert-Butyl 8-(4-cyanophenyl)-2,8-diazaspiro[4.5] decane-2-carboxylate

Cesium carbonate (1.35 g, 4.16 mmol, 2.0 eq.) was added to a stirred solution of tert-butyl 2,8-diazaspiro[4.5]decane-2-carboxylate (500 mg, 2.08 mmol, 1.0 eq.) and 4-chlorobenzonitrile (390 mg, 2.08 mmol, 1.0 eq.) in toluene (30 ml) and the reaction mixture was degassed with nitrogen for 15 min. BINAP (52 mg, 0.083 mmol, 0.04 eq.) and $Pd(OAc)_2$ (10 mg, 0.0416 mmol, 0.02 eq.) were added and the resulting reaction mixture was heated at reflux for 16 h. The reaction mixture was filtered through celite and the filtrate was evaporated under reduced pressure to afford the crude product which was purified by column chromatography (silica gel; 15-20% EtOAc hexanes) to yield the pure product as an oil. Yield: 49% (350 mg, 1.026 mmol).

Step-II

-(2,8-Diazaspiro[4.5]decan-8-yl)benzonitrile (AMN-46)

TFA (2.5 ml) was added to a solution of tert-butyl 8-(4-cyanophenyl)-2,8-diazaspiro[4.5]decane-2-carboxylate (350 mg, 1.026 mmol, 1.0 equiv.) in methylene chloride (6 ml) at 0° C. and the reaction mixture was stirred at RT for 1 h. After completion of the reaction, the solvent was evaporated under reduced pressure to give the desired product as a yellow sticky solid which was used in the next step without further purification.

Synthesis of the Amine Unit AMN-47

8-(4-Methoxyphenyl)-2,8-diazaspiro[4.5]decane (AMN-47)

Step-I tert-Butyl 8-(4-methoxyphenyl)-2,8-diazaspiro[4.5]decane-2-carboxylate Sodium t-butoxide (599 mg, 6.24 mmol, 3.0 eq.) was added to a stirred solution of tert-butyl 2,8-diazaspiro[4.5]decane-2-carboxylate (500 mg, 2.08 mmol, 1.0 eq.) and 1-chloro-4-methoxybenzene (389 mg, 2.08 mmol, 1.0 eq.) in toluene (25 ml) and the reaction mixture was degassed with Nitrogen. BINAP (51.8 mg, 0.083 mmol, 0.04 eq.) and Pd(OAc)$_2$ (10 mg, 0.0416 mmol, 0.02 equiv) were added and the resulting mixture was heated at reflux for 16 h. The reaction mixture was filtered through celite and the filtrate was evaporated under reduced pressure to afford the crude product which was purified by column chromatography (silica gel; 0-10% EtOAc/hexanes) to give the pure product as an oil. Yield: 35% (250 mg, 0.722 mmol).

Step-II 8-(4-Methoxyphenyl)-2,8-diazaspiro[4.5]decane (AMN-47)

TFA (1.2 ml) was added to a solution of tert-butyl 8-(4-methoxyphenyl)-2,8-diazaspiro[4.5]decane-2-carboxylate (200 mg, 0.57 mmol, 1.0 eq.) in methylene chloride (5 ml) at 0° C. and the reaction mixture was stirred at RT for 1 h. After completion of the reaction, the solvent was evaporated under reduced pressure to give the desired product as a yellow sticky solid which was used in the next step without further purification.

C. Syntheses of Individual Substances

General Method for Synthesis of the dihydroindene Derivatives (H)

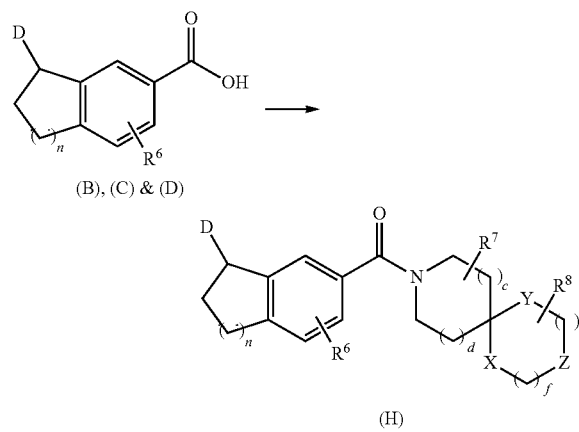

1) Synthesis of the dihydroindene Derivatives I

General Working Instructions 1 (GWI-1)

1-Hydroxybenzotriazole hydrate (0.3 eq.) and N-ethyl-diisopropylamine (4 eq.) were added to a solution of (G) (1.5 eq.) in methylene chloride. The reaction mixture was cooled to 0° C. and 1-(3-dimethylaminopropyl)-3-ethylcarbodiimide hydrochloride (1.5 eq.) was then added. The mixture was stirred at this temperature for 15 min, before the amine (1 eq.) was finally added. The reaction mixture was then stirred at room temperature overnight. For working up, the reaction mixture was washed 3× with 0.5 M KOH solution and the organic phase was dried over MgSO$_4$, filtered and concentrated. The crude product was either purified by column chromatography (silica; methylene chloride/methanol or aluminium oxide; methylene chloride/methanol) or recrystallized from methylene chloride to obtain the product (H) in a pure form.

General Working Instructions 2 (GWI-2):

O-(1H-Benzotriazol-1-yl)-N,N,N',N'-tetramethyluronium tetrafluoroborate (1 eq.) and 1-hydroxybenzotriazole hydrate (1 eq.) were added to a solution of (G) (1 eq.) in tetrahydrofuran and the reaction mixture was stirred at room temperature for 0.5 h. The amine (0.9 eq.) and N-ethyl-diisopropylamine (2.5 eq.) were then added and the mixture was stirred at room temperature overnight. For working up, the reaction mixture was concentrated, methylene chloride and sat. NaHCO$_3$ solution were added to the residue and the aqueous phase was extracted with methylene chloride a further 2×. The combined organic phases were washed with sat. NaCl solution a further 1×, dried over Na$_2$SO$_4$, filtered and concentrated. The crude product was purified by column chromatography (silica; ethyl acetate/methanol/NH$_3$ 10:1:0.05) to obtain the product (H) in a pure form.

General Working Instructions 3 (GWI-3):

1,1'-Carbonyldiimidazole (2 eq.) was added to a solution of (G) (1 eq.) in methylene chloride and N,N-dimethylformamide and the reaction mixture was stirred at room temperature for 1 h. The amine (1 eq.), dissolved in methylene chloride (230 eq.), N,N-dimethylformamide (26 eq.) and N-ethyl-diisopropylamine (5 eq.), was then added and the mixture was stirred at room temperature overnight. For working up, sat. NaHCO$_3$ solution was added to the reaction mixture and the mixture was stirred for 15 min. The aqueous phase was extracted with methylene chloride a further 1×. The combined organic phases were concentrated. The crude product was purified via HPLC to obtain the product (H) in a pure form.

General working instructions 4 (GWI-4): O-(7-Azabenzotriazol-1-yl)N,N,N',N'-tetramethyluronium hexafluorophosphate (1.1 eq.) and N-ethyl-diisopropylamine (2.5 eq.) were added to a solution of the corresponding carboxylic acid (1 eq.) in tetrahydrofuran at 0° C. and the reaction mixture was stirred at room temperature for 0.5 h. The corresponding amine (1 eq.) was then added and the mixture was stirred at room temperature overnight. For working up, the reaction mixture was diluted with ethyl acetate and washed with sat. NaHCO$_3$ solution, NH$_4$Cl solution, dist. water and sat. NaCl solution. The combined organic phases were dried over sodium sulfate, filtered and concentrated. The crude product was purified by column chromatography (silica; ethyl acetate/ethanol/ammonia (25% aq.) in order to obtain the product (H) in a pure form.

General working instructions 5 (GWI-5): N-Ethyl-diisopropylamine (4 eq.) was added to a solution of the corresponding carboxylic acid (1 eq.) in methylene chloride. The reaction mixture was cooled to 0° C. and N-ethyl-N'-3-(dimethylamino)-propyl-carbodiimide hydrochloride (1.2 eq.) and 1-hydroxybenzotriazole hydrate (0.2 eq.) were then added. The mixture was stirred at this temperature for 15 min, before the corresponding amine (1.1 eq.) was finally added. The reaction mixture was then stirred at room temperature overnight. For working up, the reaction mixture was washed in each case 1× with 10% strength NH₄Cl solution, sat. NaHCO₃ solution and sat. NaCl solution. The organic phase was dried over sodium sulfate, filtered and concentrated. The crude product was purified by column chromatography (silica; ethyl acetate/ethanol/ammonia (25% aq.) in order to obtain the product (H) in a pure form.

Notes:
(a) In most cases the no. of equivalents of amine was reduced slightly to 1 eq.
(b) In some cases the no. of equivalents of N-ethyl-diisopropylamine was adapted as required to between 3.0 and 5.0 eq., in most cases 4.5 eq. were employed.
(c) Typical reaction times were overnight to 2.5 d.
(d) Alternatively to drying the organic fraction after work-up over sodium sulfate magnesium sulfate was used in some cases.

General working instructions 6 (GWI-6): HATU (1.1 eq.) and DIPEA (2.5 eq.) were added to a suspension of the corresponding carboxylic acid (1.0 eq.) in THF (5 ml) at 0° C. and the reaction mixture was stirred for 15 min. A solution of the corresponding amine (1.0 eq.) in THF (1 ml) was added to the reaction mixture and the mixture was stirred at 25° C. for approx. 12 h or until the reaction was complete. The reaction mixture was diluted with methylene chloride or ethyl acetate, washed successively with NaHCO3 solution, NH₄Cl solution, water and sat. NaCl solution and dried over sodium sulfate. The solvent was removed in vacuo in order to obtain the crude material, which was purified by column chromatography (silica gel, methanol/methylene chloride) in order to obtain the final product (H).

General working instructions 7 (GWI-7): DIPEA (4.0 eq.) was added to a solution of the corresponding carboxylic acid (1.0 eq.) in CH₂Cl₂ at 0° C., followed by EDCl (1.5 eq.) and HOBT (1.0 eq.). The reaction mixture obtained was stirred at 25° C. for 15 min and then cooled again to 0° C. A solution of the corresponding amine (1.2 eq.) in CH₂Cl₂ was added to the reaction mixture and the mixture was stirred at 25° C. for approx. 16 h or until the reaction was complete. The mixture was diluted with methylene chloride and washed with sat. NH₄Cl solution, sat. NaHCO₃ solution and sat. NaCl solution. The organic phase was dried over sodium sulfate and concentrated in vacuo in order to obtain the crude product, which was purified by column chromatography (silica gel, methanol/methylene chloride) in order to obtain the final product (H).

General working instructions 8 (GWI-8): N-Ethyl-diisopropylamine (4 eq.) was added to a solution of the corresponding carboxylic acid (1 eq.) in methylene chloride. The reaction mixture was cooled to 0° C. and N-ethyl-N'-3-(dimethylamino)-propyl-carbodiimide hydrochloride (1.2 eq.) and 1-hydroxybenzotriazole hydrate (0.2 eq.) were then added. The mixture was stirred at this temperature for 15 min, before the corresponding amine (1 eq.) was added. The reaction mixture was stirred at room temperature overnight. Then, the reaction mixture was concentrated. The white residue was taken up in ethyl acetate and methylene chloride (1:1) and the mixture stirred at 50° C. for ½ h. The white solid was filtered out and dried in vacuo in order to obtain the final product (H).

Note: H-23 & H-24 & H-64 The hydrochloride was precipitated with 2 mol/l of HCl in diethyl ether.

TABLE

Synthesis of the dihydroindene derivatives (H)

| Example no. | Structure | Name |
|---|---|---|
| H-01 | 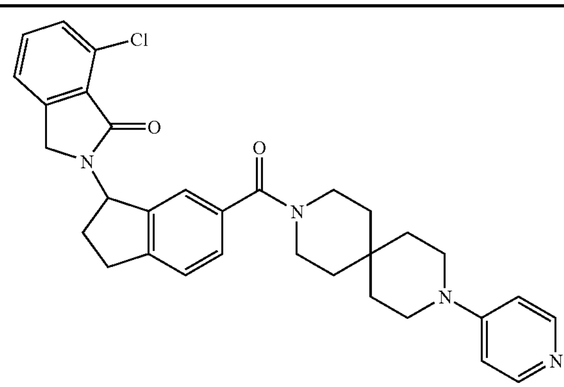 | 7-chloro-2-[6-(9-pyridin-4-yl-3,9-diazaspiro[5.5]undecane-3-carbonyl)-2,3-dihydro-1H-indan-1-yl]-2,3-dihydro-isoindol-1-one (H-01) |
| H-02 | 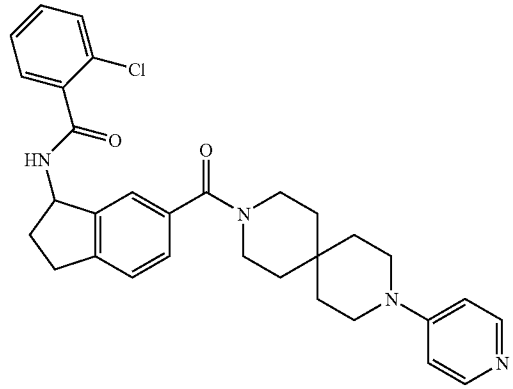 [SMILES: O=C(NC1CCc2ccc(C(=O)N3CCC4(CC3)CCN(c3ccncc3)CC4)cc21)c1ccccc1Cl] | 2-chloro-N-[6-(3-pyridin-4-yl-3,9-diazaspiro[5.5]undecane-9-carbonyl)-2,3-dihydro-1H-inden-1-yl]-benzamide (H-02) |

| | | |
|---|---|---|
| H-03 | 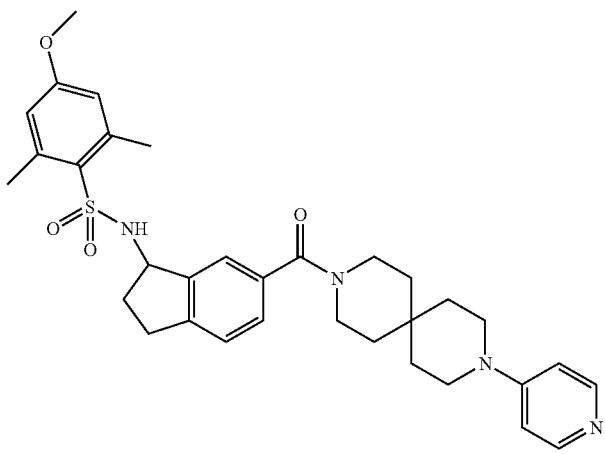 [SMILES: COc1cc(C)c(S(=O)(=O)NC2CCc3ccc(C(=O)N4CCC5(CC4)CCN(c4ccncc4)CC5)cc32)c(C)c1] | 4-methoxy-2,6-dimethyl-N-[6-(9-pyridin-4-yl-3,9-diazaspiro[5.5]undecane-3-carbonyl)-2,3-dihydro-1H-inden-1-yl)-benzenssulfonic acid amide (H-03) |
| H-04 | 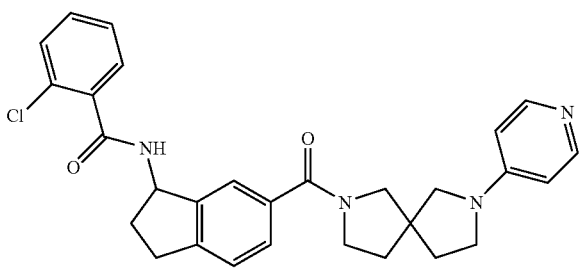 [SMILES: O=C(NC1CCc2ccc(C(=O)N3CCC4(CCN(c5ccncc5)C4)C3)cc21)c1ccccc1Cl] | 2-chloro-N-[6-(8-pyridin-4-yl-3,8-diazaspiro[4.4]nonane-3-carbonyl)-2,3-dihydro-1H-inden-1-yl]-benzamide (H-04) |
| H-05 | 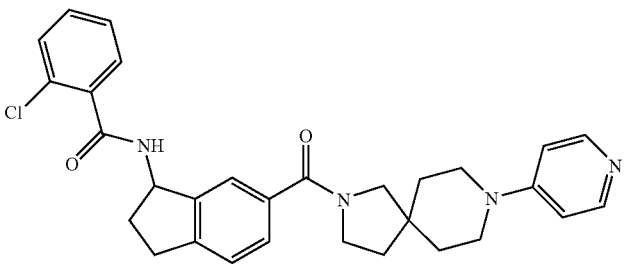 [SMILES: O=C(NC1CCc2ccc(C(=O)N3CCC4(CCN(c5ccncc5)CC4)C3)cc21)c1ccccc1Cl] | 2-chloro-N-[6-(8-pyridin-4-yl-3,8-diazaspiro[4.5]decane-3-carbonyl)-2,3-dihydro-1H-inden-1-yl]-benzamide (H-05) |
| H-06 | 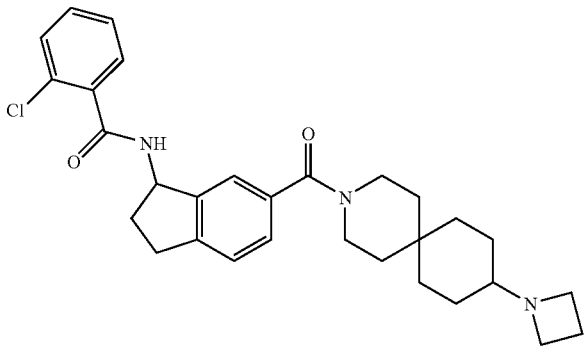 [SMILES: O=C(NC1CCc2ccc(C(=O)N3CCC4(CCC(N5CCC5)CC4)CC3)cc21)c1ccccc1Cl] | N-[6-[9-(azetidin-1-yl)-3-azaspiro[5.5]undecane-3-carbonyl)-2,3-dihydro-1H-indan-1-yl]-2-chloro-benzamide (H-06) |

| | | |
|---|---|---|
| H-07 | 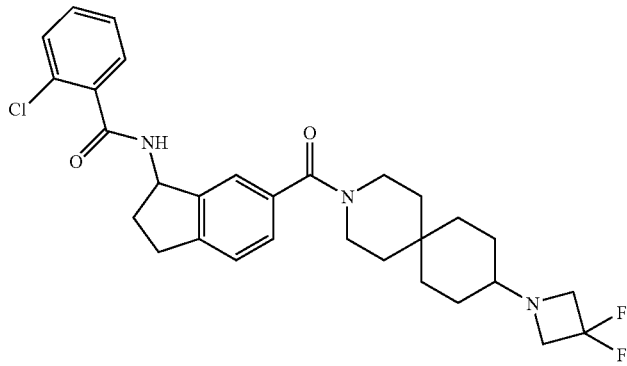 [SMILES: O=C(NC1CCc2ccc(C(=O)N3CCC4(CCC(N5CC(F)(F)C5)CC4)CC3)cc21)c1ccccc1Cl] | 2-chloro-N-[6-[9-(3,3-difluoro-azetidin-1-yl)-3-azaspiro[5.5]undecane-3-carbonyl]-2,3-dihydro-1H-inden-1-yl]-benzamide (H-07) |
| H-08 | 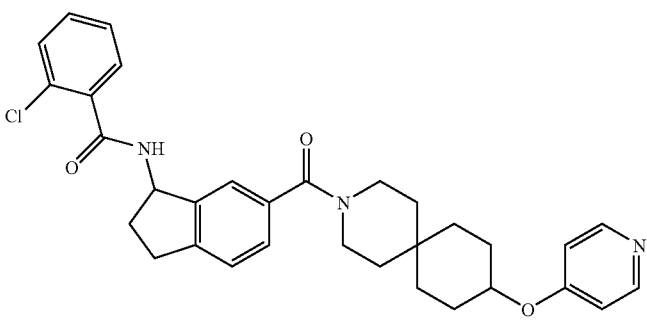 [SMILES: O=C(NC1CCc2ccc(C(=O)N3CCC4(CCC(Oc5ccncc5)CC4)CC3)cc21)c1ccccc1Cl] | 2-chloro-N-[6-(9-pyridin-4-yloxy)-3-azaspiro[5.5]undecane-3-carbonyl)-2,3-dihydro-1H-inden-1-yl]-benzamide (H-06) |
| H-09 | 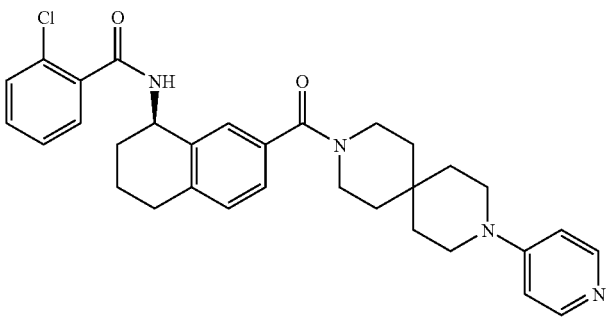 [SMILES: O=C(N[C@@H]1CCCc2ccc(C(=O)N3CCC4(CC3)CCN(c3ccncc3)CC4)cc21)c1ccccc1Cl] | 2-chloro-N-[(1R)-7-(9-pyridin-4-yl-3,9-diazaspiro[5.5]undecane-3-carbonyl)-1,2,3,4-tetrahydro-naphthalen-1-yl]-benzamide (H-09) |
| H-10 | 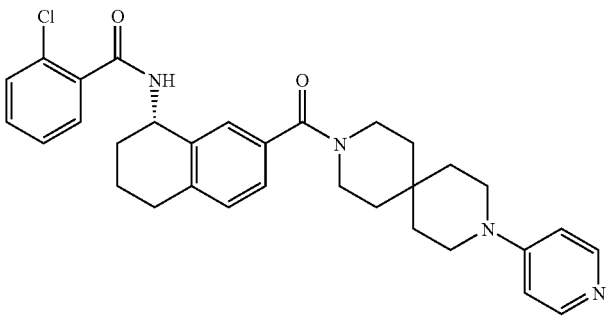 [SMILES: O=C(N[C@H]1CCCc2ccc(C(=O)N3CCC4(CC3)CCN(c3ccncc3)CC4)cc21)c1ccccc1Cl] | 2-chloro-N-[(1S)-7-(9-pyridin-4-yl-3,9-diazaspiro[5.5]undecane-3-carbonyl)-1,2,3,4-tetrahydro-naphthalen-1-yl]-benzamide (H-10) |
| H-11 | 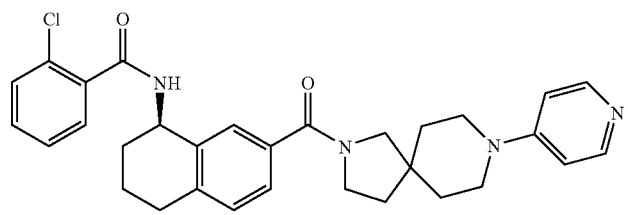 [SMILES: O=C(N[C@@H]1CCCc2ccc(C(=O)N3CCC4(CCN(c5ccncc5)CC4)C3)cc21)c1ccccc1Cl] | 2-chloro-N-[(1R)-7-(8-pyridin-4-yl-3,8-diazaspiro[4.5]decane-3-carbonyl]-1,2,3,4-tetrahydro-naphthalen-1-yl]-benzamide (H-11) |

TABLE-continued

| | | |
|---|---|---|
| H-12 | 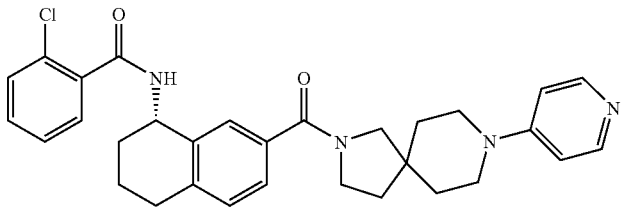 [SMILES: O=C(N[C@H]1CCCc2ccc(C(=O)N3CCC4(CCN(c5ccncc5)CC4)C3)cc21)c1ccccc1Cl] | 2-chloro-N-[(1S)-7-(8-pyridin-4-yl-3,8-diazaspiro[4.5]decane-3-carbonyl]-1,2,3,4-tetrahydro-naphthalen-1-yl]-benzamide (H-12) |
| H-13 | 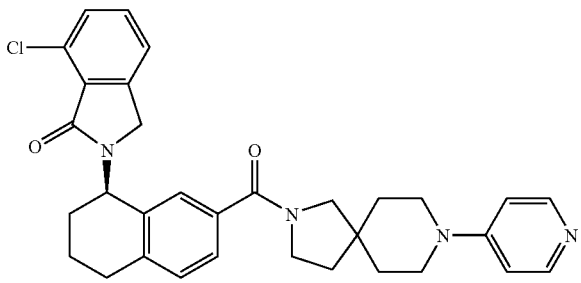 | 7-chloro-2-[(1R)-7-(8-pyridin-4-yl-3,8-diazaspiro[4.5]decane-3-carbonyl)-1,2,3,4-tetrahydro-naphthalen-1-yl]-2,3-dihydro-isoindol-1-one (H-13) |
| H-14 | 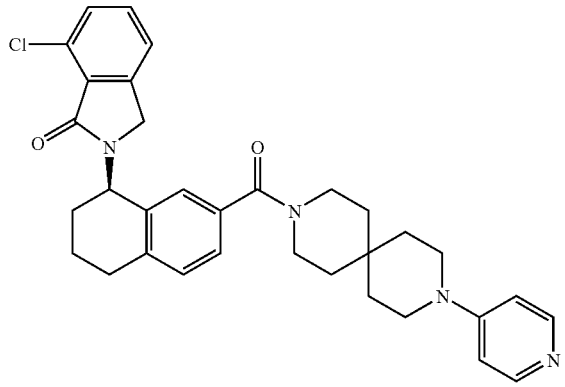 [SMILES: O=C(c1ccc2c(c1)[C@H](N1Cc3cccc(Cl)c3C1=O)CCC2)N1CCC2(CC1)CCN(c1ccncc1)CC2] | 7-chloro-2-[(1R)-7-(9-pyridin-4-yl-3,9-diazaspiro[5.5]undecane-3-carbonyl)-1,2,3,4-tetrahydro-naphthalen-1-yl]-2,3-dihydro-isoindol-1-one (H-14) |
| H-15 | 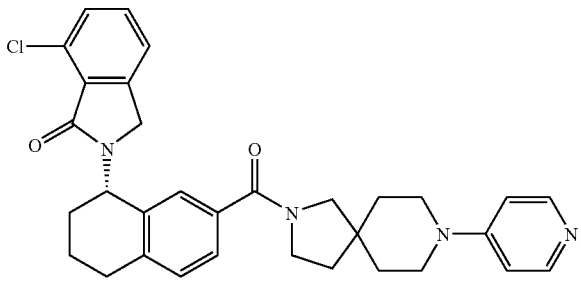 [SMILES: O=C(c1ccc2c(c1)[C@@H](N1Cc3cccc(Cl)c3C1=O)CCC2)N1CCC2(CCN(c3ccncc3)CC2)C1] | 7-chloro-2-[(1S)-7-(8-pyridin-4-yl-3,8-diazaspiro[4.5]decane-3-carbonyl)-1,2,3,4-tetrahydro-naphthalen-1-yl]-2,3-dihydro-isoindol-1-one (H-15) |
| H-16 | 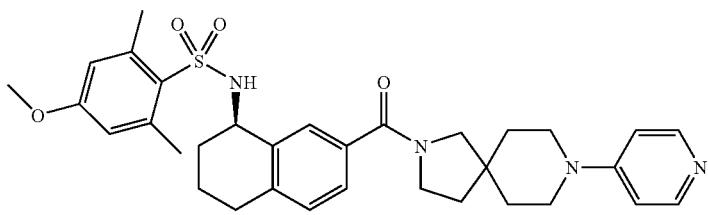 [SMILES: COc1cc(C)c(S(=O)(=O)N[C@@H]2CCCc3ccc(C(=O)N4CCC5(CCN(c6ccncc6)CC5)C4)cc32)c(C)c1] | 4-methoxy-2,6-dimehtyl-N-[(1R)-7-(8-pyridin-4-yl-3,8-diazaspiro[4.5]decane-3-carbonyl)-1,2,3,4-tetrahydro-naphthalen-1-yl]-benzenesulfonic acid amide (H-16) |

| | | |
|---|---|---|
| H-17 | 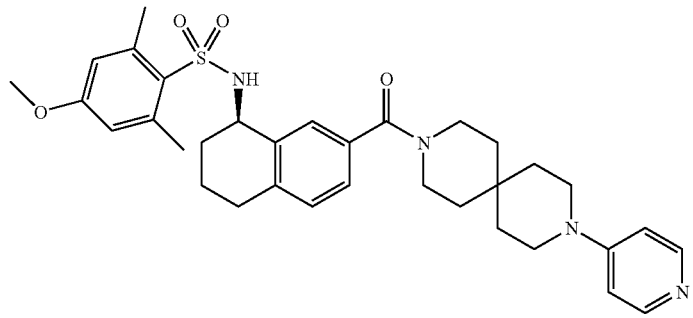 [SMILES: COc1cc(C)c(S(=O)(=O)N[C@@H]2CCCc3ccc(C(=O)N4CCC5(CC4)CCN(c4ccncc4)CC5)cc32)c(C)c1] | 4-methoxy-2,6-dimethyl-N-[(1R)-7-(9-pyridin-4-yl-3,9-diazaspiro[5.5]undecane-3-carbonyl)-1,2,3,4-tetrahydro-naphthalen-1-yl]-benzenesulfonic acid amide (H-17) |
| H-18 | 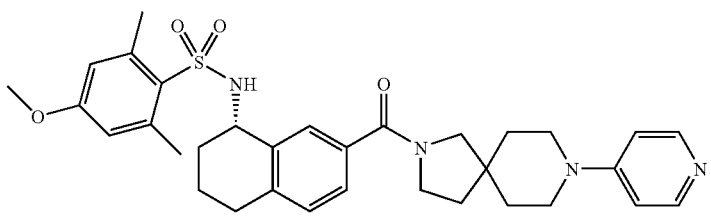 [SMILES: COc1cc(C)c(S(=O)(=O)N[C@H]2CCCc3ccc(C(=O)N4CCC5(CCN(c6ccncc6)CC5)C4)cc32)c(C)c1] | 4-methoxy-2,6-dimethyl-N-[(1S)-7-(8-pyridin-4-yl-3,8-diazaspiro[4.5]decane-3-carbonyl)-1,2,3,4-tetrahydro-naphthalen-1-yl]-benzenesulfonic acid amide (H-18) |
| H-19 | 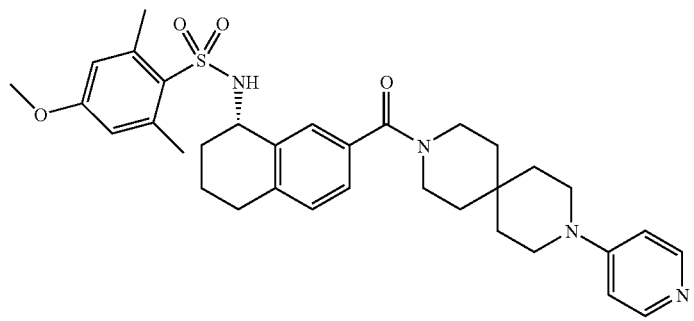 [SMILES: COc1cc(C)c(S(=O)(=O)N[C@H]2CCCc3ccc(C(=O)N4CCC5(CC4)CCN(c4ccncc4)CC5)cc32)c(C)c1] | 4-methoxy-2,6-dimethyl-N-[(1S)-7-(9-pyridin-4-yl-3,9-diazaspiro[5.5]undecane-3-carbonyl)-1,2,3,4-tetrahydro-naphthalen-1-yl]-benzenesulfonic acid amide (H-19) |
| H-20 | 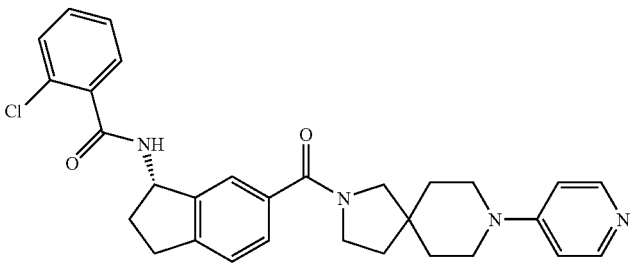 [SMILES: O=C(N[C@H]1CCc2ccc(C(=O)N3CCC4(CCN(c5ccncc5)CC4)C3)cc21)c1ccccc1Cl] | 2-chloro-N-[(1S)-6-(8-pyridin-4-yl-3,8-diazaspiro[4.5]decane-3-carbonyl)-2,3-dihydro-1H-indecn-1-yl]-benzamide (H-20) |
| H-21 | 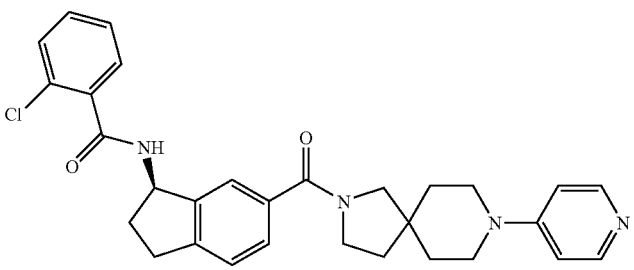 [SMILES: O=C(N[C@@H]1CCc2ccc(C(=O)N3CCC4(CCN(c5ccncc5)CC4)C3)cc21)c1ccccc1Cl] | 2-chloro-N-[(1R)-6-(8-pyridin-4-yl-3,8-diazaspiro[4.5]decane-3-carbonyl)-2,3-dihydro-1H-inden-1-yl]-benzamide (H-21) |

| | | |
|---|---|---|
| H-22 | 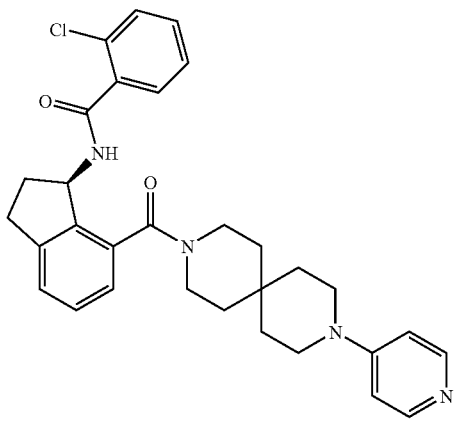 [SMILES: O=C(N[C@@H]1CCc2cccc(C(=O)N3CCC4(CC3)CCN(c3ccncc3)CC4)c21)c1ccccc1Cl] | 2-chloro-N-[(1R)-7-(9-pyridin-4-yl-3,9-diazaspiro[5.5]undecane-3-carbonyl)-2,3-dihydro-1H-inden-1-yl]-benzamide (H-22) |
| H-23 | 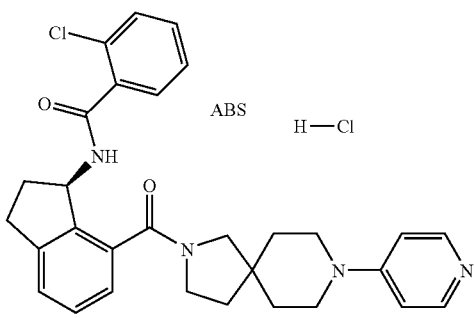 [SMILES: O=C(N[C@@H]1CCc2cccc(C(=O)N3CCC4(CCN(c5ccncc5)CC4)C3)c21)c1ccccc1Cl ; Cl] | 2-chloro-N-[(1S)-7-(8-pyridin-4-yl-3,8-diazaspiro[4.5]decane-3-carbonyl)-2,3-dihydro-1H-inden-1-yl]-benzamide hydrochloride (H-23) |
| H-24 | 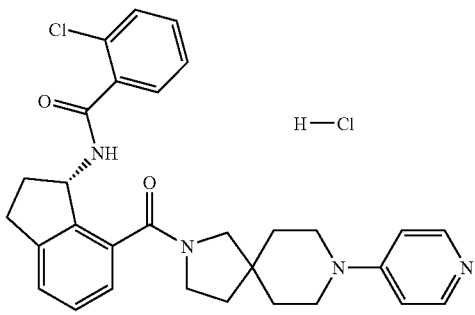 [SMILES: O=C(N[C@H]1CCc2cccc(C(=O)N3CCC4(CCN(c5ccncc5)CC4)C3)c21)c1ccccc1Cl ; Cl] | 2-chloro-N-[(1S)-7-(9-pyridin-4-yl-3,9-diazaspiro[5.5]undecane-3-carbonyl)-2,3-dihydro-1H-inden-1-yl]-benzamide (H-24) |
| H-25 | 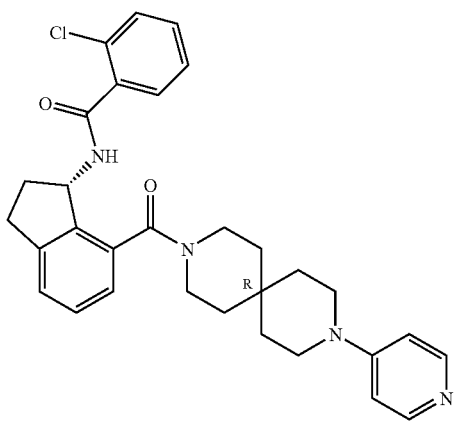 [SMILES: O=C(N[C@H]1CCc2cccc(C(=O)N3CCC4(CC3)CCN(c3ccncc3)CC4)c21)c1ccccc1Cl] | 2-chloro-N-[(1R)-7-(8-pyridin-4-yl-3,8-diazaspiro[4.5]decane-3-carbonyl)-2,3-dihydro-1H-inden-1-yl]-benzamide hydrochloride (H-25) |

| | | |
|---|---|---|
| H-26 | 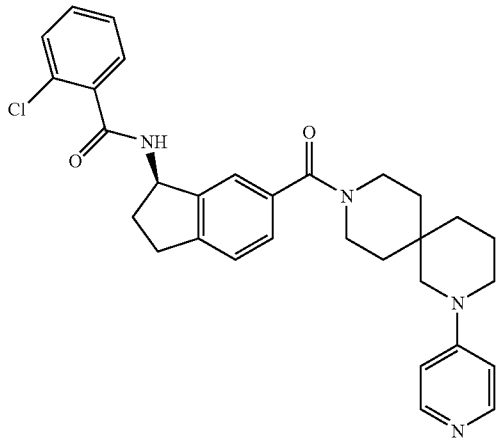 [SMILES: O=C(N[C@@H]1CCc2ccc(C(=O)N3CCC4(CCCN(c5ccncc5)C4)CC3)cc21)c1ccccc1Cl] | 2-chloro-N-[(1R)-6-(8-pyridin-4-yl-3,8-diazaspiro[5.5]undecane-3-carbonyl)-2,3-dihydro-1H-inden-1-yl]-benzamide (H-26) |
| H-27 | 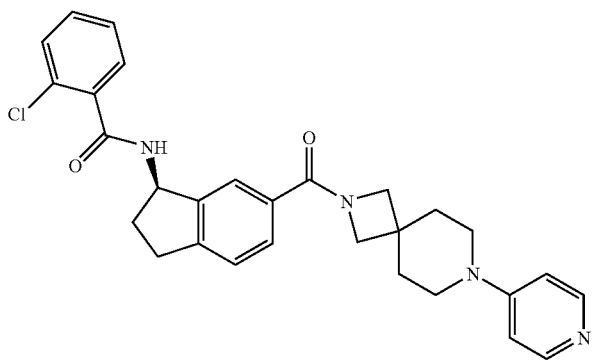 [SMILES: O=C(N[C@@H]1CCc2ccc(C(=O)N3CC4(CCN(c5ccncc5)CC4)C3)cc21)c1ccccc1Cl] | 2-chloro-N-[(1R)-6-(7-pyridin-4-yl-2,7-diazaspiro[3.5]nonane-2-carbonyl)-2,3-dihydro-1H-inden-1-yl]-benzamide (H-27) |
| H-28 | 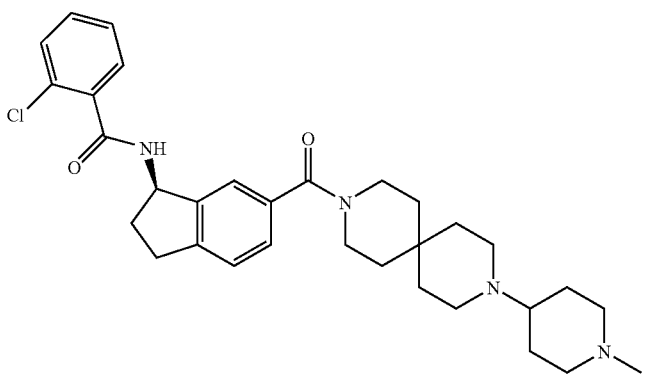 [SMILES: CN1CCC(N2CCC3(CCN(C(=O)c4ccc5c(c4)[C@H](NC(=O)c4ccccc4Cl)CC5)CC3)CC2)CC1] | 2-chloro-N-[(1R)-6-[9-(1-methyl-piperidin-4-yl)-3,9-diazaspiro[5.5]undecane-3-carobnyl]-2,3-dihydro-1H-inden-1-yl]-benzamide (H-28) |
| H-29 | 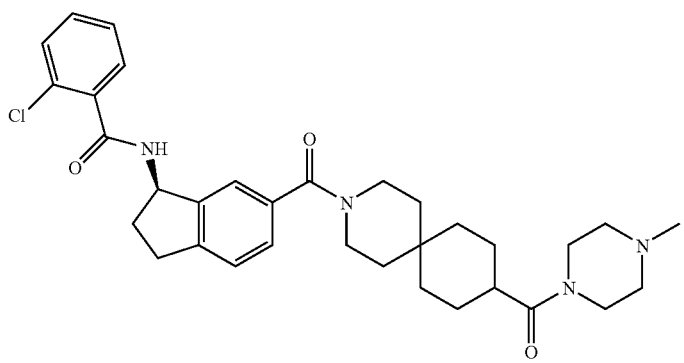 [SMILES: CN1CCN(C(=O)C2CCC3(CC2)CCN(C(=O)c2ccc4c(c2)[C@H](NC(=O)c2ccccc2Cl)CC4)CC3)CC1] | 2-chloro-N-[(1R)-6-[9-(4-methyl-piperazine-1-carbonyl)-3-azaspiro[5.5]undecane-3-carbonyl]-2,3-dihydro-1H-inden-1-yl]-benzamide (H-29) |

| | | |
|---|---|---|
| H-31 | 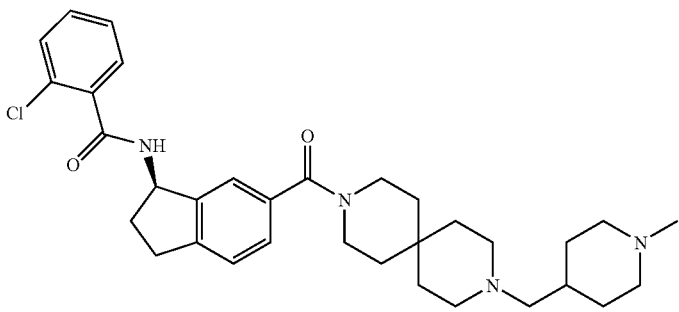 [SMILES: CN1CCC(CN2CCC3(CC2)CCN(C(=O)c2ccc4c(c2)[C@H](NC(=O)c2ccccc2Cl)CC4)CC3)CC1] | 2-chloro-N-[(1R)-6-[9-[(1-methyl-piperidin-4-yl)-methyl]-3,9-diazaspiro[5.5]undecane-3-carbonyl]-2,3-dihydro-1H-inden-1-yl]-benzamide (H-31) |
| H-32 | 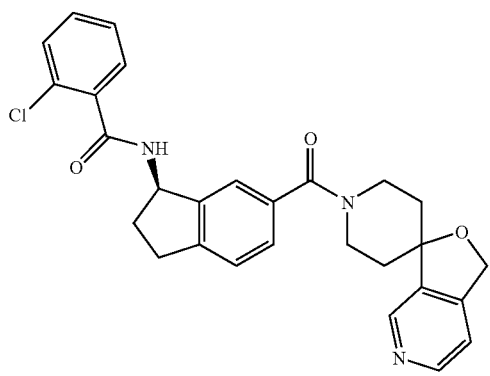 [SMILES: O=C(N[C@@H]1CCc2ccc(C(=O)N3CCC4(CC3)OCc3ccncc34)cc21)c1ccccc1Cl] | 2-chloro-N-[(1R)-6-(spiro[1H-furo[3,4-c]pyridine-3,4'-piperidine]-1'-carbonyl)-2,3-dihydro-1H-inden-1-yl]-benzamide (H-32) |
| H-33 | 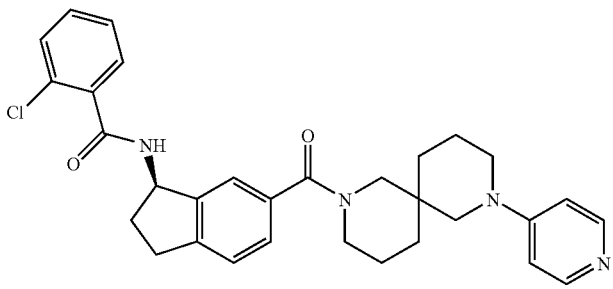 [SMILES: O=C(N[C@@H]1CCc2ccc(C(=O)N3CCCC4(CCCN(c5ccncc5)C4)C3)cc21)c1ccccc1Cl] | 2-chloro-N-[(1R)-6-(8-pyridin-4-yl-4,8-diazaspiro[5.5]undecane-4-carbonyl)-2,3-dihydro-1H-inden-1-yl]-benzamide (H-33) |
| H-34 | 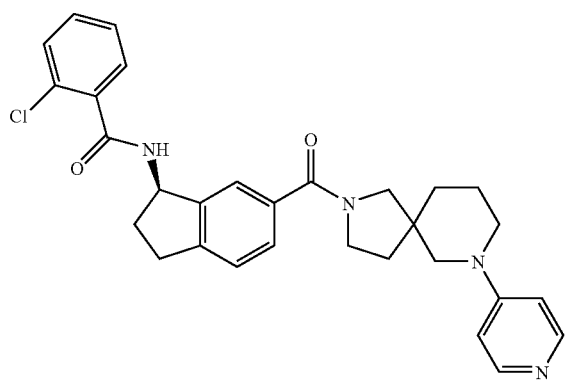 [SMILES: O=C(N[C@@H]1CCc2ccc(C(=O)N3CCC4(CCCN(c5ccncc5)C4)C3)cc21)c1ccccc1Cl] | 2-chloro-N-[(1R)-6-(7-pyridin-4-yl-3,7-diazaspiro[4.5]decane-3-carbonyl)-2,3-dihydro-1H-inden-1-yl]-benzamide (H-34) |
| H-35 | 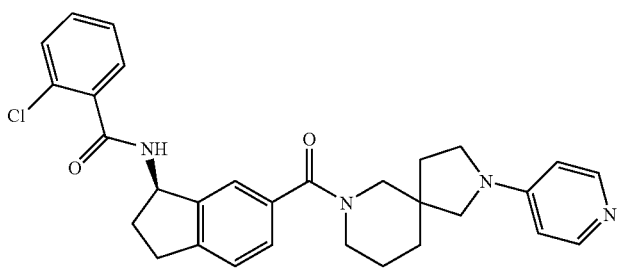 [SMILES: O=C(N[C@@H]1CCc2ccc(C(=O)N3CCCC4(CCN(c5ccncc5)C4)C3)cc21)c1ccccc1Cl] | 2-chloro-N-[(1R)-6-(2-pyridin-4-yl-2,9-diazaspiro[4.5]decane-9-carbonyl)-2,3-dihydro-1H-inden-1-yl]-benzamide (H-35) |

TABLE-continued

| H-36 | 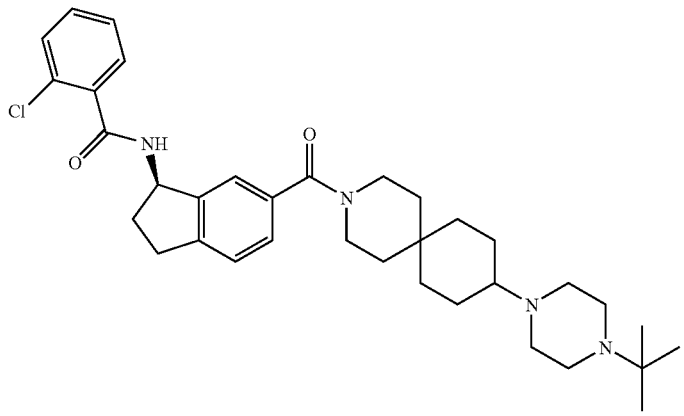 [SMILES: CC(C)(C)N1CCN(C2CCC3(CC2)CCN(C(=O)c2ccc4c(c2)[C@H](NC(=O)c2ccccc2Cl)CC4)CC3)CC1] | N-[(1R)-6-[9-(4-tert-Butyl-piperazin-1-yl)-3-azaspiro[5.5]undecane-3-carbonyl]-2,3-dihydro-1H-inden-1-yl]-2-chloro-benzamide (H-36) |
|---|---|---|
| H-37 | 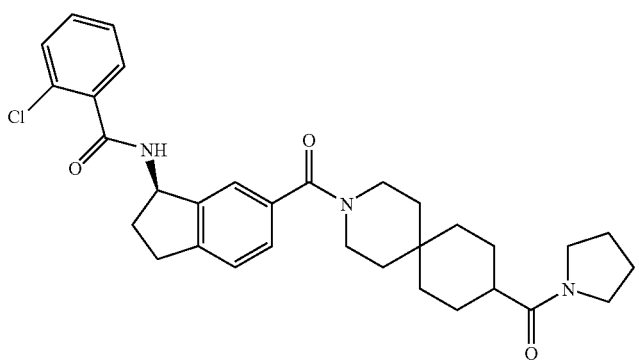 [SMILES: O=C(N[C@@H]1CCc2ccc(C(=O)N3CCC4(CCC(C(=O)N5CCCC5)CC4)CC3)cc21)c1ccccc1Cl] | 2-chloro-N-[(1R)-6-[9-(pyrrolidine-1-carbonyl)-3-azaspiro[5.5]undecane-3-carbonyl]-2,3-dihydro-1H-inden-1-yl]-benzamide (H-37) |
| H-38 | 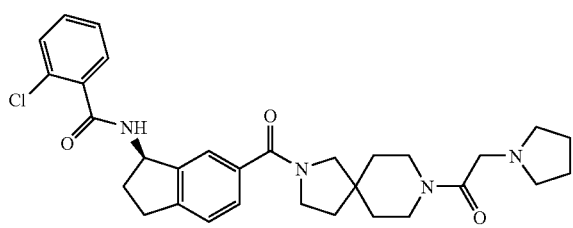 [SMILES: O=C(N[C@@H]1CCc2ccc(C(=O)N3CCC4(CCN(C(=O)CN5CCCC5)CC4)C3)cc21)c1ccccc1Cl] | 2-chloro-N-[(1R)-6-[8-(2-pyrrolidin-1-yl-acetyl)-3,8-diazaspiro[4.5]decane-3-carbonyl]-2,3-dihydro-1H-inden-1-yl]-benzamide (H-38) |
| H-39 | 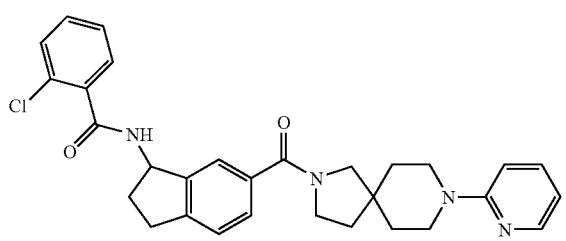 [SMILES: O=C(NC1CCc2ccc(C(=O)N3CCC4(CCN(c5ccccn5)CC4)C3)cc21)c1ccccc1Cl] | 2-chloro-N-[6-(8-pyridin-2-yl-3,8-diazaspiro[4.5]decane-3-carbonyl)-2,3-dihydro-1H-inden-1-yl]-benzamide (H-39) |
| H-40 | 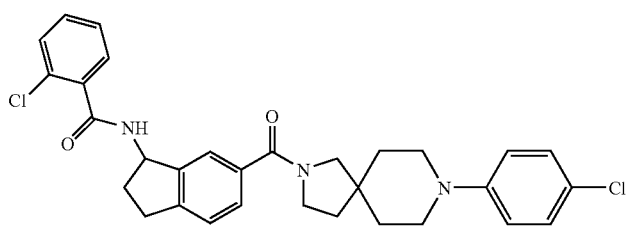 [SMILES: O=C(NC1CCc2ccc(C(=O)N3CCC4(CCN(c5ccc(Cl)cc5)CC4)C3)cc21)c1ccccc1Cl] | 2-chloro-N-[6-[8-(4-chlorophenyl)-3,8-diazaspiro[4.5]decane-3-carbonyl]-2,3-dihydro-1H-inden-1-yl]-benzamide (H-40) |

| | | |
|---|---|---|
| H-41 | | 2-chloro-N-[6-[8-(4-fluorophenyl)-3,8-diazaspiro[4.5]decane-3-carbonyl]-2,3-dihydro-1H-inden-1-yl]-benzamide (H-41) |
| H-42 | | 2-chloro-N-[6-[8-[4-(trifluoromethyl)-phenyl]-3,8-diazaspiro[4.5]decane-3-carbonyl]-2,3-dihydro-1H-inden-1-yl]-benzamide (H-42) |
| H-43 | | 2-chloro-N-[6-(8-pyridin-3-yl-3,8-diazaspiro[4.5]decane-3-carbonyl)-2,3-dihydro-1H-inden-1-yl]-benzamide (H-43) |
| H-44 | | 2-chloro-N-[6-(8-pyrimidin-2-yl-3,8-diazaspiro[4.5]decane-3-carbonyl)-2,3-dihydro-1H-inden-1-yl]-benzamide (H-44) |
| H-45 | | 2-chloro-N-[6-[8-[2-(trifluoromethyl)-pyridin-4-yl]-3,8-diazaspiro[4.5]decane-3-carbonyl]-2,3-dihydro-1H-inden-1-yl]-benzamide (H-45) |
| H-46 | | 2-chloro-N-[6-[8-[8-(trifluoromethyl)-quinolin-4-yl]-3,8-diazaspiro[4.5]decane-3-carbonyl]-2,3-dihydro-1H-inden-1-yl]-benzamide (H-46) |

| | | |
|---|---|---|
| H-47 | 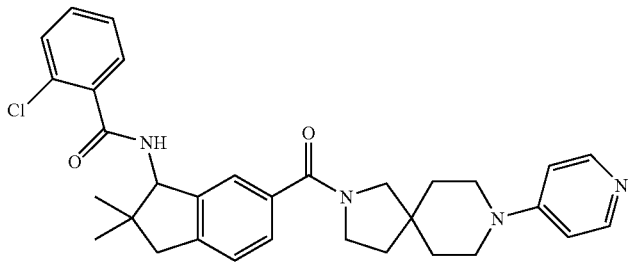 [SMILES: CC1(C)Cc2ccc(C(=O)N3CCC4(CCN(c5ccncc5)CC4)C3)cc2C1NC(=O)c1ccccc1Cl] | 2-chloro-N-[2,2-dimethyl-6-(8-pyridin-4-yl-3,8-diazaspiro[4.5]decane-3-carbonyl)-1,3-dihydro-inden-1-yl]-benzamide (H-47) |
| H-48 | 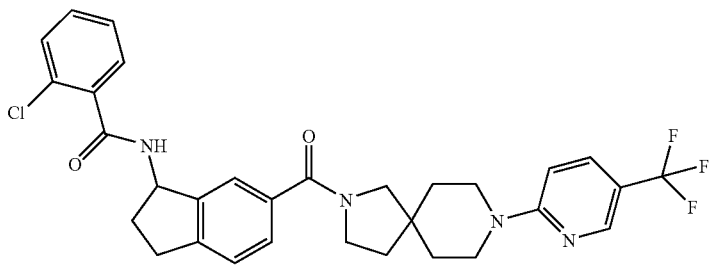 [SMILES: O=C(NC1CCc2ccc(C(=O)N3CCC4(CCN(c5ccc(C(F)(F)F)cn5)CC4)C3)cc21)c1ccccc1Cl] | 2-chloro-N-[6-[8-[5-(trifluoromethyl)-pyridin-2-yl]-3,8-diazaspiro[4.5]decane-3-carbonyl]-2,3-dihydro-1H-inden-1-yl]-benzamide (H-48) |
| H-49 | 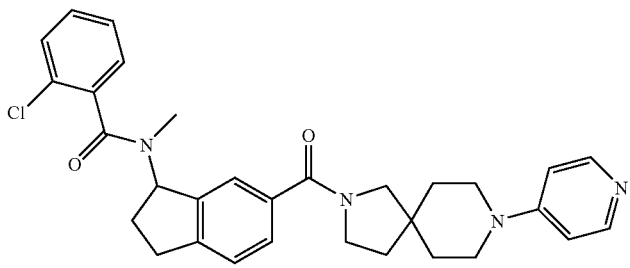 [SMILES: CN(C(=O)c1ccccc1Cl)C1CCc2ccc(C(=O)N3CCC4(CCN(c5ccncc5)CC4)C3)cc21] | 2-chloro-N-methyl-N-[6-(8-pyridin-4-yl-3,8-diazaspiro[4.5]decane-3-carbonyl)-2,3-dihydro-1H-inden-1-yl]-benzamide (H-49) |
| H-50 | 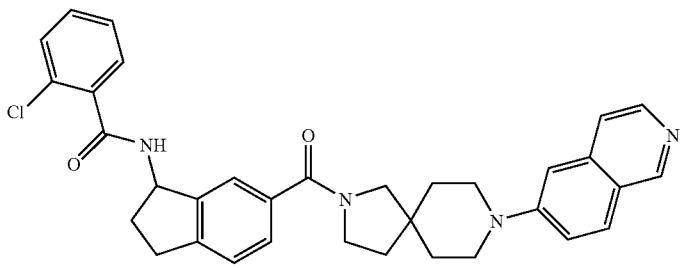 [SMILES: O=C(NC1CCc2ccc(C(=O)N3CCC4(CCN(c5ccc6cnccc6c5)CC4)C3)cc21)c1ccccc1Cl] | 2-chloro-N-[6-(8-isoquinolin-6-yl-3,8-diazaspiro[4.5]decane-3-carbonyl)-2,3-dihydro-1H-inden-1-yl]-benzamide (H-50) |
| H-51 | 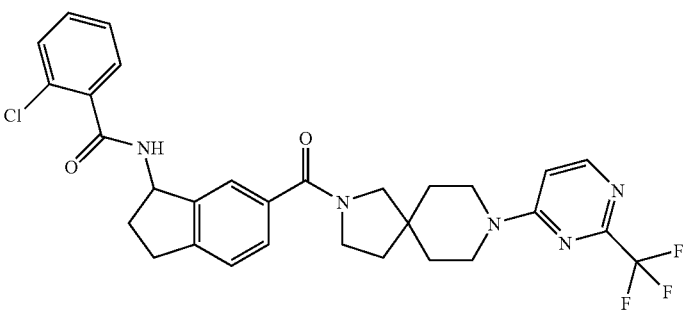 [SMILES: O=C(NC1CCc2ccc(C(=O)N3CCC4(CCN(c5ccnc(C(F)(F)F)n5)CC4)C3)cc21)c1ccccc1Cl] | 2-chloro-N-[6-[8-[2-(trifluoromethyl)-pyrimidin-4-yl]-3,8-diazaspiro[4.5]decane-3-carbonyl]-2,3-dihydro-1H-inden-1-yl]-benzamide (H-51) |

| | | |
|---|---|---|
| H-52 | 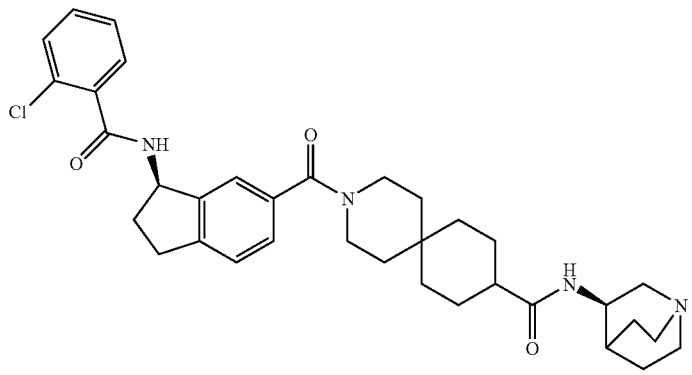 [SMILES: O=C(N[C@@H]1CCc2ccc(C(=O)N3CCC4(CCC(C(=O)N[C@H]5CN6CCC5CC6)CC4)CC3)cc21)c1ccccc1Cl] | N-[(5R)-1-Azabicyclo[2.2.2]octan-5-yl]-3-[(3R)-3-[(2-chloro-benzoyl)amino]-2,3-dihydro-1H-indene-5-carbonyl]-3-azaspiro[5.5]undecane-9-carboxylic acid amid (H-52) |
| H-53 | 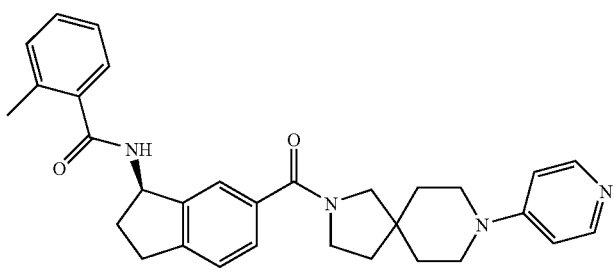 [SMILES: Cc1ccccc1C(=O)N[C@@H]1CCc2ccc(C(=O)N3CCC4(CCN(c5ccncc5)CC4)C3)cc21] | 2-Methyl-N-[(1R)-6-(8-pyridin-4-yl-3,8-diazaspiro[4.5]decane-3-carobnyl)-2,3-dihydro-1H-inden-1-yl]-benzamide (H-53) |
| H-54 | 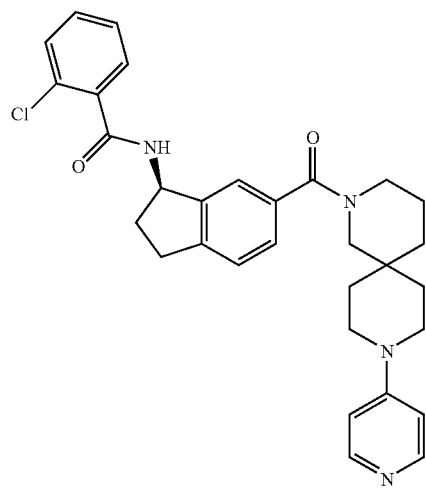 [SMILES: O=C(N[C@@H]1CCc2ccc(C(=O)N3CCCC4(CCN(c5ccncc5)CC4)C3)cc21)c1ccccc1Cl] | 2-Chloro-N-[(1R)-6-(9-pyridin-4-yl-2,9-diazaspiro[5.5]undecane-2-carbonyl)-2,3-dihydro-1H-inden-1-yl]-benzamide (H-54) |
| H-55 | 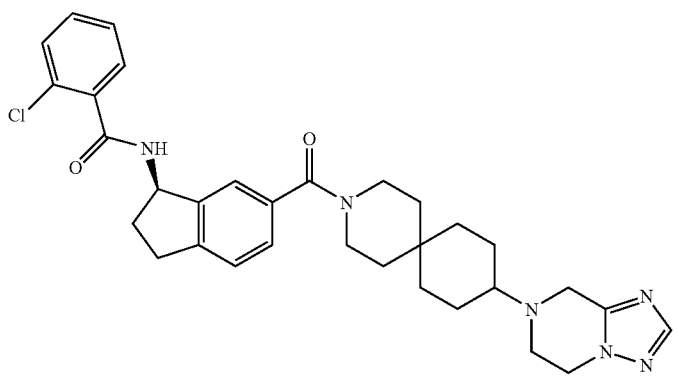 [SMILES: O=C(N[C@@H]1CCc2ccc(C(=O)N3CCC4(CCC(N5CCn6ncnc6C5)CC4)CC3)cc21)c1ccccc1Cl] | 2-Chloro-N-[(1R)-6-[9-(5,6,7,8-tetrahydro-[1,2,4]triazolo[1,5-a]pyrazin-7-yl)-3-azaspiro[5.5]undecane-3-carbonyl]-2,3-dihydro-1H-inden-1-yl]-benzamide (H-55) |

TABLE-continued

| | | |
|---|---|---|
| H-56 | 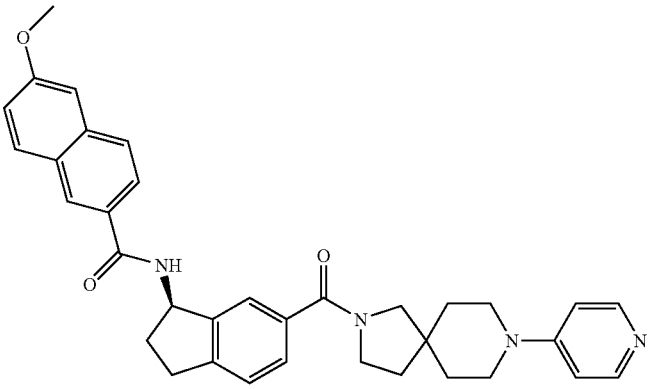 [SMILES: COc1ccc2cc(C(=O)N[C@@H]3CCc4ccc(C(=O)N5CCC6(CCN(c7ccncc7)CC6)C5)cc43)ccc2c1] | 6-Methoxy-N-[(1R)-6-(8-pyridin-4-yl-3,8-diazaspiro[4.5]decane-3-carbonyl)-2,3-dihydro-1H-inden-1-yl]-naphthalene-2-carboxylic acid amide (H-56) |
| H-57 | 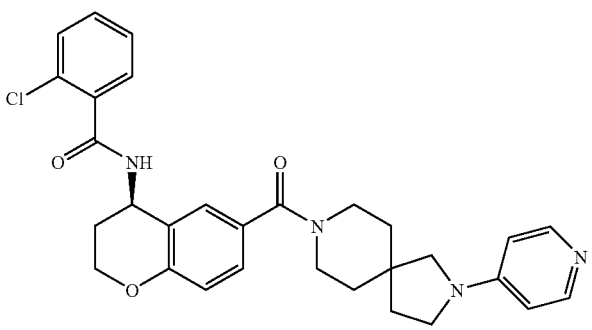 | 2-Chloro-N-[(4R)-6-(3-pyridin-4-yl-3,8-diazaspiro[4.5]decane-8-carbonyl)-3,4-dihydro-2H-chromen-4-yl]-benzamide (H-57) |
| H-58 | 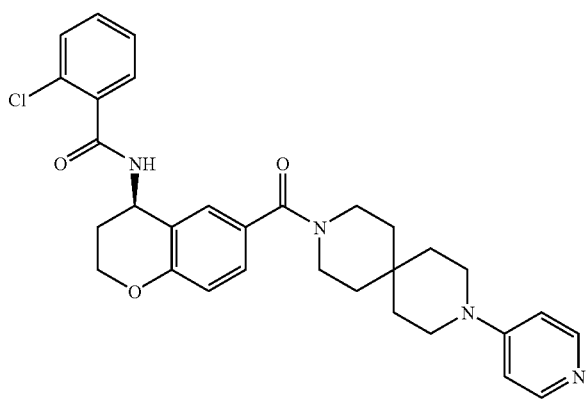 [SMILES: O=C(N[C@@H]1CCOc2ccc(C(=O)N3CCC4(CC3)CCN(c3ccncc3)CC4)cc21)c1ccccc1Cl] | 2-Chloro-N-[(4R)-6-(9-pyridin-4-yl-3,9-diazaspiro[5.5]undecane-3-carbonyl)-3,4-dihydro-2H-chromen-4-yl]-benzamide (H-58) |
| H-59 | 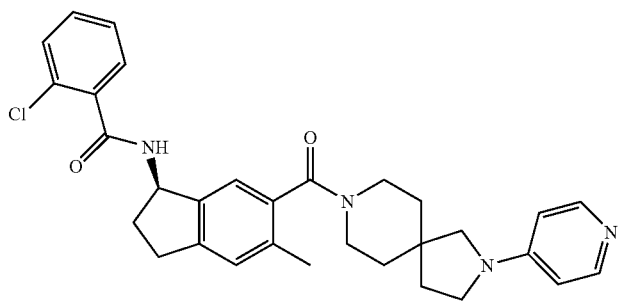 [SMILES: Cc1cc2c(cc1C(=O)N1CCC3(CC1)CCN(c1ccncc1)C3)[C@H](NC(=O)c1ccccc1Cl)CC2] | 2-Chloro-N-[(1R)-5-methyl-6-(3-pyridin-4-yl-3,8-diazaspiro[4.5]decane-8-carbonyl)-2,3-dihydro-1H-inden-1-yl]-benzamide (H-59) |

| | | |
|---|---|---|
| H-60 | 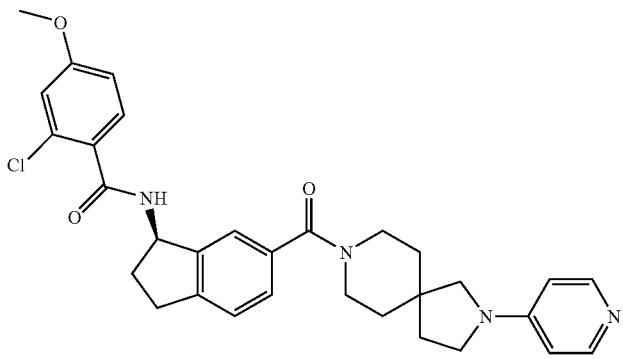 [SMILES: COc1ccc(C(=O)N[C@@H]2CCc3ccc(C(=O)N4CCC5(CC4)CCN(c4ccncc4)C5)cc32)c(Cl)c1] | 2-Chloro-4-methoxy-N-[(1R)-6-(3-pyridin-4-yl-3,8-diazaspiro[4.5]decane-8-carbonyl)-2,3-dihydro-1H-inden-1-yl]-benzamide (H-60) |
| H-61 | 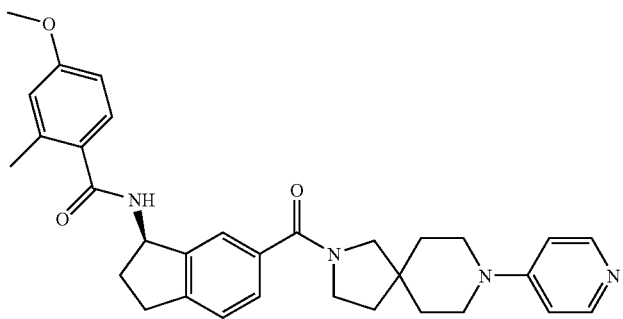 [SMILES: COc1ccc(C(=O)N[C@@H]2CCc3ccc(C(=O)N4CCC5(CCN(c6ccncc6)CC5)C4)cc32)c(C)c1] | 4-Methoxy-2-methyl-N-[(1R)-6-(8-pyridin-4-yl-3,8-diazaspiro[4.5]decane-3-carbonyl)-2,3-dihydro-1H-inden-1-yl]-benzamide (H-61) |
| H-62 | 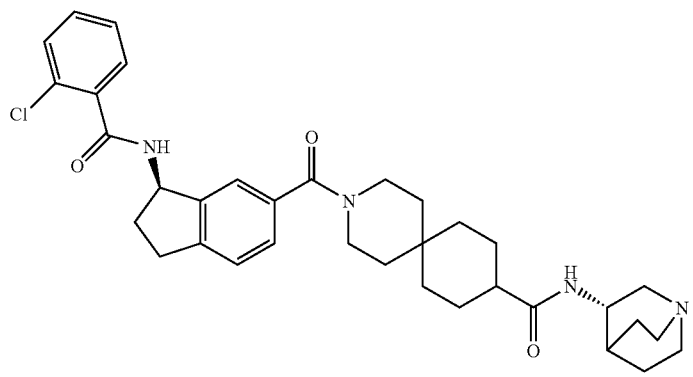 [SMILES: O=C(N[C@@H]1CCc2ccc(C(=O)N3CCC4(CCC(C(=O)N[C@@H]5CN6CCC5CC6)CC4)CC3)cc21)c1ccccc1Cl] | N-[(5S)-1-Azabicyclo[2.2.2]octan-5-yl]-3-[(3R)-3-[(2-chloro-benzoyl)amino]-2,3-dihydro-1H-indene-5-carbonyl]-3-azaspiro[5.5]undecane-9-carboxylic acid amide (H-62) |
| H-63 | 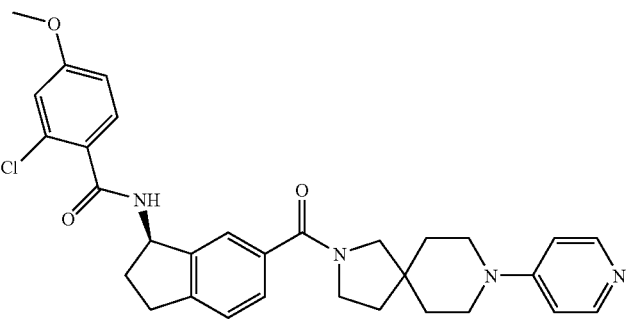 [SMILES: COc1ccc(C(=O)N[C@@H]2CCc3ccc(C(=O)N4CCC5(CCN(c6ccncc6)CC5)C4)cc32)c(Cl)c1] | 2-Chloro-4-methoxy-N-[(1R)-6-(8-pyridin-4-yl-3,8-diazaspiro[4.5]decane-3-carbonyl)-2,3-dihydro-1H-inden-1-yl]-benzamide (H-63) |

TABLE-continued

H-64 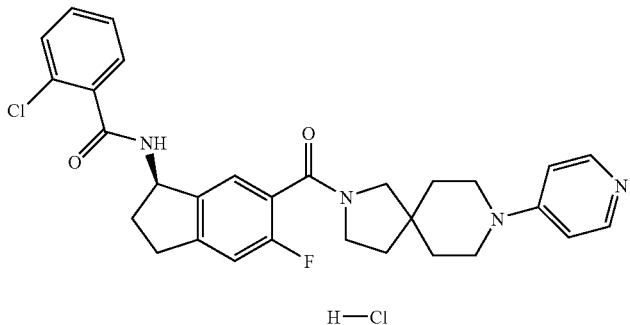 [SMILES: O=C(N[C@@H]1CCc2cc(F)c(C(=O)N3CCC4(CCN(c5ccncc5)CC4)C3)cc21)c1ccccc1Cl ; Cl]

2-Chloro-N-[(1R)-5-fluoro-6-(8-pyridin-4-yl-3,8-diazaspiro[4.5]decane-3-carbonyl)-2,3-dihydro-1H-inden-1-yl]-benzamide hydrochloride (H-64)

H-65 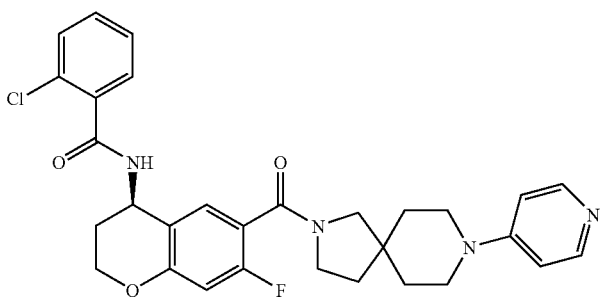 [SMILES: O=C(N[C@@H]1CCOc2cc(F)c(C(=O)N3CCC4(CCN(c5ccncc5)CC4)C3)cc21)c1ccccc1Cl]

2-Chloro-N-[(4R)-7-fluoro-6-(8-pyridin-4-yl-3,8-diazaspiro[4.5]decane-3-carbonyl)-3,4-dihydro-2H-chromen-4-yl]-benzamide (H-65)

H-66 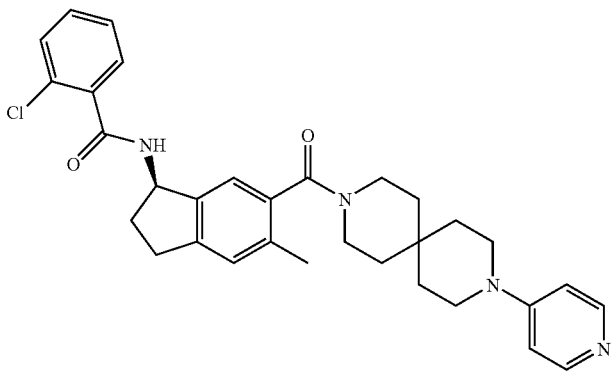

2-Chloro-N-[(1R)-5-methyl-6-(9-pyridin-4-yl-3,9-diazaspiro[5.5]undecane-3-carbonyl)-2,3-dihydro-1H-inden-1-yl]-benzamide (H-66)

H-67 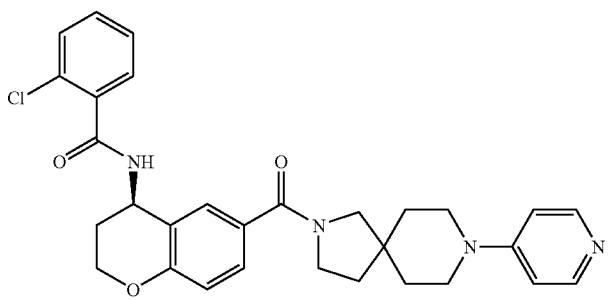 [SMILES: O=C(N[C@@H]1CCOc2ccc(C(=O)N3CCC4(CCN(c5ccncc5)CC4)C3)cc21)c1ccccc1Cl]

2-Chloro-N-[(4R)-6-(8-pyridin-4-yl-3,8-diazaspiro[4.5]decane-3-carbonyl)-3,4-dihydro-2H-chromen-4-yl]-benzamide (H-67)

TABLE-continued

H-68 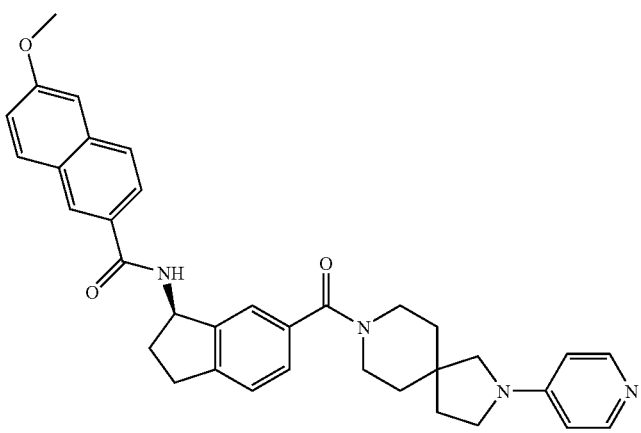 [SMILES: COc1ccc2cc(C(=O)N[C@@H]3CCc4ccc(C(=O)N5CCC6(CC5)CCN(c5ccncc5)C6)cc43)ccc2c1]

6-Methoxy-N-[(1R)-6-(3-pyridin-4-yl-3,8-diazaspiro[4.5]decane-8-carbonyl)-2,3-dihydro-1H-inden-1-yl]-naphthalene-2-carboxylic acid amid (H-68)

H-69 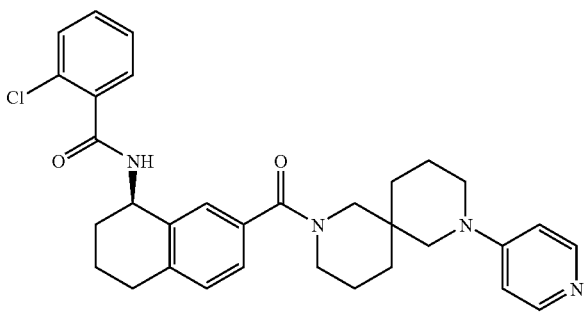 [SMILES: O=C(N[C@@H]1CCCc2ccc(C(=O)N3CCCC4(CCCN(c5ccncc5)C4)C3)cc21)c1ccccc1Cl]

2-Chloro-N-[(1R)-7-(6-pyridin-4-yl-4,6-diazaspiro[5.5]undecane-4-carbonyl)-1,2,3,4-tetrahydro-naphthalen-1-yl]-benzamide (H-69)

H-70 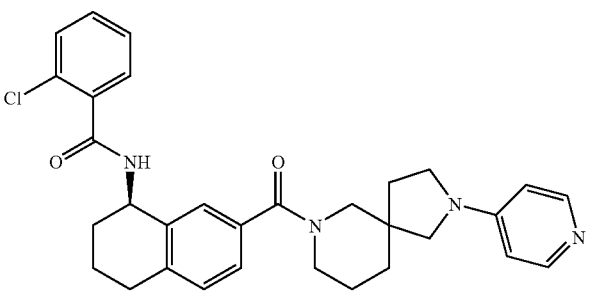 [SMILES: O=C(N[C@@H]1CCCc2ccc(C(=O)N3CCCC4(CCN(c5ccncc5)C4)C3)cc21)c1ccccc1Cl]

2-Chloro-N-[(1R)-7-(2-pyridin-4-yl-2,9-diazaspiro[4.5]decane-9-carbonyl)-1,2,3,4-tetrahydro-naphthalen-1-yl]-benzamide (H-70)

H-71 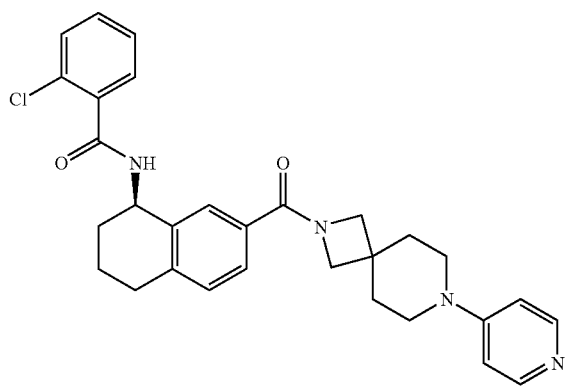 [SMILES: O=C(N[C@@H]1CCCc2ccc(C(=O)N3CC4(CCN(c5ccncc5)CC4)C3)cc21)c1ccccc1Cl]

2-Chloro-N-[(1R)-7-(7-pyridin-4-yl-2,7-diazaspiro[3.5]nonane-2-carbonyl)-1,2,3,4-tetrahydro-naphthalen-1-yl]-benzamide (H-71)

| | | |
|---|---|---|
| H-72 | 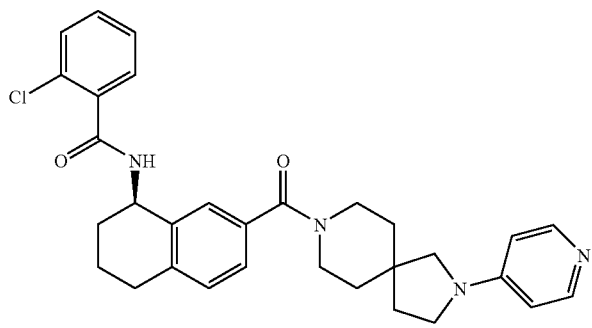 | 2-Chloro-N-[(1R)-7-(3-pyridin-4-yl-3,8-diazaspiro[4.5]decane-6-carbonyl]-1,2,3,4-tetrahydro-naphthalen-1-yl]-benzamide (H-72) |
| H-73 | 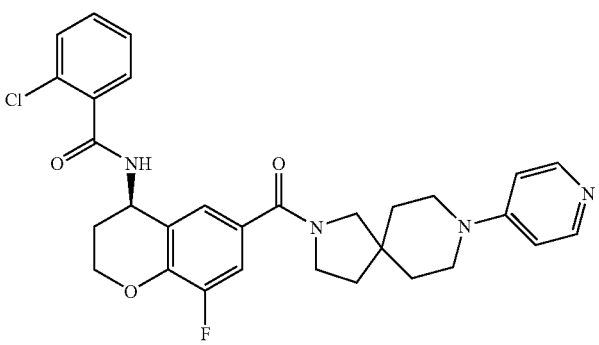 [SMILES: O=C(N[C@@H]1CCOc2c(F)cc(C(=O)N3CCC4(CCN(c5ccncc5)CC4)C3)cc21)c1ccccc1Cl] | 2-Chloro-N-[(4R)-8-fluoro-6-(8-pyridin-4-yl-3,8-diazaspiro[4.5]decane-3-carbonyl)-3,4-dihydro-2H-chromen-4-yl]-benzamide (H-73) |
| H-74 | 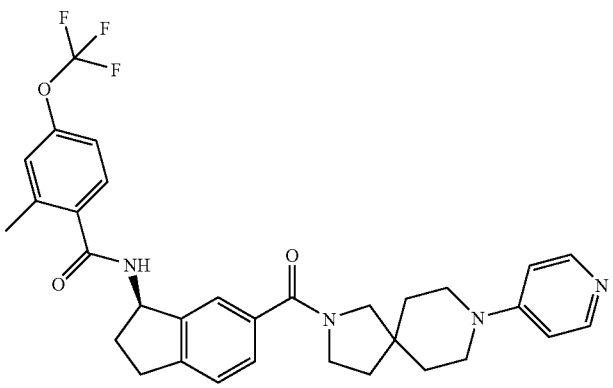 [SMILES: Cc1cc(OC(F)(F)F)ccc1C(=O)N[C@@H]1CCc2ccc(C(=O)N3CCC4(CCN(c5ccncc5)CC4)C3)cc21] | 2-Methyl-N-[(1R)-6-(8-pyridin-4-yl-3,8-diazaspiro[4.5]decane-3-carbonyl)-2,3-dihydro-1H-inden-1-yl]-4-(trifluoromethyloxy)-benzamide (H-74) |
| H-75 | 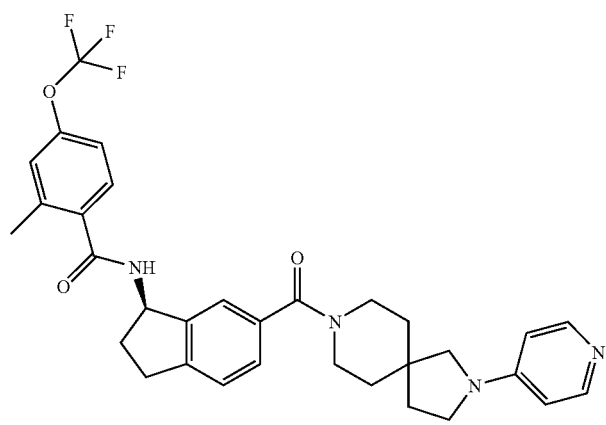 [SMILES: Cc1cc(OC(F)(F)F)ccc1C(=O)N[C@@H]1CCc2ccc(C(=O)N3CCC4(CC3)CCN(c3ccncc3)C4)cc21] | 2-Methyl-N-[(1R)-6-(3-pyridin-4-yl-3,8-diazaspiro[4.5]decane-8-carbonyl)-2,3-dihydro-1H-inden-1-yl]-4-(trifluoromethyloxy)-benzamide (H-75) |

| | | |
|---|---|---|
| H-76 | 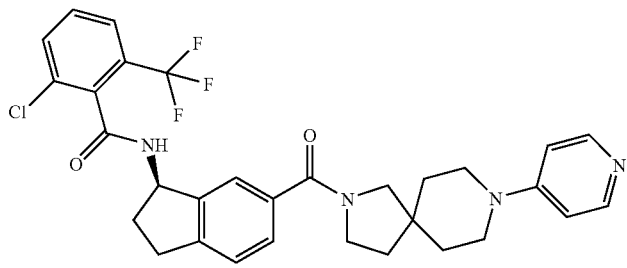 [SMILES: O=C(N[C@@H]1CCc2ccc(C(=O)N3CCC4(CCN(c5ccncc5)CC4)C3)cc21)c1c(Cl)cccc1C(F)(F)F] | 2-Chloro-N-[(1R)-6-(8-pyridin-4-yl-3,8-diazaspiro[4.5]decane-3-carbonyl)-2,3-dihydro-1H-inden-1-yl]-6-(trifluoromethyl)-benzamide (H-76) |
| H-77 | 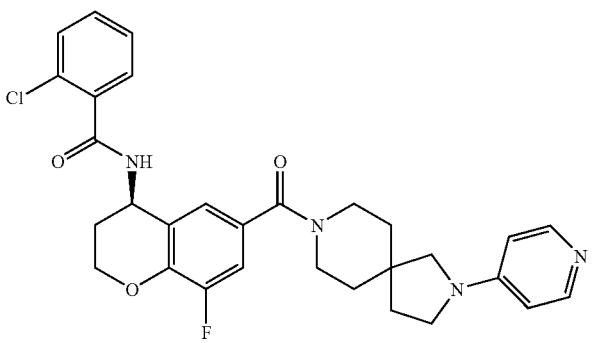 [SMILES: O=C(N[C@@H]1CCOc2c(F)cc(C(=O)N3CCC4(CC3)CCN(c3ccncc3)C4)cc21)c1ccccc1Cl] | 2-Chloro-N-[(4R)-8-fluoro-6-(3-pyridin-4-yl-3,6-diazaspiro[4.5]decane-8-carbonyl)-3,4-dihydro-2H-chromen-4-yl]-benzamide (H-77) |
| H-78 | 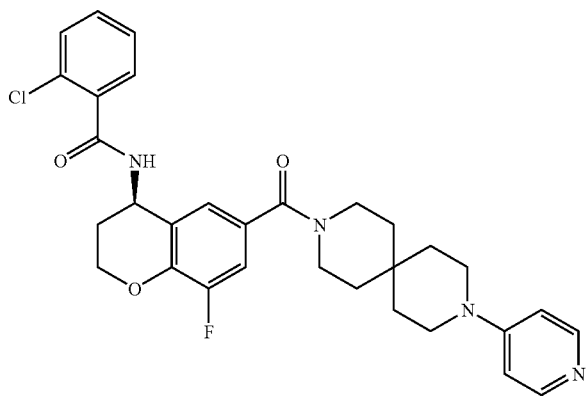 [SMILES: O=C(N[C@@H]1CCOc2c(F)cc(C(=O)N3CCC4(CC3)CCN(c3ccncc3)CC4)cc21)c1ccccc1Cl] | 2-Chloro-N-[(4R)-8-fluoro-6-(9-pyridin-4-yl-3,9-diazaspiro[4.5]undecane-3-carbonyl)-3,4-dihydro-2H-chromen-4-yl]-benzamide (H-78) |
| H-79 | 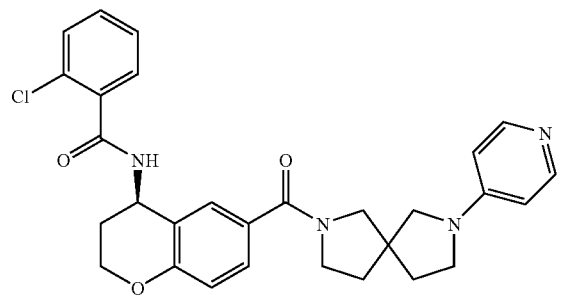 [SMILES: O=C(N[C@@H]1CCOc2ccc(C(=O)N3CCC4(CCN(c5ccncc5)C4)C3)cc21)c1ccccc1Cl] | 2-Chloro-N-[(1R)-7-(8-pyridin-4-yl-3,8-diazaspiro[4.5]nonane-3-carbonyl)-1,2,3,4-tetrahydro-naphthalen-1-yl]-benzamide (H-79) |

TABLE-continued

| H-80 | 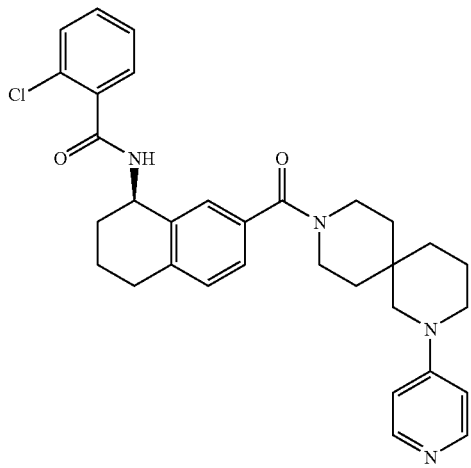 [SMILES: O=C(N[C@@H]1CCCc2ccc(C(=O)N3CCC4(CCCN(c5ccncc5)C4)CC3)cc21)c1ccccc1Cl] | 2-Chloro-N-[(1R)-7-(8-pyridin-4-yl-3,8-diazaspiro[4.5]undecane-3-carbonyl)-1,2,3,4-tetrahydro-naphthalen-1-yl]-benzamide (H-80) |
| H-81 | 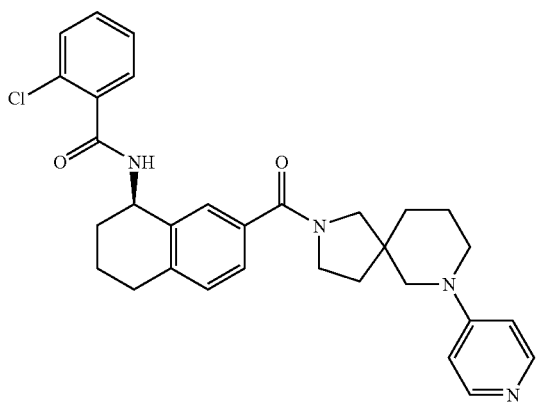 [SMILES: O=C(N[C@@H]1CCCc2ccc(C(=O)N3CCC4(CCCN(c5ccncc5)C4)C3)cc21)c1ccccc1Cl] | 2-Chloro-N-[(1R)-7-(7-pyridin-4-yl-3,7-diazaspiro[4.5]decane-3-carbonyl)-1,2,3,4-tetrahydro-naphthalen-1-yl]-benzamide (H-81) |
| H-82 | 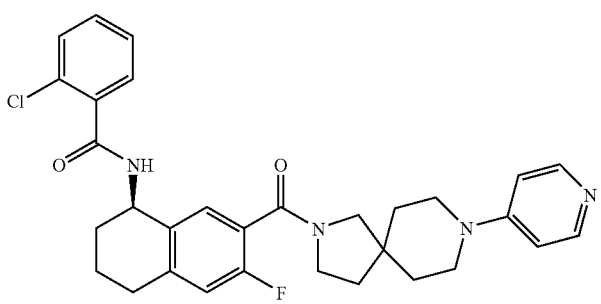 [SMILES: O=C(N[C@@H]1CCCc2cc(F)c(C(=O)N3CCC4(CCN(c5ccncc5)CC4)C3)cc21)c1ccccc1Cl] | 2-Chloro-N-[(1R)-6-fluoro-7-(8-pyridin-4-yl-3,8-diazaspiro[4.5]decane-3-carbonyl)-1,2,3,4-tetrahydro-naphthalen-1-yl]-benzamide (H-82) |
| H-83 | 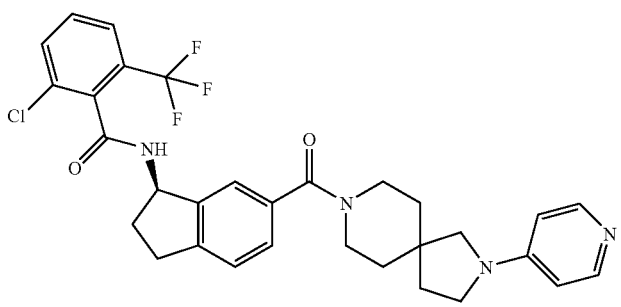 [SMILES: O=C(N[C@@H]1CCc2ccc(C(=O)N3CCC4(CC3)CCN(c3ccncc3)C4)cc21)c1c(Cl)cccc1C(F)(F)F] | 2-Chloro-N-[(1R)-6-(3-pyridin-4-yl-3,8-diazaspiro[4.5]decane-8-carbonyl)-2,3-dihydro-1H-inden-1-yl]-6-(trifluoromethyl)-benzamide (H-83) |

| | | |
|---|---|---|
| H-84 | 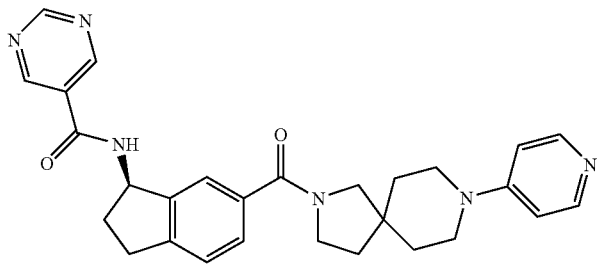 [SMILES: O=C(N[C@@H]1CCc2ccc(C(=O)N3CCC4(CCN(c5ccncc5)CC4)C3)cc21)c1cncnc1] | N-[(1R)-6-(8-Pyridin-4-yl-3,8-diazaspiro[4.5]decane-3-carbonyl)-2,3-dihydro-1H-inden-1-yl]-pyrimidine-5-carboxylic acid amide (H-84) |
| H-85 | 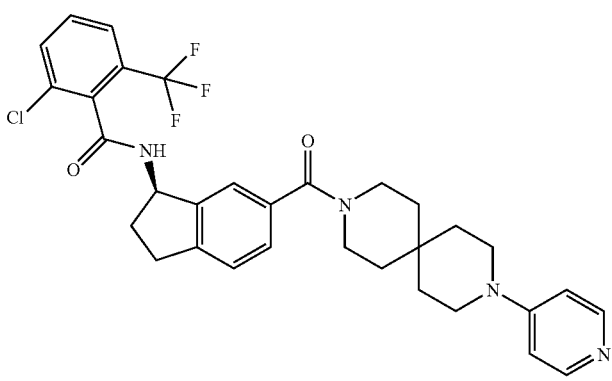 [SMILES: O=C(N[C@@H]1CCc2ccc(C(=O)N3CCC4(CC3)CCN(c3ccncc3)CC4)cc21)c1c(Cl)cccc1C(F)(F)F] | 2-Chloro-N-[(1R)-6-(9-pyridin-4-yl-3,9-diazaspiro[5.5]undecane-3-carbonyl]-2,3-dihydro-1H-inden-1-yl]-6-(trilfuoromethyl)-benzamide (H-85) |
| H-86 | 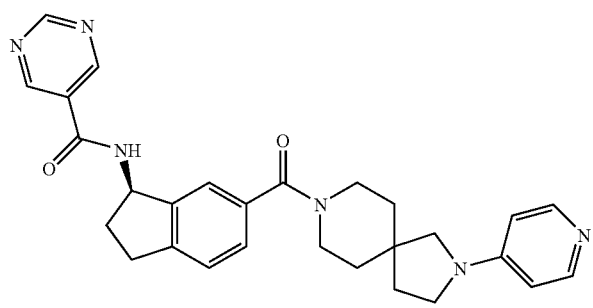 [SMILES: O=C(N[C@@H]1CCc2ccc(C(=O)N3CCC4(CC3)CCN(c3ccncc3)C4)cc21)c1cncnc1] | N-[(1R)-6-(3-Pyridin-4-yl-3,8-diazaspiro[4.5]decane-8-carbonyl)-2,3-dihydro-1H-inden-1-yl]-pyrimidine-5-carboxylic acid amide (H-86) |
| H-87 | 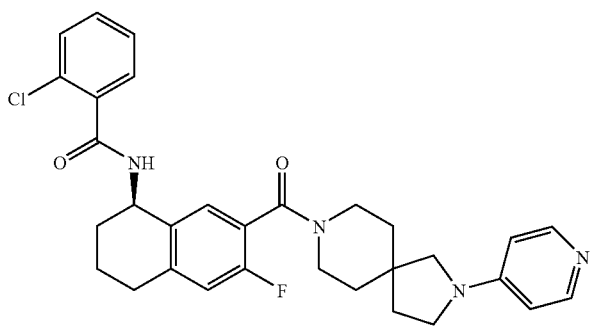 [SMILES: O=C(N[C@@H]1CCCc2cc(F)c(C(=O)N3CCC4(CC3)CCN(c3ccncc3)C4)cc21)c1ccccc1Cl] | 2-Chloro-N-[(1R)-6-fluoro-7-(3-pyridin-4-yl-3,8-diazaspiro[4.5]decane-8-carbonyl)-1,2,3,4-tetrahydro-naphthalen-1-yl]-benzamide (H-87) |

TABLE-continued

H-88 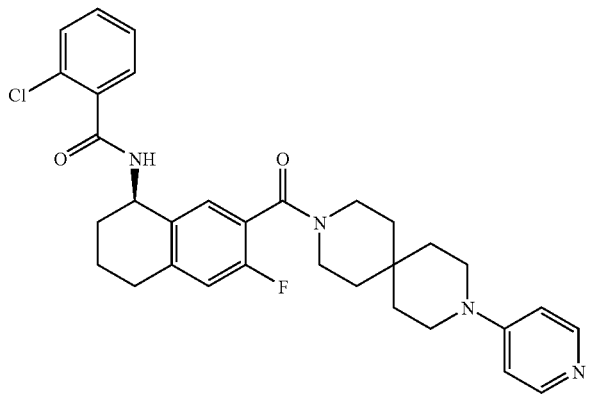 [SMILES: O=C(N[C@@H]1CCCc2cc(F)c(C(=O)N3CCC4(CC3)CCN(c3ccncc3)CC4)cc21)c1ccccc1Cl]

2-Chloro-N-[(1R)-6-fluoro-7-(9-pyridin-4-yl-3,9-diazaspiro[4.5]undecane-3-carbonyl)-1,2,3,4-tetrahydro-naphthalen-1-yl]-benzamide (H-88)

H-89 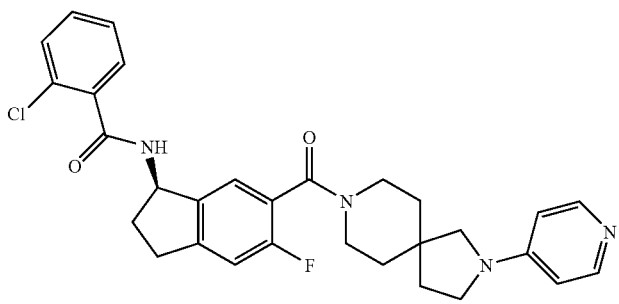

2-Chloro-N-[(1R)-5-fluoro-6-(3-pyridin-4-yl-3,8-diazaspiro[4.5]decane-8-carbonyl)-2,3-dihydro-1H-inden-1-yl]-benzamide (H-89)

H-90 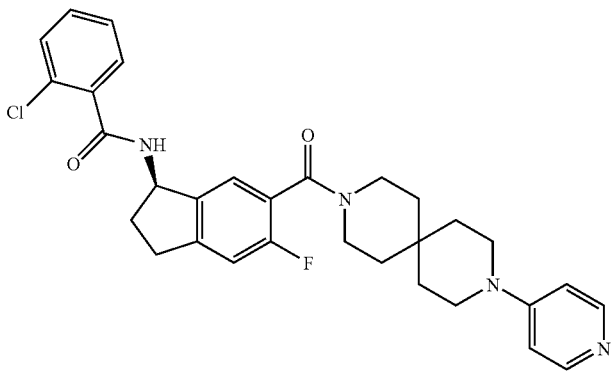 [SMILES: O=C(N[C@@H]1CCc2cc(F)c(C(=O)N3CCC4(CC3)CCN(c3ccncc3)CC4)cc21)c1ccccc1Cl]

2-Chloro-N-[(1R)-5-fluoro-6-(9-pyridin-4-yl-3,9-diazaspiro[5.5]undecane-3-carbonyl)-2,3-dihydro-1H-inden-1-yl]-benzamide (H-90)

H-91 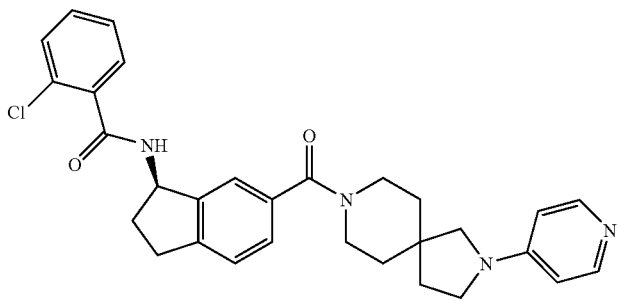 [SMILES: O=C(N[C@@H]1CCc2ccc(C(=O)N3CCC4(CC3)CCN(c3ccncc3)C4)cc21)c1ccccc1Cl]

2-Chloro-N-[(1R)-6-(3-pyridin-4-yl-3,8-diazaspiro[4.5]decane-8-carbonyl)-2,3-dihydro-1H-inden-1-yl]-benzamide (H-91)

TABLE-continued

| | | |
|---|---|---|
| H-92 | 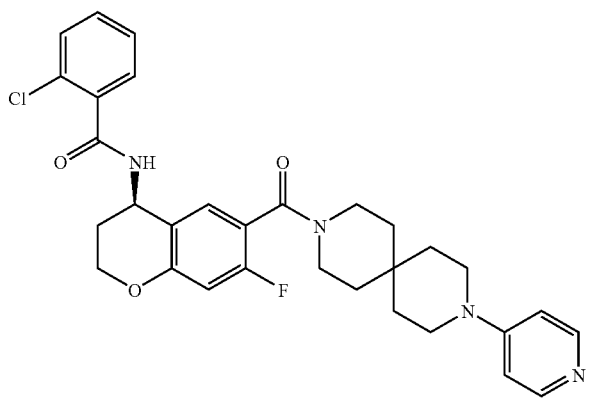 | 2-Chloro-N-[(4R)-7-fluoro-6-(9-pyridin-4-yl-3,9-diazaspiro[5.5]undecane-3-carbonyl)-3,4-dihydro-2H-chromen-4-yl]-benzamide (H-92) |
| H-93 | 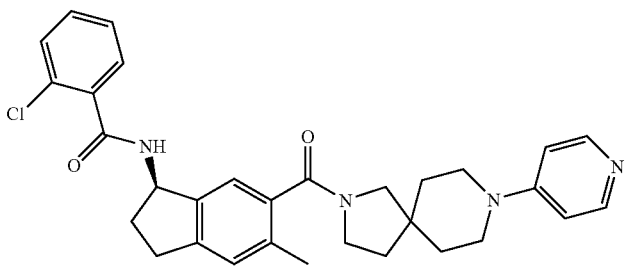 [SMILES: Cc1cc2c(cc1C(=O)N1CCC3(CCN(c4ccncc4)CC3)C1)[C@H](NC(=O)c1ccccc1Cl)CC2] | 2-Chloro-N-[(1R)-5-methyl-6-(8-pyridin-4-yl-3,8-diazaspiro[4.5]decane-3-carbonyl)-2,3-dihydro-1H-inden-1-yl]-benzamide (H-93) |
| H-94 | 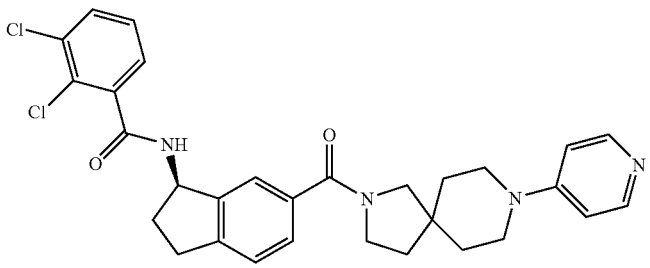 [SMILES: O=C(N[C@@H]1CCc2ccc(C(=O)N3CCC4(CCN(c5ccncc5)CC4)C3)cc21)c1cccc(Cl)c1Cl] | 2,3-Dichloro-N-[(1R)-6-(8-pyridin-4-yl-3,8-diazaspiro[4.5]decane-3-carbonyl)-2,3-dihydro-1H-inden-1-yl]-benzamide (H-94) |
| H-95 | 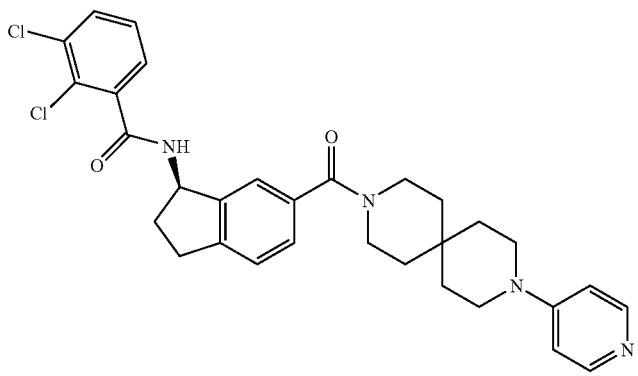 [SMILES: O=C(N[C@@H]1CCc2ccc(C(=O)N3CCC4(CC3)CCN(c3ccncc3)CC4)cc21)c1cccc(Cl)c1Cl] | 2,3-Dichloro-N-[(1R)-6-(9-pyridin-4-yl-3,9-diazaspiro[5.5]undecane-3-carbonyl)-2,3-dihydro-1H-inden-1-yl]-benzamide (H-95) |
| H-96 | 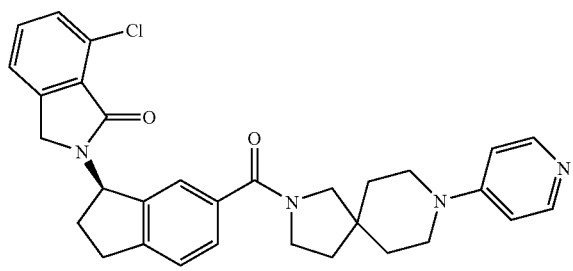 [SMILES: O=C(c1ccc2c(c1)[C@H](N1Cc3cccc(Cl)c3C1=O)CC2)N1CCC2(CCN(c3ccncc3)CC2)C1] | 7-Chloro-2-[(1R)-6-(8-pyridin-4-yl-3,8-diazaspiro[4.5]decane-3-carbonyl)-2,3-dihydro-1H-inden-1-yl]-2,3-dihydro-isoindol-1-one (H-96) |

| | | |
|---|---|---|
| H-97 | 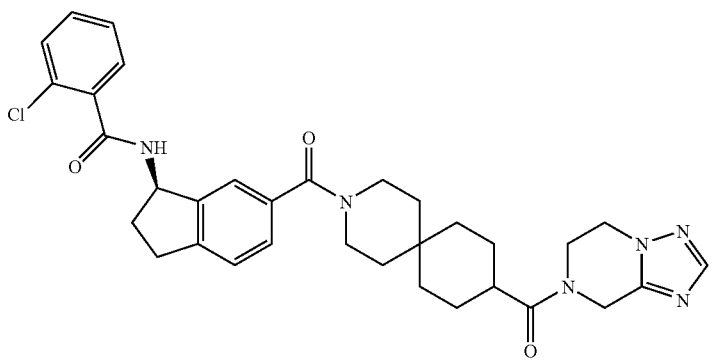 [SMILES: O=C(N[C@@H]1CCc2ccc(C(=O)N3CCC4(CCC(C(=O)N5CCn6ncnc6C5)CC4)CC3)cc21)c1ccccc1Cl] | 2-Chloro-N-[(1R)-6-[9-(5,6,7,8-tetrahydro-[1,2,4]triazolo[1,5-a]pyrazine-7-carbonyl)-3-azaspiro[5.5]undecane-3-carbonyl]-2,3-dihydro-1H-inden-1-yl]-benzamide (H-97) |
| H-98 | 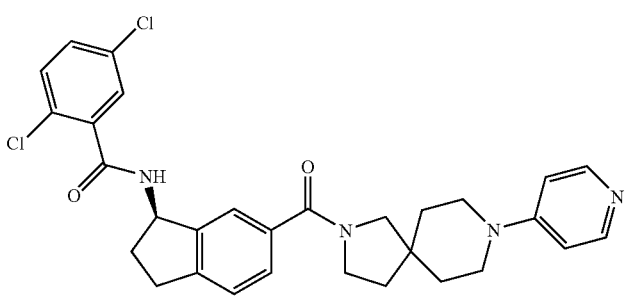 | 2,5-Dichloro-N-[(1R)-6-(8-pyridin-4-yl-3,8-diazaspiro[4.5]decane-3-carbonyl)-2,3-dihydro-1H-inden-1-yl]-benzamide (H-98) |
| H-99 | 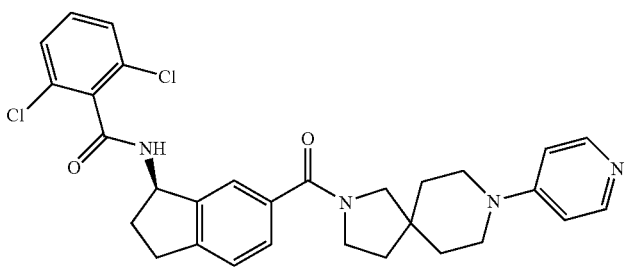 | 2,6-Dichloro-N-[(1R)-6-(8-pyridin-4-yl-3,8-diazaspiro[4.5]decane-3-carbonyl)-2,3-dihydro-1H-inden-1-yl]-benzamide (H-99) |
| H-100 | 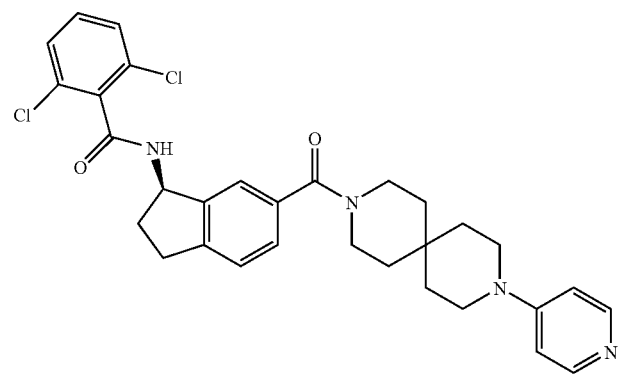 [SMILES: O=C(N[C@@H]1CCc2ccc(C(=O)N3CCC4(CC3)CCN(c3ccncc3)CC4)cc21)c1c(Cl)cccc1Cl] | 2,6-Dichloro-N-[(1R)-6-(9-pyridin-4-yl-3,9-diazaspiro[5.5]undecane-3-carbonyl)-2,3-dihydro-1H-inden-1-yl]-benzamide (H-100) |
| H-101 | 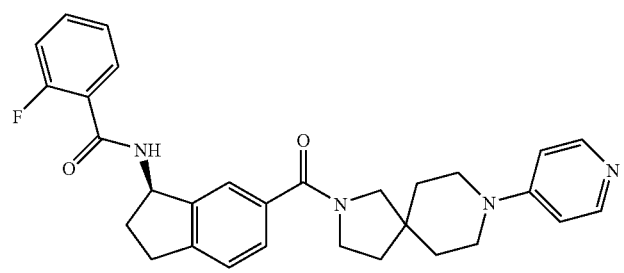 [SMILES: O=C(N[C@@H]1CCc2ccc(C(=O)N3CCC4(CCN(c5ccncc5)CC4)C3)cc21)c1ccccc1F] | 2-Fluoro-N-[(1R)-6-(8-pyridin-4-yl-3,8-diazaspiro[4.5]decane-3-carbonyl)-2,3-dihydro-1H-inden-1-yl]-benzamide (H-101) |

| | | |
|---|---|---|
| H-102 | 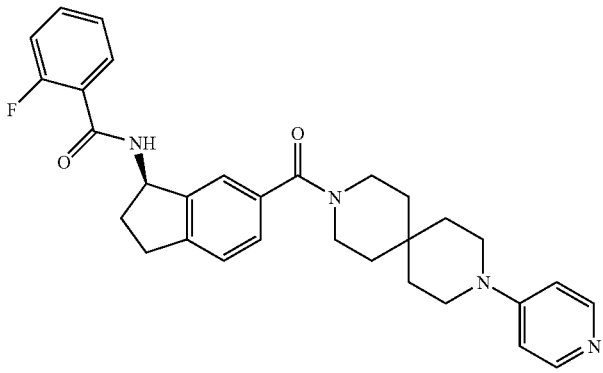 [SMILES: O=C(N[C@@H]1CCc2ccc(C(=O)N3CCC4(CC3)CCN(c3ccncc3)CC4)cc21)c1ccccc1F] | 2-Fluoro-N-[(1R)-6-(9-pyridin-4-yl-3,9-diazaspiro[5.5]undecane-3-carbonyl)-2,3-dihydro-1H-inden-1-yl]-benzamide (H-102) |
| H-103 | 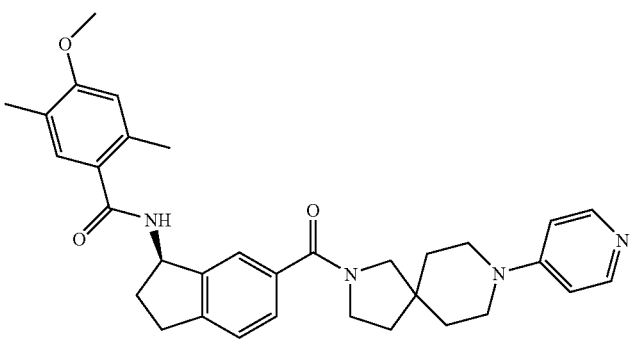 [SMILES: COc1cc(C)c(C(=O)N[C@@H]2CCc3ccc(C(=O)N4CCC5(CCN(c6ccncc6)CC5)C4)cc32)cc1C] | 4-Methoxy-2,5-dimethyl-N-[(1R)-6-(8-pyridin-4-yl-3,8-diazaspiro[4.5]decane-3-carbonyl)-2,3-dihydro-1H-inden-1-yl]-benzamide (H-103) |
| H-104 | 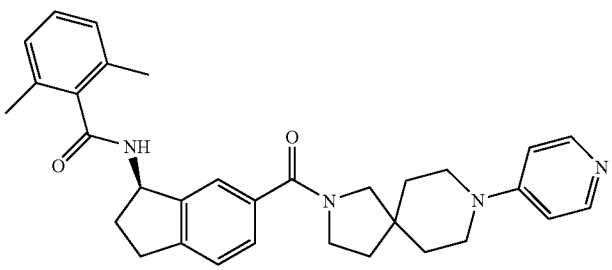 [SMILES: Cc1cccc(C)c1C(=O)N[C@@H]1CCc2ccc(C(=O)N3CCC4(CCN(c5ccncc5)CC4)C3)cc21] | 2,6-Dimethyl-N-[(1R)-6-(8-pyridin-4-yl-3,8-diazaspiro[4.5]decane-3-carbonyl)-2,3-dihydro-1H-inden-1-yl]-benzamide (H-104) |
| H-105 | 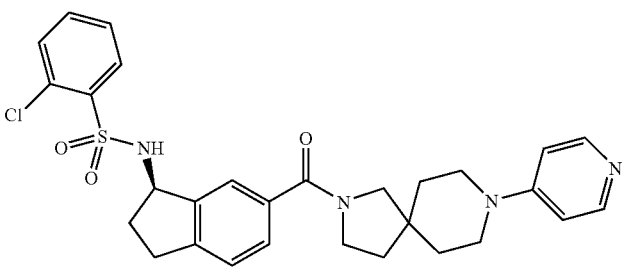 [SMILES: O=C(c1ccc2c(c1)[C@H](NS(=O)(=O)c1ccccc1Cl)CC2)N1CCC2(CCN(c3ccncc3)CC2)C1] | 2-Chloro-N-[(1R)-6-(8-pyridin-4-y-3,8-diazaspiro[4.5]decane-3-carbonyl)-2,3-dihydro-1H-inden-1-yl]-benzenesulfonic acid amide (H-105) |
| H-106 | 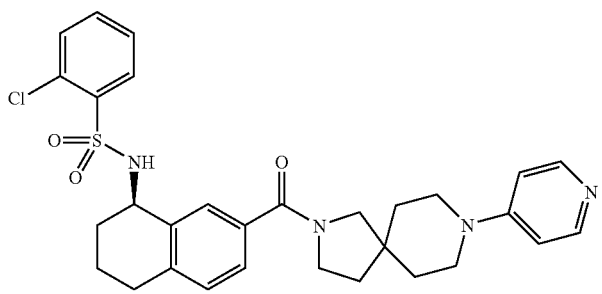 [SMILES: O=C(c1ccc2c(c1)[C@H](NS(=O)(=O)c1ccccc1Cl)CCC2)N1CCC2(CCN(c3ccncc3)CC2)C1] | 2-Chloro-N-[(1R)-7-(8-pyridin-4-yl-3,8-diazaspiro[4.5]decane-3-carbonyl)-1,2,3,4-tetrahydro-naphthalen-1-yl]-benzenesulfonic acid amide (H-106) |

| | | |
|---|---|---|
| H-107 | 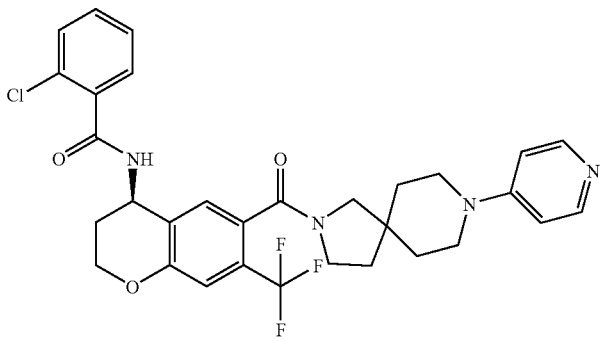 [SMILES: O=C(N[C@@H]1CCOc2cc(C(F)(F)F)c(C(=O)N3CCC4(CCN(c5ccncc5)CC4)C3)cc21)c1ccccc1Cl] | 2-Chloro-N-[(4R)-6-(8-pyridin-4-yl-3,8-diazaspiro[4.5]decane-3-carbonyl)-7-(trifluoromethyl)-3,4-dihydro-2H-chromen-4-yl]-benzamide (H-107) |
| H-108 | 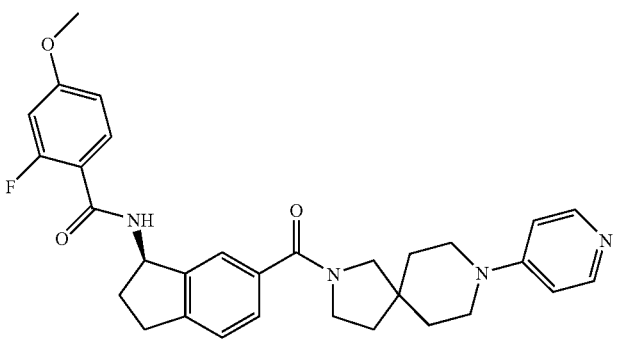 [SMILES: COc1ccc(C(=O)N[C@@H]2CCc3ccc(C(=O)N4CCC5(CCN(c6ccncc6)CC5)C4)cc32)c(F)c1] | 2-Fluoro-4-methoxy-N-[(1R)-6-(8-pyridin-4-yl-3,8-diazaspiro[4.5]decane-3-carbonyl)-2,3-dihydro-1H-inden-1-yl]-benzamide (H-108) |
| H-109 | 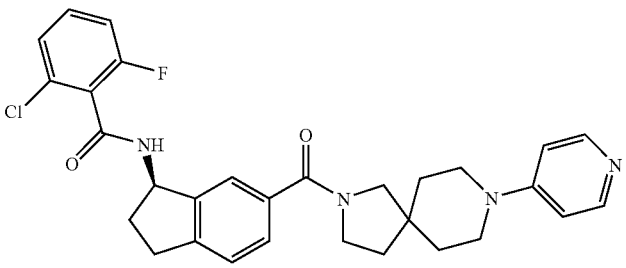 | 2-Chloro-6-fluoro-N-[(1R)-6-(8-pyridin-4-yl-3,8-diazaspiro[4.5]decane-3-carbonyl)-2,3-dihydro-1H-inden-1-yl]-benzamide (H-109) |
| H-110 | 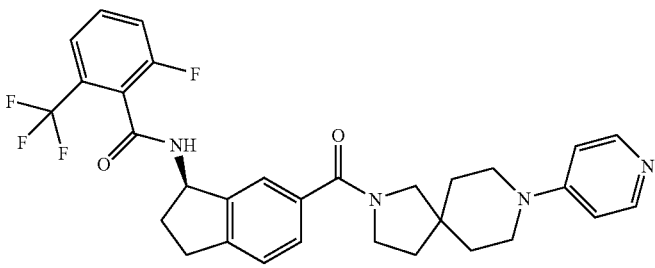 [SMILES: O=C(N[C@@H]1CCc2ccc(C(=O)N3CCC4(CCN(c5ccncc5)CC4)C3)cc21)c1c(F)cccc1C(F)(F)F] | 2-Fluoro-N-[(1R)-6-(8-pyridin-4-yl-3,8-diazaspiro[4.5]decane-3-carbonyl)-2,3-dihydro-1H-inden-1-yl]-6-(trifluoromethyl)-benzamide (H-110) |
| H-111 | 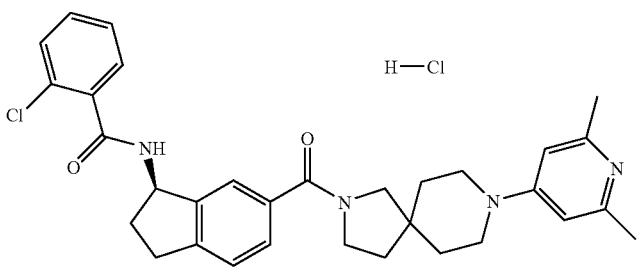 [SMILES: Cc1cc(N2CCC3(CCN(C(=O)c4ccc5c(c4)[C@H](NC(=O)c4ccccc4Cl)CC5)C3)CC2)cc(C)n1 ; Cl] | 2-Chloro-N-[(1R)-6-[8-(2,6-dimethyl-pyridin-4-yl)-3,8-diazaspiro[4.5]decane-3-carbonyl]-2,3-dihydro-1H-inden-1-yl]-benzamide hydrochloride (H-111) |

TABLE-continued

| | | |
|---|---|---|
| H-112 | 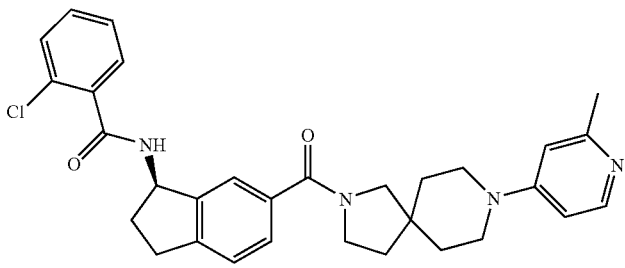 [SMILES: Cc1cc(N2CCC3(CCN(C(=O)c4ccc5c(c4)[C@H](NC(=O)c4ccccc4Cl)CC5)C3)CC2)ccn1] | 2-Chloro-N-[(1R)-6-[8-(2-methyl-pyridin-4-yl)-3,8-diazaspiro[4.5]decane-3-carbonyl]-2,3-dihydro-1H-inden-1-yl]-benzamide (H-112) |
| H-113 | 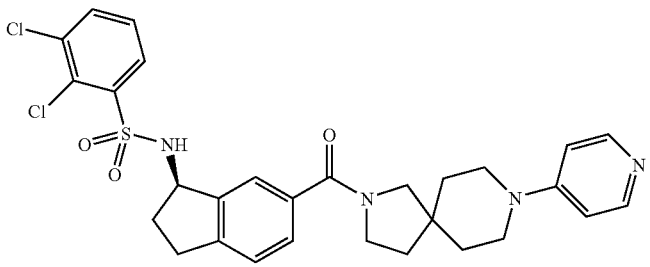 [SMILES: O=C(c1ccc2c(c1)[C@H](NS(=O)(=O)c1cccc(Cl)c1Cl)CC2)N1CCC2(CCN(c3ccncc3)CC2)C1] | 2,3-Dichloro-N-[(1R)-6-(8-pyridin-4-yl-3,8-diazaspiro[4.5]decane-3-carbonyl)-2,3-dihydro-1H-inden-1-yl]-benzenesulfonic acid amide (H-113) |
| H-114 | 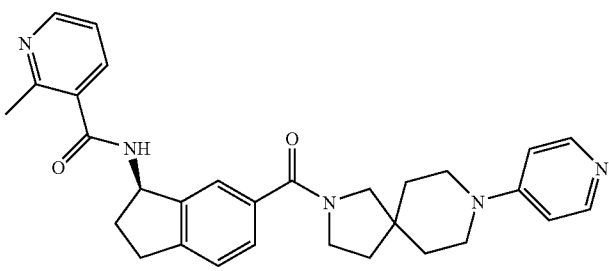 [SMILES: Cc1ncccc1C(=O)N[C@@H]1CCc2ccc(C(=O)N3CCC4(CCN(c5ccncc5)CC4)C3)cc21] | 2-Methyl-N-[(1R)-6-(8-pyridin-4-yl-3,8-diazaspiro[4.5]decane-3-carbonyl)-2,3-dihydro-1H-inden-1-yl]-pyridine-3-carboxylic acid amide (H-114) |
| H-115 | 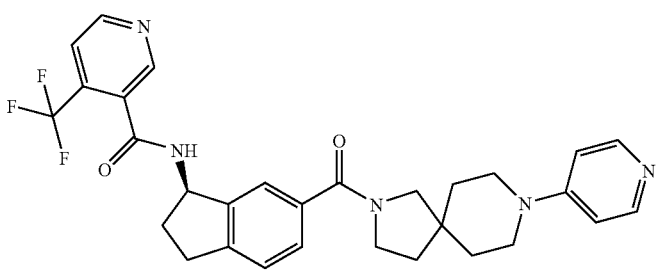 [SMILES: O=C(N[C@@H]1CCc2ccc(C(=O)N3CCC4(CCN(c5ccncc5)CC4)C3)cc21)c1cnccc1C(F)(F)F] | N-[(1R)-6-(8-Pyridin-4-yl-3,8-diazaspiro[4.5]decane-3-carbonyl)-2,3-dihydro-1H-inden-1-yl]-4-(trifluoromethyl)-pyridine-3-carboxylic acid amide (H-115) |
| H-116 | 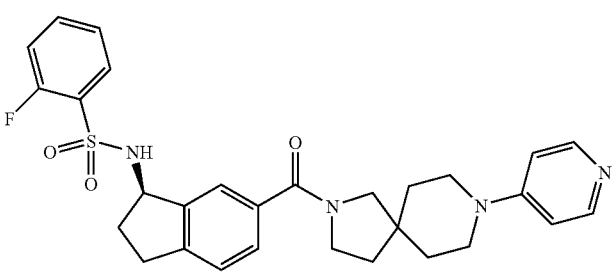 [SMILES: O=C(c1ccc2c(c1)[C@H](NS(=O)(=O)c1ccccc1F)CC2)N1CCC2(CCN(c3ccncc3)CC2)C1] | 2-Fluoro-N-[(1R)-6-(8-pyridin-4-yl-3,8-diazaspiro[4.5]decane-3-carbonyl)-2,3-dihydro-1H-inden-1-yl]-benzenesulfonic acid amide (H-116) |
| H-117 | 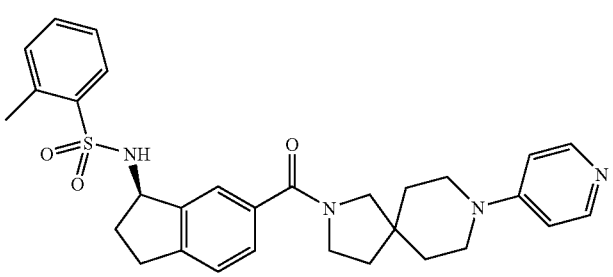 [SMILES: Cc1ccccc1S(=O)(=O)N[C@@H]1CCc2ccc(C(=O)N3CCC4(CCN(c5ccncc5)CC4)C3)cc21] | 2-Methyl-N-[(1R)-6-(8-pyridin-4-yl-3,8-diazaspiro[4.5]decane-3-carbonyl)-2,3-dihydro-1H-inden-1-yl]-benzensulfonic acid amide (H-117) |

TABLE-continued

| | | |
|---|---|---|
| H-118 | 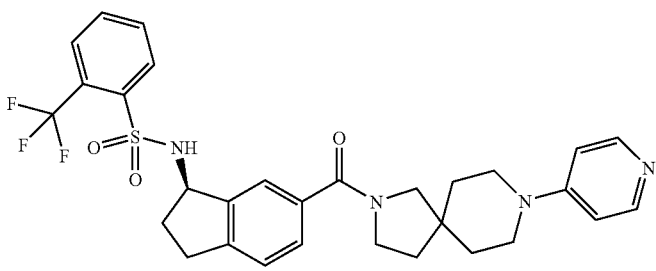 [SMILES: O=C(c1ccc2c(c1)[C@H](NS(=O)(=O)c1ccccc1C(F)(F)F)CC2)N1CCC2(CCN(c3ccncc3)CC2)C1] | N-[(1R)-6-(8-Pyridin-4-yl-3,8-diazaspiro[4.5]decane-3-carbonyl)-2,3-dihydro-1H-inden-1-yl]-2-(trifluoromethyl)-benzenesulfonic acid amide (H-118) |
| H-119 | 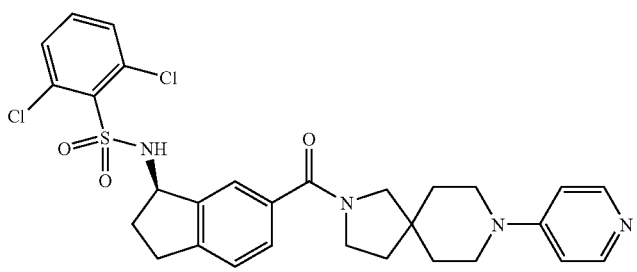 [SMILES: O=C(c1ccc2c(c1)[C@H](NS(=O)(=O)c1c(Cl)cccc1Cl)CC2)N1CCC2(CCN(c3ccncc3)CC2)C1] | 2,6-Dichloro-N-[(1R)-6-(8-pyridin-4-yl-3,8-diazaspiro[4.5]decane-3-carbonyl)-2,3-dihydro-1H-inden-1-yl]-benzenesulfonic acid amide (H-119) |
| H-120 | 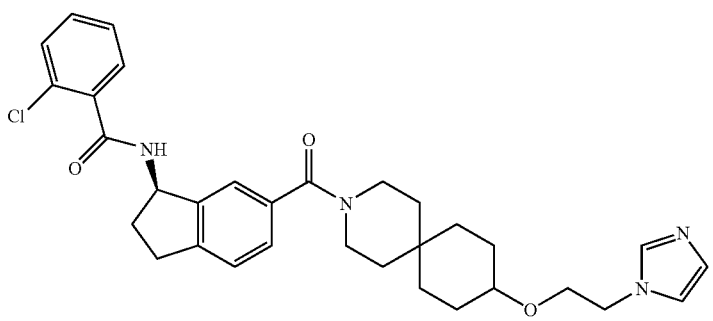 [SMILES: O=C(N[C@@H]1CCc2ccc(C(=O)N3CCC4(CCC(OCCn5ccnc5)CC4)CC3)cc21)c1ccccc1Cl] | 2-Chloro-N-[6-[9-[2-(1H-imidazol-1-yl)-ethoxy]-3-azaspiro[5.5]undecane-3-carbonyl]-2,3-dihydro-1H-inden-1-yl]-benzamide (H-120) |
| H-128 | 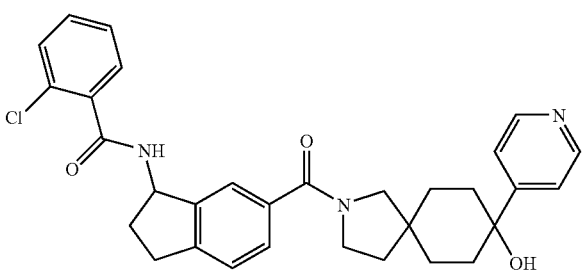 [SMILES: O=C(NC1CCc2ccc(C(=O)N3CCC4(CCC(O)(c5ccncc5)CC4)C3)cc21)c1ccccc1Cl] | 2-Chloro-N-[6-(8-hydroxy-8-pyridin-4-yl-3-azaspiro[4.5]decane-3-carbonyl)-2,3-dihydro-1H-inden-1-yl]-benzamide (H-128) |
| H-129 | 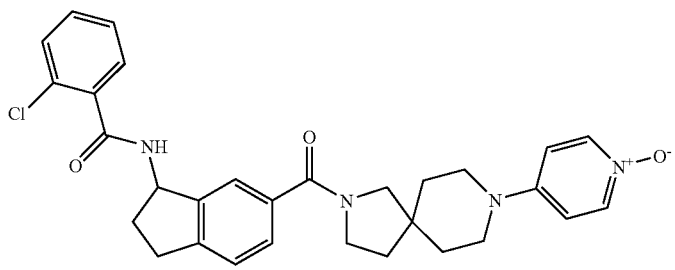 [SMILES: O=C(NC1CCc2ccc(C(=O)N3CCC4(CCN(c5cc[n+]([O-])cc5)CC4)C3)cc21)c1ccccc1Cl] | 2-Chloro-N-[6-[8-(1-oxido-pyridin-1-ium-4-yl)-3,8-diazaspiro[4.5]decane-3-carbonyl]-2,3-dihydro-1H-inden-1-yl]-benzamide (H-129) |

TABLE-continued

| H-130 | | 2-Chloro-N-[6-[8-[5-(trifluoromethyl)-pyrimidin-2-yl]-3,8-diazaspiro[4.5]decane-3-carobnyl]-2,3-dihydro-1H-inden-1-yl]-benzamide (H-10) |
| --- | --- | --- |
| H-131 | | 2-Chloro-N-[6-[9-(1H-imidazol-1-yl)-3-azaspiro[5.5]undecane-3-carbonyl]-2,3-dihydro-1H-inden-1-yl]-benzamide (H-131) |
| H-132 | | 2-Chloro-N-[3,3-dimethyl-6-(8-pyridin-4-yl-3,8-diazaspiro[4.5]decane-3-carbonyl)-1,2-dihydro-inden-1-yl]-benzamide (H-132) |
| H-133 | | 2-Chloro-N-[6-(8-pyridin-4-yl-3-azaspiro[4.5]decane-3-carbonyl)-2,3-dihydro-1H-inden-1-yl]-benzamide (H-133) |
| H-134 | | 5-Methyl-2-[(1R)-6-(8-pyridin-4-yl-3,8-diazaspiro[4.5]decane-3-carbonyl)-2,3-dihydro-1H-inden-1-yl]-1,2-dihydro-pyrrolo[2.1-e]imidazol-3-one (H-134) |

TABLE-continued

| | | |
|---|---|---|
| H-135 | 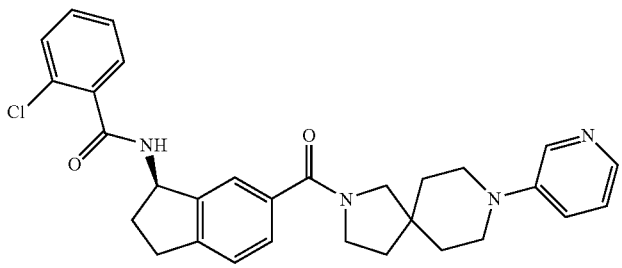 [SMILES: O=C(N[C@@H]1CCc2ccc(C(=O)N3CCC4(CCN(c5cccnc5)CC4)C3)cc21)c1ccccc1Cl] | 2-Chloro-N-[(1R)-6-(8-pyridin-3-yl-3-azaspiro[4.5]decane-3-carbonyl)-2,3-dihydro-1H-inden-1-yl]-benzamide (H-135) |
| H-136 | 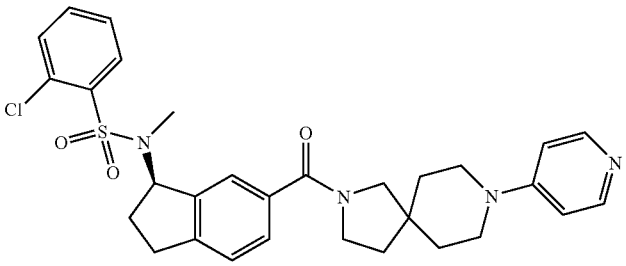 [SMILES: CN([C@@H]1CCc2ccc(C(=O)N3CCC4(CCN(c5ccncc5)CC4)C3)cc21)S(=O)(=O)c1ccccc1Cl] | 2-Chloro-N-methyl-N-[(1R)-6-(8-pyridin-4-yl-3,8-diazaspiro[4.5]decane-3-carbonyl)-2,3-dihydro-1H-inden-1-yl]-benzenesulfonic acid amide (H-136) |
| H-137 | 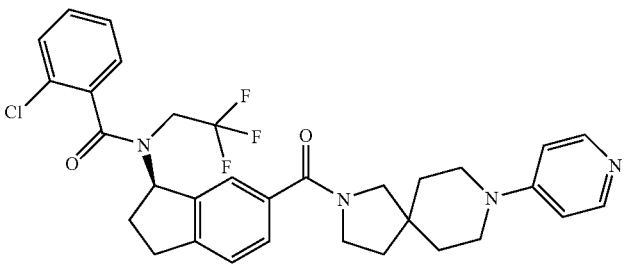 [SMILES: O=C(c1ccc2c(c1)[C@H](N(CC(F)(F)F)C(=O)c1ccccc1Cl)CC2)N1CCC2(CCN(c3ccncc3)CC2)C1] | 2-Chloro-N-[(1R)-6-(8-pyridin-4-yl-3,8-diazaspiro[4.5]decane-3-carbonyl)-2,3-dihydro-1H-inden-1-yl]-N-(2,2,2-trifluoro-ethyl)-benzamide (H-137) |
| H-138 | 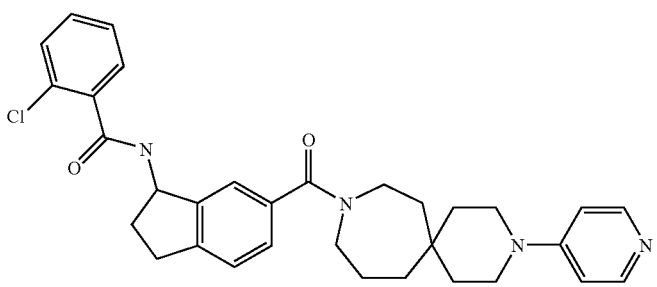 [SMILES: O=C(NC1CCc2ccc(C(=O)N3CCCC4(CC3)CCN(c3ccncc3)CC4)cc21)c1ccccc1Cl] | 2-Chloro-N-[6-(3-pyridin-4-yl-3,10-diazaspiro[5.6]dodecane-10-carbonyl)-2,3-dihydro-1H-inden-1-yl]-benzamide (H-138) |
| H-139 | 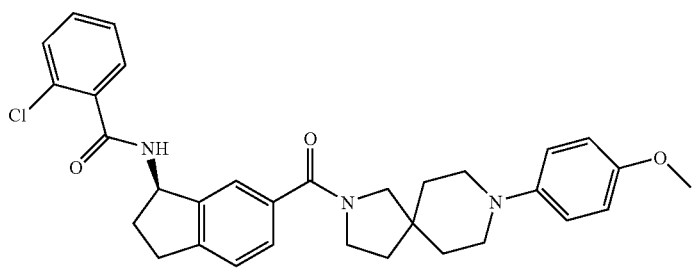 [SMILES: COc1ccc(N2CCC3(CCN(C(=O)c4ccc5c(c4)[C@H](NC(=O)c4ccccc4Cl)CC5)C3)CC2)cc1] | 2-Chloro-N-[(1R)-6-[8-(4-methoxyphenyl)-3,8-diazaspiro[4.5]decane-3-carbonyl]-2,3-dihydro-1H-inden-1-yl]-benzamide (H-139) |
| H-140 | 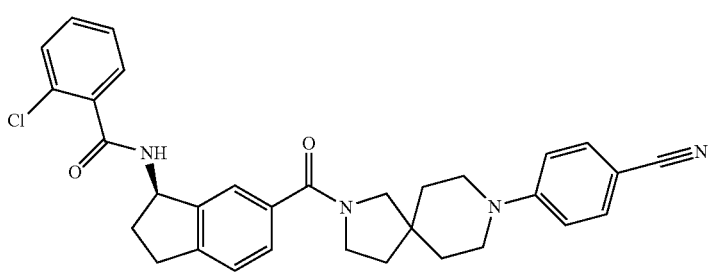 [SMILES: N#Cc1ccc(N2CCC3(CCN(C(=O)c4ccc5c(c4)[C@H](NC(=O)c4ccccc4Cl)CC5)C3)CC2)cc1] | 2-Chloro-N-[(1R)-6-[8-(4-cyano-phenyl)-3,8-diazaspiro[4.5]decane-3-carbonyl]-2,3-dihydro-1H-inden-1-yl]-benzamide (H-140) |

TABLE-continued

H-141 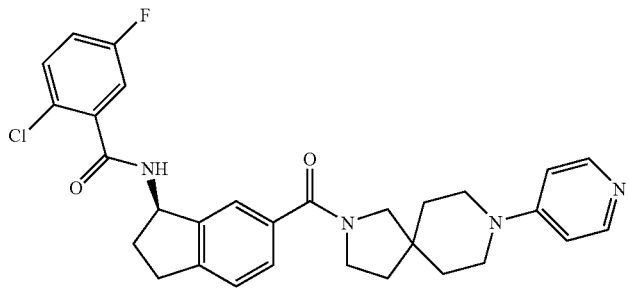 [SMILES: O=C(N[C@@H]1CCc2ccc(C(=O)N3CCC4(CCN(c5ccncc5)CC4)C3)cc21)c1cc(F)ccc1Cl] 2-Chloro-5-fluoro-N-[(1R)-6-(8-pyridin-4-yl-3,8-diazaspiro[4.5]decane-3-carbonyl)-2,3-dihydro-1H-inden-1-yl]-benzamide (H-141)

H-142 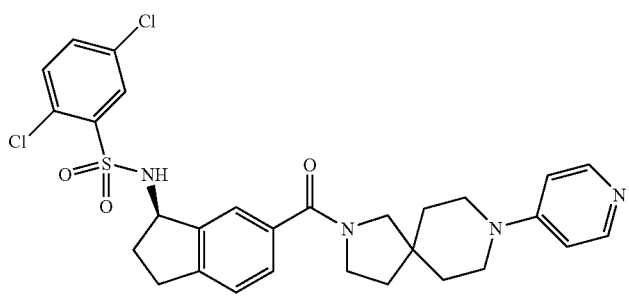 [SMILES: O=C(c1ccc2c(c1)[C@H](NS(=O)(=O)c1cc(Cl)ccc1Cl)CC2)N1CCC2(CCN(c3ccncc3)CC2)C1] 2,5-Dichloro-N-[(1R)-6-(8-pyridin-4-yl-3,8-diazaspiro[4.5]decane-3-carbonyl)-2,3-dihydro-1H-inden-1-yl]-benzenesulfonic acid amide (H-142)

H-143 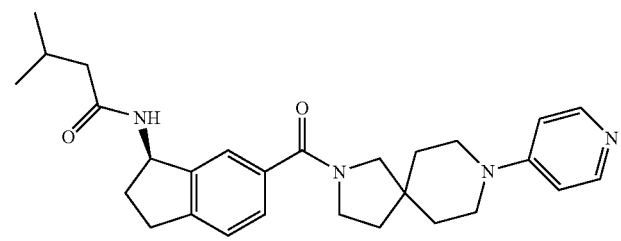 [SMILES: CC(C)CC(=O)N[C@@H]1CCc2ccc(C(=O)N3CCC4(CCN(c5ccncc5)CC4)C3)cc21] 3-Methyl-N-[(1R)-6-(8-pyridin-4-yl-3,8-diazaspiro[4.5]decane-3-carbonyl)-2,3-dihydro-1H-inden-1-yl]-butyramide (H-143)

H-144 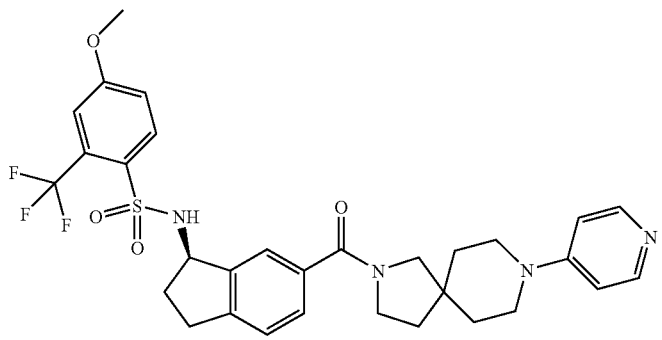 [SMILES: COc1ccc(S(=O)(=O)N[C@@H]2CCc3ccc(C(=O)N4CCC5(CCN(c6ccncc6)CC5)C4)cc32)c(C(F)(F)F)c1] 4-Methoxy-N-[(1R)-6-(8-pyridin-4-yl-3,8-diazaspiro[4.5]decane-3-carbonyl)-2,3-dihydro-1H-inden-1-yl]-2-(trifluoromethyl)-benzenesulfonic acid amide (H-144)

H-145 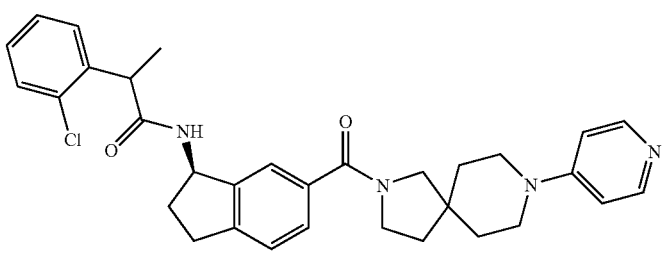 [SMILES: CC(C(=O)N[C@@H]1CCc2ccc(C(=O)N3CCC4(CCN(c5ccncc5)CC4)C3)cc21)c1ccccc1Cl] 2-(2-Chlorophenyl)-N-[(1R)-6-(8-pyridin-4-yl-3,8-diazaspiro[4.5]decane-3-carbonyl)-2,3-dihydro-H-inden-1-yl]-propionamide (H-145)

TABLE-continued

| | | |
|---|---|---|
| H-146 | | 2-(2-Chlorophenyl)-2-methyl-N-[(1R)-6-(8-pyridin-4-yl-3,8-diazaspiro[4.5]decane-3-carbonyl)-2,3-dihydro-1H-inden-1-yl]-propionamide (H-146) |
| H-147 | | 4-Methoxy-2-methyl-N-[(1R)-6-(8-pyridin-4-yl-3,8-diazaspiro[4.5]decane-3-carbonyl)-2,3-dihydro-1H-inden-1-yl]-benzenesulfonic acid amide (H-147) |
| H-148 | | 1-(2-Chlorophenyl)-N-[(1R)-6-(8-pyridin-4-yl-3,8-diazaspiro[4.5]decane-3-carbonyl)-2,3-dihydro-1H-inden-1-yl]-cyclopropane-1-carboxylic acid amide (H-148) |
| H-149 | | 2-Chloro-N-[(1R)-6-(8-pyridin-4-yl-3,8-diazaspiro[4.5]decane-3-carbonyl)-2,3-dihydro-1H-inden-1-yl]-6-(trifluoromethyl)-benzenesulfonic acid amide (H-149) |
| H-150 | | 1-(2-Chlorophenyl)-N-[(1R)-6-(8-pyridin-4-yl-3,8-diazaspiro[4.5]decane-3-carbonyl)-2,3-dihydro-1H-inden-1-yl]-methanesulfonic acid amide (H-150) |
| H-151 | | 2-(2-Chlorophenyl)-N-[(1R)-6-(8-pyridin-4-yl-3,8-diazaspiro[4.5]decane-3-carbonyl)-2,3-dihydro-1H-inden-1-yl]-acetamide H-151) |

TABLE-continued

| | | |
|---|---|---|
| H-152 | 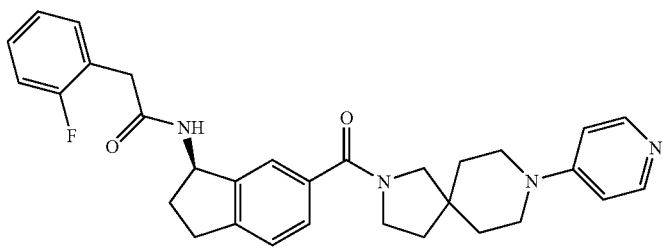 | 2-(2-Fluorophenyl)-N-[(1R)-6-(8-pyridin-4-yl-3,8-diazaspiro[4.5]decane-3-carbonyl)-2,3-dihydro-1H-inden-1-yl]-acetamide (H-152) |
| H-153 | 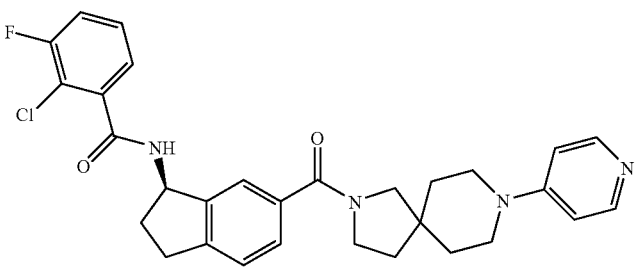 [SMILES: O=C(N[C@@H]1CCc2ccc(C(=O)N3CCC4(CCN(c5ccncc5)CC4)C3)cc21)c1cccc(F)c1Cl] | 2-Chloro-3-fluoro-N-[(1R)-6-(8-pyridin-4-yl-3,8-diazaspiro[4.5]decane-3-carbonyl)-2,3-dihydro-1H-inden-1-yl]-benzamide (H-153) |
| H-154 | 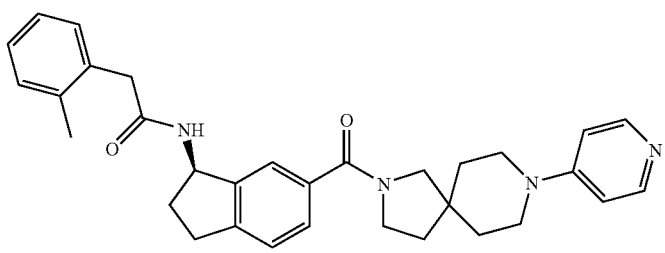 [SMILES: Cc1ccccc1CC(=O)N[C@@H]1CCc2ccc(C(=O)N3CCC4(CCN(c5ccncc5)CC4)C3)cc21] | 2-(o-Tolyl)-N-[(1R)-6-(8-pyridin-4-yl-3,8-diazaspiro[4.5]decane-3-carbonyl)-2,3-dihydro-1H-inden-1-yl]-acetamide (H-154) |
| H-155 | 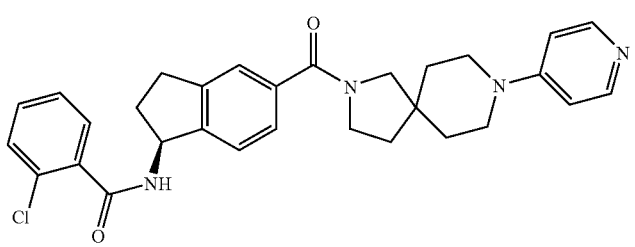 [SMILES: O=C(N[C@H]1CCc2cc(C(=O)N3CCC4(CCN(c5ccncc5)CC4)C3)ccc21)c1ccccc1Cl] | 7-Chloro-2-[(1S)-5-(8-pyridin-4-yl-3,8-diazaspiro[4.5]decane-3-carbonyl)-2,3-dihydro-1H-inden-1-yl]-2,3-dihydro-isoindol-1-one (H-155) |
| H-156 | 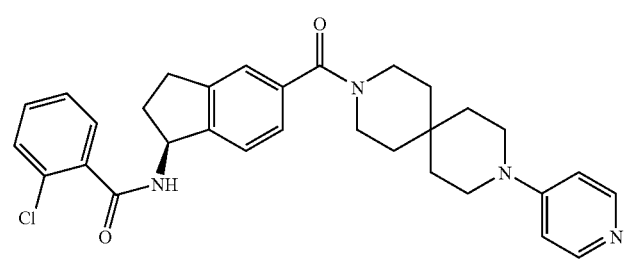 [SMILES: O=C(N[C@H]1CCc2cc(C(=O)N3CCC4(CC3)CCN(c3ccncc3)CC4)ccc21)c1ccccc1Cl] | 2-Chloro-N-[(1S)-5-(9-pyridin-4-yl-3,9-diazaspiro[5.5]undecane-3-carbonyl)-2,3-dihydro-1H-inden-1-yl]-benzamide (H-156) |
| H-157 | 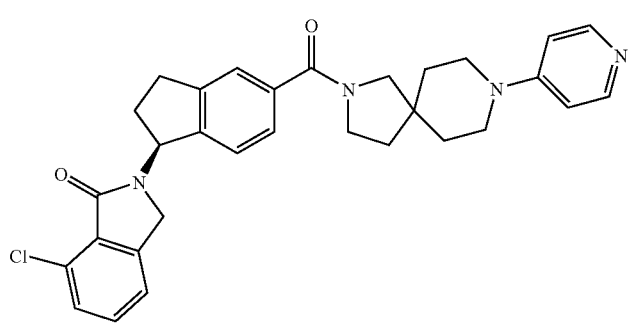 [SMILES: O=C(c1ccc2c(c1)CC[C@@H]2N1Cc2cccc(Cl)c2C1=O)N1CCC2(CCN(c3ccncc3)CC2)C1] | 2-Chloro-N-[(1S)-5-(8-pyridin-4-yl-3,8-diazaspiro[4.5]decane-3-carbonyl)-2,3-dihydro-1H-inden-1-yl]-benzamide (H-157) |

TABLE-continued

H-158 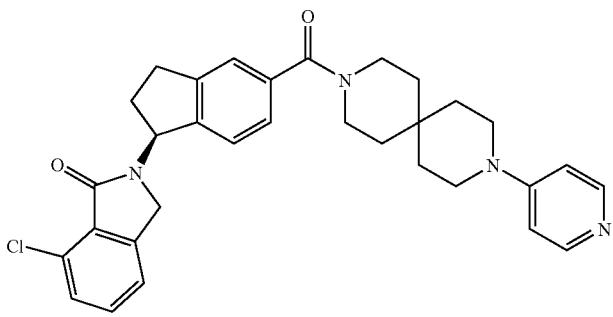 [SMILES: O=C(c1ccc2c(c1)CC[C@@H]2N1Cc2cccc(Cl)c2C1=O)N1CCC2(CC1)CCN(c1ccncc1)CC2] 7-Chloro-2-[(1S)-5-(9-pyridin-4-yl-3,9-diazaspiro[5.5]undecane-3-carbonyl)-2,3-dihydro-1H-inden-1-yl]-2,3-dihydro-isoindol-1-one (H-158)

H-159 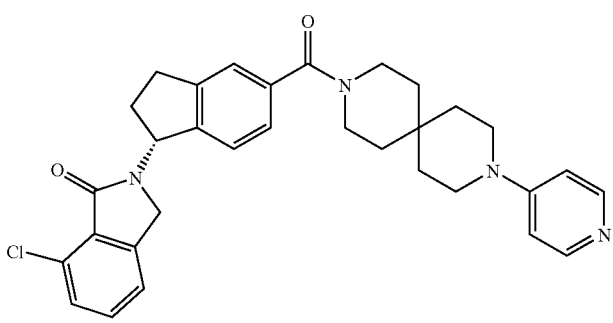 [SMILES: O=C(c1ccc2c(c1)CC[C@H]2N1Cc2cccc(Cl)c2C1=O)N1CCC2(CC1)CCN(c1ccncc1)CC2] 7-Chloro-2-[(1R)-5-(9-pyridin-4-yl-3,9-diazaspiro[5.5]undecane-3-carobnyl)-2,3-dihydro-1H-inden-1-yl]-2,3-dihydro-isoindol-1-one (H-15)

H-160 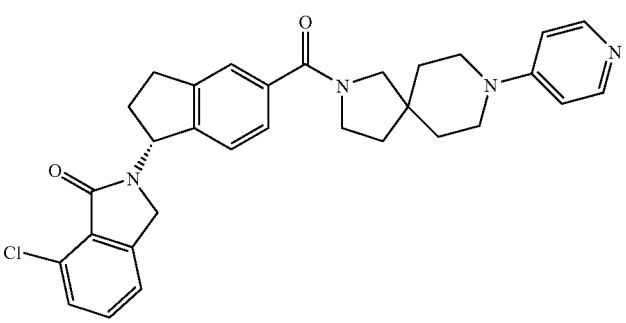 [SMILES: O=C(c1ccc2c(c1)CC[C@H]2N1Cc2cccc(Cl)c2C1=O)N1CCC2(CCN(c3ccncc3)CC2)C1] 7-Chloro-2-[(1R)-5-(8-pyridin-4-yl-3,8-diazaspiro[4.5]decane-3-carbonyl)-2,3-dihydro-1H-inden-1-yl]-2,3-dihydro-isoindol-1-one (H-160)

H-161 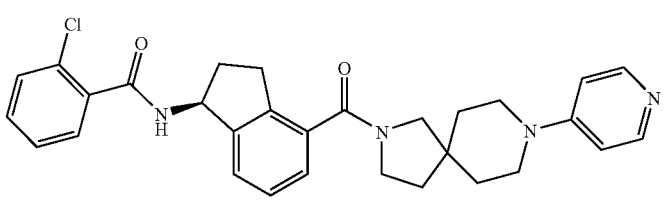 [SMILES: O=C(N[C@H]1CCc2c(C(=O)N3CCC4(CCN(c5ccncc5)CC4)C3)cccc21)c1ccccc1Cl] 2-Chloro-N-[(1S)-4-(8-pyridin-4-yl-3,8-diazaspiro[4.5]decane-3-carbonyl)-2,3-dihydro-1H-inden-1-yl]-benzamide (H-161)

H-162 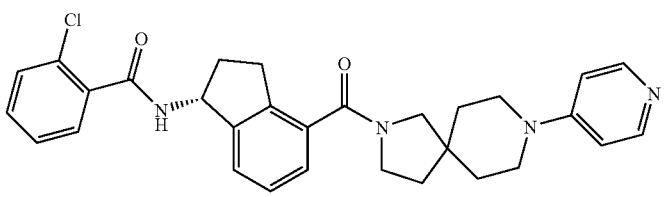 [SMILES: O=C(N[C@@H]1CCc2c(C(=O)N3CCC4(CCN(c5ccncc5)CC4)C3)cccc21)c1ccccc1Cl] 2-Chloro-N-[(1R)-4-(8-pyridin-4-yl-3,8-diazaspiro[4.5]decane-3-carbonyl)-2,3-dihydro-1H-inden-1-yl]-benzamide (H-162)

| | | |
|---|---|---|
| H-163 | 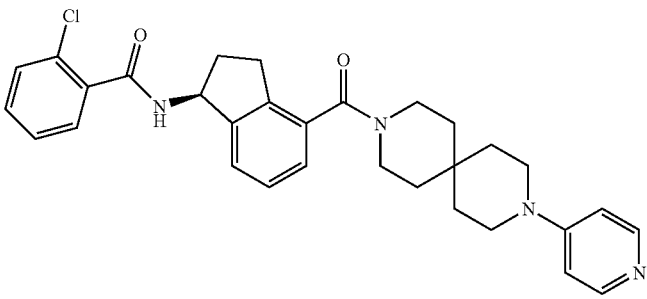 [SMILES: O=C(N[C@H]1CCc2c(C(=O)N3CCC4(CC3)CCN(c3ccncc3)CC4)cccc21)c1ccccc1Cl] | 2-Chloro-N-[(1S)-4-(9-pyridin-4-yl-3,9-diazaspiro[5.5]undecane-3-carbonyl)-2,3-dihydro-1H-inden-1-yl]-benzamide (H-163) |
| H-164 | 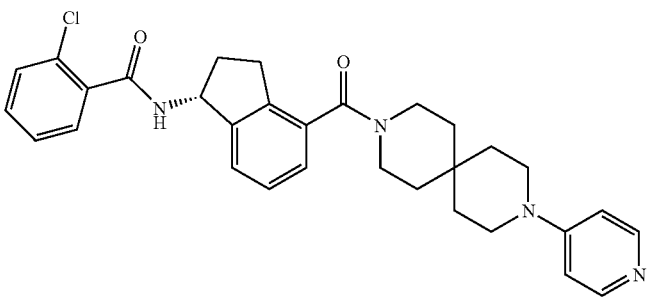 [SMILES: O=C(N[C@@H]1CCc2c(C(=O)N3CCC4(CC3)CCN(c3ccncc3)CC4)cccc21)c1ccccc1Cl] | 2-Chloro-N-[(1R)-4-(9-pyridin-4-yl-3,9-diazaspiro[5.5]undecane-3-carbonyl)-2,3-dihydro-1H-inden-1-yl]-benzamide (H-164) |
| H-165 | 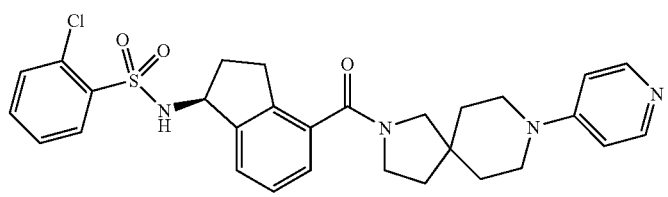 [SMILES: O=C(c1cccc2c1CC[C@@H]2NS(=O)(=O)c1ccccc1Cl)N1CCC2(CCN(c3ccncc3)CC2)C1] | 2-Chloro-N-[(1S)-4-(8-pyridin-4-yl-3,8-diazaspiro[4.5]decane-3-carbonyl)-2,3-dihydro-1H-inden-1-yl]-benzenesulfonic acid amide (H-165) |
| H-166 | 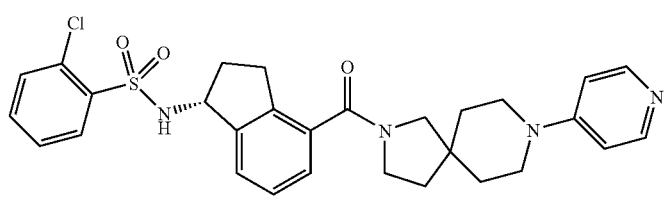 [SMILES: O=C(c1cccc2c1CC[C@H]2NS(=O)(=O)c1ccccc1Cl)N1CCC2(CCN(c3ccncc3)CC2)C1] | 2-Chloro-N-[(1R)-4-(8-pyridin-4-yl-3,8-diazaspiro[4.5]decane-3-carbonyl)-2,3-dihydro-1H-inden-1-yl]-benzenesulfonic acid amide (H-166) |
| H-167 | 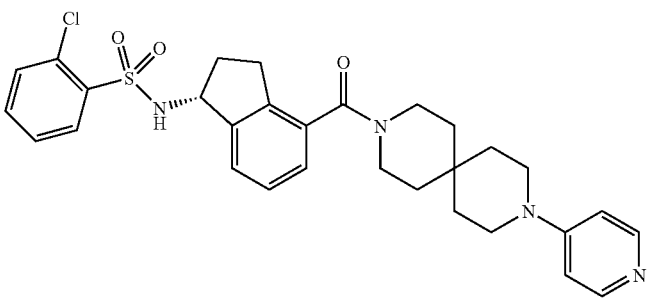 [SMILES: O=C(c1cccc2c1CC[C@H]2NS(=O)(=O)c1ccccc1Cl)N1CCC2(CC1)CCN(c1ccncc1)CC2] | 2-Chloro-N-[(1R)-4-(9-pyridin-4-yl-3,9-diazaspiro[5.5]undecane-3-carbonyl)-2,3-dihydro-1H-inden-1-yl]-benzenesulfonic acid amide (H-167) |
| H-168 | 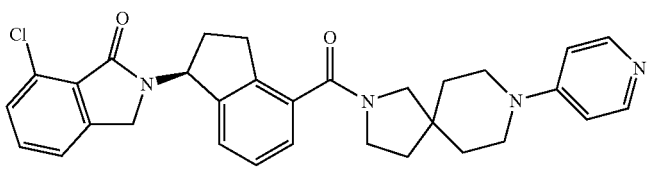 [SMILES: O=C(c1cccc2c1CC[C@@H]2N1Cc2cccc(Cl)c2C1=O)N1CCC2(CCN(c3ccncc3)CC2)C1] | 7-Chloro-2-[(1S)-4-(8-pyridin-4-yl-3,8-diazaspiro[4.5]decane-3-carbonyl)-2,3-dihydro-1H-inden-1-yl]-2,3-dihydro-isoindol-1-one (H-168) |

TABLE-continued

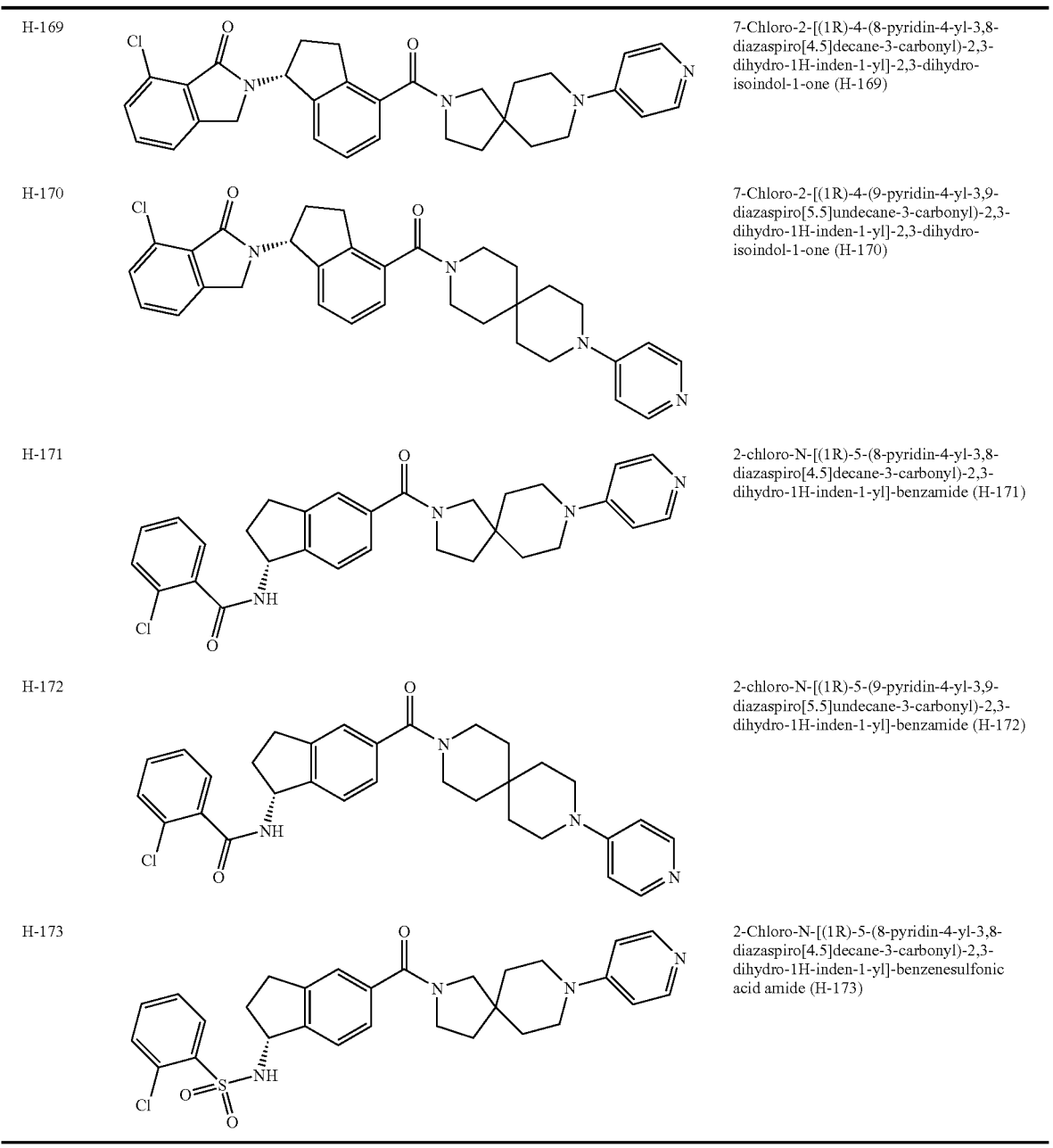

H-169 7-Chloro-2-[(1R)-4-(8-pyridin-4-yl-3,8-diazaspiro[4.5]decane-3-carbonyl)-2,3-dihydro-1H-inden-1-yl]-2,3-dihydro-isoindol-1-one (H-169)

H-170 7-Chloro-2-[(1R)-4-(9-pyridin-4-yl-3,9-diazaspiro[5.5]undecane-3-carbonyl)-2,3-dihydro-1H-inden-1-yl]-2,3-dihydro-isoindol-1-one (H-170)

H-171 2-chloro-N-[(1R)-5-(8-pyridin-4-yl-3,8-diazaspiro[4.5]decane-3-carbonyl)-2,3-dihydro-1H-inden-1-yl]-benzamide (H-171)

H-172 2-chloro-N-[(1R)-5-(9-pyridin-4-yl-3,9-diazaspiro[5.5]undecane-3-carbonyl)-2,3-dihydro-1H-inden-1-yl]-benzamide (H-172)

H-173 2-Chloro-N-[(1R)-5-(8-pyridin-4-yl-3,8-diazaspiro[4.5]decane-3-carbonyl)-2,3-dihydro-1H-inden-1-yl]-benzenesulfonic acid amide (H-173)

| Example no. | Amino acid (ACI) | Amine (AMN) | Synthesis according to | Yield | Comments |
|---|---|---|---|---|---|
| H-01 | (G-01) | (AMN-01) | GWI-1 | 69% (0.27 mmol) | purification by column chromatography MC/MeOH 99:1 → 96:4 |
| H-02 | (E-01) | (AMN-01) | GWI-1 | 27% (0.54 mmol) | purification by column chromatography:silica; MC/MeOH |
| H-03 | (F-01) | (AMN-01) | GWI-1 | 68% (0.24 mmol) | Recrystallization from MC |
| H-04 | (E-01) | (AMN-02) | GWI-2 | 80% (0.38 mmol) | purification by column chromatography:silica; EA:MeOH:ammonia 10:1:0.05 |

TABLE-continued

| | | | | | |
|---|---|---|---|---|---|
| H-05 | (E-01) | (AMN-03) | GWI-2 | 66% (0.52 mmol) | purification by column chromatography: silica; EA:MeOH:ammonia 10:1:0.05 |
| H-06 | (E-01) | (AMN-04) | GWI-2 | 81% (0.51 mmol) | purification by column chromatography:silica; ethyl acetate/methanol 4:1 + $NH_3$ |
| H-07 | (E-01) | (AMN-05) | GWI-2 | 73% (0.46 mmol) | purification by column chromatography:silica; ethyl acetate/hexane 5:1 |
| H-08 | (E-01 | (AMN-06) | GWI-2 | 77% (0.61 mmol) | purification by chromatography:silica; EA:MeOH:ammonia 10:1:0.05 |
| H-09 | (E-06) | (AMN-01) | GWI-2 | 73% (0.44 mmol) | 1 equiv. amine and 2 equiv. N-ethyl-diisopropylamine |
| H-10 | (E-07) | (AMN-01) | GWI-2 | 73% (0.44 mmol) | 1 equiv. amine and 2 equiv. N-ethyl-diisopropylamine |
| H-11 | (E-06) | (AMN-03) | GWI-2 | 99% (0.45 mmol) | 1 equiv. amine and 2 equiv. N-ethyl-diisopropylamine |
| H-12 | (E-07) | (AMN-03) | GWI-2 | 99% (0.36 mmol) | 1 equiv. amine and 2 equiv. N-ethyl-diisopropylamine |
| H-13 | (G-03) | (AMN-03) | GWI-2 | 97% (0.43 mmol) | 1 equiv. amine and 2 equiv. N-ethyl-diisopropylamine |
| H-14 | (G-03) | (AMN-01) | GWI-2 | 89% (0.46 mmol) | 1 equiv. amine and 2 equiv. N-ethyl-diisopropylamine |
| H-15 | (G-02) | (AMN-03) | GWI-2 | 93% (0.46 mmol) | 1 equiv. amine and 2 equiv. N-ethyl-diisopropylamine |
| H-16 | (F-03) | (AMN-03) | GWI-2 | 97% (0.32 mmol) | 1 equiv. amine and 2 equiv. N-ethyl-diisopropylamine |
| H-17 | (F-03) | (AMN-01) | GWI-2 | 65% (0.33 mmol) | 1 equiv. amine and 2 equiv. N-ethyl-diisopropylamine |
| H-18 | (F-02) | (AMN-03) | GWI-2 | 84% (0.32 mmol) | 1 equiv. amine and 2 equiv. N-ethyl-diisopropylamine |
| H-19 | (F-02) | (AMN-01) | GWI-2 | 86% (0.19 mmol) | 1 equiv. amine and 2 equiv. N-ethyl-diisopropylamine |
| H-20 | (E-02) | (AMN-03) | GWI-2 | 43% (0.27 mmol) | 1 equiv. amine and 2 equiv. N-ethyl-diisopropylamine |
| H-21 | (E-03) | (AMN-03) | GWI-2 | 92% (0.87 mmol) | 1 equiv. amine and 2 equiv. N-ethyl-diisopropylamine |
| H-22 | (E-05) | (AMN-01) | GWI-2 | 89% (0.28 mmol) | 1 equiv. amine and 2 equiv. N-ethyl-diisopropylamine |
| H-23 | (E-05) | (AMN-03) | GWI-2 | 69% (0.22 mmol) | 1 equiv. amine and 2 equiv. N-ethyl-diisopropylamine plus HCl precipitation |
| H-24 | (E-04) | (AMN-03) | GWI-4 | 65% (0.31 mmol) | HCl precipitation |

TABLE-continued

| | | | | | |
|---|---|---|---|---|---|
| H-25 | (E-04) | (AMN-01) | GWI-4 | 71% (0.25 mmol) | |
| H-26 | (E-03) | (AMN-07) | GWI-5 | 89% (0.28 mmol) | |
| H-27 | (E-03) | (AMN-08) | GWI-5 | 92% (0.44 mmol) | |
| H-28 | (E-03) | (AMN-09) | GWI-5 | 29% (0.09 mmol) | |
| H-29 | (E-03) | (AMN-10) | GWI-5 | 88% (0.36 mmol) | |
| H-31 | (E-03) | (AMN-12) | GWI-5 | 33% (0.11 mmol) | |
| H-32 | (E-03) | (AMN-13) | GWI-4 | 99% (0.41 mmol) | |
| H-33 | (E-03) | (AMN-14) | GWI-5 | 60% (0.28 mmol) | |
| H-34 | (E-03) | (AMN-15) | GWI-5 | 71% (0.27 mmol) | |
| H-35 | (E-03) | (AMN-16) | GWI-5 | 92% (0.35 mmol) | |
| H-36 | (E-03) | (AMN-17) | GWI-5 | 61% (0.39 mmol) | |
| H-37 | (E03) | (AMN-18) | GWI-4 | 95% (0.51 mmol) | |
| H-38 | (E03) | (AMN-19) | GWI-4 | 58% (0.109 mmol) | |
| H-39 | (E-01) | (AMN-20) | GWI-6 | 42% | |
| H-40 | (E-01) | (AMN-21) | GWI-7 | 52% | |
| H-41 | (E-01) | (AMN-22) | GWI-7 | 65% | |
| H-42 | (E-01) | (AMN-23) | GWI-7 | 50% | |
| H-43 | (E-01) | (AMN-24) | GWI-7 | 30% | |
| H-44 | (E-01) | (AMN-25) | GWI-6 | 42% | |
| H-45 | (E-01) | (AMN-26) | GWI-6 | 55% | |
| H-46 | (E-01) | (AMN-27) | GWI-6 | 30% | HATU (1 equiv), DIPEA (3 equiv.) |
| H-47 | (E-08) | (AMN-03) | GWI-7 | 30% | |
| H-48 | (E-01) | (AMN-28) | GWI-6 | 29% | HATU (1.2 equiv.), DIPEA (3 equiv.) |
| H-49 | | | | | see below |
| H-50 | (E-01) | (A-29) | GWI-6 | 58% | HATU (1.1 equiv.), DIPEA (2.5 equiv.) |
| H-51 | (E-01) | (A-30) | GWI-6 | 30% | HATU (1.1 equiv.), DIPEA (3.5 equiv.) |
| H-52 | (E03) | (AMN-31) | GWI-5 | 37% | |
| H-53 | (E-09) | (AMN-03) | GWI-5 | 56% | (reaction times were adapted) |
| H-54 | | | | | see below |
| H-55 | (E03) | (AMN-32 | GWI-5 | 77% | |
| H-56 | (E-10) | (AMN-03) | GWI-5 | 86% | |
| H-57 | (E-11) | (AMN-33) | GWI-5 | 67% | |
| H-58 | (E-11) | (AMN-01) | GWI-5 | 93% | |
| H-59 | (E-12) | (AMN-33) | GWI-5 | 62% | |
| H-60 | (E-13) | (AMN-33) | GWI-5 | 82% | |
| H-61 | (E-14) | (AMN-03) | GWI-5 | 86% | |
| H-62 | (E03) | (AMN-34) | GWI-5 | 19% | |
| H-63 | (E-13) | (AMN-03) | GWI-5 | 99% | |
| H-64 | (E-15) | (AMN-03) | GWI-5 | 28% | HCl-salt precipitation with 3 equiv. HCl in diethyl ether/acetone |
| H-65 | (E-16) | (AMN-03) | GWI-5 | 35% | |
| H-66 | (E-12) | (AMN-01) | GWI-5 | 90% | |
| H-67 | (E-11) | (AMN-03) | GWI-5 | 83% | |
| H-68 | (E-10) | (AMN-33) | GWI-5 | >99% | |
| H-69 | (E-06) | (AMN-14) | GWI-5 | 64% | |
| H-70 | (E-06) | (AMN-15) | GWI-5 | 70% | |
| H-71 | (E-06) | (AMN-08) | GWI-5 | 80% | |
| H-72 | (E-06) | (AMN-33) | GWI-8 | 75% | |
| H-73 | (E-17) | (AMN-03) | GWI-5 | 85% | |
| H-74 | (E-18) | (AMN-03) | GWI-5 | 96% | (reaction times were adapted) |

| | | | | | |
|---|---|---|---|---|---|
| H-75 | (E-18) | (AMN-33) | GWI-5 | 79% | |
| H-76 | (E-19) | (AMN-03) | GWI-5 | 87% | |
| H-77 | (E-17) | (AMN-33) | GWI-5 | 55% | |
| H-78 | (E-17) | (AMN-01) | GWI-5 | 87% | |
| H-79 | (E-06) | (AMN-02) | GWI-5 | 73% | |
| H-80 | (E-06) | (AMN-07) | GWI-5 | 85% | |
| H-81 | (E-06) | (AMN-15) | GWI-5 | 71% | |
| H-82 | (E-20) | (AMN-03) | GWI-5 | 76% | |
| H-83 | (E-19) | (AMN-33) | GWI-5 | 83% | |
| H-84 | (E-21) | (AMN-03) | GWI-5 | 59% | |
| H-85 | (E-19) | (AMN-01) | GWI-5 | 80% | (reaction times were adapted) |
| H-86 | (E-21) | (AMN-33) | GWI-5 | 12% | (reaction times were adapted) |
| H-87 | (E-20) | (AMN-33) | GWI-5 | 76% | |
| H-88 | (E-20) | (AMN-01) | GWI-5 | 80% | |
| H-89 | (E-15) | (AMN-33) | GWI-5 | 80% | |
| H-90 | (E-15) | (AMN-01) | GWI-5 | 78% | |
| H-91 | (E03) | (AMN-33) | GWI-5 | 61% | (reaction times were adapted) |
| H-92 | (E-16) | (AMN-01) | GWI-5 | 19% | |
| H-93 | (E-12) | (AMN-03) | GWI-5 | 79% | |
| H-94 | (E-22) | (AMN-03) | GWI-5 | >99% | |
| H-95 | (E-22) | (AMN-01) | GWI-5 | 93% | |
| H-96 | (G-07) | (AMN-03) | GWI-5 | 83% | |
| H-97 | (E03) | (AMN-35) | GWI-5 | 70% | |
| H-98 | (E-24) | (AMN-03) | GWI-5 | 67% | |
| H-99 | (E-25) | (AMN-03) | GWI-5 | 74% | |
| H-100 | (E-25) | (AMN-01) | GWI-5 | 83% | |
| H-101 | (E-26) | (AMN-03) | GWI-5 | 84% | |
| H-102 | (E-26) | (AMN-01) | GWI-5 | 41% | |
| H-103 | (E-27) | (AMN-03) | GWI-5 | 94% | (reation times were adapted) |
| H-104 | (E-28) | (AMN-03) | GWI-5 | 91% | |
| H-105 | (F-04) | (AMN-03) | GWI-5 | 55% | |
| H-106 | (F-05) | (AMN-03) | GWI-5 | 55% | |
| H-107 | (E-29) | (AMN-03) | GWI-5 | 84% | |
| H-108 | (E-30) | (AMN-03) | GWI-5 | 83% | |
| H-109 | (E-30) | (AMN-03) | GWI-5 | 63% | |
| H-110 | (E-31) | (AMN-03) | GWI-5 | 95% | |
| H-111 | (E03) | (AMN-36) | GWI-5 | 56% | corresponding HCl-salt was precipitated |
| H-112 | (E03) | (AMN-37) | GWI-5 | 71% | |
| H-113 | (F-06) | (AMN-03) | GWI-5 | 79% | |
| H-114 | (E-32) | (AMN-03) | GWI-5 | 49% | |
| H-115 | (E-33) | (AMN-03) | GWI-5 | 87% | |
| H-116 | (F-07) | (AMN-03) | GWI-5 | >99% | |
| H-117 | (F-08) | (AMN-03) | GWI-5 | 57% | (reaction times were adapted) |
| H-118 | (F-09) | (AMN-03) | GWI-5 | 86% | |
| H-119 | (F-10) | (AMN-03) | GWI-5 | >99% | (reaction times were adapted) |
| H-120 | (E-01) | (AMN-38) | GWI-6 | 23% | HATU (1.0 equiv.), DIPEA (3 equiv.) |
| H-128 | (E-01) | (AMN-39) | GWI-6 | 20% (0.283 mmol) | HATU (1.2 equiv.), DIPEA (3 equiv.) |
| H-129 | | | | see below | |
| H-130 | (E-01) | (AMN-41) | GWI-6 | 25% (0.19 mmol) | HATU (1.1 equiv.), DIPEA (5 equiv.) |
| H-131 | (E-01) | (AMN-42) | GWI-6 | 16% (0.55 mmol) | HATU (1.0 equiv.), DIPEA (2 equiv.) |
| H-132 | (E-39) | (AMN-03) | GWI-6 | 44% (0.34 mmol) | |
| H-133 | (E-01) | (AMN-43) | GWI-6 | 24% (0.193 mmol) | HATU (1.2 equiv.), DIPEA (3 equiv.) |
| H-134 | (G-06) | (AMN-03) | GWI-6 | 55% (0.185 mmol) | HATU (1.1 equiv.), DIPEA (5 equiv.) |
| H-135 | (E03) | (AMN-44) | GWI-6 | 25% (0.196 mmol) | HATU (1.2 equiv.), DIPEA (3 equiv.) |

TABLE-continued

| | | | | | |
|---|---|---|---|---|---|
| H-136 | (F-16) | (AMN-03) | GWI-7 | 31% (0.739 mmol) | |
| H-137 | (E-41) | (AMN-03) | GWI-7 | 22% (0.25 mmol) | (instead of HOBt HOAt (1.5 equiv.)) |
| H-138 | (E-01) | (AMN-45) | GWI-6 | 21% (0.147 mmol). | HATU (1.1 equiv.), DIPEA (4 equiv.) |
| H-139 | (E03) | (AMN-47) | GWI-6 | 58% (0.333 mmol) | HATU (1.2 equiv.), DIPEA (5 equiv.) |
| H-140 | (E03) | (AMN-46) | GWI-6 | 58% (0.59 mmol) | HATU (1.0 eqiv.), DIPEA (3 equiv.) |
| H-141 | (E-42) | (AMN-03) | GWI-5 | 72% | |
| H-142 | (F-11) | (AMN-03) | GWI-5 | 96% | |
| H-143 | (E-43) | (AMN-30) | GWI-5 | 74% | |
| H-144 | (F-12) | (AMN-03) | GWI-5 | 59% | |
| H-145 | (E-44) | (AMN-03) | GWI-5 | 87% | (reaction times were adapted) |
| H-146 | (E-45) | (AMN-03) | GWI-5 | 70% | |
| H-147 | (F-13) | (AMN-03) | GWI-5 | 20% | |
| H-148 | (E-46) | (AMN-03) | GWI-5 | 70% | |
| H-149 | (F-14) | (AMN-03) | GWI-5 | 75% | |
| H-150 | (F-15) | (AMN-03) | GWI-5 | 86% | |
| H-151 | (E-47) | (AMN-03) | GWI-5 | 87% | |
| H-152 | (E-48) | (AMN-03) | GWI-5 | 76% | |
| H-153 | (E-49) | (AMN-03) | GWI-5 | 83% | |
| H-154 | (E-50) | (AMN-03) | GWI-5 | 74% | |
| H-155 | (E-51) | (AMN-03) | GWI-5 | 80% | |
| H-156 | (E-51) | (AMN-01) | GWI-5 | 89% | |
| H-157 | (G-08) | (AMN-03) | GWI-5 | 50% | |
| H-158 | (G-08) | (AMN-01) | GWI-5 | 48% | |
| H-159 | (G-09) | (AMN-01) | GWI-5 | 76% | |
| H-160 | (G-09) | (AMN-03) | GWI-5 | 72% | |
| H-161 | (E-52) | (AMN-03) | GWI-5 | >99% | |
| H-162 | (E-53) | (AMN-03) | GWI-5 | 98% | |
| H-163 | (E-52) | (AMN-01) | GWI-5 | 83% | |
| H-164 | (E-53) | (AMN-01) | GWI-5 | 84% | |
| H-165 | (F-17) | (AMN-03) | GWI-5 | >99% | |
| H-166 | (F-18) | (AMN-03) | GWI-5 | 88% | |
| H-167 | (F-18) | (AMN-01) | GWI-5 | 68% | |
| H-168 | (G-11) | (AMN-03) | GWI-5 | 76% | |
| H-169 | (G-10) | (AMN-03) | GWI-5 | >99% | |
| H-170 | (G-10) | (AMN-01) | GWI-5 | 32% | |
| H-171 | (E-54) | (AMN-03) | GWI-5 | 74% | |
| H-172 | (E-54) | (AMN-01) | GWI-5 | 84% | |
| H-173 | (F-19) | (AMN-03) | GWI-5 | 93% | |

Notes: Typical reaction scale 0.15-0.7 mmol.

Synthesis of the Individual Substance h-49

2-Chloro-N-methyl-N-[6-(8-pyridin-4-yl-3,8-diaza-spiro[4.5]decane-3-carbonyl)-2,3-dihydro-1H-inden-1-yl]-benzamide (H-49)

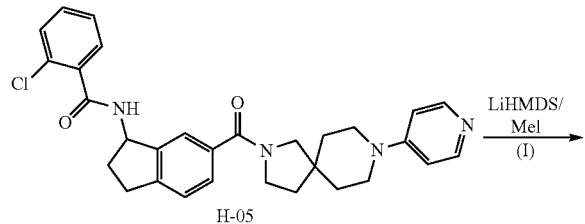

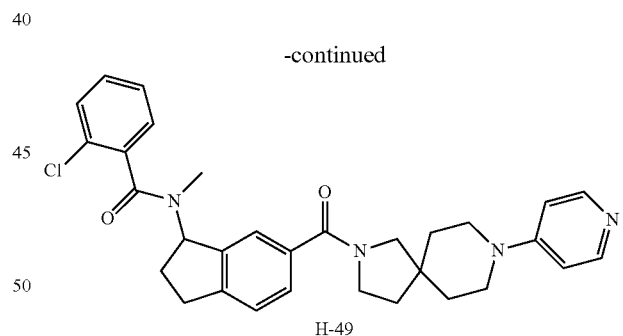

(I) LiHMDS (0.72 mmol, 1.5 eq., 1M solution in THF) was added dropwise to a cooled (0° C.) solution of compound (H-05) (0.486 mmol, 1 eq.) in THF. The reaction mixture was stirred for 20 min and MeI (0.534 mmol, 1.1 eq.) was then added at 0° C. The mixture was stirred at 25° C. for 3 h. The reaction mixture was quenched with water (5 ml) and extracted with methylene chloride (3×25 ml). The organic phase was washed successively with $NH_4Cl$ solution (15 ml), water (15 ml) and sat. NaCl solution (15 ml) and dried over sodium sulfate. The solvent was concentrated on a rotary evaporator and the crude product was purified by column chromatography (silica gel, 3% methanol in methylene chloride) in order to obtain the desired product (H-49). Yield: 46%

339
Synthesis of the Individual Substance H-54

2-Chloro-N-[(1R)-6-(9-pyridin-4-yl-2,9-diazaspiro[5.5]undecane-2-carbonyl)-2,3-dihydro-1H-inden-1-yl]-benzamide (H-54)

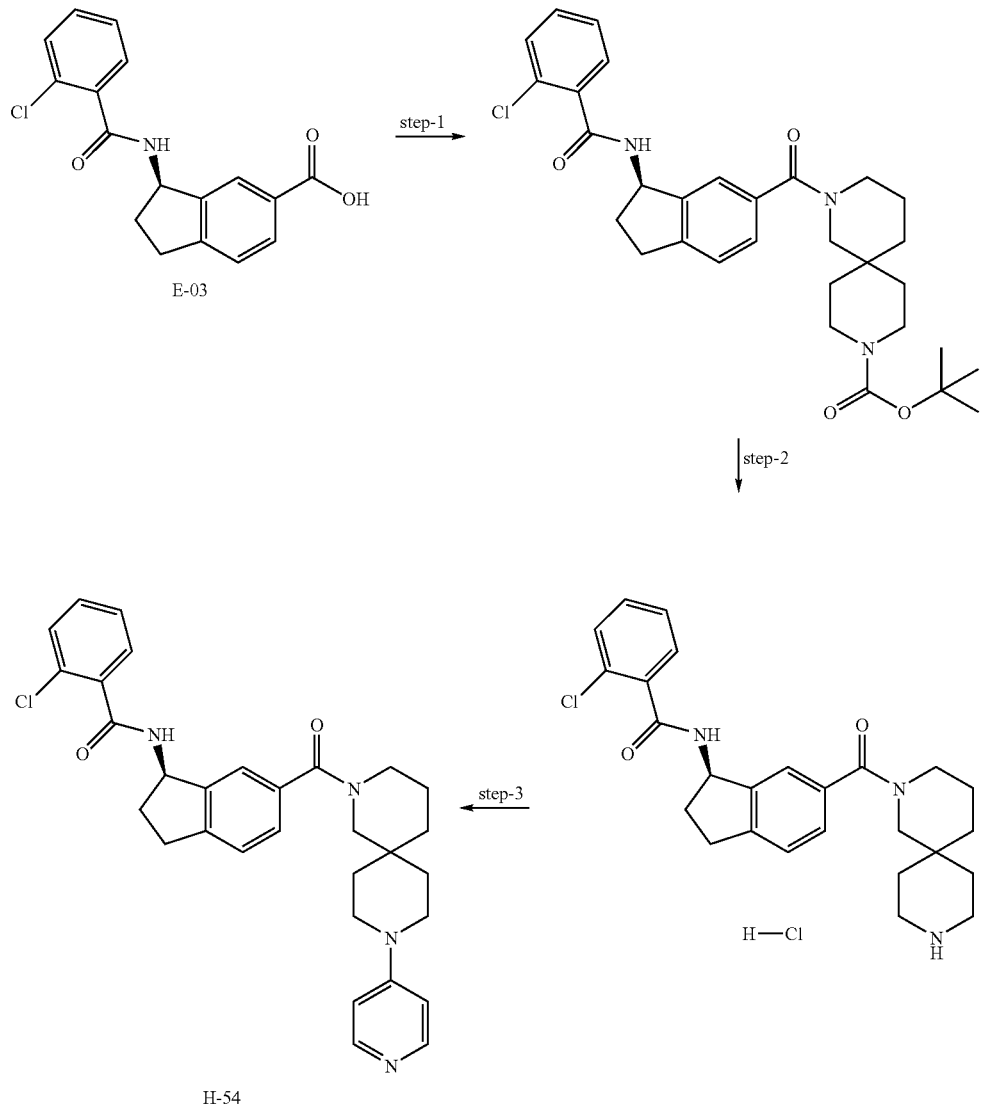

340
reaction mixture was washed in each case 1× with 10% NH₄Cl solution, sat. NaHCO₃ solution and sat. NaCl solution. The organic phase was dried over sodium sulfate, filtered and concentrated in vacuo. The crude product was purified by column chromatography (silica; ethyl acetate/hexane/ammonia (25 aq.) 70:10:0.8). Yield: 70%

Step 1

(R)-tert-Butyl 2-(3-(2-chlorobenzamido)-2,3-dihydro-1H-indene-5-carbonyl)-2,9-diazaspiro[5.5]undecane-9-carboxylate N-Ethyl-diisopropylamine (4 eq.) was added to a solution of (3R)-3-[(2-chloro-benzoyl)amino]-2,3-dihydro-1H-indene-5-carboxylic acid (E-03) (0.952 mmol, 1 eq.) in methylene chloride (18 ml). The reaction mixture was cooled to 0° C. and N-ethyl-N'-3-(dimethylamino)-propyl-carbodiimide hydrochloride (1.2 eq.) and 1-hydroxybenzotriazole hydrate (0.2 eq.) were then added. The mixture was stirred at this temperature for 15 min, before tert-butyl 2,9-diazaspiro[5.5]undecane-9-carboxylate (1.1 eq.) was added. The reaction mixture was stirred at room temperature for 2.5 d. Then, the

Step 2

(R)—N-(6-(2,9-Diazaspiro[5.5]undecane-2-carbonyl)-2,3-dihydro-1H-inden-1-yl)-2-chlorobenzamide hydrochloride Acetyl chloride (5 eq.) was added to an ice-cold solution of (R)-tert-butyl 2-(3-(2-chlorobenzamido)-2,3-dihydro-1H-indene-5-carbonyl)-2,9-diazaspiro[5.5]undecane-9-carboxylate (0.652 mmol, 1 eq.) in ethanol. The reaction mixture was then stirred at room temperature overnight. The solvent was concentrated in vacuo and the residue was dissolved in ethanol/acetone (1:3, 5 ml) and diethyl ether (100 ml) was added. The white solid was filtered out, washed with diethyl ether and dried in vacuo. Yield: 82%

Step 3

2-Chloro-N-[(1R)-6-(9-pyridin-4-yl-2,9-diazaspiro[5.5]undecane-2-carbonyl)-2,3-dihydro-1H-inden-1-yl]-benzamide (H-54)

A mixture of (R)—N-(6-(2,9-diazaspiro[5.5]undecane-2-carbonyl)-2,3-dihydro-1H-inden-1-yl)-2-chlorobenzamide hydrochloride (0.491 mmol, 1.0 eq.), triethylamine (5.0 eq.) and 4-chloropyridine hydrochloride (3.0 eq.) in n-butanol (13 ml) was stirred at 110° C. overnight. Ethyl acetate and sat. NaHCO₃ solution were added and the aqueous phase was extracted with ethyl acetate a further 4×. The combined organic phases were washed 1× with sat. NaCl solution, dried over sodium sulfate, filtered and concentrated in vacuo. The crude product was purified by column chromatography (silica, ethyl acetate/ethanol/ammonia (25% aq) 100:10:1) to obtain the desired product (H-54). Yield: 73%

Synthesis of the Individual Substance H-129

2-Chloro-N-[6-[8-(1-oxido-pyridin-1-ium-4-yl)-3,8-diazaspiro[4.5]decane-3-carbonyl]-2,3-dihydro-1H-inden-1-yl]-benzamide (H-129)

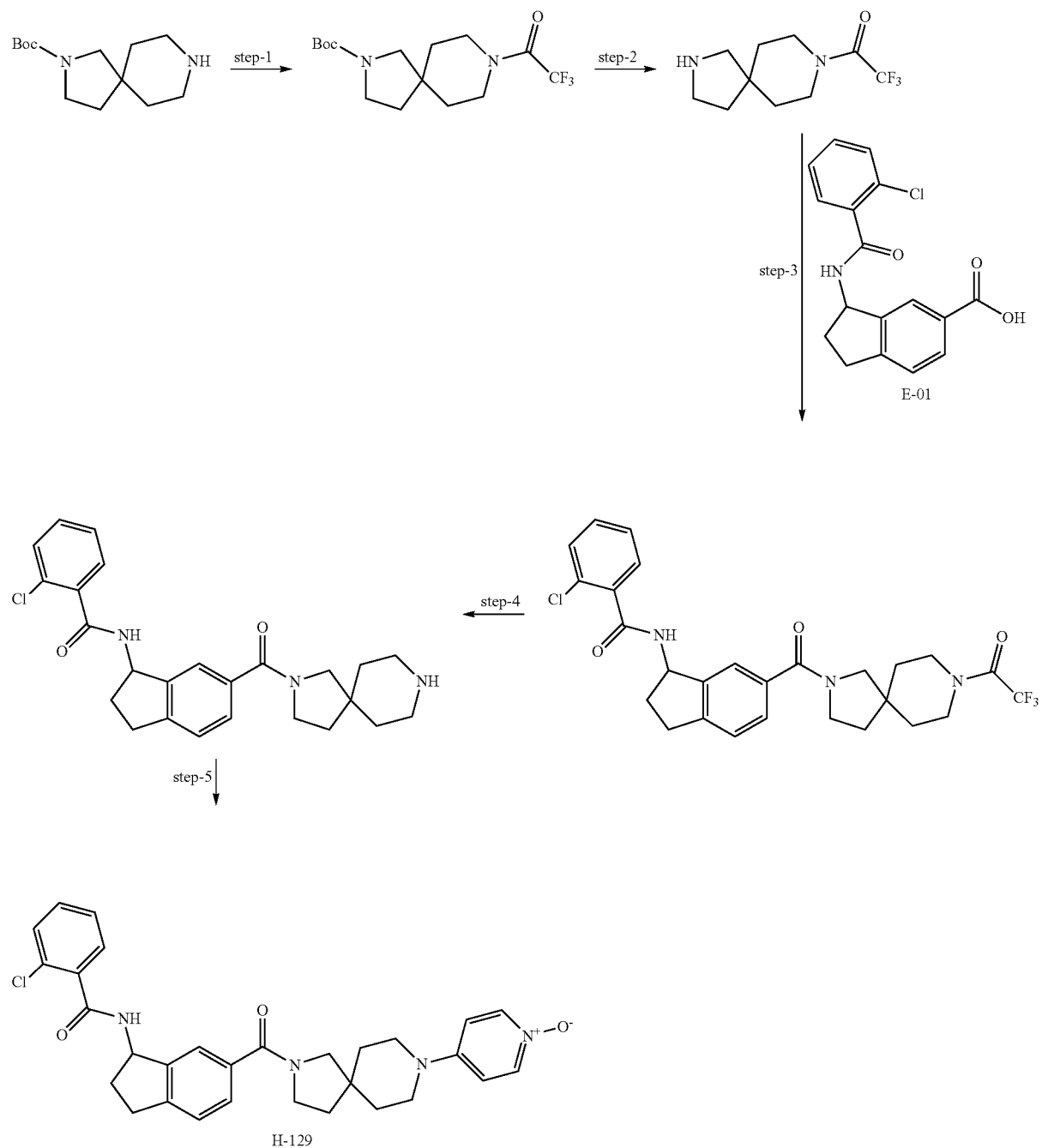

343

Step-1 tert-Butyl 8-(2,2,2-trifluoroacetyl)-2,8-diazaspiro[4.5]decane-2-carboxylate To a stirred solution of tert-butyl 2,8-diazaspiro[4.5]decane-2-carboxylate (600 mg, 2.5 mmol, 1 eq.) in MC (25 ml) DIPEA was added, the mixture stirred for 5-10 min and then TFAA (2.6 g, 12.5 mmol, 5 eq.) was added at 0° C. The reaction mixture was stirred at 25° C. for 2.5 h. The mixture was then diluted with MC (200 ml) and washed with water (2×100 ml) and brine (100 ml). The organic layer was dried over $Na_2SO_4$, filtered and evaporated to dryness to yield a yellowish oil. The crude product was used in the next step without further purification.

Step-2

2,2,2-Trifluoro-1-(2,8-diazaspiro[4.5]decan-8-yl)ethanone

TFA (1 ml) was added to a stirred solution of tert-butyl 8-(2,2,2-trifluoroacetyl)-2,8-diazaspiro[4.5]decane-2-carboxylate (840 mg, 2.5 mmol) in MC (4 ml) and the mixture was stirred at RT for 12 h. The reaction mixture was then concentrated under reduced pressure and azeotroped with MC (2×10 ml). The crude product was dried and used for the next step without further purification.

Step-3

2-Chloro-N-(6-(8-(2,2,2-trifluoroacetyl)-2,8-diazaspiro[4.5]decane-2-carbonyl)-2,3-dihydro-1H-inden-1-yl)benzamide To a suspension of 3-[(2-chloro-benzoyl)amino]-2,3-dihydro-1H-indene-5-carboxylic acid (E-01) (789 mg, 2.49 mmol, 1.0 eq.) in THF (20 ml) was added HATU (1.04 g, 2.76 mmol, 1.1 equiv.) and DIPEA (2.1 ml, 12.4 mmol, 5 eq.) at 0° C. and the reaction mixture was allowed to stir for 15 min. A solution of 2,2,2-trifluoro-1-(2,8-diazaspiro[4.5]decan-8-yl)ethanone (587 mg, 2.49 mmol, 1.0 equiv.) in THF (5 ml) was then added and the reaction mixture was stirred at 25° C. for 15 h. The mixture was diluted with MC (300 ml) and washed successively with sodium bicarbonate solution (40 ml), ammonium chloride solution (50 ml), water (50 ml) and brine (50 ml). The organic layer was dried over sodium sulfate and the solvent evaporated under reduced pressure to obtain the crude material which was purified by column chromatography (silica gel; 0-3% methanol/MC) to yield the pure final product as a white solid. Yield: 72% (1 g, 1.8 mmol).

Step-4

N-(6-(2,8-Diazaspiro[4.5]decane-2-carbonyl)-2,3-dihydro-1H-inden-1-yl)-2-chlorobenzamide 2 M KOH solution (4 ml) was added to a stirred solution of 2-chloro-N-(6-(8-(2,2,2-trifluoroacetyl)-2,8-diazaspiro[4.5]decane-2-carbonyl)-2,3-dihydro-1H-inden-1-yl)benzamide (200 mg, 0.374 mmol, 1 eq.) in MeOH (4 ml) and the mixture was stirred for 5 h. Methanol was removed under reduced pressure and it was diluted with EtOAc (100 ml) and washed with water (10 ml) and brine (20 ml). The organic layer was dried over sodium sulfate, filtered and concentrated to dryness. The crude material was used for the next step without further purification.

344

Step-5

2-Chloro-N-[6-[8-(1-oxido-pyridin-1-ium-4-yl)-3,8-diazaspiro[4.5]decane-3-carbonyl]-2,3-dihydro-1H-inden-1-yl]-benzamide (H-129)

A stirred mixture of N-(6-(2,8-diazaspiro[4.5]decane-2-carbonyl)-2,3-dihydro-1H-inden-1-yl)-2-chlorobenzamide (350 mg, 0.799 mmol, 1 eq.), DIPEA (0.34 ml, 1.99 mmol, 2.5 eq.) and 4-chloropyridine (103 mg, 0.799 mmol, 1 eq.) in EtOH (7 ml) was heated at 130° C. for 72 h. The solvent was removed and the crude material was purified by column chromatography (silica gel, 3-5% MeOH/MC) to afford the final product as a light brown solid. Yield: 23% (100 mg, 0.19 mmol).

Analytical Data:

Materials and methods for HPLC-MS analytics: HPLC: Waters Alliance 2795 with PDA Waters 2998; MS: Micromass Quattro Micro™ API; Column: Waters Atlantis® T3, 3 µm, 100 Å, 2.1×30 mm; Col. temp.: 40° C., Eluent A: purified water+0.1% formic acid; Eluent B: acetonitrile (gradient grade)+0.1% formic acid; Gradient: 0% B to 100% B in 8.8 min, 100% B for 0.4 min, 100% B to 0% B in 0.01 min, 0% B for 0.8 min; Flow: 1.0 mL/min; Ionisation: ES+, 25 V; make up: 100 µL/min 70% methanol+0.2% formic acid; UV: 200-400 nm.

| Example no. | [M+] found | R.t. [min] |
|---|---|---|
| H-01 | 541.2 | 3.0 min |
| H-02 | 515.2 | 1.56 min |
| H-03 | 589.3 | 3.4 min |
| H-04 | 501.1 | 2.7 min |
| H-05 | 515.1 | 2.7 min |
| H-06 | 506.3 | 2.9 min |
| H-07 | 542.2 | 2.9 min |
| H-08 | 544.2 | 3.2 min |
| H-09 | 543.4 | 4.4 min |
| H-10 | 543.4 | 4.5 min |
| H-11 | 529.3 | 3.0 min |
| H-12 | 529.3 | 3.0 min |
| H-13 | 541.3 | 3.2 min |
| H-14 | 555.3 | 3.3 min |
| H-15 | 541.3 | 3.2 min |
| H-16 | 589.3 | 3.6 min |
| H-17 | 603.3 | 3.8 min |
| H-18 | 589.3 | 3.5 min |
| H-19 | 603.3 | 3.7 min |
| H-20 | 515.3 | 2.8 min |
| H-21 | 515.3 | 2.8 min |
| H-22 | 529.3 | 3.0 min |
| H-23 | 515.3 | 2.9 min |
| H-24 | 529.3 | 3.0 min |
| H-25 | 515.3 | 2.9 min |
| H-26 | 529.3 | 3.1 min |
| H-27 | 501.3 | 2.8 min |
| H-28 | 549.4 | 2.1 min |
| H-29 | 577.4 | 2.9 min |
| H-31 | 563.5 | 2.1 min |
| H-32 | 563.47 | 2.11 min |
| H-33 | 488.3 | 2.7 min |
| H-34 | 515.3 | 2.9 min |
| H-35 | 515.3 | 2.9 min |
| H-36 | 591.5 | 2.5 min |
| H-37 | 548.4 | 4.1 min |
| H-38 | 549.4 | 2.7 min |
| H-39 | 515.3 | 2.9 min |
| H-40 | 548.3 | 4.5 min |
| H-41 | 532.3 | 3.5 min |
| H-42 | 582.3 | 5.2 min |
| H-43 | 515.3 | 2.8 min |
| H-44 | 516.3 | 3.7 min |
| H-45 | 583.3 | 3.6 min |

| Example no. | [M+] found | R.t. [min] |
|---|---|---|
| H-46 | 633.3 | 3.6 min |
| H-47 | 543.4 | 3.3 min |
| H-48 | 583.3 | 4.5 min |
| H-49 | 529.3 | 3.0 min |
| H-50 | 565.3 | 3.4 min |
| H-51 | 584.3 | 4.3 min |
| H-52 | 603.6 | 3.0 min |
| H-53 | 495.4 | 2.9 min |
| H-54 | 529.4 | 3.1 min |
| H-55 | 573.4 | 2.9 min |
| H-56 | 561.4 | 3.2 min |
| H-57 | 531.4 | 2.8 min |
| H-58 | 545.4 | 2.9 min |
| H-59 | 529.4 | 3.1 min |
| H-60 | 545.4 | 3.1 min |
| H-61 | 525.4 | 2.9 min |
| H-62 | 603.5 | 3.1 min |
| H-63 | 545.4 | 3.0 min |
| H-64 | 533.4 | 2.9 min |
| H-65 | 549.4 | 2.8 min |
| H-66 | 543.4 | 3.2 min |
| H-67 | 531.4 | 2.7 min |
| H-68 | 561.4 | 3.4 min |
| H-69 | 543.4 | 3.1 min |
| H-70 | 529.4 | 2.9 min |
| H-71 | 515.4 | 2.9 min |
| H-72 | 529.4 | 3.1 min |
| H-73 | 549.4 | 2.8 min |
| H-74 | 579.5 | 3.4 min |
| H-75 | 579.4 | 3.6 min |
| H-76 | 583.4 | 3.0 min |
| H-77 | 549.4 | 2.8 min |
| H-78 | 563.4 | 3.0 min |
| H-79 | 515.4 | 2.9 min |
| H-80 | 543.4 | 3.2 min |
| H-81 | 529.4 | 3.0 min |
| H-82 | 547.4 | 3.1 min |
| H-83 | 583.4 | 3.1 min |
| H-84 | 483.4 | 2.5 min |
| H-85 | 597.4 | 3.2 min |
| H-86 | 483.4 | 2.5 min |
| H-87 | 547.4 | 3.1 min |
| H-88 | 561.4 | 3.3 min |
| H-89 | 533.4 | 2.9 min |
| H-90 | 547.4 | 3.0 min |
| H-91 | 515.4 | 2.9 min |
| H-92 | 563.4 | 2.9 min |
| H-93 | 529.4 | 3.0 min |
| H-94 | 549.3 | 3.1 min |
| H-95 | 563.4 | 3.3 min |
| H-96 | 527.4 | 3.1 min |
| H-97 | 601.1 | 3.5 min |
| H-98 | 549.1 | 3.0 min |
| H-99 | 549.1 | 2.9 min |
| H-100 | 563.1 | 3.1 min |
| H-101 | 499.2 | 2.9 min |
| H-102 | 513.2 | 3.1 min |
| H-103 | 539.2 | 3.2 min |
| H-104 | 509.1 | 2.9 min |
| H-105 | 551.0 | 3.1 min |
| H-106 | 565.0 | 3.2 min |
| H-107 | 599.0 | 3.1 min |
| H-108 | 529.1 | 3.0 min |
| H-109 | 533.0 | 2.8 min |
| H-110 | 567.0 | 3.0 min |
| H-111 | 543.1 | 3.1 min |
| H-112 | 529.1 | 2.9 min |
| H-113 | 585.0 | 3.39 min |
| H-114 | 496.1 | 2.20 min |
| H-115 | 550.08 | 2.63 min |
| H-116 | 535.04 | 2.9 min |
| H-117 | 531.07 | 3.07 min |
| H-118 | 585.0 | 3.1 min |
| H-119 | 584.9 | 3.1 min |
| H-120 | 561.4 | 3.2 min |
| H-128 | 530.4 | 2.6 min |
| H-129 | 531.4 | 3.0 min |
| H-130 | 584.4 | 4.6 min |
| H-131 | 517.4 | 2.8 min |
| H-132 | 543.4 | 3.2 min |
| H-133 | 514.4 | 3.0 min |
| H-134 | 496.1 | 3.1 min |
| H-135 | 514.1 | 2.9 min |
| H-136 | 565.0 | 3.5 min |
| H-137 | 596.9 | 3.4 min |
| H-138 | 543.0 | 3.0 min |
| H-139 | 544.0 | 2.8 min |
| H-140 | 539.0 | 4.1 min |
| H-141 | 533.0 | 2.8 min |
| H-142 | 584.9 | 3.3 min |
| H-143 | 461.1 | 2.6 min |
| H-144 | 614.9 | 3.3 min |
| H-145 | 543.0 | 3.2 min |
| H-146 | 557.0 | 3.1 min |
| H-147 | 561.0 | 3.1 min |
| H-148 | 555.0 | 3.2 min |
| H-149 | 618.9 | 3.0 min |
| H-150 | 564.9 | 3.1 min |
| H-151 | 529.0 | 2.9 min |
| H-152 | 513.1 | 2.7 min |
| H-153 | 533.0 | 2.8 min |
| H-154 | 509.1 | 2.9 min |
| H-155 | 515.4 | 2.9 min |
| H-156 | 529.4 | 3.1 min |
| H-157 | 527.4 | 3.1 min |
| H-158 | 541.4 | 3.2 min |
| H-159 | 541.0 | 3.3 min |
| H-160 | 527.0 | 3.1 min |
| H-161 | 515.1 | 2.7 min |
| H-162 | 515.1 | 2.7 min |
| H-163 | 529.1 | 2.9 min |
| H-164 | 529.1 | 3.0 min |
| H-165 | 551.0 | 2.9 min |
| H-166 | 551.0 | 3.0 min |
| H-167 | 565.0 | 3.1 min |
| H-168 | 527.1 | 3.1 min |
| H-169 | 527.1 | 3.0 min |
| H-170 | 541.1 | 3.2 min |
| H-171 | 515.1 | 2.8 min |
| H-172 | 529.1 | 3.0 min |
| H-173 | 551.01 | 3.15 min |

D. Parallel Synthesis

Library No. 1:

1) Intermediate Syntheses

Synthesis of 3,9-Diazaspiro[5.5]undecane-9-carboxylic acid tert-butyl ester

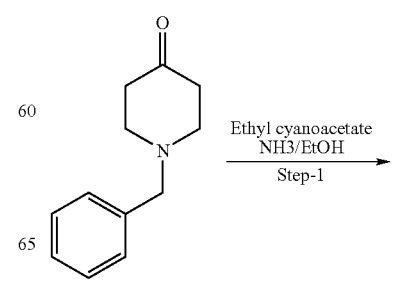

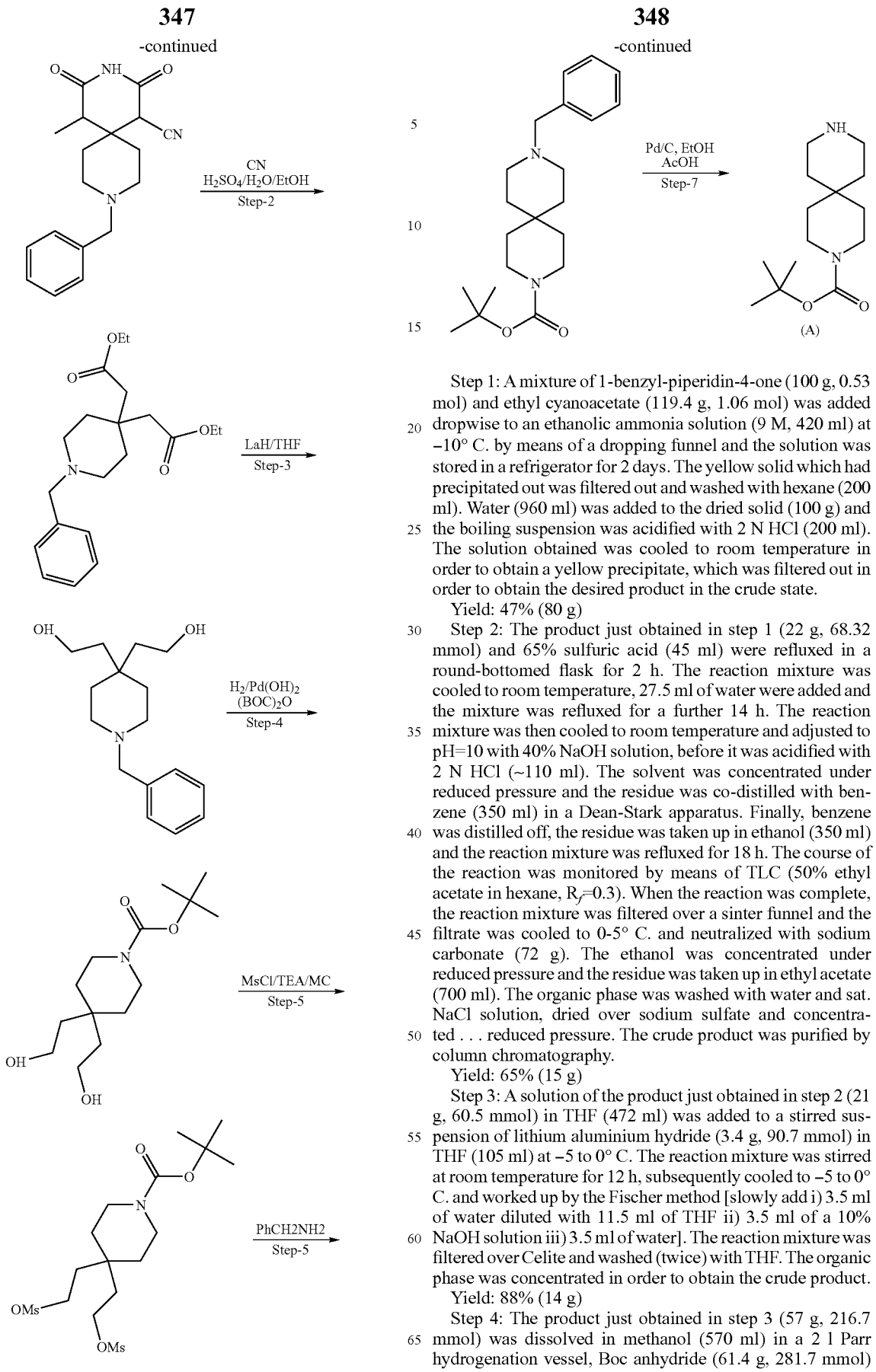

Step 1: A mixture of 1-benzyl-piperidin-4-one (100 g, 0.53 mol) and ethyl cyanoacetate (119.4 g, 1.06 mol) was added dropwise to an ethanolic ammonia solution (9 M, 420 ml) at −10° C. by means of a dropping funnel and the solution was stored in a refrigerator for 2 days. The yellow solid which had precipitated out was filtered out and washed with hexane (200 ml). Water (960 ml) was added to the dried solid (100 g) and the boiling suspension was acidified with 2 N HCl (200 ml). The solution obtained was cooled to room temperature in order to obtain a yellow precipitate, which was filtered out in order to obtain the desired product in the crude state.

Yield: 47% (80 g)

Step 2: The product just obtained in step 1 (22 g, 68.32 mmol) and 65% sulfuric acid (45 ml) were refluxed in a round-bottomed flask for 2 h. The reaction mixture was cooled to room temperature, 27.5 ml of water were added and the mixture was refluxed for a further 14 h. The reaction mixture was then cooled to room temperature and adjusted to pH=10 with 40% NaOH solution, before it was acidified with 2 N HCl (~110 ml). The solvent was concentrated under reduced pressure and the residue was co-distilled with benzene (350 ml) in a Dean-Stark apparatus. Finally, benzene was distilled off, the residue was taken up in ethanol (350 ml) and the reaction mixture was refluxed for 18 h. The course of the reaction was monitored by means of TLC (50% ethyl acetate in hexane, $R_f$=0.3). When the reaction was complete, the reaction mixture was filtered over a sinter funnel and the filtrate was cooled to 0-5° C. and neutralized with sodium carbonate (72 g). The ethanol was concentrated under reduced pressure and the residue was taken up in ethyl acetate (700 ml). The organic phase was washed with water and sat. NaCl solution, dried over sodium sulfate and concentrated . . . reduced pressure. The crude product was purified by column chromatography.

Yield: 65% (15 g)

Step 3: A solution of the product just obtained in step 2 (21 g, 60.5 mmol) in THF (472 ml) was added to a stirred suspension of lithium aluminium hydride (3.4 g, 90.7 mmol) in THF (105 ml) at −5 to 0° C. The reaction mixture was stirred at room temperature for 12 h, subsequently cooled to −5 to 0° C. and worked up by the Fischer method [slowly add i) 3.5 ml of water diluted with 11.5 ml of THF ii) 3.5 ml of a 10% NaOH solution iii) 3.5 ml of water]. The reaction mixture was filtered over Celite and washed (twice) with THF. The organic phase was concentrated in order to obtain the crude product.

Yield: 88% (14 g)

Step 4: The product just obtained in step 3 (57 g, 216.7 mmol) was dissolved in methanol (570 ml) in a 2 l Parr hydrogenation vessel, Boc anhydride (61.4 g, 281.7 mmol) and palladium-on-carbon (5.7 g, 10% Pd) were added under an N₂ atmosphere and hydrogenation was carried out for 12 h under 50 psi. The reaction mixture was filtered over Celite and washed with methanol (3×150 ml). The organic phase was concentrated in order to obtain the crude product as a yellow, tacky mass. The crude product was purified by column chromatography.

Yield: 78% (46 g)

Step 5: Triethylamine (72.5 ml, 580 mmol) was added at −20° C. to a solution of the product just obtained in step 4 (49 g, 179 mmol) in methylene chloride (1 l), followed by methanesulfonyl chloride (46.2 g, 403 mmol). The reaction mixture was stirred at −20° C. for 30 min, water was added and the organic phase was separated off, after the mixture had . . . stirred for 20 min. The aqueous phase was extracted with methylene chloride (3×150 ml). The combined organic phases were dried over sodium sulfate and concentrated in order to obtain the crude product. The crude product was purified by column chromatography.

Yield: 89% (50 g)

Step 6: The product just obtained in step 5 (70 g; 163 mmol) and benzylamine (105 ml, 962 mmol) were heated at 75° C. in a 500 ml round-bottomed flask for 2 h. The reaction mixture was cooled to 0° C. and adjusted to pH ~10 with 2% NaOH solution. Water (1,500 ml) was then added and the mixture was extracted with ethyl acetate (3×500 ml). The organic phase was washed with sat. NaCl solution, dried over sodium sulfate and concentrated under reduced pressure. The crude product was purified by column chromatography. Yield: 80% (75 g)

Step 7: Palladium-on-charcoal (2.7 g, 10% Pd/C) was added under an N₂ atmosphere to a solution of the product just obtained in step 6 (27 g, 78.488 mmol) in methanol (270 ml) and acetic acid (27 ml). Hydrogenation was carried out under a hydrogen pressure of 50 psi in a Parr apparatus for 16 h. The reaction mixture was filtered over Celite, washed with methanol (3×100 ml) and concentrated. The residue was rendered basic with 10% sodium carbonate solution and the mixture was extracted with methylene chloride (3×250 ml). The combined organic phases were dried over sodium sulfate and concentrated. The crude product was purified by column chromatography.

Yield: 90% (18 g)

Synthesis of 3-(tert-Butoxycarbonylamino)-2,3-dihydro-1H-indene-5-carboxylic acid

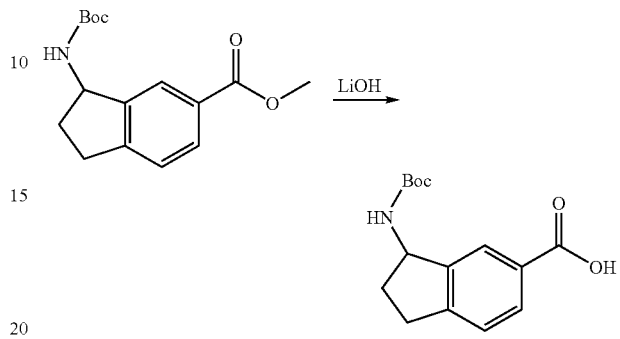

3-(tert-Butoxycarbonylamino)-2,3-dihydro-1H-indene-5-carboxylic acid methyl ester (821 g, 0.072 mol, cf. Synthesis of amino acid ester A-01) was dissolved in 110 ml of a THF-methanol-water mixture (6:4:1). The reaction mixture was cooled to 0° C., lithium hydroxide monohydrate (13.6 g, 0.32 mol) was added in portions and the mixture was stirred at room temperature for 8 h. The reaction mixture was concentrated to dryness, the residue was dissolved in a minimum of water and the solution was washed with ether. The aqueous phase was cooled to 0° C. and acidified slowly with 10% citric acid solution. The white solid which had precipitated out was filtered out, washed with water and dried in vacuo at 60° C. for 24 h in order to obtain the pure acid compound as a cream-coloured solid.

Yield: 77% (15 g)

2) Synthesis of the Amine Units (AMN_CC)

Overview:

| AMN-CC unit no. | Structure | AMN-CC name |
|---|---|---|
| AMN_CC-01 | 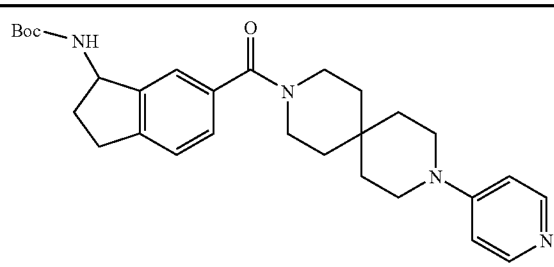 | N-[6-(3-pyridin-4-yl-3,9-diazaspiro[5.5]undecane-9-carbonyl)-2,3-dihydro-1H-inden-1-yl]-carbamic acid tert-butyl ester (AMN_CC-01) |
| AMN_CC-02 | 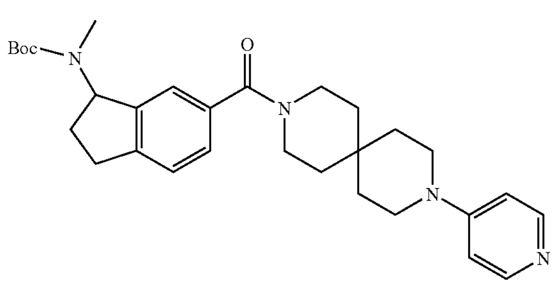 [SMILES: CN(C(=O)OC(C)(C)C)C1CCc2ccc(C(=O)N3CCC4(CC3)CCN(c3ccncc3)CC4)cc21] | N-methyl-N-[6-(3-pyridin-4-yl-3,9-diazaspiro[5.5]undecane-9-carbonyl)-2,3-dihydro-1H-inden-1-yl]-carbamic acid tert-butyl ester (AMN_CC-02) |

-continued

| AMN-CC unit no. | Structure | AMN-CC name |
| --- | --- | --- |
| AMN_CC-03 | 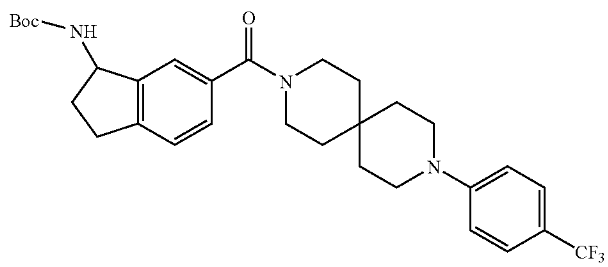 [SMILES: CC(C)(C)OC(=O)NC1CCc2ccc(C(=O)N3CCC4(CC3)CCN(c3ccc(C(F)(F)F)cc3)CC4)cc21] | N-[6-[3-[4-(trifluoromethyl)-phenyl]-3,9-diazaspiro[5.5]undecane-9-carbonyl]-2,3-dihydro-1H-inden-1-yl]-carbamic acid tert-butyl ester (AMN_CC-03) |
| AMN_CC-04 | 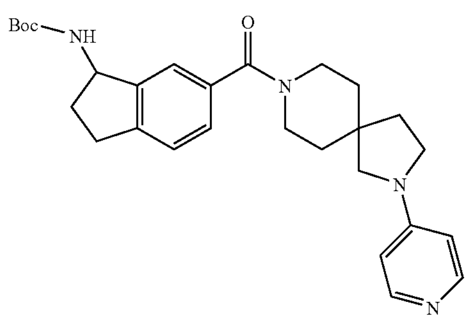 [SMILES: CC(C)(C)OC(=O)NC1CCc2ccc(C(=O)N3CCC4(CC3)CCN(c3ccncc3)C4)cc21] | N-[6-(2-pyridin-4-yl-2,8-diazaspiro[4.5]decane-8-carbonyl)-2,3-dihydro-1H-inden-1-yl]-carbamic acid tert-butyl ester (AMN_CC-04) |
| AMN_CC-13 | 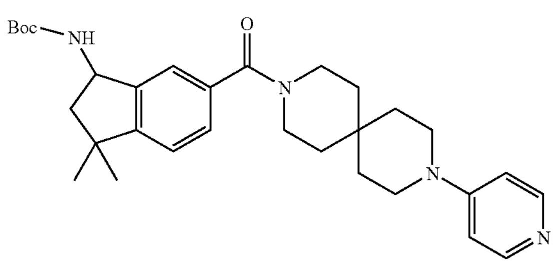 [SMILES: CC(C)(C)OC(=O)NC1CC(C)(C)c2ccc(C(=O)N3CCC4(CC3)CCN(c3ccncc3)CC4)cc21] | N-[3,3-dimethyl-6-(9-pyridin-4-yl-3,9-diazaspiro[5.5]undecane-3-carbonyl)-2,3-dihydro-inden-1-yl]-carbamic acid tert-butyl ester (AMN_CC-13) |
| AMN_CC-14 | 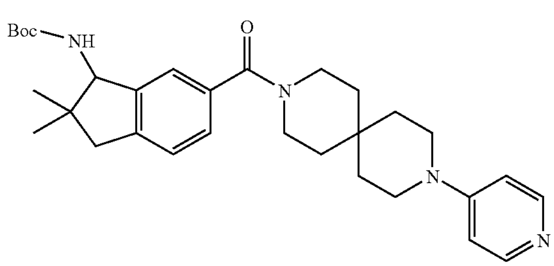 [SMILES: CC(C)(C)OC(=O)NC1c2cc(C(=O)N3CCC4(CC3)CCN(c3ccncc3)CC4)ccc2CC1(C)C] | N-[2,2-dimethyl-6-(9-pyridin-4-yl-3,9-diazaspiro[5.5]undecane-3-carbonyl)-2,3-dihydro-inden-1-yl]-carbamic acid tert-butyl ester (AMN_CC-14) |
| AMN_CC-15 | 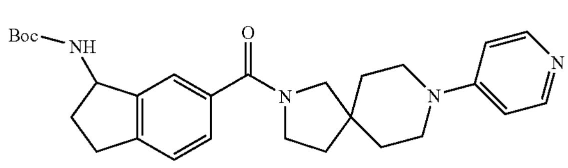 [SMILES: CC(C)(C)OC(=O)NC1CCc2ccc(C(=O)N3CCC4(CCN(c5ccncc5)CC4)C3)cc21] | N-[6-(8-pyridin-4-yl-3,8-diazaspiro[4.5]decane-3-carbonyl)-2,3-dihydro-1H-inden-1-yl]-carbamic acid tert-butyl ester (AMN_CC-15) |

Synthesis of amine (AMN_CC-01)

N-[6-(3-Pyridin-4-yl-3,9-diazaspiro[5.5]undecane-9-carbonyl)-2,3-dihydro-1H-inden-1-yl]-carbamic acid tert-butyl ester (AMN_CC-01)

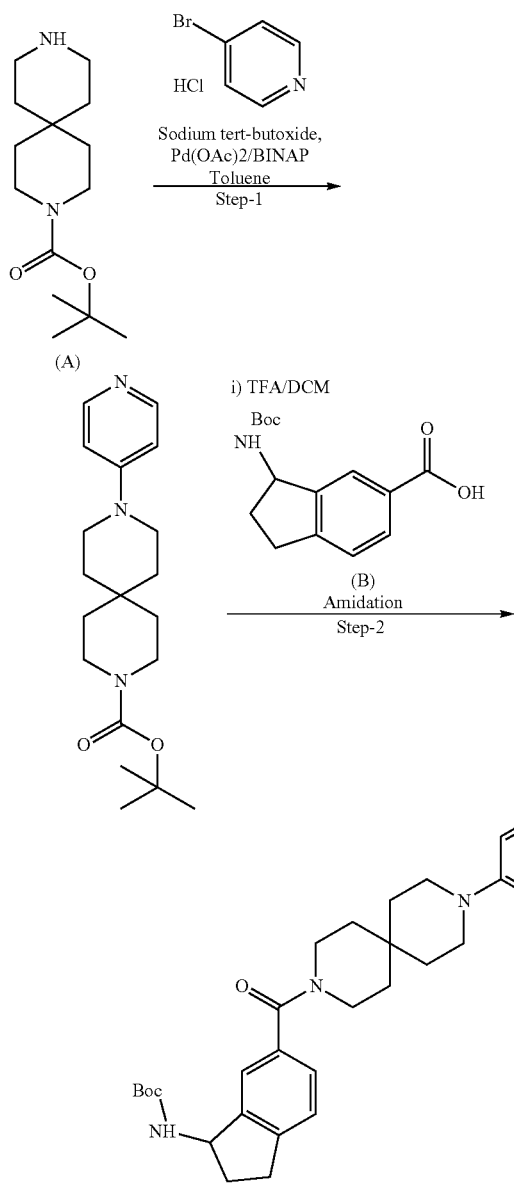

Step 1: 3,9-Diazaspiro[5.5]undecane-3-carboxylic acid tert-butyl ester (6 g, 23.6 mmol), 4-bromopyridine hydrochloride (4.58 g, 23.6 mmol) and sodium tert-butanolate (6.8 g, 70.8 mmol) were suspended in toluene and the suspension was then degassed under an argon atmosphere for 20 min. BINAP (293 mg, 0.47 mmol) and Pd(OAc)$_2$ (317 mg, 1.4 mmol) were added and the reaction mixture was first degassed for a further 20 min and then refluxed for 4 h.

The reaction was monitored by means of TLC (MeOH): CH$_2$Cl$_2$=1:9, R$_f$=0.9), and after complete consumption of the starting material the reaction mixture was cooled to room temperature, diluted with ethyl acetate, stirred for 15 min and filtered over Celite. The organic phase was washed with water and sat. NaCl solution, dried over sodium sulfate and concentrated under reduced pressure. The crude product was purified by column chromatography.

Yield: 51% (4 g)

Step 2: Trifluoroacetic acid (7 ml) was added at 0° C. to a solution of the product just obtained (3 g, 9 mmol) in methylene chloride (70 ml) and the mixture was stirred at 23° C. for 16 h. The reaction mixture was then concentrated under reduced pressure in order to obtain the crude amine compound as the TFA salt. This was employed in the next step without further purification.

EDC.HCl (3.48 g, 18.1 mmol) and HOBT (2.45 g, 18.4 mmol) were added to a solution of 3-(tert-Butoxycarbonylamino)-2,3-dihydro-1H-indene-5-carboxylic acid (3.35 g, 12.1 mmol) in THF (50 ml) and the mixture was cooled to 0° C. DIPEA (6.28 g, 8.98 ml, 48.4 mmol) was then added and the mixture was stirred for a further 10 min, before a solution of the amine TFA salt in THF (50 ml) was added dropwise to the reaction mixture and the mixture was stirred for 16 h.

For working up, water was added and the mixture was extracted with ethyl acetate (3×100 ml). The combined organic phases were washed with water and sat. NaCl solution and dried over sodium sulfate and concentrated. The crude product was purified by column chromatography.

Yield: 78% (3.5 g)

Synthesis of amine (AMN_CC-02)

N-Methyl-N-[6-(3-pyridin-4-yl-3,9-diazaspiro[5.5]undecane-9-carbonyl)-2,3-dihydro-1H-inden-1-yl]-carbamic acid tert-butyl ester (AMN_CC-02)

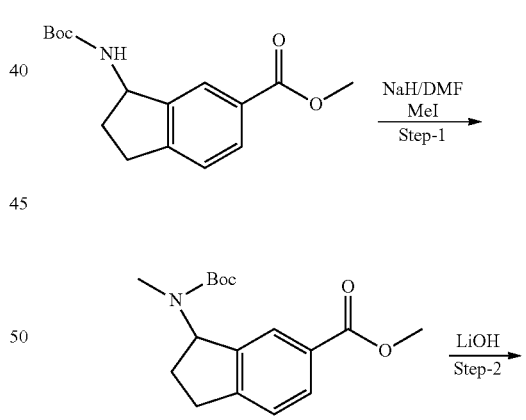

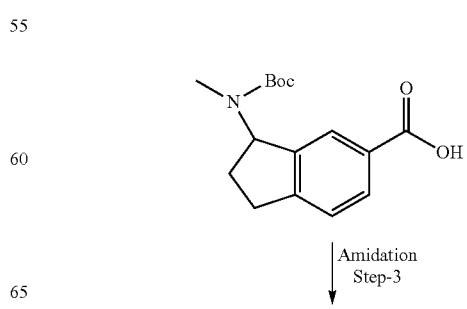

355

-continued

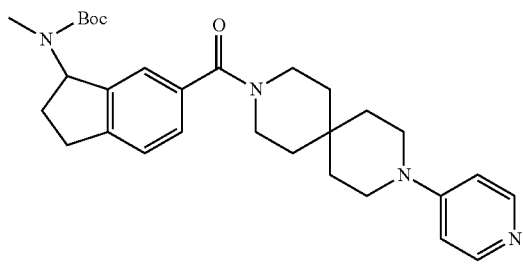

Step 1: NaH (1.4 g, 30 mmol, 60% in mineral oil) was added in portions to a solution of 3-(tert-butoxycarbonylamino)-2,3-dihydro-1H-indene-5-carboxylic acid methyl ester (3.4 g, 11.68 mmol) in DMF (60 ml) at 0° C. and the mixture was then stirred at room temperature for 2 h. The reaction mixture was cooled to 0° C., methyl iodide (2.19 ml, 30 mmol) was added and the mixture was stirred at room temperature for 16 h. The reaction mixture was quenched with ice, diluted with water and extracted with ethyl acetate. The combined organic phases were washed with water and sat. NaCL solution, dried over anhydrous sodium sulfate and concentrated under reduced pressure. The crude product was purified by column chromatography.

Yield: 61.75%

Step 2: The product just obtained in step 1 (2 g, 6.55 mmol) was dissolved in 110 ml of a THF-methanol-water mixture (6:4:1). The reaction mixture was cooled to 0° C., lithium hydroxide monohydrate (1.31 g, 30 mmol) was added in portions and the mixture was stirred at room temperature for 8 h. The reaction mixture was concentrated to dryness, the residue was dissolved in a minimum of water and the solution was washed with ether. The aqueous phase was cooled to 0° C. and acidified slowly with dilute HCl solution. The white solid which had precipitated out was filtered out, washed with water and dried in vacuo at 60° C. for 24 h in order to obtain the pure acid compound as a cream-coloured solid.

Yield: 99%

Step 3: TFA (14 ml) was added to a stirred solution of 9-pyridin-4-yl-3,9-diazaspiro[5.5]undecane-3-carboxylic acid tert-butyl ester (5.9 g, 18.09 mmol) in methylene chloride (100 ml) at 0° C. and the reaction mixture was stirred at 23° C. for 16 h. The reaction mixture was concentrated in order to obtain the TFA salt, which was employed in the next step without further purification.

EDCl.HCl (6.91 g, 36 mmol) and HOBT (2.45 g, 18.4 mmol) were added to a solution of the acid obtained in step 2 (5.26 g, 18.09 mmol) in THF (50 ml) and the mixture was cooled to 0° C. DIPEA (6.28 g, 8.98 ml, 48.4 mmol) was then added to the reaction mixture and the mixture was stirred for 10 min. A solution of the TFA salt of the amine in THF (50 ml) was added dropwise to the reaction mixture and the mixture was stirred for 16 h. For working up, water was added and the mixture was extracted with ethyl acetate (3×100 ml). The combined organic phases were washed with water and sat. NaCl solution, dried over sodium sulfate and concentrated under reduced pressure. The crude product was purified by column chromatography.

Yield: 31.57%

356

Synthesis of amine (AMN_CC-03)

N-[6-[3-[4-(Trifluoromethyl)-phenyl]-3,9-diazaspiro[5.5]undecane-9-carbonyl]-2,3-dihydro-1H-inden-1-yl]-carbamic acid tert-butyl ester (AMN_CC-03)

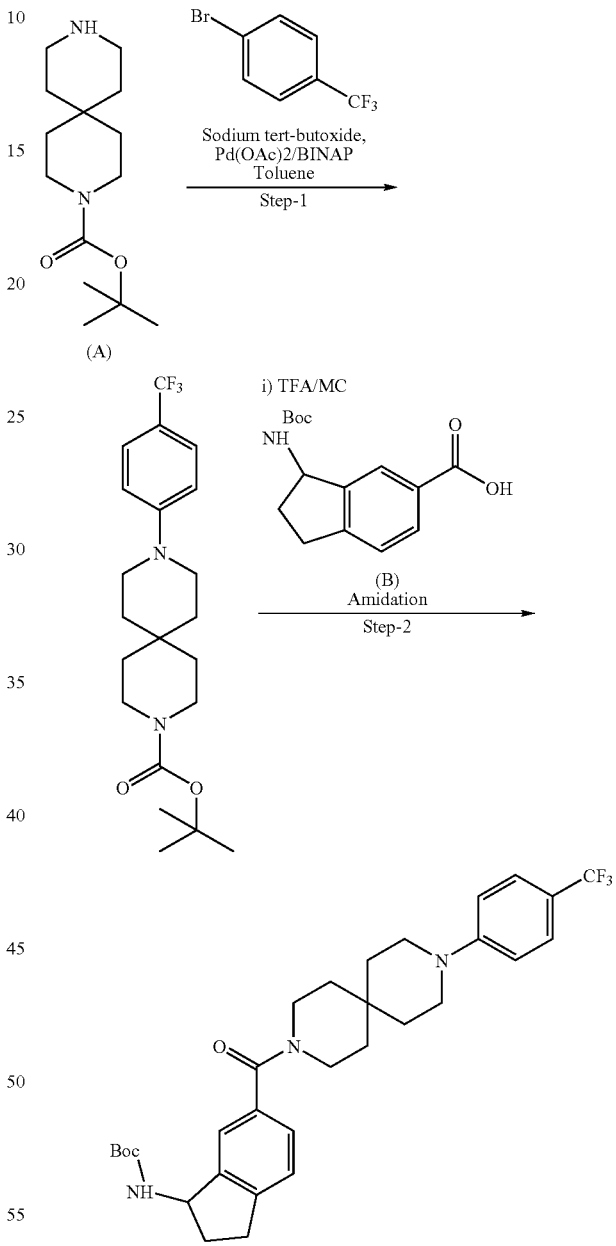

Step 1: Sodium tert-butanolate (3 eq.) and 4-trifluoromethyl bromobenzene (1.2 eq.) were added to a toluene solution (5 ml/mmol) of 3,9-diazaspiro[5.5]undecane-3-carboxylic acid tert-butyl ester (1 eq.) and the mixture was degassed under an argon atmosphere. (+/−)BINAP (0.06 eq.) and Pd(OAc)$_2$ (0.02 eq.) was then added and the mixture was refluxed for 2 h. The reaction mixture was cooled to room temperature, diluted with ethyl acetate and washed successively with water and sat. NaCl solution. After drying over sodium sulfate, it was concentrated under reduced pressure. The crude product was purified by column chromatography (5% methanol in methylene chloride).

Yield: 51%

Step 2: TFA (80 ml) was added at 0° C. to a solution of the product just obtained in step 1 (4 g, 10 mmol) in methylene chloride (320 ml) and the mixture was stirred at 23° C. for 2 h. The reaction mixture was concentrated in order to obtain the amine compound as the TFA salt, which was employed in the next step without further purification.

HATU (7.82 g, 20 mmol) was added to a solution of 3-(tert-butoxycarbonylamino)-2,3-dihydro-1H-indene-5-carboxylic acid (2.85 g, 10 mmol) in methylene chloride (25 ml), the reaction the mixture was cooled to 0° C., DIPEA (6.15 g, 30 mmol) was added and the mixture was stirred for 10 min. A solution of the amine TFA salt in methylene chloride (25 ml) was added dropwise to the reaction mixture and the mixture was stirred for 16 h. For working up, water was added and the mixture was extracted with ethyl acetate (3×100 ml). The combined organic phases were washed with water and sat. NaCl solution, dried over sodium sulfate and concentrated under reduced pressure. The crude product was purified by column chromatography.

Yield: 53%

Synthesis of amine (AMN_CC-04)

N-[6-(2-Pyridin-4-yl-2,8-diazaspiro[4.5]decane-8-carbonyl)-2,3-dihydro-1H-inden-1-yl]-carbamic acid tert-butyl ester (AMN_CC-04)

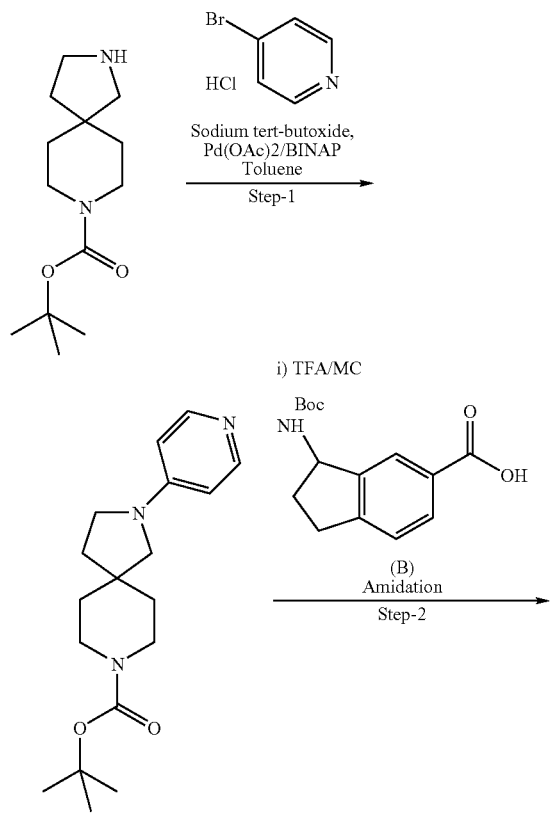

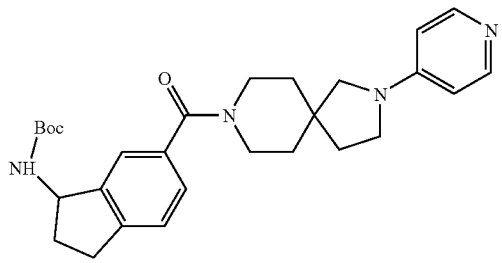

Step 1: Sodium tert-butanolate (3 eq.) and 4-bromopyridine hydrochloride (1.2 eq.) were added to a toluene solution (5 ml/mmol) of 2,8-diazaspiro[4.5]decane-8-carboxylic acid tert-butyl ester (1 eq.) and the mixture was degassed under an argon atmosphere. (+/−)BINAP (0.06 eq.) and Pd(OAc)$_2$ (0.02 eq.) was then added and the mixture was refluxed for 2 h. The reaction mixture was cooled to room temperature, diluted with ethyl acetate and washed successively with water and sat. NaCl solution. After drying over sodium sulfate, it was concentrated under reduced pressure. The crude product was purified by column chromatography (5% methanol in methylene chloride).

Yield: 53.08%

Step 2: TFA (90 ml) was added at 0° C. to a solution of the product just obtained in step 1 (4.5 g, 14.1 mmol) in methylene chloride (200 ml) and the mixture was stirred at 23° C. for 2 h. The reaction mixture was concentrated in order to obtain the amine compound as the TFA salt, which was employed in the next step without further purification.

HATU (10.8 g, 28.3 mmol) was added to a solution of 3-(tert-butoxycarbonylamino)-2,3-dihydro-1H-indene-5-carboxylic acid (3.93 g, 14.19 mmol) in methylene chloride (100 ml), the reaction the mixture was cooled to 0° C., DIPEA (2.4 ml, 14 mmol) was added and the mixture was stirred for 10 min. A solution of the amine TFA salt and DIPEA (2.4 ml, 14 mmol) in methylene chloride (50 ml) was added dropwise to the reaction mixture and the mixture was stirred for 16 h. For working up, water was added and the mixture was extracted with ethyl acetate (3×100 ml). The combined organic phases were washed with water and sat. NaCl solution, dried over sodium sulfate and concentrated under reduced pressure. The crude product was purified by column chromatography.

Yield: 78.76%

Synthesis of amine (AMN_CC-13)

N-[3,3-Dimethyl-6-(9-pyridin-4-yl-3,9-diazaspiro[5.5]undecane-3-carbonyl)-1,2-dihydro-inden-1-yl]-carbamic acid tert-butyl ester (AMN_CC-13)

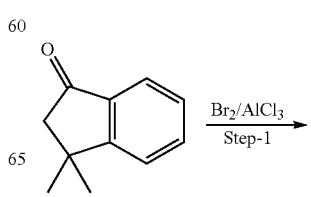

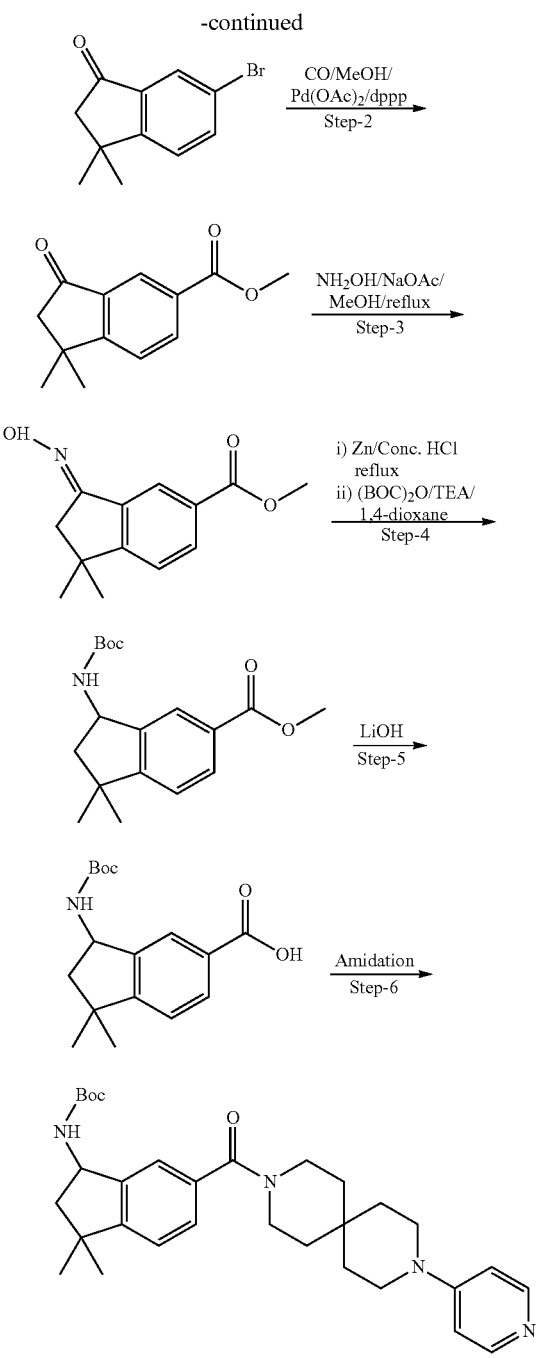

Step 1: Bromine (0.6 g, 3.75 mmol) was added to a mixture of AlCl₃ (1.04 g, 7.8 mmol) and 3,3-dimethyl-indan-1-one (0.5 g, 3.1 mmol) at 100° C. and the mixture was kept at this temperature for 40-45 min. The reaction mixture was quenched with crushed ice and extracted with ethyl acetate (3×50 ml). The organic phase was separated off, dried over sodium sulfate and concentrated under reduced pressure. The crude product was purified by column chromatography.

Yield: 26% (200 mg)

Step 2: Triethylamine was added to a solution of the product just obtained in step 1 (100 mg, 0.418 mmol) in a mixture of DMSO (5 ml) and methanol (4 ml) and the reaction mixture was degassed under an argon atmosphere for 15 min. Palladium acetate (4 mg, 0.02 mol) and dppp (1,3-bis-diphenylphosphino propane) (8 mg, 0.02 mol) were added and the mixture was degassed under a CO atmosphere for 30 min. The reaction mixture was stirred at 65° C. under a CO balloon pressure for 2 h. Methanol was removed under reduced pressure, the residue obtained was diluted with water and the mixture was extracted with diethyl ether. The organic phase was separated off, dried over sodium sulfate and concentrated under reduced pressure. The crude product was purified by column chromatography.

Yield: 44% (40 mg)

Step 3: Hydroxylamine hydrochloride (3.4 g, 49.3 mol) and sodium acetate (8 g, 98.3 mol) were added to a solution of the ester just obtained (4.3 g, 19.7 mol) in methanol (75 ml) and the reaction mixture was heated at 80° C. for 2 h. The course of the reaction was monitored by means of TLC (30% ethyl acetate in hexane) and when the conversion of the reaction was complete the reaction mixture was concentrated and the residue was extracted with ethyl acetate. The organic phase was separated off, washed with water and sat. NaCl solution, dried over sodium sulfate and concentrated under reduced pressure. The crude product was employed in the next step without further purification.

Yield: 6 g crude (IV) Zinc dust (6.6 g, 103 mmol) was added to an ethanolic solution (10 ml) of the product just obtained in step 3 (4 g, 17.1 mmol), water (10 ml) and conc. HCl (20 ml) and the mixture was refluxed for 2 h. It was then cooled to room temperature, filtered over Celite and concentrated in order to obtain the desired amine (6 g). The crude amine was dissolved in 1,4 dioxane (100 ml) and triethylamine (3.3 ml, 32.8 mmol), the solution was cooled to 5-10° C. and (Boc)₂O (6 g, 27.3 mmol) was added. This reaction mixture . . . stirred at room temperature for 12 h and then concentrated and the residue . . . taken up in ethyl acetate. The ethyl acetate phase was washed with water and sat. NaCl solution, dried over sodium sulfate and concentrated.

Yield: 51% (2.8 g)

Step 5: LiOH.H₂O (1.47 g, 35 mmol) was added to a solution of the product just obtained in step 4 (2.8 g, 8.75 mmol) in THF-MeOH—H₂O (55 ml, 6:4:1) and the mixture was stirred at room temperature for 12 h. The reaction mixture was then concentrated, the residue was dissolved in a minimum of water and the solution was washed with ether and acidified with 10% citric acid solution The reaction mixture was extracted with ethyl acetate and the combined organic phases were washed with water and sat. NaCl solution, dried over sodium sulfate and concentrated under reduced pressure. The crude product was employed in the next step without further purification.

Yield: 55% (1.5 g)

Step 6: EDCl.HCl (503 mg, 2.62 mmol), HOBT (177 mg, 1.311 mmol) and DIPEA (0.6 ml) were added to a solution of the product just obtained in step 5 (400 mg, 1.3114 mmol) in methylene chloride (10 ml). The reaction mixture was stirred at 25° C. for 30 min and then cooled to 0° C. and 3-pyridin-4-yl-3,9-diaza-spiro[5.5]undecane (364 mg, 1.57 mmol) was added. The reaction mixture was stirred at 25° C. for 12 h, subsequently diluted with methylene chloride and washed with sat. NH₄Cl solution and with NaHCO3 solution. The organic phase was washed with water and sat. NaCl solution, dried over sodium sulfate and concentrated under reduced pressure. The crude product was purified by column chromatography.

Yield: 75% (500 mg)

Synthesis of amine (AMN_CC-14)

N-[2,2-Dimethyl-6-(9-pyridin-4-yl-3,9-diazaspiro[5.5]undecane-3-carbonyl)-1,3-dihydro-inden-1-yl]-carbamic acid tert-butyl ester (AMN_CC-14)

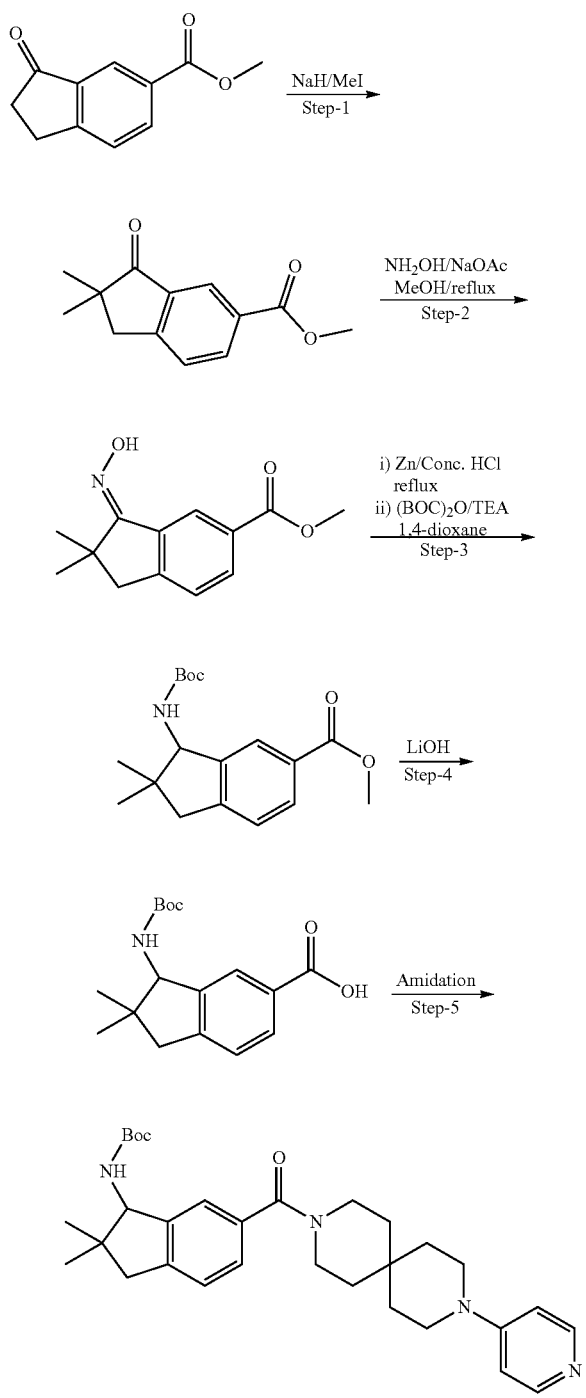

Step 1: A solution of 3-oxo-indane-5-carboxylic acid methyl ester (5 g, 26.3 mmol) in THF (40 ml) was added to a suspension of NaH (2.5 g, 2.2 eq.) in THF (25 ml) at 0° C. and the mixture was stirred at 0° C. for 15 min. Methyl iodide (9.9 ml, 184 mmol) was added and the reaction mixture was stirred at 20° C. for 4 h. The reaction mixture was diluted with water and extracted with ethyl acetate. The combined organic phases were washed with water and sat. NaCl solution, dried over sodium sulfate and concentrated under reduced pressure. The crude product was employed in the next step without further purification.

Yield: 61% (3.5 g)

Step 2: Sodium acetate (28.28 g, 0.341 mol) and hydroxylamine hydrochloride (13.2 g, 0.191 mol) were added to a solution of the product just obtained in step 1 (14 g, 0.0736 mol) in methanol (100 ml). The reaction mixture was refluxed for 16 h and then concentrated under reduced pressure and the residue was diluted with ethyl acetate. The organic phase were washed with water, dried over sodium sulfate and concentrated under reduced pressure. The crude product was employed in the next step without further purification. Yield: 60% (14 g)

Step 3: Water, more aqueous HCl (6 N, 5 ml) was added to a solution of the product just obtained in step 2 (1 g, 04.29 mmol) in ethanol (10 ml). Zinc powder (1.6 g, 25.75 mmol) was added in portions to the reaction mixture at 20° C. and the mixture was then stirred at 25° C. for 2 h. The reaction mixture was filtered and washing was carried out with methanol. The filtrate was first concentrated, the residue was then dissolved in 1,4-dioxane (50 ml) and triethylamine (3.5 ml) and Boc anhydride (34 ml, 159 mmol) were added at 0° C. The reaction mixture was stirred at 23° C. for 16 h and then concentrated under reduced pressure and the residue was diluted with ethyl acetate. The organic phase was washed with water and sat. NaCl solution, dried over sodium sulfate and concentrated under reduced pressure. The crude product was purified by column chromatography.

Yield: 73% (3 g)

Step 4: LiOH.$H_2O$ (5.2 g, 125 mmol) was added in portions at 0° C. to a solution of the product just obtained in step 3 (10 g, 31.3 mmol) in a mixture of THF-methanol-water (110 ml, ratio 6:4:1) and the mixture was stirred at 20° C. for 12 h. The reaction mixture was concentrated to dryness under reduced pressure. The residue was dissolved in a minimum of water and the solution was washed with ether and acidified with 10% citric acid solution. The reaction mixture was extracted with ethyl acetate. The organic phase was washed with water and sat. sodium chloride solution, dried over sodium sulfate and concentrated under reduced pressure. The crude product was employed in the next step without further purification.

Yield: 55% (6 g)

Step 5: EDCl.HCl (939 mg, 4.9 mmol), HOBT (660 mg, 4.9 mmol) and DIPEA (2.2 ml, 12.69 mmol) were added to a solution of the product just obtained in step 4 (1 g, 3.2 mmol) in THF (20 ml). The reaction mixture was stirred at 25° C. for 30 min, a solution of 3-pyridin-4-yl-3,9-diaza-spiro[5.5]undecane (3.2 mmol, 1 eq.) in THF (20 ml) was then added and the mixture was stirred further at 25° C. for 12 h. The reaction mixture was diluted with methylene chloride and washed with sat. $NH_4Cl$ solution and $NaHCO_3$ solution. The organic phase was washed with water and sat. NaCl solution, dried over sodium sulfate and concentrated under reduced pressure. The crude product was purified by column chromatography.

Yield: 70% (1.2 g)

Synthesis of amine (AMN_CC-15)

N-[6-(8-Pyridin-4-yl-3,8-diazaspiro[4.5]decane-3-carbonyl)-2,3-dihydro-1H-inden-1-yl]-carbamic acid tert-butyl ester (AMN_CC-15)

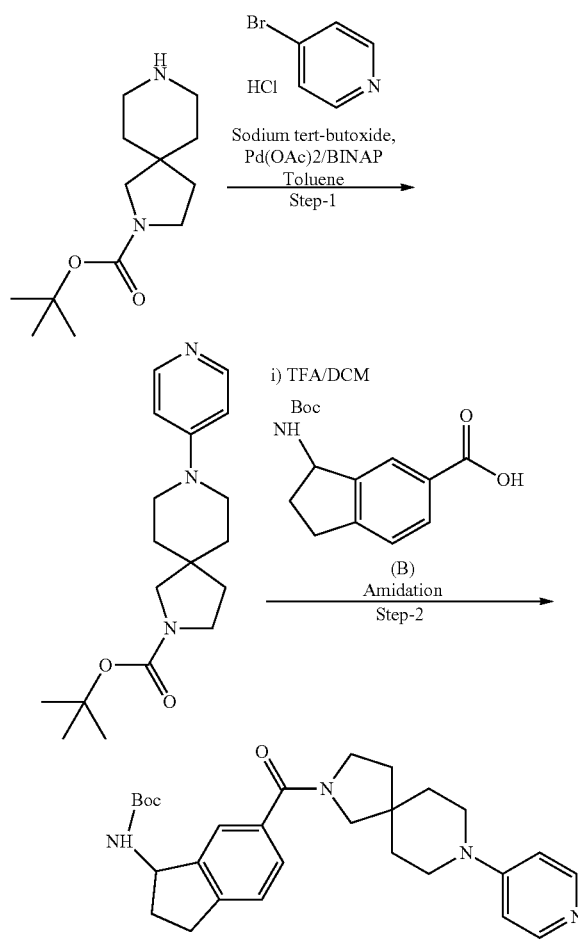

Step 1: Sodium tert-butanolate (3 eq.) and 4-bromopyridine hydrochlorides (1.2 eq.) were added to a solution of the corresponding spiro-amine (7 g, 29.12 mmol) in toluene (145 mmol). The reaction mixture was degassed under an argon atmosphere, (+/−) BINAP (0.06 eq.) and Pd(OAc)$_2$ (0.02 eq.) were added and the mixture was refluxed for 2 h and finally cooled to room temperature.

The reaction mixture was diluted with ethyl acetate, washed with water and sat. NaCl solution, dried over sodium sulfate and concentrated under reduced pressure. The crude product was purified by column chromatography.

Yield: 43.33%

Step 2: TFA (130 ml) was added at 0° C. to a solution of the product just obtained in step 1 (5.2 g, 16.40 mmol) in methylene chloride (200 ml) and the mixture was stirred at 23° C. for 16 h and finally concentrated under reduced pressure.

EDCl (6 g, 28.3 mmol) and HOBT (2.21 g, 16.40 . . . ) were added to a solution corresponding of the Boc-protected acid (4.54 g, 16.40 mmol) in methylene chloride (170 ml), the mixture was cooled to 0° C., DIPEA (11.4 ml, 64 mmol) was added and the mixture was stirred for a further 10 min. A solution of the TFA salt of the amine and DIPEA (4 ml, 23 mmol) in methylene chloride (50 ml) was added dropwise to the reaction mixture and the mixture was stirred for 16 h. Water was added to the reaction mixture and the mixture was extracted with with ethyl acetate (3×100 ml).

The combined organic phases were washed with water and sat. NaCl solution, dried over sodium sulfate and concentrated under reduced pressure. The crude product was purified by column chromatography.

Yield: 70.3%

3) Synthesis of the Acid Units, Acid Chlorides, Sulfonyl Chlorides and Isocyanates and Aldehydes (ACl_CC, ACL_CC, SCl_CC, ICN_CC, ALD_CC)

Overview:

| Unit no. | Structure | Unit name |
|---|---|---|
| ACl_CC-01 | 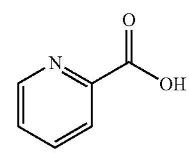 | pyridine-2-carboxylic acid |
| ACl_CC-02 | 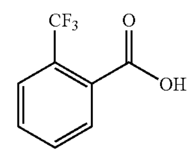 [SMILES: O=C(O)c1ccccc1C(F)(F)F] | 2-(trifluoromethyl)-benzoic acid |
| ACl_CC-03 | 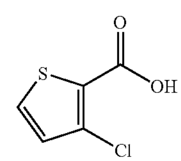 | 3-chloro-thiophene-2-carboxylic acid |
| ACl_CC-04 | 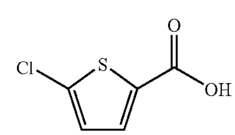 | 5-chloro-thiophene-2-carboxylic acid |
| ACl_CC-05 | 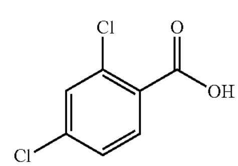 [SMILES: O=C(O)c1ccc(Cl)cc1Cl] | 2,4-dichloro-benzoic acid |
| ACl_CC-06 | 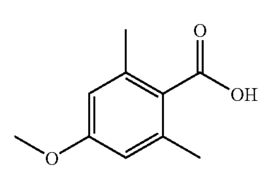 | 4-methoxy-2,6-dimethyl-benzoic acid |
| ACl_CC-07 | 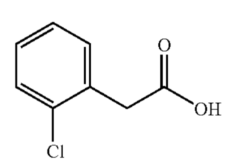 [SMILES: O=C(O)Cc1ccccc1Cl] | 2-(chlorophenyl)-acetic acid |

-continued

| ID | Structure | Name |
|---|---|---|
| ACI_CC-08 | 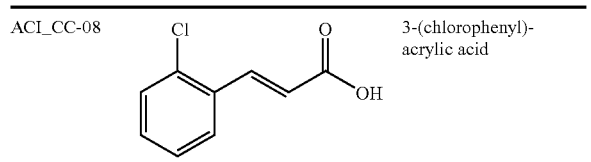 | 3-(chlorophenyl)-acrylic acid |
| ACI_CC-09 | 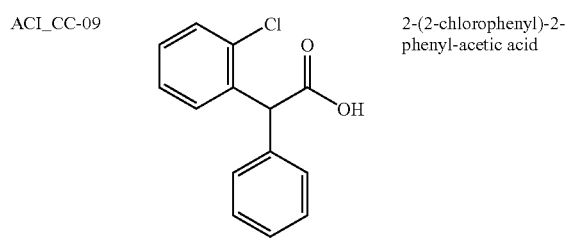 | 2-(2-chlorophenyl)-2-phenyl-acetic acid |
| SCI_CC-01 | 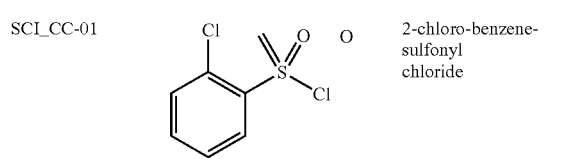 | 2-chloro-benzene-sulfonyl chloride |
| SCI_CC-02 | 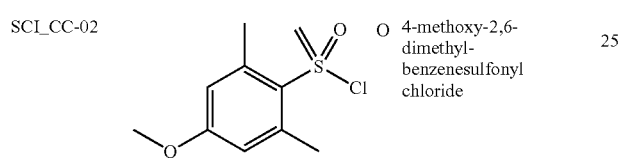 | 4-methoxy-2,6-dimethyl-benzenesulfonyl chloride |
| ICN_CC-01 | 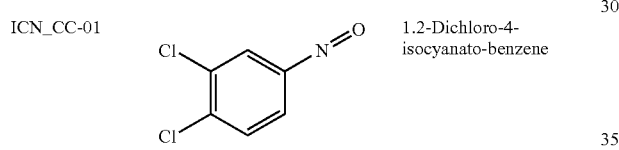 | 1,2-Dichloro-4-isocyanato-benzene |
| ICN_CC-02 | 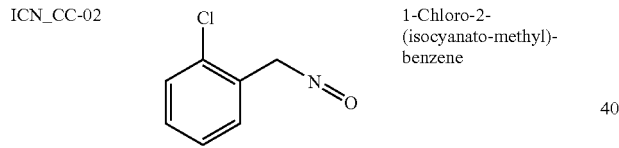 | 1-Chloro-2-(isocyanato-methyl)-benzene |

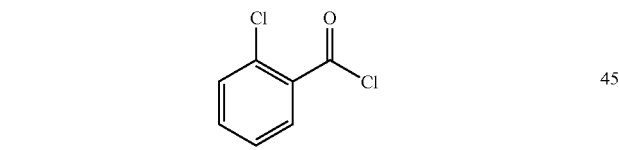

2-Chloro-benzoyl chloride (ACL_CC-01)

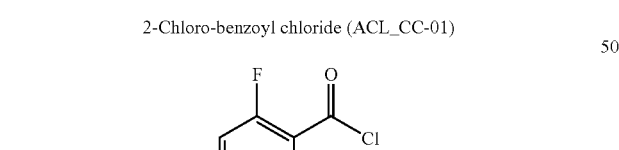

2-Fluoro-benzoyl chloride (ACL_CC-02)

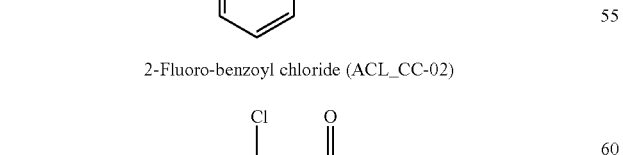

2,6-Dichloro-benzoyl chloride (ACL_CC-03)

-continued

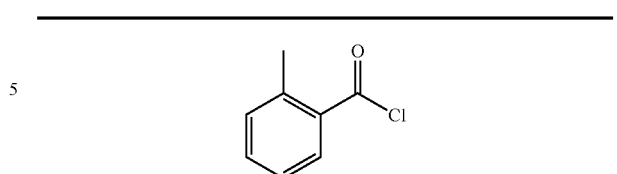

2-Methyl-benzoyl chloride (ACL_CC-04)

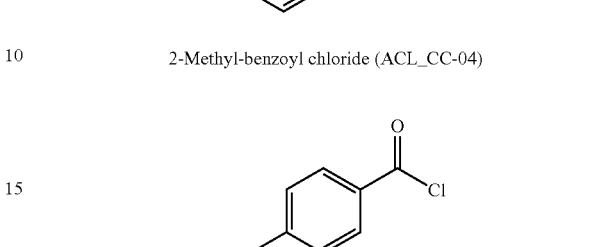

4-Cyano-benzoyl chloride (ACL_CC-05)

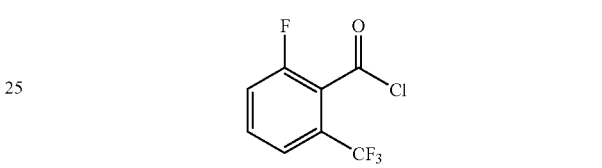

2-Fluoro-6-(trifluoromethyl)-benzoyl chloride (ACL_CC-06)

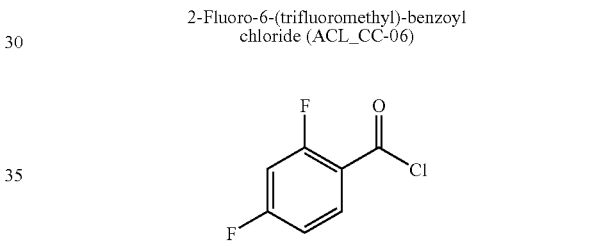

2,4-Difluoro-benzoyl chloride (ACL_CC-07)

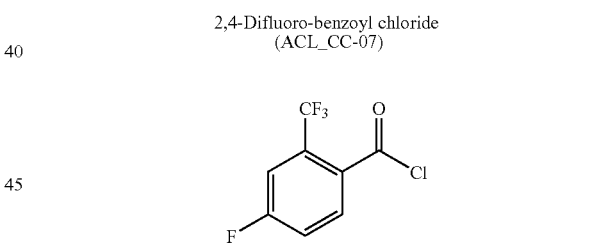

4-Fluoro-2-(trifluoromethyl)-benzoyl chloride (ACL_CC-08)

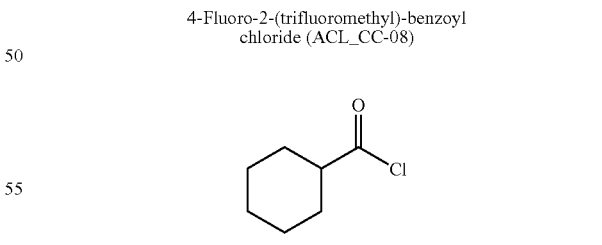

Cyclohexanecarbonyl chloride (ACL_CC-09)

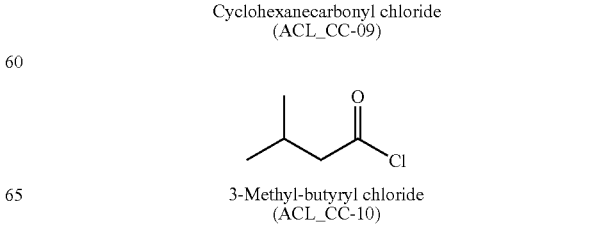

3-Methyl-butyryl chloride (ACL_CC-10)

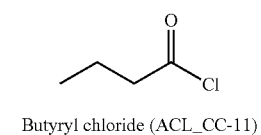

Butyryl chloride (ACL_CC-11)

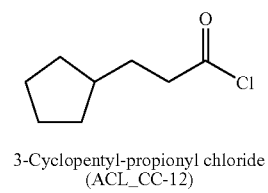

3-Cyclopentyl-propionyl chloride
(ACL_CC-12)

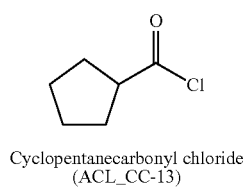

Cyclopentanecarbonyl chloride
(ACL_CC-13)

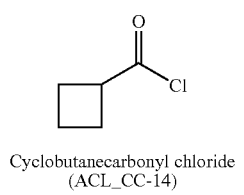

Cyclobutanecarbonyl chloride
(ACL_CC-14)

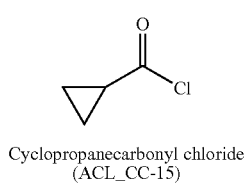

Cyclopropanecarbonyl chloride
(ACL_CC-15)

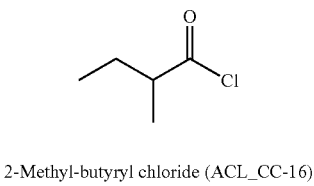

2-Methyl-butyryl chloride (ACL_CC-16)

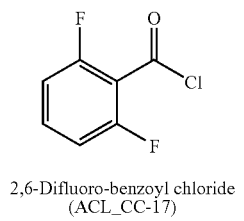 [SMILES: O=C(Cl)c1c(F)cccc1F]

2,6-Difluoro-benzoyl chloride
(ACL_CC-17)

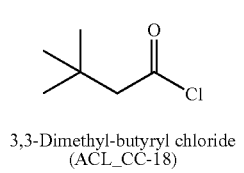

3,3-Dimethyl-butyryl chloride
(ACL_CC-18)

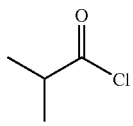

2-Methyl-propionyl chloride
(ACL_CC-19)

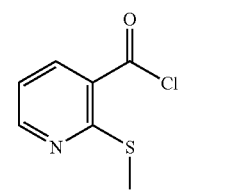

2-Methylsulfanyl-pyridine-3-carbonyl
chloride (ACL_CC-20)

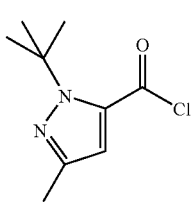

2-tert-Butyl-5-methyl-2H-pyrazole-3-
carbonyl chloride (ACL_CC-21)

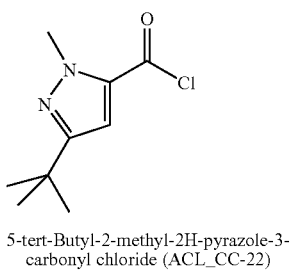

5-tert-Butyl-2-methyl-2H-pyrazole-3-
carbonyl chloride (ACL_CC-22)

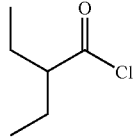

2-Ethyl-butyryl chloride
(ACL_CC-23)

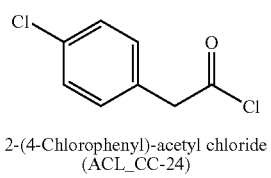 [SMILES: O=C(Cl)Cc1ccc(Cl)cc1]

2-(4-Chlorophenyl)-acetyl chloride
(ACL_CC-24)

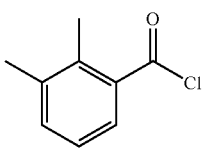

2,3-Dimethyl-benzoyl chloride
(ACL_CC-25)

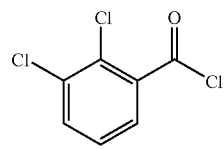

2,3-Dichloro-benzoyl chloride
(ACL_CC-26)

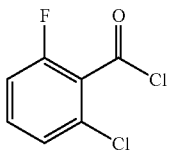

2-Chloro-6-fluoro-benzoyl chloride
(ACL_CC_27)

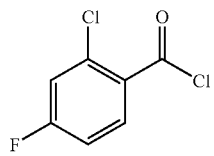

2-Chloro-4-fluoro-benzoyl chloride
(ACL_CC-28)

Acetyl chloride (ACL_CC-29)

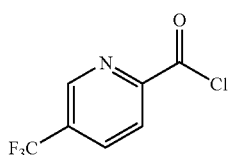

5-(Trifluoromethyl)-pyridine-2-carbonyl
chloride (ACL_CC-30)

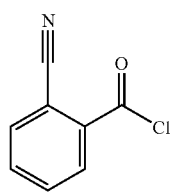

2-Cyano-benzoyl chloride
(ACL_CC-31)

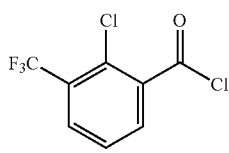

2-Chloro-3-(trifluoromethyl)-benzoyl
chloride (ACL_CC-32)

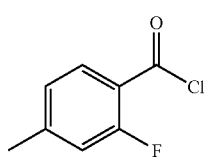

2-Fluoro-4-methyl-benzoyl chloride
(ACL_CC-33)

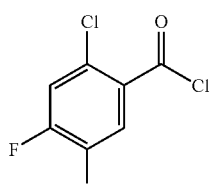

2-Chloro-4,5-difluoro-benzoyl chloride
(ACL_CC-34)

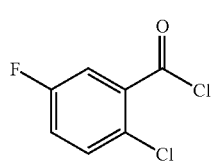

2-Chloro-5-fluoro-benzoyl chloride
(ACL_CC-35)

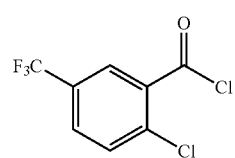

2-Chloro-5-(trifluoromethyl)-benzoyl
chloride (ACL_CC-36)

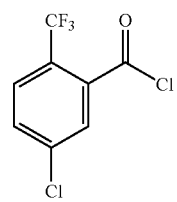

5-Chloro-2-(trifluoromethyl)-benzoyl
chloride (ACL_CC-37)

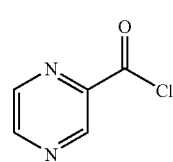

Pyrazine-2-carbonyl chloride
(ACL_CC-38)

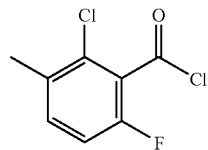

2-Chloro-6-fluoro-3-methyl-benzoyl
chloride (ACL_CC-39)

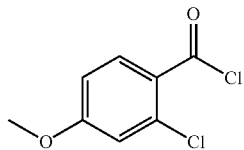

2-Chloro-4-methoxy-benzoyl chloride
(ACL_CC-40)

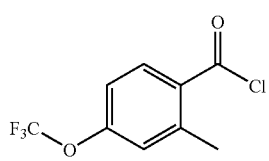

2-Methyl-4-(trifluoromethyloxy)-benzoyl
chloride (ACL_CC-41)

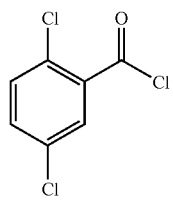

2,5-Dichloro-benzoyl chloride
(ACL_CC-42)

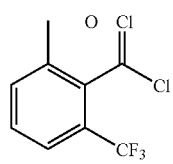

2-Chloro-6-(trifluoromethyl)-benzoyl
chloride (ACL_CC-43)

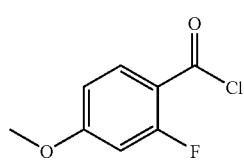

2-Fluoro-4-methoxy-benzoyl chloride
(ACL_CC-44)

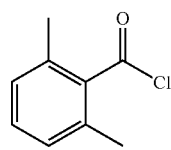

2,6-Dimethyl-benzoyl chloride
(ACL_CC-45)

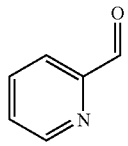

Pyridine-2-carbaldehyde (ALD_CC-01)

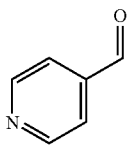

Pyridine-4-carbaldehyde (ALD_CC-02)

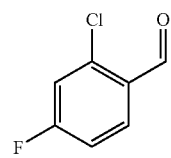

2-Chloro-4-fluoro-benzaldehyde
(ALD_CC-03)

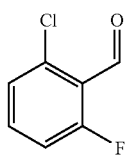

2-Chloro-6-fluoro-benzaldehyde
(ALD_CC-04)

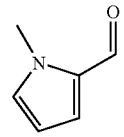

1-Methyl-1H-pyrrole-2-carbaldehyde
(ALD_CC-05)

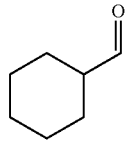

Cyclohexanecarbaldehyde
(ALD_CC-06)

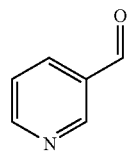

Pyridine-3-carbaldehyde (ALD_CC-07)

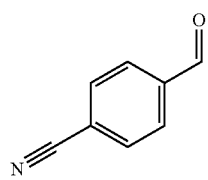

4-Formyl-benzonitrile (ALD_CC-08)

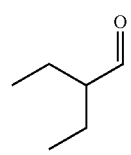

2-Ethyl-butyraldehyde (ALD_CC-09)

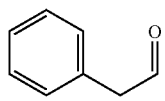

2-Phenyl-acetaldehyde (ALD_CC-10)

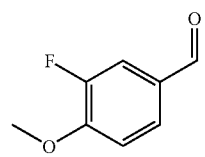

3-Fluoro-4-methoxy-benzaldehyde (ALD_CC-11)

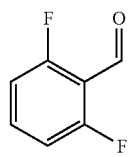

2,6-Difluoro-benzaldehyde (ALD_CC-12)

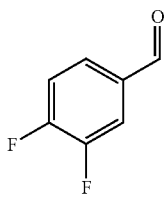

3,4-Difluoro-benzaldehyde (ALD_CC-13)

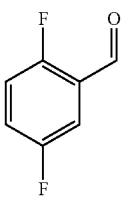

2,5-Difluoro-benzaldehyde (ALD_CC-14)

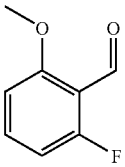

2-Fluoro-6-methoxy-benzaldehyde (ALD_CC-15)

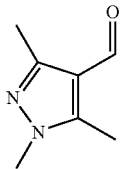

1,3,5-Trimethyl-1H-pyrazole-4-carbaldehyde (ALD_CC-16)

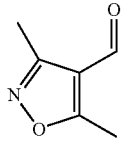

3,5-Dimethyl-isoxazole-4-carbaldehyde (ALD_CC-17)

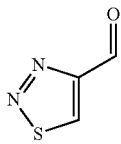

[1,2,3]Thiadiazole-4-carbaldehyde (ALD_CC-18)

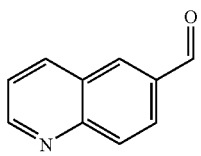

Quinoline-6-carbaldehyde (ALD_CC-19)

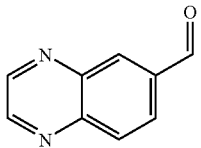

Quinoxaline-6-carbaldehyde (ALD_CC-20)

-continued

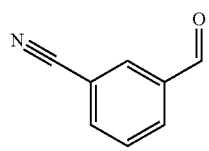

3-Formyl-benzonitrile (ALD_CC-21)

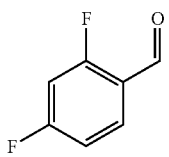

2,4-Difluoro-benzaldehyde
(ALD_CC-22)

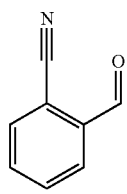

2-Formyl-benzonitrile (ALD_CC-23)

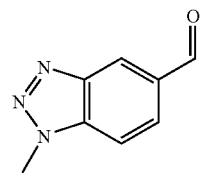

1-Methyl-1H-benzotriazole-5-
carbaldehyde (ALD_CC-24)

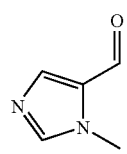

3-Methyl-3H-imidazole-4-carbaldehyde
(ALD_CC-25)

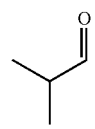

2-Methyl-propionaldehyde (ALD_CC-26)

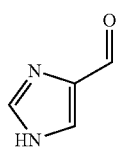

1H-Imidazole-4-carbaldehyde
(ALD_CC-27)

-continued

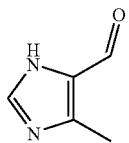

5-Methyl-3H-imidazole-4-carbaldehyde
(ALD_CC-28)

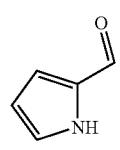

1H-Pyrrole-2-carbaldehyde
(ALD_CC-29)

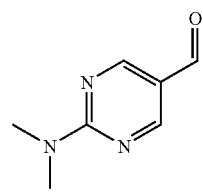

2-Dimethylamino-pyrimidine-5-
carbaldehyde (ALD_CC-30)

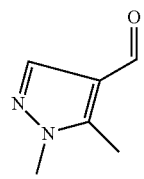

1,5-Dimethyl-1H-pyrazole-4-
carbaldehyde (ALD_CC-31)

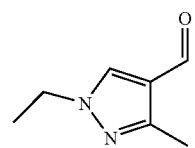

1-Ethyl-3-methyl-1H-pyrazole-4-
carbaldehyde (ALD_CC-32)

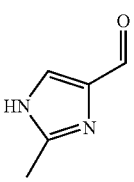

2-Methyl-1H-imidazole-4-carbaldehyde
(ALD_CC-33)

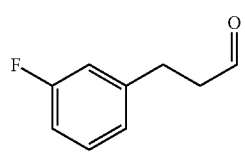

3-(3-Fluorophenyl)-propionaldehyde
(ALD_CC-34)

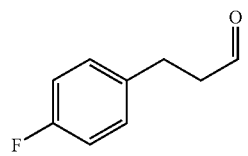

3-(4-Fluorophenyl)-propionaldehyde
(ALD_CC-35)

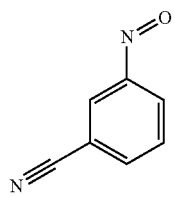

3-Isocyanato-benzonitrile (ICN_CC-03)

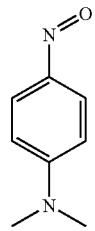

(4-Isocyanato-phenyl)-dimethyl-amine
(ICN_CC-04)

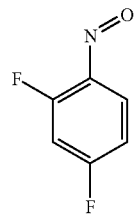

2,4-Difluoro-1-isocyanato-benzene
(ICN_CC-05)

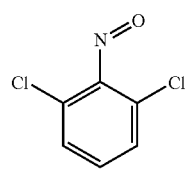

1,3-Dichloro-2-isocyanato-benzene
(ICN_CC-06)

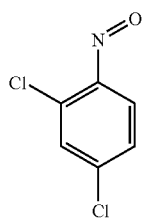

2,4-Dichloro-1-isocyanato-benzene
(ICN_CC-07)

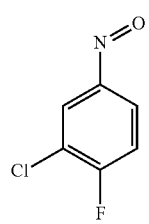

4-Chloro-1-isocyanato-2-
(trifluoromethyl)-benzene
(ICN_CC-08)

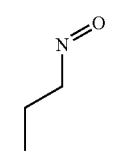

2-Chloro-1-fluoro-4-isocyanato-benzene
(ICN_CC-09)

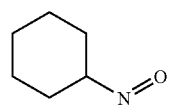

1-Isocyanato-propane
(ICN_CC-10)

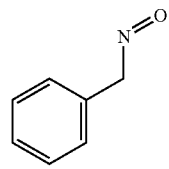

Isocyanato-cyclohexane (ICN_CC-11)

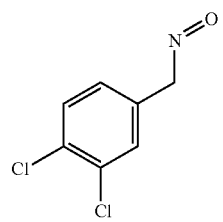

Isocyanato-methyl-benzene
(ICN_CC-12)

1,2-Dichloro-4-(isocyanato-methyl)-
benzene (ICN_CC-13)

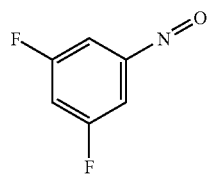

1,3-Difluoro-5-isocyanato-
benzene (ICN_CC-14)

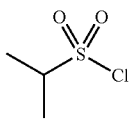

Propane-2-sulfonyl chloride
(SCI_CC-03)

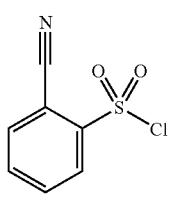

2-Cyano-benzenesulfonyl chloride
(SCI_CC-04)

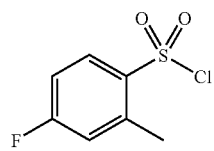

4-Fluoro-2-methyl-benzenesulfonyl
chloride (SCI_CC-05)

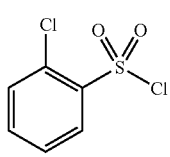

2-Chloro-benzenesulfonyl chloride
(SCI_CC-06)

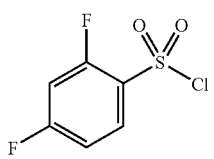

2,4-Dichloro-benzenesulfonyl
chloride (SCI_CC-07)

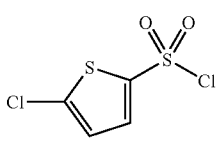

5-Chloro-thiophene-2-
sulfonyl chloride
(SCI_CC-08)

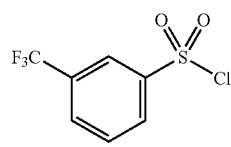

3-(Trifluoromethyl)-benzenesulfonyl
chloride (SCI_CC-09)

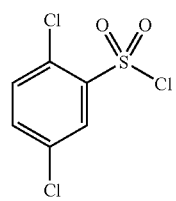

2,5-Dichloro-benzenesulfonyl chloride
(SCI_CC-10)

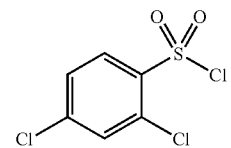

2,4-Dichloro-benzenesulfonyl chloride
(SCI_CC-11)

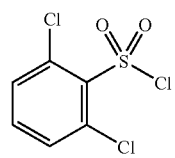

2,6-Dichloro-benzenesulfonyl chloride
(SCI_CC-12)

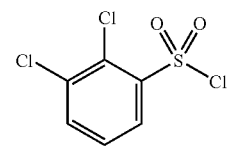

2,3-Dichloro-benzenesulfonyl chloride
(SCI_CC-13)

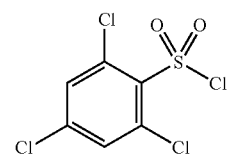

2,4,6-Trichloro-benzenesulfonyl chloride
(SCI_CC-14)

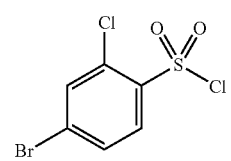

4-Bromo-2-chloro-benzenesulfonyl
chloride (SCI_CC-15)

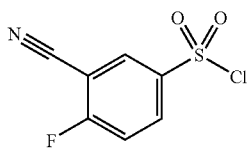

3-Cyano-4-fluoro-benzenesulfonyl
chloride (SCI_CC-16)

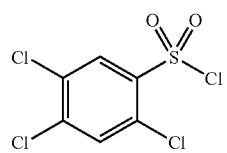

2,4,5-Trichloro-benzenesulfonyl chloride
(SCI_CC-17)

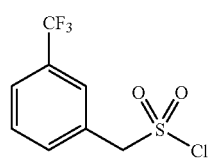

[3-(Trifluoromethyl)phenyl]-
methanesulfonyl chloride (SCI_CC-18)

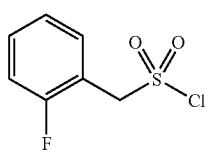

(2-Fluorophenyl)-methanesulfonyl
chloride (SCI_CC-19)

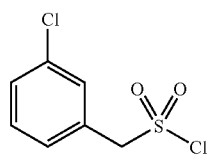

(3-Chlorophenyl)-methanesulfonyl
chloride (SCI_CC-20)

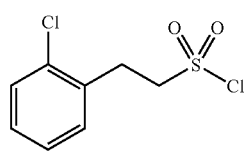

2-(2-Chlorophenyl)-ethanesulfonyl
chloride (SCI_CC-21)

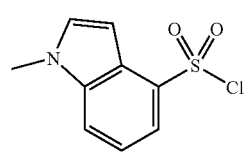

1-Methyl-1H-indole-4-sulfonyl chloride
(SCI_CC-22)

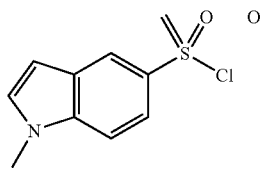

1-Methyl-1H-indole-5-sulfonyl chloride
(SCI_CC-23)

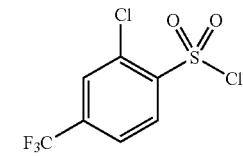

2-Chloro-4-(trifluoromethyl)-
benzenesulfonyl chloride (SCI_CC-24)

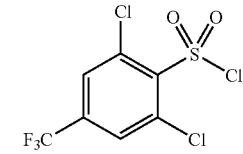

2,6-Dichloro-4-(trifluoromethyl)-
benzenesulfonyl chloride (SCI_CC-25)

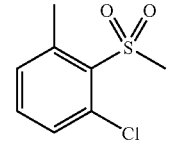

2-Chloro-6-methyl-benzenesulfonyl
chloride (SCI_CC-26)

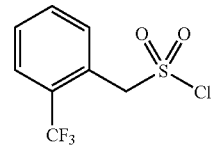

[2-(Trifluoromethyl)-phenyl]-
methanesulfonyl chloride (SCI_CC-27)

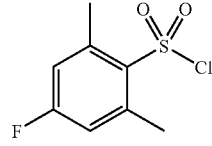

4-Fluoro-2,6-dimethyl-benzenesulfonyl
chloride (SCI_CC-28)

Carboxylic acid ACl_CC-01: Pyridine-2-carboxylic acid [CAS 4930-98-7] commercially obtainable from e.g. Acros. Carboxylic acid ACl_CC-02: 2-(Trifluoromethyl)-benzoic acid [CAS 433-97-6] commercially obtainable from e.g. Acros. Carboxylic acid ACl_C-03: 3-Chloro-thiophene-2-carboxylic acid [CAS 59337-89-2] commercially obtainable from e.g. Acros. Carboxylic acid ACl_CC-04: 5-Chloro-thiophene-2-carboxylic acid [CAS 24065-33-6] commercially obtainable from e.g. Acros. Carboxylic acid ACl_CC-05: 2,4-Dichloro-benzoic acid [CAS 50-84-0] commercially obtainable from e.g. Acros. Carboxylic acid ACl_CC-06:

4-Methoxy-2,6-dimethyl-benzoic acid [CAS 37934-89-7] commercially obtainable from e.g. Transworldchemicals. Carboxylic acid ACl_CC-07: 2-(2-Chlorophenyl)-acetic acid [CAS 2444-36-2] commercially obtainable from e.g. Acros. Carboxylic acid ACl_CC-08: (E)-3-(2-Chlorophenyl)-acrylic acid [CAS 3752-25-8] commercially obtainable from e.g. Acros.

Synthesis of carboxylic acid ACl_CC-09

2-(2-Chlorophenyl)-2-phenyl-acetic acid

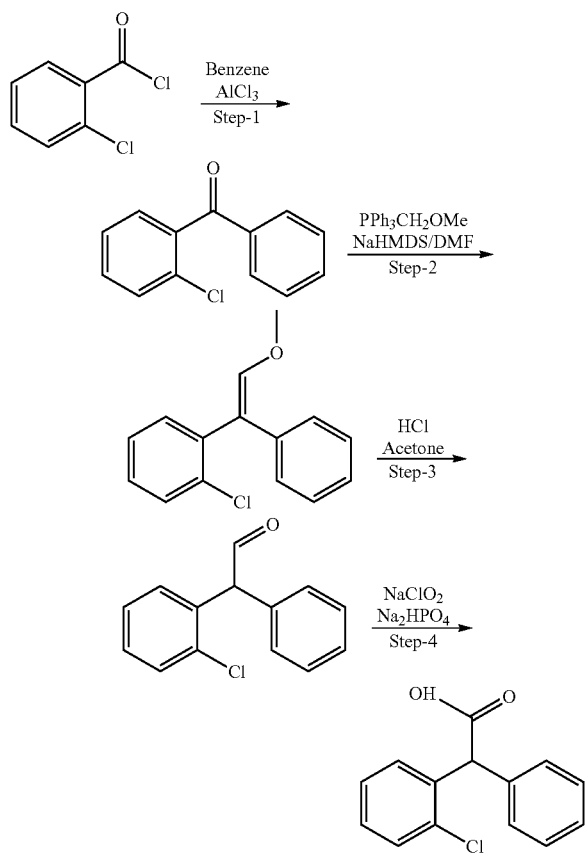

Step 1: A solution of 2-chloro benzoyl chloride (1 g, 5.75 mmol) in benzene (10 ml) was added to a suspension of AlCl$_3$ (842 mg, 6.33 mmol) in benzene (20 ml) at 20° C. and the mixture was heated under reflux for 20 h. The reaction mixture was cooled to room temperature, adjusted to pH ~3-4 with 1N hydrochloric acid and finally extracted with ethyl acetate (2×50 ml).

The combined organic phases were washed with water and sat. NaCl solution, dried over sodium sulfate and concentrated under reduced pressure. The crude product was purified by column chromatography.

Yield: 79% (1 g)

Step 2: 1M NaHMDS (13.8 ml, 13.8 mmol) was added to a suspension of methoxy methyl triphenylphosphonium chloride (3 g, 13.8 mmol) in dioxane (15 ml) and the mixture was stirred at this temperature for 30 min. A solution of the product just prepared in step 1 (81 g, 4.6 mmol) in THF (10 ml) was then added dropwise and the reaction mixture was heated under reflux for 2 h. The reaction mixture was cooled to room temperature, water was added and the mixture was extracted with ethyl acetate. The combined organic phases were washed with water and sat. NaCl solution, dried over sodium sulfate and concentrated under reduced pressure. The crude product was employed in the next step without further purification. Yield: 53% (600 mg) crude Step 3: 8 N HCl (5 ml) was added to a solution of the product just obtained in step 2 (250 mg, 1.02 mmol) in acetone (5 ml) and the mixture was stirred at 50° C. for 2 h. The reaction mixture was concentrated and the residue was adjusted to a pH of ~10 with NaHCO3 solution. The aqueous phase was extracted with ethyl acetate. The combined organic phases were washed with water and sat. NaCl solution, dried over sodium sulfate and concentrated under reduced pressure. The crude product was employed in the next step without further purification.

Yield: 27% (150 mg)

Step 4: 2-Methyl-2-butene (164 mg, 2.34 mmol) and sodium hydrogen ortho phosphate (407 mg, 2.60 mmol) were added to a solution of the products just obtained in step 3 (150 mg, 0.652 mmol) in THF/tert-butanol/water (ratio=3:3:1; 10 ml) and the reaction mixture was stirred at 20° C. for 16 h. The water was removed from the reaction mixture and the residue was diluted with ethyl acetate. The organic phase was washed with water and sat. NaCl solution, dried over sodium sulfate and concentrated under reduced pressure. The crude product was employed in the next step without further purification.

Yield: 62% (100 mg)

Sulfonyl chloride SCl_CC-01: 2-Chloro-benzenesulfonyl chloride [CAS 2905-23-9] commercially obtainable from e.g. Acros. Sulfonyl chloride SCl_CC-02: 4-Methoxy-2,6-dimethyl-benzenesulfonyl chloride [CAS-] commercially obtainable from e.g. Apolloscientific. Isocyanate ICN_CC-01: 1,2-Dichloro-4-isocyanato-benzene [CAS 102-36-3] commercially obtainable from e.g. Acros. Isocyanate ICN_CC-02: 1-Chloro-2-(isocyanato-methyl)benzene [CAS 55204-93-8] commercially obtainable from e.g. Acros.

All acid chlorides (ACL_CC-01 to ACL_CC-45), sulfonyl chlorides (SCl_CC-01 to SCl_CC-28), isocyanates (ICN_CC-01 to ICN_CC-14) and aldehydes (ALD_CC-01 to ALD_CC-35) depicted above were commercially available at the time of synthesis.

4) Parallel Synthesis of Dihydroindenes—Library No. 1:

General:

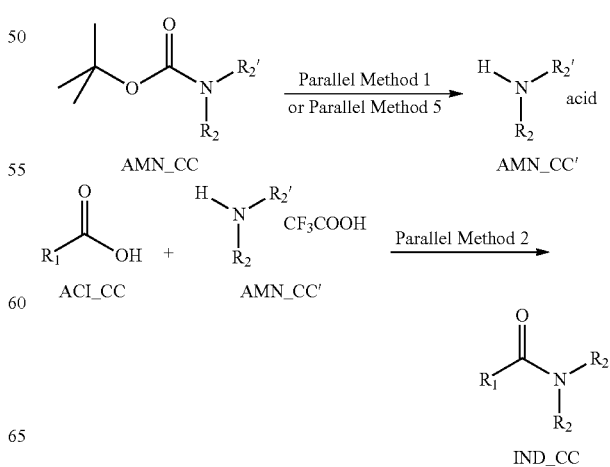

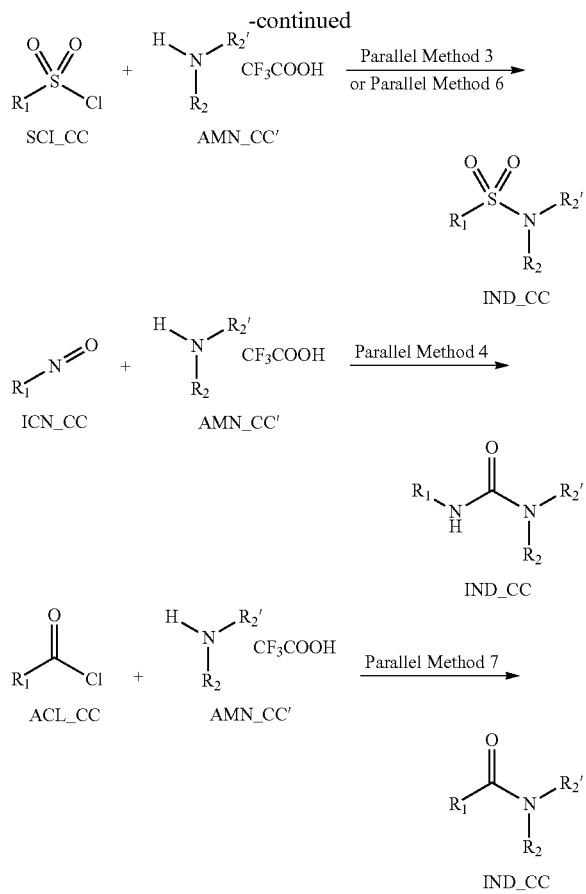

The amine units AMN_CC' were prepared from the Boc-protected amines AMN_CC by Parallel Method 1 or Parallel Method 5 in accordance with the above equation. The amine acid salts AMN_CC' obtained in this way were reacted in parallel synthesis by Parallel Method 2 with the acids ACl_CC to give the amidic products IND_CC. AMN_CC' were reacted in parallel synthesis by Parallel Method 3 or Parallel Method 6 with the sulfonyl chlorides SCl_CC to give the sulfonylated products IND_CC. AMN_CC' were reacted in parallel synthesis by Parallel Method 4 with the isocyanates ICN_CC to give the ureas IND_CC. AMN_CC' were reacted in parallel synthesis by Parallel Method 7 with the acid chlorides ACL_CC to give amidic products IND_CC. The correlation of products (IND_CC) to the units used (ACl_CC, SCl_CC, ICN_CC and AMN) and can be seen from the synthesis matrix.

The crude products of the parallel synthesis were purified by column chromatography. It was possible to demonstrate the identity of the products by analytical HPLC-MS measurements (cf. HPLC-MS data).

Parallel Method 1: Boc Deprotection

20% trifluoroacetic acid in methylene chloride (10 ml/mol) was added to the corresponding Boc-protected amine (1 eq., AMN_CC) at 0° C. The reaction mixture obtained was stirred at 25° C. for 4 h. The course of the reaction was monitored by means of thin layer chromatography. The solvent was then removed under reduced pressure and the residue was dried thoroughly in order to remove traces of trifluoroacetic acid. The crude product obtained in this way was used for synthesis of the libraries without further purification.

Parallel Method 2: Amide Formation

HATU (2 eq.) was added to a methylene chloride solution (3 ml/mmol) of the acid unit ACl_CC (1 eq.) at 0° C. and the mixture was stirred for 15 min. In a further round-bottomed flask, a methylene chloride solution (1 ml/mmol) of the Boc-deprotected amine unit AMN_CC' (1.5 eq.) was cooled in an ice bath, DIPEA (3 eq.) was added and the mixture was then added to the acid unit at 0° C. The reaction mixture was stirred at room temperature for 16 h and finally diluted with methylene chloride. The organic phase was washed successively with aqueous $NH_4Cl$ solution, $NaHCO_3$ solution and sat. NaCl solution, dried over sodium sulfate and concentrated under reduced pressure. The crude product was purified via a Biotage parallel purification system. Some compounds were purified manually by column chromatography over neutral aluminium oxide with methanol/methylene chloride as the mobile phase. A few compounds were purified via prep. HPLC with an aqueous ammonia method.

Parallel Method 3: Sulfonylation

Diisopropylethylamine (3 eq.) was added dropwise to a suspension of AMN_CC' (1 eq.) in methylene chloride (4 ml/mmol) at 0° C. and the mixture was stirred further for 15 minutes. The sulfonyl chloride (SCl_CC) (1.1 eq.) was then added at 0° C. and the reaction mixture was stirred at room temperature for 12 h. The reaction mixture was diluted with methylene chloride and the organic phase was washed successively with water, aqueous $NH_4Cl$ solution and sat. NaCl solution, dried over sodium sulfate and concentrated under reduced pressure. The crude product was purified via a Biotage parallel purification system. Some compounds were purified manually by column chromatography over neutral aluminium oxide with methanol/methylene chloride as the mobile phase. A few compounds were purified via prep. HPLC with an aqueous ammonia method.

Parallel Method 4: Urea Formation

Diisopropylethylamine (3 eq.) was added dropwise to a suspension of AMN_CC' (1 eq.) in methylene chloride (4 ml/mmol) at 0° C. and the mixture was stirred further for 15 minutes. The isocyanate (ICN_CC) (1.1 eq.) was then added at 0° C. and the reaction mixture was stirred at room temperature for 12 h. The reaction mixture was diluted with methylene chloride and the organic phase was washed successively with water and sat. NaCl solution, dried over sodium sulfate and concentrated under reduced pressure. The crude product was purified via a Biotage parallel purification system. Some compounds were purified manually by column chromatography over neutral aluminium oxide with methanol/methylene chloride as the mobile phase. A few compounds were purified via prep. HPLC with an aqueous ammonia method.

Parallel Method 5: Boc Deprotection

Acetyl chloride (500 µmol, 35.32 µl) was added at room temperature to the Boc-protected amine AMN_CC (100 µmol) dissolved in 1 ml ethanol. The reaction mixture was stirred at room temperature overnight and the solvent removed under reduced pressure. The crude product AMN_CC' obtained in this way was used for library synthesis without further purification.

Parallel Method 6: Sulfonylation

Diisopropylethylamine (500 µmol, 85 µl) was added to a suspension of AMN_CC' (100 µmol) in methylene chloride (1 ml) at room temperature. The sulfonyl chloride (SCl_CC) (150 µmol), dissolved in methylene chloride (1 ml), was then added and the reaction mixture was stirred at room temperature overnight. The reaction mixture was treated with sat. NaCl solution (1 ml) and aqueous NaOH solution (1 mol/L) and stirred at room temperature for 30 minutes. The organic layer was separated and the aqueous phase was extracted with methylene chloride for 2 times. The combined organic phases were concentrated under reduced pressure. The crude product was purified via a HPLC-MS system.

Parallel Method 7: Amide Formation

Diisopropylethylamine (500 μmol, 85 μl) was added to a suspension of AMN_CC' (100 μmol) in methylene chloride (1 ml) at room temperature. The sulfonyl chloride (ACL_CC) (150 μmol), dissolved in methylene chloride (1 ml), was then added and the reaction mixture was stirred at room temperature overnight. The reaction mixture was treated with sat. NaCl solution (1 ml) and aqueos NaOH solution (1 mol/L) and stirred at room temperature for 30 minutes. The organic layer was separated and the aqueos phase was extracted with methylene chloride for 2 times. The combined organic phases were concentrated under reduced pressure. The crude product was purified via a HPLC-MS system.

Synthesis Matrix:

| Example no. | ACI_CC, SCI_CC or ICN_CC | Amine (AMN_CC) | Method no. |
|---|---|---|---|
| Ind_CC-001 | SCI_CC-02 | AMN_CC-01 | No. 1 & No. 3 |
| Ind_CC-002 | ACI_CC-01 | AMN_CC-01 | No. 1 & No. 2 |
| Ind_CC-003 | ACI_CC-02 | AMN_CC-01 | No. 1 & No. 2 |
| Ind_CC-004 | ACI_CC-03 | AMN_CC-01 | No. 1 & No. 2 |
| Ind_CC-005 | ACI_CC-04 | AMN_CC-01 | No. 1 & No. 2 |
| Ind_CC-006 | ACI_CC-05 | AMN_CC-01 | No. 1 & No. 2 |
| Ind_CC-007 | ACI_CC-07 | AMN_CC-01 | No. 1 & No. 2 |
| Ind_CC-008 | ACI_CC-08 | AMN_CC-01 | No. 1 & No. 2 |
| Ind_CC-009 | ACI_CC-09 | AMN_CC-01 | No. 1 & No. 2 |
| Ind_CC-010 | SCI_CC-01 | AMN_CC-01 | No. 1 & No. 3 |
| Ind_CC-011 | ICN_CC-01 | AMN_CC-01 | No. 1 & No. 4 |
| Ind_CC-012 | ICN_CC-02 | AMN_CC-01 | No. 1 & No. 4 |
| Ind_CC-013 | ACI_CC-06 | AMN_CC-01 | No. 1 & No. 2 |
| Ind_CC-014 | ACI_CC-01 | AMN_CC-02 | No. 1 & No. 2 |
| Ind_CC-015 | ACI_CC-02 | AMN_CC-02 | No. 1 & No. 2 |
| Ind_CC-016 | ACI_CC-03 | AMN_CC-02 | No. 1 & No. 2 |
| Ind_CC-017 | ACI_CC-04 | AMN_CC-02 | No. 1 & No. 2 |
| Ind_CC-018 | ACI_CC-05 | AMN_CC-02 | No. 1 & No. 2 |
| Ind_CC-019 | ACI_CC-07 | AMN_CC-02 | No. 1 & No. 2 |
| Ind_CC-020 | ACI_CC-08 | AMN_CC-02 | No. 1 & No. 2 |
| Ind_CC-021 | ACI_CC-09 | AMN_CC-02 | No. 1 & No. 2 |
| Ind_CC-022 | ICN_CC-01 | AMN_CC-02 | No. 1 & No. 4 |
| Ind_CC-023 | ICN_CC-02 | AMN_CC-02 | No. 1 & No. 4 |
| Ind_CC-024 | SCI_CC-01 | AMN_CC-02 | No. 1 & No. 3 |
| Ind_CC-025 | SCI_CC-02 | AMN_CC-02 | No. 1 & No. 3 |
| Ind_CC-026 | ACI_CC-06 | AMN_CC-02 | No. 1 & No. 2 |
| Ind_CC-027 | ACI_CC-01 | AMN_CC-03 | No. 1 & No. 2 |
| Ind_CC-028 | ACI_CC-02 | AMN_CC-03 | No. 1 & No. 2 |
| Ind_CC-029 | ACI_CC-03 | AMN_CC-03 | No. 1 & No. 2 |
| Ind_CC-030 | ACI_CC-04 | AMN_CC-03 | No. 1 & No. 2 |
| Ind_CC-031 | ACI_CC-05 | AMN_CC-03 | No. 1 & No. 2 |
| Ind_CC-032 | ACI_CC-07 | AMN_CC-03 | No. 1 & No. 2 |
| Ind_CC-033 | ACI_CC-08 | AMN_CC-03 | No. 1 & No. 2 |
| Ind_CC-034 | SCI_CC-01 | AMN_CC-03 | No. 1 & No. 3 |
| Ind_CC-035 | SCI_CC-02 | AMN_CC-03 | No. 1 & No. 3 |
| Ind_CC-036 | ICN_CC-01 | AMN_CC-03 | No. 1 & No. 4 |
| Ind_CC-037 | ICN_CC-02 | AMN_CC-03 | No. 1 & No. 4 |
| Ind_CC-038 | ACI_CC-09 | AMN_CC-03 | No. 1 & No. 2 |
| Ind_CC-039 | ACI_CC-06 | AMN_CC-03 | No. 1 & No. 2 |
| Ind_CC-040 | ACI_CC-01 | AMN_CC-04 | No. 1 & No. 2 |
| Ind_CC-041 | ACI_CC-02 | AMN_CC-04 | No. 1 & No. 2 |
| Ind_CC-042 | ACI_CC-03 | AMN_CC-04 | No. 1 & No. 2 |
| Ind_CC-043 | ACI_CC-04 | AMN_CC-04 | No. 1 & No. 2 |
| Ind_CC-044 | ACI_CC-05 | AMN_CC-04 | No. 1 & No. 2 |
| Ind_CC-045 | ACI_CC-07 | AMN_CC-04 | No. 1 & No. 2 |
| Ind_CC-046 | ACI_CC-08 | AMN_CC-04 | No. 1 & No. 2 |
| Ind_CC-047 | ICN_CC-01 | AMN_CC-04 | No. 1 & No. 4 |
| Ind_CC-048 | ICN_CC-02 | AMN_CC-04 | No. 1 & No. 4 |
| Ind_CC-049 | SCI_CC-01 | AMN_CC-04 | No. 1 & No. 3 |
| Ind_CC-050 | SCI_CC-02 | AMN_CC-04 | No. 1 & No. 3 |
| Ind_CC-051 | ACI_CC-09 | AMN_CC-04 | No. 1 & No. 2 |
| Ind_CC-052 | ACI_CC-01 | AMN_CC-13 | No. 1 & No. 2 |
| Ind_CC-053 | ACI_CC-07 | AMN_CC-13 | No. 1 & No. 2 |
| Ind_CC-054 | ACI_CC-04 | AMN_CC-13 | No. 1 & No. 2 |
| Ind_CC-055 | ACI_CC-03 | AMN_CC-13 | No. 1 & No. 2 |
| Ind_CC-056 | ACI_CC-09 | AMN_CC-13 | No. 1 & No. 2 |
| Ind_CC-057 | ICN_CC-01 | AMN_CC-13 | No. 1 & No. 4 |
| Ind_CC-058 | ACI_CC-02 | AMN_CC-13 | No. 1 & No. 2 |
| Ind_CC-059 | ACI_CC-05 | AMN_CC-13 | No. 1 & No. 2 |
| Ind_CC-060 | ACI_CC-08 | AMN_CC-13 | No. 1 & No. 2 |
| Ind_CC-061 | ICN_CC-02 | AMN_CC-13 | No. 1 & No. 4 |
| Ind_CC-062 | SCI_CC-01 | AMN_CC-13 | No. 1 & No. 3 |
| Ind_CC-063 | SCI_CC-02 | AMN_CC-13 | No. 1 & No. 3 |
| Ind_CC-064 | ACI_CC-02 | AMN_CC-14 | No. 1 & No. 2 |
| Ind_CC-065 | ACI_CC-03 | AMN_CC-14 | No. 1 & No. 2 |
| Ind_CC-066 | ACI_CC-04 | AMN_CC-14 | No. 1 & No. 2 |
| Ind_CC-067 | ACI_CC-05 | AMN_CC-14 | No. 1 & No. 2 |
| Ind_CC-068 | ACI_CC-06 | AMN_CC-14 | No. 1 & No. 2 |
| Ind_CC-069 | ACI_CC-07 | AMN_CC-14 | No. 1 & No. 2 |
| Ind_CC-070 | ACI_CC-08 | AMN_CC-14 | No. 1 & No. 2 |
| Ind_CC-071 | ICN_CC-01 | AMN_CC-14 | No. 1 & No. 4 |
| Ind_CC-072 | SCI_CC-01 | AMN_CC-14 | No. 1 & No. 3 |
| Ind_CC-073 | ICN_CC-02 | AMN_CC-14 | No. 1 & No. 4 |
| Ind_CC-074 | ACI_CC-01 | AMN_CC-14 | No. 1 & No. 2 |
| Ind_CC-075 | ACI_CC-09 | AMN_CC-14 | No. 1 & No. 2 |
| Ind_CC-076 | SCI_CC-02 | AMN_CC-14 | No. 1 & No. 3 |
| Ind_CC-077 | ACI_CC-07 | AMN_CC-15 | No. 1 & No. 2 |
| Ind_CC-078 | ACI_CC-05 | AMN_CC-15 | No. 1 & No. 2 |
| Ind_CC-079 | ACI_CC-04 | AMN_CC-15 | No. 1 & No. 2 |
| Ind_CC-080 | ACI_CC-03 | AMN_CC-15 | No. 1 & No. 2 |
| Ind_CC-081 | ACI_CC-02 | AMN_CC-15 | No. 1 & No. 2 |
| Ind_CC-082 | ACI_CC-09 | AMN_CC-15 | No. 1 & No. 2 |
| Ind_CC-083 | ACI_CC-08 | AMN_CC-15 | No. 1 & No. 2 |
| Ind_CC-084 | ACI_CC-01 | AMN_CC-15 | No. 1 & No. 2 |
| Ind_CC-085 | ICN_CC-01 | AMN_CC-15 | No. 1 & No. 4 |
| Ind_CC-086 | ICN_CC-02 | AMN_CC-15 | No. 1 & No. 4 |
| Ind_CC-087 | SCI_CC-02 | AMN_CC-15 | No. 1 & No. 3 |
| Ind_CC-088 | ACI_CC-06 | AMN_CC-15 | No. 1 & No. 2 |
| Ind_CC-089 | SCI_CC-01 | AMN_CC-15 | No. 1 & No. 3 |
| IND_CC-200 | ACL_CC-42 | AMN_CC-02 | No. 5 & No. 7 |
| IND_CC-201 | ACL_CC-40 | AMN_CC-02 | No. 5 & No. 7 |
| IND_CC-202 | ACL_CC-36 | AMN_CC-02 | No. 5 & No. 7 |
| IND_CC-203 | ACL_CC-35 | AMN_CC-02 | No. 5 & No. 7 |
| IND_CC-204 | ACL_CC-43 | AMN_CC-01 | No. 5 & No. 7 |
| IND_CC-205 | ACL_CC-43 | AMN_CC-04 | No. 5 & No. 7 |
| IND_CC-206 | ACL_CC-43 | AMN_CC-14 | No. 5 & No. 7 |
| IND_CC-207 | ACL_CC-42 | AMN_CC-01 | No. 5 & No. 7 |
| IND_CC-208 | ACL_CC-42 | AMN_CC-04 | No. 5 & No. 7 |
| IND_CC-209 | ACL_CC-42 | AMN_CC-03 | No. 5 & No. 7 |
| IND_CC-210 | ACL_CC-42 | AMN_CC-14 | No. 5 & No. 7 |
| IND_CC-211 | ACL_CC-40 | AMN_CC-01 | No. 5 & No. 7 |
| IND_CC-212 | ACL_CC-40 | AMN_CC-04 | No. 5 & No. 7 |
| IND_CC-213 | ACL_CC-40 | AMN_CC-03 | No. 5 & No. 7 |
| IND_CC-214 | ACL_CC-39 | AMN_CC-01 | No. 5 & No. 7 |
| IND_CC-215 | ACL_CC-39 | AMN_CC-04 | No. 5 & No. 7 |
| IND_CC-216 | ACL_CC-39 | AMN_CC-14 | No. 5 & No. 7 |
| IND_CC-217 | ACL_CC-36 | AMN_CC-01 | No. 5 & No. 7 |
| IND_CC-218 | ACL_CC-36 | AMN_CC-04 | No. 5 & No. 7 |
| IND_CC-219 | ACL_CC-36 | AMN_CC-14 | No. 5 & No. 7 |
| IND_CC-220 | ACL_CC-35 | AMN_CC-01 | No. 5 & No. 7 |
| IND_CC-221 | ACL_CC-35 | AMN_CC-04 | No. 5 & No. 7 |
| IND_CC-222 | ACL_CC-35 | AMN_CC-03 | No. 5 & No. 7 |
| IND_CC-223 | ACL_CC-35 | AMN_CC-14 | No. 5 & No. 7 |
| IND_CC-224 | ACL_CC-34 | AMN_CC-02 | No. 5 & No. 7 |
| IND_CC-225 | ACL_CC-32 | AMN_CC-02 | No. 5 & No. 7 |
| IND_CC-226 | SCI_CC-27 | AMN_CC-02 | No. 5 & No. 6 |
| IND_CC-227 | SCI_CC-26 | AMN_CC-02 | No. 5 & No. 6 |
| IND_CC-228 | ACL_CC-34 | AMN_CC-01 | No. 5 & No. 7 |
| IND_CC-229 | ACL_CC-34 | AMN_CC-04 | No. 5 & No. 7 |
| IND_CC-230 | ACL_CC-34 | AMN_CC-03 | No. 5 & No. 7 |
| IND_CC-231 | ACL_CC-34 | AMN_CC-14 | No. 5 & No. 7 |
| IND_CC-232 | ACL_CC-32 | AMN_CC-01 | No. 5 & No. 7 |
| IND_CC-233 | ACL_CC-32 | AMN_CC-04 | No. 5 & No. 7 |
| IND_CC-234 | ACL_CC-32 | AMN_CC-14 | No. 5 & No. 7 |
| IND_CC-235 | ACL_CC-31 | AMN_CC-03 | No. 5 & No. 7 |
| IND_CC-236 | SCI_CC-27 | AMN_CC-01 | No. 5 & No. 6 |
| IND_CC-237 | SCI_CC-27 | AMN_CC-04 | No. 5 & No. 6 |
| IND_CC-238 | SCI_CC-27 | AMN_CC-14 | No. 5 & No. 6 |
| IND_CC-239 | SCI_CC-26 | AMN_CC-03 | No. 5 & No. 6 |
| IND_CC-240 | SCI_CC-26 | AMN_CC-14 | No. 5 & No. 6 |
| IND_CC-241 | SCI_CC-21 | AMN_CC-01 | No. 5 & No. 6 |
| IND_CC-242 | SCI_CC-21 | AMN_CC-14 | No. 5 & No. 6 |
| IND_CC-243 | ACL_CC-43 | AMN_CC-13 | No. 5 & No. 7 |

| Example no. | ACI_CC, SCI_CC or ICN_CC | Amine (AMN_CC) | Method no. |
|---|---|---|---|
| IND_CC-244 | ACL_CC-42 | AMN_CC-13 | No. 5 & No. 7 |
| IND_CC-245 | ACL_CC-42 | AMN_CC-15 | No. 5 & No. 7 |
| IND_CC-246 | ACL_CC-40 | AMN_CC-13 | No. 5 & No. 7 |
| IND_CC-247 | ACL_CC-40 | AMN_CC-15 | No. 5 & No. 7 |
| IND_CC-248 | ACL_CC-39 | AMN_CC-13 | No. 5 & No. 7 |
| IND_CC-249 | ACL_CC-39 | AMN_CC-15 | No. 5 & No. 7 |
| IND_CC-250 | ACL_CC-36 | AMN_CC-13 | No. 5 & No. 7 |
| IND_CC-251 | ACL_CC-36 | AMN_CC-15 | No. 5 & No. 7 |
| IND_CC-252 | ACL_CC-35 | AMN_CC-13 | No. 5 & No. 7 |
| IND_CC-253 | ACL_CC-35 | AMN_CC-15 | No. 5 & No. 7 |
| IND_CC-254 | ACL_CC-32 | AMN_CC-13 | No. 5 & No. 7 |
| IND_CC-255 | ACL_CC-32 | AMN_CC-15 | No. 5 & No. 7 |
| IND_CC-256 | SCI_CC-27 | AMN_CC-13 | No. 5 & No. 6 |
| IND_CC-258 | SCI_CC-27 | AMN_CC-15 | No. 5 & No. 6 |
| IND_CC-259 | SCI_CC-26 | AMN_CC-13 | No. 5 & No. 6 |
| IND_CC-260 | SCI_CC-21 | AMN_CC-13 | No. 5 & No. 6 |
| IND_CC-261 | ACL_CC-28 | AMN_CC-02 | No. 5 & No. 7 |
| IND_CC-262 | ACL_CC-28 | AMN_CC-01 | No. 5 & No. 7 |
| IND_CC-263 | ACL_CC-28 | AMN_CC-04 | No. 5 & No. 7 |
| IND_CC-264 | ACL_CC-27 | AMN_CC-04 | No. 5 & No. 7 |
| IND_CC-265 | ACL_CC-26 | AMN_CC-02 | No. 5 & No. 7 |
| IND_CC-266 | ACL_CC-26 | AMN_CC-01 | No. 5 & No. 7 |
| IND_CC-267 | ACL_CC-26 | AMN_CC-04 | No. 5 & No. 7 |
| IND_CC-268 | ACL_CC-03 | AMN_CC-02 | No. 5 & No. 7 |
| IND_CC-269 | ACL_CC-03 | AMN_CC-01 | No. 5 & No. 7 |
| IND_CC-270 | ACL_CC-03 | AMN_CC-04 | No. 5 & No. 7 |
| IND_CC-271 | ACL_CC-01 | AMN_CC-04 | No. 5 & No. 7 |
| IND_CC-272 | ACL_CC-01 | AMN_CC-02 | No. 5 & No. 7 |
| IND_CC-273 | ACL_CC-01 | AMN_CC-01 | No. 5 & No. 7 |
| IND_CC-274 | ACL_CC-28 | AMN_CC-03 | No. 5 & No. 7 |
| IND_CC-275 | ACL_CC-28 | AMN_CC-14 | No. 5 & No. 7 |
| IND_CC-276 | ACL_CC-28 | AMN_CC-13 | No. 5 & No. 7 |
| IND_CC-277 | ACL_CC-28 | AMN_CC-15 | No. 5 & No. 7 |
| IND_CC-278 | ACL_CC-27 | AMN_CC-03 | No. 5 & No. 7 |
| IND_CC-279 | ACL_CC-27 | AMN_CC-13 | No. 5 & No. 7 |
| IND_CC-280 | ACL_CC-27 | AMN_CC-15 | No. 5 & No. 7 |
| IND_CC-281 | ACL_CC-26 | AMN_CC-03 | No. 5 & No. 7 |
| IND_CC-282 | ACL_CC-26 | AMN_CC-14 | No. 5 & No. 7 |
| IND_CC-283 | ACL_CC-26 | AMN_CC-13 | No. 5 & No. 7 |
| IND_CC-284 | ACL_CC-26 | AMN_CC-15 | No. 5 & No. 7 |
| IND_CC-286 | ACL_CC-03 | AMN_CC-03 | No. 5 & No. 7 |
| IND_CC-287 | ACL_CC-03 | AMN_CC-14 | No. 5 & No. 7 |
| IND_CC-288 | ACL_CC-03 | AMN_CC-13 | No. 5 & No. 7 |
| IND_CC-289 | ACL_CC-03 | AMN_CC-15 | No. 5 & No. 7 |
| IND_CC-290 | ACL_CC-01 | AMN_CC-03 | No. 5 & No. 7 |
| IND_CC-291 | ACL_CC-01 | AMN_CC-14 | No. 5 & No. 7 |
| IND_CC-292 | ACL_CC-01 | AMN_CC-13 | No. 5 & No. 7 |
| IND_CC-293 | ACL_CC-01 | AMN_CC-15 | No. 5 & No. 7 |
| IND_CC-294 | ACL_CC-45 | AMN_CC-01 | No. 5 & No. 7 |
| IND_CC-295 | ACL_CC-45 | AMN_CC-04 | No. 5 & No. 7 |
| IND_CC-296 | ACL_CC-44 | AMN_CC-02 | No. 5 & No. 7 |
| IND_CC-297 | ACL_CC-44 | AMN_CC-01 | No. 5 & No. 7 |
| IND_CC-298 | ACL_CC-44 | AMN_CC-04 | No. 5 & No. 7 |
| IND_CC-299 | ACL_CC-41 | AMN_CC-02 | No. 5 & No. 7 |
| IND_CC-300 | ACL_CC-41 | AMN_CC-01 | No. 5 & No. 7 |
| IND_CC-301 | ACL_CC-37 | AMN_CC-02 | No. 5 & No. 7 |
| IND_CC-302 | ACL_CC-37 | AMN_CC-01 | No. 5 & No. 7 |
| IND_CC-303 | ACL_CC-37 | AMN_CC-04 | No. 5 & No. 7 |
| IND_CC-304 | ACL_CC-33 | AMN_CC-02 | No. 5 & No. 7 |
| IND_CC-305 | ACL_CC-33 | AMN_CC-01 | No. 5 & No. 7 |
| IND_CC-306 | ACL_CC-33 | AMN_CC-04 | No. 5 & No. 7 |
| IND_CC-307 | ACL_CC-45 | AMN_CC-03 | No. 5 & No. 7 |
| IND_CC-308 | ACL_CC-45 | AMN_CC-14 | No. 5 & No. 7 |
| IND_CC-309 | ACL_CC-45 | AMN_CC-13 | No. 5 & No. 7 |
| IND_CC-310 | ACL_CC-45 | AMN_CC-15 | No. 5 & No. 7 |
| IND_CC-311 | ACL_CC-44 | AMN_CC-14 | No. 5 & No. 7 |
| IND_CC-312 | ACL_CC-44 | AMN_CC-13 | No. 5 & No. 7 |
| IND_CC-313 | ACL_CC-44 | AMN_CC-15 | No. 5 & No. 7 |
| IND_CC-314 | ACL_CC-37 | AMN_CC-14 | No. 5 & No. 7 |
| IND_CC-315 | ACL_CC-37 | AMN_CC-13 | No. 5 & No. 7 |
| IND_CC-316 | ACL_CC-37 | AMN_CC-15 | No. 5 & No. 7 |
| IND_CC-317 | ACL_CC-33 | AMN_CC-14 | No. 5 & No. 7 |
| IND_CC-318 | ACL_CC-33 | AMN_CC-13 | No. 5 & No. 7 |
| IND_CC-319 | ACL_CC-33 | AMN_CC-15 | No. 5 & No. 7 |
| IND_CC-320 | SCI_CC-24 | AMN_CC-02 | No. 5 & No. 6 |
| IND_CC-321 | SCI_CC-12 | AMN_CC-02 | No. 5 & No. 6 |
| IND_CC-322 | SCI_CC-12 | AMN_CC-01 | No. 5 & No. 6 |
| IND_CC-323 | SCI_CC-12 | AMN_CC-04 | No. 5 & No. 6 |
| IND_CC-324 | SCI_CC-11 | AMN_CC-02 | No. 5 & No. 6 |
| IND_CC-325 | SCI_CC-06 | AMN_CC-02 | No. 5 & No. 6 |
| IND_CC-326 | SCI_CC-05 | AMN_CC-02 | No. 5 & No. 6 |
| IND_CC-327 | SCI_CC-09 | AMN_CC-02 | No. 5 & No. 6 |
| IND_CC-328 | SCI_CC-09 | AMN_CC-01 | No. 5 & No. 6 |
| IND_CC-329 | SCI_CC-09 | AMN_CC-04 | No. 5 & No. 6 |
| IND_CC-330 | SCI_CC-24 | AMN_CC-14 | No. 5 & No. 6 |
| IND_CC-331 | SCI_CC-24 | AMN_CC-13 | No. 5 & No. 6 |
| IND_CC-332 | SCI_CC-12 | AMN_CC-13 | No. 5 & No. 6 |
| IND_CC-333 | SCI_CC-12 | AMN_CC-15 | No. 5 & No. 6 |
| IND_CC-334 | SCI_CC-11 | AMN_CC-14 | No. 5 & No. 6 |
| IND_CC-335 | SCI_CC-11 | AMN_CC-13 | No. 5 & No. 6 |
| IND_CC-336 | SCI_CC-06 | AMN_CC-14 | No. 5 & No. 6 |
| IND_CC-337 | SCI_CC-06 | AMN_CC-13 | No. 5 & No. 6 |
| IND_CC-338 | SCI_CC-05 | AMN_CC-14 | No. 5 & No. 6 |
| IND_CC-339 | SCI_CC-05 | AMN_CC-13 | No. 5 & No. 6 |
| IND_CC-340 | SCI_CC-09 | AMN_CC-13 | No. 5 & No. 6 |
| IND_CC-341 | SCI_CC-09 | AMN_CC-14 | No. 5 & No. 6 |
| IND_CC-342 | SCI_CC-09 | AMN_CC-15 | No. 5 & No. 6 |
| IND_CC-343 | SCI_CC-13 | AMN_CC-02 | No. 5 & No. 6 |
| IND_CC-344 | SCI_CC-10 | AMN_CC-02 | No. 5 & No. 6 |
| IND_CC-345 | ACL_CC-04 | AMN_CC-02 | No. 5 & No. 7 |
| IND_CC-346 | ACL_CC-04 | AMN_CC-01 | No. 5 & No. 7 |
| IND_CC-347 | ACL_CC-04 | AMN_CC-04 | No. 5 & No. 7 |
| IND_CC-348 | SCI_CC-19 | AMN_CC-02 | No. 5 & No. 6 |
| IND_CC-349 | SCI_CC-19 | AMN_CC-01 | No. 5 & No. 6 |
| IND_CC-350 | SCI_CC-19 | AMN_CC-04 | No. 5 & No. 6 |
| IND_CC-351 | SCI_CC-20 | AMN_CC-02 | No. 5 & No. 6 |
| IND_CC-352 | SCI_CC-20 | AMN_CC-01 | No. 5 & No. 6 |
| IND_CC-353 | SCI_CC-20 | AMN_CC-04 | No. 5 & No. 6 |
| IND_CC-354 | SCI_CC-28 | AMN_CC-02 | No. 5 & No. 6 |
| IND_CC-355 | SCI_CC-28 | AMN_CC-01 | No. 5 & No. 6 |
| IND_CC-356 | SCI_CC-28 | AMN_CC-04 | No. 5 & No. 6 |
| IND_CC-357 | SCI_CC-10 | AMN_CC-15 | No. 5 & No. 6 |
| IND_CC-358 | ACL_CC-04 | AMN_CC-15 | No. 5 & No. 7 |
| IND_CC-359 | SCI_CC-19 | AMN_CC-15 | No. 5 & No. 6 |
| IND_CC-360 | SCI_CC-20 | AMN_CC-15 | No. 5 & No. 6 |
| IND_CC-361 | SCI_CC-28 | AMN_CC-15 | No. 5 & No. 6 |
| IND_CC-362 | SCI_CC-17 | AMN_CC-02 | No. 5 & No. 6 |
| IND_CC-363 | SCI_CC-17 | AMN_CC-04 | No. 5 & No. 6 |
| IND_CC-364 | ACL_CC-09 | AMN_CC-01 | No. 5 & No. 7 |
| IND_CC-365 | ACL_CC-09 | AMN_CC-02 | No. 5 & No. 7 |
| IND_CC-366 | ACL_CC-09 | AMN_CC-04 | No. 5 & No. 7 |
| IND_CC-367 | ACL_CC-09 | AMN_CC-15 | No. 5 & No. 7 |
| IND_CC-368 | ACL_CC-15 | AMN_CC-01 | No. 5 & No. 7 |
| IND_CC-369 | ACL_CC-15 | AMN_CC-02 | No. 5 & No. 7 |
| IND_CC-370 | ACL_CC-15 | AMN_CC-15 | No. 5 & No. 7 |
| IND_CC-371 | ACL_CC-18 | AMN_CC-01 | No. 5 & No. 7 |
| IND_CC-372 | ACL_CC-18 | AMN_CC-02 | No. 5 & No. 7 |
| IND_CC-373 | ACL_CC-18 | AMN_CC-04 | No. 5 & No. 7 |
| IND_CC-374 | ACL_CC-18 | AMN_CC-15 | No. 5 & No. 7 |
| IND_CC-375 | ACL_CC-29 | AMN_CC-15 | No. 5 & No. |
| IND_CC-376 | ACL_CC-06 | AMN_CC-01 | No. 5 & No. 7 |
| IND_CC-377 | ACL_CC-06 | AMN_CC-04 | No. 5 & No. 7 |
| IND_CC-378 | ACL_CC-06 | AMN_CC-15 | No. 5 & No. 7 |
| IND_CC-379 | ACL_CC-08 | AMN_CC-01 | No. 5 & No. 7 |
| IND_CC-380 | ACL_CC-08 | AMN_CC-02 | No. 5 & No. 7 |
| IND_CC-381 | ACL_CC-08 | AMN_CC-04 | No. 5 & No. 7 |
| IND_CC-382 | ACL_CC-08 | AMN_CC-15 | No. 5 & No. 7 |
| IND_CC-383 | ACL_CC-17 | AMN_CC-01 | No. 5 & No. 7 |
| IND_CC-384 | ACL_CC-17 | AMN_CC-02 | No. 5 & No. 7 |
| IND_CC-385 | ACL_CC-17 | AMN_CC-04 | No. 5 & No. 7 |
| IND_CC-386 | ACL_CC-17 | AMN_CC-15 | No. 5 & No. 7 |
| IND_CC-387 | ACL_CC-25 | AMN_CC-02 | No. 5 & No. 7 |
| IND_CC-388 | ACL_CC-25 | AMN_CC-04 | No. 5 & No. 7 |
| IND_CC-389 | ACL_CC-25 | AMN_CC-15 | No. 5 & No. 7 |
| IND_CC-390 | SCI_CC-18 | AMN_CC-02 | No. 5 & No. 6 |
| IND_CC-391 | ACL_CC-13 | AMN_CC-01 | No. 5 & No. 7 |
| IND_CC-392 | ACL_CC-13 | AMN_CC-02 | No. 5 & No. 7 |
| IND_CC-393 | ACL_CC-13 | AMN_CC-04 | No. 5 & No. 7 |
| IND_CC-394 | ACL_CC-13 | AMN_CC-15 | No. 5 & No. 7 |
| IND_CC-395 | ACL_CC-30 | AMN_CC-02 | No. 5 & No. 7 |
| IND_CC-396 | ACL_CC-30 | AMN_CC-15 | No. 5 & No. 7 |
| IND_CC-397 | ACL_CC-38 | AMN_CC-01 | No. 5 & No. 7 |
| IND_CC-398 | ACL_CC-38 | AMN_CC-15 | No. 5 & No. 7 |
| IND_CC-399 | ACL_CC-02 | AMN_CC-01 | No. 5 & No. 7 |

-continued

| Example no. | ACI_CC, SCI_CC or ICN_CC | Amine (AMN_CC) | Method no. |
|---|---|---|---|
| IND_CC-400 | ACL_CC-02 | AMN_CC-02 | No. 5 & No. 7 |
| IND_CC-401 | ACL_CC-02 | AMN_CC-04 | No. 5 & No. 7 |
| IND_CC-402 | ACL_CC-02 | AMN_CC-15 | No. 5 & No. 7 |
| IND_CC-403 | SCI_CC-25 | AMN_CC-02 | No. 5 & No. 6 |
| IND_CC-404 | SCI_CC-25 | AMN_CC-15 | No. 5 & No. 6 |
| IND_CC-405 | SCI_CC-15 | AMN_CC-02 | No. 5 & No. 6 |
| IND_CC-406 | SCI_CC-14 | AMN_CC-02 | No. 5 & No. 6 |
| IND_CC-407 | SCI_CC-14 | AMN_CC-15 | No. 5 & No. 6 |
| IND_CC-408 | ACL_CC-10 | AMN_CC-02 | No. 5 & No. 7 |
| IND_CC-409 | ACL_CC-10 | AMN_CC-15 | No. 5 & No. 7 |
| IND_CC-410 | ACL_CC-11 | AMN_CC-02 | No. 5 & No. 7 |
| IND_CC-411 | ACL_CC-11 | AMN_CC-15 | No. 5 & No. 7 |
| IND_CC-412 | ACL_CC-12 | AMN_CC-02 | No. 5 & No. 7 |
| IND_CC-413 | ACL_CC-12 | AMN_CC-15 | No. 5 & No. 7 |
| IND_CC-414 | ACL_CC-14 | AMN_CC-02 | No. 5 & No. 7 |
| IND_CC-415 | ACL_CC-14 | AMN_CC-15 | No. 5 & No. 7 |
| IND_CC-416 | ACL_CC-16 | AMN_CC-02 | No. 5 & No. 7 |
| IND_CC-417 | ACL_CC-16 | AMN_CC-15 | No. 5 & No. 7 |
| IND_CC-418 | ACL_CC-19 | AMN_CC-02 | No. 5 & No. 7 |
| IND_CC-419 | ACL_CC-19 | AMN_CC-15 | No. 5 & No. 7 |
| IND_CC-420 | ACL_CC-23 | AMN_CC-15 | No. 5 & No. 7 |

Analytical Data:

| Example no. | [M+] found | R.t. [min] |
|---|---|---|
| Ind_CC-001 | 589.4 | 2.83 |
| Ind_CC-002 | 496 | 2.65 |
| Ind_CC-003 | 563 | 2.76 |
| Ind_CC-004 | 535 | 2.77 |
| Ind_CC-005 | 535 | 2.81 |
| Ind_CC-006 | 563 | 2.8 |
| Ind_CC-007 | 543.2 | 2.74 |
| Ind_CC-008 | 555.2 | 2.84 |
| Ind_CC-009 | 619.3 | 2.92 |
| Ind_CC-010 | 565.4 | 2.78 |
| Ind_CC-011 | 578.2 | 2.89 |
| Ind_CC-012 | 558.4 | 2.75 |
| Ind_CC-013 | 553.2 | 2.73 |
| Ind_CC-014 | 510.2 | 2.52 |
| Ind_CC-015 | 577.2 | 2.79 |
| Ind_CC-016 | 549.4 | 2.76 |
| Ind_CC-017 | 549.2 | 2.83 |
| Ind_CC-018 | 577.2 | 2.85 |
| Ind_CC-019 | 557.2 | 2.8 |
| Ind_CC-020 | 569.2 | 2.86 |
| Ind_CC-021 | 633.3 | 2.98 |
| Ind_CC-022 | 592.2 | 2.93 |
| Ind_CC-023 | 572.2 | 2.8 |
| Ind_CC-024 | 579.2 | 2.86 |
| Ind_CC-025 | 603.4 | 2.91 |
| Ind_CC-027 | 563.2 | 3.93 |
| Ind_CC-028 | 630.3 | 3.94 |
| Ind_CC-029 | 602.1 | 4.07 |
| Ind_CC-030 | 602.3 | 4.13 |
| Ind_CC-031 | 630.3 | 4.07 |
| Ind_CC-032 | 610.4 | 3.98 |
| Ind_CC-033 | 622.3 | 4.08 |
| Ind_CC-034 | 632.2 | 4.05 |
| Ind_CC-035 | 656.3 | 4.14 |
| Ind_CC-036 | 645.3 | 4.28 |
| Ind_CC-037 | 625.2 | 3.92 |
| Ind_CC-038 | 686.3 | 4.2 |
| Ind_CC-040 | 482.2 | 2.62 |
| Ind_CC-041 | 549.4 | 2.71 |
| Ind_CC-042 | 521.2 | 2.74 |
| Ind_CC-043 | 521.2 | 2.78 |
| Ind_CC-044 | 549.4 | 2.78 |
| Ind_CC-045 | 529.2 | 2.71 |
| Ind_CC-046 | 541.4 | 2.81 |
| Ind_CC-047 | 564.2 | 2.89 |
| Ind_CC-048 | 544.2 | 2.74 |
| Ind_CC-049 | 551.2 | 2.77 |
| Ind_CC-050 | 575.2 | 2.82 |
| Ind_CC-051 | 605.4 | 2.9 |
| Ind_CC-052 | 524.4 | 2.78 |
| Ind_CC-053 | 571.2 | 2.84 |
| Ind_CC-054 | 563 | 2.9 |
| Ind_CC-055 | 563 | 2.87 |
| Ind_CC-056 | 647.4 | 3 |
| Ind_CC-057 | 606.4 | 2.99 |
| Ind_CC-058 | 591.2 | 6.73 |
| Ind_CC-059 | 591.2 | 2.89 |
| Ind_CC-060 | 583.2 | 2.92 |
| Ind_CC-061 | 586.2 | 2.84 |
| Ind_CC-062 | 593.4 | 2.89 |
| Ind_CC-064 | 591.2 | 2.9 |
| Ind_CC-065 | 563 | 2.93 |
| Ind_CC-066 | 563.2 | 2.97 |
| Ind_CC-067 | 591.4 | 2.94 |
| Ind_CC-068 | 581.6 | 2.85 |
| Ind_CC-069 | 571.2 | 2.89 |
| Ind_CC-070 | 583.4 | 2.98 |
| Ind_CC-071 | 606.3 | 3.06 |
| Ind_CC-072 | 593.2 | 2.93 |
| Ind_CC-073 | 586.4 | 2.87 |
| Ind_CC-074 | 524.4 | 2.79 |
| Ind_CC-075 | 647.4 | 3.01 |
| Ind_CC-076 | 617.4 | 2.92 |
| Ind_CC-077 | 529.2 | 2.69 |
| Ind_CC-078 | 549.4 | 2.74 |
| Ind_CC-079 | 521.2 | 2.74 |
| Ind_CC-080 | 521.2 | 2.7 |
| Ind_CC-081 | 549.2 | 2.69 |
| Ind_CC-082 | 605.4 | 2.88 |
| Ind_CC-083 | 541.4 | 2.77 |
| Ind_CC-084 | 482 | 2.55 |
| Ind_CC-085 | 564.2 | 2.86 |
| Ind_CC-086 | 544.4 | 2.71 |
| IND_CC-200 | 577.3 | 0.57 |
| IND_CC-201 | 573.4 | 0.55 |
| IND_CC-202 | 611.4 | 0.58 |
| IND_CC-203 | 561.3 | 0.54 |
| IND_CC-204 | 597.3 | 0.54 |
| IND_CC-205 | 538.3 | 0.53 |
| IND_CC-206 | 625.4 | 0.58 |
| IND_CC-207 | 563.3 | 0.53 |
| IND_CC-208 | 549.3 | 0.52 |
| IND_CC-209 | 630.3 | 0.89 |
| IND_CC-210 | 591.3 | 0.57 |
| IND_CC-211 | 559.3 | 0.52 |
| IND_CC-212 | 545.3 | 0.51 |
| IND_CC-213 | 626.4 | 0.86 |
| IND_CC-214 | 561.3 | 0.53 |
| IND_CC-215 | 547.3 | 0.52 |
| IND_CC-216 | 589.4 | 0.57 |
| IND_CC-217 | 597.3 | 0.55 |
| IND_CC-218 | 583.3 | 0.54 |
| IND_CC-219 | 625.4 | 0.59 |
| IND_CC-220 | 547.3 | 0.51 |
| IND_CC-221 | 533.3 | 0.50 |
| IND_CC-222 | 614.3 | 0.86 |
| IND_CC-223 | 575.4 | 0.55 |
| IND_CC-224 | 579.3 | 0.55 |
| IND_CC-225 | 611.4 | 0.56 |
| IND_CC-226 | 627.4 | 0.59 |
| IND_CC-227 | 593.3 | 0.59 |
| IND_CC-228 | 565.3 | 0.52 |
| IND_CC-229 | 551.3 | 0.51 |
| IND_CC-230 | 632.3 | 0.87 |
| IND_CC-231 | 593.4 | 0.58 |
| IND_CC-232 | 597.4 | 0.56 |
| IND_CC-233 | 583.3 | 0.55 |
| IND_CC-234 | 525.4 | 0.60 |
| IND_CC-235 | 587.4 | 0.77 |
| IND_CC-236 | 613.4 | 0.57 |
| IND_CC-237 | 599.4 | 0.57 |
| IND_CC-238 | 641.4 | 0.61 |
| IND_CC-239 | 646.3 | 0.90 |
| IND_CC-240 | 607.4 | 0.61 |
| IND_CC-241 | 593.4 | 0.58 |

| Example no. | [M+] found | R.t. [min] |
|---|---|---|
| IND_CC-242 | 621.4 | 0.61 |
| IND_CC-243 | 625.4 | 0.59 |
| IND_CC-244 | 591.4 | 0.59 |
| IND_CC-245 | 549.3 | 0.52 |
| IND_CC-246 | 587.4 | 0.57 |
| IND_CC-247 | 545.3 | 0.51 |
| IND_CC-248 | 589.4 | 0.58 |
| IND_CC-249 | 547.3 | 0.51 |
| IND_CC-250 | 625.4 | 0.59 |
| IND_CC-251 | 583.3 | 0.54 |
| IND_CC-252 | 575.4 | 0.56 |
| IND_CC-253 | 533.3 | 0.50 |
| IND_CC-254 | 625.4 | 0.60 |
| IND_CC-255 | 583.3 | 0.54 |
| IND_CC-256 | 641.4 | 0.61 |
| IND_CC-258 | 599.4 | 0.56 |
| IND_CC-259 | 607.4 | 0.60 |
| IND_CC-260 | 621.4 | 0.61 |
| IND_CC-261 | 561.4 | 0.55 |
| IND_CC-262 | 547.3 | 0.52 |
| IND_CC-263 | 533.3 | 0.52 |
| IND_CC-264 | 533.3 | 0.51 |
| IND_CC-265 | 577.3 | 0.57 |
| IND_CC-266 | 563.3 | 0.54 |
| IND_CC-267 | 549.3 | 0.54 |
| IND_CC-268 | 577.3 | 0.56 |
| IND_CC-269 | 563.3 | 0.53 |
| IND_CC-270 | 549.3 | 0.52 |
| IND_CC-271 | 515.3 | 0.50 |
| IND_CC-272 | 543.3 | 0.54 |
| IND_CC-273 | 529.3 | 0.51 |
| IND_CC-274 | 614.3 | 0.86 |
| IND_CC-275 | 575.4 | 0.56 |
| IND_CC-276 | 575.4 | 0.56 |
| IND_CC-277 | 533.3 | 0.50 |
| IND_CC-278 | 614.3 | 0.86 |
| IND_CC-279 | 575.4 | 0.56 |
| IND_CC-280 | 533.3 | 0.49 |
| IND_CC-281 | 630.2 | 0.88 |
| IND_CC-282 | 591.3 | 0.58 |
| IND_CC-283 | 591.3 | 0.58 |
| IND_CC-284 | 549.3 | 0.52 |
| IND_CC-286 | 630.3 | 0.87 |
| IND_CC-287 | 591.3 | 0.57 |
| IND_CC-288 | 591.3 | 0.57 |
| IND_CC-289 | 549.3 | 0.51 |
| IND_CC-290 | 596.3 | 0.85 |
| IND_CC-291 | 557.3 | 0.51 |
| IND_CC-292 | 557.3 | 0.55 |
| IND_CC-293 | 515.3 | 0.49 |
| IND_CC-294 | 523.4 | 0.52 |
| IND_CC-295 | 509.4 | 0.52 |
| IND_CC-296 | 557.4 | 0.54 |
| IND_CC-297 | 543.4 | 0.52 |
| IND_CC-298 | 529.3 | 0.52 |
| IND_CC-299 | 607.4 | 0.59 |
| IND_CC-300 | 593.4 | 0.57 |
| IND_CC-301 | 611.3 | 0.58 |
| IND_CC-302 | 597.3 | 0.56 |
| IND_CC-303 | 583.3 | 0.55 |
| IND_CC-304 | 541.4 | 0.56 |
| IND_CC-305 | 527.4 | 0.54 |
| IND_CC-306 | 513.3 | 0.54 |
| IND_CC-307 | 590.4 | 0.86 |
| IND_CC-308 | 551.4 | 0.57 |
| IND_CC-309 | 551.4 | 0.58 |
| IND_CC-310 | 509.4 | 0.51 |
| IND_CC-311 | 571.4 | 0.57 |
| IND_CC-312 | 571.4 | 0.57 |
| IND_CC-313 | 529.3 | 0.51 |
| IND_CC-314 | 625.4 | 0.61 |
| IND_CC-315 | 625.4 | 0.61 |
| IND_CC-316 | 583.3 | 0.56 |
| IND_CC-317 | 555.4 | 0.59 |
| IND_CC-318 | 555.4 | 0.59 |
| IND_CC-319 | 513.4 | 0.53 |
| IND_CC-320 | 647.3 | 0.63 |
| IND_CC-321 | 613.3 | 0.60 |
| IND_CC-322 | 599.3 | 0.58 |
| IND_CC-323 | 585.3 | 0.57 |
| IND_CC-324 | 613.3 | 0.62 |
| IND_CC-325 | 579.4 | 0.59 |
| IND_CC-326 | 577.4 | 0.60 |
| IND_CC-327 | 613.4 | 0.61 |
| IND_CC-328 | 599.4 | 0.59 |
| IND_CC-329 | 585.3 | 0.58 |
| IND_CC-330 | 661.4 | 0.64 |
| IND_CC-331 | 661.4 | 0.65 |
| IND_CC-332 | 627.3 | 0.62 |
| IND_CC-333 | 585.2 | 0.56 |
| IND_CC-334 | 627.3 | 0.63 |
| IND_CC-335 | 627.3 | 0.64 |
| IND_CC-336 | 593.4 | 0.60 |
| IND_CC-337 | 593.4 | 0.60 |
| IND_CC-338 | 591.4 | 0.61 |
| IND_CC-339 | 591.4 | 0.61 |
| IND_CC-340 | 627.4 | 0.62 |
| IND_CC-341 | 627.4 | 0.62 |
| IND_CC-342 | 585.3 | 0.57 |
| IND_CC-343 | 616.3 | 0.62 |
| IND_CC-344 | 613.3 | 0.62 |
| IND_CC-345 | 523.4 | 0.55 |
| IND_CC-346 | 509.4 | 0.53 |
| IND_CC-347 | 495.4 | 0.52 |
| IND_CC-348 | 577.4 | 0.57 |
| IND_CC-349 | 563.4 | 0.55 |
| IND_CC-350 | 549.3 | 0.54 |
| IND_CC-351 | 593.4 | 0.60 |
| IND_CC-352 | 579.3 | 0.57 |
| IND_CC-353 | 565.3 | 0.57 |
| IND_CC-354 | 591.4 | 0.62 |
| IND_CC-355 | 577.4 | 0.59 |
| IND_CC-356 | 563.3 | 0.58 |
| IND_CC-357 | 585.3 | 0.58 |
| IND_CC-358 | 514.3 | 0.54 |
| IND_CC-359 | 549.3 | 0.53 |
| IND_CC-360 | 565.3 | 0.56 |
| IND_CC-361 | 563.4 | 0.58 |
| IND_CC-362 | 647.3 | 0.65 |
| IND_CC-363 | 619.2 | 0.63 |
| IND_CC-364 | 501.4 | 0.53 |
| IND_CC-365 | 515.4 | 0.56 |
| IND_CC-366 | 487.4 | 0.52 |
| IND_CC-367 | 487.4 | 0.51 |
| IND_CC-368 | 459.4 | 0.46 |
| IND_CC-369 | 473.4 | 0.49 |
| IND_CC-370 | 445.4 | 0.44 |
| IND_CC-371 | 489.4 | 0.51 |
| IND_CC-372 | 503.4 | 0.55 |
| IND_CC-373 | 475.4 | 0.51 |
| IND_CC-374 | 475.4 | 0.49 |
| IND_CC-375 | 419.3 | 0.40 |
| IND_CC-376 | 581.3 | 0.54 |
| IND_CC-377 | 567.3 | 0.53 |
| IND_CC-378 | 567.3 | 0.52 |
| IND_CC-379 | 581.3 | 0.54 |
| IND_CC-380 | 595.4 | 0.57 |
| IND_CC-381 | 567.3 | 0.53 |
| IND_CC-382 | 567.3 | 0.53 |
| IND_CC-383 | 531.3 | 0.51 |
| IND_CC-384 | 545.3 | 0.54 |
| IND_CC-385 | 517.3 | 0.51 |
| IND_CC-386 | 517.3 | 0.49 |
| IND_CC-387 | 537.4 | 0.57 |
| IND_CC-388 | 509.3 | 0.54 |
| IND_CC-389 | 509.3 | 0.52 |
| IND_CC-390 | 627.3 | 0.62 |
| IND_CC-391 | 487.4 | 0.50 |
| IND_CC-392 | 501.4 | 0.54 |
| IND_CC-393 | 473.4 | 0.50 |
| IND_CC-394 | 473.3 | 0.49 |
| IND_CC-395 | 578.3 | 0.55 |
| IND_CC-396 | 550.3 | 0.55 |
| IND_CC-397 | 497.3 | 0.47 |
| IND_CC-398 | 483.3 | 0.46 |
| IND_CC-399 | 513.3 | 0.52 |

| Example no. | [M+] found | R.t. [min] |
|---|---|---|
| IND_CC-400 | 527.3 | 0.54 |
| IND_CC-401 | 499.3 | 0.51 |
| IND_CC-402 | 499.3 | 0.50 |
| IND_CC-403 | 681.3 | 0.65 |
| IND_CC-404 | 653.2 | 0.61 |
| IND_CC-405 | 657.2 | 0.62 |
| IND_CC-406 | 647.2 | 0.64 |
| IND_CC-407 | 619.2 | 0.60 |
| IND_CC-408 | 589.4 | 0.53 |
| IND_CC-409 | 461.4 | 0.48 |
| IND_CC-410 | 475.4 | 0.51 |
| IND_CC-411 | 447.3 | 0.45 |
| IND_CC-412 | 529.4 | 0.59 |
| IND_CC-413 | 501.4 | 0.54 |
| IND_CC-414 | 487.4 | 0.52 |
| IND_CC-415 | 459.3 | 0.46 |
| IND_CC-416 | 489.4 | 0.53 |
| IND_CC-417 | 461.3 | 0.48 |
| IND_CC-418 | 475.4 | 0.51 |
| IND_CC-419 | 447.3 | 0.45 |
| IND_CC-420 | 475.4 | 0.49 |

E. Parallel Synthesis

Library No. 2:

1) Intermediate Syntheses

Synthesis of

3-Amino-2,3-dihydro-1H-indene-5-carboxylic acid tert-butyl ester

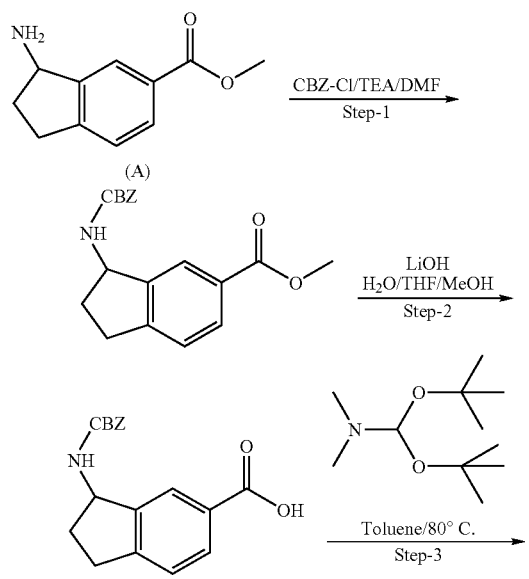

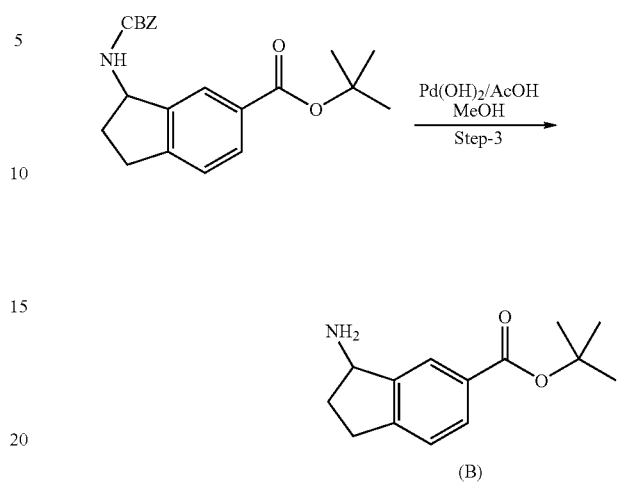

Step 1: Triethylamine (10.3 mmol, 3 eq.) and benzyl chloroformate (5.15 mmol, 1.5 eq.) was added to a solution of amine ester A (3.434 mmol) in DMF at 0° C. and the mixture was then stirred at room temperature for 16 h. The mixture was then diluted with ethyl acetate, washed with water and sat. NaCl solution, dried over sodium sulfate and concentrated under reduced pressure. The crude product was purified by column chromatography (mobile phase ethyl acetate/hexane). Yield: 80%

Step 2: The product just obtained in step 1 (0.33 g, 1.015 mmol) was dissolved in 10 ml of a THF-methanol-water mixture (3:1:1), LiOH.H$_2$O (0.127 g, 3.046 mmol) was added in portions at 0° C. and the mixture was stirred at room temperature for 8 h. The reaction mixture was concentrated under reduced pressure, the residue was taken up in water and the mixture was washed with ether and acidified with 10% strength citric acid at 0° C. in order to obtain the desired acid in the form of a white solid. This was filtered out, washed with water and dried at 60° C. for 24 h. Yield: 85%

Step 3: The product just obtained in step 2 (1 g, 3.2 mmol) was dissolved in methylene chloride (20 ml), oxalyl chloride (3.37 ml, 3.53 mmol) and DMF (0.25 ml) were added and the mixture was stirred at room temperature for 2 h. The solvent was removed under reduced pressure and the residue was taken up in chloroform (10 ml) and tert-butanol (9 ml). Pyridine was added at 10° C. and the mixture was stirred for 30 minutes. The reaction mixture was concentrated and the residue was taken up in toluene, and washed with 2 M HCl, sat. NaHCO$_3$ solution and sat. NaCl solution, dried over sodium sulfate and concentrated under reduced pressure. The crude product was purified by column chromatography (mobile phase: ethyl acetate/hexane). Yield: 50%

Step 4: The product just obtained in step 3 (610 mg, 1.66 mmol) was dissolved in methanol (30 ml) and the solution was degassed under argon. Pd(OH)$_2$ (300 mg) and acetic acid (0.1 ml) were added and the reaction mixture was hydrogenated for 2 h (2 kg of h$_2$). The reaction mixture was filtered over Celite and the filtrate was concentrated to dryness. The crude product was employed in the next step without further purification.

Yield: 100%

2) Synthesis of the Amine Units (AMN_CC)

Overview:

| AMN-CC unit no. | Structure | AMN-CC name |
|---|---|---|
| AMN_CC-20 | 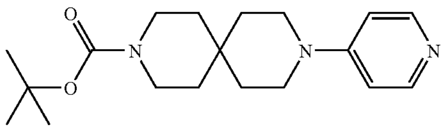 [SMILES: CC(C)(C)OC(=O)N1CCC2(CC1)CCN(c1ccncc1)CC2] | 9-pyridin-4-yl-3,9-diazaspiro[5.5]undecane-3-carboxylic acid tert-butyl ester |
| AMN_CC-21 | 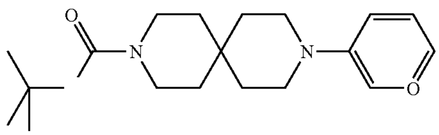 | 9-pyridin-3-yl-3,9-diazaspiro[5.5]undecane-3-carboxylic acid tert-butyl ester |
| AMN_CC-22 | 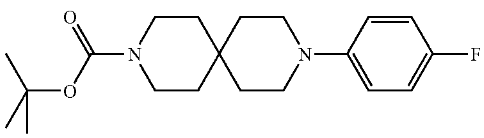 [SMILES: CC(C)(C)OC(=O)N1CCC2(CC1)CCN(c1ccc(F)cc1)CC2] | 9-(4-fluorophenyl)-3,9-diazaspiro[5.5]undecane-3-carboxylic acid tert-butyl ester |
| AMN_CC-23 | 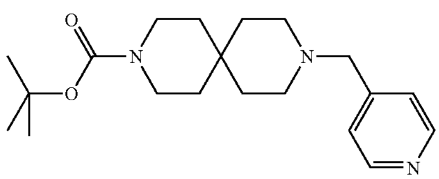 [SMILES: CC(C)(C)OC(=O)N1CCC2(CCN(Cc3ccncc3)CC2)CC1] | 9-(pyridin-4-yl-methyl)-3,9-diazaspiro[5.5]undecane-3-carboxylic acid tert-butyl ester |
| AMN_CC-24 | 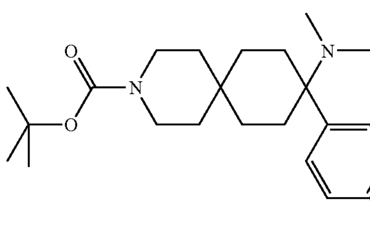 | 9-dimethylamino-9-(4-fluorophenyl)-3-azaspiro[5.5]undecane-3-carboxylic acid tert-butyl ester |
| AMN_CC-25 | 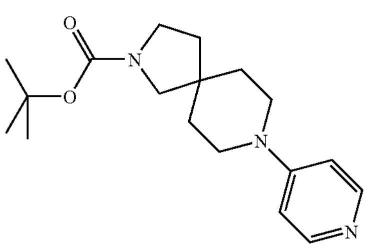 [SMILES: CC(C)(C)OC(=O)N1CCC2(CCN(c3ccncc3)CC2)C1] | 8-pyridin-4-yl-2,8-diazaspiro[4.5]decane-2-carboxylic acid tert-butyl ester |
| AMN_CC-26 | 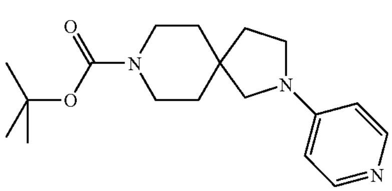 [SMILES: CC(C)(C)OC(=O)N1CCC2(CC1)CCN(c1ccncc1)C2] | 2-pyridin-4-yl-2,8-diazaspiro[4.5]decane-8-carboxylic acid tert-butyl ester |

Synthesis of amine (AMN_CC-20)

9-Pyridin-4-yl-3,9-diazaspiro[5.5]undecane-3-carboxylic acid tert-butyl ester (AMN_CC-20)

The synthesis of AMN_CC-20 was carried out as described in the context of the synthesis of AMN-01.

Synthesis of amine (AMN_CC-21)

9-Pyridin-3-yl-3,9-diazaspiro[5.5]undecane-3-carboxylic acid tert-butyl ester (AMN_CC-21)

BINAP (147 mg, 0.23 mmol) and Pd(OAc)$_2$ (159 mg, 0.74 mmol) was added to a mixture of 3,9-diazaspiro[5.5]undecane-3-carboxylic acid tert-butyl ester (3 g, 11.81 mmol), 3-bromopyridine HCl (2.29 g, 11.81 mmol) and sodium tert-butylate (3.4 g, 35.45 mmol) in toluene and the reaction mixture was degassed under argon for 20 minutes and heated under reflux for 4 h. After cooling to room temperature, the mixture was diluted with ethyl acetate, stirred for 15 minutes and filtered over Celite. The reaction mixture was washed with water and sat. NaCl solution, dried over sodium sulfate and concentrated under reduced pressure. The crude product was purified by column chromatography. Yield: 31%

Synthesis of amine (AMN_CC-22)

9-(4-Fluorophenyl)-3,9-diazaspiro[5.5]undecane-3-carboxylic acid tert-butyl ester (AMN_CC-22)

BINAP (350 mg, 0.47 mmol) and Pd$_2$dba$_3$ (317 mg, 1.57 mmol) was added to a mixture of 3,9-diazaspiro[5.5]undecane-3-carboxylic acid tert-butyl ester (2 g, 7.87 mmol), 1-bromo-4-fluoro-benzene (1.3 g, 7.87 mmol) and sodium tert-butylate (2.26 g, 23.61 mmol) in toluene (25 ml) and the reaction mixture was degassed under argon for 20 minutes and heated under reflux for 4 h. The mixture was then diluted with ethyl acetate, stirred for 15 minutes and filtered over Celite. The reaction mixture was washed with water and sat. NaCl solution, dried over sodium sulfate and concentrated under reduced pressure. The crude product was purified by column chromatography. Yield: 43%

Synthesis of amine (AMN_CC-23)

9-(Pyridin-4-yl-methyl)-3,9-diazaspiro[5.5]undecane-3-carboxylic acid tert-butyl ester (AMN_CC-23)

NaH (60% strength in mineral oil, 709 mg, 29.52 mmol) was added to a mixture of 3,9-diazaspiro[5.5]undecane-3-carboxylic acid tert-butyl ester (2.5 g, 9.84 mmol) in DMF (50 ml) at 0° C., the mixture was stirred at room temperature for 2 h, 4-(bromomethyl)-pyridine HCl (2.42 mg, 14.76 mmol) was then added and the mixture was stirred at room temperature for 16 h. Finally, ice was added and the reaction mixture was extracted with ethyl acetate. The combined organic phases were washed with water and sat. NaCl solution, dried over sodium sulfate and concentrated under reduced pressure. The crude product was purified by column chromatography (mobile phase methanol/methylene chloride). Yield: 35%

Synthesis of amine (AMN_CC-24)

9-Dimethylamino-9-(4-fluorophenyl)-3-azaspiro[5.5]undecane-3-carboxylic acid tert-buty ester (AMN_CC-24)

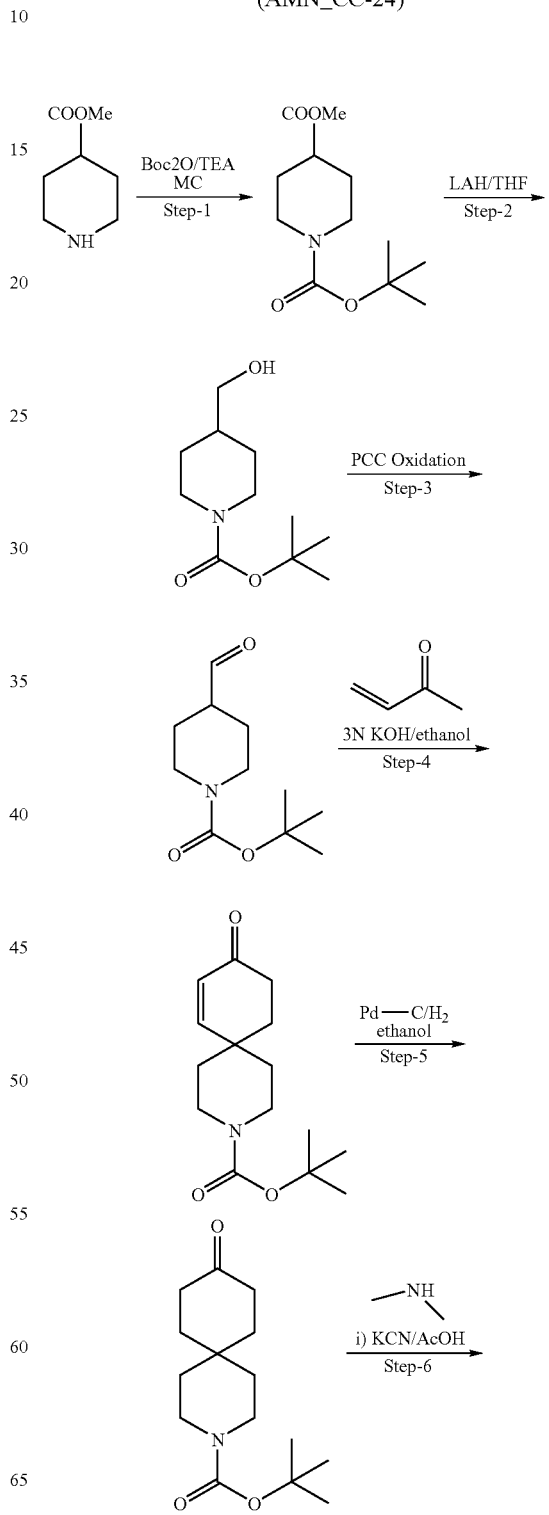

-continued

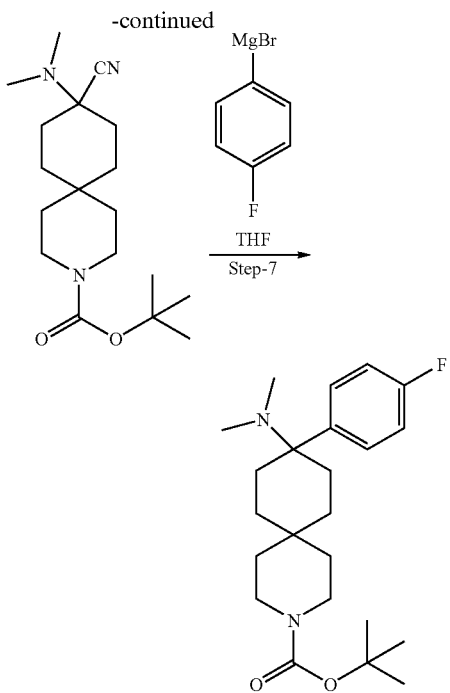

Step 1: Boc anhydride (190.8 mmol, 1.5 eq.) and triethylamine (254.4 mmol, 2 eq.) was added to a solution of piperidine-4-carboxylic acid methyl ester (127.2 mmol, 1 eq.) in methylene chloride (200 ml) and the mixture was stirred at room temperature for 12 h. The reaction mixture was diluted with methylene chloride (100 ml) and washed with dist. water and sat. NaCl solution and the organic phase was dried over sodium sulfate. The crude product was employed in the next step without further purification. Yield: 98%

Step 2: The product just obtained in step 1 (171.3 mmol, 1 eq.) was dissolved in THF (250 ml), lithium aluminium hydride (342.6 mmol, 2 eq.) was added at 0° C. and the mixture was heated under reflux for 2 h. It was then cooled to 0° C., ice-water (100 g) was added, the mixture was diluted with ethyl acetate and the phases were separated. The aqueous phase was extracted with ethyl acetate. The combined organic phases were diluted with methylene chloride (100 ml), washed with dist. water and sat. NaCl solution and dried over sodium sulfate. The crude product was employed in the next step without further purification.
Yield: 82%

Step 3: The product just obtained in step 2 (139.5 mmol) was dissolved in methylene chloride (300 ml), PCC (209.3 mmol, 1.5 eq.) was added and the mixture was stirred at 25° C. for 16 h. The reaction mixture was filtered over Celite and washed with methylene chloride (2×200 ml) and the filtrate was concentrated. The crude product was purified by column chromatography (mobile phase 20% ethyl acetate in methylene chloride). Yield: 42%

Step 4: The product just obtained in step 3 (5.87 mmol, 1 eq.) was dissolved in THF (250 ml), methyl vinyl ketone (7.63 mmol, 1.3 eq.) and 3 N KOH in ethanol (7.7 ml) were added at 0° C. and the mixture was stirred at room temperature for 16 h. The solution was concentrated to ⅓ and acidified with 0.5N HCl at 0° C. The aqueous phase was extracted with ethyl acetate (2×100 ml) and the combined organic phases were washed with dist. water and sat. NaCl solution and dried over sodium sulfate. The crude product was employed in the next step without further purification. Yield: 91%

Step 5: The product just obtained in step 4 (6.41 mmol, 1 eq.) was dissolved in ethanol (500 ml), 10% Pd/C (3.4 g) was added and hydrogenation was carried out at room temperature for 16 h. The mixture was finally filtered over Celite, the filtrate was concentrated and the crude product was purified by column chromatography. Yield: 38%

Step 6 & 7: Dimethylamine (29.9 mmol, 10 eq.) was added at 0° C. to a solution of the spiro-ketone just prepared in step 5 (2.99 mmol, 1 eq.) in methanol (15 ml) and acetic acid (1.5 ml). Potassium cyanide (7.47 mmol, 2.5 eq.) was added and the mixture was stirred for 16 h. NH₄OH solution (50 g of ice+50 ml of 25% strength ammonia solution) was cautiously added at 0° C. and the mixture was stirred for 30 minutes. The reaction mixture was extracted with ethyl acetate and the combined organic phases were washed with dist. water (15 ml), saturated iron sulfate solution (15 ml) and sat. NaCl solution (20 ml), dried over sodium sulfate and concentrated. This crude product (1.1 g crude) was dissolved in THF (30 ml), the solution was added dropwise to a bromo-(4-fluorophenyl)-magnesium solution (5 eq. of a 1M solution in THF) at 0° C. and the mixture was stirred at room temperature under nitrogen for 16 h. Finally, saturated ammonia solution was added and the mixture was extracted with ethyl acetate. The combined organic phases were washed with water and sat. NaCl solution, dried over sodium sulfate and concentrated under reduced pressure. The crude product was purified by column chromatography (25% ethyl acetate/hexane). Yield: 14%

Synthesis of amine (AMN_CC-25)

8-Pyridin-4-yl-2,8-diazaspiro[4.5]decane-2-carboxylic acid tert-butyl ester (AMN_CC-25)

BINAP (293 mg, 0.47 mmol) and Pd(OAc)₂ (317 mg, 1.4 mmol) was added to a mixture of tert-butyl 2,8-diazaspiro[4.5]decane-2-carboxylate (5.66 g, 23.6 mmol), 4-bromopyridine HCl (4.58 g, 23.6 mmol) and sodium tert-butylate (6.8 g, 70.8 mmol) in toluene and the reaction mixture was degassed under argon for 20 minutes and heated under reflux for 4 h. The mixture was then diluted with ethyl acetate, stirred for 15 minutes and filtered over Celite. The organic phase was washed with water and sat. NaCl solution, dried over sodium sulfate and concentrated under reduced pressure. The crude product was purified by column chromatography. Yield: 43.3%

Synthesis of amine (AMN_CC-26)

2-Pyridin-4-yl-2,8-diazaspiro[4.5]decane-8-carboxylic acid tert-butyl ester (AMN_CC-26)

BINAP (293 mg, 0.47 mmol) and Pd(OAc)₂ (317 mg, 1.4 mmol) was added to a mixture of 2,8-diazaspiro[4.5]decane-8-carboxylic acid tert-butyl ester (5.66 g, 23.6 mmol), 4-bromopyridine HCl (4.58 g; 23.6 mmol) and sodium tert-butylate (6.8 g, 70.8 mmol) in toluene and the reaction mixture was degassed under argon for 20 minutes and heated under reflux for 4 h. The mixture was then diluted with ethyl acetate, stirred for 15 minutes and filtered over Celite. The organic phase was washed with water and sat. NaCl solution, dried over sodium sulfate and concentrated under reduced pressure. The crude product was purified by column chromatography. Yield: 53%

3) Synthesis of the Acid Units (ACl_CC)

Overview:

| Unit no. | Structure | Unit name |
|---|---|---|
| ACI_CC-20 | 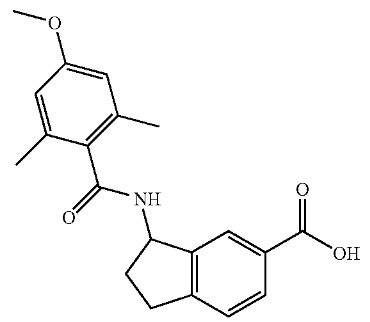 [SMILES: COc1cc(C)c(C(=O)NC2CCc3ccc(C(=O)O)cc32)c(C)c1] | 3-[(4-methoxy-2,6-dimethyl-benzoyl)amino]-2,3-dihydro-1H-indene-5-carboxylic acid |
| ACI_CC-21 | 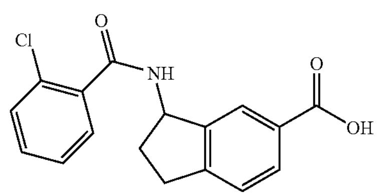 [SMILES: O=C(O)c1ccc2c(c1)C(NC(=O)c1ccccc1Cl)CC2] | 3-[(2-chloro-benzoyl)amino]-2,3-dihydro-1H-indene-5-carboxylic acid |
| ACI_CC-22 | 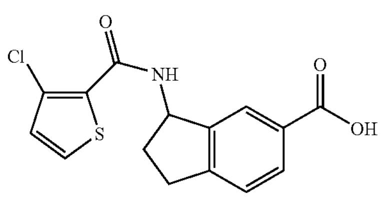 [SMILES: O=C(O)c1ccc2c(c1)C(NC(=O)c1sccc1Cl)CC2] | 3-[(3-chloro-thiophene-2-carbonyl)amino]-2,3-dihydro-1H-indene-5-carboxylic acid |
| ACI_CC-23 | 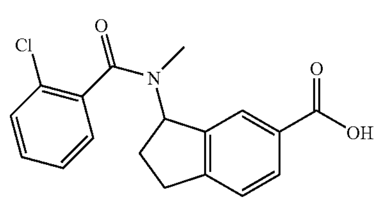 [SMILES: CN(C(=O)c1ccccc1Cl)C1CCc2ccc(C(=O)O)cc21] | 3-[(2-chloro-benzoyl)-methyl-amino]-2,3-dihydro-1H-indene-5-carboxylic acid |
| ACI_CC-24 | 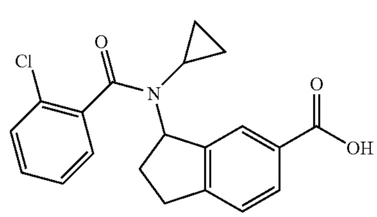 [SMILES: O=C(O)c1ccc2c(c1)C(N(C(=O)c1ccccc1Cl)C1CC1)CC2] | 3-[(2-chloro-benzoyl)-cyclopropyl-amino]-2,3-dihydro-1H-indene-5-carboxylic acid |
| ACI_CC-25 | 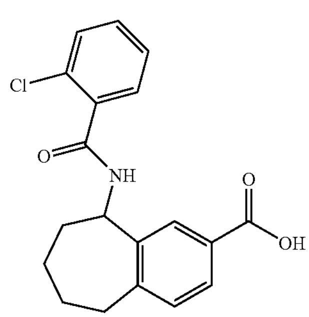 [SMILES: O=C(O)c1ccc2c(c1)C(NC(=O)c1ccccc1Cl)CCCC2] | 9-[(2-chloro-benzoyl)amino]-6,7,8,9-tetrahydro-5H-benzocycloheptene-2-carboxylic acid |

-continued

| Unit no. | Structure | Unit name |
|---|---|---|
| ACI_CC-26 | 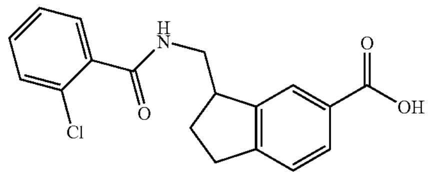 [SMILES: O=C(O)c1ccc2c(c1)C(CNC(=O)c1ccccc1Cl)CC2] | 3-[[(2-chloro-benzoyl)amino]-methyl]-2,3-dihydro-1H-indene-5-carboxylic acid |
| ACI_CC-27 | 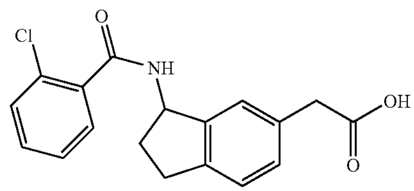 [SMILES: O=C(O)Cc1ccc2c(c1)C(NC(=O)c1ccccc1Cl)CC2] | 2-[3-[(2-chloro-benzoyl)amino]-2,3-dihydro-1H-inden-5-yl]-acetic acid |
| ACI_CC-28 | 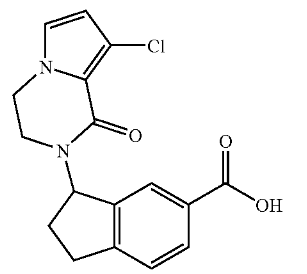 [SMILES: O=C(O)c1ccc2c(c1)C(N1CCn3ccc(Cl)c3C1=O)CC2] | 3-(8-chloro-1-oxo-3,4-dihydro-2H-pyrrolo[1,2-a]pyrazin-2-yl)-2,3-dihydro-1H-indene-5-carboxylic acid |
| ACI_CC-29 | 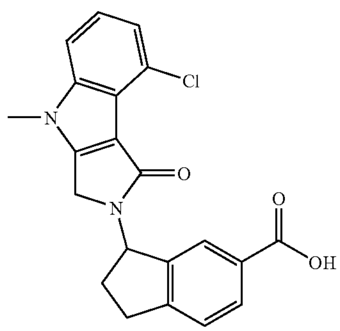 [SMILES: Cn1c2c(c3c(Cl)cccc31)C(=O)N(C1CCc3ccc(C(=O)O)cc31)C2] | 3-(8-chloro-4-methyl-1-oxo-3,4-dihydro-2H-pyrrolo[3,4-b]indol-2-yl)-2,3-dihydro-1H-indene-5-carboxylic acid |
| ACI_CC-30 | 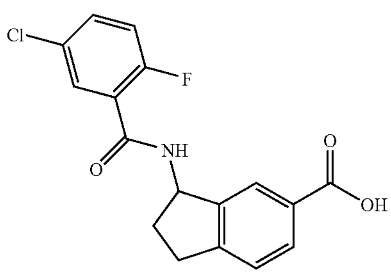 [SMILES: O=C(O)c1ccc2c(c1)C(NC(=O)c1cc(Cl)ccc1F)CC2] | 3-(5-chloro-2-fluorobenzamido)-2,3-dihydro-1H-indene-5-carboxylic acid |
| ACI_CC-31 | 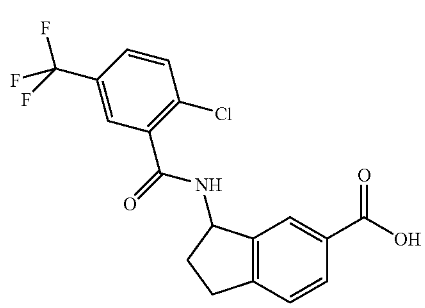 [SMILES: O=C(O)c1ccc2c(c1)C(NC(=O)c1cc(C(F)(F)F)ccc1Cl)CC2] | 3-(2-chloro-5-(trifluoromethyl)benzamido)-2,3-dihydro-1H-indene-5-carboxylic acid |

-continued

| Unit no. | Structure | Unit name |
|---|---|---|
| ACI_CC-32 | 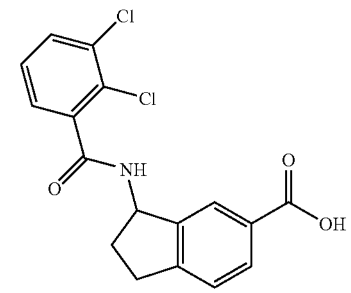 [SMILES: O=C(O)c1ccc2c(c1)C(NC(=O)c1cccc(Cl)c1Cl)CC2] | 3-(2,3-dichlorobenzamido)-2,3-dihydro-1H-indene-5-carboxylic acid |
| ACI_CC-33 | 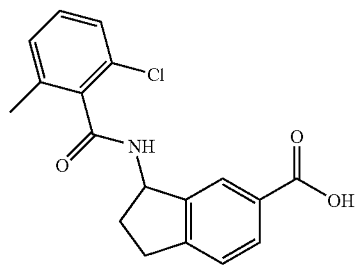 [SMILES: Cc1cccc(Cl)c1C(=O)NC1CCc2ccc(C(=O)O)cc21] | 3-(2-chloro-6-methylbenzamido)-2,3-dihydro-1H-indene-5-carboxylic acid |
| ACI_CC-34 | 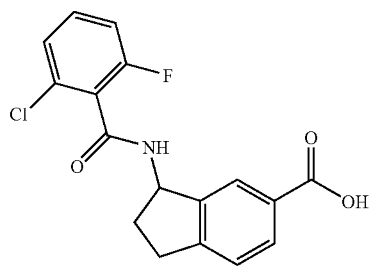 [SMILES: O=C(O)c1ccc2c(c1)C(NC(=O)c1c(F)cccc1Cl)CC2] | 3-(2-chloro-6-fluorobenzamido)-2,3-dihydro-1H-indene-5-carboxylic acid |

Synthesis of acid unit (ACI_CC-20)

3-[(4-Methoxy-2,6-dimethyl-benzoyl)amino]-2,3-dihydro-1H-indene-5-carboxylic acid (ACI_CC-20)

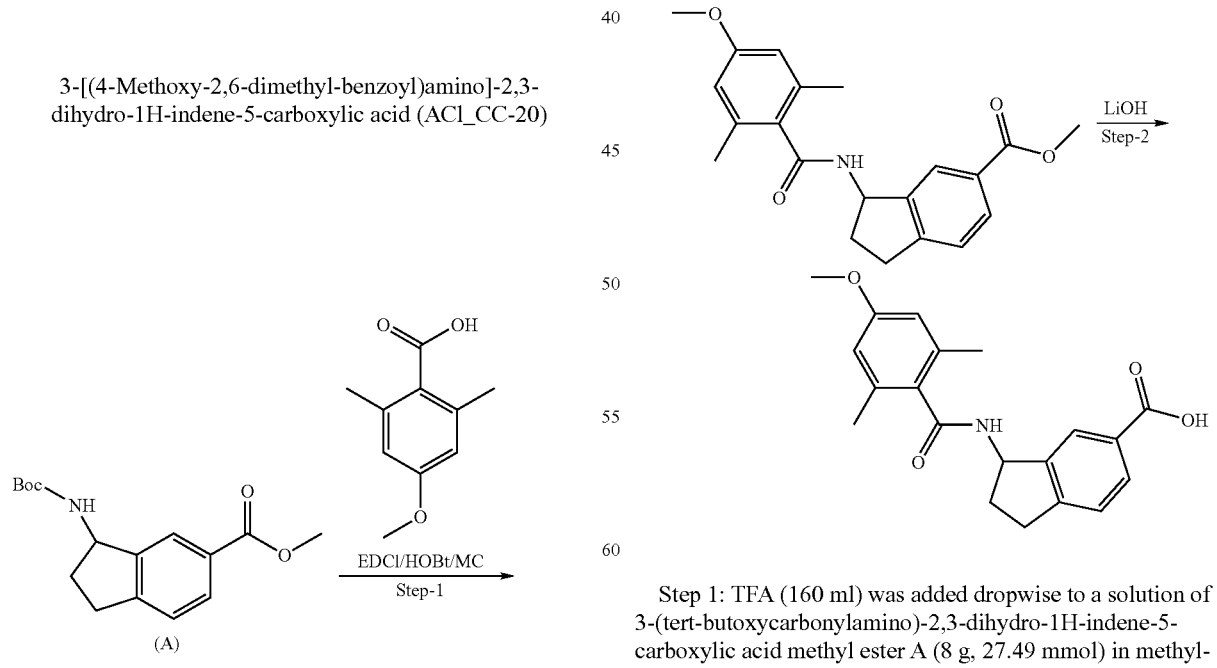

Step 1: TFA (160 ml) was added dropwise to a solution of 3-(tert-butoxycarbonylamino)-2,3-dihydro-1H-indene-5-carboxylic acid methyl ester A (8 g, 27.49 mmol) in methylene chloride (200 ml) at 0° C. and the mixture was stirred at room temperature for 4 h. The reaction mixture was concentrated and the desired TFA salt was obtained. Diisopropylamine (14 ml, 81.66 mmol) was added to a solution of 4-methoxy-2,6-dimethyl benzoic acid (4.9 g, 27.22 mmol), EDCl (10.39 g, 54.44 mmol) and HOBT (3.67 g, 27.22 mmol) in methylene chloride (125 ml) and the mixture was stirred at 0° C. for 10 minutes. A solution of the TFA salt just prepared in diisopropylamine (14 ml) and methylene chloride (125 ml) was then added and the mixture was stirred for 12 h. The reaction mixture was extracted with methylene chloride, the combined organic phases were washed with NH₄Cl solution, sodium hydrogen sulfate solution, water and sat. NaCl solution, dried over sodium sulfate and concentrated under reduced pressure. The crude product was purified by column chromatography (mobile phase: ethyl acetate 20% in hexane). Yield: 49.95%

Step 2: The product just obtained in step 1 (5.3 g, 15.01 mmol) was dissolved in 265 ml of THF-methanol-water (3:1:1) and the solution was cooled to 0° C. Lithium hydroxide hydrate (1.89 g, 45.03 mmol) was added in portions and the mixture was stirred at room temperature for 8 h. The reaction mixture was then concentrated to dryness, the residue was taken up in a little dist. water and the mixture was washed with diethyl ether. HCl solution was added to the aqueous phase at 0° C. and the white solid formed was filtered out, washed with dist. water and dried in vacuo at 60° C. for 24 h. Yield: 84.50%

Synthesis of acid unit (ACl_CC-21)

3-[(2-Chloro-benzoyl)amino]-2,3-dihydro-1H-indene-5-carboxylic acid (ACl_CC-21)

The acid unit ACl_CC-21 corresponds to the acid unit E-01 already described.

Synthesis of acid unit (ACl_CC-22)

3-[(3-Chloro-thiophene-2-carbonyl)amino]-2,3-dihydro-1H-indene-5-carboxylic acid (ACl_CC-22)

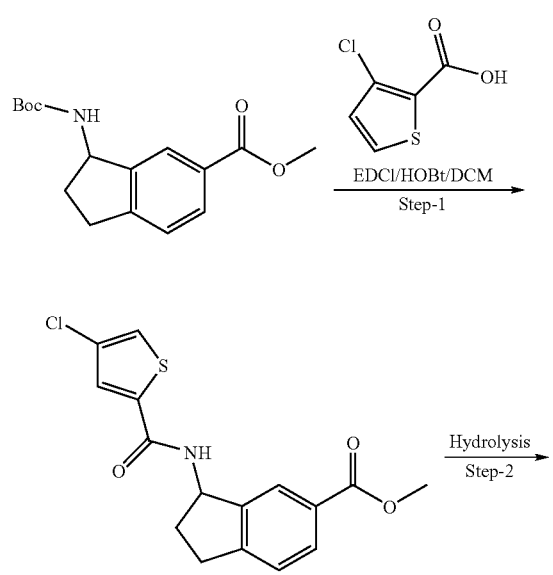

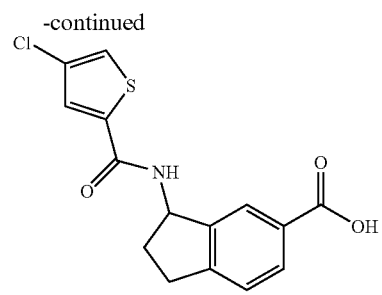

Step 1: TFA (120 ml) was added dropwise to a solution of 3-(tert-butoxycarbonylamino)-2,3-dihydro-1H-indene-5-carboxylic acid methyl ester A (5.7 g, 19.58 mmol) in methylene chloride (150 ml) at 0° C. and the mixture was stirred at room temperature for 4 h. The reaction mixture was concentrated and the desired TFA salt was obtained. Diisopropylamine (14 ml, 81.66 mmol) was added to a solution of 3-chloro-thiophene-2-carboxylic acid (2.6 g, 16.04 mmol), EDCl (6.13 g, 32.08 mmol) and HOBT (2.16 g, 16.04 mmol) in methylene chloride (50 ml) and the mixture was stirred at 0° C. for 10 minutes. A solution of the TFA salt just prepared in diisopropylamine (14 ml) and methylene chloride (50 ml) was then added and the mixture was stirred for 12 h. The reaction mixture was extracted with methylene chloride and the combined organic phases were washed with NH₄Cl solution, sodium hydrogen sulfate solution, water and sat. NaCl solution, dried over sodium sulfate and concentrated under reduced pressure. The crude product was purified by column chromatography (mobile phase: ethyl acetate 20% in hexane). Yield: 65.13%

Step 2: The product just obtained in step 1 (3.11 g, 9.28 mmol) was dissolved in 150 ml of THF-methanol-water (6:3:1) and the solution was cooled to 0° C. Lithium hydroxide hydrate (1.16 g, 27.84 mmol) was added in portions and the mixture was stirred at room temperature for 8 h. The reaction mixture was then concentrated to dryness, the residue was taken up in a little dist. water and the mixture was washed with diethyl ether. HCl solution was added to the aqueous phase at 0° C. and the white solid formed was filtered out, washed with dist. water and dried in vacuo at 60° C. for 24 h. Yield: 96%

Synthesis of acid unit (ACl_CC-23)

3-[(2-Chloro-benzoyl)-methyl-amino]-2,3-dihydro-1H-indene-5-carboxylic acid (ACl_CC-23)

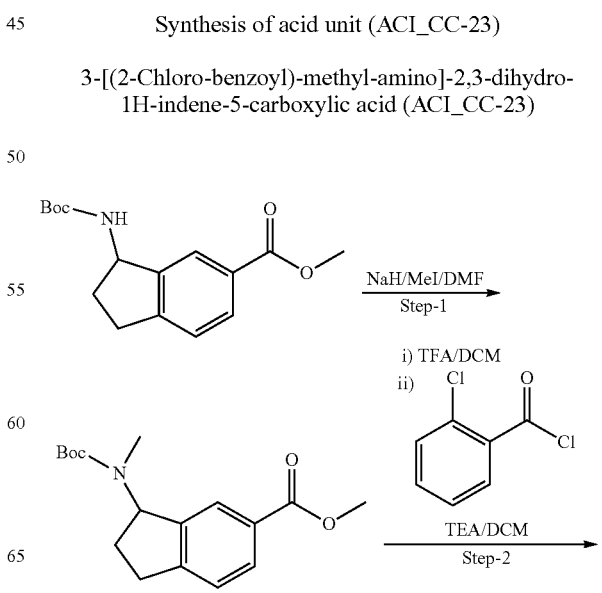

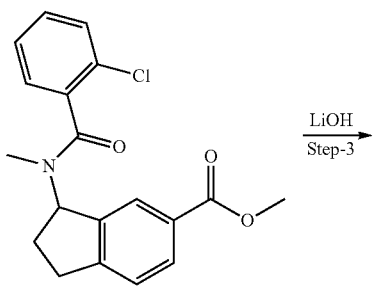

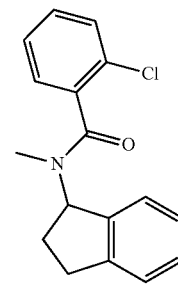

Step 1: NaH (2.05 g, 42.95 mmol) was added in portions to a solution of 3-(tert-butoxycarbonylamino)-2,3-dihydro-1H-indene-5-carboxylic acid methyl ester (5 g, 17.18 mmol) in DMF (80 ml) at 0° C. and the mixture was then stirred at room temperature for 2 h. The reaction mixture was cooled to 0° C., methyl iodide (3.24 ml, 51.54 mmol) was added dropwise and the mixture was stirred at room temperature for 16 h. Hydrolysis was then carried out with ice and dist. water and the mixture was extracted with ethyl acetate. The combined organic phases were washed with water and sat. NaCl solution, dried over sodium sulfate and concentrated under reduced pressure. The crude product was purified by column chromatography (mobile phase: ethyl acetate/hexane). Yield: 61.75%

Step 2: The product just obtained in step 1 (4 g, 13.11 mmol) was dissolved in methylene chloride (200 ml), the solution was cooled to 0° C. and trifluoroacetic acid (100 ml) was added. The reaction mixture was stirred at room temperature for 4 h and then concentrated. The TFA salt of the splitting off of the Boc protective group was dissolved in methylene chloride (70 ml), the solution was cooled to 0° C. and diisopropylamine (22.6 ml, 70 mmol) was added. Thereafter, 2-chlorobenzene-acid chloride was added and the mixture was stirred at 20° C. for 12 h. The reaction mixture was extracted with methylene chloride and the combined organic phases were washed with water and sat. NaCl solution, dried over sodium sulfate and concentrated under reduced pressure. The crude product was purified by column chromatography (mobile phase: ethyl acetate 20% in hexane). Yield: 89%

Step 3: The product just obtained in step 2 (3.5 g, 10.34 mmol) was dissolved in 150 ml of THF-methanol-water (3:1:1). LiOH.H$_2$O was added in portions at 0° C. (1.30 g, 31.02 mmol) and the mixture was stirred at room temperature for 8 h. The reaction mixture was concentrated under reduced pressure, the residue was taken up in water and the mixture was washed with ether. The aqueous phase was acidified with aqueous HCl solution at 0° C. A white solid precipitated out, which was filtered out, washed with water and dried in vacuo at 60° C. for 24 h. Yield: 96%

Synthesis of acid unit (ACl_CC-24)

3-[(2-Chloro-benzoyl)-cyclopropyl-amino]-2,3-dihydro-1H-indene-5-carboxylic acid (ACl_CC-24)

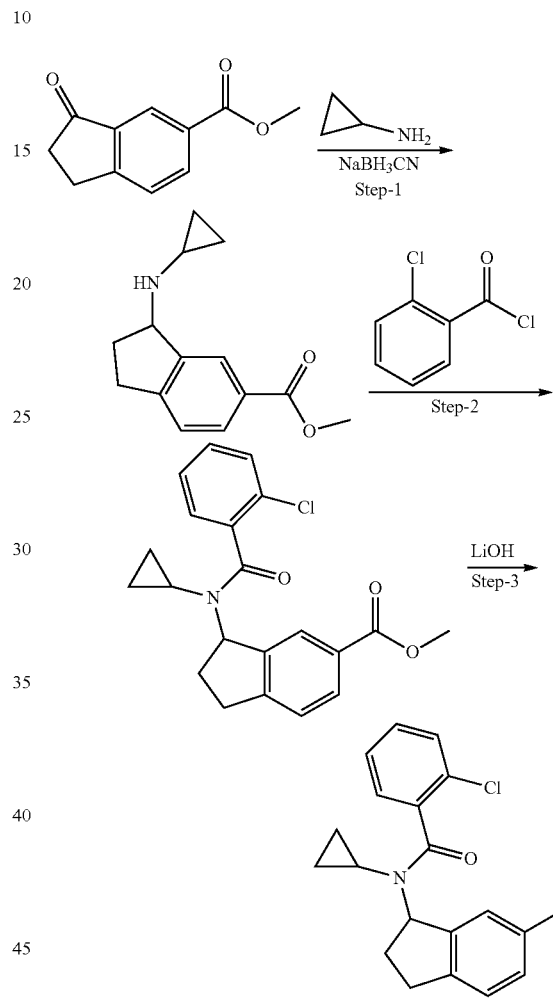

Step 1: Cyclopropylamine (360 mg, 6.36 mmol) and acetic acid (315 mg, 5.26 mmol) were added to a solution of 3-oxo-1,2-dihydro-indene-5-carboxylic acid methyl ester (1 g, 5.26 mmol) in methylene chloride (25 ml) at 5-10° C. After stirring for 20 minutes, sodium triacetoxyborohydride (4.45 g, 21 mmol) was added and the mixture was warmed to room temperature and stirred for 16 h. Dist. water was then added, the mixture was stirred for a further 30 minutes, the phases were separated and the aqueous part was rendered basic with 10% strength NaOH solution and extracted with ethyl acetate. The combined organic phases washed with dist. water and sat. NaCl solution and dried over sodium sulfate. The crude product was employed in the next step without further purification. Yield: 25%

Step 2: The product just obtained in step 1 (300 mg, 1.29 mmol) was dissolved in methylene chloride (10 ml) and diisopropylamine (4 eq.) was added at 0° C. 2-Chlorobenzoyl chloride (340 mg, 1.97 mmol) was added and the mixture was stirred at room temperature for 16 h. The mixture was diluted with methylene chloride (10 ml) and then washed with dist. water and sat. NaCl solution, dried over sodium sulfate and concentrated under reduced pressure. The crude product was employed in the next step without further purification. Yield: 62%

Step 3: The product just obtained in step 2 (3 g, 8.13 mmol) was dissolved in 50 ml of THF-methanol-water (6:3:1). LiOH.H$_2$O (1.50 g, 35 mmol, 4 eq.) was added in portions at 0° C. an the mixture was stirred at room temperature for 16 h. The reaction mixture was concentrated under reduced pressure, the residue was taken up in water and the mixture was washed with ether and acidified with 10% citric acid solution to obtain the desired acid. Yield: 95%

Synthesis of acid unit (ACl_CC-25)

9-[(2-Chloro-benzoyl)amino]-6,7,8,9-tetrahydro-5H-benzocycloheptene-2-carboxylic (ACl_CC-25)

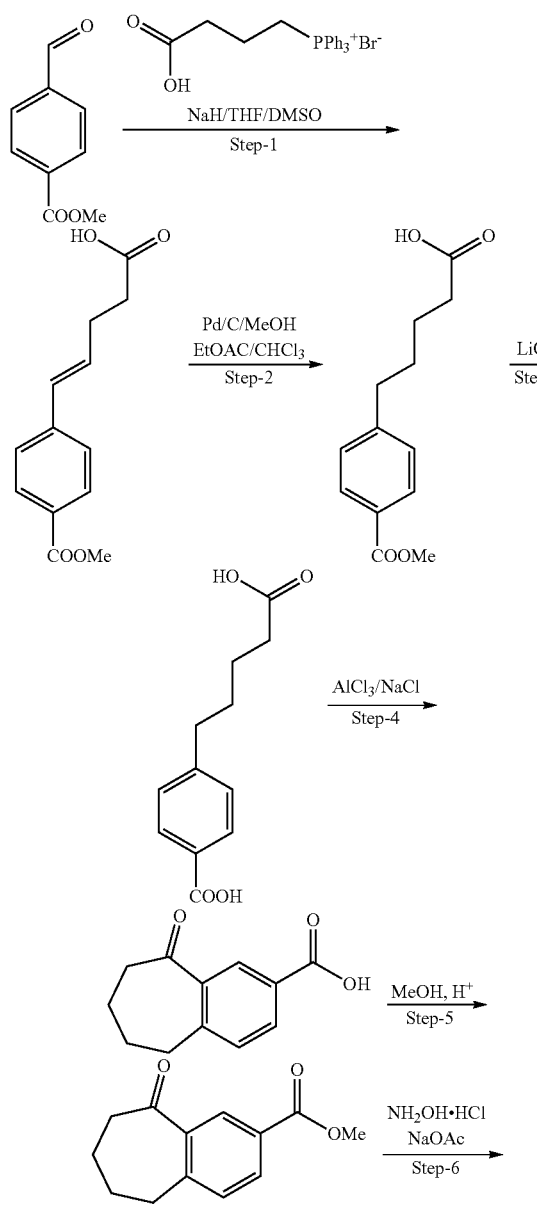
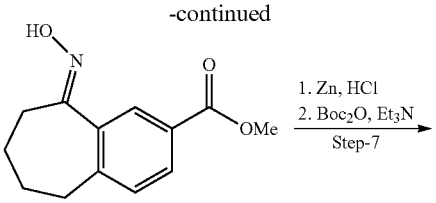
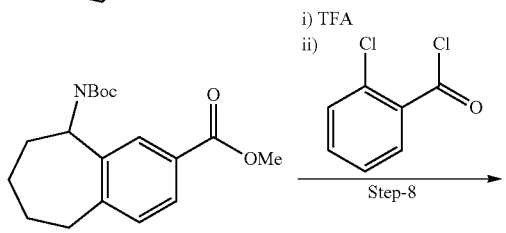
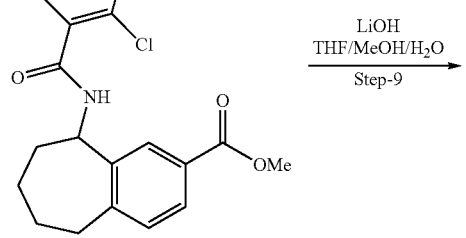
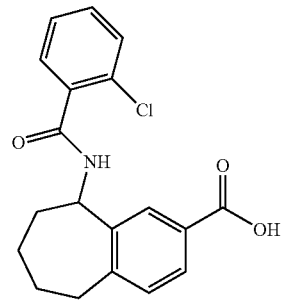

Step 1: NaH (60% strength in mineral oil, 1.5 g, 40 mmol) was added to a suspension of 4-formyl-benzoic acid methyl ester (3.2 g, 20 mmol) and (3-carboxy propyl)-triphenyl phosphonium bromide (8.6 g, 20 mmol) in 80 ml of DMSO/THF 1:1 and the mixture was stirred first at 0-5° C. for 30 minutes and then at room temperature for 6 h. Thereafter, the reaction mixture was cooled to 0° C., dist. water (10 ml) and 6 M HCl 10 ml) were added and the mixture was stirred for 20 minutes. The reaction mixture was extracted with ethyl acetate and the combined organic phases were dried over sodium sulfate and concentrated under reduced pressure. The crude product was purified by column chromatography (mobile phase: ethyl acetate 10% in hexane). Yield: 66% (3 g)

Step 2: 10% Pd/C was added to a solution of the product just obtained in step 2 (1 g, 4.27 mmol) in ethyl acetate/methylene chloride 2:1 and the mixture was degassed under argon. The reaction mixture was hydrogenated at 25° C. for 12 h, the catalyst was filtered out over Celite and the residue was rinsed with ethyl acetate. The filtrate was concentrated to dryness under reduced pressure and the combined organic phases were dried over sodium sulfate and concentrated under reduced pressure. Yield: 100% (1 g)

Step 3: The product just obtained in step 2 (1 g, 4.2 mmol) was dissolved in 20 ml of THF-methanol-water (6:3:1). LiOH.H$_2$O (0.75 g, 17 mmol) was added in portions at 0° C. and the mixture was stirred at room temperature for 16 h. The reaction mixture was concentrated under reduced pressure, the residue was taken up in water and the mixture was washed with ether and acidified with 10% strength citric acid in order to obtain the desired acid. Yield: 72% (700 mg)

Step 4: A mixture of the product just obtained in step 3 (700 mg, 3.16 mmol), AlCl₃ (2.94 g, 22.17 mmol) and NaCl (295 mg, 3.2 mmol) was heated at 180° C. for 1 hour. It was then cooled to 100° C. and poured on to ice in portions. The reaction mixture was acidified with 6 M HCl and extracted with ethyl acetate and the combined organic phases were dried over sodium sulfate and concentrated under reduced pressure. The combined organic phases were dried over sodium sulfate and concentrated under reduced pressure.
Yield: 31% (200 mg)

Step 5: H₂SO₄ (catalytic) was added to a solution of the product just obtained in step 4 (200 mg, 0.98 mmol) in methanol (8 ml) and the mixture was heated under reflux for 16 h. The organic phase was concentrated under reduced pressure and the crude product was purified by column chromatography. Yield: 51% (110 mg)

Step 6: Hydroxylamine (1.4 g, 20.6 mmol) and sodium acetate (3.4 g, 41.28 mmol) were added at room temperature to a solution of the product just obtained in step 5 (1.5 g, 6.88 mmol) in methanol (50 ml) and the mixture was then heated under reflux for 2 h. The reaction mixture was concentrated under reduced pressure, the residue was taken up in ethyl acetate and the mixture was washed with dist. water and sat. NaCl solution. The organic phase was dried over sodium sulfate and concentrated in order to obtain the crude product.
Yield: 90% (1.4 g)

Step 7: Dist. water (3.5 ml) and conc. HCl (7.2 ml) were added to a solution of the product just obtained in step 6 (1.2 g, 5.15 mmol) in ethanol (15 ml) and the mixture was stirred for 15 minutes. The reaction mixture was cooled, Zn powder (2 g, 31 mmol) was slowly added and the mixture was then heated under reflux for 1 hour. After it had cooled to room temperature, it was filtered over Celite and the residue was rinsed with ethanol. The filtrate was concentrated, the residue was taken up again in toluene and the mixture was concentrated to dryness again in order to obtain the desired crude amine. The crude amine (4 g) was dissolved in 1,4-dioxane (12 ml) and the solution was cooled to 0° C. Triethylamine (2 eq.) and Boc anhydride (3.98 g, 18.2 mmol) were added and the mixture was stirred at room temperature for 12 h. The 1,4-dioxane was concentrated under reduced pressure and the residue was taken up in ethyl acetate and water (50 ml of each). The phases were separated and the organic phase was washed with dist. water and sat. NaCl solution, dried over sodium sulfate and concentrated under reduced pressure. The crude product was purified by column chromatography. Yield: 85% (1.6 g)

Step 8:: A solution of the product just obtained in step 7 (1.8 g, 5.6 mmol) in methylene chloride (25 ml) was cooled to 0° C., trifluoroacetic acid (2.5 ml) was added and the mixture was stirred at room temperature for 1 hour. The reaction mixture was concentrated to dryness under reduced pressure (TFA salt). The TFA salt was dissolved in methylene chloride, the solution was cooled to 0° C. and diisopropylamine (4 eq.) was added. 2-Chlorobenzoyl chloride (1.5 eq.) was added and the mixture was stirred at room temperature for 4 h. The reaction mixture was diluted with methylene chloride and washed with dist. water and sat. NaCl solution, and the organic phase was dried over sodium sulfate and concentrated under reduced pressure. The crude product was purified by column chromatography (mobile phase: ethyl acetate 20% in hexane). Yield: 80% (1.6 g)

Step 9: LiOH.H₂O (2.4 g, 56 mmol, 4 eq.) was added at 0° C. to a solution of the product obtained in step 8 (5 g, 14 mmol) in 75 ml of THF-methanol-water (6:3:1) and the mixture was stirred at room temperature for 16 h. The reaction mixture was concentrated under reduced pressure, the residue was taken up in water and the mixture was washed with ether and acidified with 10% strength citric acid in order to obtain the desired acid in the form of a white solid. Yield: 62%

Synthesis of acid unit (ACl_CC-26)

3-[[(2-Chloro-benzoyl)amino]-methyl]-2,3-dihydro-1H-indene-5-carboxylic acid (ACl_CC-26)

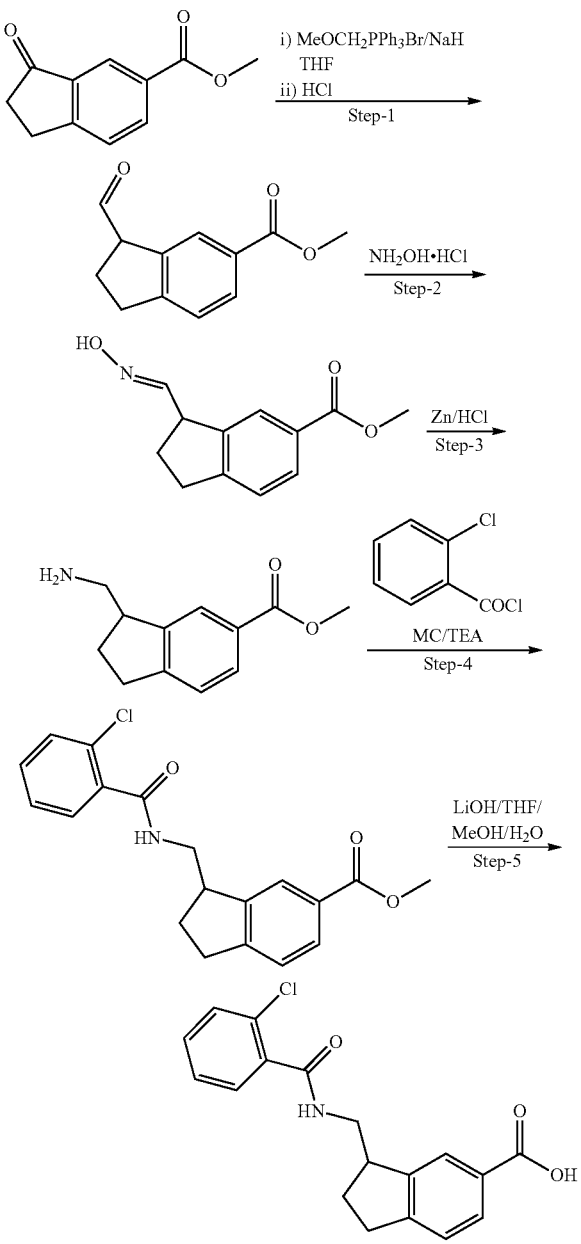

Synthesis of acid unit (ACI_CC-27)

2-[3-[(2-Chloro-benzoyl)amino]-2,3-dihydro-1H-inden-5-yl]-acetic acid (ACI_CC-27)

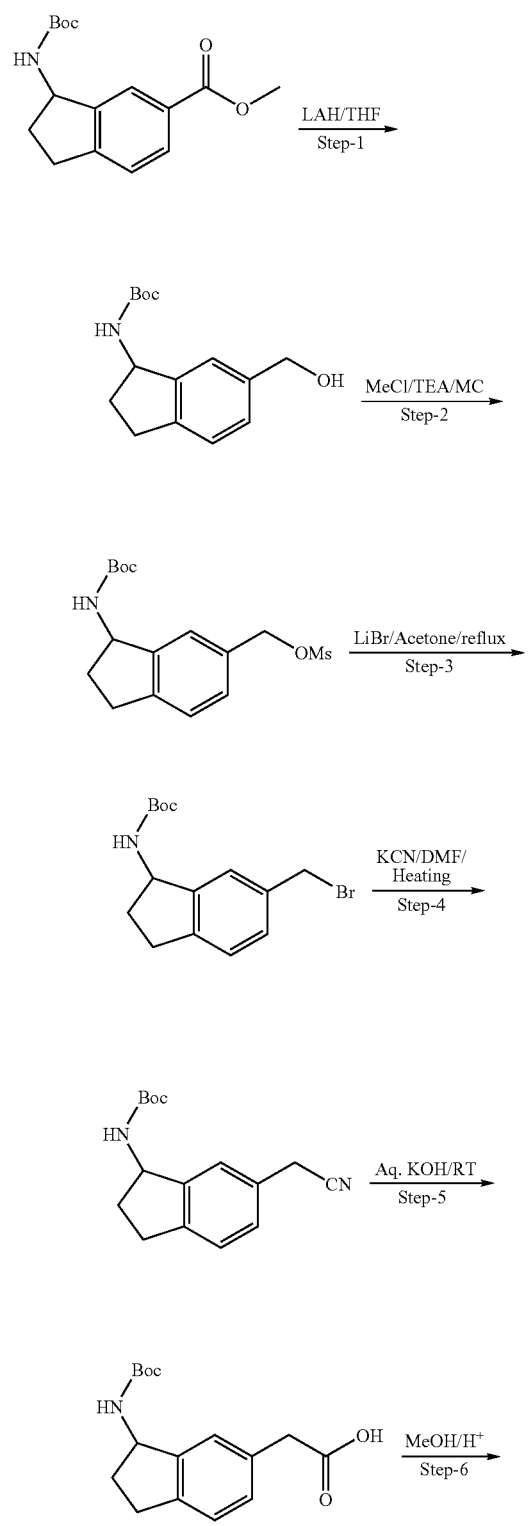

Step 1: NaH (6.31 g, 0.15 mol) was added to a solution of methoxymethyl triphenylphosphorus chloride (36 g, 0.10 mol) in THF (400 ml) at 0° C. and the mixture was stirred for 30 minutes. 3-Oxo-1,2-dihydro-indene-5-carboxylic acid methyl ester (10 g, 0.052 mmol) was dissolved in THF (50 ml) and added, and the mixture was stirred at room temperature for 16 h. Ethyl acetate was added and the organic phase was washed with sat. $NH_4Cl$ solution, dist. water and sat. sodium chloride solution and dried over sodium sulfate. The organic phase was concentrated under reduced pressure and the residue was purified by column chromatography (mobile phase: methanol/methylene chloride). The ether intermediate (6.9 g) was obtained. This intermediate was dissolved in acetone (100 ml), 6 M HCl (20 ml) was added and the mixture was stirred at 50° C. for 3 h. The reaction mixture was concentrated under reduced pressure and the residue was neutralized with sodium bicarbonate solution. The aqueous phase was extracted with methylene chloride and the combined organic phases were washed with sat. $NH_4Cl$ solution, dist. water and sat. NaCl solution, dried over sodium sulfate and concentrated to dryness under reduced pressure. The crude product was employed in the next step without further purification. Yield: 56%

Step 2: Hydroxylamine HCl (4.7 g, 67.74 mmol) and Amberlyst-A-21 resin (23 g) were added at room temperature to a solution of the product just obtained in step 1 (4.6 g, 22.54 mmol) in methanol (50 ml) and the mixture was heated under reflux for 2 h. The reaction mixture was filtered and the filtrate was concentrated under reduced pressure. The crude product was purified by column chromatography (mobile phase: ethyl acetate/hexane). Yield: 93%

Step 3 & 4: Dist. water (11 ml) and conc. HCl (24 ml) was added to a solution of the product just obtained in step 2 (4.6 g, 0.21 mol) in ethanol (50 ml) and the mixture was stirred for 15 minutes. The reaction solution was cooled, Zn powder (7.36 g, 112 mmol) was slowly added and the mixture was then refluxed for 1 hour. The reaction mixture was cooled to room temperature and filtered over Celite, the residue was rinsed with ethanol and the filtrate was concentrated under reduced pressure. The residue was taken up in toluene and the mixture was concentrated to dryness again. The crude product (amine) was dissolved in methylene chloride (100 ml), the solution was cooled to 0° C., triethylamine (4 ml, 29.5 mmol) and 2-chlorobenzoyl chloride (4.1 g, 23.4 mmol) were added and the mixture was stirred at room temperature for 2 h. Dist. water was added, the phases were separated and the organic phase was washed with dist. water, sat. sodium bicarbonate solution and sat. NaCl solution, dried over sodium sulfate and concentrated under reduced pressure. The crude product was purified by column chromatography (mobile phase ethyl acetate/hexane). Yield: 56%

Step 5: $LiOH.H_2O$ (1.17 g, 27.98 mmol) was added in portions at 0° C. to a solution of the product just obtained in step 4 (2.4 g, 6.997 mmol) in 40 ml of THF-methanol-water (6:4:1) and the mixture was stirred at room temperature for 8 h. The reaction mixture was concentrated under reduced pressure, the residue was taken up in water and the mixture was washed with ether. The aqueous phase was acidified with 2 M HCl at 0° C., during which a white solid precipitated out. This was filtered out, washed with water and dried at 60° C. for 24 h.

Yield: 87%

-continued

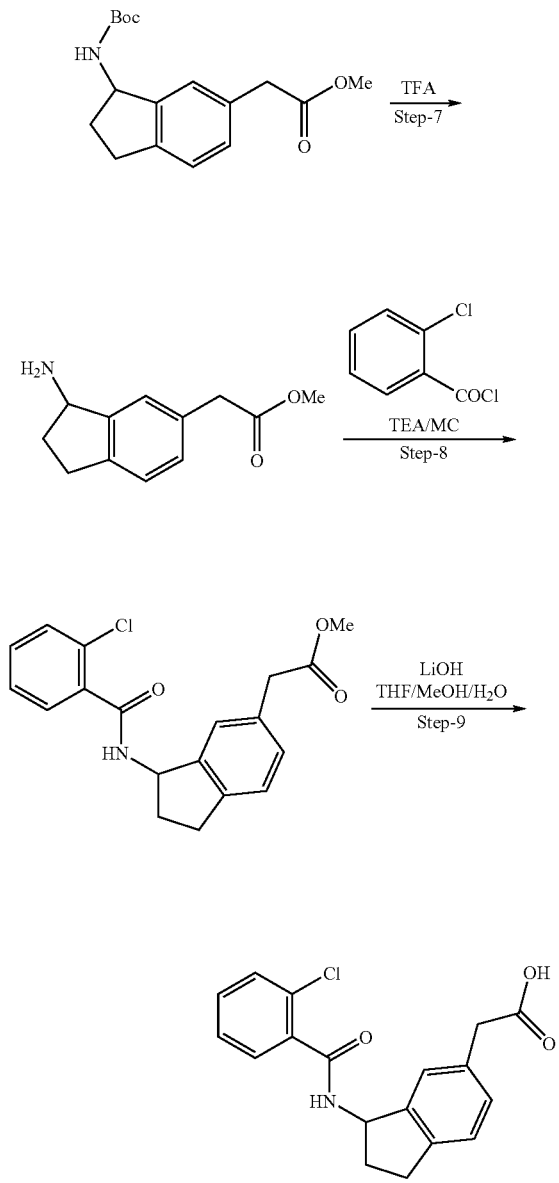

Step 1: A solution of 3-(tert-butoxycarbonylamino)-2,3-dihydro-1H-indene-5-carboxylic acid methyl ester (to which acetic acid tert-butyl ester was added) (10 g, 34.36 mmol) in THF (50 ml) was added dropwise to a suspension of lithium aluminium hydride (1.56 g, 41.23 mmol) in THF (40 ml) at 0° C. and the mixture was then stirred at room temperature for 2 h. The reaction was quenched with sat. sodium sulfate solution, the mixture was filtered over Celite and the residue was rinsed with THF. The filtrate was concentrated to dryness in order to obtain the desired product. Yield: 62% (7.7 g)

Step 2: Triethylamine (6.1 ml, 45.05 mmol) was added to a solution of the product just obtained in step 1 (7.9 g, 30.03 mmol) in methylene chloride (150 ml) and the mixture was then cooled to −20° C. Methanesulfonyl chloride (4.2 ml, 36.03 mmol) was added dropwise and the reaction mixture was stirred for one hour. The mixture was diluted with methylene chloride and washed with dist. water & sat. NaCl solution. The organic phase was dried over sodium sulfate and concentrated under reduced pressure. The crude product was purified by column chromatography (mobile phase: ethyl acetate/hexane). Yield: 97%

Step 3: LiBr (5 g, 58.65 mmol) was added at room temperature to a solution of the product just obtained in step 2 (10 g, 29.32 mmol) in acetone (150 ml) and the mixture was heated under reflux for 2 h. The reaction mixture was cooled to room temperature and filtered over Celite, the filtrate was concentrated and the residue was taken up in ethyl acetate. The organic phase was washed with dist. water and sat. NaCl solution, dried over sodium sulfate and concentrated under reduced pressure. The crude product was employed in the next step without further purification. Yield: 93%

Step 4: KCN (3.55 g, 54.6 mmol) was added at room temperature to a solution of the product just obtained in step 3 (8.9 g, 27.3 mmol) in DMF (190 ml). The reaction mixture was heated at 100° C. for 16 h. It was then cooled to room temperature and diluted with ethyl acetate. The organic phase was washed with dist. water and sat. NaCl solution, dried over sodium sulfate and concentrated under reduced pressure. The crude product was employed in the next step without further purification. Yield: 44%

Step 5 & 6: 1N NaOH (64.4 ml, 64.3 mmol)) was added to a solution of the product just obtained in step 4 (7 g, 25.73 mmol) in ethanol (250 ml) and the mixture was refluxed for 16 h. It was then cooled to room temperature and concentrated under reduced pressure. The residue was taken up in dist. water and the mixture was extracted with ethyl acetate. The aqueous phase was acidified with citric acid and extracted with ethyl acetate. The organic phase was washed with dist. water and sat. NaCl solution, dried over sodium sulfate and concentrated under reduced pressure. The crude product was dissolved in acetone (50 ml), potassium carbonate (4 g) was added, the mixture was cooled to 0° C., methyl iodide (1.7 ml, 27 mmol) was added and the mixture was stirred at room temperature for 16 h. The reaction mixture was filtered, the filtrate was concentrated under reduced pressure and the residue was purified by column chromatography (mobile phase ethyl acetate/hexane). Yield: 20%

Step 7 & 8: Trifluoroacetic acid (18 ml) was added to a solution of the product just obtained in step 6 (900 mg, 2.95 mmol) in methylene chloride (50 ml) and the mixture was stirred at room temperature for 4 h. The reaction mixture was concentrated under reduced pressure, the residue was taken up in methylene chloride (20 ml) and triethylamine (1.2 ml, 8.85 mmol), 2-chlorobenzoyl chloride (0.45 ml, 3.54 mmol) was added and the mixture was stirred at room temperature for 1 hour. Dist. water was added to the reaction mixture and the phases were separated. The organic phase was washed with dist. water and sat. NaCl solution, dried over sodium sulfate and concentrated under reduced pressure. The crude product was purified by column chromatography (mobile phase ethyl acetate/hexane). Yield: 49%

Step 9: LiOH.H$_2$O (0.167 g, 5.83 mmol) was added in portions at 0° C. to a solution of the product just obtained in step 6 (0.5 g, 1.457 mmol) in 15 ml of THF-methanol-water (6:4:1) and the mixture was stirred at room temperature for 4 h. The reaction mixture was concentrated under reduced pressure, the residue was taken up in water and the mixture was washed with ether. The aqueous phase was acidified with 2 M HCl at 0° C., during which a white solid precipitated out. This was filtered out, washed with water and dried at 60° C. for 24 h. Yield: 74%

Synthesis of acid unit (ACl_CC-28): 3-(8-Chloro-1-oxo-3,4-dihydro-2H-pyrrolo[1,2-a]pyrazin-2-yl)-2,3-dihydro-1H-indene-5-carboxylic acid (ACl_CC-28)

Step 4: The product just obtained in step 3 (1.287 mmol/1 eq.) was dissolved in DMF (6 ml), BOP reagent (2.57 mmol, 2 eq.) and N-methylmorpholine (3.86 mmol, 3 eq.) were

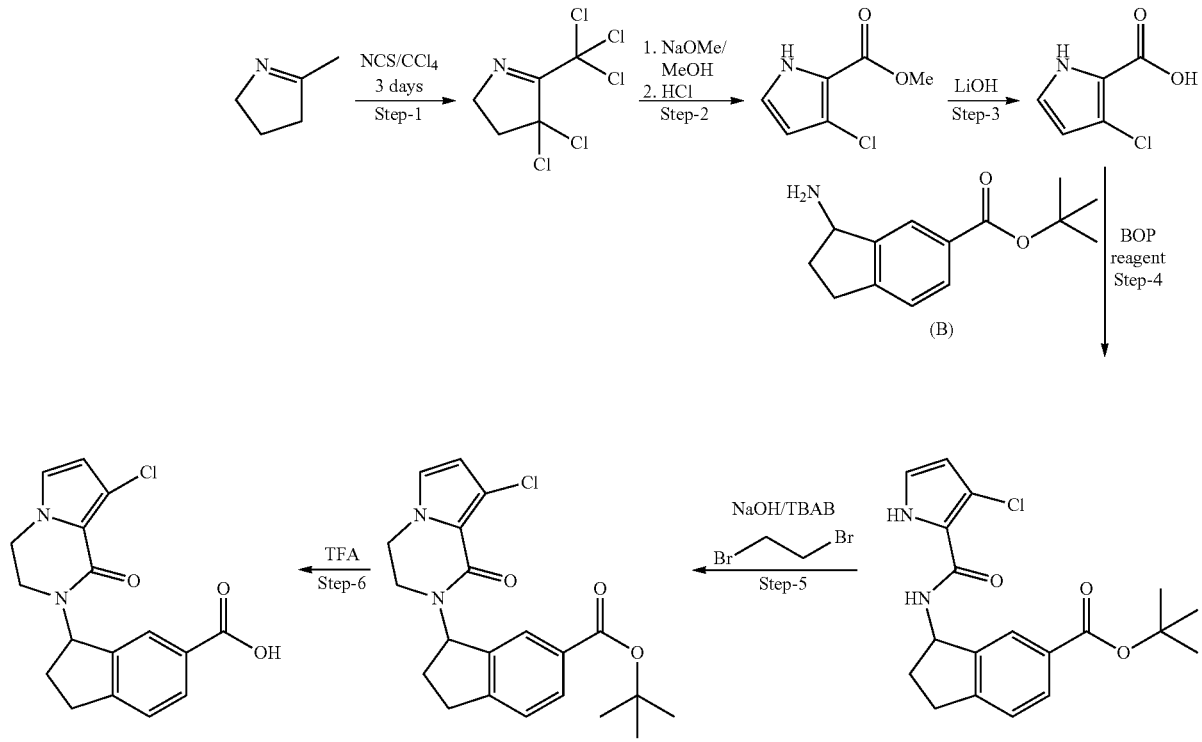

(B)

Step 1: 5-Methyl-3,4-dihydro-2H-pyrrole (24.06 mmol, 1 eq.) was dissolved in CCl$_4$ and N-chlorosucdinimide (8 eq.) was added in portions at 0° C. The suspension was refluxed for 3 days, the reaction mixture was then cooled to 0° C. and the succinimide was filtered out and rinsed with carbon tetrachloride. The filtrate was concentrated to dryness under reduced pressure. The crude product was employed in the next step without further purification. Yield: 90%

Step 2: The product just obtained in step 1 (27.31 mmol) was added to a solution of sodium methanolate in methanol (2 M, 6 eq.) and the mixture was heated under reflux for 1.5 h. After cooling to room temperature, the solvent was distilled off under reduced pressure. The residue was taken up in ether (10 ml) and the mixture was stirred at room temperature for 30 minutes. The precipitate obtained was filtered out and the filtrate was dried over potassium carbonate and concentrated under reduced pressure. This residue was taken up in 2 M HCl and the mixture was extracted with methylene chloride (3×). The combined organic phases were dried over sodium sulfate and concentrated to dryness. The crude product was employed in the next step without further purification. Yield: 83%

Step 3: The product just obtained in step 2 (4.32 g, 27 mmol) was dissolved in 110 ml of THF-methanol-water (6:4:1), LiOH.H$_2$O (3.42 g, 81 mmol) was added in portions at 0° C. and the mixture was stirred at room temperature for 8 h. The reaction mixture was concentrated under reduced pressure, the residue was taken up in water and the mixture was washed with ether and acidified with 10% strength citric acid at 0° C. in order to obtain the desired acid in the form of a white solid. This was filtered out, washed with water and dried at 60° C. for 24 h. Yield: 77% added and the mixture was stirred at room temperature for 15 minutes. A solution of 3-amino-2,3-dihydro-1H-indene-5-carboxylic acid tert-butyl ester (1.287 mmol, 1 eq.) in DMF (1 ml) was added and the mixture was stirred at room temperature for 12 h. The reaction mixture was poured on to dist. water and the mixture was extracted with ethyl acetate. The combined organic phases were washed with water and sat. NaCl solution, dried over sodium sulfate and concentrated under reduced pressure. The crude product was purified by column chromatography. Yield: 59%

Step 5: 1,2-Dibromoethane (21.66 mmol, 10 eq.) was added to a mixture of the product just obtained in step 4 (21.6 mmol, 1 eq.) and tetrabutylammonium bromide (1 eq.) in 1M NaOH (13 ml) and the mixture was stirred at room temperature for 12 h. The reaction mixture was diluted with dist. water and the mixture was extracted with ethyl acetate. The combined organic phases were washed with water and sat. NaCl solution, dried over sodium sulfate and concentrated under reduced pressure. The crude product was purified by column chromatography. Yield: 95%

Step 6: The product obtained in step 5 (1,554 mmol) was dissolved in methylene chloride (10 ml), the solution was cooled to 0° C. and trifluoroacetic acid (2.1 ml) was added. The mixture was stirred at room temperature for 6 h. The solvent was removed under reduced pressure, dist. water was added to the residue and the mixture was extracted with ethyl acetate. The combined organic phases were washed with water and sat. NaCl solution, dried over sodium sulfate and concentrated under reduced pressure. The crude product was purified by column chromatography. Yield: 96%

Synthesis of acid unit (ACl_CC-29)

3-(8-Chloro-4-methyl-1-oxo-3,4-dihydro-2H-pyrrolo[3,4-b]indol-2-yl)-2,3-dihydro-1H-indene-5-carboxylic acid (ACl_CC-29)

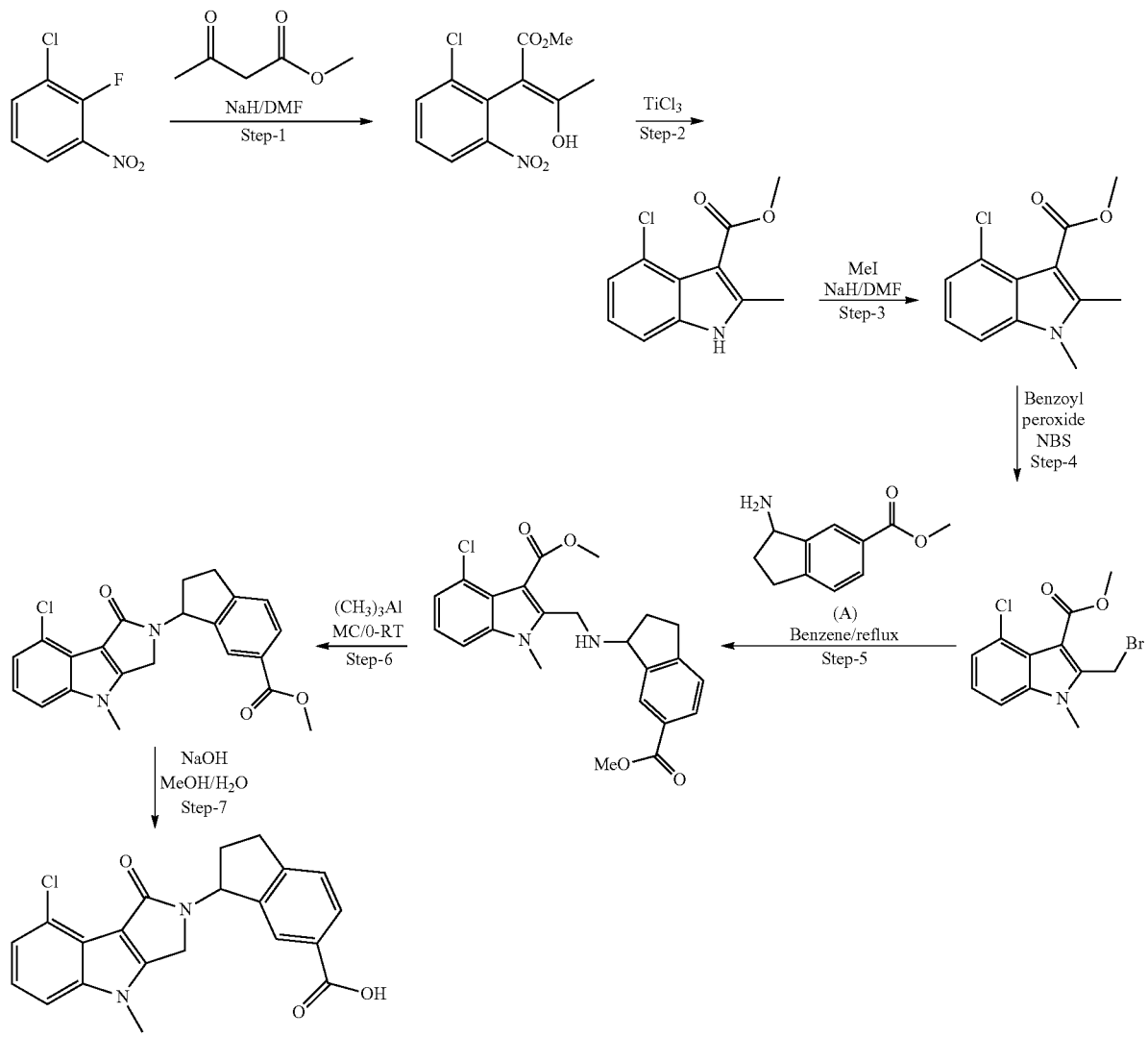

Step 1: Methyl acetoacetate (59.82 mmol, 2.1 eq.) was added dropwise to a suspension of NaH (65.52 mmol, 23 eq.) in DMF (40 ml) at 0° C. The mixture was stirred for 10 minutes, 1-chloro-2-fluoro-3-nitro-benzene (28.49 mmol, 1 eq.) was added and the mixture was finally stirred at room temperature for 16 h. 2 M HCl and water were added to the reaction mixture and the mixture was extracted with diethyl ether. The combined organic phases were washed with water and sat. NaCl solution, dried over sodium sulfate and concentrated under reduced pressure. The crude product was purified by column chromatography. Yield: 51%

Step 2: The product just obtained in step 1 (14.76 mmol) was dissolved in acetic acid (96 ml), a 20% strength $TiCl_3$ solution (20%—w/w in 2 N HCl, 71.6 ml) was added and the mixture was heated at 90° C. for 5-10 minutes. The reaction mixture was then cooled in an ice bath, and water and methylene chloride/methanol (9:1) were added. The organic phase was washed with water and sat. NaCl solution, dried over sodium sulfate and concentrated under reduced pressure. The crude product was titrated with hexane in order to obtain the desired product in a pure form. Yield: 53%

Step 3: A solution of the product obtained in step 2 (13.45 mmol, 1 eq.) in DMF (70 ml) was added to a suspension (0° C.) of NaH (26.90 mmol, 2 eq.) in DMF (13 ml) and the mixture was stirred for 30 minutes. Methyl iodide (20.17 mmol, 1.5 eq.) was added dropwise at 0° C. and the reaction mixture was stirred at room temperature for 2 h. The reaction mixture was quenched with $NH_4Cl$ solution and extracted with ethyl acetate. The combined organic phases were washed with water and sat. NaCl solution, dried over sodium sulfate and concentrated under reduced pressure. The crude product was employed in the next step without further purification. Yield: 60%

Step 4: The product just obtained in step 3 (9.70 mmol, 1 eq.) was dissolved in carbon tetrachloride (97 ml), NBS (9.70 mmol, 1 eq.) and benzoyl peroxide (0.19 mmol, 0.02 eq.) were added and the mixture was stirred at 85° C. for 1 hour. The precipitate formed was filtered out and the filtrate was concentrated under reduced pressure. The crude product was purified by column chromatography. Yield: 51%

Step 5: Triethylamine (10.59 mmol, 1.2 eq.) was added to a solution of the product just obtained in step 4 (8.83 mmol, 1.0 eq.) and 3-amino-2,3-dihydro-1H-indene-5-carboxylic acid methyl ester A (8.83 mmol, 1.0 eq.) in benzene (36 ml) and the mixture was heated under reflux for 16 h. The reaction mixture was then diluted with ethyl acetate and the organic phase was washed with water and sat. NaCl solution, dried over sodium sulfate and concentrated under reduced pressure. The crude product was purified by column chromatography. Yield: 80%

Step 6: The product just obtained in step 5 (5.59 mmol, 1 eq.) was dissolved in methylene chloride (38 ml), the solution was cooled to 0° C., AlMe$_3$ (2 M solution in toluene, 2.0 eq.) was added under an inert gas atmosphere and the mixture was stirred for 10 minutes in the cold and 2 h at room temperature. The reaction mixture was quenched with 2 N HCl, while cooling, and diluted with methylene chloride. The organic phase was washed with water and sat. NaCl solution, dried over sodium sulfate and concentrated under reduced pressure. The crude product was titrated with ethyl acetate in order to obtain the desired product in a pure form. Yield: 75%

Step 7: The product just obtained in step 6 (2.25 mmol, 1 eq.) was dissolved in methanol (34 ml), 3 M NaOH (3.3 ml.) was added and the mixture was heated under reflux for 15 h. Methanol was removed under reduced pressure, the residue was diluted with dist. water and the mixture was acidified with 1M HCl. The precipitate formed was filtered out and dried. The crude product was employed in the next step without further purification. Yield: 96%

Synthesis of Acid Unit (ACI_CC-30)

3-(5-chloro-2-fluorobenzamido)-2,3-dihydro-1H-indene-5-carboxylic acid (ACI_CC-30)

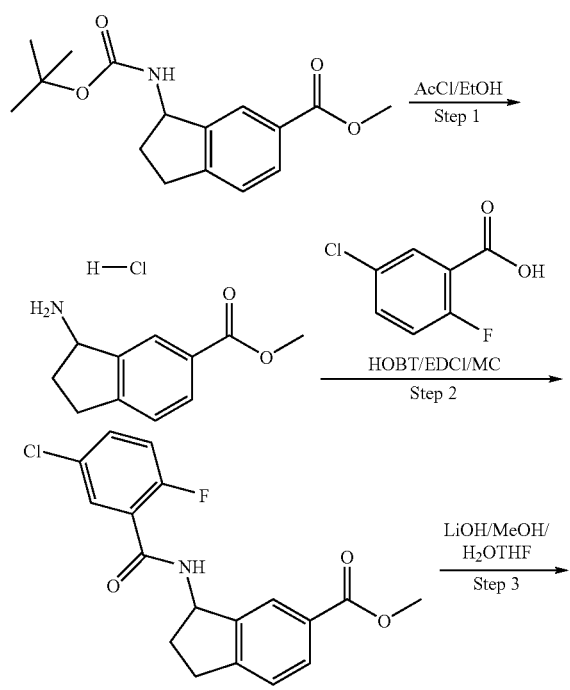

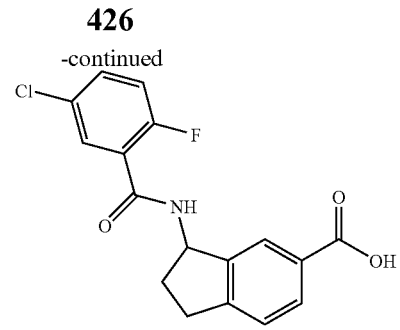

Step 1: Methyl 3-(tert-butoxycarbonylamino)-2,3-dihydro-1H-indene-5-carboxylate (25.3 g, 80 mmol) was dissolved in ethanol (280 ml) and cooled to 0° C. Acetylchloride (28.3 ml) was added, the reaction mixture was stirred at room temperature over night and finally concentrated under reduced pressure. Yield: 69.5 mmol/86.9%

Step 2: 5-Chloro-2-fluoro benzoic acid (5.0 g, 28.6 mmol), 1-Hydroxybenzotriazole hydrate (0.90 g, 6.87 mmol) and N,N-diisopropylethylamine (15.6 ml, 91.6 mmol) were dissolved in methylene chloride (600 ml) and the solution cooled to 0° C. 1-(3-Dimethylaminopropyl)-3-ethylcarbdiimide hydrochloride (6.57 g, 34.4 mmol) was added and the solution stirred for at least 15 minutes before the amine hydrochloride obtained in step 1 (5.22 g, 22.9 mmol) was added and the mixture stirred at room temperature over night. The reaction mixture was washed three times with 0.5 M aqueous KOH solution, dried over sodium sulfate and concentrated under reduced pressure. The crude product was purified by column chromatography (mobile phase: methylene chloride/methanol). Yield: 25.2 mmol/110%

Step 3: The product obtained in step 2 (8.76 g, 25.2 mmol) was dissolved in 185 ml of methanol-water-THF (3:1:2) and cooled to 0° C. LiOH 2H$_2$O (1.20 g, 50.4 mmol) was added and the mixture was stirred at room temperature over night. The reaction mixture was then heated to 60° C. for 3 h. After cooling to room temperature the mixture was concentrated under reduced pressure, the residue was taken up in water and washed with ether. The aqueous phase was acified with 1M aqueous HCl. A white solid precipitated, which was filtered out, washed with water and dried in vacuo. Yield: 25.5 mmol/101%

Synthesis of Acid Unit (ACI_CC-31)

3-(2-chloro-5-(trifluoromethyl)benzamido)-2,3-dihydro-1H-indene-5-carboxylic acid (ACI_CC-31)

Step 1: See step 1 of acid unit ACI_CC-30
Yield: 69.5 mmol/86.9%

Step 2: The amine hydrochloride obtained in step 1 (4.53 g, 17.15 mmol) was suspended in methylene chloride (66 ml) and then cooled to 0° C. under nitrogen. Triethylamine (7.12 ml, 51.5 mmol) and 2-Chloro-5-(trifluoromethyl)benzoyl chloride (5.00 g, 20.6 mmol) were added and the solution was stirred for 2 hours at room temperature. The reaction mixture was diluted with methylene chloride and washed with water and brine, dried over magnesium sulfate and concentrated under reduced pressure. The crude product was purified by column chromatography (mobile phase: methylene chloride/methanol). Yield: 19.1 mmol/111%

Step 3: In analogy to step 3 of acid unit ACI_CC-30
Yield: 18.6 mmol/97.8%

Synthesis of Acid Unit (ACI_CC-32)

3-(2,3-dichlorobenzamido)-2,3-dihydro-1H-indene-5-carboxylic acid (ACI_CC-32)

Step 1: See step 1 of acid unit ACI_CC-30
Yield: 69.5 mmol/86.9%
Step 2: In analogy to step 2 of acid unit ACI_CC-31 utilizing 2,3-Dichlorobenzoyl chloride
Yield: 22.7 mmol/114%
Step 3: In analogy to step 3 of acid unit ACI_CC-30
Yield: 22.4 mmol/98.9%

Synthesis of Acid Unit (ACI_CC-33)

3-(2-chloro-6-methylbenzamido)-2,3-dihydro-1H-indene-5-carboxylic acid (ACI_CC-33)

Step 1: See step 1 of acid unit ACI_CC-30
Yield: 69.5 mmol/86.9%
Step 2: In analogy to step 2 of acid unit ACI_CC-30 utilizing 2-Chloro-6-methyl benzoic acid
Yield: 17.8 mmol/70.4%
Step 3: In analogy to step 3 of acid unit ACI_CC-30
Yield: 17.1 mmol/96.3%

Synthesis of Acid Unit (ACI_CC-34)

3-(2-chloro-6-fluorobenzamido)-2,3-dihydro-1H-indene-5-carboxylic acid (ACI_CC-34)

Step 1: See step 1 of acid unit ACI_CC-30
Yield: 69.5 mmol/86.9%
Step 2: In analogy to step 2 of acid unit ACI_CC-31 utilizing 2-Chloro-6-fluorobenzoyl chloride
Yield: 20.2 mmol/93.8%
Step 3: In analogy to step 3 of acid unit ACI_CC-30
Yield: 19.8 mmol/97.8%

4) Parallel Synthesis
General:

The amine units AMN_CC' were prepared from the Boc-protected amines AMN_CC by Parallel Method 1 in accordance with the above equation. The amine trifluoroacetic acid salts AMN_CC' obtained in this way were reacted in parallel synthesis by Parallel Method 2 with the acids ACI_CC to give the amidic products IND_CC. The correlation of products (IND_CC) to the units used (ACI_CC) and can be seen from the synthesis matrix. The crude products of the parallel synthesis were purified by column chromatography. It was possible to demonstrate the identity of the products by analytical HPLC-MS measurements (cf. HPLC-MS data).

Parallel Method 1: Boc Deprotection

20% trifluoroacetic acid in methylene chloride (10 ml/mol) was added to the corresponding Boc-protected amine (1 eq., AMN_CC) at 0° C. The reaction mixture obtained was stirred at 25° C. for 4 h. The course of the reaction was monitored by means of thin layer chromatography. The solvent was then removed under reduced pressure and the residue was dried thoroughly in order to remove traces of trifluoroacetic acid. The crude product obtained in this way was used for synthesis of the libraries without further purification.

Parallel Method 2: Amide Formation

HATU (2 eq.) was added to a methylene chloride solution (3 ml/mmol) of the acid unit ACI_CC (1 eq.) at 0° C. and the mixture was stirred for 15 min. In a further round-bottomed flask, a methylene chloride solution (1 ml/mmol) of the Boc-deprotected amine unit AMN_CC' (1.5 eq.) was cooled in an ice bath, DIPEA (3 eq.) was added and the mixture was then added to the acid unit at 0° C. The reaction mixture was stirred at room temperature for 16 h and finally diluted with methylene chloride. The organic phase was washed successively with aqueous $NH_4Cl$ solution, $NaHCO_3$ solution and sat. NaCl solution, dried over $Na_2SO_4$ and concentrated under reduced pressure. The crude product was purified via a Biotage parallel purification system. Some compounds were purified manually by column chromatography over neutral aluminium oxide with methanol/methylene chloride as the mobile phase. A few compounds were purified via prep. HPLC with an aqueous ammonia method.

Synthesis Matrix:

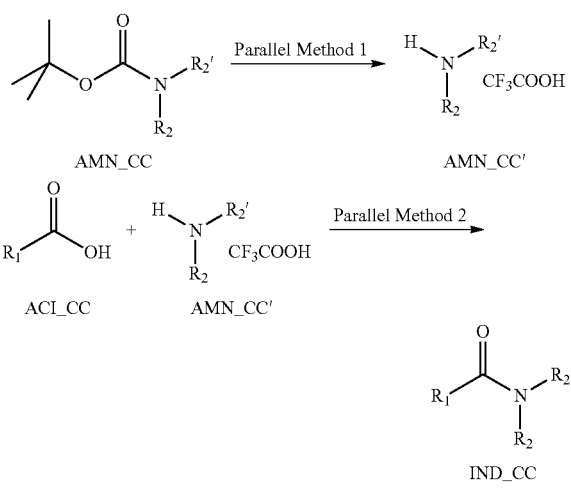

| Example no. | ACI_CC | Amine (AMN_CC) | Method no. |
|---|---|---|---|
| Ind_CC-090 | ACI_CC-20 | AMN_CC-21 | No. 1 & No. 2 |
| Ind_CC-091 | ACI_CC-20 | AMN_CC-22 | No. 1 & No. 2 |
| Ind_CC-092 | ACI_CC-20 | AMN_CC-23 | No. 1 & No. 2 |
| Ind_CC-093 | ACI_CC-20 | AMN_CC-24 | No. 1 & No. 2 |
| Ind_CC-094 | ACI_CC-20 | AMN_CC-26 | No. 1 & No. 2 |
| Ind_CC-095 | ACI_CC-21 | AMN_CC-20 | No. 1 & No. 2 |
| Ind_CC-096 | ACI_CC-21 | AMN_CC-21 | No. 1 & No. 2 |
| Ind_CC-097 | ACI_CC-21 | AMN_CC-22 | No. 1 & No. 2 |
| Ind_CC-098 | ACI_CC-21 | AMN_CC-23 | No. 1 & No. 2 |
| Ind_CC-099 | ACI_CC-21 | AMN_CC-24 | No. 1 & No. 2 |
| Ind_CC-100 | ACI_CC-21 | AMN_CC-25 | No. 1 & No. 2 |
| Ind_CC-101 | ACI_CC-21 | AMN_CC-26 | No. 1 & No. 2 |
| Ind_CC-102 | ACI_CC-22 | AMN_CC-21 | No. 1 & No. 2 |
| Ind_CC-103 | ACI_CC-22 | AMN_CC-22 | No. 1 & No. 2 |
| Ind_CC-104 | ACI_CC-22 | AMN_CC-23 | No. 1 & No. 2 |

| Example no. | ACI_CC | Amine (AMN_CC) | Method no. |
|---|---|---|---|
| Ind_CC-105 | ACI_CC-22 | AMN_CC-24 | No. 1 & No. 2 |
| Ind_CC-106 | ACI_CC-23 | AMN_CC-20 | No. 1 & No. 2 |
| Ind_CC-107 | ACI_CC-23 | AMN_CC-21 | No. 1 & No. 2 |
| Ind_CC-108 | ACI_CC-23 | AMN_CC-22 | No. 1 & No. 2 |
| Ind_CC-109 | ACI_CC-23 | AMN_CC-23 | No. 1 & No. 2 |
| Ind_CC-110 | ACI_CC-23 | AMN_CC-24 | No. 1 & No. 2 |
| Ind_CC-111 | ACI_CC-23 | AMN_CC-25 | No. 1 & No. 2 |
| Ind_CC-112 | ACI_CC-23 | AMN_CC-26 | No. 1 & No. 2 |
| Ind_CC-113 | ACI_CC-24 | AMN_CC-20 | No. 1 & No. 2 |
| Ind_CC-114 | ACI_CC-24 | AMN_CC-21 | No. 1 & No. 2 |
| Ind_CC-115 | ACI_CC-24 | AMN_CC-22 | No. 1 & No. 2 |
| Ind_CC-116 | ACI_CC-24 | AMN_CC-23 | No. 1 & No. 2 |
| Ind_CC-117 | ACI_CC-24 | AMN_CC-24 | No. 1 & No. 2 |
| Ind_CC-118 | ACI_CC-24 | AMN_CC-25 | No. 1 & No. 2 |
| Ind_CC-119 | ACI_CC-24 | AMN_CC-26 | No. 1 & No. 2 |
| Ind_CC-120 | ACI_CC-25 | AMN_CC-20 | No. 1 & No. 2 |
| Ind_CC-121 | ACI_CC-25 | AMN_CC-21 | No. 1 & No. 2 |
| Ind_CC-122 | ACI_CC-25 | AMN_CC-22 | No. 1 & No. 2 |
| Ind_CC-123 | ACI_CC-25 | AMN_CC-23 | No. 1 & No. 2 |
| Ind_CC-124 | ACI_CC-25 | AMN_CC-24 | No. 1 & No. 2 |
| Ind_CC-125 | ACI_CC-25 | AMN_CC-25 | No. 1 & No. 2 |
| Ind_CC-126 | ACI_CC-25 | AMN_CC-26 | No. 1 & No. 2 |
| Ind_CC-127 | ACI_CC-26 | AMN_CC-20 | No. 1 & No. 2 |
| Ind_CC-128 | ACI_CC-26 | AMN_CC-21 | No. 1 & No. 2 |
| Ind_CC-129 | ACI_CC-26 | AMN_CC-22 | No. 1 & No. 2 |
| Ind_CC-130 | ACI_CC-26 | AMN_CC-23 | No. 1 & No. 2 |
| Ind_CC-131 | ACI_CC-26 | AMN_CC-24 | No. 1 & No. 2 |
| Ind_CC-132 | ACI_CC-26 | AMN_CC-25 | No. 1 & No. 2 |
| Ind_CC-133 | ACI_CC-26 | AMN_CC-26 | No. 1 & No. 2 |
| Ind_CC-134 | ACI_CC-27 | AMN_CC-20 | No. 1 & No. 2 |
| Ind_CC-135 | ACI_CC-27 | AMN_CC-21 | No. 1 & No. 2 |
| Ind_CC-136 | ACI_CC-27 | AMN_CC-22 | No. 1 & No. 2 |
| Ind_CC-137 | ACI_CC-27 | AMN_CC-23 | No. 1 & No. 2 |
| Ind_CC-138 | ACI_CC-27 | AMN_CC-24 | No. 1 & No. 2 |
| Ind_CC-139 | ACI_CC-27 | AMN_CC-25 | No. 1 & No. 2 |
| Ind_CC-140 | ACI_CC-27 | AMN_CC-26 | No. 1 & No. 2 |
| Ind_CC-141 | ACI_CC-28 | AMN_CC-20 | No. 1 & No. 2 |
| Ind_CC-142 | ACI_CC-28 | AMN_CC-21 | No. 1 & No. 2 |
| Ind_CC-143 | ACI_CC-28 | AMN_CC-22 | No. 1 & No. 2 |
| Ind_CC-144 | ACI_CC-28 | AMN_CC-23 | No. 1 & No. 2 |
| Ind_CC-145 | ACI_CC-28 | AMN_CC-24 | No. 1 & No. 2 |
| Ind_CC-146 | ACI_CC-28 | AMN_CC-25 | No. 1 & No. 2 |
| Ind_CC-147 | ACI_CC-28 | AMN_CC-26 | No. 1 & No. 2 |
| Ind_CC-148 | ACI_CC-29 | AMN_CC-20 | No. 1 & No. 2 |
| Ind_CC-149 | ACI_CC-29 | AMN_CC-21 | No. 1 & No. 2 |
| Ind_CC-150 | ACI_CC-29 | AMN_CC-22 | No. 1 & No. 2 |
| Ind_CC-151 | ACI_CC-29 | AMN_CC-23 | No. 1 & No. 2 |
| Ind_CC-152 | ACI_CC-29 | AMN_CC-24 | No. 1 & No. 2 |
| Ind_CC-153 | ACI_CC-29 | AMN_CC-25 | No. 1 & No. 2 |
| Ind_CC-154 | ACI_CC-29 | AMN_CC-26 | No. 1 & No. 2 |

Analytical Data:

| Example no. | [M+] found | R.t. [min] |
|---|---|---|
| Ind_CC-090 | 553.4 | 2.74 |
| Ind_CC-091 | 570.4 | 2.87 |
| Ind_CC-092 | 567.4 | 2.37 |
| Ind_CC-093 | 612.5 | 2.85 |
| Ind_CC-094 | 539.4 | 2.7 |
| Ind_CC-095 | 529.2 | 2.69 |
| Ind_CC-096 | 529.2 | 2.71 |
| Ind_CC-097 | 546.3 | 6.51 |
| Ind_CC-098 | 543.4 | 2.23 |
| Ind_CC-099 | 588.4 | 2.81 |
| Ind_CC-100 | 515.2 | 2.65 |
| Ind_CC-101 | 515.2 | 2.66 |
| Ind_CC-102 | 535.2 | 2.77 |
| Ind_CC-103 | 552.3 | 6.89 |
| Ind_CC-104 | 549.4 | 2.42 |
| Ind_CC-105 | 594.4 | 2.87 |
| Ind_CC-106 | 543.4 | 2.76 |
| Ind_CC-107 | 543.4 | 2.77 |
| Ind_CC-108 | 560.4 | 2.91 |
| Ind_CC-109 | 557.4 | 2.4 |
| Ind_CC-110 | 602.4 | 2.86 |
| Ind_CC-111 | 529.2 | 2.72 |
| Ind_CC-112 | 529.2 | 2.73 |
| Ind_CC-113 | 569.4 | 2.83 |
| Ind_CC-114 | 569.2 | 2.85 |
| Ind_CC-115 | 586.4 | 3.03 |
| Ind_CC-116 | 583.4 | 2.6 |
| Ind_CC-117 | 628.4 | 2.96 |
| Ind_CC-118 | 555.2 | 2.8 |
| Ind_CC-119 | 555.2 | 2.81 |
| Ind_CC-120 | 557.4 | 2.77 |
| Ind_CC-121 | 557.4 | 2.79 |
| Ind_CC-122 | 574.4 | 2.93 |
| Ind_CC-123 | 571.4 | 2.49 |
| Ind_CC-124 | 616.4 | 2.89 |
| Ind_CC-125 | 543.2 | 2.73 |
| Ind_CC-126 | 543.1 | 6.22 |
| Ind_CC-127 | 543.2 | 2.77 |
| Ind_CC-128 | 543.2 | 2.76 |
| Ind_CC-129 | 560.4 | 2.9 |
| Ind_CC-130 | 557.4 | 2.32 |
| Ind_CC-131 | 557.4 | 2.88 |
| Ind_CC-132 | 529.2 | 2.7 |
| Ind_CC-133 | 529.2 | 2.7 |
| Ind_CC-134 | 543.2 | 2.72 |
| Ind_CC-135 | 543.2 | 2.72 |
| Ind_CC-136 | 560.2 | 2.86 |
| Ind_CC-137 | 557.4 | 1.7 |
| Ind_CC-138 | 602.4 | 2.83 |
| Ind_CC-139 | 529.2 | 2.2 |
| Ind_CC-140 | 529.2 | 2.7 |
| Ind_CC-141 | 544.2 | 2.69 |
| Ind_CC-142 | 544.2 | 2.71 |
| Ind_CC-143 | 561.2 | 2.82 |
| Ind_CC-144 | 558.4 | 2.22 |
| Ind_CC-145 | 603.4 | 2.83 |
| Ind_CC-146 | 530.2 | 2.62 |
| Ind_CC-147 | 530.2 | 2.65 |
| Ind_CC-148 | 594.2 | 2.78 |
| Ind_CC-149 | 594.2 | 2.79 |
| Ind_CC-150 | 611.3 | 2.94 |
| Ind_CC-151 | 608.4 | 2.57 |
| Ind_CC-152 | 653.6 | 2.88 |
| Ind_CC-153 | 580.4 | 2.76 |
| Ind_CC-154 | 580.2 | 2.76 |

F) Parallel Synthesis Library No. 3:

1) Synthesis of the Secondary Amine Units (ASN_CC)

Overview:

| Unit no. | Structure | Unit name |
|---|---|---|
| ASN_CC-01 | 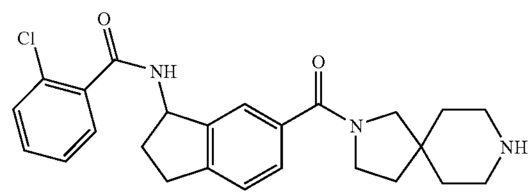 [SMILES: O=C(NC1CCc2ccc(C(=O)N3CCC4(CCNCC4)C3)cc21)c1ccccc1Cl] | 2-Chloro-N-[6-(3,8-diazaspiro[4.5]decane-3-carbonyl)-2,3-dihydro-1H-inden-1-yl]-benzamide (ASN_CC-01) |
| ASN_CC-02 | 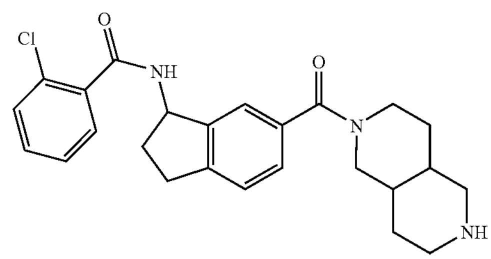 [SMILES: O=C(NC1CCc2ccc(C(=O)N3CCC4CNCCC4C3)cc21)c1ccccc1Cl] | 2-Chloro-N-[6-(3,9-diazaspiro[5.5]undecane-3-carbonyl)-2,3-dihydro-1H-inden-1-yl]-benzamide (ASN_CC-02) |
| ASN_CC-03 | 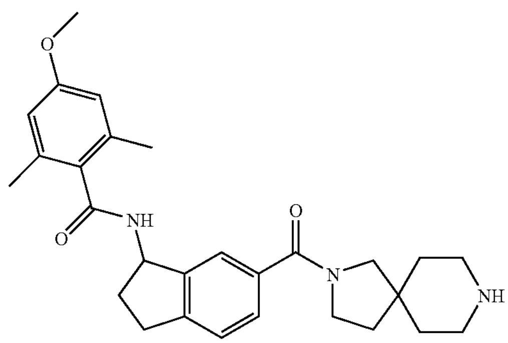 [SMILES: COc1cc(C)c(C(=O)NC2CCc3ccc(C(=O)N4CCC5(CCNCC5)C4)cc32)c(C)c1] | N-[6-(3,8-Diazaspiro[4.5]decane-3-carbonyl)-2,3-dihydro-1H-inden-1-yl]-4-methoxy-2,6-dimethyl-benzamide (ASN_CC-03) |
| ASN_CC-04 | 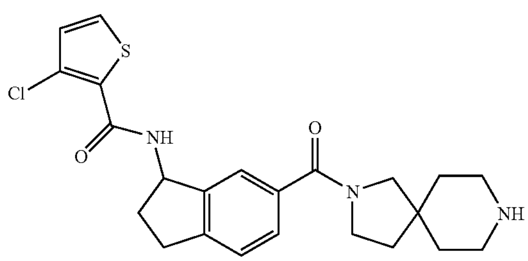 [SMILES: O=C(NC1CCc2ccc(C(=O)N3CCC4(CCNCC4)C3)cc21)c1sccc1Cl] | 3-Chloro-N-[6-(3,8-diazaspiro[4.5]decane-3-carbonyl)-2,3-dihydro-1H-inden-1-yl]-thiophene-2-carboxylic acid amide (ASN_CC-04) |
| ASN_CC-05 | 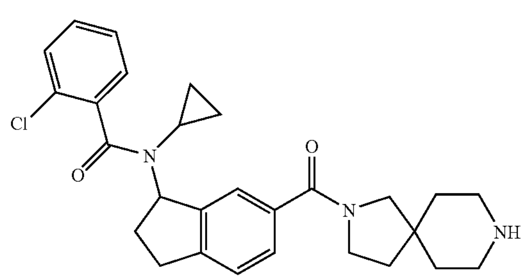 [SMILES: O=C(c1ccc2c(c1)C(N(C(=O)c1ccccc1Cl)C1CC1)CC2)N1CCC2(CCNCC2)C1] | 2-Chloro-N-cyclopropyl-N-[6-(3,8-diazaspiro[4.5]decane-3-carbonyl)-2,3-dihydro-1H-inden-1-yl]-benzamide (ASN_CC_05) |

-continued

| Unit no. | Structure | Unit name |
| --- | --- | --- |
| ASN_CC-06 | 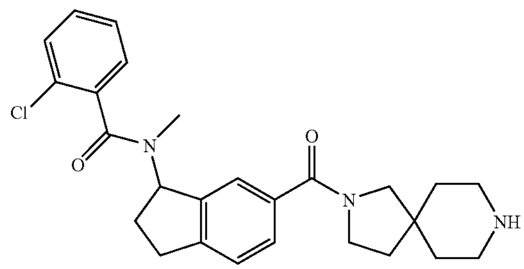 [SMILES: CN(C(=O)c1ccccc1Cl)C1CCc2ccc(C(=O)N3CCC4(CCNCC4)C3)cc21] | 2-Chloro-N-[6-(3,8-diazaspiro[4.5]decane-3-carbonyl)-2,3-dihydro-1H-inden-1-yl]-N-methyl-benzamide (ASN_CC-06) |
| ASN_CC-07 | 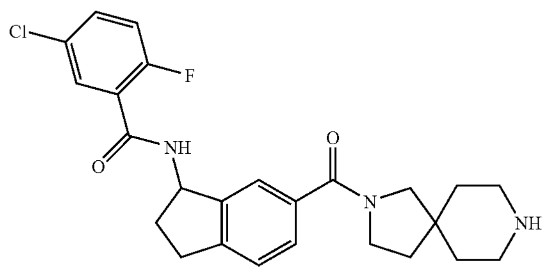 [SMILES: O=C(NC1CCc2ccc(C(=O)N3CCC4(CCNCC4)C3)cc21)c1cc(Cl)ccc1F] | 5-Chloro-N-[6-(3,8-diazaspiro[4.5]decane-3-carbonyl)-3,4-dihydro-1H-inden-1-yl]-2-fluoro-benzamide (ASN_CC-07) |
| ASN_CC-08 | 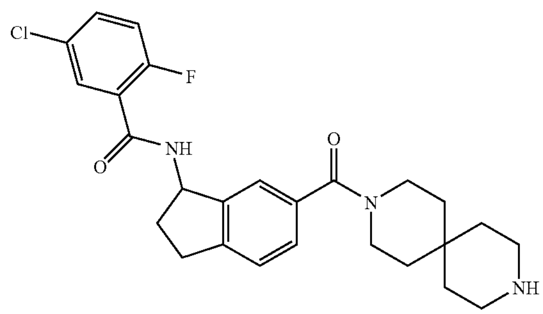 [SMILES: O=C(NC1CCc2ccc(C(=O)N3CCC4(CCNCC4)CC3)cc21)c1cc(Cl)ccc1F] | 5-Chloro-N-[6-(3,9-diazaspiro[5.5]undecane-3-carbonyl)-2,3-dihydro-1H-inden-1-yl]-2-fluoro-benzamide (ASN_CC-08) |
| ASN_CC-09 | 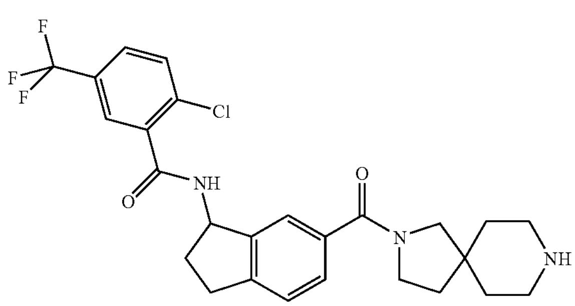 [SMILES: O=C(NC1CCc2ccc(C(=O)N3CCC4(CCNCC4)C3)cc21)c1cc(C(F)(F)F)ccc1Cl] | 2-Chloro-N-[6-(3,8-diazaspiro[4.5]decane-3-carbonyl)-2,3-dihydro-1H-inden-1-yl]-5-(trifluoromethyl)-benzamide (ASN_CC-09) |
| ASN_CC-10 | 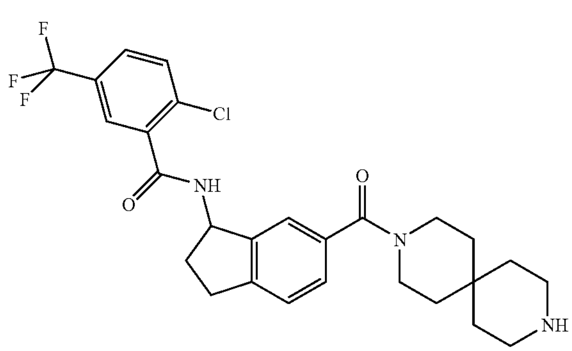 [SMILES: O=C(NC1CCc2ccc(C(=O)N3CCC4(CCNCC4)CC3)cc21)c1cc(C(F)(F)F)ccc1Cl] | 2-Chloro-N-[6-(3,9-diazaspiro[5.5]undecane-3-carbonyl)-2,3-dihydro-1H-inden-1-yl]-5-(trifluoromethyl)-benzamide (ASN_CC-10) |

-continued

| Unit no. | Structure | Unit name |
|---|---|---|
| ASN_CC-11 | 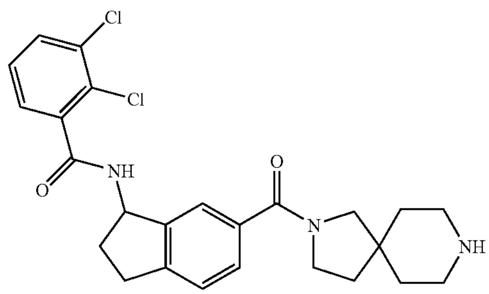 [SMILES: O=C(NC1CCc2ccc(C(=O)N3CCC4(CCNCC4)C3)cc21)c1cccc(Cl)c1Cl] | 2,3-Dichloro-N-[6-(3,8-diazaspiro[4.5]decane-3-carbonyl)-2,3-dihydro-1H-inden-1-yl]-benzamide (ASN_CC-11) |
| ASN_CC-12 | 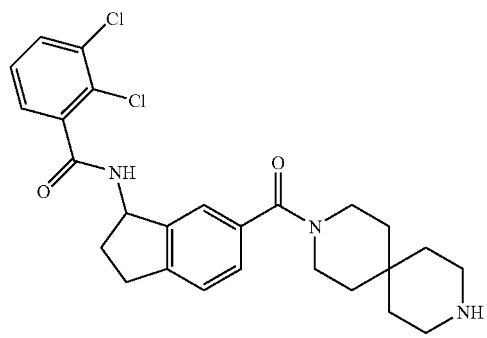 [SMILES: O=C(NC1CCc2ccc(C(=O)N3CCC4(CCNCC4)CC3)cc21)c1cccc(Cl)c1Cl] | 2,3-Dichloro-N-[6-(3,9-diazaspiro[5.5]undecane-3-carbonyl)-2,3-dihydro-1H-inden-1-yl]-benzamide (ASN_CC-12) |
| ASN_CC-13 | 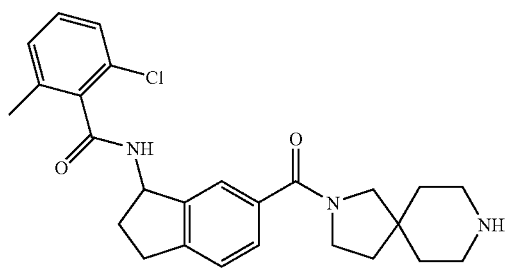 [SMILES: Cc1cccc(Cl)c1C(=O)NC1CCc2ccc(C(=O)N3CCC4(CCNCC4)C3)cc21] | 2-Chloro-N-[6-(3,8-diazaspiro[4.5]decane-3-carbonyl)-2,3-dihydro-1H-inden-1-yl]-6-methyl-benzamide (ASN_CC-13) |
| ASN_CC-14 | 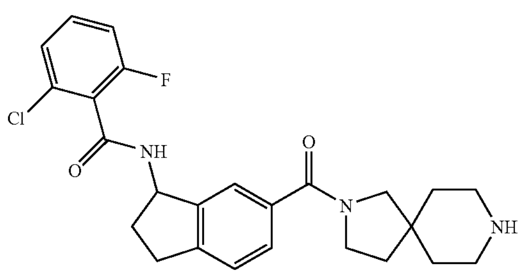 [SMILES: O=C(NC1CCc2ccc(C(=O)N3CCC4(CCNCC4)C3)cc21)c1c(F)cccc1Cl] | 2-Chloro-N-[6-(3,8-diazaspiro[4.5]decane-3-carbonyl)-2,3-dihydro-1H-inden-1-yl]-6-fluoro-benzamide (ASN_CC-14) |
| ASN_CC-15 | 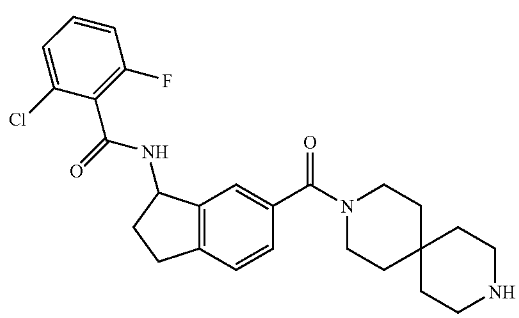 [SMILES: O=C(NC1CCc2ccc(C(=O)N3CCC4(CCNCC4)CC3)cc21)c1c(F)cccc1Cl] | 2-Chloro-N-[6-(3,9-diazaspiro[5.5]undecane-3-carbonyl)-2,3-dihydro-1H-inden-1-yl]-6-fluoro-benzamide (ASN_CC-15) |

-continued

| Unit no. | Structure | Unit name |
|---|---|---|
| ASN_CC-16 | 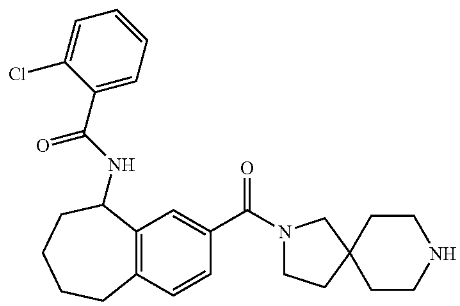 [SMILES: O=C(NC1CCCCc2ccc(C(=O)N3CCC4(CCNCC4)C3)cc21)c1ccccc1Cl] | 2-Chloro-N-[2-(3,8-diazaspiro[4.5]decane-3-carbonyl)-6,7,8,9-tetrahydro-5H-benzocyclohepten-9-yl]-benzamide (ASN_CC-16) |
| ASN_CC-17 | 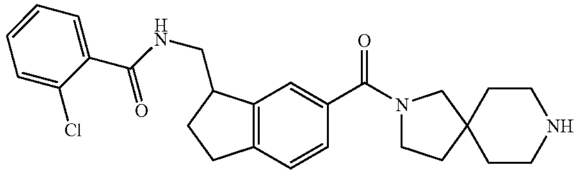 [SMILES: O=C(NCC1CCc2ccc(C(=O)N3CCC4(CCNCC4)C3)cc21)c1ccccc1Cl] | 2-Chloro-N-[[6-(3,8-diazaspiro[4.5]decane-3-carbonyl)-2,3-dihydro-1H-inden-1-yl]-methyl]-benzamide (ASN_CC-17) |
| ASN_CC-18 | 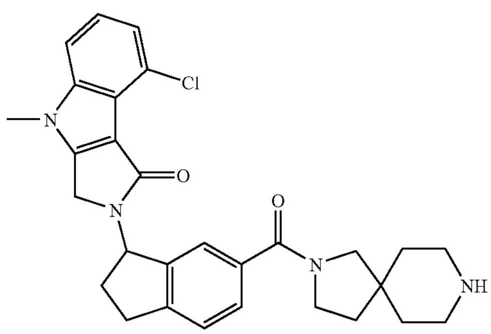 [SMILES: Cn1c2c(c3c(Cl)cccc31)C(=O)N(C1CCc3ccc(C(=O)N4CCC5(CCNCC5)C4)cc31)C2] | 8-Chloro-2-[6-(3,8-diazaspiro[4.5]decane-3-carbonyl)-2,3-dihydro-1H-inden-1-yl]-4-methyl-3,4-dihydro-2H-pyrrolo[3,4-b]indol-1-one (ASN_CC-18) |
| ASN_CC-19 | 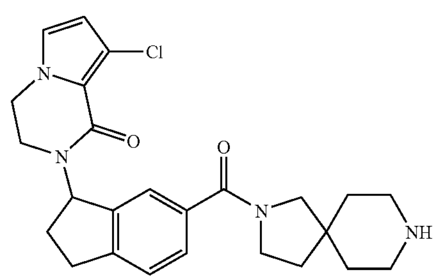 [SMILES: O=C(c1ccc2c(c1)C(N1CCn3ccc(Cl)c3C1=O)CC2)N1CCC2(CCNCC2)C1] | 8-Chloro-2-[6-(3,8-diazaspiro[4.5]decane-3-carbonyl)-2,3-dihydro-1H-inden-1-yl]-3,4-dihydro-2H-pyrrolo[1,2-a]pyrazin-1-one (ASN_CC-19) |
| ASN_CC-20 | 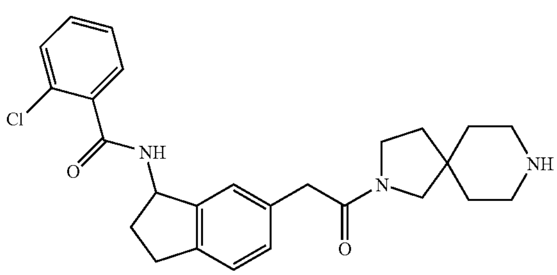 [SMILES: O=C(NC1CCc2ccc(CC(=O)N3CCC4(CCNCC4)C3)cc21)c1ccccc1Cl] | 2-Chloro-N-[6-[2-(2,8-diazaspiro[4.5]decane-2-yl)-2-oxo-ethyl]-2,3-dihydro-1H-inden-1-yl]-benzamide (ASN_CC-20) |

General Procedure for the Synthesis of the Secondary Amine Units (ASN_CC):

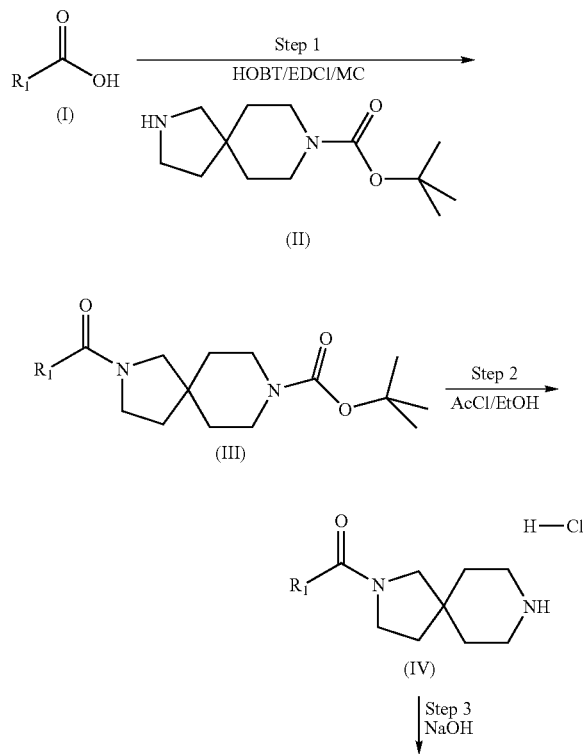

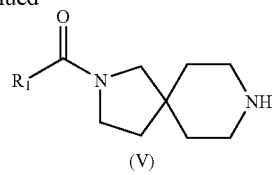

Step 1: 1-Hydroxybenzotriazole hydrate (0.35 g, 2.62 mmol), the corresponding acid (I) (3.5 g, 10.5 mmol) and N,N-diisopropylethylamine (3.0 ml, 17.5 mmol) were dissolved in methylene chloride (230 ml) and cooled to 0° C. 1-(3-Dimethylaminopropyl)-3-ethylcarbdiimide hydrochloride (2.51 g, 13.1 mmol) was added and the reaction mixture stirred for at least 15 minutes before the desired secondary amine (II) (2.1 g, 8.74 mmol) was added. Stirring was continued at room temperature over night. The reaction mixture was washed three times with 0.5 M aqueous KOH solution, dried over sodium sulfate and concentrated under reduced pressure. The crude product (III) was purified by column chromatography (methylene chloride/methanol).

Step 2: Boc protected amine (III) (4.55 g, 8.18 mmol) was dissolved in ethanol (40 ml) and cooled to 0° C. Acetylchloride (2.9 ml) was added, the reaction mixture was stirred at room temperature over night and afterwards concentrated under reduced pressure. The obtained amine hydrochloride (IV) was used in the next step without further purification.

Step 3: Amine hydrochloride (IV) (4.26 g, 8.06 mmol) was dissolved in water, 1M NaOH was added until pH 9 has been reached and extracted with methylene chloride. The organic layer was dried over sodium sulfate and concentrated under reduced pressure.

All secondary amine units (ASN_CC) depicted in the following table were synthesized according to the general procedure described above.

| Unit no. | Structure | Unit name | Acid (ACI_CC) | Amine (AMN) | Yield |
|---|---|---|---|---|---|
| ASN_CC-01 | 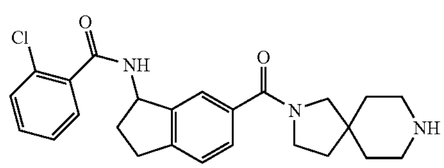 [SMILES: O=C(NC1CCc2ccc(C(=O)N3CCC4(CCNCC4)C3)cc21)c1ccccc1Cl] | 2-Chloro-N-[6-(3,8-diazaspiro[4.5]decane-3-carbonyl)-2,3-dihydro-1H-inden-1-yl]-benzamide (ASN_CC-01) | (ACI_CC-21) | tert-butyl 2,8-diazaspiro[4.5]decane-8-carboxylate | Step 1: 96% (7.27 mmol) Step 2: 106% (7.62 mmol) Step 3: 90% (6.84 mmol) |
| ASN_CC-02 | 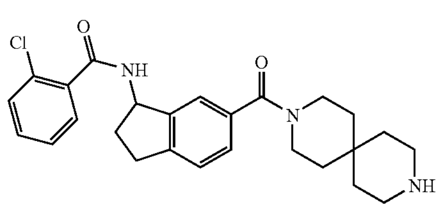 [SMILES: O=C(NC1CCc2ccc(C(=O)N3CCC4(CCNCC4)CC3)cc21)c1ccccc1Cl] | 2-Chloro-N-[6-(3,9-diazaspiro[5.5]undecane-3-carbonyl)-2,3-dihydro-1H-inden-1-yl]benzamide (ASN_CC-02) | (ACI_CC-21) | tert-butyl 3,9-diazaspiro[5.5]undecane-3-carboxylate | Step 1: 100% (7.83 mmol) Step 2: 105% (7.12 mmol) Step 3: 95% (6.79 mmol) |

-continued

| Unit no. | Structure | Unit name | Acid (ACI_CC) | Amine (AMN) | Yield |
|---|---|---|---|---|---|
| ASN_CC-03 | 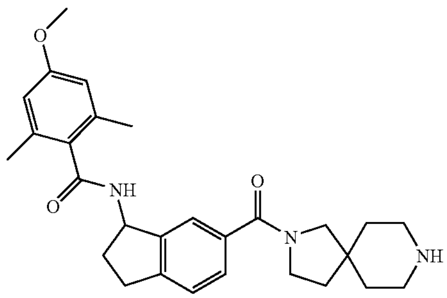 [SMILES: COc1cc(C)c(C(=O)NC2CCc3ccc(C(=O)N4CCC5(CCNCC5)C4)cc32)c(C)c1] | N-[6-(3,8-Diazaspiro[4.5]decane-3-carbonyl)-2,3-dihydro-1H-inden-1-yl]-4-methoxy-2,6-dimethyl-benzamide (ASN_CC-03) | (ACI_CC-20) | tert-butyl 2,8-diazaspiro[4.5]decane-8-carboxylate | Step 1: 97% (7.71 mmol) Step 2: 101% (7.77 mmol) Step 3: 101% (7.83 mmol) |
| ASN_CC-04 | 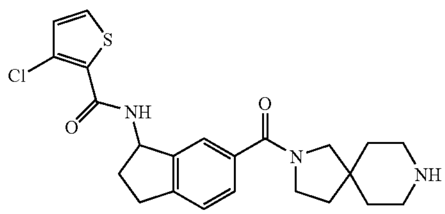 [SMILES: O=C(NC1CCc2ccc(C(=O)N3CCC4(CCNCC4)C3)cc21)c1sccc1Cl] | 3-Chloro-N-[6-(3,8-diazaspiro[4.5]decane-3-carbonyl)-2,3-dihydro-1H-inden-1-yl]-thiophene-2-carboxylic acid amide (ASN_CC-04) | (ACI_CC-22) | tert-butyl 2,8-diazaspiro[4.5]decane-8-carboxylate | Step 1: 91% (7.83 mmol) Step 2: 106% (8.66 mmol) Step 3: 93% (8.09 mmol) |
| ASN_CC-05 | 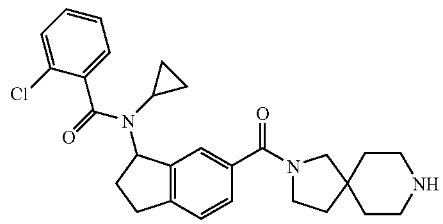 [SMILES: O=C(c1ccc2c(c1)C(N(C(=O)c1ccccc1Cl)C1CC1)CC2)N1CCC2(CCNCC2)C1] | 2-Chloro-N-cyclopropyl-N-[6-(3,8-diazaspiro[4.5]decane-3-carbonyl)-2,3-dihydro-1H-inden-1-yl]-benzamide (ASN_CC-05) | (ACI_CC-24) | tert-butyl 2,8-diazaspiro[4.5]decane-8-carboxylate | Step 1: 90% (5.86 mmol) Step 2: 104% (6.07 mmol) Step 3: 96% (5.81 mmol) |
| ASN_CC-06 | 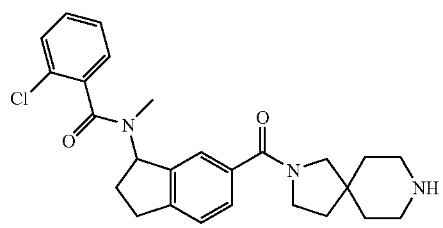 [SMILES: CN(C(=O)c1ccccc1Cl)C1CCc2ccc(C(=O)N3CCC4(CCNCC4)C3)cc21] | 2-Chloro-N-[6-(3,8-diazaspiro[4.5]decane-3-carbonyl)-2,3-dihydro-1H-inden-1-yl]-N-methyl-benzamide (ASN_CC-06) | (ACI_CC-23) | tert-butyl 2,8-diazaspiro[4.5]decane-8-carboxylate | Step 1: 80% (5.86 mmol) Step 2: 104% (6.91 mmol) Step 3: 102% (7.04 mmol) |
| ASN_CC-07) | 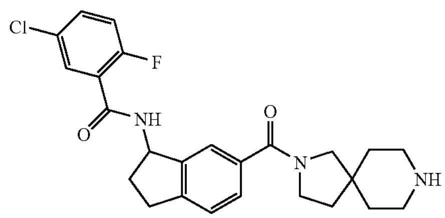 [SMILES: O=C(NC1CCc2ccc(C(=O)N3CCC4(CCNCC4)C3)cc21)c1cc(Cl)ccc1F] | 5-Chloro-N-[6-(3,8-diazaspiro[4.5]decane-3-carbonyl)-2,3-dihydro-1H-inden-1-yl]-2-fluoro-benzamide (ASN_CC-07) | (ACI_CC-30) | tert-butyl 2,8-diazaspiro[4.5]decane-8-carboxylate | Step 1: 94% (8.19 mmol) Step 2: 98% (8.06 mmol) Step 3: 99% (7.97 mmol) |
| ASN_CC-08) | 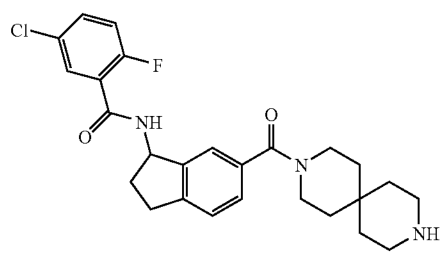 [SMILES: O=C(NC1CCc2ccc(C(=O)N3CCC4(CCNCC4)CC3)cc21)c1cc(Cl)ccc1F] | 5-Chloro-N-[6-(3,9-diazaspiro[5.5]undecane-3-carbonyl)-2,3-dihydro-1H-inden-1-yl]-2-fluoro-benzamide (ASN_CC-08) | (ACI_CC-30) | tert-butyl 3,9-diazaspiro[5.5]undecane-3-carboxylate | Step 1: 78% (6.81 mmol) Step 2: 100% (6.83 mmol) Step 3: 100% (6.81 mmol) |

-continued

| Unit no. | Structure | Unit name | Acid (ACI_CC) | Amine (AMN) | Yield |
|---|---|---|---|---|---|
| ASN_CC-09 | 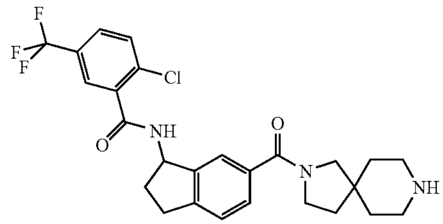 [SMILES: O=C(NC1CCc2ccc(C(=O)N3CCC4(CCNCC4)C3)cc21)c1cc(C(F)(F)F)ccc1Cl] | 2-Chloro-N-[6-(3,8-diazaspiro[4.5]decane-3-carbonyl)-2,3-dihydro-1H-inden-1-yl]-5-(trifluoromethyl)-benzamide (ASN_CC-09) | (ACI_CC-31) | tert-butyl 2,8-diazaspiro[4.5]decane-8-carboxylate | Step 1: 95% (7.35 mmol) Step 2: 107% (7.83 mmol) Step 3: 94% (7.36 mmol) |
| ASN_CC-10 | 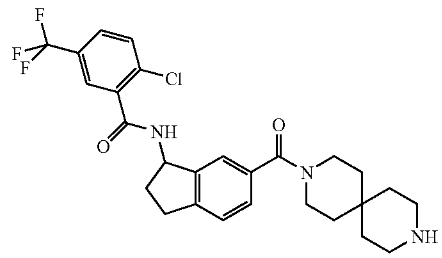 [SMILES: O=C(NC1CCc2ccc(C(=O)N3CCC4(CCNCC4)CC3)cc21)c1cc(C(F)(F)F)ccc1Cl] | 2-Chloro-N-[6-(3,9-diazaspiro[5.5]undecane-3-carbonyl)-2,3-dihydro-1H-inden-1-yl]-5-(trifluoromethyl)-benzamide (ASN_CC-10) | (ACI_CC-31) | tert-butyl 3,9-diazaspiro[5.5]undecane-3-carboxylate | Step 1: 90% (6.98 mmol) Step 2: 105% (7.31 mmol) Step 3: 95% (6.94 mmol) |
| ASN_CC-11 | 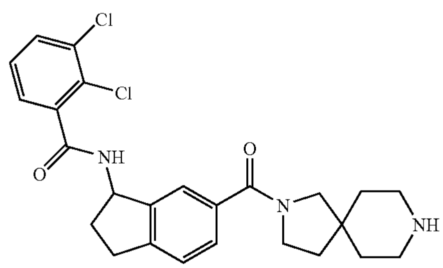 [SMILES: O=C(NC1CCc2ccc(C(=O)N3CCC4(CCNCC4)C3)cc21)c1cccc(Cl)c1Cl] | 2,3-Dichloro-N-[6-(3,8-diazaspiro[4.5]decane-3-carbonyl)-2,3-dihydro-1H-inden-1-yl]-benzamide (ASN_CC-11) | (ACI_CC-32) | tert-butyl 2,8-diazaspiro[4.5]decane-8-carboxylate | Step 1: 97% (9.04 mmol) Step 2: 104% (9.40 mmol) Step 3: 97% (9.11 mmol) |
| ASN_CC-12 | 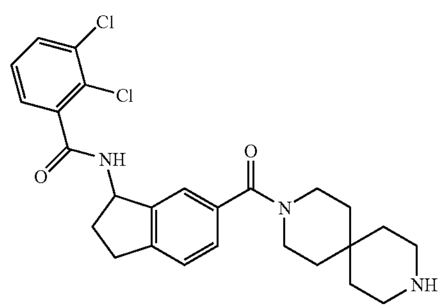 [SMILES: O=C(NC1CCc2ccc(C(=O)N3CCC4(CCNCC4)CC3)cc21)c1cccc(Cl)c1Cl] | 2,3-Dichloro-N-[6-(3,9-diazaspiro[5.5]undecane-3-carbonyl)-2,3-dihydro-1H-inden-1-yl]-benzamide (ASN_CC-12) | (ACI_CC-32) | tert-butyl 3,9-diazaspiro[5.5]undecane-3-carboxylate | Step 1: 81% (7.60 mmol) Step 2: 99% (7.50 mmol) Step 3: 100% (7.50 mmol) |
| ASN_CC-13 | 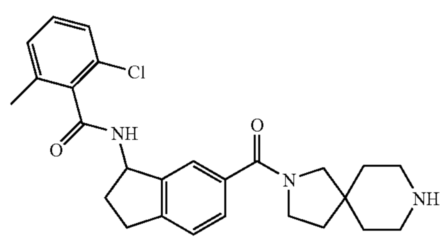 [SMILES: Cc1cccc(Cl)c1C(=O)NC1CCc2ccc(C(=O)N3CCC4(CCNCC4)C3)cc21] | 2-Chloro-N-[6-(3,8-diazaspiro[4.5]decane-3-carbonyl)-2,3-dihydro-1H-inden-1-yl]-6-methyl-benzamide (ASN_CC-13) | (ACI_CC-33) | tert-butyl 2,8-diazaspiro[4.5]decane-8-carboxylate | Step 1: 87% (8.83 mmol) Step 2: 103% (9.06 mmol) Step 3: 102% (9.23 mmol) |
| ASN_CC-14 | 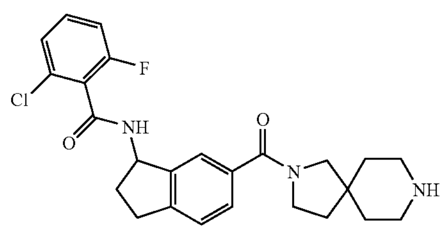 [SMILES: O=C(NC1CCc2ccc(C(=O)N3CCC4(CCNCC4)C3)cc21)c1c(F)cccc1Cl] | 2-Chloro-N-[6-(3,8-diazaspiro[4.5]decane-3-carbonyl)-2,3-dihydro-1H-inden-1-yl]-6-fluoro-benzamide (ASN_CC-14) | (ACI_CC-34) | tert-butyl 2,8-diazaspiro[4.5]decane-8-carboxylate | Step 1: 99% (8.13 mmol) Step 2: 101% (8.18 mmol) Step 3: 100% (8.22 mmol) |

-continued

| Unit no. | Structure | Unit name | Acid (ACI_CC) | Amine (AMN) | Yield |
|---|---|---|---|---|---|
| ASN_CC-15 | 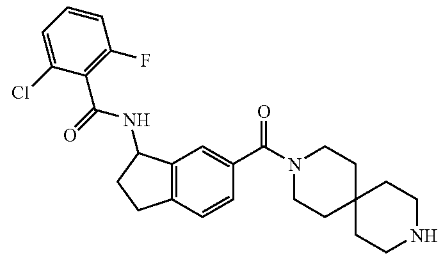 [SMILES: O=C(NC1CCc2ccc(C(=O)N3CCC4(CCNCC4)CC3)cc21)c1c(F)cccc1Cl] | 2-Chloro-N-[6-(3,9-diazaspiro[5.5]undecane-3-carbonyl)-2,3-dihydro-1H-inden-1-yl]-6-fluoro-benzamide (ASN_CC-15) | (ACI_CC-34) | tert-butyl 3,9-diazaspiro[5.5]undecane-3-carboxylate | Step 1: 74% (6.07 mmol) Step 2: 113% (6.84 mmol) Step 3: 100% (6.85 mmol) |
| ASN_CC-16 | 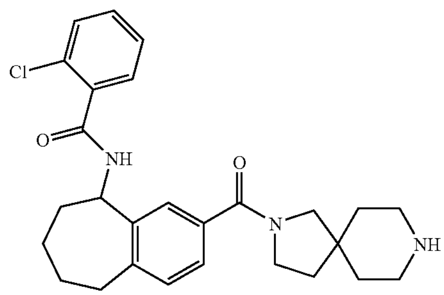 [SMILES: O=C(NC1CCCCc2ccc(C(=O)N3CCC4(CCNCC4)C3)cc21)c1ccccc1Cl] | 2-Chloro-N-[2-(3,8-diazaspiro[4.5]decane-3-carbonyl)-6,7,8,9-tetrahydro-5H-benzocyclohepten-9-yl]-benzamide (ASN_CC-16) | (ACI_CC-25) | tert-butyl 2,8-diazaspiro[4.5]decane-8-carboxylate | Step 1: 89% (6.46 mmol) Step 2: 113% (7.28 mmol) Step 3: 92% (6.67 mmol) |
| ASN_CC-17 | 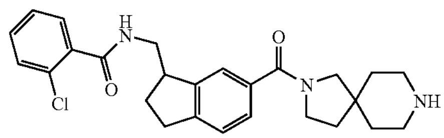 [SMILES: O=C(NCC1CCc2ccc(C(=O)N3CCC4(CCNCC4)C3)cc21)c1ccccc1Cl] | 2-Chloro-N-[[6-(3,8-diazaspiro[4.5]decane-3-carbonyl)-2,3-dihydro-1H-inden-1-yl]-methyl]-benzamide (ASN_CC-17) | (ACI_CC-26) | tert-butyl 2,8-diazaspiro[4.5]decane-8-carboxylate | Step 1: 88% (7.15 mmol) Step 2: 106% (7.59 mmol) Step 3: 96% (7.30 mmol) |
| ASN_CC-18 | 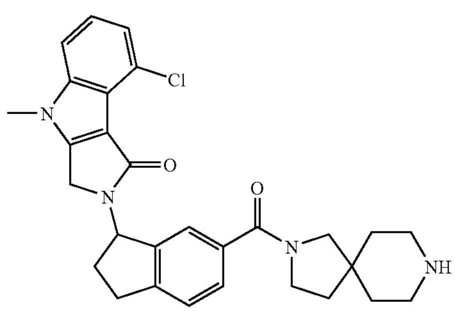 [SMILES: Cn1c2c(c3c(Cl)cccc31)C(=O)N(C1CCc3ccc(C(=O)N4CCC5(CCNCC5)C4)cc31)C2] | 8-Chloro-2-[6-(3,8-diazaspiro[4.5]decane-3-carbonyl)-2,3-dihydro-1H-inden-1-yl]-4-methyl-3,4-dihydro-2H-pyrrolo[3,4-b]indol-1-one (ASN_CC-18) | (ACI_CC-29) | tert-butyl 2,8-diazaspiro[4.5]decane-8-carboxylate | Step 1: 101% (6.17 mmol) Step 2: 97% (6.01 mmol) Step 3: 105% (6.30 mmol) |
| ASN_CC-19 | 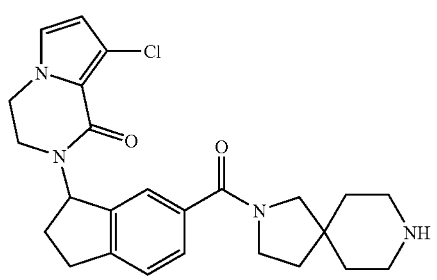 [SMILES: O=C(c1ccc2c(c1)C(N1CCn3ccc(Cl)c3C1=O)CC2)N1CCC2(CCNCC2)C1] | 8-Chloro-2-[6-(3,8-diazaspiro[4.5]decane-3-carbonyl)-2,3-dihydro-1H-inden-1-yl]-3,4-dihydro-2H-pyrrolo[1,2-a]pyrazin-1-one (ASN_CC-19) | (ACI_CC-28) | tert-butyl 2,8-diazaspiro[4.5]decane-8-carboxylate | Step 1: 91% (1.67 mmol) Step 2: 98% (1.62 mmol) Step 3: 109% (1.76 mmol) |
| ASN_CC-20 | 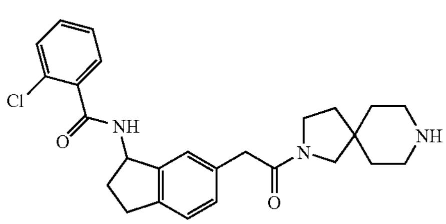 [SMILES: O=C(NC1CCc2ccc(CC(=O)N3CCC4(CCNCC4)C3)cc21)c1ccccc1Cl] | 2-Chloro-N-[6-[2-(2,8-diazaspiro[4.5]decan-2-yl)-2-oxo-ethyl]-2,3-dihydro-1H-inden-1-yl]-benzamide (ASN_CC-20) | (ACI_CC-27) | tert-butyl 2,8-diazaspiro[4.5]decane-8-carboxylate | Step 1: 96% (7.27 mmol) Step 2: 106% (7.62 mmol) Step 3: 90% (6.84 mmol) |

2) Synthesis of Acid Units, acid chlorides, sulfonyl chlorides and isocyanates and aldehydes (ACl_CC, ACL_CC, SCl_CC, ICN_CC, ALD_CC)

All building blocks (aldehyde, acid chloride, sulfonyl chloride and isocyanate) required for the synthesis of library no. 3 have been described and depicted under library no. 1 (→3) Synthesis of the acid units, acid chlorides, sulfonyl chlorides and isocyanates and aldehydes (ACl_CC, ACL_CC, ALD_CC).

3) Parallel Synthesis

General:

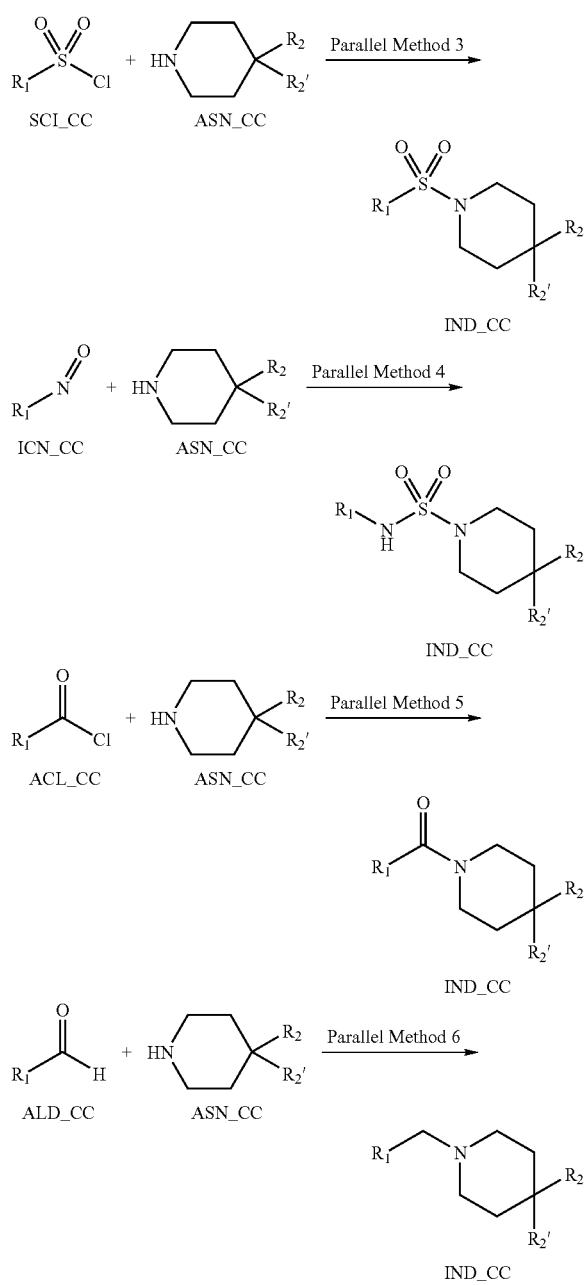

The spiroamines amine ASN_CC were reacted in parallel fashion via Parallel Method 3 with sulfonyl chlorides SCl_CC to give the sulfonamidic products IND_CC. ASN_CC were reacted in parallel fashion via Parallel Method 4 with isocyanates ISN_CC to give the urea products IND_CC. ASN_CC were reacted in parallel fashion via Parallel Method 5 with acid chlorides ACL_CC to give the amidic products IND_CC. ASN_CC were reacted in parallel fashion via Parallel Method 6 with aldehydes ALD_CC to give the reductively aminated products IND_CC. The crude products of the parallel synthesis were purified by column chromatography. It was possible to demonstrate the identity of the products by analytical HPLC-MS measurements (cf. HPLC-MS data).

Parallel Method 3: Sulfonylation

To a solution of ASN_CC (100 µmol) in methylene chloride (1 ml) was added a mixture of the sulfonyl chloride (SCl_CC) (150 µmol) and diisopropylethylamine (300 µmol) in methylene chloride (1.5 ml). The reaction mixture was stirred at room temperature for 12 h. The reaction mixture was treated with aqueous NaOH solution (1.5 ml, 1 mol/l) and sat. NaCl solution (1.5 ml) and stirred at room temperature for 30 min. The organic phase was separated, the aqueous phase was extracted with methylene chloride for two times. The combined organic phases were concentrated under reduced pressure. The crude product was purified via a HPLCMS system.

Parallel Method 4: Urea Formation

To a solution of ASN_CC (100 µmol) in methylene chloride (1 ml) was added a mixture of the sulfonyl chloride (ICN_CC) (150 µmol) and diisopropylethylamine (300 µmol) in methylene chloride (1.5 ml). The reaction mixture was stirred at room temperature for 12 h. The reaction mixture was treated with aqueous NaOH solution (1.5 ml, 1 mol/l) and sat. NaCl solution (1.5 ml) and stirred at room temperature for 30 min. The organic phase was separated, the aqueous phase was extracted with methylene chloride for two times. The combined organic phases were concentrated under reduced pressure. The crude product was purified via a HPLCMS system.

Parallel Method 5: Amide Formation

To a solution of ASN_CC (100 µmol) in methylene chloride (1 ml) was added a mixture of the sulfonyl chloride (ACL_CC) (150 µmol) and diisopropylethylamine (300 µmol) in methylene chloride (1.5 ml). The reaction mixture was stirred at room temperature for 12 h. The reaction mixture was treated with aqueous NaOH solution (1.5 ml, 1 mol/l) and sat. NaCl solution (1.5 ml) and stirred at room temperature for 30 min. The organic phase was separated, the aqueous phase was extracted with methylene chloride for two times. The combined organic phases were concentrated under reduced pressure. The crude product was purified via a HPLCMS system.

Parallel Method 6: Reductive Amination

To a solution of ALD_CC (150 µmol) in methylene chloride (2.5 ml) were added the amine (ASN_CC) (100 µmol) in methylene chloride (1 ml) and acetic acid (12.5 µmol) in methylene chloride (0.5 ml). The reaction mixture was stirred at room temperature for 1 h. Sodium triacetoxyborohydride (250 µmol) was added and the reaction mixture was stirred at room temperature for 12 h. The reaction mixture was treated with halfsat. NaHCO$_3$ solution (2 ml) and sat. NaCl solution (1 ml) and stirred at room temperature for 15 min. The organic phase was separated, the aqueous phase was extracted with methylene chloride for two times. The combined organic phases were concentrated under reduced pressure. The crude product was purified via a HPLCMS system.

Synthesis Matrix:

| Example no. | ACI_CC, SCI_CC, ICN_CC or ALD_CC | Amine (ASN_CC) | Method no. |
|---|---|---|---|
| IND_CC-500 | SCI_CC-07 | ASN_CC__04 | No. 3 |
| IND_CC-501 | SCI_CC-04 | ASN_CC__04 | No. 3 |
| IND_CC-502 | ICN_CC-09 | ASN_CC__04 | No. 4 |
| IND_CC-503 | ICN_CC-03 | ASN_CC__04 | No. 4 |
| IND_CC-504 | ALD_CC-12 | ASN_CC__04 | No. 6 |
| IND_CC-505 | ALD_CC-23 | ASN_CC__05 | No. 6 |
| IND_CC-506 | ALD_CC-20 | ASN_CC__05 | No. 6 |
| IND_CC-507 | ALD_CC-29 | ASN_CC__06 | No. 6 |
| IND_CC-508 | ALD_CC-27 | ASN_CC__06 | No. 6 |
| IND_CC-509 | ALD_CC-01 | ASN_CC__06 | No. 6 |
| IND_CC-510 | ALD_CC-02 | ASN_CC__06 | No. 6 |
| IND_CC-511 | ALD_CC-07 | ASN_CC__06 | No. 6 |
| IND_CC-512 | ALD_CC-05 | ASN_CC__06 | No. 6 |
| IND_CC-513 | ALD_CC-12 | ASN_CC__06 | No. 6 |
| IND_CC-514 | ALD_CC-13 | ASN_CC__06 | No. 6 |
| IND_CC-515 | ALD_CC-14 | ASN_CC__06 | No. 6 |
| IND_CC-516 | ALD_CC-22 | ASN_CC__06 | No. 6 |
| IND_CC-517 | ALD_CC-15 | ASN_CC__06 | No. 6 |
| IND_CC-518 | ALD_CC-07 | ASN_CC__03 | No. 6 |
| IND_CC-519 | ALD_CC-05 | ASN_CC__03 | No. 6 |
| IND_CC-520 | ALD_CC-12 | ASN_CC__03 | No. 6 |
| IND_CC-521 | ALD_CC-13 | ASN_CC__03 | No. 6 |
| IND_CC-522 | ALD_CC-14 | ASN_CC__03 | No. 6 |
| IND_CC-523 | ALD_CC-22 | ASN_CC__03 | No. 6 |
| IND_CC-524 | ALD_CC-11 | ASN_CC__03 | No. 6 |
| IND_CC-525 | ALD_CC-15 | ASN_CC__03 | No. 6 |
| IND_CC-526 | ALD_CC-25 | ASN_CC__06 | No. 6 |
| IND_CC-527 | ALD_CC-28 | ASN_CC__06 | No. 6 |
| IND_CC-528 | ALD_CC-33 | ASN_CC__06 | No. 6 |
| IND_CC-529 | ALD_CC-03 | ASN_CC__06 | No. 6 |
| IND_CC-530 | ALD_CC-04 | ASN_CC__06 | No. 6 |
| IND_CC-531 | ALD_CC-31 | ASN_CC__06 | No. 6 |
| IND_CC-532 | ALD_CC-17 | ASN_CC__06 | No. 6 |
| IND_CC-533 | ALD_CC-08 | ASN_CC__06 | No. 6 |
| IND_CC-534 | ALD_CC-21 | ASN_CC__06 | No. 6 |
| IND_CC-535 | ALD_CC-23 | ASN_CC__06 | No. 6 |
| IND_CC-536 | ALD_CC-25 | ASN_CC__03 | No. 6 |
| IND_CC-537 | ALD_CC-03 | ASN_CC__03 | No. 6 |
| IND_CC-538 | ALD_CC-04 | ASN_CC__03 | No. 6 |
| IND_CC-539 | ALD_CC-08 | ASN_CC__03 | No. 6 |
| IND_CC-540 | ALD_CC-21 | ASN_CC__03 | No. 6 |
| IND_CC-541 | ALD_CC-23 | ASN_CC__03 | No. 6 |
| IND_CC-542 | ALD_CC-13 | ASN_CC__04 | No. 6 |
| IND_CC-543 | ALD_CC-14 | ASN_CC__04 | No. 6 |
| IND_CC-544 | ALD_CC-22 | ASN_CC__04 | No. 6 |
| IND_CC-545 | ALD_CC-11 | ASN_CC__04 | No. 6 |
| IND_CC-546 | ALD_CC-15 | ASN_CC__04 | No. 6 |
| IND_CC-547 | ALD_CC-14 | ASN_CC__02 | No. 6 |
| IND_CC-548 | ALD_CC-11 | ASN_CC__02 | No. 6 |
| IND_CC-549 | ALD_CC-13 | ASN_CC__05 | No. 6 |
| IND_CC-550 | ALD_CC-14 | ASN_CC__05 | No. 6 |
| IND_CC-551 | ALD_CC-22 | ASN_CC__05 | No. 6 |
| IND_CC-552 | ALD_CC-11 | ASN_CC__05 | No. 6 |
| IND_CC-553 | ALD_CC-28 | ASN_CC__04 | No. 6 |
| IND_CC-554 | ALD_CC-33 | ASN_CC__04 | No. 6 |
| IND_CC-555 | ALD_CC-18 | ASN_CC__04 | No. 6 |
| IND_CC-556 | ALD_CC-03 | ASN_CC__04 | No. 6 |
| IND_CC-557 | ALD_CC-04 | ASN_CC__04 | No. 6 |
| IND_CC-558 | ALD_CC-04 | ASN_CC__05 | No. 6 |
| IND_CC-559 | ALD_CC-31 | ASN_CC__04 | No. 6 |
| IND_CC-560 | ALD_CC-17 | ASN_CC__04 | No. 6 |
| IND_CC-561 | ALD_CC-08 | ASN_CC__04 | No. 6 |
| IND_CC-562 | ALD_CC-21 | ASN_CC__04 | No. 6 |
| IND_CC-563 | ALD_CC-23 | ASN_CC__04 | No. 6 |
| IND_CC-564 | ALD_CC-16 | ASN_CC__04 | No. 6 |
| IND_CC-565 | ALD_CC-32 | ASN_CC__04 | No. 6 |
| IND_CC-566 | ALD_CC-30 | ASN_CC__04 | No. 6 |
| IND_CC-567 | ALD_CC-19 | ASN_CC__04 | No. 6 |
| IND_CC-568 | ALD_CC-20 | ASN_CC__04 | No. 6 |
| IND_CC-569 | ALD_CC-08 | ASN_CC__02 | No. 6 |
| IND_CC-570 | ALD_CC-19 | ASN_CC__02 | No. 6 |
| IND_CC-571 | ALD_CC-20 | ASN_CC__02 | No. 6 |
| IND_CC-572 | ALD_CC-21 | ASN_CC__05 | No. 6 |
| IND_CC-573 | ACL_CC-15 | ASN_CC__04 | No. 5 |
| IND_CC-574 | ACL_CC-18 | ASN_CC__04 | No. 5 |
| IND_CC-575 | ACL_CC-28 | ASN_CC__04 | No. 5 |
| IND_CC-576 | ACL_CC-07 | ASN_CC__04 | No. 5 |
| IND_CC-577 | ACL_CC-24 | ASN_CC__04 | No. 5 |
| IND_CC-578 | ACL_CC-22 | ASN_CC__04 | No. 5 |
| IND_CC-579 | ACL_CC-21 | ASN_CC__04 | No. 5 |
| IND_CC-580 | ACL_CC-22 | ASN_CC__01 | No. 5 |
| IND_CC-581 | ACL_CC-21 | ASN_CC__01 | No. 5 |
| IND_CC-582 | ACL_CC-15 | ASN_CC__02 | No. 5 |
| IND_CC-583 | ACL_CC-18 | ASN_CC__02 | No. 5 |
| IND_CC-584 | ACL_CC-28 | ASN_CC__02 | No. 5 |
| IND_CC-585 | ACL_CC-07 | ASN_CC__02 | No. 5 |
| IND_CC-586 | ACL_CC-24 | ASN_CC__02 | No. 5 |
| IND_CC-587 | ACL_CC-22 | ASN_CC__02 | No. 5 |
| IND_CC-588 | ACL_CC-21 | ASN_CC__02 | No. 5 |
| IND_CC-589 | ACL_CC-15 | ASN_CC__05 | No. 5 |
| IND_CC-590 | ACL_CC-18 | ASN_CC__05 | No. 5 |
| IND_CC-591 | ACL_CC-28 | ASN_CC__05 | No. 5 |
| IND_CC-592 | ACL_CC-24 | ASN_CC__05 | No. 5 |
| IND_CC-593 | ACL_CC-22 | ASN_CC__05 | No. 5 |
| IND_CC-594 | ACL_CC-38 | ASN_CC__06 | No. 5 |
| IND_CC-595 | ACL_CC-20 | ASN_CC__06 | No. 5 |
| IND_CC-596 | ACL_CC-05 | ASN_CC__06 | No. 5 |
| IND_CC-597 | ACL_CC-15 | ASN_CC__06 | No. 5 |
| IND_CC-598 | ACL_CC-18 | ASN_CC__06 | No. 5 |
| IND_CC-599 | ACL_CC-28 | ASN_CC__06 | No. 5 |
| IND_CC-600 | ACL_CC-07 | ASN_CC__06 | No. 5 |
| IND_CC-601 | ACL_CC-22 | ASN_CC__06 | No. 5 |
| IND_CC-602 | ACL_CC-21 | ASN_CC__06 | No. 5 |
| IND_CC-603 | ACL_CC-15 | ASN_CC__03 | No. 5 |
| IND_CC-604 | ACL_CC-18 | ASN_CC__03 | No. 5 |
| IND_CC-605 | ACL_CC-28 | ASN_CC__03 | No. 5 |
| IND_CC-606 | ACL_CC-07 | ASN_CC__03 | No. 5 |
| IND_CC-607 | ACL_CC-22 | ASN_CC__03 | No. 5 |
| IND_CC-608 | SCI_CC-08 | ASN_CC__06 | No. 3 |
| IND_CC-609 | SCI_CC-07 | ASN_CC__06 | No. 3 |
| IND_CC-610 | SCI_CC-16 | ASN_CC__06 | No. 3 |
| IND_CC-611 | SCI_CC-04 | ASN_CC__06 | No. 3 |
| IND_CC-612 | SCI_CC-22 | ASN_CC__06 | No. 3 |
| IND_CC-613 | SCI_CC-03 | ASN_CC__06 | No. 3 |
| IND_CC-614 | SCI_CC-23 | ASN_CC__06 | No. 3 |
| IND_CC-615 | SCI_CC-08 | ASN_CC__03 | No. 3 |
| IND_CC-616 | SCI_CC-07 | ASN_CC__03 | No. 3 |
| IND_CC-617 | SCI_CC-16 | ASN_CC__03 | No. 3 |
| IND_CC-618 | SCI_CC-04 | ASN_CC__03 | No. 3 |
| IND_CC-619 | SCI_CC-23 | ASN_CC__03 | No. 3 |
| IND_CC-620 | ALD_CC-29 | ASN_CC__07 | No. 6 |
| IND_CC-621 | ALD_CC-13 | ASN_CC__07 | No. 6 |
| IND_CC-622 | ALD_CC-22 | ASN_CC__07 | No. 6 |
| IND_CC-623 | ALD_CC-11 | ASN_CC__07 | No. 6 |
| IND_CC-624 | ALD_CC-29 | ASN_CC__08 | No. 6 |
| IND_CC-625 | ALD_CC-27 | ASN_CC__08 | No. 6 |
| IND_CC-626 | ALD_CC-01 | ASN_CC__08 | No. 6 |
| IND_CC-627 | ALD_CC-02 | ASN_CC__08 | No. 6 |
| IND_CC-628 | ALD_CC-13 | ASN_CC__08 | No. 6 |
| IND_CC-629 | ALD_CC-22 | ASN_CC__08 | No. 6 |
| IND_CC-630 | ALD_CC-11 | ASN_CC__08 | No. 6 |
| IND_CC-631 | ALD_CC-27 | ASN_CC__09 | No. 6 |
| IND_CC-632 | ALD_CC-12 | ASN_CC__09 | No. 6 |
| IND_CC-633 | ALD_CC-13 | ASN_CC__09 | No. 6 |
| IND_CC-634 | ALD_CC-14 | ASN_CC__09 | No. 6 |
| IND_CC-635 | ALD_CC-22 | ASN_CC__09 | No. 6 |
| IND_CC-636 | ALD_CC-11 | ASN_CC__09 | No. 6 |
| IND_CC-637 | ALD_CC-15 | ASN_CC__09 | No. 6 |
| IND_CC-638 | ALD_CC-29 | ASN_CC__10 | No. 6 |
| IND_CC-639 | ALD_CC-27 | ASN_CC__10 | No. 6 |
| IND_CC-640 | ALD_CC-01 | ASN_CC__10 | No. 6 |
| IND_CC-641 | ALD_CC-02 | ASN_CC__10 | No. 6 |
| IND_CC-642 | ALD_CC-07 | ASN_CC__10 | No. 6 |
| IND_CC-643 | ALD_CC-05 | ASN_CC__10 | No. 6 |
| IND_CC-644 | ALD_CC-12 | ASN_CC__10 | No. 6 |
| IND_CC-645 | ALD_CC-13 | ASN_CC__10 | No. 6 |
| IND_CC-646 | ALD_CC-14 | ASN_CC__10 | No. 6 |
| IND_CC-647 | ALD_CC-22 | ASN_CC__10 | No. 6 |
| IND_CC-648 | ALD_CC-11 | ASN_CC__10 | No. 6 |
| IND_CC-649 | ALD_CC-15 | ASN_CC__10 | No. 6 |
| IND_CC-650 | ALD_CC-08 | ASN_CC__07 | No. 6 |

| Example no. | ACI_CC, SCI_CC, ICN_CC or ALD_CC | Amine (ASN_CC) | Method no. |
|---|---|---|---|
| IND_CC-651 | ALD_CC-21 | ASN_CC_07 | No. 6 |
| IND_CC-652 | ALD_CC-18 | ASN_CC_08 | No. 6 |
| IND_CC-653 | ALD_CC-08 | ASN_CC_08 | No. 6 |
| IND_CC-654 | ALD_CC-21 | ASN_CC_08 | No. 6 |
| IND_CC-655 | ALD_CC-28 | ASN_CC_09 | No. 6 |
| IND_CC-656 | ALD_CC-18 | ASN_CC_09 | No. 6 |
| IND_CC-657 | ALD_CC-17 | ASN_CC_09 | No. 6 |
| IND_CC-658 | ALD_CC-08 | ASN_CC_09 | No. 6 |
| IND_CC-659 | ALD_CC-21 | ASN_CC_09 | No. 6 |
| IND_CC-660 | ALD_CC-23 | ASN_CC_09 | No. 6 |
| IND_CC-661 | ALD_CC-28 | ASN_CC_10 | No. 6 |
| IND_CC-662 | ALD_CC-33 | ASN_CC_10 | No. 6 |
| IND_CC-663 | ALD_CC-18 | ASN_CC_10 | No. 6 |
| IND_CC-664 | ALD_CC-31 | ASN_CC_10 | No. 6 |
| IND_CC-665 | ALD_CC-17 | ASN_CC_10 | No. 6 |
| IND_CC-666 | ALD_CC-08 | ASN_CC_10 | No. 6 |
| IND_CC-667 | ALD_CC-21 | ASN_CC_10 | No. 6 |
| IND_CC-668 | ALD_CC-23 | ASN_CC_10 | No. 6 |
| IND_CC-669 | ALD_CC-03 | ASN_CC_10 | No. 6 |
| IND_CC-670 | ALD_CC-04 | ASN_CC_10 | No. 6 |
| IND_CC-671 | ALD_CC-19 | ASN_CC_07 | No. 6 |
| IND_CC-672 | ALD_CC-20 | ASN_CC_07 | No. 6 |
| IND_CC-673 | ALD_CC-24 | ASN_CC_07 | No. 6 |
| IND_CC-674 | ALD_CC-34 | ASN_CC_07 | No. 6 |
| IND_CC-675 | ALD_CC-35 | ASN_CC_07 | No. 6 |
| IND_CC-676 | ALD_CC-30 | ASN_CC_08 | No. 6 |
| IND_CC-677 | ALD_CC-19 | ASN_CC_08 | No. 6 |
| IND_CC-678 | ALD_CC-20 | ASN_CC_08 | No. 6 |
| IND_CC-679 | ALD_CC-24 | ASN_CC_08 | No. 6 |
| IND_CC-680 | ALD_CC-26 | ASN_CC_08 | No. 6 |
| IND_CC-681 | ALD_CC-10 | ASN_CC_08 | No. 6 |
| IND_CC-682 | ALD_CC-16 | ASN_CC_09 | No. 6 |
| IND_CC-683 | ALD_CC-30 | ASN_CC_09 | No. 6 |
| IND_CC-684 | ALD_CC-19 | ASN_CC_09 | No. 6 |
| IND_CC-685 | ALD_CC-20 | ASN_CC_09 | No. 6 |
| IND_CC-686 | ALD_CC-24 | ASN_CC_09 | No. 6 |
| IND_CC-687 | ALD_CC-26 | ASN_CC_09 | No. 6 |
| IND_CC-688 | ALD_CC-09 | ASN_CC_09 | No. 6 |
| IND_CC-689 | ALD_CC-06 | ASN_CC_09 | No. 6 |
| IND_CC-690 | ALD_CC-10 | ASN_CC_09 | No. 6 |
| IND_CC-691 | ALD_CC-34 | ASN_CC_09 | No. 6 |
| IND_CC-692 | ALD_CC-35 | ASN_CC_09 | No. 6 |
| IND_CC-693 | ALD_CC-32 | ASN_CC_10 | No. 6 |
| IND_CC-694 | ALD_CC-30 | ASN_CC_10 | No. 6 |
| IND_CC-695 | ALD_CC-19 | ASN_CC_10 | No. 6 |
| IND_CC-696 | ALD_CC-20 | ASN_CC_10 | No. 6 |
| IND_CC-697 | ALD_CC-24 | ASN_CC_10 | No. 6 |
| IND_CC-698 | ALD_CC-26 | ASN_CC_10 | No. 6 |
| IND_CC-699 | ALD_CC-09 | ASN_CC_10 | No. 6 |
| IND_CC-700 | ALD_CC-06 | ASN_CC_10 | No. 6 |
| IND_CC-701 | ALD_CC-10 | ASN_CC_10 | No. 6 |
| IND_CC-702 | ALD_CC-34 | ASN_CC_10 | No. 6 |
| IND_CC-703 | ALD_CC-35 | ASN_CC_10 | No. 6 |
| IND_CC-704 | ICN_CC-10 | ASN_CC_06 | No. 4 |
| IND_CC-705 | ICN_CC-03 | ASN_CC_06 | No. 4 |
| IND_CC-706 | ICN_CC-12 | ASN_CC_06 | No. 4 |
| IND_CC-707 | ICN_CC-04 | ASN_CC_06 | No. 4 |
| IND_CC-708 | ICN_CC-11 | ASN_CC_06 | No. 4 |
| IND_CC-709 | ICN_CC-06 | ASN_CC_06 | No. 4 |
| IND_CC-710 | ICN_CC-07 | ASN_CC_06 | No. 4 |
| IND_CC-711 | ICN_CC-05 | ASN_CC_06 | No. 4 |
| IND_CC-712 | ICN_CC-10 | ASN_CC_03 | No. 4 |
| IND_CC-713 | ICN_CC-09 | ASN_CC_03 | No. 4 |
| IND_CC-714 | ICN_CC-08 | ASN_CC_03 | No. 4 |
| IND_CC-715 | ICN_CC-03 | ASN_CC_03 | No. 4 |
| IND_CC-716 | ICN_CC-12 | ASN_CC_03 | No. 4 |
| IND_CC-717 | ICN_CC-11 | ASN_CC_03 | No. 4 |
| IND_CC-718 | ICN_CC-06 | ASN_CC_03 | No. 4 |
| IND_CC-719 | ICN_CC-05 | ASN_CC_03 | No. 4 |
| IND_CC-720 | ICN_CC-14 | ASN_CC_03 | No. 4 |
| IND_CC-721 | ICN_CC-13 | ASN_CC_03 | No. 4 |
| IND_CC-722 | ALD_CC-31 | ASN_CC_11 | No. 6 |
| IND_CC-723 | ALD_CC-17 | ASN_CC_11 | No. 6 |
| IND_CC-724 | ALD_CC-23 | ASN_CC_11 | No. 6 |
| IND_CC-725 | ALD_CC-04 | ASN_CC_11 | No. 6 |
| IND_CC-726 | ALD_CC-03 | ASN_CC_12 | No. 6 |
| IND_CC-727 | ALD_CC-04 | ASN_CC_12 | No. 6 |
| IND_CC-728 | ALD_CC-33 | ASN_CC_13 | No. 6 |
| IND_CC-729 | ALD_CC-31 | ASN_CC_13 | No. 6 |
| IND_CC-730 | ALD_CC-17 | ASN_CC_13 | No. 6 |
| IND_CC-731 | ALD_CC-08 | ASN_CC_13 | No. 6 |
| IND_CC-732 | ALD_CC-21 | ASN_CC_13 | No. 6 |
| IND_CC-733 | ALD_CC-23 | ASN_CC_13 | No. 6 |
| IND_CC-734 | ALD_CC-03 | ASN_CC_13 | No. 6 |
| IND_CC-735 | ALD_CC-04 | ASN_CC_13 | No. 6 |
| IND_CC-736 | ALD_CC-33 | ASN_CC_14 | No. 6 |
| IND_CC-737 | ALD_CC-31 | ASN_CC_14 | No. 6 |
| IND_CC-738 | ALD_CC-17 | ASN_CC_14 | No. 6 |
| IND_CC-739 | ALD_CC-08 | ASN_CC_14 | No. 6 |
| IND_CC-740 | ALD_CC-23 | ASN_CC_14 | No. 6 |
| IND_CC-741 | ALD_CC-03 | ASN_CC_14 | No. 6 |
| IND_CC-742 | ALD_CC-32 | ASN_CC_11 | No. 6 |
| IND_CC-743 | ALD_CC-30 | ASN_CC_11 | No. 6 |
| IND_CC-744 | ALD_CC-19 | ASN_CC_11 | No. 6 |
| IND_CC-745 | ALD_CC-20 | ASN_CC_11 | No. 6 |
| IND_CC-746 | ALD_CC-24 | ASN_CC_11 | No. 6 |
| IND_CC-747 | ALD_CC-26 | ASN_CC_11 | No. 6 |
| IND_CC-748 | ALD_CC-09 | ASN_CC_11 | No. 6 |
| IND_CC-749 | ALD_CC-10 | ASN_CC_11 | No. 6 |
| IND_CC-750 | ALD_CC-34 | ASN_CC_11 | No. 6 |
| IND_CC-751 | ALD_CC-35 | ASN_CC_11 | No. 6 |
| IND_CC-752 | ALD_CC-32 | ASN_CC_12 | No. 6 |
| IND_CC-753 | ALD_CC-30 | ASN_CC_12 | No. 6 |
| IND_CC-754 | ALD_CC-19 | ASN_CC_12 | No. 6 |
| IND_CC-755 | ALD_CC-20 | ASN_CC_12 | No. 6 |
| IND_CC-756 | ALD_CC-24 | ASN_CC_12 | No. 6 |
| IND_CC-757 | ALD_CC-26 | ASN_CC_12 | No. 6 |
| IND_CC-758 | ALD_CC-10 | ASN_CC_12 | No. 6 |
| IND_CC-759 | ALD_CC-34 | ASN_CC_12 | No. 6 |
| IND_CC-760 | ALD_CC-35 | ASN_CC_12 | No. 6 |
| IND_CC-761 | ALD_CC-16 | ASN_CC_13 | No. 6 |
| IND_CC-762 | ALD_CC-32 | ASN_CC_13 | No. 6 |
| IND_CC-763 | ALD_CC-30 | ASN_CC_13 | No. 6 |
| IND_CC-764 | ALD_CC-19 | ASN_CC_13 | No. 6 |
| IND_CC-765 | ALD_CC-20 | ASN_CC_13 | No. 6 |
| IND_CC-766 | ALD_CC-24 | ASN_CC_13 | No. 6 |
| IND_CC-767 | ALD_CC-26 | ASN_CC_13 | No. 6 |
| IND_CC-768 | ALD_CC-09 | ASN_CC_13 | No. 6 |
| IND_CC-769 | ALD_CC-10 | ASN_CC_13 | No. 6 |
| IND_CC-770 | ALD_CC-34 | ASN_CC_13 | No. 6 |
| IND_CC-771 | ALD_CC-35 | ASN_CC_13 | No. 6 |
| IND_CC-772 | ALD_CC-32 | ASN_CC_14 | No. 6 |
| IND_CC-773 | ALD_CC-30 | ASN_CC_14 | No. 6 |
| IND_CC-774 | ALD_CC-19 | ASN_CC_14 | No. 6 |
| IND_CC-775 | ALD_CC-20 | ASN_CC_14 | No. 6 |
| IND_CC-776 | ALD_CC-24 | ASN_CC_14 | No. 6 |
| IND_CC-777 | ALD_CC-26 | ASN_CC_14 | No. 6 |
| IND_CC-778 | ALD_CC-09 | ASN_CC_14 | No. 6 |
| IND_CC-779 | ALD_CC-06 | ASN_CC_14 | No. 6 |
| IND_CC-780 | ALD_CC-10 | ASN_CC_14 | No. 6 |
| IND_CC-781 | ALD_CC-34 | ASN_CC_14 | No. 6 |
| IND_CC-782 | ALD_CC-35 | ASN_CC_14 | No. 6 |
| IND_CC-783 | ALD_CC-29 | ASN_CC_15 | No. 6 |
| IND_CC-784 | ALD_CC-01 | ASN_CC_15 | No. 6 |
| IND_CC-785 | ALD_CC-02 | ASN_CC_15 | No. 6 |
| IND_CC-786 | ALD_CC-07 | ASN_CC_15 | No. 6 |
| IND_CC-787 | ALD_CC-05 | ASN_CC_15 | No. 6 |
| IND_CC-788 | ALD_CC-12 | ASN_CC_15 | No. 6 |
| IND_CC-789 | ALD_CC-13 | ASN_CC_15 | No. 6 |
| IND_CC-790 | ALD_CC-14 | ASN_CC_15 | No. 6 |
| IND_CC-791 | ALD_CC-22 | ASN_CC_15 | No. 6 |
| IND_CC-792 | ALD_CC-11 | ASN_CC_15 | No. 6 |
| IND_CC-793 | ALD_CC-15 | ASN_CC_15 | No. 6 |
| IND_CC-794 | ALD_CC-11 | ASN_CC_18 | No. 6 |
| IND_CC-795 | ALD_CC-15 | ASN_CC_18 | No. 6 |
| IND_CC-796 | ALD_CC-25 | ASN_CC_15 | No. 6 |
| IND_CC-797 | ALD_CC-18 | ASN_CC_15 | No. 6 |
| IND_CC-798 | ALD_CC-31 | ASN_CC_15 | No. 6 |
| IND_CC-799 | ALD_CC-17 | ASN_CC_15 | No. 6 |
| IND_CC-800 | ALD_CC-21 | ASN_CC_15 | No. 6 |
| IND_CC-801 | ALD_CC-23 | ASN_CC_15 | No. 6 |
| IND_CC-802 | ALD_CC-03 | ASN_CC_15 | No. 6 |
| IND_CC-803 | ALD_CC-04 | ASN_CC_15 | No. 6 |
| IND_CC-804 | ALD_CC-19 | ASN_CC_20 | No. 6 |

-continued

| Example no. | ACI_CC, SCI_CC, ICN_CC or ALD_CC | Amine (ASN_CC) | Method no. |
|---|---|---|---|
| IND_CC-805 | ALD_CC-20 | ASN_CC_20 | No. 6 |
| IND_CC-806 | ALD_CC-09 | ASN_CC_20 | No. 6 |
| IND_CC-807 | ALD_CC-06 | ASN_CC_20 | No. 6 |

Analytical Data:

| Example no. | [M+] found | R.t. [min] |
|---|---|---|
| IND_CC-500 | 614.3 | 0.74 |
| IND_CC-501 | 603.3 | 0.71 |
| IND_CC-502 | 609.4 | 0.74 |
| IND_CC-503 | 582.3 | 0.68 |
| IND_CC-504 | 564.3 | 0.51 |
| IND_CC-505 | 567.4 | 0.53 |
| IND_CC-506 | 594.4 | 0.51 |
| IND_CC-507 | 531.4 | 0.50 |
| IND_CC-508 | 532.4 | 0.41 |
| IND_CC-509 | 543.4 | 0.49 |
| IND_CC-510 | 543.4 | 0.44 |
| IND_CC-511 | 543.4 | 0.46 |
| IND_CC-512 | 545.4 | 0.52 |
| IND_CC-513 | 578.4 | 0.52 |
| IND_CC-514 | 578.4 | 0.54 |
| IND_CC-515 | 578.3 | 0.53 |
| IND_CC-516 | 578.3 | 0.53 |
| IND_CC-517 | 590.4 | 0.54 |
| IND_CC-518 | 569.4 | 0.52 |
| IND_CC-519 | 571.4 | 0.57 |
| IND_CC-520 | 604.4 | 0.57 |
| IND_CC-521 | 604.4 | 0.59 |
| IND_CC-522 | 604.4 | 0.57 |
| IND_CC-523 | 604.4 | 0.58 |
| IND_CC-524 | 616.4 | 0.59 |
| IND_CC-525 | 616.4 | 0.59 |
| IND_CC-526 | 546.4 | 0.38 |
| IND_CC-527 | 546.4 | 0.39 |
| IND_CC-528 | 546.4 | 0.38 |
| IND_CC-529 | 594.3 | 0.54 |
| IND_CC-530 | 594.3 | 0.53 |
| IND_CC-531 | 560.4 | 0.48 |
| IND_CC-532 | 561.4 | 0.49 |
| IND_CC-533 | 567.3 | 0.52 |
| IND_CC-534 | 567.4 | 0.51 |
| IND_CC-535 | 567.4 | 0.51 |
| IND_CC-536 | 572.4 | 0.45 |
| IND_CC-537 | 620.4 | 0.59 |
| IND_CC-538 | 620.4 | 0.58 |
| IND_CC-539 | 593.4 | 0.56 |
| IND_CC-540 | 593.4 | 0.56 |
| IND_CC-541 | 593.4 | 0.56 |
| IND_CC-542 | 564.4 | 0.53 |
| IND_CC-543 | 564.3 | 0.51 |
| IND_CC-544 | 564.3 | 0.51 |
| IND_CC-545 | 576.4 | 0.52 |
| IND_CC-546 | 576.4 | 0.53 |
| IND_CC-547 | 570.3 | 0.53 |
| IND_CC-548 | 582.3 | 0.54 |
| IND_CC-549 | 578.4 | 0.55 |
| IND_CC-550 | 578.4 | 0.54 |
| IND_CC-551 | 578.4 | 0.54 |
| IND_CC-552 | 590.4 | 0.54 |
| IND_CC-553 | 532.4 | 0.39 |
| IND_CC-554 | 532.4 | 0.37 |
| IND_CC-555 | 536.3 | 0.46 |
| IND_CC-556 | 580.3 | 0.59 |
| IND_CC-557 | 580.3 | 0.52 |
| IND_CC-558 | 594.3 | 0.54 |
| IND_CC-559 | 546.4 | 0.46 |
| IND_CC-560 | 547.3 | 0.47 |
| IND_CC-561 | 553.3 | 0.49 |
| IND_CC-562 | 553.3 | 0.49 |
| IND_CC-563 | 553.3 | 0.50 |
| IND_CC-564 | 560.4 | 0.47 |
| IND_CC-565 | 560.4 | 0.48 |
| IND_CC-566 | 573.4 | 0.49 |
| IND_CC-567 | 579.3 | 0.47 |
| IND_CC-568 | 580.4 | 0.47 |
| IND_CC-569 | 559.3 | 0.52 |
| IND_CC-570 | 585.3 | 0.49 |
| IND_CC-571 | 586.3 | 0.50 |
| IND_CC-572 | 567.4 | 0.52 |
| IND_CC-573 | 506.3 | 0.68 |
| IND_CC-574 | 536.4 | 0.72 |
| IND_CC-575 | 594.3 | 0.72 |
| IND_CC-576 | 578.3 | 0.70 |
| IND_CC-577 | 590.3 | 0.74 |
| IND_CC-578 | 602.4 | 0.73 |
| IND_CC-579 | 602.4 | 0.73 |
| IND_CC-580 | 626.5 | 0.74 |
| IND_CC-581 | 626.5 | 0.74 |
| IND_CC-582 | 512.3 | 0.68 |
| IND_CC-583 | 542.3 | 0.75 |
| IND_CC-584 | 600.2 | 0.75 |
| IND_CC-585 | 584.3 | 0.73 |
| IND_CC-586 | 596.3 | 0.77 |
| IND_CC-587 | 608.4 | 0.76 |
| IND_CC-588 | 608.4 | 0.76 |
| IND_CC-589 | 520.3 | 0.69 |
| IND_CC-590 | 550.4 | 0.75 |
| IND_CC-591 | 608.3 | 0.75 |
| IND_CC-592 | 604.4 | 0.77 |
| IND_CC-593 | 616.4 | 0.76 |
| IND_CC-594 | 558.4 | 0.63 |
| IND_CC-595 | 603.4 | 0.70 |
| IND_CC-596 | 581.3 | 0.69 |
| IND_CC-597 | 520.4 | 0.67 |
| IND_CC-598 | 550.4 | 0.74 |
| IND_CC-599 | 608.3 | 0.74 |
| IND_CC-600 | 592.3 | 0.73 |
| IND_CC-601 | 616.4 | 0.75 |
| IND_CC-602 | 616.4 | 0.75 |
| IND_CC-603 | 546.3 | 0.72 |
| IND_CC-604 | 576.4 | 0.78 |
| IND_CC-605 | 634.3 | 0.79 |
| IND_CC-606 | 618.4 | 0.77 |
| IND_CC-607 | 642.4 | 0.80 |
| IND_CC-608 | 632.2 | 0.80 |
| IND_CC-609 | 628.3 | 0.77 |
| IND_CC-610 | 635.3 | 0.76 |
| IND_CC-611 | 617.3 | 0.74 |
| IND_CC-612 | 645.4 | 0.76 |
| IND_CC-613 | 558.3 | 0.71 |
| IND_CC-614 | 645.4 | 0.76 |
| IND_CC-615 | 658.3 | 0.84 |
| IND_CC-616 | 654.3 | 0.81 |
| IND_CC-617 | 661.3 | 0.80 |
| IND_CC-618 | 643.3 | 0.78 |
| IND_CC-619 | 671.4 | 0.80 |
| IND_CC-620 | 535.4 | 0.52 |
| IND_CC-621 | 582.3 | 0.57 |
| IND_CC-622 | 582.3 | 0.57 |
| IND_CC-623 | 594.4 | 0.57 |
| IND_CC-624 | 549.3 | 0.54 |
| IND_CC-625 | 550.3 | 0.45 |
| IND_CC-626 | 561.4 | 0.53 |
| IND_CC-627 | 561.4 | 0.49 |
| IND_CC-628 | 596.4 | 0.58 |
| IND_CC-629 | 596.3 | 0.57 |
| IND_CC-630 | 608.4 | 0.58 |
| IND_CC-631 | 586.3 | 0.48 |
| IND_CC-632 | 632.3 | 0.57 |
| IND_CC-633 | 632.3 | 0.60 |
| IND_CC-634 | 632.3 | 0.59 |
| IND_CC-635 | 632.3 | 0.60 |
| IND_CC-636 | 644.4 | 0.59 |
| IND_CC-637 | 644.4 | 0.60 |
| IND_CC-638 | 599.4 | 0.57 |
| IND_CC-639 | 600.4 | 0.48 |
| IND_CC-640 | 611.4 | 0.56 |
| IND_CC-641 | 611.4 | 0.52 |
| IND_CC-642 | 611.4 | 0.53 |

| Example no. | [M+] found | R.t. [min] |
|---|---|---|
| IND_CC-643 | 613.4 | 0.58 |
| IND_CC-644 | 646.4 | 0.59 |
| IND_CC-645 | 646.4 | 0.60 |
| IND_CC-646 | 646.4 | 0.59 |
| IND_CC-647 | 646.4 | 0.59 |
| IND_CC-648 | 658.4 | 0.60 |
| IND_CC-649 | 658.4 | 0.61 |
| IND_CC-650 | 571.3 | 0.55 |
| IND_CC-651 | 571.3 | 0.55 |
| IND_CC-652 | 568.3 | 0.53 |
| IND_CC-653 | 585.3 | 0.55 |
| IND_CC-654 | 585.3 | 0.56 |
| IND_CC-655 | 600.4 | 0.46 |
| IND_CC-656 | 604.3 | 0.54 |
| IND_CC-657 | 615.3 | 0.55 |
| IND_CC-658 | 621.4 | 0.56 |
| IND_CC-659 | 621.4 | 0.57 |
| IND_CC-660 | 621.3 | 0.58 |
| IND_CC-661 | 614.4 | 0.48 |
| IND_CC-662 | 614.2 | 0.46 |
| IND_CC-663 | 618.3 | 0.56 |
| IND_CC-664 | 628.3 | 0.56 |
| IND_CC-665 | 629.3 | 0.57 |
| IND_CC-666 | 635.3 | 0.58 |
| IND_CC-667 | 635.3 | 0.59 |
| IND_CC-668 | 635.3 | 0.59 |
| IND_CC-669 | 662.3 | 0.62 |
| IND_CC-670 | 662.3 | 0.60 |
| IND_CC-671 | 597.3 | 0.52 |
| IND_CC-672 | 598.3 | 0.53 |
| IND_CC-673 | 601.3 | 0.54 |
| IND_CC-674 | 529.3 | 0.61 |
| IND_CC-675 | 592.3 | 0.61 |
| IND_CC-676 | 605.3 | 0.56 |
| IND_CC-677 | 611.3 | 0.53 |
| IND_CC-678 | 612.3 | 0.55 |
| IND_CC-679 | 615.3 | 0.55 |
| IND_CC-680 | 526.3 | 0.56 |
| IND_CC-681 | 574.3 | 0.60 |
| IND_CC-682 | 628.3 | 0.55 |
| IND_CC-683 | 641.4 | 0.57 |
| IND_CC-684 | 647.3 | 0.55 |
| IND_CC-685 | 648.3 | 0.56 |
| IND_CC-686 | 651.3 | 0.55 |
| IND_CC-687 | 562.3 | 0.56 |
| IND_CC-688 | 590.3 | 0.60 |
| IND_CC-689 | 602.4 | 0.62 |
| IND_CC-690 | 610.3 | 0.60 |
| IND_CC-691 | 642.3 | 0.61 |
| IND_CC-692 | 642.3 | 0.61 |
| IND_CC-693 | 642.4 | 0.56 |
| IND_CC-694 | 655.4 | 0.57 |
| IND_CC-695 | 661.4 | 0.55 |
| IND_CC-696 | 662.4 | 0.56 |
| IND_CC-697 | 656.4 | 0.56 |
| IND_CC-698 | 576.3 | 0.57 |
| IND_CC-699 | 604.4 | 0.61 |
| IND_CC-700 | 616.4 | 0.63 |
| IND_CC-701 | 624.4 | 0.61 |
| IND_CC-702 | 656.4 | 0.63 |
| IND_CC-703 | 656.4 | 0.63 |
| IND_CC-704 | 537.3 | 0.67 |
| IND_CC-705 | 596.3 | 0.71 |
| IND_CC-706 | 585.3 | 0.71 |
| IND_CC-707 | 614.4 | 0.55 |
| IND_CC-708 | 577.4 | 0.73 |
| IND_CC-709 | 639.2 | 0.73 |
| IND_CC-710 | 639.2 | 0.80 |
| IND_CC-711 | 607.3 | 0.72 |
| IND_CC-712 | 563.3 | 0.72 |
| IND_CC-713 | 649.3 | 0.81 |
| IND_CC-714 | 699.3 | 0.83 |
| IND_CC-715 | 622.3 | 0.75 |
| IND_CC-716 | 611.4 | 0.76 |
| IND_CC-717 | 603.4 | 0.78 |
| IND_CC-718 | 665.3 | 0.78 |
| IND_CC-719 | 633.3 | 0.77 |
| IND_CC-720 | 633.4 | 0.80 |
| IND_CC-721 | 679.3 | 0.82 |
| IND_CC-722 | 580.3 | 0.52 |
| IND_CC-723 | 581.2 | 0.54 |
| IND_CC-724 | 587.3 | 0.56 |
| IND_CC-725 | 614.3 | 0.58 |
| IND_CC-726 | 628.3 | 0.60 |
| IND_CC-727 | 628.3 | 0.59 |
| IND_CC-728 | 546.3 | 0.41 |
| IND_CC-729 | 560.4 | 0.50 |
| IND_CC-730 | 561.3 | 0.52 |
| IND_CC-731 | 567.3 | 0.53 |
| IND_CC-732 | 567.3 | 0.54 |
| IND_CC-733 | 567.3 | 0.54 |
| IND_CC-734 | 594.3 | 0.57 |
| IND_CC-735 | 594.3 | 0.56 |
| IND_CC-736 | 550.2 | 0.40 |
| IND_CC-737 | 564.3 | 0.49 |
| IND_CC-738 | 565.3 | 0.50 |
| IND_CC-739 | 571.3 | 0.52 |
| IND_CC-740 | 571.3 | 0.54 |
| IND_CC-741 | 577.3 | 0.57 |
| IND_CC-742 | 594.3 | 0.53 |
| IND_CC-743 | 607.3 | 0.54 |
| IND_CC-744 | 613.3 | 0.51 |
| IND_CC-745 | 614.3 | 0.53 |
| IND_CC-746 | 617.3 | 0.53 |
| IND_CC-747 | 528.3 | 0.54 |
| IND_CC-748 | 556.3 | 0.59 |
| IND_CC-749 | 576.3 | 0.58 |
| IND_CC-750 | 608.3 | 0.60 |
| IND_CC-751 | 608.3 | 0.60 |
| IND_CC-752 | 608.3 | 0.54 |
| IND_CC-753 | 621.3 | 0.56 |
| IND_CC-754 | 627.3 | 0.52 |
| IND_CC-755 | 628.3 | 0.54 |
| IND_CC-756 | 631.4 | 0.54 |
| IND_CC-757 | 542.3 | 0.55 |
| IND_CC-758 | 590.3 | 0.59 |
| IND_CC-759 | 622.3 | 0.61 |
| IND_CC-760 | 622.3 | 0.61 |
| IND_CC-761 | 574.3 | 0.51 |
| IND_CC-762 | 574.4 | 0.52 |
| IND_CC-763 | 587.3 | 0.53 |
| IND_CC-764 | 593.4 | 0.50 |
| IND_CC-765 | 594.4 | 0.51 |
| IND_CC-766 | 597.4 | 0.52 |
| IND_CC-767 | 508.3 | 0.52 |
| IND_CC-768 | 536.4 | 0.57 |
| IND_CC-769 | 556.4 | 0.57 |
| IND_CC-770 | 588.4 | 0.59 |
| IND_CC-771 | 588.4 | 0.59 |
| IND_CC-772 | 578.4 | 0.51 |
| IND_CC-773 | 591.4 | 0.51 |
| IND_CC-774 | 597.4 | 0.48 |
| IND_CC-775 | 598.3 | 0.50 |
| IND_CC-776 | 601.3 | 0.51 |
| IND_CC-777 | 512.3 | 0.51 |
| IND_CC-778 | 540.3 | 0.56 |
| IND_CC-779 | 552.4 | 0.57 |
| IND_CC-780 | 560.3 | 0.56 |
| IND_CC-781 | 592.4 | 0.58 |
| IND_CC-782 | 592.3 | 0.58 |
| IND_CC-783 | 549.3 | 0.52 |
| IND_CC-784 | 561.3 | 0.51 |
| IND_CC-785 | 561.3 | 0.46 |
| IND_CC-786 | 561.3 | 0.47 |
| IND_CC-787 | 563.2 | 0.52 |
| IND_CC-788 | 596.2 | 0.53 |
| IND_CC-789 | 596.2 | 0.55 |
| IND_CC-790 | 596.2 | 0.54 |
| IND_CC-791 | 596.2 | 0.54 |
| IND_CC-792 | 608.2 | 0.55 |
| IND_CC-793 | 608.2 | 0.56 |
| IND_CC-794 | 641.2 | 0.57 |
| IND_CC-795 | 641.2 | 0.58 |
| IND_CC-796 | 564.2 | 0.38 |
| IND_CC-797 | 568.2 | 0.48 |
| IND_CC-798 | 578.2 | 0.48 |

| Example no. | [M+] found | R.t. [min] |
|---|---|---|
| IND_CC-799 | 579.2 | 0.49 |
| IND_CC-800 | 585.2 | 0.51 |
| IND_CC-801 | 585.2 | 0.52 |
| IND_CC-802 | 612.1 | 0.55 |
| IND_CC-803 | 612.1 | 0.55 |
| IND_CC-804 | 593.2 | 0.48 |
| IND_CC-805 | 594.2 | 0.50 |
| IND_CC-806 | 536.2 | 0.56 |
| IND_CC-807 | 548.2 | 0.58 |

Pharmacological Data

The pharmacological data were determined as described above. The following data are given in the table below by way of example:

| Example no. | % Inhibition (rat B1R) at 10 μM | % Inhibition (human B1R) at 10 μM |
|---|---|---|
| H-01 | 97 | 100 |
| H-02 | 100 | 100 |
| H-03 | 104 | 98 |
| H-04 | 106 | 100 |
| H-05 | 105 | 100 |
| H-06 | 98 | 60 |
| H-07 | 69 | 34 |
| H-08 | 100 | 71 |
| H-09 | 102 | 100 |
| H-10 | 103 | 49 |
| H-11 | 103 | 99 |
| H-12 | 102 | 97 |
| H-13 | 101 | 100 |
| H-14 | 101 | 91 |
| H-15 | 11 | 59 |
| H-16 | 102 | 100 |
| H-17 | 102 | 98 |
| H-18 | 104 | 96 |
| H-19 | 102 | 99 |
| H-20 | 105 | 100 |
| H-21 | 105 | 100 |
| H-26 | 101 | 46 |
| H-27 | 102 | 100 |
| H-28 | 102 | 57 |
| H-29 | 55 | 33 |
| H-47 | 101 | 99 |
| H-48 | 97 | 63 |
| H-49 | 100 | 99 |
| H-50 | 98 | 98 |
| H-51 | 96 | 98 |
| Ind_CC-001 | 98 | 99 |
| Ind_CC-002 | 85 | 97 |
| Ind_CC-003 | 101 | 99 |
| Ind_CC-004 | 98 | 99 |
| Ind_CC-005 | 98 | 97 |
| Ind_CC-006 | 98 | 98 |
| Ind_CC-007 | 102 | 99 |
| Ind_CC-008 | 74 | 72 |
| Ind_CC-009 | 99 | 87 |
| Ind_CC-010 | 100 | 97 |
| Ind_CC-011 | 76 | 36 |
| Ind_CC-012 | 100 | 100 |
| Ind_CC-013 | 71 | 68 |
| Ind_CC-014 | 101 | 93 |
| Ind_CC-015 | 101 | 100 |
| Ind_CC-016 | 102 | 100 |
| Ind_CC-017 | 102 | 99 |
| Ind_CC-018 | 98 | 98 |
| Ind_CC-019 | 95 | 99 |
| Ind_CC-020 | 88 | 89 |
| Ind_CC-021 | 96 | 94 |
| Ind_CC-022 | 75 | 91 |
| Ind_CC-023 | 93 | 98 |
| Ind_CC-042 | 101 | 98 |
| Ind_CC-043 | 88 | 79 |
| Ind_CC-044 | 100 | 97 |
| Ind_CC-045 | 101 | 100 |
| Ind_CC-046 | 68 | 98 |
| Ind_CC-047 | 60 | 94 |
| Ind_CC-048 | 88 | 98 |
| Ind_CC-049 | 101 | 99 |
| Ind_CC-050 | 93 | 100 |
| Ind_CC-051 | 99 | 71 |
| Ind_CC-052 | 81 | 62 |
| Ind_CC-053 | 103 | 99 |
| Ind_CC-054 | 102 | 96 |
| Ind_CC-055 | 102 | 99 |
| Ind_CC-056 | 94 | 41 |
| Ind_CC-057 | 80 | 35 |
| Ind_CC-058 | 101 | 100 |
| Ind_CC-059 | 102 | 100 |
| Ind_CC-060 | 94 | 93 |
| Ind_CC-061 | 103 | 100 |
| Ind_CC-062 | 104 | |
| Ind_CC-064 | 101 | 95 |
| Ind_CC-065 | 98 | 94 |
| Ind_CC-066 | 98 | 82 |
| Ind_CC-067 | 101 | 94 |
| Ind_CC-081 | 101 | 99 |
| Ind_CC-082 | 101 | 100 |
| Ind_CC-083 | 85 | 90 |
| Ind_CC-084 | 100 | 99 |
| Ind_CC-085 | 77 | 91 |
| Ind_CC-086 | 99 | 100 |
| Ind_CC-087 | 100 | |
| Ind_CC-088 | 93 | |
| Ind_CC-089 | 100 | |
| Ind_CC-090 | 100 | 42 |
| Ind_CC-091 | 50 | 24 |
| Ind_CC-092 | 101 | 78 |
| Ind_CC-093 | 74 | 34 |
| Ind_CC-094 | 65 | 42 |
| Ind_CC-095 | 99 | 99 |
| Ind_CC-096 | 101 | 91 |
| Ind_CC-097 | 90 | 33 |
| Ind_CC-098 | 98 | 34 |
| Ind_CC-099 | 103 | 39 |
| Ind_CC-100 | 104 | 100 |
| Ind_CC-101 | 102 | 100 |
| Ind_CC-102 | 100 | 87 |
| Ind_CC-103 | 62 | 93 |
| Ind_CC-104 | 102 | 33 |
| Ind_CC-105 | 86 | 61 |
| Ind_CC-106 | 100 | 100 |
| Ind_CC-107 | 100 | 78 |
| Ind_CC-108 | 51 | 23 |
| Ind_CC-109 | 29 | 33 |
| Ind_CC-110 | 79 | 52 |
| Ind_CC-111 | 101 | 100 |
| Ind_CC-112 | 104 | 100 |
| Ind_CC-113 | 100 | 98 |
| Ind_CC-114 | 101 | 99 |
| Ind_CC-115 | 64 | 22 |
| Ind_CC-116 | 77 | 68 |
| Ind_CC-117 | 77 | 56 |
| Ind_CC-118 | 103 | 100 |
| Ind_CC-119 | 104 | 99 |
| Ind_CC-120 | 99 | 56 |
| Ind_CC-121 | 103 | 46 |
| H-52 | 46 | 28 |
| H-53 | 104 | 100 |
| H-54 | 102 | 98 |
| H-55 | 87 | 42 |
| H-56 | 68 | 94 |
| H-57 | 105 | 99 |
| H-58 | 106 | 99 |
| H-59 | 105 | 99 |
| H-60 | 101 | 82 |

| Example no. | % Inhibition (rat B1R) at 10 μM | % Inhibition (human B1R) at 10 μM | Example no. | % Inhibition (rat B1R) at 10 μM | % Inhibition (human B1R) at 10 μM |
|---|---|---|---|---|---|
| H-61 | 104 | 100 | H-143 | 105 | 100 |
| H-62 | 102 | 30 | H-144 | 104 | 99 |
| H-63 | 104 | 100 | H-145 | 101 | 100 |
| H-64 | 105 | 100 | H-146 | 102 | 100 |
| H-65 | 105 | 100 | H-147 | 104 | 100 |
| H-66 | 102 | 99 | H-148 | 101 | 100 |
| H-67 | 102 | 100 | H-149 | 103 | 100 |
| H-68 | 93 | 96 | H-150 | 100 | 97 |
| H-69 | 102 | 98 | H-151 | 103 | 99 |
| H-70 | 103 | 90 | H-152 | 101 | 99 |
| H-71 | 103 | 100 | H-153 | 105 | 99 |
| H-72 | 104 | 100 | H-154 | 105 | 99 |
| H-73 | 103 | 100 | H-155 | 100 | 87 |
| H-74 | 100 | 94 | H-156 | 75 | 24 |
| H-75 | 64 | 29 | H-157 | 98 | 100 |
| H-76 | 102 | 100 | H-158 | 100 | 92 |
| H-77 | 104 | 96 | H-159 | 103 | 98 |
| H-78 | 104 | 100 | H-160 | 105 | 98 |
| H-79 | 104 | 100 | H-161 | 104 | 89 |
| H-80 | 105 | 57 | H-162 | 61 | 13 |
| H-81 | 103 | 78 | H-163 | 105 | 63 |
| H-82 | 104 | 100 | H-164 | 77 | 25 |
| H-83 | 105 | 100 | H-165 | 44 | 44 |
| H-84 | 104 | 100 | H-166 | −4 | 21 |
| H-85 | 103 | 100 | H-167 | 81 | 35 |
| H-86 | 79 | 95 | H-168 | 55 | 96 |
| H-87 | 103 | 99 | H-169 | 12 | 54 |
| H-88 | 104 | 100 | H-170 | 47 | 56 |
| H-89 | 103 | 99 | H-171 | 104 | 100 |
| H-90 | 103 | 100 | H-172 | 105 | 99 |
| H-91 | 104 | 100 | H-173 | 89 | 100 |
| H-92 | 104 | 96 | IND_CC-200 | 102 | 100 |
| H-93 | 103 | 100 | IND_CC-201 | 99 | |
| H-94 | 98 | 100 | IND_CC-202 | 103 | 86 |
| H-95 | 98 | 100 | IND_CC-203 | 103 | 99 |
| H-96 | 104 | 100 | IND_CC-204 | 102 | 99 |
| H-97 | 90 | 6 | IND_CC-205 | 103 | 100 |
| H-98 | 108 | 100 | IND_CC-206 | 103 | 100 |
| H-99 | 105 | 100 | IND_CC-207 | 101 | 98 |
| H-100 | 108 | 100 | IND_CC-208 | 100 | 99 |
| H-101 | 107 | 97 | IND_CC-209 | 102 | 20 |
| H-102 | 109 | 100 | IND_CC-210 | 104 | 97 |
| H-103 | 106 | 99 | IND_CC-211 | 104 | |
| H-104 | 109 | 101 | IND_CC-212 | 102 | 58 |
| H-105 | 107 | 100 | IND_CC-213 | 73 | |
| H-106 | 105 | 100 | IND_CC-214 | 102 | 83 |
| H-107 | 108 | 72 | IND_CC-215 | 103 | 48 |
| H-108 | 111 | 100 | IND_CC-216 | 103 | 58 |
| H-109 | 109 | 100 | IND_CC-217 | 95 | 99 |
| H-110 | 108 | 101 | IND_CC-218 | 103 | 94 |
| H-111 | 102 | 100 | IND_CC-219 | 104 | 53 |
| H-112 | 102 | 100 | IND_CC-220 | 104 | 100 |
| H-113 | 92 | 99 | IND_CC-221 | 104 | 100 |
| H-114 | 102 | 100 | IND_CC-222 | 60 | |
| H-115 | 101 | 100 | IND_CC-223 | 105 | 97 |
| H-116 | 101 | 100 | IND_CC-224 | 103 | 100 |
| H-117 | 101 | 100 | IND_CC-225 | 103 | 71 |
| H-118 | 101 | 100 | IND_CC-226 | 101 | 98 |
| H-119 | 100 | 100 | IND_CC-227 | 97 | |
| H-120 | 104 | 65 | IND_CC-228 | 104 | 100 |
| H-128 | 36 | 38 | IND_CC-229 | 102 | 100 |
| H-129 | 102 | 100 | IND_CC-230 | 104 | |
| H-130 | 99 | 94 | IND_CC-231 | 102 | 100 |
| H-131 | 102 | 74 | IND_CC-232 | 101 | 96 |
| H-132 | 102 | 100 | IND_CC-233 | 98 | 86 |
| H-133 | 100 | 65 | IND_CC-234 | 99 | 85 |
| H-134 | 103 | 99 | IND_CC-235 | 89 | |
| H-135 | 101 | 80 | IND_CC-236 | 96 | 98 |
| H-136 | 101 | 99 | IND_CC-237 | 98 | 100 |
| H-137 | 103 | 99 | IND_CC-238 | 100 | 99 |
| H-138 | 102 | 100 | IND_CC-239 | 71 | |
| H-139 | 98 | 31 | IND_CC-240 | 99 | 95 |
| H-140 | 100 | 70 | IND_CC-241 | 101 | 95 |
| H-141 | 101 | 99 | IND_CC-242 | 101 | 94 |
| H-142 | 103 | 98 | IND_CC-243 | 99 | 100 |

| Example no. | % Inhibition (rat B1R) at 10 μM | % Inhibition (human B1R) at 10 μM |
|---|---|---|
| IND_CC-244 | 103 | 99 |
| IND_CC-245 | 101 | 100 |
| IND_CC-246 | 100 | 99 |
| IND_CC-247 | 102 | 99 |
| IND_CC-248 | 102 | 90 |
| IND_CC-249 | 99 | 99 |
| IND_CC-250 | 100 | 94 |
| IND_CC-251 | 99 | 100 |
| IND_CC-252 | 102 | 100 |
| IND_CC-253 | 100 | 100 |
| IND_CC-254 | 105 | 97 |
| IND_CC-255 | 100 | 100 |
| IND_CC-256 | 100 | 99 |
| IND_CC-258 | 95 | 100 |
| IND_CC-259 | 100 | 99 |
| IND_CC-260 | 100 | 100 |
| IND_CC-261 | 103 | 100 |
| IND_CC-262 | 105 | 100 |
| IND_CC-263 | 81 | 100 |
| IND_CC-264 | 106 | 97 |
| IND_CC-265 | 107 | 88 |
| IND_CC-266 | 106 | 98 |
| IND_CC-267 | 106 | 86 |
| IND_CC-268 | 108 | 99 |
| IND_CC-269 | 107 | 100 |
| IND_CC-270 | 108 | 100 |
| IND_CC-271 | 106 | 100 |
| IND_CC-272 | 107 | 99 |
| IND_CC-273 | 106 | 99 |
| IND_CC-274 | 102 | 8 |
| IND_CC-275 | 107 | 100 |
| IND_CC-276 | 107 | 100 |
| IND_CC-277 | 105 | 100 |
| IND_CC-278 | 101 | 35 |
| IND_CC-279 | 106 | 100 |
| IND_CC-280 | 108 | 100 |
| IND_CC-281 | 105 | 84 |
| IND_CC-282 | 107 | 69 |
| IND_CC-283 | 107 | 96 |
| IND_CC-284 | 107 | 100 |
| IND_CC-286 | 90 | |
| IND_CC-287 | 105 | 99 |
| IND_CC-288 | 106 | 100 |
| IND_CC-289 | 104 | 100 |
| IND_CC-290 | 100 | 35 |
| IND_CC-291 | 104 | 98 |
| IND_CC-292 | 105 | 99 |
| IND_CC-293 | 106 | 100 |
| IND_CC-294 | 105 | 99 |
| IND_CC-295 | 106 | 96 |
| IND_CC-296 | 103 | 59 |
| IND_CC-297 | 107 | |
| IND_CC-298 | 74 | |
| IND_CC-299 | 106 | 27 |
| IND_CC-300 | 65 | |
| IND_CC-301 | 107 | 94 |
| IND_CC-302 | 106 | 99 |
| IND_CC-303 | 106 | 92 |
| IND_CC-304 | 104 | 49 |
| IND_CC-305 | 104 | 67 |
| IND_CC-306 | 106 | |
| IND_CC-307 | 103 | 14 |
| IND_CC-308 | 106 | 97 |
| IND_CC-309 | 104 | 97 |
| IND_CC-310 | 104 | 100 |
| IND_CC-311 | 83 | |
| IND_CC-312 | 102 | 44 |
| IND_CC-313 | 95 | |
| IND_CC-314 | 80 | |
| IND_CC-315 | 101 | |
| IND_CC-316 | 100 | |
| IND_CC-317 | 60 | |
| IND_CC-318 | 100 | |
| IND_CC-319 | 102 | |
| IND_CC-320 | 83 | |
| IND_CC-321 | 95 | |
| IND_CC-322 | 102 | |
| IND_CC-323 | 100 | |
| IND_CC-324 | 98 | |
| IND_CC-325 | 102 | |
| IND_CC-326 | 100 | |
| IND_CC-327 | 101 | |
| IND_CC-328 | 98 | |
| IND_CC-329 | 97 | |
| IND_CC-330 | 67 | |
| IND_CC-331 | 94 | |
| IND_CC-332 | 97 | |
| IND_CC-333 | 92 | |
| IND_CC-334 | 90 | |
| IND_CC-335 | 102 | |
| IND_CC-336 | 103 | |
| IND_CC-337 | 104 | |
| IND_CC-338 | 103 | |
| IND_CC-339 | 103 | |
| IND_CC-340 | 101 | |
| IND_CC-341 | 87 | |
| IND_CC-342 | 103 | |
| IND_CC-343 | 97 | |
| IND_CC-344 | 99 | |
| IND_CC-345 | 105 | |
| IND_CC-346 | 104 | |
| IND_CC-347 | 106 | |
| IND_CC-348 | 102 | |
| IND_CC-349 | 105 | |
| IND_CC-350 | 106 | |
| IND_CC-351 | 99 | |
| IND_CC-352 | 98 | |
| IND_CC-353 | 97 | |
| IND_CC-354 | 84 | |
| IND_CC-355 | 65 | |
| IND_CC-356 | 69 | |
| IND_CC-357 | 95 | |
| IND_CC-358 | 104 | |
| IND_CC-359 | 104 | |
| IND_CC-360 | 69 | |
| IND_CC-361 | 99 | |
| IND_CC-362 | 81 | |
| IND_CC-363 | 74 | |
| IND_CC-364 | 103 | |
| IND_CC-365 | 105 | |
| IND_CC-366 | 104 | |
| IND_CC-367 | 104 | |
| IND_CC-368 | 87 | |
| IND_CC-369 | 74 | |
| IND_CC-370 | 100 | |
| IND_CC-371 | 104 | |
| IND_CC-372 | 105 | |
| IND_CC-373 | 102 | |
| IND_CC-374 | 103 | |
| IND_CC-375 | 59 | |
| IND_CC-376 | 102 | |
| IND_CC-377 | 104 | |
| IND_CC-378 | 104 | |
| IND_CC-379 | 103 | |
| IND_CC-380 | 103 | |
| IND_CC-381 | 104 | |
| IND_CC-382 | 103 | |
| IND_CC-383 | 102 | |
| IND_CC-384 | 104 | |
| IND_CC-385 | 104 | |
| IND_CC-386 | 104 | |
| IND_CC-387 | 104 | |
| IND_CC-388 | 101 | |
| IND_CC-389 | 103 | |
| IND_CC-390 | 100 | |
| IND_CC-391 | 103 | |
| IND_CC-392 | 102 | |
| IND_CC-393 | 103 | |
| IND_CC-394 | 103 | |
| IND_CC-395 | 58 | |

| Example no. | % Inhibition (rat B1R) at 10 μM | % Inhibition (human B1R) at 10 μM |
|---|---|---|
| IND_CC-396 | 81 | |
| IND_CC-397 | 68 | |
| IND_CC-398 | 88 | |
| IND_CC-399 | 101 | |
| IND_CC-400 | 103 | |
| IND_CC-401 | 103 | |
| IND_CC-402 | 102 | |
| IND_CC-403 | 97 | |
| IND_CC-404 | 92 | |
| IND_CC-405 | 96 | |
| IND_CC-406 | 102 | |
| IND_CC-407 | 101 | |
| IND_CC-408 | 101 | |
| IND_CC-409 | 102 | |
| IND_CC-410 | 97 | |
| IND_CC-411 | 101 | |
| IND_CC-412 | 99 | |
| IND_CC-413 | 103 | |
| IND_CC-414 | 102 | |
| IND_CC-415 | 100 | |
| IND_CC-416 | 101 | |
| IND_CC-417 | 102 | |
| IND_CC-418 | 99 | |
| IND_CC-419 | 101 | |
| IND_CC-420 | 100 | |
| IND_CC-500 | 51 | |
| IND_CC-501 | 56 | |
| IND_CC-502 | 71 | |
| IND_CC-503 | 66 | |
| IND_CC-504 | 51 | |
| IND_CC-505 | 67 | |
| IND_CC-506 | 61 | |
| IND_CC-507 | 100 | 2 |
| IND_CC-508 | 100 | |
| IND_CC-509 | 101 | |
| IND_CC-510 | 95 | |
| IND_CC-511 | 94 | |
| IND_CC-512 | 92 | |
| IND_CC-513 | 98 | |
| IND_CC-514 | 102 | |
| IND_CC-515 | 104 | |
| IND_CC-516 | 102 | |
| IND_CC-517 | 90 | |
| IND_CC-518 | 86 | |
| IND_CC-519 | 53 | |
| IND_CC-520 | 72 | |
| IND_CC-521 | 66 | |
| IND_CC-522 | 55 | |
| IND_CC-523 | 68 | |
| IND_CC-524 | 62 | |
| IND_CC-525 | 62 | |
| IND_CC-526 | 87 | 25 |
| IND_CC-527 | 98 | |
| IND_CC-528 | 102 | 24 |
| IND_CC-529 | 104 | |
| IND_CC-530 | 96 | |
| IND_CC-531 | 81 | |
| IND_CC-532 | 62 | |
| IND_CC-533 | 74 | |
| IND_CC-534 | 102 | |
| IND_CC-535 | 90 | 49 |
| IND_CC-536 | 54 | |
| IND_CC-537 | 62 | |
| IND_CC-538 | 72 | |
| IND_CC-539 | 75 | |
| IND_CC-540 | 82 | |
| IND_CC-541 | 65 | |
| IND_CC-542 | 104 | 27 |
| IND_CC-543 | 102 | |
| IND_CC-544 | 99 | |
| IND_CC-545 | 105 | |
| IND_CC-546 | 99 | |
| IND_CC-547 | 71 | |
| IND_CC-548 | 66 | |
| IND_CC-549 | 60 | |
| IND_CC-550 | 62 | |
| IND_CC-551 | 55 | |
| IND_CC-552 | 68 | |
| IND_CC-553 | 90 | −2 |
| IND_CC-554 | 73 | |
| IND_CC-555 | 91 | |
| IND_CC-556 | 100 | 7 |
| IND_CC-557 | 103 | |
| IND_CC-558 | 62 | |
| IND_CC-559 | 56 | |
| IND_CC-560 | 95 | |
| IND_CC-561 | 85 | |
| IND_CC-562 | 104 | 27 |
| IND_CC-563 | 92 | |
| IND_CC-564 | 81 | |
| IND_CC-565 | 68 | |
| IND_CC-566 | 90 | |
| IND_CC-567 | 100 | |
| IND_CC-568 | 105 | 20 |
| IND_CC-569 | 52 | |
| IND_CC-570 | 57 | |
| IND_CC-571 | 52 | |
| IND_CC-572 | 80 | |
| IND_CC-573 | 100 | 43 |
| IND_CC-574 | 101 | 14 |
| IND_CC-575 | 78 | |
| IND_CC-576 | 79 | |
| IND_CC-577 | 96 | 21 |
| IND_CC-578 | 79 | |
| IND_CC-579 | 57 | |
| IND_CC-580 | 81 | |
| IND_CC-581 | 67 | |
| IND_CC-582 | 58 | |
| IND_CC-583 | 75 | |
| IND_CC-584 | 63 | |
| IND_CC-585 | 52 | |
| IND_CC-586 | 76 | |
| IND_CC-587 | 71 | |
| IND_CC-588 | 61 | |
| IND_CC-589 | 81 | |
| IND_CC-590 | 86 | |
| IND_CC-591 | 62 | |
| IND_CC-592 | 85 | |
| IND_CC-593 | 50 | |
| IND_CC-594 | 91 | |
| IND_CC-595 | 91 | |
| IND_CC-596 | 94 | |
| IND_CC-597 | 101 | |
| IND_CC-598 | 96 | |
| IND_CC-599 | 96 | |
| IND_CC-600 | 100 | |
| IND_CC-601 | 77 | |
| IND_CC-602 | 95 | |
| IND_CC-603 | 75 | |
| IND_CC-604 | 94 | |
| IND_CC-605 | 66 | |
| IND_CC-606 | 66 | |
| IND_CC-607 | 67 | |
| IND_CC-608 | 102 | |
| IND_CC-609 | 101 | |
| IND_CC-610 | 103 | |
| IND_CC-611 | 98 | |
| IND_CC-612 | 65 | |
| IND_CC-613 | 102 | |
| IND_CC-614 | 67 | |
| IND_CC-615 | 67 | |
| IND_CC-616 | 81 | |
| IND_CC-617 | 67 | |
| IND_CC-618 | 61 | |
| IND_CC-619 | 57 | |
| IND_CC-620 | 54 | |
| IND_CC-621 | 67 | |
| IND_CC-622 | 69 | |
| IND_CC-623 | 59 | |
| IND_CC-624 | 62 | |

| Example no. | % Inhibition (rat B1R) at 10 μM | % Inhibition (human B1R) at 10 μM |
|---|---|---|
| IND_CC-625 | 50 | |
| IND_CC-626 | 55 | |
| IND_CC-627 | 54 | |
| IND_CC-628 | 63 | |
| IND_CC-629 | 71 | |
| IND_CC-630 | 53 | |
| IND_CC-631 | 57 | |
| IND_CC-632 | 64 | |
| IND_CC-633 | 86 | |
| IND_CC-634 | 75 | |
| IND_CC-635 | 72 | |
| IND_CC-636 | 79 | |
| IND_CC-637 | 69 | |
| IND_CC-638 | 80 | |
| IND_CC-639 | 78 | |
| IND_CC-640 | 73 | |
| IND_CC-641 | 74 | |
| IND_CC-642 | 77 | |
| IND_CC-643 | 78 | |
| IND_CC-644 | 59 | |
| IND_CC-645 | 78 | |
| IND_CC-646 | 66 | |
| IND_CC-647 | 73 | |
| IND_CC-648 | 78 | |
| IND_CC-649 | 76 | |
| IND_CC-650 | 54 | |
| IND_CC-651 | 76 | |
| IND_CC-652 | 53 | |
| IND_CC-653 | 64 | |
| IND_CC-654 | 60 | |
| IND_CC-655 | 59 | |
| IND_CC-656 | 51 | |
| IND_CC-657 | 66 | |
| IND_CC-658 | 51 | |
| IND_CC-659 | 81 | |
| IND_CC-660 | 50 | |
| IND_CC-661 | 95 | |
| IND_CC-662 | 76 | |
| IND_CC-663 | 85 | |
| IND_CC-664 | 54 | |
| IND_CC-665 | 67 | |
| IND_CC-666 | 78 | |
| IND_CC-667 | 85 | |
| IND_CC-668 | 57 | |
| IND_CC-669 | 60 | |
| IND_CC-670 | 67 | |
| IND_CC-671 | 80 | |
| IND_CC-672 | 88 | |
| IND_CC-673 | 67 | |
| IND_CC-674 | 67 | |
| IND_CC-675 | 87 | |
| IND_CC-676 | 74 | |
| IND_CC-677 | 72 | |
| IND_CC-678 | 82 | |
| IND_CC-679 | 82 | |
| IND_CC-680 | 54 | |
| IND_CC-681 | 53 | |
| IND_CC-682 | 51 | |
| IND_CC-683 | 62 | |
| IND_CC-684 | 67 | |
| IND_CC-685 | 68 | |
| IND_CC-686 | 69 | |
| IND_CC-687 | 76 | |
| IND_CC-688 | 88 | |
| IND_CC-689 | 55 | |
| IND_CC-690 | 85 | |
| IND_CC-691 | 95 | |
| IND_CC-692 | 99 | |
| IND_CC-693 | 68 | |
| IND_CC-694 | 100 | |
| IND_CC-695 | 100 | |
| IND_CC-696 | 102 | |
| IND_CC-697 | 98 | |
| IND_CC-698 | 90 | |
| IND_CC-699 | 75 | |
| IND_CC-700 | 64 | |
| IND_CC-701 | 96 | |
| IND_CC-702 | 80 | |
| IND_CC-703 | 70 | |
| IND_CC-704 | 91 | |
| IND_CC-705 | 101 | |
| IND_CC-706 | 103 | |
| IND_CC-707 | 92 | |
| IND_CC-708 | 99 | |
| IND_CC-709 | 91 | |
| IND_CC-710 | 90 | |
| IND_CC-711 | 94 | |
| IND_CC-712 | 76 | |
| IND_CC-713 | 77 | |
| IND_CC-714 | 51 | |
| IND_CC-715 | 79 | |
| IND_CC-716 | 80 | |
| IND_CC-717 | 72 | |
| IND_CC-718 | 52 | |
| IND_CC-719 | 59 | |
| IND_CC-720 | 80 | |
| IND_CC-721 | 70 | |
| IND_CC-722 | 81 | |
| IND_CC-723 | 55 | |
| IND_CC-724 | 86 | |
| IND_CC-725 | 56 | |
| IND_CC-726 | 67 | |
| IND_CC-727 | 74 | |
| IND_CC-728 | 58 | |
| IND_CC-729 | 76 | |
| IND_CC-730 | 75 | |
| IND_CC-731 | 83 | |
| IND_CC-732 | 100 | |
| IND_CC-733 | 83 | |
| IND_CC-734 | 95 | |
| IND_CC-735 | 81 | |
| IND_CC-736 | 93 | |
| IND_CC-737 | 55 | |
| IND_CC-738 | 89 | |
| IND_CC-739 | 83 | |
| IND_CC-740 | 88 | |
| IND_CC-741 | 100 | |
| IND_CC-742 | 50 | |
| IND_CC-743 | 80 | |
| IND_CC-744 | 71 | |
| IND_CC-745 | 70 | |
| IND_CC-746 | 78 | |
| IND_CC-747 | 59 | |
| IND_CC-748 | 70 | |
| IND_CC-749 | 70 | |
| IND_CC-750 | 99 | |
| IND_CC-751 | 98 | |
| IND_CC-752 | 69 | |
| IND_CC-753 | 90 | |
| IND_CC-754 | 87 | |
| IND_CC-755 | 92 | |
| IND_CC-756 | 104 | |
| IND_CC-757 | 52 | |
| IND_CC-758 | 86 | |
| IND_CC-759 | 78 | |
| IND_CC-760 | 93 | |
| IND_CC-761 | 57 | |
| IND_CC-762 | 55 | |
| IND_CC-763 | 74 | |
| IND_CC-764 | 71 | |
| IND_CC-765 | 105 | |
| IND_CC-766 | 93 | |
| IND_CC-767 | 73 | |
| IND_CC-768 | 79 | |
| IND_CC-769 | 91 | |
| IND_CC-770 | 109 | |
| IND_CC-771 | 108 | |
| IND_CC-772 | 52 | |
| IND_CC-773 | 80 | |
| IND_CC-774 | 81 | |

-continued

| Example no. | % Inhibition (rat B1R) at 10 μM | % Inhibition (human B1R) at 10 μM |
|---|---|---|
| IND_CC-775 | 98 | |
| IND_CC-776 | 99 | |
| IND_CC-777 | 83 | |
| IND_CC-778 | 105 | |
| IND_CC-779 | 69 | |
| IND_CC-780 | 101 | |
| IND_CC-781 | 106 | |
| IND_CC-782 | 107 | |
| IND_CC-783 | 102 | |
| IND_CC-784 | 99 | |
| IND_CC-785 | 98 | |
| IND_CC-786 | 104 | |
| IND_CC-787 | 93 | |
| IND_CC-788 | 71 | |
| IND_CC-789 | 98 | |
| IND_CC-790 | 96 | |
| IND_CC-791 | 91 | |
| IND_CC-792 | 89 | |
| IND_CC-793 | 79 | |
| IND_CC-794 | 59 | |
| IND_CC-795 | 54 | |
| IND_CC-796 | 66 | |
| IND_CC-797 | 91 | |
| IND_CC-798 | 71 | |
| IND_CC-799 | 52 | |
| IND_CC-800 | 97 | |
| IND_CC-801 | 92 | |
| IND_CC-802 | 89 | |
| IND_CC-803 | 76 | |
| IND_CC-804 | 61 | |
| IND_CC-805 | 51 | |
| IND_CC-806 | 75 | |
| IND_CC-807 | 53 | |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A substituted spiro-amide compound corresponding to formula (I)

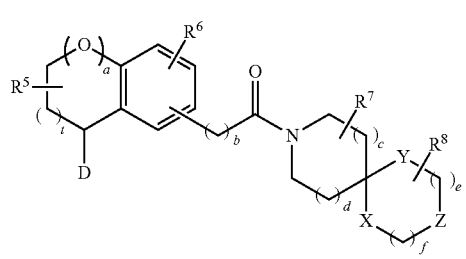

wherein a represents 0 or 1;

t represents 1, 2 or 3; and b represents 0 or 1;

such that the partial structure (Ac)

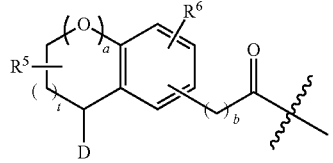

represents a partial structure selected from the group consisting of:

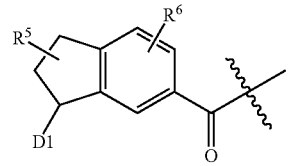

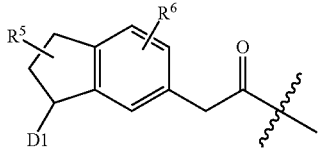

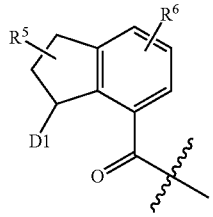

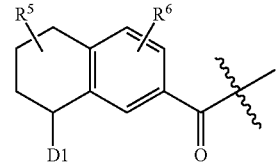

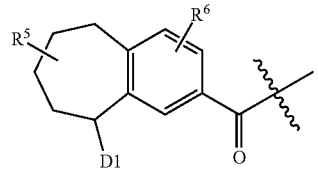

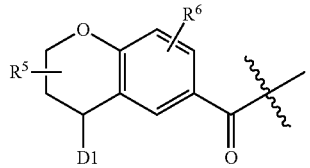

-continued
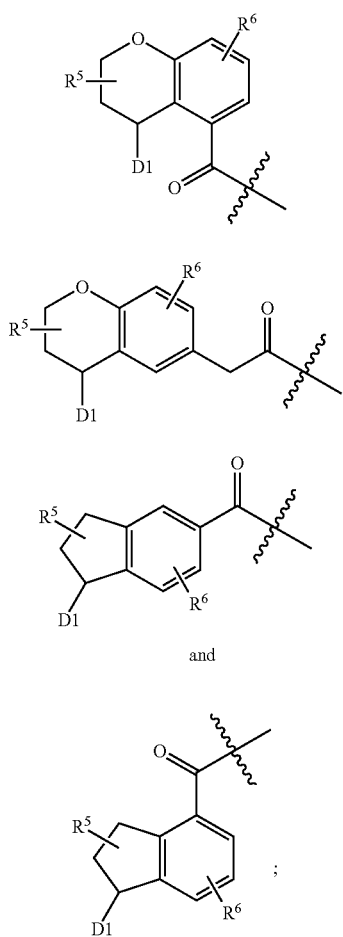
(Ac 27)
(Ac 28)
(Ac 33)
(Ac 37)
c, d, e and f each independently represent 0, 1 or 2;
X represents $CR^{10a}R^{10b}$;
Y represents $CR^{12a}R^{12b}$; and
Z represents $NR^{15}$;
such that the partial structure (SP)
(SP)
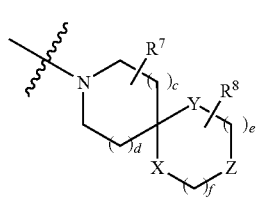
represents a structure selected from the group consisting of:
SP 5
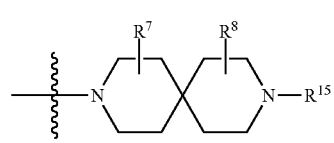
-continued
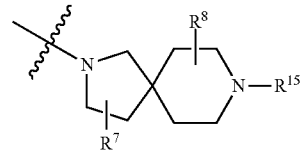
SP 6
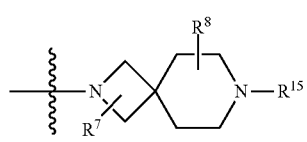
SP 7
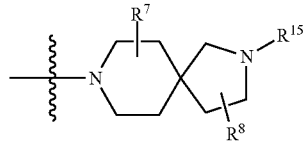
SP 8
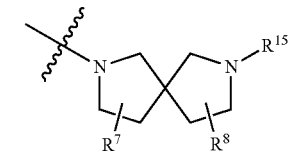
SP 9
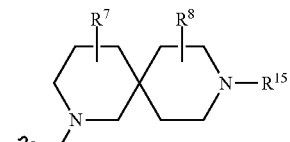
SP 34
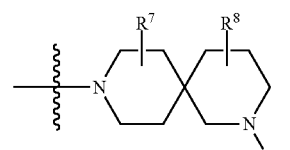
SP 35
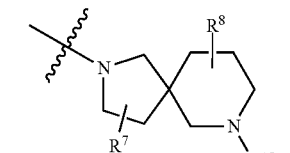
SP 36
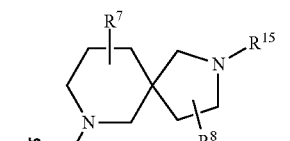
SP 37
and

SP 38

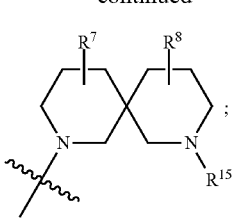

D represents D1

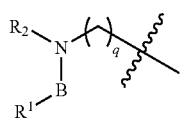

q represents 0 or 1;

B represents C(=O), S(=O)$_2$ or the group —C(=O)—N(R$^9$), wherein the nitrogen atom thereof is bonded to R$^1$;

R$^1$ represents C$_{1-6}$-alkyl, aryl, heteroaryl, —CH(aryl)$_2$, C$_{3-8}$-cycloalkyl or an aryl, heteroaryl or C$_{3-8}$-cycloalkyl bonded via a C$_{1-6}$-alkylene group or C$_{2-6}$-alkenylene group;

R$^2$ represents H, C$_{1-6}$-alkyl, C$_{3-8}$-cycloalkyl, aryl, heteroaryl or a C$_{3-8}$-cycloalkyl, aryl or heteroaryl group bonded via a C$_{1-6}$-alkylene group;

R$^5$ represents 0, 1 or 2 substituents independently selected from the group consisting of F, Cl, CF$_3$, OCF$_3$, OH, C$_{1-6}$-alkyl and O—C$_{1-6}$-alkyl;

R$^6$ represents 0, 1 or 2 substituents independently selected from the group consisting of F, Cl, CF$_3$, OCF$_3$, OH, C$_{1-6}$-alkyl, and O—C$_{1-6}$-alkyl;

R$^7$ and R$^8$ each independently represent 0, 1 or 2 substituents each independently selected from the group consisting of F, Cl, OH, and C$_{1-6}$-alkyl;

R$^9$ represents H, C$_{1-6}$-alkyl, C$_{3-8}$-cycloalkyl, aryl, heteroaryl or a C$_{3-8}$-cycloalkyl, aryl or heteroaryl group bonded via a C$_{1-3}$-alkylene group;

R$^{10a}$, R$^{10b}$, R$^{12a}$ and R$^{12b}$ each independently denote H, F, Cl, OH, O$_{1-6}$-alkyl, O—C$_{1-6}$-alkyl, C$_{3-8}$-cycloalkyl, aryl or heteroaryl, or represent a C$_{3-8}$-cycloalkyl, aryl or heteroaryl group bonded via a C$_{1-6}$-alkylene group; or R$^{10a}$ and R$^{10b}$ together can represent =O; or R$^{12a}$ and R$^{12b}$ together can represent =O;

R$^{15}$ represents H, —C(=O)—R$^{19}$, —S(=O)$_2$—R$^{19}$, —C(=O)—N(R$^{20}$)—R$^{19}$, CHR$^{25}$R$^{26}$, C$_{1-10}$-alkyl, C$_{3-8}$-cycloalkyl, heterocyclyl, aryl or heteroaryl or denotes a CHR$^{25}$R$^{26}$, C$_{3-8}$-cycloalkyl, heterocyclyl, aryl or heteroaryl group bonded via a C$_{1-6}$-alkylene group;

R$^{19}$ represents C$_{1-6}$-alkyl, aryl, heteroaryl, —CH(aryl)$_2$, C$_{3-8}$-cycloalkyl, heterocyclyl or an aryl, heteroaryl, C$_{3-8}$-cycloalkyl or heterocyclyl group bonded via a C$_{1-6}$-alkylene group, C$_{2-6}$-alkenylene group or C$_{2-6}$-alkynylene group;

R$^{20}$ represents H, C$_{1-6}$-alkyl, C$_{3-8}$-cycloalkyl, aryl, heteroaryl or a C$_{3-8}$-cycloalkyl, aryl or heteroaryl group bonded via a C$_{1-3}$-alkylene group;

R$^{25}$ and R$^{26}$ each independently represent H, C$_{1-4}$-alkyl, C$_{3-8}$-cycloalkyl, aryl or heteroaryl, or R$^{25}$ and R$^{26}$ together with the CH grouping joining them form a 4-, 5-, 6- or 7-membered ring, which may be unsubstituted or substituted on one or more of its carbon ring members by one or more substituents independently selected from the group consisting of F, Cl, Br, I, CF$_3$, C$_{1-6}$-alkyl, O—C$_{1-6}$-alkyl, OH, OCF$_3$, SH, SCF$_3$, NR$^A$R$^B$, aryl and heteroaryl, wherein the ring may be saturated or unsaturated one or more times, but is not aromatic, and optionally may contain one or more hetero atoms or hetero atom groups independently selected from the group consisting of N, NR$^{50b}$, O, S, S(=O) and S(=O)$_2$; wherein R$^{50b}$ denotes H, C$_{1-6}$-alkyl, —C(=O)—R$^{51b}$, C$_{3-8}$-cycloalkyl, aryl, heteroaryl or a C$_{3-8}$-cycloalkyl, aryl or heteroaryl group bonded via a C$_{1-3}$-alkylene group, and R$^{51b}$ denotes C$_{1-6}$-alkyl, C$_{3-8}$-cycloalkyl, aryl, heteroaryl or a C$_{3-8}$-cycloalkyl, aryl or heteroaryl group bonded via a C$_{1-3}$-alkylene group;

R$^A$ and R$^B$ each independently represent H, C$_{1-6}$-alkyl or C$_{3-8}$-cycloalkyl, or R$^A$ and R$^B$ together with the nitrogen atom to which they are bound form a 4-, 5-, 6- or 7-membered heterocyclic ring, which may be unsubstituted or substituted on one or more of its carbon ring members by one or more substituents independently selected from the group consisting of F, Cl, Br, I, CF$_3$, C$_{1-6}$-alkyl, O—C$_{1-6}$-alkyl, OH, OCF$_3$, SH, SCF$_3$, aryl and heteroaryl, wherein the heterocyclic ring may be saturated or unsaturated one or more times, but is not aromatic, and optionally may contain one or more hetero atoms or hetero atom groups independently selected from the group consisting of N, NR$^C$, O, S, S(=O) and S(=O)$_2$; wherein R$^C$ denotes H, C$_{1-6}$-alkyl, —C(=O)—R$^D$, C$_{3-8}$-cycloalkyl, aryl, heteroaryl or a C$_{3-8}$-cycloalkyl, aryl or heteroaryl group bonded via a C$_{1-3}$-alkylene group, and R$^D$ denotes C$_{1-6}$-alkyl, C$_{3-8}$-cycloalkyl, aryl, heteroaryl or a C$_{3-8}$-cycloalkyl, aryl or heteroaryl group bonded via a C$_{1-3}$-alkylene group;

wherein the aforementioned C$_{1-4}$-alkyl, C$_{1-6}$-alkyl, C$_{1-10}$-alkyl, C$_{1-3}$-alkylene, C$_{1-6}$-alkylene, C$_{2-6}$-alkenylene, C$_{2-6}$-alkynylene, C$_{3-8}$-cycloalkyl, heterocyclyl, aryl and heteroaryl groups may each be unsubstituted or substituted one or more times by identical or different substituents, and the abovementioned C$_{1-4}$-alkyl, C$_{1-6}$-alkyl, C$_{1-10}$-alkyl, C$_{1-3}$-alkylene, C$_{1-6}$-alkylene, C$_{2-6}$-alkenylene and C$_{2-6}$-alkynylene groups may each be branched or unbranched;

or a physiologically acceptable salt thereof.

2. A compound as claimed in claim 1, wherein said compound is in the form of an isolated stereoisomer.

3. A compound as claimed in claim 1, wherein said compound is in the form of a mixture of stereoisomers in any mixing ratio.

4. A compound as claimed in claim 3, wherein said mixture is a racemic mixture.

5. A compound as claimed in claim 1, wherein R$^1$ represents C$_{1-6}$-alkyl, —CH(phenyl)$_2$, C$_{3-8}$-cycloalkyl, phenyl, naphthyl, chromanyl, indolyl, benzofuranyl, benzothiophenyl, benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothiophenyl or a phenyl or naphthyl group bonded via a C$_{1-3}$-alkylene group or a C$_{2-3}$-alkenylene group;

wherein the aforementioned aryl or heteroaryl groups may each be unsubstituted or substituted one or more times by identical or different substituents independently selected from the group consisting of O—C$_{1-3}$-alkyl, C$_{1-6}$-alkyl, F, Cl, Br, I, CF$_3$, OCF$_3$, OH, SH, phenyl, phenoxy, naphthyl, furyl, thienyl and pyridinyl, and wherein the aforementioned alkyl, alkylene, alkenylene and alkynylene groups may each be unsubstituted or substituted one or more times by identical or different substituents independently selected from the group consisting of O—$C_{1-3}$-alkyl, F, Cl, Br, I, $CF_3$, $OCF_3$, OH, SH, phenyl, phenoxy, naphthyl, furyl, thienyl and pyridinyl.

6. A compound as claimed in claim 5, wherein $R^1$ represents $C_{1-4}$-alkyl, —CH(phenyl)$_2$, $C_{3-6}$-cycloalkyl, phenyl, naphthyl, chromanyl, benzothiophenyl, benzooxadiazolyl, thienyl, pyridinyl, imidazothiazolyl, dibenzofuranyl or a phenyl bonded via a $C_{1-3}$-alkylene group or a $C_{2-3}$-alkenylene group.

7. A compound as claimed in claim 5, wherein $R^2$ represents H, —$CF_3$, —$CH_2$—$CF_3$, methyl, ethyl, n-propyl, iso-propyl, n-butyl, iso-butyl, sec-butyl, tert-butyl, cyclopropyl, cyclobutyl, cyclopentyl or cyclohexyl.

8. A compound as claimed in claim 1, wherein $R^9$ represents H, methyl, ethyl, n-propyl, iso-propyl, n-butyl, iso-butyl, sec-butyl, tert-butyl, cyclopropyl, cyclobutyl, cyclopentyl or cyclohexyl.

9. A compound as claimed in claim 1, wherein $R^{15}$ represents H, $C_{1-6}$-alkyl, —$CHR^{25}R^{26}$, $C_{1-3}$-alkylene-$CHR^{25}R^{26}$, aryl, heteroaryl, $C_{1-3}$-alkylene-aryl, $C_{1-3}$-alkylene-heteroaryl, —C(=O)—$R^{19}$, —S(=O)$_2$—$R^{19}$ or the group —C(=O)—N($R^{20}$)—$R^{19}$;

$R^{25}$ and $R^{26}$ each independently represent H, $C_{1-4}$-alkyl, $C_{3-6}$-cycloalkyl, aryl or heteroaryl, or $R^{25}$ and $R^{26}$ together with the CH group joining them form a structure selected from the group consisting of:

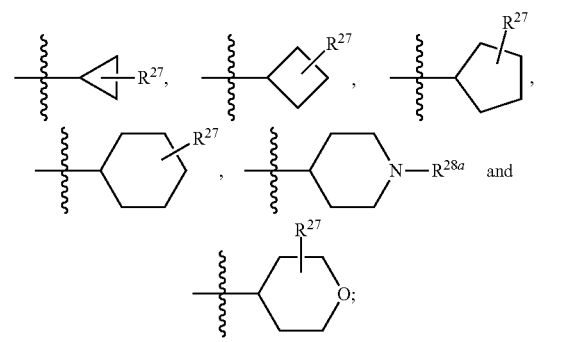

$R^{27}$ represents 0, 1 or 2 substituents each independently selected from the group consisting of F, Cl, $CF_3$, $OCF_3$, $C_{1-6}$-alkyl, O—$C_{1-3}$-alkyl and $NR^{48a}R^{48b}$;

$R^{28a}$ represents a substituent selected from the group consisting of H, methyl, ethyl, n-propyl, iso-propyl, n-butyl, iso-butyl, sec-butyl, tert-butyl, aryl and heteroaryl;

$R^{48a}$ and $R^{48b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, $R^{48a}$ and $R^{48b}$ together with the nitrogen atom to which they are bound form a structure selected from the group consisting of:

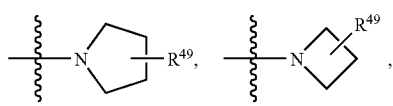

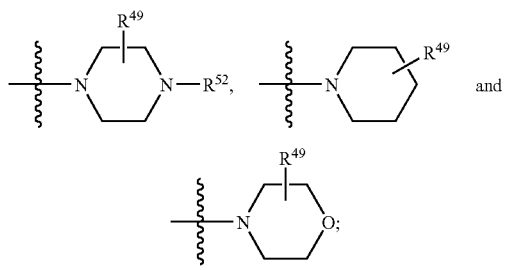

$R^{49}$ represents 0, 1 or 2 substituents each independently selected from the group consisting of F, Cl, $CF_3$, $OCF_3$, $C_{1-6}$-alkyl and O—$C_{1-3}$-alkyl;

$R^{52}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

$R^{19}$ represents $C_{1-6}$-alkyl, aryl, heteroaryl, —CH(aryl)$_2$, $C_{3-8}$-cycloalkyl, heterocyclyl or an aryl, heteroaryl, $C_{3-8}$-cycloalkyl or heterocyclyl group bonded via a $C_{1-6}$-alkylene group, $C_{2-6}$-alkenylene group or $C_{2-6}$-alkynylene group; and $R^{20}$ represents H, methyl, ethyl, n-propyl, iso-propyl, n-butyl, iso-butyl, sec-butyl, tert-butyl, cyclopropyl, cyclobutyl, cyclopentyl or cyclohexyl.

10. A compound as claimed in claim 1, wherein the following partial structure (SP)

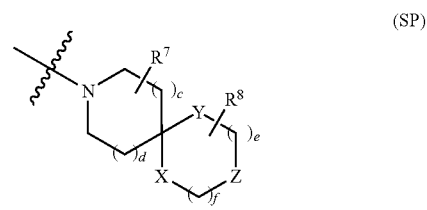

is selected from the group consisting of:

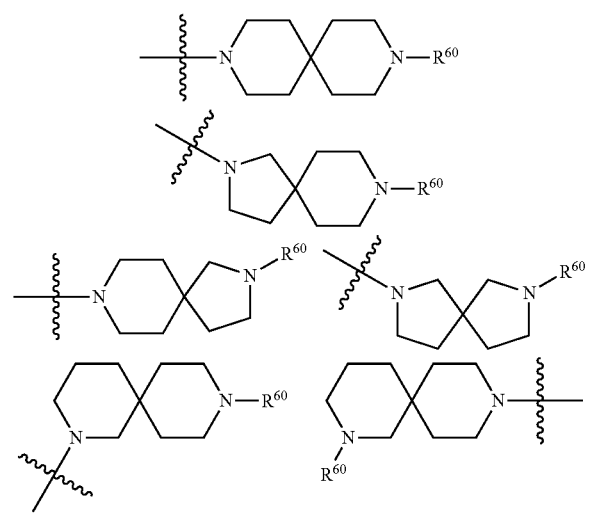

-continued

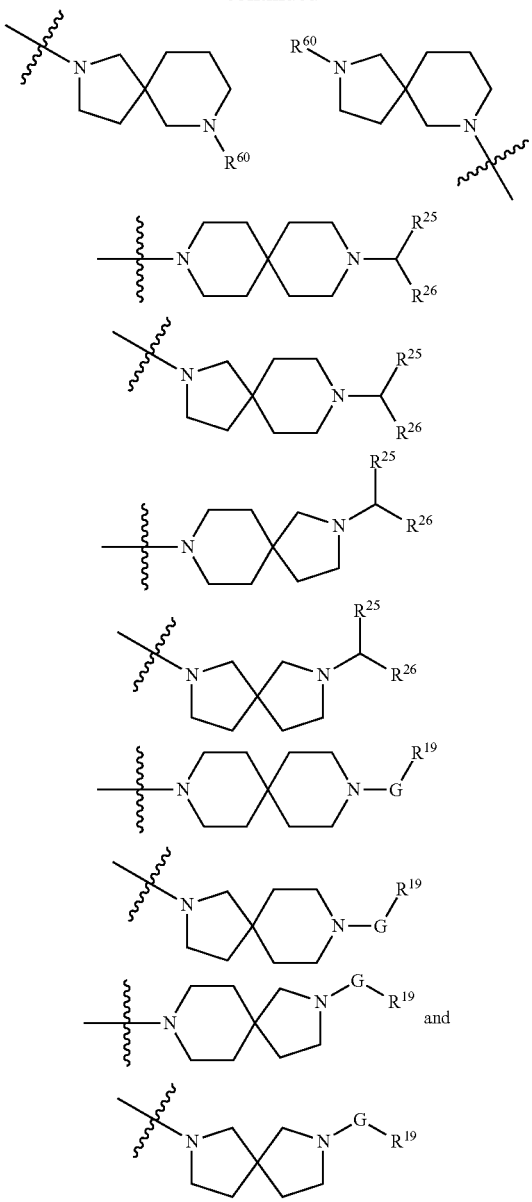

wherein $R^{60}$ in each case represents (het)aryl or $C_{1-3}$-alkylene-(het)aryl;

$R^{25}$ and $R^{26}$ each independently represent H, $C_{1-6}$-alkyl, $C_{3-6}$-cycloalkyl or (het)aryl, or $R^{25}$ and $R^{26}$ together with the CH to which they are bound form a structure selected from the group consisting of:

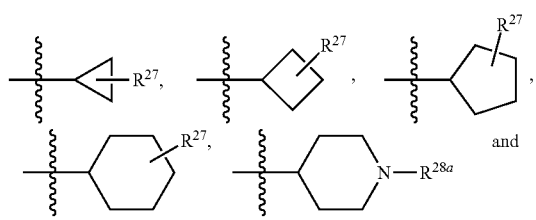

-continued

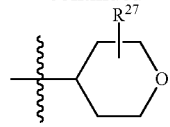

$R^{27}$ represents 0, 1 or 2 substituents each independently selected from the group consisting of F, Cl, $CF_3$, $OCF_3$, $C_{1-6}$-alkyl, O—$C_{1-3}$-alkyl and $NR^{48a}R^{48b}$;

$R^{28a}$ represents a substituent selected from the group consisting of H, methyl, ethyl, n-propyl, iso-propyl, n-butyl, iso-butyl, sec-butyl, tert-butyl and het(aryl);

$R^{48a}$ and $R^{48b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, $R^{48a}$ and $R^{48b}$ together with the nitrogen atom to which they are bound form a structure selected from the arouo consistina of:

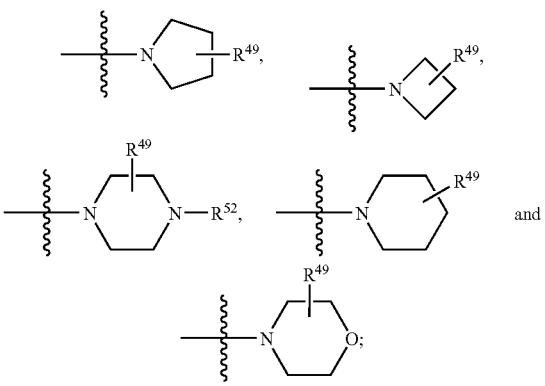

$R^{49}$ represents 0, 1 or 2 substituents each independantly selected from the group consisiting of F, Cl, $CF_3$, $OCF_3$, $C_{1-6}$-alkyl and O—$C_{1-3}$-alkyl;

$R^{52}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl and (het)aryl;

G represents C(=O), S(=O)$_2$ or the group —C(=O)—N($R^{20}$), wherein the nitrogen atom thereof is bonded to $R^{19}$;

$R^{19}$ represents $C_{1-8}$-alkyl, (het)aryl, —CH(aryl)$_2$, $C_{3-8}$-cycloalkyl, heterocyclyl or a (het)aryl, $C_{3-8}$-cycloalkyl or heterocyclyl bonded via a $C_{1-8}$-alkylene group, $C_{2-8}$-alkenylene group or $C_{2-6}$-alkynylene group;

$R^{20}$ represents H, methyl, ethyl, n-propyl, iso-propyl, n-butyl, iso-butyl, sec-butyl, tert-butyl, cyclopropyl, cyclobutyl, cyclopentyl or cyclohexyl; and (1)

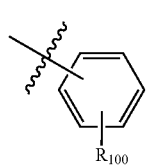

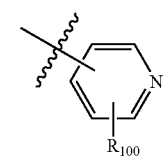 (2)
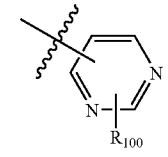 (3)
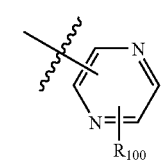 (4)
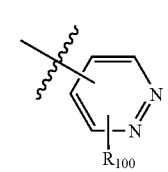 (5)
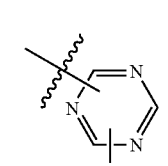 (6)
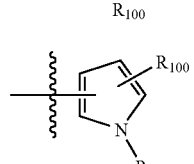 (7)
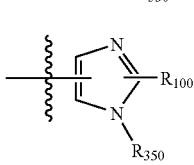 (8)
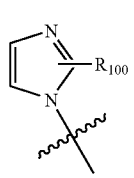 (9)
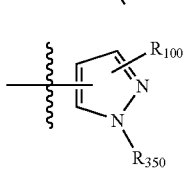 (10)
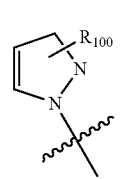 (11)
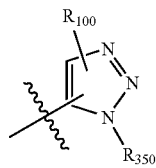 (12)
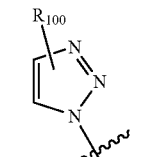 (13)
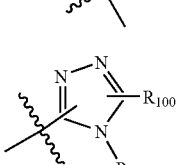 (14)
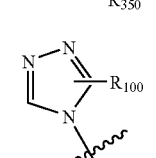 (15)
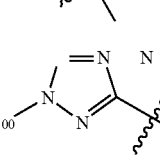 (16)
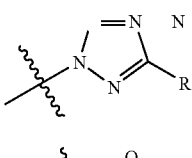 (17)
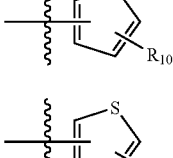 (18)
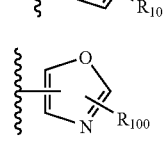 (19)
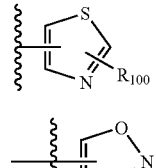 (20)
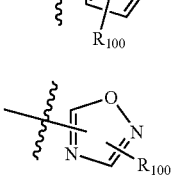 (21)
(22)
(23)

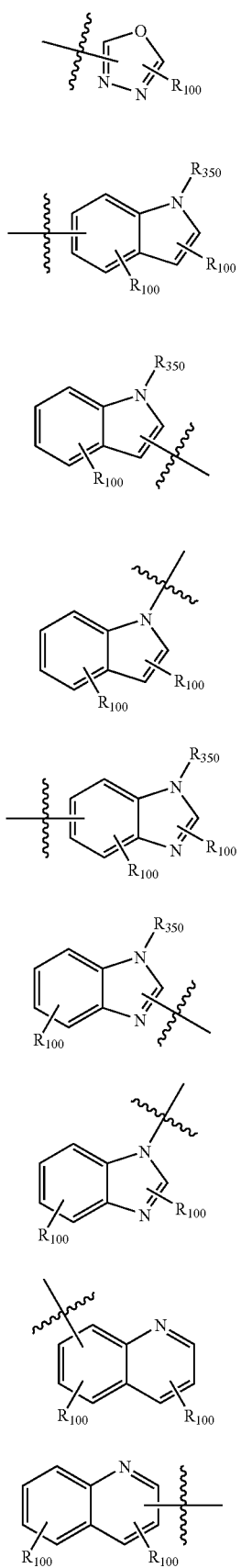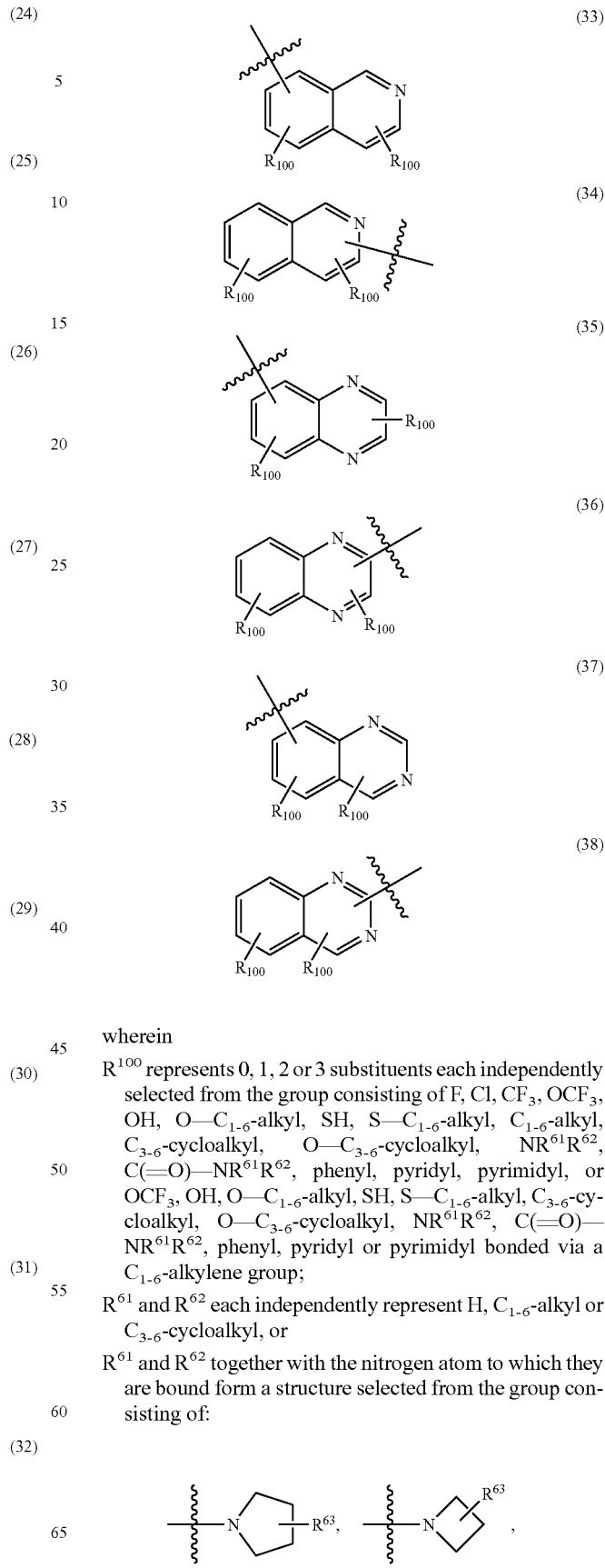

wherein

R[100] represents 0, 1, 2 or 3 substituents each independently selected from the group consisting of F, Cl, CF$_3$, OCF$_3$, OH, O—C$_{1-6}$-alkyl, SH, S—C$_{1-6}$-alkyl, C$_{1-6}$-alkyl, C$_{3-6}$-cycloalkyl, O—C$_{3-6}$-cycloalkyl, NR$^{61}$R$^{62}$, C(=O)—NR$^{61}$R$^{62}$, phenyl, pyridyl, pyrimidyl, or OCF$_3$, OH, O—C$_{1-6}$-alkyl, SH, S—C$_{1-6}$-alkyl, C$_{3-6}$-cycloalkyl, O—C$_{3-6}$-cycloalkyl, NR$^{61}$R$^{62}$, C(=O)—NR$^{61}$R$^{62}$, phenyl, pyridyl or pyrimidyl bonded via a C$_{1-6}$-alkylene group;

R$^{61}$ and R$^{62}$ each independently represent H, C$_{1-6}$-alkyl or C$_{3-6}$-cycloalkyl, or R$^{61}$ and R$^{62}$ together with the nitrogen atom to which they are bound form a structure selected from the group consisting of:

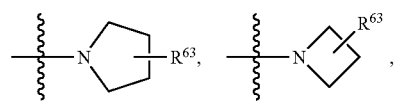

-continued

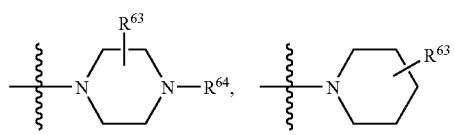 and

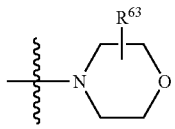

R$^{63}$ represents 0, 1 or 2 substituents each independently selected from the group consisting of F, Cl, CF$_3$, OCF$_3$, C$_{1-6}$-alkyl and O—C$_{1-3}$-alkyl;

R$^{64}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl and cyclohexyl; and R$^{350}$ represents H, CF$_3$, phenyl, pyridyl, pyrimidyl or a phenyl, pyridyl or pyrimidyl group bonded via a C$_{1-6}$-alkylene group.

11. A compound as claimed in claim 1, wherein the following partial structure (SP):

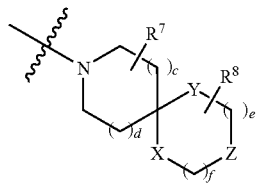 (SP)

is selected from the group consisting of:

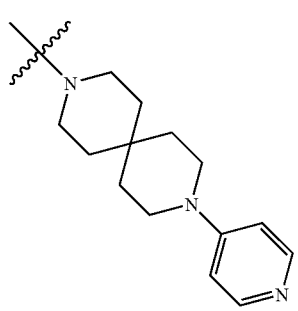 (1)

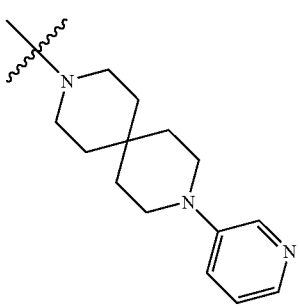 (2)

-continued

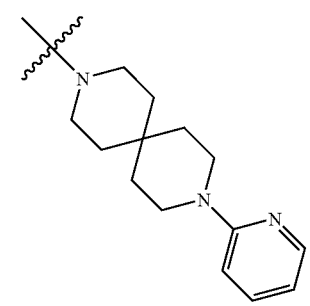 (3)

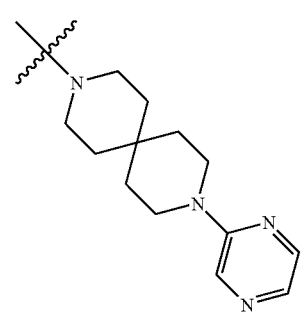 (4)

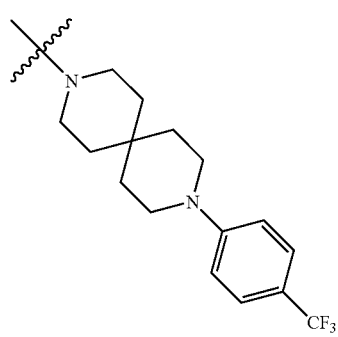 (5)

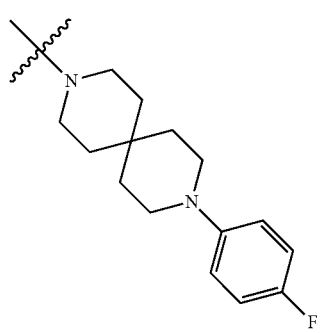 (6)

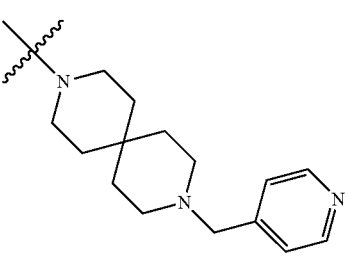 (7)

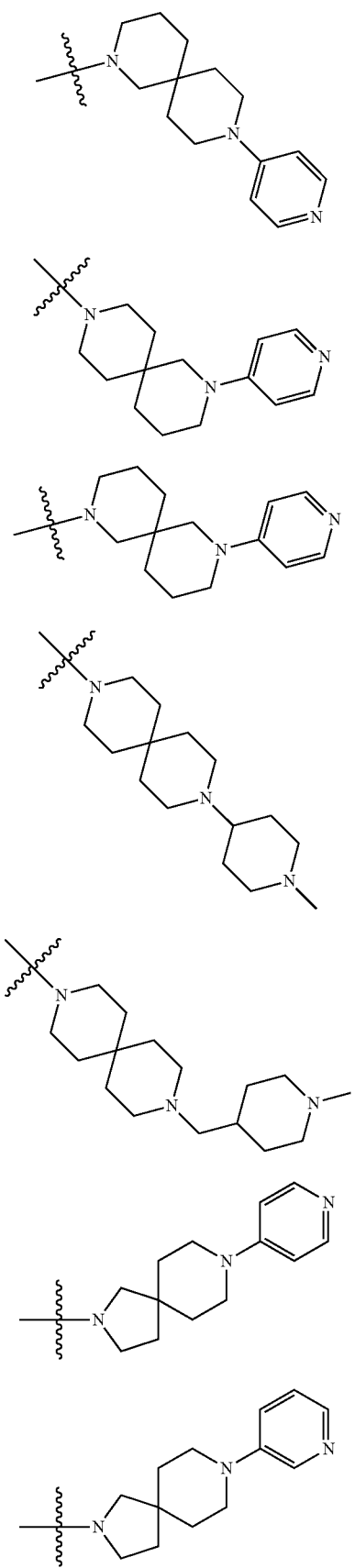
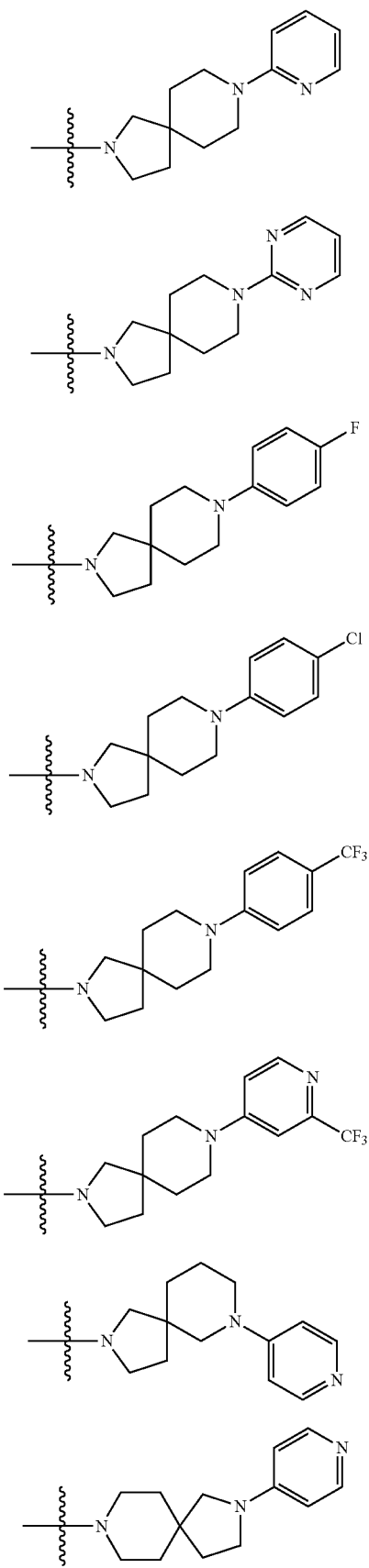

(29) 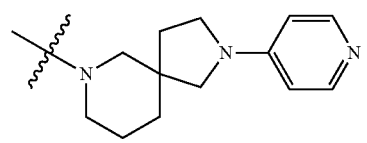
(30) 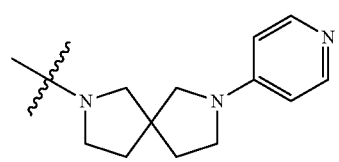
(31) 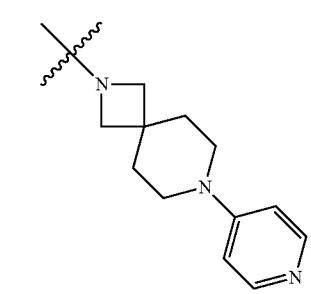
(37) 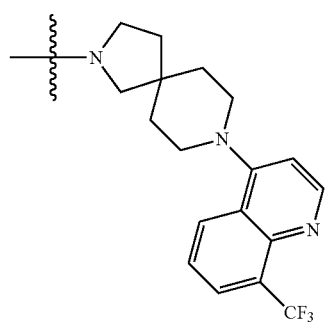
(38) 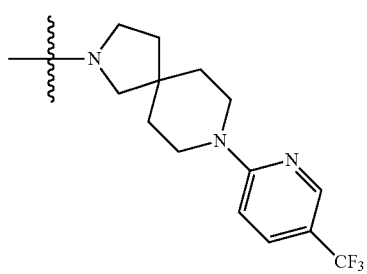
(39) 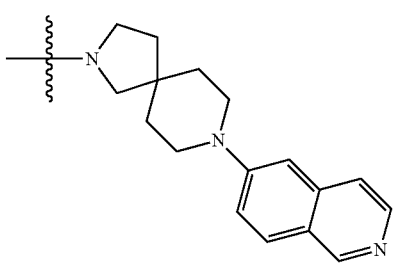
(40) 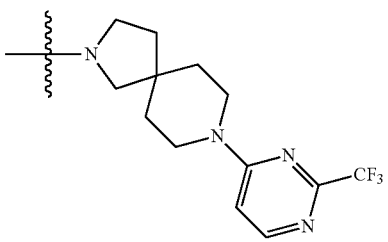
(44) 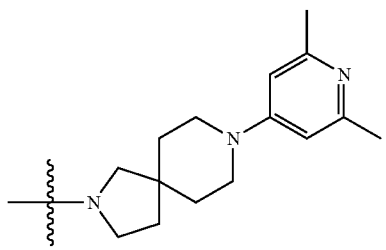
(45) 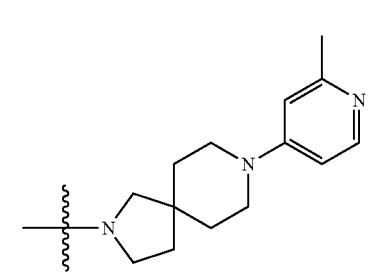
(47) 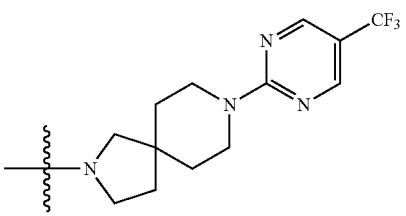
(49) 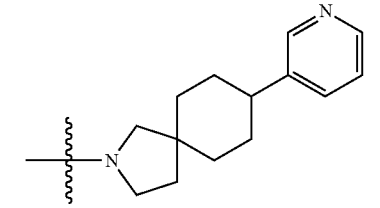
(50) 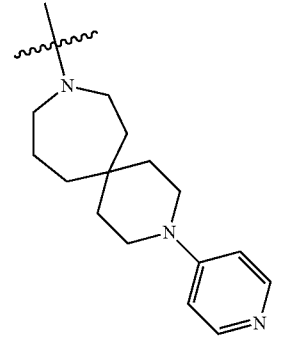

-continued

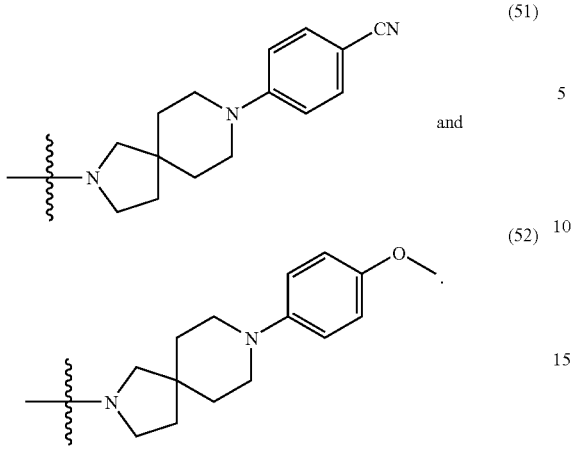

12. A compound selected from the group consisiting of:

[H-01] 7-chloro-2-[6-(9-pyridin-4-yl-3,9-diazaspiro[5.5]undecane-3-carbonyl)-2,3-dihydro-1H-inden-1-yl]-2,3-dihydro-isoindol-1-one,

[H-02] 2-chloro-N-[6-(3-pyridin-4-yl-3,9-diazaspiro[5.5]undecane-9-carbonyl)-2,3-dihydro-1H-inden-1-yl]-benzamide,

[H-03] 4-methoxy-2,6-dimethyl-N-[6-(9-pyridin-4-yl-3,9-diazaspiro[5.5]undecane-3-carbonyl)-2,3-dihydro-1H-inden-1-yl]-benzenesulfonic acid amide,

[H-04] 2-chloro-N-[6-(8-pyridin-4-yl-3,8-diazaspiro[4.4]nonane-3-carbonyl)-2,3-dihydro-1H-inden-1-yl]-benzamide,

[H-05] 2-chloro-N-[6-(8-pyridin-4-yl-3,8-diazaspiro[4.5]decane-3-carbonyl)-2,3-dihydro-1H-inden-1-yl]-benzamide,

[H-06] N-[6-[9-(azetidin-1-yl)-3-azaspiro[5.5]undecane-3-carbonyl]-2,3-dihydro-1H-inden-1-yl]-2-chloro-benzamide,

[H-07] 2-chloro-N-[6-[9-(3,3-difluoro-azetidin-1-yl)-3-azaspiro[5.5]undecane-3-carbonyl]-2,3-dihydro-1H-inden-1-yl]-benzamide,

[H-08] 2-chloro-N-[6-(9-pyridin-4-yloxy-3-azaspiro[5.5]undecane-3-carbonyl)-2,3-dihydro-1H-inden-1-yl]-benzamide,

[H-09] 2-chloro-N-[(1R)-7-(9-pyridin-4-yl-3,9-diazaspiro[5.5]undecane-3-carbonyl)-1,2,3,4-tetrahydro-naphthalen-1-yl]-benzamide,

[H-10] 2-chloro-N-[(1S)-7-(9-pyridin-4-yl-3,9-diazaspiro[5.5]undecane-3-carbonyl)-1,2,3,4-tetrahydro-naphthalen-1-yl]-benzamide,

[H-11] 2-chloro-N-[(1R)-7-(8-pyridin-4-yl-3,8-diazaspiro[4.5]decane-3-carbonyl)-1,2,3,4-tetrahydro-naphthalen-1-yl]-benzamide,

[H-12] 2-chloro-N-[(1S)-7-(8-pyridin-4-yl-3,8-diazaspiro[4.5]decane-3-carbonyl)-1,2,3,4-tetrahydro-naphthalen-1-yl]-benzamide,

[H-13] 7-chloro-2-[(1R)-7-(8-pyridin-4-yl-3,8-diazaspiro[4.5]decane-3-carbonyl)-1,2,3,4-tetrahydro-naphthalen-1-yl]-2,3-dihydro-isoindol-1-one,

[H-14] 7-chloro-2-[(1R)-7-(9-pyridin-4-yl-3,9-diazaspiro[5.5]undecane-3-carbonyl)-1,2,3,4-tetrahydro-naphthalen-1-yl]-2,3-dihydro-isoindol-1-one,

[H-15] 7-chloro-2-[(1S)-7-(8-pyridin-4-yl-3,8-diazaspiro[4.5]decane-3-carbonyl)-1,2,3,4-tetrahydro-naphthalen-1-yl]-2,3-dihydro-isoindol-1-one,

[H-16] 4-methoxy-2,6-dimethyl-N-[(1R)-7-(8-pyridin-4-yl-3,8-diazaspiro[4.5]decane-3-carbonyl)-1,2,3,4-tetrahydro-naphthalen-1-yl]-benzenesulfonic acid amide,

[H-17]-methoxy-2,6-dimethyl-N-[(1R)-7-(9-pyridin-4-yl-3,9-diazaspiro[5.5]undecane-3-carbonyl)-1,2,3,4-tetrahydro-naphthalen-1-yl]-benzenesulfonic acid amide,

[H-18] 4-methoxy-2,6-dimethyl-N-[(1S)-7-(8-pyridin-4-yl-3,8-diazaspiro[4.5]decane-3-carbonyl)-1,2,3,4-tetrahydro-naphthalen-1-yl]-benzenesulfonic acid amide,

[H-19] 4-methoxy-2,6-dimethyl-N-[(1S)-7-(9-pyridin-4-yl-3,9-diazaspiro[5.5]undecane-3-carbonyl)-1,2,3,4-tetrahydro-naphthalen-1-yl]-benzenesulfonic acid amide,

[H-20] 2-chloro-N-[(1S)-6-(8-pyridin-4-yl-3,8-diazaspiro[4.5]decane-3-carbonyl)-2,3-dihydro-1H-inden-1-yl]-benzamide,

[H-21] 2-chloro-N-[(1R)-6-(8-pyridin-4-yl-3,8-diazaspiro[4.5]decane-3-carbonyl)-2,3-dihydro-1H-inden-1-yl]-benzamide

[H-22] 2-chloro-N-[(1R)-7-(9-pyridin-4-yl-3,9-diazaspiro[5.5]undecane-3-carbonyl)-2,3-dihydro-1H-inden-1-yl]-benzamide,

[H-23] 2-chloro-N-[(1S)-7-(8-pyridin-4-yl-3,8-diazaspiro[4.5]decane-3-carbonyl)-2,3-dihydro-1H-inden-1-yl]-benzamide

[H-24] 2-chloro-N-[(1S)-7-(9-pyridin-4-yl-3,9-diazaspiro[5.5]undecane-3-carbonyl)-2,3-dihydro-1H-inden-1-yl]-benzamide,

[H-25] 2-chloro-N-[(1R)-7-(8-pyridin-4-yl-3,8-diazaspiro[4.5]decane-3-carbonyl)-2,3-dihydro-1H-inden-1-yl]-benzamide

[H-26] 2-chloro-N-[(1R)-6-(8-pyridin-4-yl-3,8-diazaspiro[5.5]undecane-3-carbonyl)-2,3-dihydro-1H-inden-1-yl]-benzamide,

[H-27] 2-chloro-N-[(1R)-6-(7-pyridin-4-yl-2,7-diazaspiro[3.5]nonane-2-carbonyl)-2,3-dihydro-1H-inden-1-yl]-benzamide,

[H-28] 2-chloro-N-[(1R)-6-[9-(1-methyl-piperidin-4-yl)-3,9-diazaspiro[5.5]undecane-3-carbonyl]-2,3-dihydro-1H-inden-1-yl]-benzamide,

[H-29] 2-chloro-N-[(1R)-6-[9-(4-methyl-piperazine-1-carbonyl)-3-azaspiro[5.5]undecane-3-carbonyl]-2,3-dihydro-1H-inden-1-yl]-benzamide,

[H-31] 2-chloro-N-[(1R)-6-[9-[(1-methyl-piperidin-4-yl)-methyl]-3,9-diazaspiro[5.5]undecane-3-carbonyl]-2,3-dihydro-1H-inden-1-yl]-benzamide,

[H-32] 2-chloro-N-[(1R)-6-(spiro[1H-furo[3,4-c]pyridine-3,4'-piperidine]-1'-carbonyl)-2,3-dihydro-1H-inden-1-yl]-benzamide,

[H-33] 2-chloro-N-[(1R)-6-(8-pyridin-4-yl-4,8-diazaspiro[5.5]undecane-4-carbonyl)-2,3-dihydro-1H-inden-1-yl]-benzamide,

[H-34] 2-chloro-N-[(1R)-6-(7-pyridin-4-yl-3,7-diazaspiro[4.5]decane-3-carbonyl)-2,3-dihydro-1H-inden-1-yl]-benzamide,

[H-35] 2-chloro-N-[(1R)-6-(2-pyridin-4-yl-2,9-diazaspiro[4.5]decane-9-carbonyl)-2,3-dihydro-1H-inden-1-yl]-benzamide,

[H-36] N-[(1R)-6-[9-(4-tert-butyl-piperazin-1-yl)-3-azaspiro[5.5]undecane-3-carbonyl]-2,3-dihydro-1H-inden-1-yl]-2-chloro-benzamide,

[H-37] 2-chloro-N-[(1R)-6-[9-(pyrrolidine-1-carbonyl)-3-azaspiro[5.5]undecane-3-carbonyl]-2,3-dihydro-1H-inden-1-yl]-benzamide,

[H-38] 2-chloro-N-[(1R)-6-[8-(2-pyrrolidin-1-yl-acetyl)-3,8-diazaspiro[4.5]decane-3-carbonyl]-2,3-dihydro-1H-inden-1-yl]-benzamide,

[H-39] 2-chloro-N-[6-(8-pyridin-2-yl-3,8-diazaspiro[4.5]decane-3-carbonyl)-2,3-dihydro-1H-inden-1-yl]-benzamide,

[H-40] 2-chloro-N-[6-[8-(4-chlorophenyl)-3,8-diazaspiro[4.5]decane-3-carbonyl]-2,3-dihydro-1H-inden-1-yl]-benzamide,

[H-41] 2-chloro-N-[6-[8-(4-fluorophenyl)-3,8-diazaspiro[4.5]decane-3-carbonyl]-2,3-dihydro-1H-inden-1-yl]-benzamide,

[H-42] 2-chloro-N-[6-[8-[4-(trifluoromethyl)-phenyl]-3,8-diazaspiro[4.5]decane-3-carbonyl]-2,3-dihydro-1H-inden-1-yl]-benzamide,

[H-43] 2-chloro-N-[6-(8-pyridin-3-yl-3,8-diazaspiro[4.5]decane-3-carbonyl)-2,3-dihydro-1H-inden-1-yl]-benzamide,

[H-44] 2-chloro-N-[6-(8-pyrimidin-2-yl-3,8-diazaspiro[4.5]decane-3-carbonyl)-2,3-dihydro-1H-inden-1-yl]-benzamide,

[H-45] 2-chloro-N-[6-[8-[2-(trifluoromethyl)-pyridin-4-yl]-3,8-diazaspiro[4.5]decane-3-carbonyl]-2,3-dihydro-1H-inden-1-yl]-benzamide,

[H-46] 2-chloro-N-[6-[8-[8-(trifluoromethyl)-quinolin-4-yl]-3,8-diazaspiro[4.5]decane-3-carbonyl]-2,3-dihydro-1H-inden-1-yl]-benzamide,

[H-47] 2-chloro-N-[2,2-dimethyl-6-(8-pyridin-4-yl-3,8-diazaspiro[4.5]decane-3-carbonyl)-1,3-dihydro-inden-1-yl]-benzamide,

[H-48] 2-chloro-N-[6-[8-[5-(trifluoromethyl)-pyridin-2-yl]-3,8-diazaspiro[4.5]decane-3-carbonyl]-2,3-dihydro-1H-inden-1-yl]-benzamide,

[H-49] 2-chloro-N-methyl-N-[6-(8-pyridin-4-yl-3,8-diazaspiro[4.5]decane-3-carbonyl)-2,3-dihydro-1H-inden-1-yl]-benzamide,

[H-50] 2-chloro-N-[6-(8-isoquinolin-6-yl-3,8-diazaspiro[4.5]decane-3-carbonyl)-2,3-dihydro-1H-inden-1-yl]-benzamide,

[H-51] 2-chloro-N-[6-[8-[2-(trifluoromethyl)-pyrimidin-4-yl]-3,8-diazaspiro[4.5]-decane-3-carbonyl]-2,3-dihydro-1H-inden-1-yl]-benzamide,

[H-52] N-[(5R)-1-Azabicyclo[2.2.2]octan-5-yl]-3-[(3R)-3-[(2-chloro-benzoyl)amino]-2,3-dihydro-1H-indene-5-carbonyl]-3-azaspiro[5.5]undecane-9-carboxylic acid amide,

[H-53] 2-Methyl-N-[(1R)-6-(8-pyridin-4-yl-3,8-diazaspiro[4.5]decane-3-carbonyl)-2,3-dihydro-1H-inden-1-yl]-benzamide,

[H-54] 2-Chloro-N-[(1R)-6-(9-pyridin-4-yl-2,9-diazaspiro[5.5]undecane-2-carbonyl)-2,3-dihydro-1H-inden-1-yl]-benzamide,

[H-55] 2-Chloro-N-[(1R)-6-[9-(5,6,7,8-tetrahydro-[1,2,4]triazolo[1,5-a]pyrazin-7-yl)-3-azaspiro[5.5]undecane-3-carbonyl]-2,3-dihydro-1H-inden-1-yl]-benzamide,

[H-56] 6-Methoxy-N-[(1R)-6-(8-pyridin-4-yl-3,8-diazaspiro[4.5]decane-3-carbonyl)-2,3-dihydro-1H-inden-1-yl]-naphthalene-2-carboxylic acid amide,

[H-57] 2-Chloro-N-[(4R)-6-(3-pyridin-4-O-3,8-diazaspiro[4.5]decane-8-carbonyl)-3,4-dihydro-2H-chromen-4-yl]-benzamide,

[H-58] 2-Chloro-N-[(4R)-6-(9-pyridin-4-O-3,9-diazaspiro[5.5]undecane-3-carbonyl)-3,4-dihydro-2H-chromen-4-yl]-benzamide,

[H-59] 2-Chloro-N-[(1R)-5-methyl-6-(3-pyridin-4-yl-3,8-diazaspiro[4.5]decane-8-carbonyl)-2,3-dihydro-1H-inden-1-yl]-benzamide,

[H-60] 2-Chloro-4-methoxy-N-[(1R)-6-(3-pyridin-4-yl-3,8-diazaspiro[4.5]decane-8-carbonyl)-2,3-dihydro-1H-inden-1-yl]-benzamide,

[H-61] 4-Methoxy-2-methyl-N-[(1R)-6-(8-pyridin-4-yl-3,8-diazaspiro[4.5]decane-3-carbonyl)-2,3-dihydro-1H-inden-1-yl]-benzamide,

[H-62] N-[(5S)-1-Azabicyclo[2.2.2]octan-5-yl]-3-[(3R)-3-[(2-chloro-benzoyl)amino]-2,3-dihydro-1H-indene-5-carbonyl]-3-azaspiro[5.5]undecane-9-carboxylic acid amide,

[H-63] 2-Chloro-4-methoxy-N-[(1R)-6-(8-pyridin-4-yl-3,8-diazaspiro[4.5]decane-3-carbonyl)-2,3-dihydro-1H-inden-1-yl]-benzamide,

[H-64] 2-Chloro-N-[(1R)-5-fluoro-6-(8-pyridin-4-yl-3,8-diazaspiro[4.5]decane-3-carbonyl)-2,3-dihydro-1H-inden-1-yl]-benzamide hydrochloride,

[H-65] 2-Chloro-N-[(4R)-7-fluoro-6-(8-pyridin-4-yl-3,8-diazaspiro[4.5]decane-3-carbonyl)-3,4-dihydro-2H-chromen-4-yl]-benzamide,

[H-66] 2-Chloro-N-[(1R)-5-methyl-6-(9-pyridin-4-yl-3,9-diazaspiro[5.5]undecane-3-carbonyl)-2,3-dihydro-1H-inden-1-yl]-benzamide,

[H-67] 2-Chloro-N-[(4R)-6-(8-pyridin-4-yl-3,8-diazaspiro[4.5]decane-3-carbonyl)-3,4-dihydro-2H-chromen-4-yl]-benzamide,

[H-68] 6-Methoxy-N-[(1R)-6-(3-pyridin-4-yl-3,8-diazaspiro[4.5]decane-8-carbonyl)-2,3-dihydro-1H-inden-1-yl]-naphthalene-2-carboxylic acid amide,

[H-69] 2-Chloro-N-[(1R)-7-(8-pyridin-4-yl-4,8-diazaspiro[5.5]undecane-4-carbonyl)-1,2,3,4-tetrahydro-naphthalen-1-yl]-benzamide,

[H-70] 2-Chloro-N-[(1R)-7-(2-pyridin-4-yl-2,9-diazaspiro[4.5]decane-9-carbonyl)-1,2,3,4-tetrahydro-naphthalen-1-yl]-benzamide,

[H-71] 2-Chloro-N-[(1R)-7-(7-pyridin-4-yl-2,7-diazaspiro[3.5]nonane-2-carbonyl)-1,2,3,4-tetrahydro-naphthalen-1-yl]-benzamide,

[H-72] 2-Chloro-N-[(1R)-7-(3-pyridin-4-yl-3,8-diazaspiro[4.5]decane-8-carbonyl)-1,2,3,4-tetrahydro-naphthalen-1-yl]-benzamide,

[H-73] 2-Chloro-N-[(4R)-8-fluoro-6-(8-pyridin-4-O-3,8-diazaspiro[4.5]decane-3-carbonyl)-3,4-dihydro-2H-chromen-4-yl]-benzamide,

[H-74] 2-Methyl-N-[(1R)-6-(8-pyridin-4-yl-3,8-diazaspiro[4.5]decane-3-carbonyl)-2,3-dihydro-1H-inden-1-yl]-4-(trifluoromethyloxy)-benzamide,

[H-75] 2-Methyl-N-[(1R)-6-(3-pyridin-4-yl-3,8-diazaspiro[4.5]decane-8-carbonyl)-2,3-dihydro-1H-inden-1-yl]-4-(trifluoromethyloxy)-benzamide,

[H-76] 2-Chloro-N-[(1R)-6-(8-pyridin-4-yl-3,8-diazaspiro[4.5]decane-3-carbonyl)-2,3-dihydro-1H-inden-1-yl]-6-(trifluoromethyl)-benzamide,

[H-77] 2-Chloro-N-[(4R)-8-fluoro-6-(3-pyridin-4-O-3,8-diazaspiro[4.5]decane-8-carbonyl)-3,4-dihydro-2H-chromen-4-yl]-benzamide,

[H-78] 2-Chloro-N-[(4R)-8-fluoro-6-(9-pyridin-4-O-3,9-diazaspiro[5.5]undecane-3-carbonyl)-3,4-dihydro-2H-chromen-4-yl]-benzamide,

[H-79] 2-Chloro-N-[(1R)-7-(8-pyridin-4-yl-3,8-diazaspiro[4.4]nonane-3-carbonyl)-1,2,3,4-tetrahydro-naphthalen-1-yl]-benzamide,

[H-80] 2-Chloro-N-[(1R)-7-(8-pyridin-4-yl-3,8-diazaspiro[5.5]undecane-3-carbonyl)-1,2,3,4-tetrahydro-naphthalen-1-yl]-benzamide,

[H-81] 2-Chloro-N-[(1R)-7-(7-pyridin-4-yl-3,7-diazaspiro[4.5]decane-3-carbonyl)-1,2,3,4-tetrahydro-naphthalen-1-yl]-benzamide,

[H-82] 2-Chloro-N-[(1R)-6-fluoro-7-(8-pyridin-4-yl-3,8-diazaspiro[4.5]decane-3-carbonyl)-1,2,3,4-tetrahydro-naphthalen-1-yl]-benzamide,

[H-83] 2-Chloro-N-[(1R)-6-(3-pyridin-4-yl-3,8-diazaspiro[4.5]decane-8-carbonyl)-2,3-dihydro-1H-inden-1-yl]-6-(trifluoromethyl)-benzamide,

[H-84] N-[(1R)-6-(8-Pyridin-4-yl-3,8-diazaspiro[4.5]decane-3-carbonyl)-2,3-dihydro-1H-inden-1-yl]-pyrimidine-5-carboxylic acid amide,

[H-85] 2-Chloro-N-[(1R)-6-(9-pyridin-4-yl-3,9-diazaspiro[5.5]undecane-3-carbonyl)-2,3-dihydro-1H-inden-1-yl]-6-(trifluoromethyl)-benzamide,

[H-86] N-[(1R)-6-(3-Pyridin-4-yl-3,8-diazaspiro[4.5]decane-8-carbonyl)-2,3-dihydro-1H-inden-1-yl]-pyrimidine-5-carboxylic acid amide,

[H-87] 2-Chloro-N-[(1R)-6-fluoro-7-(3-pyridin-4-yl-3,8-diazaspiro[4.5]decane-8-carbonyl)-1,2,3,4-tetrahydro-naphthalen-1-yl]-benzamide,

[H-88] 2-Chloro-N-[(1R)-6-fluoro-7-(9-pyridin-4-yl-3,9-diazaspiro[5.5]undecane-3-carbonyl)-1,2,3,4-tetrahydro-naphthalen-1-yl]-benzamide,

[H-89] 2-Chloro-N-[(1R)-5-fluoro-6-(3-pyridin-4-yl-3,8-diazaspiro[4.5]decane-8-carbonyl)-2,3-dihydro-1H-inden-1-yl]-benzamide,

[H-90] 2-Chloro-N-[(1R)-5-fluoro-6-(9-pyridin-4-yl-3,9-diazaspiro[5.5]undecane-3-carbonyl)-2,3-dihydro-1H-inden-1-yl]-benzamide,

[H-91] 2-Chloro-N-[(1R)-6-(3-pyridin-4-yl-3,8-diazaspiro[4.5]decane-8-carbonyl)-2,3-dihydro-1H-inden-1-yl]-benzamide,

[H-92] 2-Chloro-N-[(4R)-7-fluoro-6-(9-pyridin-4,1-3,9-diazaspiro[5.5]undecane-3-carbonyl)-3,4-dihydro-2H-chromen-4-yl]-benzamide,

[H-93] 2-Chloro-N-[(1R)-5-methyl-6-(8-pyridin-4-yl-3,8-diazaspiro[4.5]decane-3-carbonyl)-2,3-dihydro-1H-inden-1-yl]-benzamide,

[H-94] 2,3-Dichloro-N-[(1R)-6-(8-pyridin-4-yl-3,8-diazaspiro[4.5]decane-3-carbonyl)-2,3-dihydro-1H-inden-1-yl]-benzamide,

[H-95] 2,3-Dichloro-N-[(1R)-6-(9-pyridin-4-yl-3,9-diazaspiro[5.5]undecane-3-carbonyl)-2,3-dihydro-1H-inden-1-yl]-benzamide,

[H-96] 7-Chloro-2-[(1R)-6-(8-pyridin-4-yl-3,8-diazaspiro[4.5]decane-3-carbonyl)-2,3-dihydro-1H-inden-1-yl]-2,3-dihydro-isoindol-1-one,

[H-97] 2-Chloro-N-[(1R)-6-[9-(5,6,7,8-tetrahydro-[1,2,4]triazolo[1,5-a]pyrazine-7-carbonyl)-3-azaspiro[5.5]undecane-3-carbonyl]-2,3-dihydro-1H-inden-1-yl]-benzamide,

[H-98] 2,5-Dichloro-N-[(1R)-6-(8-pyridin-4-yl-3,8-diazaspiro[4.5]decane-3-carbonyl)-2,3-dihydro-1H-inden-1-yl]-benzamide,

[H-99] 2,6-Dichloro-N-[(1R)-6-(8-pyridin-4-yl-3,8-diazaspiro[4.5]decane-3-carbonyl)-2,3-dihydro-1H-inden-1-yl]-benzamide,

[H-100] 2,6-Dichloro-N-[(1R)-6-(9-pyridin-4-yl-3,9-diazaspiro[5.5]undecane-3-carbonyl)-2,3-dihydro-1H-inden-1-yl]-benzamide,

[H-101] 2-Fluoro-N-[(1R)-6-(8-pyridin-4-yl-3,8-diazaspiro[4.5]decane-3-carbonyl)-2,3-dihydro-1H-inden-1-yl]-benzamide,

[H-102] 2-Fluoro-N-[(1R)-6-(9-pyridin-4-yl-3,9-diazaspiro[5.5]undecane-3-carbonyl)-2,3-dihydro-1H-inden-1-yl]-benzamide,

[H-103] 4-Methoxy-2,5-dimethyl-N-[(1R)-6-(8-pyridin-4-yl-3,8-diazaspiro[4.5]decane-3-carbonyl)-2,3-dihydro-1H-inden-1-yl]-benzamide,

[H-104] 2,6-Dimethyl-N-[(1R)-6-(8-pyridin-4-yl-3,8-diazaspiro[4.5]decane-3-carbonyl)-2,3-dihydro-1H-inden-1-yl]-benzamide,

[H-105] 2-Chloro-N-[(1R)-6-(8-pyridin-4-yl-3,8-diazaspiro[4.5]decane-3-carbonyl)-2,3-dihydro-1H-inden-1-yl]-benzenesulfonic acid amide,

[H-106] 2-Chloro-N-[(1R)-7-(8-pyridin-4-yl-3,8-diazaspiro[4.5]decane-3-carbonyl)-1,2,3,4-tetrahydro-naphthalen-1-yl]-benzenesulfonic acid amide,

[H-107] 2-Chloro-N-[(4R)-6-(8-pyridin-4-O-3,8-diazaspiro[4.5]decane-3-carbonyl)-7-(trifluoromethyl)-3,4-dihydro-2H-chromen-4-yl]-benzamide,

[H-108] 2-Fluoro-4-methoxy-N-[(1R)-6-(8-pyridin-4-yl-3,8-diazaspiro[4.5]decane-3-carbonyl)-2,3-dihydro-1H-inden-1-yl]-benzamide,

[H-109] 2-Chloro-6-fluoro-N-[(1R)-6-(8-pyridin-4-yl-3,8-diazaspiro[4.5]decane-3-carbonyl)-2,3-dihydro-1H-inden-1-yl]-benzamide,

[H-110] 2-Fluoro-N-[(1R)-6-(8-pyridin-4-yl-3,8-diazaspiro[4.5]decane-3-carbonyl)-2,3-dihydro-1H-inden-1-yl]-6-(trifluoromethyl)-benzamide,

[H-111] 2-Chloro-N-[(1R)-6-[8-(2,6-dimethyl-pyridin-4-yl)-3,8-diazaspiro[4.5]decane-3-carbonyl]-2,3-dihydro-1H-inden-1-yl]-benzamide hydrochloride,

[H-112] 2-Chloro-N-[(1R)-6-[8-(2-methyl-pyridin-4-yl)-3,8-diazaspiro[4.5]decane-3-carbonyl]-2,3-dihydro-1H-inden-1-yl]-benzamide,

[H-113] 2,3-Dichloro-N-[(1R)-6-(8-pyridin-4-yl-3,8-diazaspiro[4.5]decane-3-carbonyl)-2,3-dihydro-1H-inden-1-yl]-benzenesulfonic acid amide,

[H-114] 2-Methyl-N-[(1R)-6-(8-pyridin-4-yl-3,8-diazaspiro[4.5]decane-3-carbonyl)-2,3-dihydro-1H-inden-1-yl]-pyridine-3-carboxylic acid amide,

[H-115] N-[(1R)-6-(8-Pyridin-4-yl-3,8-diazaspiro[4.5]decane-3-carbonyl)-2,3-dihydro-1H-inden-1-yl]-4-(trifluoromethyl)-pyridine-3-carboxylic acid amide,

[H-116] 2-Fluoro-N-[(1R)-6-(8-pyridin-4-yl-3,8-diazaspiro[4.5]decane-3-carbonyl)-2,3-dihydro-1H-inden-1-yl]-benzenesulfonic acid amide,

[H-117] 2-Methyl-N-[(1R)-6-(8-pyridin-4-yl-3,8-diazaspiro[4.5]decane-3-carbonyl)-2,3-dihydro-1H-inden-1-yl]-benzenesulfonic acid amide,

[H-118] N-[(1R)-6-(8-Pyridin-4-yl-3,8-diazaspiro[4.5]decane-3-carbonyl)-2,3-dihydro-1H-inden-1-yl]-2-(trifluoromethyl)-benzenesulfonic acid amide,

[H-119] 2,6-Dichloro-N-[(1R)-6-(8-pyridin-4-yl-3,8-diazaspiro[4.5]decane-3-carbonyl)-2,3-dihydro-1H-inden-1-yl]-benzenesulfonic acid amide,

[H-120] 2-Chloro-N-[6-[9-[2-(1H-imidazol-1-yl)-ethoxy]-3-azaspiro[5.5]undecane-3-carbonyl]-2,3-dihydro-1H-inden-1-yl]-benzamide,

[H-128] 2-Chloro-N-[6-(8-hydroxy-8-pyridin-4-yl-3-azaspiro[4.5]decane-3-carbonyl)-2,3-dihydro-1H-inden-1-yl]-benzamide,

[H-129] 2-Chloro-N-[6-[8-(1-oxido-pyridin-1-ium-4-yl)-3,8-diazaspiro[4.5]decane-3-carbonyl]-2,3-dihydro-1H-inden-1-yl]-benzamide,

[H-130] 2-Chloro-N-[6-[8-[5-(trifluoromethyl)-pyrimidin-2-yl]-3,8-diazaspiro[4.5]decane-3-carbonyl]-2,3-dihydro-1H-inden-1-yl]-benzamide,

[H-131] 2-Chloro-N-[6-[9-(1H-imidazol-1-yl)-3-azaspiro[5.5]undecane-3-carbonyl]-2,3-dihydro-1H-inden-1-yl]-benzamide,

[H-132] 2-Chloro-N-[3,3-dimethyl-6-(8-pyridin-4-yl-3,8-diazaspiro[4.5]decane-3-carbonyl)-1,2-dihydro-inden-1-yl]-benzamide,

[H-133] 2-Chloro-N-[6-(8-pyridin-4-yl-3-azaspiro[4.5]decane-3-carbonyl)-2,3-dihydro-1H-inden-1-yl]-benzamide,

[H-134] 5-Methyl-2-[(1R)-6-(8-pyridin-4-yl-3,8-diazaspiro[4.5]decane-3-carbonyl)-2,3-dihydro-1H-inden-1-yl]-1,2-dihydro-pyrrolo[2,1-e]imidazol-3-one,

[H-135] 2-Chloro-N-[(1R)-6-(8-pyridin-3-yl-3-azaspiro[4.5]decane-3-carbonyl)-2,3-dihydro-1H-inden-1-yl]-benzamide,

[H-136] 2-Chloro-N-methyl-N-[(1R)-6-(8-pyridin-4-yl-3,8-diazaspiro[4.5]decane-3-carbonyl)-2,3-dihydro-1H-inden-1-yl]-benzenesulfonic acid amide,

[H-137] 2-Chloro-N-[(1R)-6-(8-pyridin-4-yl-3,8-diazaspiro[4.5]decane-3-carbonyl)-2,3-dihydro-1H-inden-1-yl]-N-(2,2,2-trifluoro-ethyl)-benzamide,

[H-138] 2-Chloro-N-[6-(3-pyridin-4-yl-3,10-diazaspiro[5.6]dodecane-10-carbonyl)-2,3-dihydro-1H-inden-1-yl]-benzamide,

[H-139] 2-Chloro-N-[(1R)-6-[8-(4-methoxyphenyl)-3,8-diazaspiro[4.5]decane-3-carbonyl]-2,3-dihydro-1H-inden-1-yl]-benzamide,

[H-140] 2-Chloro-N-[(1R)-6-[8-(4-cyano-phenyl)-3,8-diazaspiro[4.5]decane-3-carbonyl]-2,3-dihydro-1H-inden-1-yl]-benzamide,

[H-141] 2-Chloro-5-fluoro-N-[(1R)-6-(8-pyridin-4-yl-3,8-diazaspiro[4.5]decane-3-carbonyl)-2,3-dihydro-1H-inden-1-yl]-benzamide,

[H-142] 2,5-Dichloro-N-[(1R)-6-(8-pyridin-4-yl-3,8-diazaspiro[4.5]decane-3-carbonyl)-2,3-dihydro-1H-inden-1-yl]-benzenesulfonic acid amide,

[H-143] 3-Methyl-N-[(1R)-6-(8-pyridin-4-yl-3,8-diazaspiro[4.5]decane-3-carbonyl)-2,3-dihydro-1H-inden-1-yl]-butyramide,

[H-144] 4-Methoxy-N-[(1R)-6-(8-pyridin-4-yl-3,8-diazaspiro[4.5]decane-3-carbonyl)-2,3-dihydro-1H-inden-1-yl]-2-(trifluoromethyl)-benzenesulfonic acid amide,

[H-145] 2-(2-Chlorophenyl)-N-[(1R)-6-(8-pyridin-4-yl-3,8-diazaspiro[4.5]decane-3-carbonyl)-2,3-dihydro-1H-inden-1-yl]-propionamide,

[H-146] 2-(2-Chlorophenyl)-2-methyl-N-[(1R)-6-(8-pyridin-4-yl-3,8-diazaspiro[4.5]decane-3-carbonyl)-2,3-dihydro-1H-inden-1-yl]-propionamide,

[H-147] 4-Methoxy-2-methyl-N-[(1R)-6-(8-pyridin-4-yl-3,8-diazaspiro[4.5]decane-3-carbonyl)-2,3-dihydro-1H-inden-1-yl]-benzenesulfonic acid amide,

[H-148] 1-(2-Chlorophenyl)-N-[(1R)-6-(8-pyridin-4-yl-3,8-diazaspiro[4.5]decane-3-carbonyl)-2,3-dihydro-1H-inden-1-yl]-cyclopropane-1-carboxylic acid amide,

[H-149] 2-Chloro-N-[(1R)-6-(8-pyridin-4-yl-3,8-diazaspiro[4.5]decane-3-carbonyl)-2,3-dihydro-1H-inden-1-yl]-6-(trifluoromethyl)-benzenesulfonic acid amide,

[H-150] 1-(2-Chlorophenyl)-N-[(1R)-6-(8-pyridin-4-yl-3,8-diazaspiro[4.5]decane-3-carbonyl)-2,3-dihydro-1H-inden-1-yl]-methanesulfonic acid amide,

[H-151] 2-(2-Chlorophenyl)-N-[(1R)-6-(8-pyridin-4-yl-3,8-diazaspiro[4.5]decane-3-carbonyl)-2,3-dihydro-1H-inden-1-yl-]acetamide,

[H-152] 2-(2-Fluorophenyl)-N-[(1R)-6-(8-pyridin-4-yl-3,8-diazaspiro[4.5]decane-3-carbonyl)-2,3-dihydro-1H-inden-1-yl]-acetamide,

[H-153] 2-Chloro-3-fluoro-N-[(1R)-6-(8-pyridin-4-yl-3,8-diazaspiro[4.5]decane-3-carbonyl)-2,3-dihydro-1H-inden-1-yl]-benzamide,

[H-154] 2-(o-Tolyl)-N-[(1R)-6-(8-pyridin-4-yl-3,8-diazaspiro[4.5]decane-3-carbonyl)-2,3-dihydro-1H-inden-1-yl]-acetamide,

[H-155] 2-Chloro-N-[(1S)-5-(8-pyridin-4-yl-3,8-diazaspiro[4.5]decane-3-carbonyl)-2,3-dihydro-1H-inden-1-yl]-benzamide,

[H-156] 2-Chloro-N-[(1S)-5-(9-pyridin-4-yl-3,9-diazaspiro[5.5]undecane-3-carbonyl)-2,3-dihydro-1H-inden-1-yl]-benzamide,

[H-157] 7-Chloro-2-[(1S)-5-(8-pyridin-4-yl-3,8-diazaspiro[4.5]decane-3-carbonyl)-2,3-dihydro-1H-inden-1-yl]-2,3-dihydro-isoindol-1-one,

[H-158] 7-Chloro-2-[(1S)-5-(9-pyridin-4-yl-3,9-diazaspiro[5.5]undecane-3-carbonyl)-2,3-dihydro-1H-inden-1-yl]-2,3-dihydro-isoindol-1-one,

[H-159] 7-Chloro-2-[(1R)-5-(9-pyridin-4-yl-3,9-diazaspiro[5.5]undecane-3-carbonyl)-2,3-dihydro-1H-inden-1-yl]-2,3-dihydro-isoindol-1-one,

[H-160] 7-Chloro-2-[(1R)-5-(8-pyridin-4-yl-3,8-diazaspiro[4.5]decane-3-carbonyl)-2,3-dihydro-1H-inden-1-yl]-2,3-dihydro-isoindol-1-one,

[H-161] 2-Chloro-N-[(1S)-4-(8-pyridin-4-yl-3,8-diazaspiro[4.5]decane-3-carbonyl)-2,3-dihydro-1H-inden-1-yl]-benzamide,

[H-162] 2-Chloro-N-[(1R)-4-(8-pyridin-4-yl-3,8-diazaspiro[4.5]decane-3-carbonyl)-2,3-dihydro-1H-inden-1-yl]-benzamide,

[H-163] 2-Chloro-N-[(1S)-4-(9-pyridin-4-yl-3,9-diazaspiro[5.5]undecane-3-carbonyl)-2,3-dihydro-1H-inden-1-yl]-benzamide,

[H-164] 2-Chloro-N-[(1R)-4-(9-pyridin-4-yl-3,9-diazaspiro[5.5]undecane-3-carbonyl)-2,3-dihydro-1H-inden-1-yl]-benzamide,

[H-165] 2-Chloro-N-[(1S)-4-(8-pyridin-4-yl-3,8-diazaspiro[4.5]decane-3-carbonyl)-2,3-dihydro-1H-inden-1-yl]-benzenesulfonic acid amide,

[H-166] 2-Chloro-N-[(1R)-4-(8-pyridin-4-yl-3,8-diazaspiro[4.5]decane-3-carbonyl)-2,3-dihydro-1H-inden-1-yl]-benzenesulfonic acid amide,

[H-167] 2-Chloro-N-[(1R)-4-(9-pyridin-4-yl-3,9-diazaspiro[5.5]undecane-3-carbonyl)-2,3-dihydro-1H-inden-1-yl]-benzenesulfonic acid amide,

[H-168] 7-Chloro-2-[(1S)-4-(8-pyridin-4-yl-3,8-diazaspiro[4.5]decane-3-carbonyl)-2,3-dihydro-1H-inden-1-yl]-2,3-dihydro-isoindol-1-one,

[H-169] 7-Chloro-2-[(1R)-4-(8-pyridin-4-yl-3,8-diazaspiro[4.5]decane-3-carbonyl)-2,3-dihydro-1H-inden-1-yl]-2,3-dihydro-isoindol-1-one,

[H-170] 7-Chloro-2-[(1R)-4-(9-pyridin-4-yl-3,9-diazaspiro[5.5]undecane-3-carbonyl)-2,3-dihydro-1H-inden-1-yl]-2,3-dihydro-isoindol-1-one,

[H-171] 2-Chloro-N-[(1R)-5-(8-pyridin-4-yl-3,8-diazaspiro[4.5]decane-3-carbonyl)-2,3-dihydro-1H-inden-1-yl]-benzamide,

[H-172] 2-Chloro-N-[(1R)-5-(9-pyridin-4-yl-3,9-diazaspiro[5.5]undecane-3-carbonyl)-2,3-dihydro-1H-inden-1-yl]-benzamide,

[H-173] 2-Chloro-N-[(1R)-5-(8-pyridin-4-yl-3,8-diazaspiro[4.5]decane-3-carbonyl)-2,3-dihydro-1H-inden-1-yl]-benzenesulfonic acid amide,

[Ind_CC-001] 4-methoxy-2,6-dimethyl-N-[6-(9-pyridin-4-yl-3,9-diazaspiro[5.5]undecane-3-carbonyl)-2,3-dihydro-1H-inden-1-yl]-benzenesulfonic acid amide,

[Ind_CC-002] N-[6-(9-pyridin-4-yl-3,9-diazaspiro[5.5]undecane-3-carbonyl)-2,3-dihydro-1H-inden-1-yl]-pyridine-2-carboxylic acid amide,

[Ind_CC-003] N-[6-(9-pyridin-4-yl-3,9-diazaspiro[5.5]undecane-3-carbonyl)-2,3-dihydro-1H-inden-1-yl]-2-(trifluoromethyl)-benzamide,

[Ind_CC-004] 3-chloro-N-[6-(9-pyridin-4-yl-3,9-diazaspiro[5.5]undecane-3-carbonyl)-2,3-dihydro-1H-inden-1-yl]-thiophene-2-carboxylic acid amide,

[Ind_CC-005] 5-chloro-N-[6-(9-pyridin-4-yl-3,9-diazaspiro[5.5]undecane-3-carbonyl)-2,3-dihydro-1H-inden-1-yl]-thiophene-2-carboxylic acid amide,

[Ind_CC-006] 2,4-dichloro-N-[6-(9-pyridin-4-yl-3,9-diazaspiro[5.5]undecane-3-carbonyl)-2,3-dihydro-1H-inden-1-yl]-benzamide,

[Ind_CC-007] 2-(2-chlorophenyl)-N-[6-(9-pyridin-4-yl-3,9-diazaspiro[5.5]undecane-3-carbonyl)-2,3-dihydro-1H-inden-1-yl]-acetamide,

[Ind_CC-008] (E)-3-(2-chlorophenyl)-N-[6-(9-pyridin-4-yl-3,9-diazaspiro[5.5]undecane-3-carbonyl)-2,3-dihydro-1H-inden-1-yl-]acrylamide,

[Ind_CC-009] 2-(2-chlorophenyl)-2-phenyl-N-[6-(9-pyridin-4-yl-3,9-diazaspiro[5.5]undecane-3-carbonyl)-2,3-dihydro-1H-inden-1-yl-]acetamide,

[Ind_CC-010] 2-chloro-N-[6-(9-pyridin-4-yl-3,9-diazaspiro[5.5]undecane-3-carbonyl)-2,3-dihydro-1H-inden-1-yl]-benzenesulfonic acid amide,

[Ind_CC-011] 1-(3,4-dichlorophenyl)-3-[6-(9-pyridin-4-yl-3,9-diazaspiro[5.5]undecane-3-carbonyl)-2,3-dihydro-1H-inden-1-yl]-urea,

[Ind_CC-012] 1-[(2-chlorophenyl)-methyl]-3-[6-(9-pyridin-4-yl-3,9-diazaspiro[5.5]undecane-3-carbonyl)-2,3-dihydro-1H-inden-1-yl]-urea,

[Ind_CC-013] 4-methoxy-2,6-dimethyl-N-[6-(9-pyridin-4-yl-3,9-diazaspiro[5.5]undecane-3-carbonyl)-2,3-dihydro-1H-inden-1-yl]-benzamide,

[Ind_CC-014] N-methyl-N-[6-(9-pyridin-4-yl-3,9-diazaspiro[5.5]undecane-3-carbonyl)-2,3-dihydro-1H-inden-1-yl]-pyridine-2-carboxylic acid amide,

[Ind_CC-015] N-methyl-N-[6-(9-pyridin-4-yl-3,9-diazaspiro[5.5]undecane-3-carbonyl)-2,3-dihydro-1H-inden-1-yl]-2-(trifluoromethyl)-benzamide,

[Ind_CC-016] 3-chloro-N-methyl-N-[6-(9-pyridin-4-yl-3,9-diazaspiro[5.5]undecane-3-carbonyl)-2,3-dihydro-1H-inden-1-yl]-thiophene-2-carboxylic acid amide,

[Ind_CC-017] 5-chloro-N-methyl-N-[6-(9-pyridin-4-yl-3,9-diazaspiro[5.5]undecane-3-carbonyl)-2,3-dihydro-1H-inden-1-yl]-thiophene-2-carboxylic acid amide,

[Ind_CC-018] 2,4-dichloro-N-methyl-N-[6-(9-pyridin-4-yl-3,9-diazaspiro[5.5]undecane-3-carbonyl)-2,3-dihydro-1H-inden-1-yl]-benzamide,

[Ind_CC-019] 2-(2-chlorophenyl)-N-methyl-N-[6-(9-pyridin-4-yl-3,9-diazaspiro[5.5]undecane-3-carbonyl)-2,3-dihydro-1H-inden-1-yl-]acetamide,

[Ind_CC-020] (E)-3-(2-chlorophenyl)-N-methyl-N-[6-(9-pyridin-4-yl-3,9-diazaspiro[5.5]undecane-3-carbonyl)-2,3-dihydro-1H-inden-1-yl-]acrylamide,

[Ind_CC-021] 2-(2-chlorophenyl)-N-methyl-2-phenyl-N-[6-(9-pyridin-4-yl-3,9-diazaspiro[5.5]undecane-3-carbonyl)-2,3-dihydro-1H-inden-1-yl-]acetamide,

[Ind_CC-022] 3-(3,4-dichlorophenyl)-1-methyl-1-[6-(9-pyridin-4-yl-3,9-diazaspiro[5.5]undecane-3-carbonyl)-2,3-dihydro-1H-inden-1-yl]-urea,

[Ind_CC-023] 3-[(2-chlorophenyl)-methyl]-1-methyl-1-[6-(9-pyridin-4-yl-3,9-diazaspiro[5.5]undecane-3-carbonyl)-2,3-dihydro-1H-inden-1-yl]-urea,

[Ind_CC-024] 2-chloro-N-methyl-N-[6-(9-pyridin-4-yl-3,9-diazaspiro[5.5]undecane-3-carbonyl)-2,3-dihydro-1H-inden-1-yl]-benzenesulfonic acid amide,

[Ind_CC-025] 4-methoxy-N,2,6-trimethyl-N-[6-(9-pyridin-4-yl-3,9-diazaspiro[5.5]undecane-3-carbonyl)-2,3-dihydro-1H-inden-1-yl]-benzenesulfonic acid amide,

[Ind_CC-026] 4-methoxy-N,2,6-trimethyl-N-[6-(9-pyridin-4-yl-3,9-diazaspiro[5.5]undecane-3-carbonyl)-2,3-dihydro-1H-inden-1-yl]-benzamide,

[Ind_CC-027] N-[6-[9-[4-(trifluoromethyl)-phenyl]-3,9-diazaspiro[5.5]undecane-3-carbonyl]-2,3-dihydro-1H-inden-1-yl]-pyridine-2-carboxylic acid amide,

[Ind_CC-028] 2-(trifluoromethyl)-N-[6-[9-[4-(trifluoromethyl)-phenyl]-3,9-diazaspiro[5.5]undecane-3-carbonyl]-2,3-dihydro-1H-inden-1-yl]-benzamide,

[Ind_CC-029] 3-chloro-N-[6-[9-[4-(trifluoromethyl)-phenyl]-3,9-diazaspiro[5.5]undecane-3-carbonyl]-2,3-dihydro-1H-inden-1-yl]-thiophene-2-carboxylic acid amide,

[Ind_CC-030] 5-chloro-N-[6-[9-[4-(trifluoromethyl)-phenyl]-3,9-diazaspiro[5.5]undecane-3-carbonyl]-2,3-dihydro-1H-inden-1-yl]-thiophene-2-carboxylic acid amide,

[Ind_CC-031] 2,4-dichloro-N-[6-[9-[4-(trifluoromethyl)-phenyl]-3,9-diazaspiro[5.5]undecane-3-carbonyl]-2,3-dihydro-1H-inden-1-yl]-benzamide,

[Ind_CC-032] 2-(2-chlorophenyl)-N-[6-[9-[4-(trifluoromethyl)-phenyl]-3,9-diazaspiro[5.5]undecane-3-carbonyl]-2,3-dihydro-1H-inden-1-yl-]acetamide,

[Ind_CC-033] (E)-3-(2-chlorophenyl)-N-[6-[9-[4-(trifluoromethyl)-phenyl]-3,9-diazaspiro[5.5]undecane-3-carbonyl]-2,3-dihydro-1H-inden-1-yl-]acrylamide,

[Ind_CC-034] 2-chloro-N-[6-[9-[4-(trifluoromethyl)-phenyl]-3,9-diazaspiro[5.5]undecane-3-carbonyl]-2,3-dihydro-1H-inden-1-yl]-benzenesulfonic acid amide,

[Ind_CC-035] 4-methoxy-2,6-dimethyl-N-[6-[9-[4-(trifluoromethyl)-phenyl]-3,9-diazaspiro[5.5]undecane-3-carbonyl]-2,3-dihydro-1H-inden-1-yl]-benzenesulfonic acid amide,

[Ind_CC-036] 1-(3,4-dichlorophenyl)-3-[6-[9-[4-(trifluoromethyl)-phenyl]-3,9-diazaspiro[5.5]undecane-3-carbonyl]-2,3-dihydro-1H-inden-1-yl]-urea,

[Ind_CC-037] 1-[(2-chlorophenyl)-methyl]-3-[6-[9-[4-(trifluoromethyl)-phenyl]-3,9-diazaspiro[5.5]undecane-3-carbonyl]-2,3-dihydro-1H-inden-1-yl]-urea,

[Ind_CC-038] 2-(2-chlorophenyl)-2-phenyl-N-[6-[9-[4-(trifluoromethyl)-phenyl]-3,9-diazaspiro[5.5]undecane-3-carbonyl]-2,3-dihydro-1H-inden-1-yl-]acetamide,

[Ind_CC-039] 4-methoxy-2,6-dimethyl-N-[6-[9-[4-(trifluoromethyl)-phenyl]-3,9-diazaspiro[5.5]undecane-3-carbonyl]-2,3-dihydro-1H-inden-1-yl]-benzamide,

[Ind_CC-040] N-[6-(2-pyridin-4-yl-2,8-diazaspiro[4.5]decane-8-carbonyl)-2,3-dihydro-1H-inden-1-yl]-pyridine-2-carboxylic acid amide,

[Ind_CC-041] N-[6-(2-pyridin-4-yl-2,8-diazaspiro[4.5]decane-8-carbonyl)-2,3-dihydro-1H-inden-1-yl]-2-(trifluoromethyl)-benzamide,

[Ind_CC-042] 3-chloro-N-[6-(2-pyridin-4-yl-2,8-diazaspiro[4.5]decane-8-carbonyl)-2,3-dihydro-1H-inden-1-yl]-thiophene-2-carboxylic acid amide,

[Ind_CC-043] 5-chloro-N-[6-(2-pyridin-4-yl-2,8-diazaspiro[4.5]decane-8-carbonyl)-2,3-dihydro-1H-inden-1-yl]-thiophene-2-carboxylic acid amide,

[Ind_CC-044] 2,4-dichloro-N-[6-(2-pyridin-4-yl-2,8-diazaspiro[4.5]decane-8-carbonyl)-2,3-dihydro-1H-inden-1-yl]-benzamide,

[Ind_CC-045] 2-(2-chlorophenyl)-N-[6-(2-pyridin-4-yl-2,8-diazaspiro[4.5]decane-8-carbonyl)-2,3-dihydro-1H-inden-1-yl-]acetamide,

[Ind_CC-046] (E)-3-(2-chlorophenyl)-N-[6-(2-pyridin-4-yl-2,8-diazaspiro[4.5]decane-8-carbonyl)-2,3-dihydro-1H-inden-1-yl-]acrylamide,

[Ind_CC-047] 1-(3,4-dichlorophenyl)-3-[6-(2-pyridin-4-yl-2,8-diazaspiro[4.5]decane-8-carbonyl)-2,3-dihydro-1H-inden-1-yl]-urea,
[Ind_CC-048] 1-[(2-chlorophenyl)-methyl]-3-[6-(2-pyridin-4-yl-2,8-diazaspiro[4.5]decane-8-carbonyl)-2,3-dihydro-1H-inden-1-yl]-urea,
[Ind_CC-049] 2-chloro-N-[6-(2-pyridin-4-yl-2,8-diazaspiro[4.5]decane-8-carbonyl)-2,3-dihydro-1H-inden-1-yl]-benzenesulfonic acid amide,
[Ind_CC-050] 4-methoxy-2,6-dimethyl-N-[6-(2-pyridin-4-yl-2,8-diazaspiro[4.5]decane-8-carbonyl)-2,3-dihydro-1H-inden-1-yl]-benzenesulfonic acid amide,
[Ind_CC-051] 2-(2-chlorophenyl)-2-phenyl-N-[6-(2-pyridin-4-yl-2,8-diazaspiro[4.5]decane-8-carbonyl)-2,3-dihydro-1H-inden-1-yl]-acetamide,
[Ind_CC-052] N-[3,3-dimethyl-6-(9-pyridin-4-yl-3,9-diazaspiro[5.5]undecane-3-carbonyl)-1,2-dihydro-inden-1-yl]-pyridine-2-carboxylic acid amide,
[Ind_CC-053] 2-(2-chlorophenyl)-N-[3,3-dimethyl-6-(9-pyridin-4-yl-3,9-diazaspiro[5.5]undecane-3-carbonyl)-1,2-dihydro-inden-1-yl-]acetamide,
[Ind_CC-054] 5-chloro-N-[3,3-dimethyl-6-(9-pyridin-4-yl-3,9-diazaspiro[5.5]undecane-3-carbonyl)-1,2-dihydro-inden-1-yl]-thiophene-2-carboxylic acid amide,
[Ind_CC-055] 3-chloro-N-[3,3-dimethyl-6-(9-pyridin-4-yl-3,9-diazaspiro[5.5]undecane-3-carbonyl)-1,2-dihydro-inden-1-yl]-thiophene-2-carboxylic acid amide,
[Ind_CC-056] 2-(2-chlorophenyl)-N-[3,3-dimethyl-6-(9-pyridin-4-yl-3,9-diazaspiro-[5.5]undecane-3-carbonyl)-1,2-dihydro-inden-1-yl]-2-phenyl-acetamide,
[Ind_CC-057] 1-(3,4-dichlorophenyl)-3-[3,3-dimethyl-6-(9-pyridin-4-yl-3,9-diazaspiro[5.5]undecane-3-carbonyl)-1,2-dihydro-inden-1-yl]-urea,
[Ind_CC-058] N-[3,3-dimethyl-6-(9-pyridin-4-yl-3,9-diazaspiro[5.5]undecane-3-carbonyl)-1,2-dihydro-inden-1-yl]-2-(trifluoromethyl)-benzamide,
[Ind_CC-059] 2,4-dichloro-N-[3,3-dimethyl-6-(9-pyridin-4-yl-3,9-diazaspiro[5.5]undecane-3-carbonyl)-1,2-dihydro-inden-1-yl]-benzamide,
[Ind_CC-060] (E)-3-(2-chlorophenyl)-N-[3,3-dimethyl-6-(9-pyridin-4-yl-3,9-diazaspiro[5.5]undecane-3-carbonyl)-1,2-dihydro-inden-1-yl-]acrylamide,
[Ind_CC-061] 1-[(2-chlorophenyl)-methyl]-3-[3,3-dimethyl-6-(9-pyridin-4-yl-3,9-diazaspiro[5.5]undecane-3-carbonyl)-1,2-dihydro-inden-1-yl]-urea,
[Ind_CC-062] 2-chloro-N-[3,3-dimethyl-6-(9-pyridin-4-yl-3,9-diazaspiro[5.5]undecane-3-carbonyl)-1,2-dihydro-inden-1-yl]-benzenesulfonic acid amide,
[Ind_CC-063] N-[3,3-dimethyl-6-(9-pyridin-4-yl-3,9-diazaspiro[5.5]undecane-3-carbonyl)-1,2-dihydro-inden-1-yl]-4-methoxy-2,6-dimethyl-benzenesulfonic acid amide,
[Ind_CC-064] N-[2,2-dimethyl-6-(9-pyridin-4-yl-3,9-diazaspiro[5.5]undecane-3-carbonyl)-1,3-dihydro-inden-1-yl]-2-(trifluoromethyl)-benzamide,
[Ind_CC-065] 3-chloro-N-[2,2-dimethyl-6-(9-pyridin-4-yl-3,9-diazaspiro[5.5]undecane-3-carbonyl)-1,3-dihydro-inden-1-yl]-thiophene-2-carboxylic acid amide,
[Ind_CC-066] 5-chloro-N-[2,2-dimethyl-6-(9-pyridin-4-yl-3,9-diazaspiro[5.5]undecane-3-carbonyl)-1,3-dihydro-inden-1-yl]-thiophene-2-carboxylic acid amide,
[Ind_CC-067] 2,4-dichloro-N-[2,2-dimethyl-6-(9-pyridin-4-yl-3,9-diazaspiro[5.5]undecane-3-carbonyl)-1,3-dihydro-inden-1-yl]-benzamide,
[Ind_CC-068] N-[2,2-dimethyl-6-(9-pyridin-4-yl-3,9-diazaspiro[5.5]undecane-3-carbonyl)-1,3-dihydro-inden-1-yl]-4-methoxy-2,6-dimethyl-benzamide,
[Ind_CC-069] 2-(2-chlorophenyl)-N-[2,2-dimethyl-6-(9-pyridin-4-yl-3,9-diazaspiro[5.5]undecane-3-carbonyl)-1,3-dihydro-inden-1-yl-]acetamide,
[Ind_CC-070] (E)-3-(2-chlorophenyl)-N-[2,2-dimethyl-6-(9-pyridin-4-yl-3,9-diazaspiro[5.5]undecane-3-carbonyl)-1,3-dihydro-inden-1-yl-]acrylamide,
[Ind_CC-071] 1-(3,4-dichlorophenyl)-3-[2,2-dimethyl-6-(9-pyridin-4-yl-3,9-diazaspiro[5.5]undecane-3-carbonyl)-1,3-dihydro-inden-1-yl]-urea,
[Ind_CC-072] 2-chloro-N-[2,2-dimethyl-6-(9-pyridin-4-yl-3,9-diazaspiro[5.5]undecane-3-carbonyl)-1,3-dihydro-inden-1-yl]-benzenesulfonic acid amide,
[Ind_CC-073] 1-[(2-chlorophenyl)-methyl]-3-[2,2-dimethyl-6-(9-pyridin-4-yl-3,9-diazaspiro[5.5]undecane-3-carbonyl)-1,3-dihydro-inden-1-yl]-urea,
[Ind_CC-074] N-[2,2-dimethyl-6-(9-pyridin-4-yl-3,9-diazaspiro[5.5]undecane-3-carbonyl)-1,3-dihydro-inden-1-yl]-pyridine-2-carboxylic acid amide,
[Ind_CC-075] 2-(2-chlorophenyl)-N-[2,2-dimethyl-6-(9-pyridin-4-yl-3,9-diazaspiro-[5.5]undecane-3-carbonyl)-1,3-dihydro-inden-1-yl]-2-phenyl-acetamide,
[Ind_CC-076] N-[2,2-dimethyl-6-(9-pyridin-4-yl-3,9-diazaspiro[5.5]undecane-3-carbonyl)-1,3-dihydro-inden-1-yl]-4-methoxy-2,6-dimethyl-benzenesulfonic acid amide,
[Ind_CC-077] 2-(2-chlorophenyl)-N-[6-(8-pyridin-4-yl-2,8-diazaspiro[4.5]decane-2-carbonyl)-2,3-dihydro-1H-inden-1-yl-]acetamide,
[Ind_CC-078] 2,4-dichloro-N-[6-(8-pyridin-4-yl-3,8-diazaspiro[4.5]decane-3-carbonyl)-2,3-dihydro-1H-inden-1-yl]-benzamide,
[Ind_CC-079] 5-chloro-N-[6-(8-pyridin-4-yl-3,8-diazaspiro[4.5]decane-3-carbonyl)-2,3-dihydro-1H-inden-1-yl]-thiophene-2-carboxylic acid amide,
[Ind_CC-080] 3-chloro-N-[6-(8-pyridin-4-yl-3,8-diazaspiro[4.5]decane-3-carbonyl)-2,3-dihydro-1H-inden-1-yl]-thiophene-2-carboxylic acid amide,
[Ind_CC-081] N-[6-(8-pyridin-4-yl-3,8-diazaspiro[4.5]decane-3-carbonyl)-2,3-dihydro-1H-inden-1-yl]-2-(trifluoromethyl)-benzamide,
[Ind_CC-082] 2-(2-chlorophenyl)-2-phenyl-N-[6-(8-pyridin-4-yl-3,8-diazaspiro[4.5]decane-3-carbonyl)-2,3-dihydro-1H-inden-1-yl-]acetamide,
[Ind_CC-083] (E)-3-(2-chlorophenyl)-N-[6-(8-pyridin-4-yl-2,8-diazaspiro[4.5]decane-2-carbonyl)-2,3-dihydro-1H-inden-1-yl-]acrylamide,
[Ind_CC-084] N-[6-(8-pyridin-4-yl-3,8-diazaspiro[4.5]decane-3-carbonyl)-2,3-dihydro-1H-inden-1-yl]-pyridine-2-carboxylic acid amide,
[Ind_CC-085] 1-(3,4-dichlorophenyl)-3-[6-(8-pyridin-4-yl-2,8-diazaspiro[4.5]decane-2-carbonyl)-2,3-dihydro-1H-inden-1-yl]-urea,
[Ind_CC-086] 1-[(2-chlorophenyl)-methyl]-3-[6-(8-pyridin-4-yl-2,8-diazaspiro[4.5]decane-2-carbonyl)-2,3-dihydro-1H-inden-1-yl]-urea,
[Ind_CC-087] 4-methoxy-2,6-dimethyl-N-[6-(8-pyridin-4-yl-2,8-diazaspiro[4.5]decane-2-carbonyl)-2,3-dihydro-1H-inden-1-yl]-benzenesulfonic acid amide,
[Ind_CC-088] 4-methoxy-2,6-dimethyl-N-[6-(8-pyridin-4-yl-2,8-diazaspiro[4.5]decane-2-carbonyl)-2,3-dihydro-1H-inden-1-yl]-benzamide,
[Ind_CC-089] 2-chloro-N-[6-(8-pyridin-4-yl-3,8-diazaspiro[4.5]decane-3-carbonyl)-2,3-dihydro-1H-inden-1-yl]-benzenesulfonic acid amide,
[Ind_CC-090] 4-methoxy-2,6-dimethyl-N-[6-(9-pyridin-3-yl-3,9-diazaspiro[5.5]undecane-3-carbonyl)-2,3-dihydro-1H-inden-1-yl]-benzamide,

[Ind_CC-091] N-[6-[9-(4-fluorophenyl)-3,9-diazaspiro[5.5]undecane-3-carbonyl]-2,3-dihydro-1H-inden-1-yl]-4-methoxy-2,6-dimethyl-benzamide,

[Ind_CC-092] 4-methoxy-2,6-dimethyl-N-[6-[9-(pyridin-4-yl-methyl)-3,9-diazaspiro[5.5]undecane-3-carbonyl]-2,3-dihydro-1H-inden-1-yl]-benzamide,

[Ind_CC-093] N-[6-[9-dimethylamino-9-(4-fluorophenyl)-3-azaspiro[5.5]undecane-3-carbonyl]-2,3-dihydro-1H-inden-1-yl]-4-methoxy-2,6-dimethyl-benzamide,

[Ind_CC-094] 4-methoxy-2,6-dimethyl-N-[6-(2-pyridin-4-yl-2,8-diazaspiro[4.5]decane-8-carbonyl)-2,3-dihydro-1H-inden-1-yl]-benzamide,

[Ind_CC-095] 2-chloro-N-[6-(9-pyridin-4-yl-3,9-diazaspiro[5.5]undecane-3-carbonyl)-2,3-dihydro-1H-inden-1-yl]-benzamide,

[Ind_CC-096] 2-chloro-N-[6-(9-pyridin-3-yl-3,9-diazaspiro[5.5]undecane-3-carbonyl)-2,3-dihydro-1H-inden-1-yl]-benzamide,

[Ind_CC-097] 2-chloro-N-[6-[9-(4-fluorophenyl)-3,9-diazaspiro[5.5]undecane-3-carbonyl]-2,3-dihydro-1H-inden-1-yl]-benzamide,

[Ind_CC-098] 2-chloro-N-[6-[9-(pyridin-4-yl-methyl)-3,9-diazaspiro[5.5]undecane-3-carbonyl]-2,3-dihydro-1H-inden-1-yl]-benzamide,

[Ind_CC-099] 2-chloro-N-[6-[9-dimethylamino-9-(4-fluorophenyl)-3-azaspiro[5.5]undecane-3-carbonyl]-2,3-dihydro-1H-inden-1-yl]-benzamide,

[Ind_CC-100] 2-chloro-N-[6-(8-pyridin-4-yl-2,8-diazaspiro[4.5]decane-2-carbonyl)-2,3-dihydro-1H-inden-1-yl]-benzamide,

[Ind_CC-101] 2-chloro-N-[6-(2-pyridin-4-yl-2,8-diazaspiro[4.5]decane-8-carbonyl)-2,3-dihydro-1H-inden-1-yl]-benzamide,

[Ind_CC-102] 3-chloro-N-[6-(9-pyridin-3-yl-3,9-diazaspiro[5.5]undecane-3-carbonyl)-2,3-dihydro-1H-inden-1-yl]-thiophene-2-carboxylic acid amide,

[Ind_CC-103] 3-chloro-N-[6-[9-(4-fluorophenyl)-3,9-diazaspiro[5.5]undecane-3-carbonyl]-2,3-dihydro-1H-inden-1-yl]-thiophene-2-carboxylic acid amide,

[Ind_CC-104] 3-chloro-N-[6-[9-(pyridin-4-yl-methyl)-3,9-diazaspiro[5.5]undecane-3-carbonyl]-2,3-dihydro-1H-inden-1-yl]-thiophene-2-carboxylic acid amide,

[Ind_CC-105] 3-chloro-N-[6-[9-dimethylamino-9-(4-fluorophenyl)-3-azaspiro[5.5]undecane-3-carbonyl]-2,3-dihydro-1H-inden-1-yl]-thiophene-2-carboxylic acid amide,

[Ind_CC-106] 2-chloro-N-methyl-N-[6-(9-pyridin-4-yl-3,9-diazaspiro[5.5]undecane-3-carbonyl)-2,3-dihydro-1H-inden-1-yl]-benzamide,

[Ind_CC-107] 2-chloro-N-methyl-N-[6-(9-pyridin-3-yl-3,9-diazaspiro[5.5]undecane-3-carbonyl)-2,3-dihydro-1H-inden-1-yl]-benzamide,

[Ind_CC-108] 2-chloro-N-[6-[9-(4-fluorophenyl)-3,9-diazaspiro[5.5]undecane-3-carbonyl]-2,3-dihydro-1H-inden-1-yl]-N-methyl-benzamide,

[Ind_CC-109] 2-chloro-N-methyl-N-[6-[9-(pyridin-4-yl-methyl)-3,9-diazaspiro[5.5]undecane-3-carbonyl]-2,3-dihydro-1H-inden-1-yl]-benzamide,

[Ind_CC-110] 2-chloro-N-[6-[9-dimethylamino-9-(4-fluorophenyl)-3-azaspiro[5.5]undecane-3-carbonyl]-2,3-dihydro-1H-inden-1-yl]-N-methyl-benzamide,

[Ind_CC-111] 2-chloro-N-methyl-N-[6-(8-pyridin-4-yl-2,8-diazaspiro[4.5]decane-2-carbonyl)-2,3-dihydro-1H-inden-1-yl]-benzamide,

[Ind_CC-112] 2-chloro-N-methyl-N-[6-(2-pyridin-4-yl-2,8-diazaspiro[4.5]decane-8-carbonyl)-2,3-dihydro-1H-inden-1-yl]-benzamide,

[Ind_CC-113] 2-chloro-N-cyclopropyl-N-[6-(9-pyridin-4-yl-3,9-diazaspiro[5.5]undecane-3-carbonyl)-2,3-dihydro-1H-inden-1-yl]-benzamide,

[Ind_CC-114] 2-chloro-N-cyclopropyl-N-[6-(9-pyridin-3-yl-3,9-diazaspiro[5.5]undecane-3-carbonyl)-2,3-dihydro-1H-inden-1-yl]-benzamide,

[Ind_CC-115] 2-chloro-N-cyclopropyl-N-[6-[9-(4-fluorophenyl)-3,9-diazaspiro[5.5]undecane-3-carbonyl]-2,3-dihydro-1H-inden-1-yl]-benzamide,

[Ind_CC-116] 2-chloro-N-cyclopropyl-N-[6-[9-(pyridin-4-yl-methyl)-3,9-diazaspiro[5.5]undecane-3-carbonyl]-2,3-dihydro-1H-inden-1-yl]-benzamide,

[Ind_CC-117] 2-chloro-N-cyclopropyl-N-[6-[9-dimethylamino-9-(4-fluorophenyl)-3-azaspiro[5.5]undecane-3-carbonyl]-2,3-dihydro-1H-inden-1-yl]-benzamide,

[Ind_CC-118] 2-chloro-N-cyclopropyl-N-[6-(8-pyridin-4-yl-2,8-diazaspiro[4.5]decane-2-carbonyl)-2,3-dihydro-1H-inden-1-yl]-benzamide,

[Ind_CC-119] 2-chloro-N-cyclopropyl-N-[6-(2-pyridin-4-yl-2,8-diazaspiro[4.5]decane-8-carbonyl)-2,3-dihydro-1H-inden-1-yl]-benzamide,

[Ind_CC-120] 2-chloro-N-[3-(9-pyridin-4-yl-3,9-diazaspiro[5.5]undecane-3-carbonyl)-6,7,8,9-tetrahydro-5H-benzocyclohepten-5-yl]-benzamide,

[Ind_CC-121] 2-chloro-N-[3-(9-pyridin-3-yl-3,9-diazaspiro[5.5]undecane-3-carbonyl)-6,7,8,9-tetrahydro-5H-benzocyclohepten-5-yl]-benzamide,

[Ind_CC-122] 2-chloro-N-[3-[9-(4-fluorophenyl)-3,9-diazaspiro[5.5]undecane-3-carbonyl]-6,7,8,9-tetrahydro-5H-benzocyclohepten-5-yl]-benzamide,

[Ind_CC-123] 2-chloro-N-[3-[9-(pyridin-4-yl-methyl)-3,9-diazaspiro[5.5]undecane-3-carbonyl]-6,7,8,9-tetrahydro-5H-benzocyclohepten-5-yl]-benzamide

[Ind_CC-124] 2-chloro-N-[3-[9-dimethylamino-9-(4-fluorophenyl)-3-azaspiro[5.5]undecane-3-carbonyl]-6,7,8,9-tetrahydro-5H-benzocyclohepten-5-yl]-benzamide,

[Ind_CC-125] 2-chloro-N-[3-(8-pyridin-4-yl-2,8-diazaspiro[4.5]decane-2-carbonyl)-6,7,8,9-tetrahydro-5H-benzocyclohepten-5-yl]-benzamide,

[Ind_CC-126] 2-chloro-N-[3-(2-pyridin-4-yl-2,8-diazaspiro[4.5]decane-8-carbonyl)-6,7,8,9-tetrahydro-5H-benzocyclohepten-5-yl]-benzamide,

[Ind_CC-127] 2-chloro-N-[[6-(9-pyridin-4-yl-3,9-diazaspiro[5.5]undecane-3-carbonyl)-2,3-dihydro-1H-inden-1-yl]-methyl]-benzamide,

[Ind_CC-128] 2-chloro-N-[[6-(9-pyridin-3-yl-3,9-diazaspiro[5.5]undecane-3-carbonyl)-2,3-dihydro-1H-inden-1-yl]-methyl-]benzamide,

[Ind_CC-129] 2-chloro-N[[6-[9-(4-fluorophenyl)-3,9-diazaspiro[5.5]undecane-3-carbonyl]-2,3-dihydro-1H-inden-1-yl]-methyl]-benzamide,

[Ind_CC-130] 2-chloro-N-[[6-[9-(pyridin-4-yl-methyl)-3,9-diazaspiro[5.5]undecane-3-carbonyl]-2,3-dihydro-1H-inden-1-yl]-methyl]-benzamide,

[Ind_CC-131] 2-chloro-N-[[6-[9-dimethylamino-9-(4-fluorophenyl)-3-azaspiro[5.5]-undecane-3-carbonyl]-2,3-dihydro-1H-inden-1-yl]-methyl]-benzamide,

[Ind_CC-132] 2-chloro-N-[[6-(8-pyridin-4-yl-2,8-diazaspiro[4.5]decane-2-carbonyl)-2,3-dihydro-1H-inden-1-yl]-methyl]-benzamide,

[Ind_CC-133] 2-chloro-N-[[6-(2-pyridin-4-yl-2,8-diazaspiro[4.5]decane-8-carbonyl)-2,3-dihydro-1H-inden-1-yl]-methyl]-benzamide,

[Ind_CC-134] 2-chloro-N-[6-[2-oxo-2-(9-pyridin-4-yl-3,9-diazaspiro[5.5]undecane-3-yl)-ethyl]-2,3-dihydro-1H-inden-1-yl]-benzamide,

[Ind_CC-135] 2-chloro-N-[6-[2-oxo-2-(9-pyridin-3-yl-3,9-diazaspiro[5.5]undecane-3-yl)-ethyl]-2,3-dihydro-1H-inden-1-yl]-benzamide,

[Ind_CC-136] 2-chloro-N-[6-[2-[9-(4-fluorophenyl)-3,9-diazaspiro[5.5]undecane-3-yl]-2-oxo-ethyl]-2,3-dihydro-1H-inden-1-yl]-benzamide,

[Ind_CC-137] 2-chloro-N-[6-[2-[9-(pyridin-4-yl-methyl)-3,9-diazaspiro[5.5]undecane-3-yl]ethyl]-2,3-dihydro-1H-inden-1-yl]-benzamide,

[Ind_CC-138] 2-chloro-N-[6-[2-[9-dimethylamino-9-(4-fluorophenyl)-3-azaspiro[5.5]-undecane-3-yl]-2-oxo-ethyl]-2,3-dihydro-1H-inden-1-yl]-benzamide,

[Ind_CC-139] 2-chloro-N-[6-[2-oxo-2-(8-pyridin-4-yl-2,8-diazaspiro[4.5]decane-2-yl)-ethyl]-2,3-dihydro-1H-inden-1-yl]-benzamide,

[Ind_CC-140] 2-chloro-N-[6-[2-oxo-2-(2-pyridin-4-yl-2,8-diazaspiro[4.5]decane-8-yl)-ethyl]-2,3-dihydro-1H-inden-1-yl]-benzamide,

[Ind_CC-141] 8-chloro-2-[6-(9-pyridin-4-yl-3,9-diazaspiro[5.5]undecane-3-carbonyl)-2,3-dihydro-1H-inden-1-yl]-3,4-dihydro-2H-pyrrolo[1,2-a]pyrazin-1-one,

[Ind_CC-142] 8-chloro-2-[6-(9-pyridin-3-yl-3,9-diazaspiro[5.5]undecane-3-carbonyl)-2,3-dihydro-1H-inden-1-yl]-3,4-dihydro-2H-pyrrolo[1,2-a]pyrazin-1-one,

[Ind_CC-143] 8-chloro-2-[6-[9-(4-fluorophenyl)-3,9-diazaspiro[5.5]undecane-3-carbonyl]-2,3-dihydro-1H-inden-1-yl]-3,4-dihydro-2H-pyrrolo[1,2-a]pyrazin-1-one,

[Ind_CC-144] 8-chloro-2-[6-[9-(pyridin-4-yl-methyl)-3,9-diazaspiro[5.5]undecane-3-carbonyl]-2,3-dihydro-1H-inden-1-yl]-3,4-dihydro-2H-pyrrolo[1,2-a]pyrazin-1-one,

[Ind_CC-145] 8-chloro-2-[6-[9-dimethylamino-9-(4-fluorophenyl)-3-azaspiro[5.5]undecane-3-carbonyl]-2,3-dihydro-1H-inden-1-yl]-3,4-dihydro-2H-pyrrolo[1,2-a]pyrazin-1-one,

[Ind_CC-146] 8-chloro-2-[6-(8-pyridin-4-yl-2,8-diazaspiro[4.5]decane-2-carbonyl)-2,3-dihydro-1H-inden-1-yl]-3,4-dihydro-2H-pyrrolo[1,2-a]pyrazin-1-one,

[Ind_CC-147] 8-chloro-2-[6-(2-pyridin-4-yl-2,8-diazaspiro[4.5]decane-8-carbonyl)-2,3-dihydro-1H-inden-1-yl]-3,4-dihydro-2H-pyrrolo[1,2-a]pyrazin-1-one,

[Ind_CC-148] 8-chloro-4-methyl-2-[6-(9-pyridin-4-yl-3,9-diazaspiro[5.5]undecane-3-carbonyl)-2,3-dihydro-1H-inden-1-yl]-3,4-dihydro-2H-pyrrolo[3,4-b]indol-1-one,

[Ind_CC-149] 8-chloro-4-methyl-2-[6-(9-pyridin-3-yl-3,9-diazaspiro[5.5]undecane-3-carbonyl)-2,3-dihydro-1H-inden-1-yl]-3,4-dihydro-2H-pyrrolo[3,4-b]indol-1-one,

[Ind_CC-150] 8-chloro-2-[6-[9-(4-fluorophenyl)-3,9-diazaspiro[5.5]undecane-3-carbonyl]-2,3-dihydro-1H-inden-1-yl]-4-methyl-3,4-dihydro-2H-pyrrolo[3,4-b]indol-1-one,

[Ind_CC-151] 8-chloro-4-methyl-2-[6-[9-(pyridin-4-yl-methyl)-3,9-diazaspiro[5.5]undecane-3-carbonyl]-2,3-dihydro-1H-inden-1-yl]-3,4-dihydro-2H-pyrrolo[3,4-b]indol-1-one,

[Ind_CC-152] 8-chloro-2-[6-[9-dimethylamino-9-(4-fluorophenyl)-3-azaspiro[5.5]undecane-3-carbonyl]-2,3-dihydro-1H-inden-1-yl]-4-methyl-3,4-dihydro-2H-pyrrolo[3,4-b]indol-1-one,

[Ind_CC-153] 8-chloro-4-methyl-2-[6-(8-pyridin-4-yl-2,8-diazaspiro[4.5]decane-2-carbonyl)-2,3-dihydro-1H-inden-1-yl]-3,4-dihydro-2H-pyrrolo[3,4-b]indol-1-one and

[Ind_CC-154] 8-chloro-4-methyl-2-[6-(2-pyridin-4-yl-2,8-diazaspiro[4.5]decane-8-carbonyl)-2,3-dihydro-1H-inden-1-yl]-3,4-dihydro-2H-pyrrolo[3,4-b]indol-1-one.

[IND_CC-200] 2,5-Dichloro-N-methyl-N-[6-(9-pyridin-4-yl-3,9-diazaspiro[5.5]undecane-3-carbonyl)-2,3-dihydro-1H-inden-1-yl]-benzamide

[IND_CC-201] 2-Chloro-4-methoxy-N-methyl-N-[6-(9-pyridin-4-yl-3,9-diazaspiro[5.5]undecane-3-carbonyl)-2,3-dihydro-1H-inden-1-yl]-benzamide

[IND_CC-202] 2-Chloro-N-methyl-N-[6-(9-pyridin-4-yl-3,9-diazaspiro[5.5]undecane-3-carbonyl)-2,3-dihydro-1H-inden-1-yl]-5-(trifluoromethyl)-benzamide

[IND_CC-203] 2-Chloro-5-fluoro-N-methyl-N-[6-(9-pyridin-4-yl-3,9-diazaspiro[5.5]undecane-3-carbonyl)-2,3-dihydro-1H-inden-1-yl]-benzamide

[IND_CC-204] 2-Chloro-N-[6-(9-pyridin-4-yl-3,9-diazaspiro[5.5]undecane-3-carbonyl)-2,3-dihydro-1H-inden-1-yl]-6-(trifluoromethyl)-benzamide

[IND_CC-205] 2-Chloro-N-[6-(2-pyridin-4-yl-2,8-diazaspiro[4.5]decane-8-carbonyl)-2,3-dihydro-1H-inden-1-yl]-6-(trifluoromethyl)-benzamide

[IND_CC-206] 2-Chloro-N-[2,2-dimethyl-6-(9-pyridin-4-yl-3,9-diazaspiro[5.5]undecane-3-carbonyl)-1,3-dihydro-inden-1-yl]-6-(trifluoromethyl)-benzamide

[IND_CC-207] 2,5-Dichloro-N-[6-(9-pyridin-4-yl-3,9-diazaspiro[5.5]undecane-3-carbonyl)-2,3-dihydro-1H-inden-1-yl]-benzamide

[IND_CC-208] 2,5-Dichloro-N-[6-(2-pyridin-4-yl-2,8-diazaspiro[4.5]decane-8-carbonyl)-2,3-dihydro-1H-inden-1-yl]-benzamide

[IND_CC-209] 2,5-Dichloro-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-210] 2,5-Dichloro-N-[2,2-dimethyl-6-(9-pyridin-4-yl-3,9-diazaspiro[5.5]undecane-3-carbonyl)-1,3-dihydro-inden-1-yl]-benzamide

[IND_CC-211] 2-Chloro-4-methoxy-N-[6-(9-pyridin-4-yl-3,9-diazaspiro[5.5]undecane-3-carbonyl)-2,3-dihydro-1H-inden-1-yl]-benzamide

[IND_CC-212] 2-Chloro-4-methoxy-N-[6-(2-pyridin-4-yl-2,8-diazaspiro[4.5]decane-8-carbonyl)-2,3-dihydro-1H-inden-1-yl]-benzamide

[IND_CC-213] 2-Chloro-4-methoxy-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-214] 2-Chloro-6-fluoro-3-methyl-N-[6-(9-pyridin-4-yl-3,9-diazaspiro[5.5]undecane-3-carbonyl)-2,3-dihydro-1H-inden-1-yl]-benzamide

[IND_CC-215] 2-Chloro-6-fluoro-3-methyl-N-[6-(2-pyridin-4-yl-2,8-diazaspiro[4.5]decane-8-carbonyl)-2,3-dihydro-1H-inden-1-yl]-benzamide

[IND_CC-216] 2-Chloro-N-[2,2-dimethyl-6-(9-pyridin-4-yl-3,9-diazaspiro[5.5]undecane-3-carbonyl)-1,3-dihydro-inden-1-yl]-6-fluoro-3-methyl-benzamide

[IND_CC-217] 2-Chloro-N-[6-(9-pyridin-4-yl-3,9-diazaspiro[5.5]undecane-3-carbonyl)-2,3-dihydro-1H-inden-1-yl]-5-(trifluoromethyl)-benzamide

[IND_CC-218] 2-Chloro-N-[6-(2-pyridin-4-yl-2,8-diazaspiro[4.5]decane-8-carbonyl)-2,3-dihydro-1H-inden-1-yl]-5-(trifluoromethyl)-benzamide

[IND_CC-219] 2-Chloro-N-[2,2-dimethyl-6-(9-pyridin-4-yl-3,9-diazaspiro[5.5]undecane-3-carbonyl)-1,3-dihydro-inden-1-yl]-5-(trifluoromethyl)-benzamide

[IND_CC-220] 2-Chloro-5-fluoro-N-[6-(9-pyridin-4-yl-3,9-diazaspiro[5.5]undecane-3-carbonyl)-2,3-dihydro-1H-inden-1-yl]-benzamide

[IND_CC-221] 2-Chloro-5-fluoro-N-[6-(2-pyridin-4-yl-2,8-diazaspiro[4.5]decane-8-carbonyl)-2,3-dihydro-1H-inden-1-yl]-benzamide

[IND_CC-222] 2-Chloro-5-fluoro-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-223] 2-Chloro-N-[2,2-dimethyl-6-(9-pyridin-4-yl-3,9-diazaspiro[5.5]undecane-3-carbonyl)-1,3-dihydro-inden-1-yl]-5-fluoro-benzamide

[IND_CC-224] 2-Chloro-4,5-difluoro-N-methyl-N-[6-(9-pyridin-4-yl-3,9-diazaspiro[5.5]undecane-3-carbonyl)-2,3-dihydro-1H-inden-1-yl]-benzamide

[IND_CC-225] 2-Chloro-N-methyl-N-[6-(9-pyridin-4-yl-3,9-diazaspiro[5.5]undecane-3-carbonyl)-2,3-dihydro-1H-inden-1-yl]-3-(trifluoromethyl)-benzamide

[IND_CC-226] N-Methyl-N-[6-(9-pyridin-4-yl-3,9-diazaspiro[5.5]undecane-3-carbonyl)-2,3-dihydro-1H-inden-1-yl]-1-[2-(trifluoromethyl)-phenyl]methanesulfonic acid amide

[IND_CC-227] 2-Chloro-N,6-dimethyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-228] 2-Chloro-4,5-difluoro-N-[6-(9-pyridin-4-yl-3,9-diazaspiro[5.5]undecane-3-carbonyl)-2,3-dihydro-1H-inden-1-yl]-benzamide

[IND_CC-229] 2-Chloro-4,5-difluoro-N-[6-(2-pyridin-4-yl-2,8-diazaspiro[4.5]decane-8-carbonyl)-2,3-dihydro-1H-inden-1-yl]-benzamide

[IND_CC-230] 2-Chloro-4,5-difluoro-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-231] 2-Chloro-N-[2,2-dimethyl-6-(9-pyridin-4-yl-3,9-diazaspiro[5.5]undecane-3-carbonyl)-1,3-dihydro-inden-1-yl]-4,5-difluoro-benzamide

[IND_CC-232] 2-Chloro-N-[6-(9-pyridin-4-yl-3,9-diazaspiro[5.5]undecane-3-carbonyl)-2,3-dihydro-1H-inden-1-yl]-3-(trifluoromethyl)-benzamide

[IND_CC-233] 2-Chloro-N-[6-(2-pyridin-4-yl-2,8-diazaspiro[4.5]decane-8-carbonyl)-2,3-dihydro-1H-inden-1-yl]-3-(trifluoromethyl)-benzamide

[IND_CC-234] 2-Chloro-N-[2,2-dimethyl-6-(9-pyridin-4-yl-3,9-diazaspiro[5.5]undecane-3-carbonyl)-1,3-dihydro-inden-1-yl]-3-(trifluoromethyl)-benzamide

[IND_CC-235] 2-Cyano-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-236] N-[6-(9-Pyridin-4-yl-3,9-diazaspiro[5.5]undecane-3-carbonyl)-2,3-dihydro-1H-inden-1-yl]-1-[2-(trifluoromethyl)-phenyl]-methanesulfonic acid amide

[IND_CC-237] N-[6-(2-Pyridin-4-yl-2,8-diazaspiro[4.5]decane-8-carbonyl)-2,3-dihydro-1H-inden-1-yl]-1-[2-(trifluoromethyl)-phenyl]-methanesulfonic acid amide

[IND_CC-238] N-[2,2-Dimethyl-6-(9-pyridin-4-yl-3,9-diazaspiro[5.5]undecane-3-carbonyl)-1,3-dihydro-inden-1-yl]-1-[2-(trifluoromethyl)-phenyl]methanesulfonic acid amide

[IND_CC-239] 2-Chloro-6-methyl-N-[6-[9-[4-(trifluoromethyl)-phenyl]-3,9-diazaspiro[5.5]undecane-3-carbonyl]-2,3-dihydro-1H-inden-1-yl]-benzenesulfonic acid amide

[IND_CC-240] 2-Chloro-N-[2,2-dimethyl-6-(9-pyridin-4-yl-3,9-diazaspiro[5.5]undecane-3-carbonyl)-1,3-dihydro-inden-1-yl]-6-methyl-benzenesulfonic acid amide

[IND_CC-241] 2-(2-Chlorophenyl)-N-[6-(9-pyridin-4-yl-3,9-diazaspiro[5.5]undecane-3-carbonyl)-2,3-dihydro-1H-inden-1-yl]-ethanesulfonic acid amide

[IND_CC-242] 2-(2-Chlorophenyl)-N-[2,2-dimethyl-6-(9-pyridin-4-yl-3,9-diazaspiro[5.5]-undecane-3-carbonyl)-1,3-dihydro-inden-1-yl]-ethanesulfonic acid amide

[IND_CC-243] 2-Chloro-N-[3,3-dimethyl-6-(3-pyridin-4-yl-3,9-diazaspiro[5.5]undecane-9-carbonyl)-1,2-dihydro-inden-1-yl]-6-(trifluoromethyl)-benzamide

[IND_CC-244] 2,5-Dichloro-N-[3,3-dimethyl-6-(3-pyridin-4-yl-3,9-diazaspiro[5.5]undecane-9-carbonyl)-1,2-dihydro-inden-1-yl]-benzamide

[IND_CC-245] 2,5-Dichloro-N-[6-(8-pyridin-4-yl-2,8-diazaspiro[4.5]decane-2-carbonyl)-2,3-dihydro-1H-inden-1-yl]-benzamide

[IND_CC-246] 2-Chloro-N-[3,3-dimethyl-6-(3-pyridin-4-yl-3,9-diazaspiro[5.5]undecane-9-carbonyl)-1,2-dihydro-inden-1-yl]-4-methoxy-benzamide

[IND_CC-247] 2-Chloro-4-methoxy-N-[6-(8-pyridin-4-yl-2,8-diazaspiro[4.5]decane-2-carbonyl)-2,3-dihydro-1H-inden-1-yl]-benzamide

[IND_CC-248] 2-Chloro-N-[3,3-dimethyl-6-(3-pyridin-4-yl-3,9-diazaspiro[5.5]undecane-9-carbonyl)-1,2-dihydro-inden-1-yl]-6-fluoro-3-methyl-benzamide

[IND_CC-249] 2-Chloro-6-fluoro-3-methyl-N-[6-(8-pyridin-4-yl-2,8-diazaspiro[4.5]decane-2-carbonyl)-2,3-dihydro-1H-inden-1-yl]-benzamide

[IND_CC-250] 2-Chloro-N-[3,3-dimethyl-6-(3-pyridin-4-yl-3,9-diazaspiro[5.5]undecane-9-carbonyl)-1,2-dihydro-inden-1-yl]-5-(trifluoromethyl)-benzamide

[IND_CC-251] 2-Chloro-N-[6-(8-pyridin-4-yl-2,8-diazaspiro[4.5]decane-2-carbonyl)-2,3-dihydro-1H-inden-1-yl]-5-(trifluoromethyl)-benzamide

[IND_CC-252] 2-Chloro-N-[3,3-dimethyl-6-(3-pyridin-4-yl-3,9-diazaspiro[5.5]undecane-9-carbonyl)-1,2-dihydro-inden-1-yl]-5-fluoro-benzamide

[IND_CC-253] 2-Chloro-5-fluoro-N-[6-(8-pyridin-4-yl-2,8-diazaspiro[4.5]decane-2-carbonyl)-2,3-dihydro-1H-inden-1-yl]-benzamide

[IND_CC-254] 2-Chloro-N-[3,3-dimethyl-6-(3-pyridin-4-yl-3,9-diazaspiro[5.5]undecane-9-carbonyl)-1,2-dihydro-inden-1-yl]-3-(trifluoromethyl)-benzamide

[IND_CC-255] 2-Chloro-N-[6-(8-pyridin-4-yl-2,8-diazaspiro[4.5]decane-2-carbonyl)-2,3-dihydro-1H-inden-1-yl]-3-(trifluoromethyl)-benzamide

[IND_CC-256] N-[3,3-Dimethyl-6-(3-pyridin-4-yl-3,9-diazaspiro[5.5]undecane-9-carbonyl)-1,2-dihydro-inden-1-yl]-1-[2-(trifluoromethyl)-phenyl]-methanesulfonic acid amide

[IND_CC-257] N-[6-(8-Pyridin-4-yl-2,8-diazaspiro[4.5]decane-2-carbonyl)-2,3-dihydro-1H-inden-1-yl]-1-[2-(trifluoromethyl)-phenyl]-methanesulfonic acid amide

[IND_CC-259] 2-Chloro-N-[3,3-dimethyl-6-(3-pyridin-4-yl-3,9-diazaspiro[5.5]undecane-9-carbonyl)-1,2-dihydro-inden-1-yl]-6-methyl-benzenesulfonic acid amide

[IND_CC-260] 2-(2-Chlorophenyl)-N-[3,3-dimethyl-6-(3-pyridin-4-yl-3,9-diazaspiro[5.5]-undecane-9-carbonyl)-1,2-dihydro-inden-1-yl]-ethanesulfonic acid amide

[IND_CC-261] 2-Chloro-4-fluoro-N-methyl-N-[6-(9-pyridin-4-yl-3,9-diazaspiro[5.5]undecane-3-carbonyl)-2,3-dihydro-1H-inden-1-yl]-benzamide

[IND_CC-262] 2-Chloro-4-fluoro-N-[6-(9-pyridin-4-yl-3,9-diazaspiro[5.5]undecane-3-carbonyl)-2,3-dihydro-1H-inden-1-yl]-benzamide

[IND_CC-263] 2-Chloro-4-fluoro-N-[6-(2-pyridin-4-yl-2,8-diazaspiro[4.5]decane-8-carbonyl)-2,3-dihydro-1H-inden-1-yl]-benzamide

[IND_CC-264] 2-Chloro-6-fluoro-N-[6-(2-pyridin-4-yl-2,8-diazaspiro[4.5]decane-8-carbonyl)-2,3-dihydro-1H-inden-1-yl]-benzamide

[IND_CC-265] 2,3-Dichloro-N-methyl-N-[6-(9-pyridin-4-yl-3,9-diazaspiro[5.5]undecane-3-carbonyl)-2,3-dihydro-1H-inden-1-yl]-benzamide

[IND_CC-266] 2,3-Dichloro-N-[6-(9-pyridin-4-yl-3,9-diazaspiro[5.5]undecane-3-carbonyl)-2,3-dihydro-1H-inden-1-yl]-benzamide

[IND_CC-267] 2,3-Dichloro-N-[6-(2-pyridin-4-yl-2,8-diazaspiro[4.5]decane-8-carbonyl)-2,3-dihydro-1H-inden-1-yl]-benzamide

[IND_CC-268] 2,6-Dichloro-N-methyl-N-[6-(9-pyridin-4-yl-3,9-diazaspiro[5.5]undecane-3-carbonyl)-2,3-dihydro-1H-inden-1-yl]-benzamide

[IND_CC-269] 2,6-Dichloro-N-[6-(9-pyridin-4-yl-3,9-diazaspiro[5.5]undecane-3-carbonyl)-2,3-dihydro-1H-inden-1-yl]-benzamide

[IND_CC-270] 2,6-Dichloro-N-[6-(2-pyridin-4-yl-2,8-diazaspiro[4.5]decane-8-carbonyl)-2,3-dihydro-1H-inden-1-yl]-benzamide

[IND_CC-271] 2-Chloro-N-[6-(2-pyridin-4-yl-2,8-diazaspiro[4.5]decane-8-carbonyl)-2,3-dihydro-1H-inden-1-yl]-benzamide

[IND_CC-272] 2-Chloro-N-methyl-N-[6-(9-pyridin-4-yl-3,9-diazaspiro[5.5]undecane-3-carbonyl)-2,3-dihydro-1H-inden-1-yl]-benzamide

[IND_CC-273] 2-Chloro-N-[6-(9-pyridin-4-yl-3,9-diazaspiro[5.5]undecane-3-carbonyl)-2,3-dihydro-1H-inden-1-yl]-benzamide

[IND_CC-274] 2-Chloro-4-fluoro-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-275] 2-Chloro-N-[2,2-dimethyl-6-(9-pyridin-4-yl-3,9-diazaspiro[5.5]undecane-3-carbonyl)-1,3-dihydro-inden-1-yl]-4-fluoro-benzamide

[IND_CC-276] 2-Chloro-N-[3,3-dimethyl-6-(3-pyridin-4-yl-3,9-diazaspiro[5.5]undecane-9-carbonyl)-1,2-dihydro-inden-1-yl]-4-fluoro-benzamide

[IND_CC-277] 2-Chloro-4-fluoro-N-[6-(8-pyridin-4-yl-2,8-diazaspiro[4.5]decane-2-carbonyl)-2,3-dihydro-1H-inden-1-yl]-benzamide

[IND_CC-278] 2-Chloro-6-fluoro-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-279] 2-Chloro-N-[3,3-dimethyl-6-(3-pyridin-4-yl-3,9-diazaspiro[5.5]undecane-9-carbonyl)-1,2-dihydro-inden-1-yl]-6-fluoro-benzamide

[IND_CC-280] 2-Chloro-6-fluoro-N-[6-(8-pyridin-4-yl-2,8-diazaspiro[4.5]decane-2-carbonyl)-2,3-dihydro-1H-inden-1-yl]-benzamide

[IND_CC-281] 2,3-Dichloro-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-282] 2,3-Dichloro-N-[2,2-dimethyl-6-(9-pyridin-4-yl-3,9-diazaspiro[5.5]undecane-3-carbonyl)-1,3-dihydro-inden-1-yl]-benzamide

[IND_CC-283] 2,3-Dichloro-N-[3,3-dimethyl-6-(3-pyridin-4-yl-3,9-diazaspiro[5.5]undecane-9-carbonyl)-1,2-dihydro-inden-1-yl]-benzamide

[IND_CC-284] 2,3-Dichloro-N-[6-(8-pyridin-4-yl-2,8-diazaspiro[4.5]decane-2-carbonyl)-2,3-dihydro-1H-inden-1-yl]-benzamide

[IND_CC-286] 2,6-Dichloro-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-287] 2,6-Dichloro-N-[2,2-dimethyl-6-(9-pyridin-4-yl-3,9-diazaspiro[5.5]undecane-3-carbonyl)-1,3-dihydro-inden-1-yl]-benzamide

[IND_CC-288] 2,6-Dichloro-N-[3,3-dimethyl-6-(3-pyridin-4-yl-3,9-diazaspiro[5.5]undecane-9-carbonyl)-1,2-dihydro-inden-1-yl]-benzamide

[IND_CC-289] 2,6-Dichloro-N-[6-(8-pyridin-4-yl-2,8-diazaspiro[4.5]decane-2-carbonyl)-2,3-dihydro-1H-inden-1-yl]-benzamide

[IND_CC-290] 2-Chloro-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-291] 2-Chloro-N-[2,2-dimethyl-6-(9-pyridin-4-yl-3,9-diazaspiro[5.5]undecane-3-carbonyl)-1,3-dihydro-inden-1-yl]-benzamide

[IND_CC-292] 2-Chloro-N-[3,3-dimethyl-6-(3-pyridin-4-yl-3,9-diazaspiro[5.5]undecane-9-carbonyl)-1,2-dihydro-inden-1-yl]-benzamide

[IND_CC-293] 2-Chloro-N-[6-(8-pyridin-4-yl-2,8-diazaspiro[4.5]decane-2-carbonyl)-2,3-dihydro-1H-inden-1-yl]-benzamide

[IND_CC-294] 2,6-Dimethyl-N-[6-(9-pyridin-4-yl-3,9-diazaspiro[5.5]undecane-3-carbonyl)-2,3-dihydro-1H-inden-1-yl]-benzamide

[IND_CC-295] 2,6-Dimethyl-N-[6-(2-pyridin-4-yl-2,8-diazaspiro[4.5]decane-8-carbonyl)-2,3-dihydro-1H-inden-1-yl]-benzamide

[IND_CC-296] 2-Fluoro-4-methoxy-N-methyl-N-[6-(9-pyridin-4-yl-3,9-diazaspiro[5.5]undecane-3-carbonyl)-2,3-dihydro-1H-inden-1-yl]-benzamide

[IND_CC-297] 2-Fluoro-4-methoxy-N-[6-(9-pyridin-4-yl-3,9-diazaspiro[5.5]undecane-3-carbonyl)-2,3-dihydro-1H-inden-1-yl]-benzamide

[IND_CC-298] 2-Fluoro-4-methoxy-N-[6-(2-pyridin-4-yl-2,8-diazaspiro[4.5]decane-8-carbonyl)-2,3-dihydro-1H-inden-1-yl]-benzamide

[IND_CC-299] N,2-Dimethyl-N-[6-(9-pyridin-4-yl-3,9-diazaspiro[5.5]undecane-3-carbonyl)-2,3-dihydro-1H-inden-1-yl]-4-(trifluoromethyloxy)-benzamide

[IND_CC-300] 2-Methyl-N-[6-(9-pyridin-4-yl-3,9-diazaspiro[5.5]undecane-3-carbonyl)-2,3-dihydro-1H-inden-1-yl]-4-(trifluoromethyloxy)-benzamide

[IND_CC-301] 5-Chloro-N-methyl-N-[6-(9-pyridin-4-yl-3,9-diazaspiro[5.5]undecane-3-carbonyl)-2,3-dihydro-1H-inden-1-yl]-2-(trifluoromethyl)-benzamide

[IND_CC-302] 5-Chloro-N-[6-(9-pyridin-4-yl-3,9-diazaspiro[5.5]undecane-3-carbonyl)-2,3-dihydro-1H-inden-1-yl]-2-(trifluoromethyl)-benzamide

[IND_CC-303] 5-Chloro-N-[6-(2-pyridin-4-yl-2,8-diazaspiro[4.5]decane-8-carbonyl)-2,3-dihydro-1H-inden-1-yl]-2-(trifluoromethyl)-benzamide

[IND_CC-304] 2-Fluoro-N,4-dimethyl-N-[6-(9-pyridin-4-yl-3,9-diazaspiro[5.5]undecane-3-carbonyl)-2,3-dihydro-1H-inden-1-yl]-benzamide

[IND_CC-305] 2-Fluoro-4-methyl-N-[6-(9-pyridin-4-yl-3,9-diazaspiro[5.5]undecane-3-carbonyl)-2,3-dihydro-1H-inden-1-yl]-benzamide

[IND_CC-306] 2-Fluoro-4-methyl-N-[6-(2-pyridin-4-yl-2,8-diazaspiro[4.5]decane-8-carbonyl)-2,3-dihydro-1H-inden-1-yl]-benzamide

[IND_CC-307] 2,6-Dimethyl-N-[6-[9-[4-(trifluoromethyl)-phenyl]-3,9-diazaspiro[5.5]undecane-3-carbonyl]-2,3-dihydro-1H-inden-1-yl]-benzamide

[IND_CC-308] N-[2,2-Dimethyl-6-(9-pyridin-4-yl-3,9-diazaspiro[5.5]undecane-3-carbonyl)-1,3-dihydro-inden-1-yl]-2,6-dimethyl-benzamide

[IND_CC-309] N-[3,3-Dimethyl-6-(3-pyridin-4-yl-3,9-diazaspiro[5.5]undecane-9-carbonyl)-1,2-dihydro-inden-1-yl]-2,6-dimethyl-benzamide

[IND_CC-310] 2,6-Dimethyl-N-[6-(8-pyridin-4-yl-2,8-diazaspiro[4.5]decane-2-carbonyl)-2,3-dihydro-1H-inden-1-yl]-benzamide

[IND_CC-311] N-[2,2-Dimethyl-6-(9-pyridin-4-yl-3,9-diazaspiro[5.5]undecane-3-carbonyl)-1,3-dihydro-inden-1-yl]-2-fluoro-4-methoxy-benzamide

[IND_CC-312] N-[3,3-Dimethyl-6-(3-pyridin-4-yl-3,9-diazaspiro[5.5]undecane-9-carbonyl)-1,2-dihydro-inden-1-yl]-2-fluoro-4-methoxy-benzamide

[IND_CC-313] 2-Fluoro-4-methoxy-N-[6-(8-pyridin-4-yl-2,8-diazaspiro[4.5]decane-2-carbonyl)-2,3-dihydro-1H-inden-1-yl]-benzamide

[IND_CC-314] 5-Chloro-N-[2,2-dimethyl-6-(9-pyridin-4-yl-3,9-diazaspiro[5.5]undecane-3-carbonyl)-1,3-dihydro-inden-1-yl]-2-(trifluoromethyl)-benzamide

[IND_CC-315] 5-Chloro-N-[3,3-dimethyl-6-(3-pyridin-4-yl-3,9-diazaspiro[5.5]undecane-9-carbonyl)-1,2-dihydro-inden-1-yl]-2-(trifluoromethyl)-benzamide

[IND_CC-316] 5-Chloro-N-[6-(8-pyridin-4-yl-2,8-diazaspiro[4.5]decane-2-carbonyl)-2,3-dihydro-1H-inden-1-yl]-2-(trifluoromethyl)-benzamide

[IND_CC-317] N-[2,2-Dimethyl-6-(9-pyridin-4-yl-3,9-diazaspiro[5.5]undecane-3-carbonyl)-1,3-dihydro-inden-1-yl]-2-fluoro-4-methyl-benzamide

[IND_CC-318] N-[3,3-Dimethyl-6-(3-pyridin-4-yl-3,9-diazaspiro[5.5]undecane-9-carbonyl)-1,2-dihydro-inden-1-yl]-2-fluoro-4-methyl-benzamide

[IND_CC-319] 2-Fluoro-4-methyl-N-[6-(8-pyridin-4-yl-2,8-diazaspiro[4.5]decane-2-carbonyl)-2,3-dihydro-1H-inden-1-yl]-benzamide

[IND_CC-320] 2-Chloro-N-methyl-N-[6-(9-pyridin-4-yl-3,9-diazaspiro[5.5]undecane-3-carbonyl)-2,3-dihydro-1H-inden-1-yl]-4-(trifluoromethyl)-benzenesulfonic acid amide

[IND_CC-321] 2,6-Dichloro-N-methyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-322] 2,6-Dichloro-N-[6-(9-pyridin-4-yl-3,9-diazaspiro[5.5]undecane-3-carbonyl)-2,3-dihydro-1H-inden-1-yl]-benzenesulfonic acid amide

[IND_CC-323] 2,6-Dichloro-N-[6-(2-pyridin-4-yl-2,8-diazaspiro[4.5]decane-8-carbonyl)-2,3-dihydro-1H-inden-1-yl]-benzenesulfonic acid amide

[IND_CC-324] 2,4-Dichloro-N-methyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-325] 2-Chloro-N-methyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-326] 4-Fluoro-N,2-dimethyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-327] N-Methyl-N-[6-(9-pyridin-4-yl-3,9-diazaspiro[5.5]undecane-3-carbonyl)-2,3-dihydro-1H-inden-1-yl]-3-(trifluoromethyl)-benzenesulfonic acid amide

[IND_CC-328] N-[6-(9-Pyridin-4-yl-3,9-diazaspiro[5.5]undecane-3-carbonyl)-2,3-dihydro-1H-inden-1-yl]-3-(trifluoromethyl)-benzenesulfonic acid amide

[IND_CC-329] N-[6-(2-Pyridin-4-yl-2,8-diazaspiro[4.5]decane-8-carbonyl)-2,3-dihydro-1H-inden-1-yl]-3-(trifluoromethyl)-benzenesulfonic acid amide

[IND_CC-330] 2-Chloro-N-[2,2-dimethyl-6-(9-pyridin-4-yl-3,9-diazaspiro[5.5]undecane-3-carbonyl)-1,3-dihydro-inden-1-yl]-4-(trifluoromethyl)-benzenesulfonic acid amide

[IND_CC-331] 2-Chloro-N-[3,3-dimethyl-6-(3-pyridin-4-yl-3,9-diazaspiro[5.5]undecane-9-carbonyl)-1,2-dihydro-inden-1-yl]-4-(trifluoromethyl)-benzenesulfonic acid amide

[IND_CC-332] 2,6-Dichloro-N-[3,3-dimethyl-6-(3-pyridin-4-yl-3,9-diazaspiro[5.5]undecane-9-carbonyl)-1,2-dihydro-inden-1-yl]-benzenesulfonic acid amide

[IND_CC-333] 2,6-Dichloro-N-[6-(8-pyridin-4-yl-2,8-diazaspiro[4.5]decane-2-carbonyl)-2,3-dihydro-1H-inden-1-yl]-benzenesulfonic acid amide

[IND_CC-334] 2,4-Dichloro-N-[2,2-dimethyl-6-(9-pyridin-4-yl-3,9-diazaspiro[5.5]undecane-3-carbonyl)-1,3-dihydro-inden-1-yl]-benzenesulfonic acid amide

[IND_CC-335] 2,4-Dichloro-N-[3,3-dimethyl-6-(3-pyridin-4-yl-3,9-diazaspiro[5.5]undecane-9-carbonyl)-1,2-dihydro-inden-1-yl]-benzenesulfonic acid amide

[IND_CC-336] 2-Chloro-N-[2,2-dimethyl-6-(9-pyridin-4-yl-3,9-diazaspiro[5.5]undecane-3-carbonyl)-1,3-dihydro-inden-1-yl]-benzenesulfonic acid amide

[IND_CC-337] 2-Chloro-N-[3,3-dimethyl-6-(3-pyridin-4-yl-3,9-diazaspiro[5.5]undecane-9-carbonyl)-1,2-dihydro-inden-1-yl]-benzenesulfonic acid amide

[IND_CC-338] N-[2,2-Dimethyl-6-(9-pyridin-4-yl-3,9-diazaspiro[5.5]undecane-3-carbonyl)-1,3-dihydro-inden-1-yl]-4-fluoro-2-methyl-benzenesulfonic acid amide

[IND_CC-339] N-[3,3-Dimethyl-6-(3-pyridin-4-yl-3,9-diazaspiro[5.5]undecane-9-carbonyl)-1,2-dihydro-inden-1-yl]-4-fluoro-2-methyl-benzenesulfonic acid amide

[IND_CC-340] N-[3,3-Dimethyl-6-(3-pyridin-4-yl-3,9-diazaspiro[5.5]undecane-9-carbonyl)-1,2-dihydro-inden-1-yl]-3-(trifluoromethyl)-benzenesulfonic acid amide

[IND_CC-341] N-[2,2-Dimethyl-6-(9-pyridin-4-yl-3,9-diazaspiro[5.5]undecane-3-carbonyl)-1,3-dihydro-inden-1-yl]-3-(trifluoromethyl)-benzenesulfonic acid amide

[IND_CC-342] N-[6-(8-Pyridin-4-yl-2,8-diazaspiro[4.5]decane-2-carbonyl)-2,3-dihydro-1H-inden-1-yl]-3-(trifluoromethyl)-benzenesulfonic acid amide

[IND_CC-343] 2,3-Dichloro-N-methyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-344] 2,5-Dichloro-N-methyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-345] N,2-Dimethyl-N-[6-(9-pyridin-4-yl-3,9-diazaspiro[5.5]undecane-3-carbonyl)-2,3-dihydro-1H-inden-1-yl]-benzamide

[IND_CC-346] 2-Methyl-N-[6-(9-pyridin-4-yl-3,9-diazaspiro[5.5]undecane-3-carbonyl)-2,3-dihydro-1H-inden-1-yl]-benzamide

[IND_CC-347] 2-Methyl-N-[6-(2-pyridin-4-yl-2,8-diazaspiro[4.5]decane-8-carbonyl)-2,3-dihydro-1H-inden-1-yl]-benzamide
[IND_CC-348] 1-(2-Fluorophenyl)-N-methyl-N-[6-(9-pyridin-4-yl-3,9-diazaspiro[5.5]-undecane-3-carbonyl)-2,3-dihydro-1H-inden-1-yl]-methanesulfonic acid amide
[IND_CC-349] 1-(2-Fluorophenyl)-N-[6-(9-pyridin-4-yl-3,9-diazaspiro[5.5]undecane-3-carbonyl)-2,3-dihydro-1H-inden-1-yl]-methanesulfonic acid amide
[IND_CC-350] 1-(2-Fluorophenyl)-N-[6-(2-pyridin-4-yl-2,8-diazaspiro[4.5]decane-8-carbonyl)-2,3-dihydro-1H-inden-1-yl]-methanesulfonic acid amide
[IND_CC-351] 1-(3-Chlorophenyl)-N-methyl-N-[6-(9-pyridin-4-yl-3,9-diazaspiro[5.5]-undecane-3-carbonyl)-2,3-dihydro-1H-inden-1-yl]-methanesulfonic acid amide
[IND_CC-352] 1-(3-Chlorophenyl)-N-[6-(9-pyridin-4-yl-3,9-diazaspiro[5.5]undecane-3-carbonyl)-2,3-dihydro-1H-inden-1-yl]-methanesulfonic acid amide
[IND_CC-353] 1-(3-Chlorophenyl)-N-[6-(2-pyridin-4-yl-2,8-diazaspiro[4.5]decane-8-carbonyl)-2,3-dihydro-1H-inden-1-yl]-methanesulfonic acid amide
[IND_CC-354] 4-Fluoro-N,2,6-trimethyl-N-[6-(9-pyridin-4-yl-3,9-diazaspiro[5.5]undecane-3-carbonyl)-2,3-dihydro-1H-inden-1-yl]-benzenesulfonic acid amide
[IND_CC-355] 4-Fluoro-2,6-dimethyl-N-[6-(9-pyridin-4-yl-3,9-diazaspiro[5.5]undecane-3-carbonyl)-2,3-dihydro-1H-inden-1-yl]-benzenesulfonic acid amide
[IND_CC-356] 4-Fluoro-2,6-dimethyl-N-[6-(2-pyridin-4-yl-2,8-diazaspiro[4.5]decane-8-carbonyl)-2,3-dihydro-1H-inden-1-yl]-benzenesulfonic acid amide
[IND_CC-357] 2,5-Dichloro-N-[6-(8-pyridin-4-yl-2,8-diazaspiro[4.5]decane-2-carbonyl)-2,3-dihydro-1H-inden-1-yl]-benzenesulfonic acid amide
[IND_CC-358] 2-Methyl-N-[6-(8-pyridin-4-yl-2,8-diazaspiro[4.5]decane-2-carbonyl)-2,3-dihydro-1H-inden-1-yl]-benzamide
[IND_CC-359] 1-(2-Fluorophenyl)-N-[6-(8-pyridin-4-yl-2,8-diazaspiro[4.5]decane-2-carbonyl)-2,3-dihydro-1H-inden-1-yl]-methanesulfonic acid amide
[IND_CC-360] 1-(3-Chlorophenyl)-N-[6-(8-pyridin-4-yl-2,8-diazaspiro[4.5]decane-2-carbonyl)-2,3-dihydro-1H-inden-1-yl]-methanesulfonic acid amide
[IND_CC-361] 4-Fluoro-2,6-dimethyl-N-[6-(8-pyridin-4-yl-2,8-diazaspiro[4.5]decane-2-carbonyl)-2,3-dihydro-1H-inden-1-yl]-benzenesulfonic acid amide
[IND_CC-362] 2,4,5-Trichloro-N-methyl-N-[6-(9-pyridin-4-yl-3,9-diazaspiro[5.5]undecane-3-carbonyl)-2,3-dihydro-1H-inden-1-yl]-benzenesulfonic acid amide
[IND_CC-363] 2,4,5-Trichloro-N-[6-(2-pyridin-4-yl-2,8-diazaspiro[4.5]decane-8-carbonyl)-2,3-dihydro-1H-inden-1-yl]-benzenesulfonic acid amide
[IND_CC-364] N-[6-(9-Pyridin-4-yl-3,9-diazaspiro[5.5]undecane-3-carbonyl)-2,3-dihydro-1H-inden-1-yl]-cyclohexanecarboxylic acid amide
[IND_CC-365] N-Methyl-N-[6-(9-pyridin-4-yl-3,9-diazaspiro[5.5]undecane-3-carbonyl)-2,3-dihydro-1H-inden-1-yl]-cyclohexanecarboxylic acid amide
[IND_CC-366] N-[6-(2-Pyridin-4-yl-2,8-diazaspiro[4.5]decane-8-carbonyl)-2,3-dihydro-1H-inden-1-yl]-cyclohexanecarboxylic acid amide
[IND_CC-367] N-[6-(8-Pyridin-4-yl-2,8-diazaspiro[4.5]decane-2-carbonyl)-2,3-dihydro-1H-inden-1-yl]-cyclohexanecarboxylic acid amide
[IND_CC-368] N-[6-(9-Pyridin-4-yl-3,9-diazaspiro[5.5]undecane-3-carbonyl)-2,3-dihydro-1H-inden-1-yl]-cyclopropanecarboxylic acid amide
[IND_CC-369] N-Methyl-N-[6-(9-pyridin-4-yl-3,9-diazaspiro[5.5]undecane-3-carbonyl)-2,3-dihydro-1H-inden-1-yl]-cyclopropanecarboxylic acid amide
[IND_CC-370] N-[6-(8-Pyridin-4-yl-2,8-diazaspiro[4.5]decane-2-carbonyl)-2,3-dihydro-1H-inden-1-yl]-cyclopropanecarboxylic acid amide
[IND_CC-371] 3,3-Dimethyl-N-[6-(9-pyridin-4-yl-3,9-diazaspiro[5.5]undecane-3-carbonyl)-2,3-dihydro-1H-inden-1-yl]-butyramide
[IND_CC-372] N,3,3-Trimethyl-N-[6-(9-pyridin-4-yl-3,9-diazaspiro[5.5]undecane-3-carbonyl)-2,3-dihydro-1H-inden-1-yl]-butyramide
[IND_CC-373] 3,3-Dimethyl-N-[6-(2-pyridin-4-yl-2,8-diazaspiro[4.5]decane-8-carbonyl)-2,3-dihydro-1H-inden-1-yl]-butyramide
[IND_CC-374] 3,3-Dimethyl-N-[6-(8-pyridin-4-yl-2,8-diazaspiro[4.5]decane-2-carbonyl)-2,3-dihydro-1H-inden-1-yl]-butyramide
[IND_CC-375] N-[6-(8-Pyridin-4-yl-2,8-diazaspiro[4.5]decane-2-carbonyl)-2,3-dihydro-1H-inden-1-yl-]acetamide
[IND_CC-376] 2-Fluoro-N-[6-(9-pyridin-4-yl-3,9-diazaspiro[5.5]undecane-3-carbonyl)-2,3-dihydro-1H-inden-1-yl]-6-(trifluoromethyl)-benzamide
[IND_CC-377] 2-Fluoro-N-[6-(2-pyridin-4-yl-2,8-diazaspiro[4.5]decane-8-carbonyl)-2,3-dihydro-1H-inden-1-yl]-6-(trifluoromethyl)-benzamide
[IND_CC-378] 2-Fluoro-N-[6-(8-pyridin-4-yl-2,8-diazaspiro[4.5]decane-2-carbonyl)-2,3-dihydro-1H-inden-1-yl]-6-(trifluoromethyl)-benzamide
[IND_CC-379] 4-Fluoro-N-[6-(9-pyridin-4-yl-3,9-diazaspiro[5.5]undecane-3-carbonyl)-2,3-dihydro-1H-inden-1-yl]-2-(trifluoromethyl)-benzamide
[IND_CC-380] 4-Fluoro-N-methyl-N-[6-(9-pyridin-4-yl-3,9-diazaspiro[5.5]undecane-3-carbonyl)-2,3-dihydro-1H-inden-1-yl]-2-(trifluoromethyl)-benzamide
[IND_CC-381] 4-Fluoro-N-[6-(2-pyridin-4-yl-2,8-diazaspiro[4.5]decane-8-carbonyl)-2,3-dihydro-1H-inden-1-yl]-2-(trifluoromethyl)-benzamide
[IND_CC-382] 4-Fluoro-N-[6-(8-pyridin-4-yl-2,8-diazaspiro[4.5]decane-2-carbonyl)-2,3-dihydro-1H-inden-1-yl]-2-(trifluoromethyl)-benzamide
[IND_CC-383] 2,6-Difluoro-N-[6-(9-pyridin-4-yl-3,9-diazaspiro[5.5]undecane-3-carbonyl)-2,3-dihydro-1H-inden-1-yl]-benzamide
[IND_CC-384] 2,6-Difluoro-N-methyl-N-[6-(9-pyridin-4-yl-3,9-diazaspiro[5.5]undecane-3-carbonyl)-2,3-dihydro-1H-inden-1-yl]-benzamide
[IND_CC-385] 2,6-Difluoro-N-[6-(2-pyridin-4-yl-2,8-diazaspiro[4.5]decane-8-carbonyl)-2,3-dihydro-1H-inden-1-yl]-benzamide
[IND_CC-386] 2,6-Difluoro-N-[6-(8-pyridin-4-yl-2,8-diazaspiro[4.5]decane-2-carbonyl)-2,3-dihydro-1H-inden-1-yl]-benzamide
[IND_CC-387] N,2,3-Trimethyl-N-[6-(9-pyridin-4-yl-3,9-diazaspiro[5.5]undecane-3-carbonyl)-2,3-dihydro-1H-inden-1-yl]-benzamide
[IND_CC-388] 2,3-Dimethyl-N-[6-(2-pyridin-4-yl-2,8-diazaspiro[4.5]decane-8-carbonyl)-2,3-dihydro-1H-inden-1-yl]-benzamide
[IND_CC-389] 2,3-Dimethyl-N-[6-(8-pyridin-4-yl-2,8-diazaspiro[4.5]decane-2-carbonyl)-2,3-dihydro-1H-inden-1-yl]-benzamide

[IND_CC-390] N-Methyl-N-[6-(9-pyridin-4-yl-3,9-diazaspiro[5.5]undecane-3-carbonyl)-2,3-dihydro-1H-inden-1-yl]-1-[3-(trifluoromethyl)phenyl]-methanesulfonic acid amide

[IND_CC-391] N-[6-(9-Pyridin-4-yl-3,9-diazaspiro[5.5]undecane-3-carbonyl)-2,3-dihydro-1H-inden-1-yl]-cyclopentanecarboxylic acid amide

[IND_CC-392] N-Methyl-N-[6-(9-pyridin-4-yl-3,9-diazaspiro[5.5]undecane-3-carbonyl)-2,3-dihydro-1H-inden-1-A-cyclopentanecarboxylic acid amide

[IND_CC-393] N-[6-(2-Pyridin-4-yl-2,8-diazaspiro[4.5]decane-8-carbonyl)-2,3-dihydro-1H-inden-1-yl]-cyclopentanecarboxylic acid amide

[IND_CC-394] N-[6-(8-Pyridin-4-yl-2,8-diazaspiro[4.5]decane-2-carbonyl)-2,3-dihydro-1H-inden-1-yl]-cyclopentanecarboxylic acid amide

[IND_CC-395] N-Methyl-N-[6-(9-pyridin-4-yl-3,9-diazaspiro[5.5]undecane-3-carbonyl)-2,3-dihydro-1H-inden-1-yl]-5-(trifluoromethyl)-pyridine-2-carboxylic acid amide

[IND_CC-396] N-[6-(8-Pyridin-4-yl-2,8-diazaspiro[4.5]decane-2-carbonyl)-2,3-dihydro-1H-inden-1-yl]-5-(trifluoromethyl)-pyridine-2-carboxylic acid amide

[IND_CC-397] N-[6-(9-Pyridin-4-yl-3,9-diazaspiro[5.5]undecane-3-carbonyl)-2,3-dihydro-1H-inden-1-yl]-pyrazine-2-carboxylic acid amide

[IND_CC-398] N-[6-(8-Pyridin-4-yl-2,8-diazaspiro[4.5]decane-2-carbonyl)-2,3-dihydro-1H-inden-1-yl]-pyrazine-2-carboxylic acid amide

[IND_CC-399] 2-Fluoro-N-[6-(9-pyridin-4-yl-3,9-diazaspiro[5.5]undecane-3-carbonyl)-2,3-dihydro-1H-inden-1-yl]-benzamide

[IND_CC-400] 2-Fluoro-N-methyl-N-[6-(9-pyridin-4-yl-3,9-diazaspiro[5.5]undecane-3-carbonyl)-2,3-dihydro-1H-inden-1-yl]-benzamide

[IND_CC-401] 2-Fluoro-N-[6-(2-pyridin-4-yl-2,8-diazaspiro[4.5]decane-8-carbonyl)-2,3-dihydro-1H-inden-1-yl]-benzamide

[IND_CC-402] 2-Fluoro-N-[6-(8-pyridin-4-yl-2,8-diazaspiro[4.5]decane-2-carbonyl)-2,3-dihydro-1H-inden-1-yl]-benzamide

[IND_CC-403] 2,6-Dichloro-N-methyl-N-[6-(9-pyridin-4-yl-3,9-diazaspiro[5.5]undecane-3-carbonyl)-2,3-dihydro-1H-inden-1-yl]-4-(trifluoromethyl)-benzenesulfonic acid amide

[IND_CC-404] 2,6-Dichloro-N-[6-(8-pyridin-4-yl-2,8-diazaspiro[4.5]decane-2-carbonyl)-2,3-dihydro-1H-inden-1-yl]-4-(trifluoromethyl)-benzenesulfonic acid amide

[IND_CC-405] 4-Bromo-2-chloro-N-methyl-N-[6-(9-pyridin-4-yl-3,9-diazaspiro[5.5]-undecane-3-carbonyl)-2,3-dihydro-1H-inden-1-yl]-benzenesulfonic acid amide

[IND_CC-406] 2,4,6-Trichloro-N-methyl-N-[6-(9-pyridin-4-yl-3,9-diazaspiro[5.5]undecane-3-carbonyl)-2,3-dihydro-1H-inden-1-yl]-benzenesulfonic acid amide

[IND_CC-407] 2,4,6-Trichloro-N-[6-(8-pyridin-4-yl-2,8-diazaspiro[4.5]decane-2-carbonyl)-2,3-dihydro-1H-inden-1-yl]-benzenesulfonic acid amide

[IND_CC-408] N,3-Dimethyl-N-[6-(9-pyridin-4-yl-3,9-diazaspiro[5.5]undecane-3-carbonyl)-2,3-dihydro-1H-inden-1-yl]-butyramide

[IND_CC-409] 3-Methyl-N-[6-(8-pyridin-4-yl-2,8-diazaspiro[4.5]decane-2-carbonyl)-2,3-dihydro-1H-inden-1-yl]-butyramide

[IND_CC-410] N-Methyl-N-[6-(9-pyridin-4-yl-3,9-diazaspiro[5.5]undecane-3-carbonyl)-2,3-dihydro-1H-inden-1-yl]-butyramide

[IND_CC-411] N-[6-(8-Pyridin-4-yl-2,8-diazaspiro[4.5]decane-2-carbonyl)-2,3-dihydro-1H-inden-1-yl]-butyramide

[IND_CC-412] 3-Cyclopentyl-N-methyl-N-[6-(9-pyridin-4-yl-3,9-diazaspiro[5.5]undecane-3-carbonyl)-2,3-dihydro-1H-inden-1-yl]-propionamide

[IND_CC-413] 3-Cyclopentyl-N-[6-(8-pyridin-4-yl-2,8-diazaspiro[4.5]decane-2-carbonyl)-2,3-dihydro-1H-inden-1-yl]-propionamide

[IND_CC-414] N-Methyl-N-[6-(9-pyridin-4-yl-3,9-diazaspiro[5.5]undecane-3-carbonyl)-2,3-dihydro-1H-inden-1-yl]-cyclobutanecarboxylic acid amide

[IND_CC-415] N-[6-(8-Pyridin-4-yl-2,8-diazaspiro[4.5]decane-2-carbonyl)-2,3-dihydro-1H-inden-1-yl]-cyclobutanecarboxylic acid amide

[IND_CC-416] N,2-Dimethyl-N-[6-(9-pyridin-4-yl-3,9-diazaspiro[5.5]undecane-3-carbonyl)-2,3-dihydro-1H-inden-1-yl]-butyramide

[IND_CC-417] 2-Methyl-N-[6-(8-pyridin-4-yl-2,8-diazaspiro[4.5]decane-2-carbonyl)-2,3-dihydro-1H-inden-1-yl]-butyramide

[IND_CC-418] N,2-Dimethyl-N-[6-(9-pyridin-4-yl-3,9-diazaspiro[5.5]undecane-3-carbonyl)-2,3-dihydro-1H-inden-1-yl]-propionamide

[IND_CC-419] 2-Methyl-N-[6-(8-pyridin-4-yl-2,8-diazaspiro[4.5]decane-2-carbonyl)-2,3-dihydro-1H-inden-1-yl]-propionamide

[IND_CC-420] 2-Ethyl-N-[6-(8-pyridin-4-yl-2,8-diazaspiro[4.5]decane-2-carbonyl)-2,3-dihydro-1H-inden-1-yl]-butyramide

[IND_CC-500] 2-Chloro-N-[6-[8-[(2,4-difluoro-phenyl)sulfonyl]-2,8-diazaspiro[4.5]decane-2-carbonyl]-2,3-dihydro-1H-inden-1-yl]-benzamide

[IND_CC-501] 2-Chloro-N-[6-[8-[(2-cyano-phenyl)sulfonyl]-2,8-diazaspiro[4.5]decane-2-carbonyl]-2,3-dihydro-1H-inden-1-yl]-benzamide

[IND_CC-502] 2-[3-[(2-Chloro-benzoyl)amino]-2,3-dihydro-1H-indene-5-carbonyl]-N-(3-chloro-4-fluoro-phenyl)-2,8-diazaspiro[4.5]decane-8-carboxylic acid amide

[IND_CC-503] 2-[3-[(2-Chloro-benzoyl)amino]-2,3-dihydro-1H-indene-5-carbonyl]-N-(3-cyano-phenyl)-2,8-diazaspiro[4.5]decane-8-carboxylic acid amide

[IND_CC-504] 2-Chloro-N-[6-[8-[(2,6-difluoro-phenyl)-methyl]-2,8-diazaspiro[4.5]decane-2-carbonyl]-2,3-dihydro-1H-inden-1-yl]-benzamide

[IND_CC-505] 2-Chloro-N-[6-[8-[(2-cyano-phenyl)-methyl]-2,8-diazaspiro[4.5]decane-2-carbonyl]-2,3-dihydro-1H-inden-1-yl]-N-methyl-benzamide

[IND_CC-506] 2-Chloro-N-methyl-N-[6-[8-(quinoxalin-6-yl-methyl)-2,8-diazaspiro[4.5]decane-2-carbonyl]-2,3-dihydro-1H-inden-1-yl]-benzamide

[IND_CC-507] 2-Chloro-N-[6-[9-(1H-pyrrol-2-yl-methyl)-3,9-diazaspiro[5.5]undecane-3-carbonyl]-2,3-dihydro-1H-inden-1-yl]-benzamide

[IND_CC-508] 2-Chloro-N-[6-[9-(1H-imidazol-4-yl-methyl)-3,9-diazaspiro[5.5]undecane-3-carbonyl]-2,3-dihydro-1H-inden-1-yl]-benzamide

[IND_CC-509] 2-Chloro-N-[6-[9-(pyridin-2-yl-methyl)-3,9-diazaspiro[5.5]undecane-3-carbonyl]-2,3-dihydro-1H-inden-1-yl]-benzamide

[IND_CC-510] 2-Chloro-N-[6-[9-(pyridin-4-yl-methyl)-3,9-diazaspiro[5.5]undecane-3-carbonyl]-2,3-dihydro-1H-inden-1-yl]-benzamide

[IND_CC-511] 2-Chloro-N-[6-[9-(pyridin-3-yl-methyl)-3,9-diazaspiro[5.5]undecane-3-carbonyl]-2,3-dihydro-1H-inden-1-yl]-benzamide

[IND_CC-512] 2-Chloro-N-[6-[9-[(1-methyl-1H-pyrrol-2-yl)-methyl]-3,9-diazaspiro[5.5]undecane-3-carbonyl]-2,3-dihydro-1H-inden-1-yl]-benzamide
[IND_CC-513] 2-Chloro-N-[6-[9-[(2,6-difluoro-phenyl)-methyl]-3,9-diazaspiro[5.5]undecane-3-carbonyl]-2,3-dihydro-1H-inden-1-yl]-benzamide
[IND_CC-514] 2-Chloro-N-[6-[9-[(3,4-difluoro-phenyl)-methyl]-3,9-diazaspiro[5.5]undecane-3-carbonyl]-2,3-dihydro-1H-inden-1-yl]-benzamide
[IND_CC-515] 2-Chloro-N-[6-[9-[(2,5-difluoro-phenyl)-methyl]-3,9-diazaspiro[5.5]undecane-3-carbonyl]-2,3-dihydro-1H-inden-1-yl]-benzamide
[IND_CC-516] 2-Chloro-N-[6-[9-[(2,4-difluoro-phenyl)-methyl]-3,9-diazaspiro[5.5]undecane-3-carbonyl]-2,3-dihydro-1H-inden-1-yl]-benzamide
[IND_CC-517] 2-Chloro-N-[6-[9-[(2-fluoro-6-methoxy-phenyl)-methyl]-3,9-diazaspiro[5.5]undecane-3-carbonyl]-2,3-dihydro-1H-inden-1-yl]-benzamide
[IND_CC-518] 2-Chloro-N-cyclopropyl-N-[6-[8-(pyridin-3-yl-methyl)-2,8-diazaspiro[4.5]decane-2-carbonyl]-2,3-dihydro-1H-inden-1-yl]-benzamide
[IND_CC-519] 2-Chloro-N-cyclopropyl-N-[6-[8-[(1-methyl-1H-pyrrol-2-yl)-methyl]-2,8-diazaspiro[4.5]decane-2-carbonyl]-2,3-dihydro-1H-inden-1-yl]-benzamide
[IND_CC-520] 2-Chloro-N-cyclopropyl-N-[6-[8-[(2,6-difluoro-phenyl)-methyl]-2,8-diazaspiro[4.5]decane-2-carbonyl]-2,3-dihydro-1H-inden-1-yl]-benzamide
[IND_CC-521] 2-Chloro-N-cyclopropyl-N-[6-[8-[(3,4-difluoro-phenyl)-methyl]-2,8-diazaspiro[4.5]decane-2-carbonyl]-2,3-dihydro-1H-inden-1-yl]-benzamide
[IND_CC-522] 2-Chloro-N-cyclopropyl-N-[6-[8-[(2,5-difluoro-phenyl)-methyl]-2,8-diazaspiro[4.5]decane-2-carbonyl]-2,3-dihydro-1H-inden-1-yl]-benzamide
[IND_CC-523] 2-Chloro-N-cyclopropyl-N-[6-[8-[(2,4-difluoro-phenyl)-methyl]-2,8-diazaspiro[4.5]decane-2-carbonyl]-2,3-dihydro-1H-inden-1-yl]-benzamide
[IND_CC-524] 2-Chloro-N-cyclopropyl-N-[6-[8-[(3-fluoro-4-methoxy-phenyl)-methyl]-2,8-diazaspiro[4.5]decane-2-carbonyl]-2,3-dihydro-1H-inden-1-yl]-benzamide
[IND_CC-525] 2-Chloro-N-cyclopropyl-N-[6-[8-[(2-fluoro-6-methoxy-phenyl)-methyl]-2,8-diazaspiro[4.5]decane-2-carbonyl]-2,3-dihydro-1H-inden-1-yl]-benzamide
[IND_CC-526] 2-Chloro-N-[6-[9-[(3-methyl-3H-imidazol-4-yl)-methyl]-3,9-diazaspiro[5.5]undecane-3-carbonyl]-2,3-dihydro-1H-inden-1-yl]-benzamide
[IND_CC-527] 2-Chloro-N-[6-[9-[(5-methyl-3H-imidazol-4-yl)-methyl]-3,9-diazaspiro[5.5]undecane-3-carbonyl]-2,3-dihydro-1H-inden-1-yl]-benzamide
[IND_CC-528] 2-Chloro-N-[6-[9-[(2-methyl-1H-imidazol-4-yl)-methyl]-3,9-diazaspiro[5.5]undecane-3-carbonyl]-2,3-dihydro-1H-inden-1-yl]-benzamide
[IND_CC-529] 2-Chloro-N-[6-[9-[(2-chloro-4-fluoro-phenyl)-methyl]-3,9-diazaspiro[5.5]undecane-3-carbonyl]-2,3-dihydro-1H-inden-1-yl]-benzamide
[IND_CC-530] 2-Chloro-N-[6-[9-[(2-chloro-6-fluoro-phenyl)-methyl]-3,9-diazaspiro[5.5]undecane-3-carbonyl]-2,3-dihydro-1H-inden-1-yl]-benzamide
[IND_CC-531] 2-Chloro-N-[6-[9-[(1,5-dimethyl-1H-pyrazol-4-yl)-methyl]-3,9-diazaspiro[5.5]undecane-3-carbonyl]-2,3-dihydro-1H-inden-1-yl]-benzamide
[IND_CC-532] 2-Chloro-N-[6-[9-[(3,5-dimethyl-isoxazol-4-yl)-methyl]-3,9-diazaspiro[5.5]undecane-3-carbonyl]-2,3-dihydro-1H-inden-1-yl]-benzamide
[IND_CC-533] 2-Chloro-N-[6-[9-[(4-cyano-phenyl)-methyl]-3,9-diazaspiro[5.5]undecane-3-carbonyl]-2,3-dihydro-1H-inden-1-yl]-benzamide
[IND_CC-534] 2-Chloro-N-[6-[9-[(3-cyano-phenyl)-methyl]-3,9-diazaspiro[5.5]undecane-3-carbonyl]-2,3-dihydro-1H-inden-1-yl]-benzamide
[IND_CC-535] 2-Chloro-N-[6-[9-[(2-cyano-phenyl)-methyl]-3,9-diazaspiro[5.5]undecane-3-carbonyl]-2,3-dihydro-1H-inden-1-yl]-benzamide
[IND_CC-536] 2-Chloro-N-cyclopropyl-N-[6-[8-[(3-methyl-3H-imidazol-4-yl)-methyl]-2,8-diazaspiro[4.5]decane-2-carbonyl]-2,3-dihydro-1H-inden-1-yl]-benzamide
[IND_CC-537] 2-Chloro-N-[6-[8-[(2-chloro-4-fluoro-phenyl)-methyl]-2,8-diazaspiro[4.5]-decane-2-carbonyl]-2,3-dihydro-1H-inden-1-yl]-N-cyclopropyl-benzamide
[IND_CC-538] 2-Chloro-N-[6-[8-[(2-chloro-6-fluoro-phenyl)-methyl]-2,8-diazaspiro[4.5]-decane-2-carbonyl]-2,3-dihydro-1H-inden-1-yl]-N-cyclopropyl-benzamide
[IND_CC-539] 2-Chloro-N-[6-[8-[(4-cyano-phenyl)-methyl]-2,8-diazaspiro[4.5]decane-2-carbonyl]-2,3-dihydro-1H-inden-1-yl]-N-cyclopropyl-benzamide
[IND_CC-540] 2-Chloro-N-[6-[8-[(3-cyano-phenyl)-methyl]-2,8-diazaspiro[4.5]decane-2-carbonyl]-2,3-dihydro-1H-inden-1-yl]-N-cyclopropyl-benzamide
[IND_CC-541] 2-Chloro-N-[6-[8-[(2-cyano-phenyl)-methyl]-2,8-diazaspiro[4.5]decane-2-carbonyl]-2,3-dihydro-1H-inden-1-yl]-N-cyclopropyl-benzamide
[IND_CC-542] 2-Chloro-N-[6-[8-[(3,4-difluoro-phenyl)-methyl]-2,8-diazaspiro[4.5]decane-2-carbonyl]-2,3-dihydro-1H-inden-1-yl]-benzamide
[IND_CC-543] 2-Chloro-N-[6-[8-[(2,5-difluoro-phenyl)-methyl]-2,8-diazaspiro[4.5]decane-2-carbonyl]-2,3-dihydro-1H-inden-1-yl]-benzamide
[IND_CC-544] 2-Chloro-N-[6-[8-[(2,4-difluoro-phenyl)-methyl]-2,8-diazaspiro[4.5]decane-2-carbonyl]-2,3-dihydro-1H-inden-1-yl]-benzamide
[IND_CC-545] 2-Chloro-N-[6-[8-[(3-fluoro-4-methoxy-phenyl)-methyl]-2,8-diazaspiro[4.5]decane-2-carbonyl]-2,3-dihydro-1H-inden-1-yl]-benzamide
[IND_CC-546] 2-Chloro-N-[6-[8-[(2-fluoro-6-methoxy-phenyl)-methyl]-2,8-diazaspiro[4.5]decane-2-carbonyl]-2,3-dihydro-1H-inden-1-yl]-benzamide
[IND_CC-547] 3-Chloro-N-[6-[8-[(2,5-difluoro-phenyl)-methyl]-2,8-diazaspiro[4.5]decane-2-carbonyl]-2,3-dihydro-1H-inden-1-yl]-thiophene-2-carboxylic acid amide
[IND_CC-548] 3-Chloro-N-[6-[8-[(3-fluoro-4-methoxy-phenyl)-methyl]-2,8-diazaspiro[4.5]-decane-2-carbonyl]-2,3-dihydro-1H-inden-1-yl]-thiophene-2-carboxylic acid amide
[IND_CC-549] 2-Chloro-N-[6-[8-[(3,4-difluoro-phenyl)-methyl]-2,8-diazaspiro[4.5]decane-2-carbonyl]-2,3-dihydro-1H-inden-1-yl]-N-methyl-benzamide
[IND_CC-550] 2-Chloro-N-[6-[8-[(2,5-difluoro-phenyl)-methyl]-2,8-diazaspiro[4.5]decane-2-carbonyl]-2,3-dihydro-1H-inden-1-yl]-N-methyl-benzamide
[IND_CC-551] 2-Chloro-N-[6-[8-[(2,4-difluoro-phenyl)-methyl]-2,8-diazaspiro[4.5]decane-2-carbonyl]-2,3-dihydro-1H-inden-1-yl]-N-methyl-benzamide
[IND_CC-552] 2-Chloro-N-[6-[8-[(3-fluoro-4-methoxy-phenyl)-methyl]-2,8-diazaspiro[4.5]-decane-2-carbonyl]-2,3-dihydro-1H-inden-1-yl]-N-methyl-benzamide

[IND_CC-553] 2-Chloro-N-[6-[8-[(5-methyl-3H-imidazol-4-yl)-methyl]-2,8-diazaspiro[4.5]decane-2-carbonyl]-2,3-dihydro-1H-inden-1-yl]-benzamide
[IND_CC-554] 2-Chloro-N-[6-[8-[(2-methyl-1H-imidazol-4-yl)-methyl]-2,8-diazaspiro[4.5]decane-2-carbonyl]-2,3-dihydro-1H-inden-1-yl]-benzamide
[IND_CC-555] 2-Chloro-N-[6-[8-([1,2,3]thiadiazol-4-yl-methyl)-2,8-diazaspiro[4.5]decane-2-carbonyl]-2,3-dihydro-1H-inden-1-yl]-benzamide
[IND_CC-556] 2-Chloro-N-[6-[8-[(2-chloro-4-fluoro-phenyl)-methyl]-2,8-diazaspiro[4.5]decane-2-carbonyl]-2,3-dihydro-1H-inden-1-yl]-benzamide
[IND_CC-557] 2-Chloro-N-[6-[8-[(2-chloro-6-fluoro-phenyl)-methyl]-2,8-diazaspiro[4.5]decane-2-carbonyl]-2,3-dihydro-1H-inden-1-yl]-benzamide
[IND_CC-558] 2-Chloro-N-[6-[8-[(2-chloro-6-fluoro-phenyl)-methyl]-2,8-diazaspiro[4.5]-decane-2-carbonyl]-2,3-dihydro-1H-inden-1-yl]-N-methyl-benzamide
[IND_CC-559] 2-Chloro-N-[6-[8-[(1,5-dimethyl-1H-pyrazol-4-yl)-methyl]-2,8-diazaspiro[4.5]decane-2-carbonyl]-2,3-dihydro-1H-inden-1-yl]-benzamide
[IND_CC-560] 2-Chloro-N-[6-[8-[(3,5-dimethyl-isoxazol-4-yl)-methyl]-2,8-diazaspiro[4.5]decane-2-carbonyl]-2,3-dihydro-1H-inden-1-yl]-benzamide
[IND_CC-561] 2-Chloro-N-[6-[8-[(4-cyano-phenyl)-methyl]-2,8-diazaspiro[4.5]decane-2-carbonyl]-2,3-dihydro-1H-inden-1-yl]-benzamide
[IND_CC-562] 2-Chloro-N-[6-[8-[(3-cyano-phenyl)-methyl]-2,8-diazaspiro[4.5]decane-2-carbonyl]-2,3-dihydro-1H-inden-1-yl]-benzamide
[IND_CC-563] 2-Chloro-N-[6-[8-[(2-cyano-phenyl)-methyl]-2,8-diazaspiro[4.5]decane-2-carbonyl]-2,3-dihydro-1H-inden-1-yl]-benzamide
[IND_CC-564] 2-Chloro-N-[6-[8-[(1,3,5-trimethyl-1H-pyrazol-4-yl)-methyl]-2,8-diazaspiro[4.5]decane-2-carbonyl]-2,3-dihydro-1H-inden-1-yl]-benzamide
[IND_CC-565] 2-Chloro-N-[6-[8-[(1-ethyl-3-methyl-1H-pyrazol-4-yl)-methyl]-2,8-diazaspiro[4.5]decane-2-carbonyl]-2,3-dihydro-1H-inden-1-yl]-benzamide
[IND_CC-566] 2-Chloro-N-[6-[8-[(2-dimethylamino-pyrimidin-5-yl)-methyl]-2,8-diazaspiro[4.5]decane-2-carbonyl]-2,3-dihydro-1H-inden-1-yl]-benzamide
[IND_CC-567] 2-Chloro-N-[6-[8-(quinolin-6-yl-methyl)-2,8-diazaspiro[4.5]decane-2-carbonyl]-2,3-dihydro-1H-inden-1-yl]-benzamide
[IND_CC-568] 2-Chloro-N-[6-[8-(quinoxalin-6-yl-methyl)-2,8-diazaspiro[4.5]decane-2-carbonyl]-2,3-dihydro-1H-inden-1-yl]-benzamide
[IND_CC-569] 3-Chloro-N-[6-[8-[(4-cyano-phenyl)-methyl]-2,8-diazaspiro[4.5]decane-2-carbonyl]-2,3-dihydro-1H-inden-1-yl]-thiophene-2-carboxylic acid amide
[IND_CC-570] 3-Chloro-N-[6-[8-(quinolin-6-yl-methyl)-2,8-diazaspiro[4.5]decane-2-carbonyl]-2,3-dihydro-1H-inden-1-yl]-thiophene-2-carboxylic acid amide
[IND_CC-571] 3-Chloro-N-[6-[8-(quinoxalin-6-yl-methyl)-2,8-diazaspiro[4.5]decane-2-carbonyl]-2,3-dihydro-1H-inden-1-yl]-thiophene-2-carboxylic acid amide
[IND_CC-572] 2-Chloro-N-[6-[8-[(3-cyano-phenyl)-methyl]-2,8-diazaspiro[4.5]decane-2-carbonyl]-2,3-dihydro-1H-inden-1-yl]-N-methyl-benzamide
[IND_CC-573] 2-Chloro-N-[6-[8-(cyclopropanecarbonyl)-2,8-diazaspiro[4.5]decane-2-carbonyl]-2,3-dihydro-1H-inden-1-yl]-benzamide
[IND_CC-574] 2-Chloro-N-[6-[8-(3,3-dimethyl-butanoyl)-2,8-diazaspiro[4.5]decane-2-carbonyl]-2,3-dihydro-1H-inden-1-yl]-benzamide
[IND_CC-575] 2-Chloro-N-[6-[8-(2-chloro-4-fluoro-benzoyl)-2,8-diazaspiro[4.5]decane-2-carbonyl]-2,3-dihydro-1H-inden-1-yl]-benzamide
[IND_CC-576] 2-Chloro-N-[6-[8-(2,4-difluoro-benzoyl)-2,8-diazaspiro[4.5]decane-2-carbonyl]-2,3-dihydro-1H-inden-1-yl]-benzamide
[IND_CC-577] 2-Chloro-N-[6-[8-[2-(4-chlorophenyl)-acetyl]-2,8-diazaspiro[4.5]decane-2-carbonyl]-2,3-dihydro-1H-inden-1-yl]-benzamide
[IND_CC-578] N-[6-[8-(5-tert-Butyl-2-methyl-2H-pyrazole-3-carbonyl)-2,8-diazaspiro[4.5]-decane-2-carbonyl]-2,3-dihydro-1H-inden-1-yl]-2-chlorobenzamide
[IND_CC-579] N-[6-[8-(2-tert-Butyl-5-methyl-2H-pyrazole-3-carbonyl)-2,8-diazaspiro-[4.5]decane-2-carbonyl]-2,3-dihydro-1H-inden-1-yl]-2-chlorobenzamide
[IND_CC-580] N-[6-[8-(5-tert-Butyl-2-methyl-2H-pyrazole-3-carbonyl)-2,8-diazaspiro[4.5]decane-2-carbonyl]-2,3-dihydro-1H-inden-1-yl]-4-methoxy-2,6-dimethylbenzamide
[IND_CC-581] N-[6-[8-(2-tert-Butyl-5-methyl-2H-pyrazole-3-carbonyl)-2,8-diazaspiro[4.5]decane-2-carbonyl]-2,3-dihydro-1H-inden-1-yl]-4-methoxy-2,6-dimethylbenzamide
[IND_CC-582] 3-Chloro-N-[6-[8-(cyclopropanecarbonyl)-2,8-diazaspiro[4.5]decane-2-carbonyl]-2,3-dihydro-1H-inden-1-yl]-thiophene-2-carboxylic acid amide
[IND_CC-583] 3-Chloro-N-[6-[8-(3,3-dimethyl-butanoyl)-2,8-diazaspiro[4.5]decane-2-carbonyl]-2,3-dihydro-1H-inden-1-yl]-thiophene-2-carboxylic acid amide
[IND_CC-584] 3-Chloro-N-[6-[8-(2-chloro-4-fluoro-benzoyl)-2,8-diazaspiro[4.5]decane-2-carbonyl]-2,3-dihydro-1H-inden-1-yl]-thiophene-2-carboxylic acid amide
[IND_CC-585] 3-Chloro-N-[6-[8-(2,4-difluoro-benzoyl)-2,8-diazaspiro[4.5]decane-2-carbonyl]-2,3-dihydro-1H-inden-1-yl]-thiophene-2-carboxylic acid amide
[IND_CC-586] 3-Chloro-N-[6-[8-[2-(4-chlorophenyl)-acetyl]-2,8-diazaspiro[4.5]decane-2-carbonyl]-2,3-dihydro-1H-inden-1-yl]-thiophene-2-carboxylic acid amide
[IND_CC-587] N-[6-[8-(5-tert-Butyl-2-methyl-2H-pyrazole-3-carbonyl)-2,8-diazaspiro[4.5]decane-2-carbonyl]-2,3-dihydro-1H-inden-1-yl]-3-chloro-thiophene-2-carboxylic acid amide
[IND_CC-588] N-[6-[8-(2-tert-Butyl-5-methyl-2H-pyrazole-3-carbonyl)-2,8-diazaspiro[4.5]decane-2-carbonyl]-2,3-dihydro-1H-inden-1-yl]-3-chloro-thiophene-2-carboxylic acid amide
[IND_CC-589] 2-Chloro-N-[6-[8-(cyclopropanecarbonyl)-2,8-diazaspiro[4.5]decane-2-carbonyl]-2,3-dihydro-1H-inden-1-yl]-N-methyl-benzamide
[IND_CC-590] 2-Chloro-N-[6-[8-(3,3-dimethyl-butanoyl)-2,8-diazaspiro[4.5]decane-2-carbonyl]-2,3-dihydro-1H-inden-1-yl]-N-methyl-benzamide
[IND_CC-591] 2-Chloro-N-[6-[8-(2-chloro-4-fluoro-benzoyl)-2,8-diazaspiro[4.5]decane-2-carbonyl]-2,3-dihydro-1H-inden-1-yl]-N-methyl-benzamide
[IND_CC-592] 2-Chloro-N-[6-[8-[2-(4-chlorophenyl)-acetyl]-2,8-diazaspiro[4.5]decane-2-carbonyl]-2,3-dihydro-1H-inden-1-yl]-N-methyl-benzamide
[IND_CC-593] N-[6-[8-(5-tert-Butyl-2-methyl-2H-pyrazole-3-carbonyl)-2,8-diazaspiro[4.5]-decane-2-carbonyl]-2,3-dihydro-1H-inden-1-yl]-2-chloro-N-methyl-benzamide

[IND_CC-594] 2-Chloro-N-[6-[9-(pyrazine-2-carbonyl)-3,9-diazaspiro[5.5]undecane-3-carbonyl]-2,3-dihydro-1H-inden-1-yl]-benzamide

[IND_CC-595] 2-Chloro-N-[6-[9-(2-methylsulfanyl-pyridine-3-carbonyl)-3,9-diazaspiro[5.5]undecane-3-carbonyl]-2,3-dihydro-1H-inden-1-yl]-benzamide

[IND_CC-596] 2-Chloro-N-[6-[9-(4-cyano-benzoyl)-3,9-diazaspiro[5.5]undecane-3-carbonyl]-2,3-dihydro-1H-inden-1-yl]-benzamide

[IND_CC-597] 2-Chloro-N-[6-[9-(cyclopropanecarbonyl)-3,9-diazaspiro[5.5]undecane-3-carbonyl]-2,3-dihydro-1H-inden-1-yl]-benzamide

[IND_CC-598] 2-Chloro-N-[6-[9-(3,3-dimethyl-butanoyl)-3,9-diazaspiro[5.5]undecane-3-carbonyl]-2,3-dihydro-1H-inden-1-yl]-benzamide

[IND_CC-599] 2-Chloro-N-[6-[9-(2-chloro-4-fluoro-benzoyl)-3,9-diazaspiro[5.5]undecane-3-carbonyl]-2,3-dihydro-1H-inden-1-yl]-benzamide

[IND_CC-600] 2-Chloro-N-[6-[9-(2,4-difluoro-benzoyl)-3,9-diazaspiro[5.5]undecane-3-carbonyl]-2,3-dihydro-1H-inden-1-yl]-benzamide

[IND_CC-601] N-[6-[9-(5-tert-Butyl-2-methyl-2H-pyrazole-3-carbonyl)-3,9-diazaspiro-[5.5]undecane-3-carbonyl]-2,3-dihydro-1H-inden-1-yl]-2-chloro-benzamide

[IND_CC-602] N-[6-[9-(2-tert-Butyl-5-methyl-2H-pyrazole-3-carbonyl)-3,9-diazaspiro-[5.5]undecane-3-carbonyl]-2,3-dihydro-1H-inden-1-yl]-2-chloro-benzamide

[IND_CC-603] 2-Chloro-N-[6-[8-(cyclopropanecarbonyl)-2,8-diazaspiro[4.5]decane-2-carbonyl]-2,3-dihydro-1H-inden-1-yl]-N-cyclopropyl-benzamide

[IND_CC-604] 2-Chloro-N-cyclopropyl-N-[6-[8-(3,3-dimethyl-butanoyl)-2,8-diazaspiro[4.5]decane-2-carbonyl]-2,3-dihydro-1H-inden-1-yl]-benzamide

[IND_CC-605] 2-Chloro-N-[6-[8-(2-chloro-4-fluoro-benzoyl)-2,8-diazaspiro[4.5]decane-2-carbonyl]-2,3-dihydro-1H-inden-1-yl]-N-cyclopropyl-benzamide

[IND_CC-606] 2-Chloro-N-cyclopropyl-N-[6-[8-(2,4-difluoro-benzoyl)-2,8-diazaspiro[4.5]decane-2-carbonyl]-2,3-dihydro-1H-inden-1-yl]-benzamide

[IND_CC-607] N-[6-[8-(5-tert-Butyl-2-methyl-2H-pyrazole-3-carbonyl)-2,8-diazaspiro[4.5]-decane-2-carbonyl]-2,3-dihydro-1H-inden-1-yl]-2-chloro-N-cyclopropylbenzamide

[IND_CC-608] 2-Chloro-N-[6-[9-[(5-chloro-thiophen-2-yl)sulfonyl]-3,9-diazaspiro[5.5]undecane-3-carbonyl]-2,3-dihydro-1H-inden-1-yl]-benzamide

[IND_CC-609] 2-Chloro-N-[6-[9-[(2,4-difluoro-phenyl)sulfonyl]-3,9-diazaspiro[5.5]undecane-3-carbonyl]-2,3-dihydro-1H-inden-1-yl]-benzamide

[IND_CC-610] 2-Chloro-N-[6-[9-[(3-cyano-4-fluoro-phenyl)sulfonyl]-3,9-diazaspiro[5.5]-undecane-3-carbonyl]-2,3-dihydro-1H-inden-1-yl]-benzamide

[IND_CC-611] 2-Chloro-N-[6-[9-[(2-cyano-phenyl)sulfonyl]-3,9-diazaspiro[5.5]undecane-3-carbonyl]-2,3-dihydro-1H-inden-1-yl]-benzamide

[IND_CC-612] 2-Chloro-N-[6-[9-[(1-methyl-1H-indol-4-yl)sulfonyl]-3,9-diazaspiro[5.5]undecane-3-carbonyl]-2,3-dihydro-1H-inden-1-yl]-benzamide

[IND_CC-613] 2-Chloro-N-[6-[9-(isopropylsulfonyl)-3,9-diazaspiro[5.5]undecane-3-carbonyl]-2,3-dihydro-1H-inden-1-yl]-benzamide

[IND_CC-614] 2-Chloro-N-[6-[9-[(1-methyl-1H-indol-5-yl)sulfonyl]-3,9-diazaspiro[5.5]undecane-3-carbonyl]-2,3-dihydro-1H-inden-1-yl]-benzamide

[IND_CC-615] 2-Chloro-N-[6-[8-[(5-chloro-thiophen-2-Asulfonyl]-2,8-diazaspiro[4.5]-decane-2-carbonyl]-2,3-dihydro-1H-inden-1-yl]-N-cyclopropyl-benzamide

[IND_CC-616] 2-Chloro-N-cyclopropyl-N-[6-[8-[(2,4-difluoro-phenyl)sulfonyl]-2,8-diazaspiro[4.5]decane-2-carbonyl]-2,3-dihydro-1H-inden-1-yl]-benzamide

[IND_CC-617] 2-Chloro-N-[6-[8-[(3-cyano-4-fluoro-phenyl)sulfonyl]-2,8-diazaspiro[4.5]-decane-2-carbonyl]-2,3-dihydro-1H-inden-1-yl]-N-cyclopropyl-benzamide

[IND_CC-618] 2-Chloro-N-[6-[8-[(2-cyano-phenyl)sulfonyl]-2,8-diazaspiro[4.5]decane-2-carbonyl]-2,3-dihydro-1H-inden-1-yl]-N-cyclopropyl-benzamide

[IND_CC-619] 2-Chloro-N-cyclopropyl-N-[6-[8-[(1-methyl-1H-indol-5-yl)sulfonyl]-2,8-diazaspiro[4.5]decane-2-carbonyl]-2,3-dihydro-1H-inden-1-yl]-benzamide

[IND_CC-620] 5-Chloro-2-fluoro-N-[6-[8-(1H-pyrrol-2-yl-methyl)-2,8-diazaspiro[4.5]decane-2-carbonyl]-2,3-dihydro-1H-inden-1-yl]-benzamide

[IND_CC-621] 5-Chloro-N-[6-[8-[(3,4-difluoro-phenyl)-methyl]-2,8-diazaspiro[4.5]decane-2-carbonyl]-2,3-dihydro-1H-inden-1-yl]-2-fluoro-benzamide

[IND_CC-622] 5-Chloro-N-[6-[8-[(2,4-difluoro-phenyl)-methyl]-2,8-diazaspiro[4.5]decane-2-carbonyl]-2,3-dihydro-1H-inden-1-yl]-2-fluoro-benzamide

[IND_CC-623] 5-Chloro-2-fluoro-N-[6-[8-[(3-fluoro-4-methoxy-phenyl)-methyl]-2,8-diazaspiro[4.5]decane-2-carbonyl]-2,3-dihydro-1H-inden-1-yl]-benzamide

[IND_CC-624] 5-Chloro-2-fluoro-N-[6-[9-(1H-pyrrol-2-yl-methyl)-3,9-diazaspiro[5.5]undecane-3-carbonyl]-2,3-dihydro-1H-inden-1-yl]-benzamide

[IND_CC-625] 5-Chloro-2-fluoro-N-[6-[9-(1H-imidazol-4-yl-methyl)-3,9-diazaspiro[5.5]undecane-3-carbonyl]-2,3-dihydro-1H-inden-1-yl]-benzamide

[IND_CC-626] 5-Chloro-2-fluoro-N-[6-[9-(pyridin-2-yl-methyl)-3,9-diazaspiro[5.5]undecane-3-carbonyl]-2,3-dihydro-1H-inden-1-yl]-benzamide

[IND_CC-627] 5-Chloro-2-fluoro-N-[6-[9-(pyridin-4-yl-methyl)-3,9-diazaspiro[5.5]undecane-3-carbonyl]-2,3-dihydro-1H-inden-1-yl]-benzamide

[IND_CC-628] 5-Chloro-N-[6-[9-[(3,4-difluoro-phenyl)-methyl]-3,9-diazaspiro[5.5]undecane-3-carbonyl]-2,3-dihydro-1H-inden-1-yl]-2-fluoro-benzamide

[IND_CC-629] 5-Chloro-N-[6-[9-[(2,4-difluoro-phenyl)-methyl]-3,9-diazaspiro[5.5]undecane-3-carbonyl]-2,3-dihydro-1H-inden-1-yl]-2-fluoro-benzamide

[IND_CC-630] 5-Chloro-2-fluoro-N-[6-[9-[(3-fluoro-4-methoxy-phenyl)-methyl]-3,9-diazaspiro[5.5]undecane-3-carbonyl]-2,3-dihydro-1H-inden-1-yl]-benzamide

[IND_CC-631] 2-Chloro-N-[6-[8-(1H-imidazol-4-yl-methyl)-2,8-diazaspiro[4.5]decane-2-carbonyl]-2,3-dihydro-1H-inden-1-yl]-5-(trifluoromethyl)-benzamide

[IND_CC-632] 2-Chloro-N-[6-[8-[(2,6-difluoro-phenyl)-methyl]-2,8-diazaspiro[4.5]decane-2-carbonyl]-2,3-dihydro-1H-inden-1-yl]-5-(trifluoromethyl)-benzamide

[IND_CC-633] 2-Chloro-N-[6-[8-[(3,4-difluoro-phenyl)-methyl]-2,8-diazaspiro[4.5]decane-2-carbonyl]-2,3-dihydro-1H-inden-1-yl]-5-(trifluoromethyl)-benzamide

[IND_CC-634] 2-Chloro-N-[6-[8-[(2,5-difluoro-phenyl)-methyl]-2,8-diazaspiro[4.5]decane-2-carbonyl]-2,3-dihydro-1H-inden-1-yl]-5-(trifluoromethyl)-benzamide

[IND_CC-635] 2-Chloro-N-[6-[8-[(2,4-difluoro-phenyl)-methyl]-2,8-diazaspiro[4.5]decane-2-carbonyl]-2,3-dihydro-1H-inden-1-yl]-5-(trifluoromethyl)-benzamide

[IND_CC-636] 2-Chloro-N-[6-[8-[(3-fluoro-4-methoxy-phenyl)-methyl]-2,8-diazaspiro[4.5]-decane-2-carbonyl]-2,3-dihydro-1H-inden-1-yl]-5-(trifluoromethyl)-benzamide

[IND_CC-637] 2-Chloro-N-[6-[8-[(2-fluoro-6-methoxy-phenyl)-methyl]-2,8-diazaspiro[4.5]-decane-2-carbonyl]-2,3-dihydro-1H-inden-1-yl]-5-(trifluoromethyl)-benzamide

[IND_CC-638] 2-Chloro-N-[6-[9-(1H-pyrrol-2-yl-methyl)-3,9-diazaspiro[5.5]undecane-3-carbonyl]-2,3-dihydro-1H-inden-1-yl]-5-(trifluoromethyl)-benzamide

[IND_CC-639] 2-Chloro-N-[6-[9-(1H-imidazol-4-yl-methyl)-3,9-diazaspiro[5.5]undecane-3-carbonyl]-2,3-dihydro-1H-inden-1-yl]-5-(trifluoromethyl)-benzamide

[IND_CC-640] 2-Chloro-N-[6-[9-(pyridin-2-yl-methyl)-3,9-diazaspiro[5.5]undecane-3-carbonyl]-2,3-dihydro-1H-inden-1-yl]-5-(trifluoromethyl)-benzamide

[IND_CC-641] 2-Chloro-N-[6-[9-(pyridin-4-yl-methyl)-3,9-diazaspiro[5.5]undecane-3-carbonyl]-2,3-dihydro-1H-inden-1-yl]-5-(trifluoromethyl)-benzamide

[IND_CC-642] 2-Chloro-N-[6-[9-(pyridin-3-yl-methyl)-3,9-diazaspiro[5.5]undecane-3-carbonyl]-2,3-dihydro-1H-inden-1-yl]-5-(trifluoromethyl)-benzamide

[IND_CC-643] 2-Chloro-N-[6-[9-[(1-methyl-1H-pyrrol-2-yl)-methyl]-3,9-diazaspiro[5.5]undecane-3-carbonyl]-2,3-dihydro-1H-inden-1-yl]-5-(trifluoromethyl)-benzamide

[IND_CC-644] 2-Chloro-N-[6-[9-[(2,6-difluoro-phenyl)-methyl]-3,9-diazaspiro[5.5]undecane-3-carbonyl]-2,3-dihydro-1H-inden-1-yl]-5-(trifluoromethyl)-benzamide

[IND_CC-645] 2-Chloro-N-[6-[9-[(3,4-difluoro-phenyl)-methyl]-3,9-diazaspiro[5.5]undecane-3-carbonyl]-2,3-dihydro-1H-inden-1-yl]-5-(trifluoromethyl)-benzamide

[IND_CC-646] 2-Chloro-N-[6-[9-[(2,5-difluoro-phenyl)-methyl]-3,9-diazaspiro[5.5]undecane-3-carbonyl]-2,3-dihydro-1H-inden-1-yl]-5-(trifluoromethyl)-benzamide

[IND_CC-647] 2-Chloro-N-[6-[9-[(2,4-difluoro-phenyl)-methyl]-3,9-diazaspiro[5.5]undecane-3-carbonyl]-2,3-dihydro-1H-inden-1-yl]-5-(trifluoromethyl)-benzamide

[IND_CC-648] 2-Chloro-N-[6-[9-[(3-fluoro-4-methoxy-phenyl)-methyl]-3,9-diazaspiro[5.5]-undecane-3-carbonyl]-2,3-dihydro-1H-inden-1-yl]-5-(trifluoromethyl) benzamide

[IND_CC-649] 2-Chloro-N-[6-[9-[(2-fluoro-6-methoxy-phenyl)-methyl]-3,9-diazaspiro[5.5]-undecane-3-carbonyl]-2,3-dihydro-1H-inden-1-yl]-5-(trifluoromethyl) benzamide

[IND_CC-650] 5-Chloro-N-[6-[8-[(4-cyano-phenyl)-methyl]-2,8-diazaspiro[4.5]decane-2-carbonyl]-2,3-dihydro-1H-inden-1-yl]-2-fluoro-benzamide

[IND_CC-651] 5-Chloro-N-[6-[8-[(3-cyano-phenyl)-methyl]-2,8-diazaspiro[4.5]decane-2-carbonyl]-2,3-dihydro-1H-inden-1-yl]-2-fluoro-benzamide

[IND_CC-652] 5-Chloro-2-fluoro-N-[6-[9-([1,2,3]thiadiazol-4-yl-methyl)-3,9-diazaspiro[5.5]undecane-3-carbonyl]-2,3-dihydro-1H-inden-1-yl]-benzamide

[IND_CC-653] 5-Chloro-N-[6-[9-[(4-cyano-phenyl)-methyl]-3,9-diazaspiro[5.5]undecane-3-carbonyl]-2,3-dihydro-1H-inden-1-yl]-2-fluoro-benzamide

[IND_CC-654] 5-Chloro-N-[6-[9-[(3-cyano-phenyl)-methyl]-3,9-diazaspiro[5.5]undecane-3-carbonyl]-2,3-dihydro-1H-inden-1-yl]-2-fluoro-benzamide

[IND_CC-655] 2-Chloro-N-[6-[8-[(5-methyl-3H-imidazol-4-yl)-methyl]-2,8-diazaspiro[4.5]-decane-2-carbonyl]-2,3-dihydro-1H-inden-1-yl]-5-(trifluoromethyl)-benzamide

[IND_CC-656] 2-Chloro-N-[6-[8-([1,2,3]thiadiazol-4-yl-methyl)-2,8-diazaspiro[4.5]decane-2-carbonyl]-2,3-dihydro-1H-inden-1-yl]-5-(trifluoromethyl)-benzamide

[IND_CC-657] 2-Chloro-N-[6-[8-[(3,5-dimethyl-isoxazol-4-yl)-methyl]-2,8-diazaspiro[4.5]-decane-2-carbonyl]-2,3-dihydro-1H-inden-1-yl]-5-(trifluoromethyl)-benzamide

[IND_CC-658] 2-Chloro-N-[6-[8-[(4-cyano-phenyl)-methyl]-2,8-diazaspiro[4.5]decane-2-carbonyl]-2,3-dihydro-1H-inden-1-yl]-5-(trifluoromethyl)-benzamide

[IND_CC-659] 2-Chloro-N-[6-[8-[(3-cyano-phenyl)-methyl]-2,8-diazaspiro[4.5]decane-2-carbonyl]-2,3-dihydro-1H-inden-1-yl]-5-(trifluoromethyl)-benzamide

[IND_CC-660] 2-Chloro-N-[6-[8-[(2-cyano-phenyl)-methyl]-2,8-diazaspiro[4.5]decane-2-carbonyl]-2,3-dihydro-1H-inden-1-yl]-5-(trifluoromethyl)-benzamide

[IND_CC-661] 2-Chloro-N-[6-[9-[(5-methyl-3H-imidazol-4-yl)-methyl]-3,9-diazaspiro[5.5]-undecane-3-carbonyl]-2,3-dihydro-1H-inden-1-yl]-5-(trifluoromethyl) benzamide

[IND_CC-662] 2-Chloro-N-[6-[9-[(2-methyl-1H-imidazol-4-yl)-methyl]-3,9-diazaspiro[5.5]-undecane-3-carbonyl]-2,3-dihydro-1H-inden-1-yl]-5-(trifluoromethyl) benzamide

[IND_CC-663] 2-Chloro-N-[6-[9-([1,2,3]thiadiazol-4-yl-methyl)-3,9-diazaspiro[5.5]undecane-3-carbonyl]-2,3-dihydro-1H-inden-1-yl]-5-(trifluoromethyl)-benzamide

[IND_CC-664] 2-Chloro-N-[6-[9-[(1,5-dimethyl-1H-pyrazol-4-yl)-methyl]-3,9-diazaspiro[5.5]-undecane-3-carbonyl]-2,3-dihydro-1H-inden-1-yl]-5-(trifluoromethyl)benzamide

[IND_CC-665] 2-Chloro-N-[6-[9-[(3,5-dimethyl-isoxazol-4-yl)-methyl]-3,9-diazaspiro[5.5]-undecane-3-carbonyl]-2,3-dihydro-1H-inden-1-yl]-5-(trifluoromethyl)benzamide

[IND_CC-666] 2-Chloro-N-[6-[9-[(4-cyano-phenyl)-methyl]-3,9-diazaspiro[5.5]undecane-3-carbonyl]-2,3-dihydro-1H-inden-1-yl]-5-(trifluoromethyl)-benzamide

[IND_CC-667] 2-Chloro-N-[6-[9-[(3-cyano-phenyl)-methyl]-3,9-diazaspiro[5.5]undecane-3-carbonyl]-2,3-dihydro-1H-inden-1-yl]-5-(trifluoromethyl)-benzamide

[IND_CC-668] 2-Chloro-N-[6-[9-[(2-cyano-phenyl)-methyl]-3,9-diazaspiro[5.5]undecane-3-carbonyl]-2,3-dihydro-1H-inden-1-yl]-5-(trifluoromethyl)-benzamide

[IND_CC-669] 2-Chloro-N-[6-[9-[(2-chloro-4-fluoro-phenyl)-methyl]-3,9-diazaspiro[5.5]-undecane-3-carbonyl]-2,3-dihydro-1H-inden-1-yl]-5-(trifluoromethyl) benzamide

[IND_CC-670] 2-Chloro-N-[6-[9-[(2-chloro-6-fluoro-phenyl)-methyl]-3,9-diazaspiro[5.5]-undecane-3-carbonyl]-2,3-dihydro-1H-inden-1-yl]-5-(trifluoromethyl) benzamide

[IND_CC-671] 5-Chloro-2-fluoro-N-[6-[8-(quinolin-6-yl-methyl)-2,8-diazaspiro[4.5]decane-2-carbonyl]-2,3-dihydro-1H-inden-1-yl]-benzamide

[IND_CC-672] 5-Chloro-2-fluoro-N-[6-[8-(quinoxalin-6-yl-methyl)-2,8-diazaspiro[4.5]decane-2-carbonyl]-2,3-dihydro-1H-inden-1-yl]-benzamide

[IND_CC-673] 5-Chloro-2-fluoro-N-[6-[8-[(1-methyl-1H-benzotriazol-5-yl)-methyl]-2,8-diazaspiro[4.5]decane-2-carbonyl]-2,3-dihydro-1H-inden-1-yl]-benzamide

[IND_CC-674] 5-Chloro-2-fluoro-N-[6-[8-[3-(3-fluorophenyl)-propyl]-2,8-diazaspiro[4.5]decane-2-carbonyl]-2,3-dihydro-1H-inden-1-yl]-benzamide

[IND_CC-675] 5-Chloro-2-fluoro-N-[6-[8-[3-(4-fluorophenyl)-propyl]-2,8-diazaspiro[4.5]decane-2-carbonyl]-2,3-dihydro-1H-inden-1-yl]-benzamide

[IND_CC-676] 5-Chloro-N-[6-[9-[(2-dimethylamino-pyrimidin-5-yl)-methyl]-3,9-diazaspiro-[5.5]undecane-3-carbonyl]-2,3-dihydro-1H-inden-1-yl]-2-fluoro-benzamide

[IND_CC-677] 5-Chloro-2-fluoro-N-[6-[9-(quinolin-6-yl-methyl)-3,9-diazaspiro[5.5]undecane-3-carbonyl]-2,3-dihydro-1H-inden-1-yl]-benzamide

[IND_CC-678] 5-Chloro-2-fluoro-N-[6-[9-(quinoxalin-6-yl-methyl)-3,9-diazaspiro[5.5]undecane-3-carbonyl]-2,3-dihydro-1H-inden-1-yl]-benzamide

[IND_CC-679] 5-Chloro-2-fluoro-N-[6-[9-[(1-methyl-1H-benzotriazol-5-yl)-methyl]-3,9-diazaspiro[5.5]undecane-3-carbonyl]-2,3-dihydro-1H-inden-1-yl]-benzamide

[IND_CC-680] 5-Chloro-2-fluoro-N-[6-[9-(2-methyl-propyl)-3,9-diazaspiro[5.5]undecane-3-carbonyl]-2,3-dihydro-1H-inden-1-yl]-benzamide

[IND_CC-681] 5-Chloro-2-fluoro-N-[6-(9-phenethyl-3,9-diazaspiro[5.5]undecane-3-carbonyl)-2,3-dihydro-1H-inden-1-yl]-benzamide

[IND_CC-682] 2-Chloro-5-(trifluoromethyl)-N-[6-[8-[(1,3,5-trimethyl-1H-pyrazol-4-yl)-methyl]-2,8-diazaspiro[4.5]decane-2-carbonyl]-2,3-dihydro-1H-inden-1-yl]-benzamide

[IND_CC-683] 2-Chloro-N-[6-[8-[(2-dimethylamino-pyrimidin-5-yl)-methyl]-2,8-diazaspiro[4.5]-decane-2-carbonyl]-2,3-dihydro-1H-inden-1-yl]-5-(trifluoromethyl)-benzamide

[IND_CC-684] 2-Chloro-N-[6-[8-(quinolin-6-yl-methyl)-2,8-diazaspiro[4.5]decane-2-carbonyl]-2,3-dihydro-1H-inden-1-yl]-5-(trifluoromethyl)-benzamide

[IND_CC-685] 2-Chloro-N-[6-[8-(quinoxalin-6-yl-methyl)-2,8-diazaspiro[4.5]decane-2-carbonyl]-2,3-dihydro-1H-inden-1-yl]-5-(trifluoromethyl)-benzamide

[IND_CC-686] 2-Chloro-N-[6-[8-[(1-methyl-1H-benzotriazol-5-yl)-methyl]-2,8-diazaspiro[4.5]-decane-2-carbonyl]-2,3-dihydro-1H-inden-1-yl]-5-(trifluoromethyl)benzamide

[IND_CC-687] 2-Chloro-N-[6-[8-(2-methyl-propyl)-2,8-diazaspiro[4.5]decane-2-carbonyl]-2,3-dihydro-1H-inden-1-yl]-5-(trifluoromethyl)-benzamide

[IND_CC-688] 2-Chloro-N-[6-[8-(2-ethyl-butyl)-2,8-diazaspiro[4.5]decane-2-carbonyl]-2,3-dihydro-1H-inden-1-yl]-5-(trifluoromethyl)-benzamide

[IND_CC-689] 2-Chloro-N-[6-[8-(cyclohexyl-methyl)-2,8-diazaspiro[4.5]decane-2-carbonyl]-2,3-dihydro-1H-inden-1-yl]-5-(trifluoromethyl)-benzamide

[IND_CC-690] 2-Chloro-N-[6-(8-phenethyl-2,8-diazaspiro[4.5]decane-2-carbonyl)-2,3-dihydro-1H-inden-1-yl]-5-(trifluoromethyl)-benzamide

[IND_CC-691] 2-Chloro-N-[6-[8-[3-(3-fluorophenyl)-propyl]-2,8-diazaspiro[4.5]decane-2-carbonyl]-2,3-dihydro-1H-inden-1-yl]-5-(trifluoromethyl)-benzamide

[IND_CC-692] 2-Chloro-N-[6-[8-[3-(4-fluorophenyl)-propyl]-2,8-diazaspiro[4.5]decane-2-carbonyl]-2,3-dihydro-1H-inden-1-yl]-5-(trifluoromethyl)-benzamide

[IND_CC-693] 2-Chloro-N-[6-[9-[(1-ethyl-3-methyl-1H-pyrazol-4-yl)-methyl]-3,9-diazaspiro[5.5]-undecane-3-carbonyl]-2,3-dihydro-1H-inden-1-yl]-5-(trifluoromethyl)-benzamide

[IND_CC-694] 2-Chloro-N-[6-[9-[(2-dimethylamino-pyrimidin-5-yl)-methyl]-3,9-diazaspiro[5.5]-undecane-3-carbonyl]-2,3-dihydro-1H-inden-1-yl]-5-(trifluoromethyl)benzamide

[IND_CC-695] 2-Chloro-N-[6-[9-(quinolin-6-yl-methyl)-3,9-diazaspiro[5.5]undecane-3-carbonyl]-2,3-dihydro-1H-inden-1-yl]-5-(trifluoromethyl)-benzamide

[IND_CC-696] 2-Chloro-N-[6-[9-(quinoxalin-6-yl-methyl)-3,9-diazaspiro[5.5]undecane-3-carbonyl]-2,3-dihydro-1H-inden-1-yl]-5-(trifluoromethyl)-benzamide

[IND_CC-697] 2-Chloro-N-[6-[9-[(1-methyl-1H-benzotriazol-5-yl)-methyl]-3,9-diazaspiro[5.5]-undecane-3-carbonyl]-2,3-dihydro-1H-inden-1-yl]-5-(trifluoromethyl)benzamide

[IND_CC-698] 2-Chloro-N-[6-[9-(2-methyl-propyl)-3,9-diazaspiro[5.5]undecane-3-carbonyl]-2,3-dihydro-1H-inden-1-yl]-5-(trifluoromethyl)-benzamide

[IND_CC-699] 2-Chloro-N-[6-[9-(2-ethyl-butyl)-3,9-diazaspiro[5.5]undecane-3-carbonyl]-2,3-dihydro-1H-inden-1-yl]-5-(trifluoromethyl)-benzamide

[IND_CC-700] 2-Chloro-N-[6-[9-(cyclohexyl-methyl)-3,9-diazaspiro[5.5]undecane-3-carbonyl]-2,3-dihydro-1H-inden-1-yl]-5-(trifluoromethyl)-benzamide

[IND_CC-701] 2-Chloro-N-[6-(9-phenethyl-3,9-diazaspiro[5.5]undecane-3-carbonyl)-2,3-dihydro-1H-inden-1-yl]-5-(trifluoromethyl)-benzamide

[IND_CC-702] 2-Chloro-N-[6-[9-[3-(3-fluorophenyl)-propyl]-3,9-diazaspiro[5.5]undecane-3-carbonyl]-2,3-dihydro-1H-inden-1-yl]-5-(trifluoromethyl)-benzamide

[IND_CC-703] 2-Chloro-N-[6-[9-[3-(4-fluorophenyl)-propyl]-3,9-diazaspiro[5.5]undecane-3-carbonyl]-2,3-dihydro-1H-inden-1-yl]-5-(trifluoromethyl)-benzamide

[IND_CC-704] 3-[3-[(2-Chloro-benzoyl)amino]-2,3-dihydro-1H-indene-5-carbonyl]-N-propyl-3,9-diazaspiro[5.5]undecane-9-carboxylic acid amide

[IND_CC-705] 3-[3-[(2-Chloro-benzoyl)amino]-2,3-dihydro-1H-indene-5-carbonyl]-N-(3-cyano-phenyl)-3,9-diazaspiro[5.5]undecane-9-carboxylic acid amide

[IND_CC-706] N-Benzyl-3-[3-[(2-chloro-benzoyl)amino]-2,3-dihydro-1H-indene-5-carbonyl]-3,9-diazaspiro[5.5]undecane-9-carboxylic acid amide

[IND_CC-707] 3-[3-[(2-Chloro-benzoyl)amino]-2,3-dihydro-1H-indene-5-carbonyl]-N-(4-dimethylaminophenyl)-3,9-diazaspiro[5.5]undecane-9-carboxylic acid amide

[IND_CC-708] 3-[3-[(2-Chloro-benzoyl)amino]-2,3-dihydro-1H-indene-5-carbonyl]-N-cyclohexyl-3,9-diazaspiro[5.5]undecane-9-carboxylic acid amide

[IND_CC-709] 3-[3-[(2-Chloro-benzoyl)amino]-2,3-dihydro-1H-indene-5-carbonyl]-N-(2,6-dichloro-phenyl)-3,9-diazaspiro[5.5]undecane-9-carboxylic acid amide

[IND_CC-710] 3-[3-[(2-Chloro-benzoyl)amino]-2,3-dihydro-1H-indene-5-carbonyl]-N-(2,4-dichlorophenyl)-3,9-diazaspiro[5.5]undecane-9-carboxylic acid amide

[IND_CC-711] 3-[3-[(2-Chloro-benzoyl)amino]-2,3-dihydro-1H-indene-5-carbonyl]-N-(2,4-difluoro-phenyl)-3,9-diazaspiro[5.5]undecane-9-carboxylic acid amide

[IND_CC-712] 2-[3-[(2-Chloro-benzoyl)-cyclopropyl-amino]-2,3-dihydro-1H-indene-5-carbonyl]-N-propyl-2,8-diazaspiro[4.5]decane-8-carboxylic acid amide

[IND_CC-713] 2-[3-[(2-Chloro-benzoyl)-cyclopropyl-amino]-2,3-dihydro-1H-indene-5-carbonyl]-N-(3-chloro-4-fluoro-phenyl)-2,8-diazaspiro[4.5]decane-8-carboxylic acid amide

[IND_CC-714] 2-[3-[(2-Chloro-benzoyl)-cyclopropyl-amino]-2,3-dihydro-1H-indene-5-carbonyl]-N-[4-chloro-2-(trifluoromethyl)-phenyl]-2,8-diazaspiro[4.5]decane-8-carboxylic acid amide

[IND_CC-715] 2-[3-[(2-Chloro-benzoyl)-cyclopropyl-amino]-2,3-dihydro-1H-indene-5-carbonyl]-N-(3-cyano-phenyl)-2,8-diazaspiro[4.5]decane-8-carboxylic acid amide

[IND_CC-716] N-Benzyl-2-[3-[(2-chloro-benzoyl)-cyclopropyl-amino]-2,3-dihydro-1H-indene-5-carbonyl]-2,8-diazaspiro[4.5]decane-8-carboxylic acid amide

[IND_CC-717] 2-[3-[(2-Chloro-benzoyl)-cyclopropyl-amino]-2,3-dihydro-1H-indene-5-carbonyl]-N-cyclohexyl-2,8-diazaspiro[4.5]decane-8-carboxylic acid amide

[IND_CC-718] 2-[3-[(2-Chloro-benzoyl)-cyclopropyl-amino]-2,3-dihydro-1H-indene-5-carbonyl]-N-(2,6-dichloro-phenyl)-2,8-diazaspiro[4.5]decane-8-carboxylic acid amide

[IND_CC-719] 2-[3-[(2-Chloro-benzoyl)-cyclopropyl-amino]-2,3-dihydro-1H-indene-5-carbonyl]-N-(2,4-difluoro-phenyl)-2,8-diazaspiro[4.5]decane-8-carboxylic acid amide

[IND_CC-720] 2-[3-[(2-Chloro-benzoyl)-cyclopropyl-amino]-2,3-dihydro-1H-indene-5-carbonyl]-N-(3,5-difluoro-phenyl)-2,8-diazaspiro[4.5]decane-8-carboxylic acid amide

[IND_CC-721] 2-[3-[(2-Chloro-benzoyl)-cyclopropyl-amino]-2,3-dihydro-1H-indene-5-carbonyl]-N-[(3,4-dichlorophenyl)-methyl]-2,8-diazaspiro[4.5]decane-8-carboxylic acid amide

[IND_CC-722] 2,3-Dichloro-N-[6-[8-[(1,5-dimethyl-1H-pyrazol-4-yl)-methyl]-2,8-diazaspiro[4.5]decane-2-carbonyl]-2,3-dihydro-1H-inden-1-yl]-benzamide

[IND_CC-723] 2,3-Dichloro-N-[6-[8-[(3,5-dimethyl-isoxazol-4-yl)-methyl]-2,8-diazaspiro[4.5]decane-2-carbonyl]-2,3-dihydro-1H-inden-1-yl]-benzamide

[IND_CC-724] 2,3-Dichloro-N-[6-[8-[(2-cyano-phenyl)-methyl]-2,8-diazaspiro[4.5]decane-2-carbonyl]-2,3-dihydro-1H-inden-1-yl]-benzamide

[IND_CC-725] 2,3-Dichloro-N-[6-[8-[(2-chloro-6-fluoro-phenyl)-methyl]-2,8-diazaspiro[4.5]decane-2-carbonyl]-2,3-dihydro-1H-inden-1-yl]-benzamide

[IND_CC-726] 2,3-Dichloro-N-[6-[9-[(2-chloro-4-fluoro-phenyl)-methyl]-3,9-diazaspiro[5.5]undecane-3-carbonyl]-2,3-dihydro-1H-inden-1-yl]-benzamide

[IND_CC-727] 2,3-Dichloro-N-[6-[9-[(2-chloro-6-fluoro-phenyl)-methyl]-3,9-diazaspiro[5.5]undecane-3-carbonyl]-2,3-dihydro-1H-inden-1-yl]-benzamide

[IND_CC-728] 2-Chloro-6-methyl-N-[6-[8-[(2-methyl-1H-imidazol-4-yl)-methyl]-2,8-diazaspiro[4.5]decane-2-carbonyl]-2,3-dihydro-1H-inden-1-yl]-benzamide

[IND_CC-729] 2-Chloro-N-[6-[8-[(1,5-dimethyl-1H-pyrazol-4-yl)-methyl]-2,8-diazaspiro-[4.5]decane-2-carbonyl]-2,3-dihydro-1H-inden-1-yl]-6-methyl-benzamide

[IND_CC-730] 2-Chloro-N-[6-[8-[(3,5-dimethyl-isoxazol-4-yl)-methyl]-2,8-diazaspiro-[4.5]decane-2-carbonyl]-2,3-dihydro-1H-inden-1-yl]-6-methyl-benzamide

[IND_CC-731] 2-Chloro-N-[6-[8-[(4-cyano-phenyl)-methyl]-2,8-diazaspiro[4.5]decane-2-carbonyl]-2,3-dihydro-1H-inden-1-yl]-6-methyl-benzamide

[IND_CC-732] 2-Chloro-N-[6-[8-[(3-cyano-phenyl)-methyl]-2,8-diazaspiro[4.5]decane-2-carbonyl]-2,3-dihydro-1H-inden-1-yl]-6-methyl-benzamide

[IND_CC-733] 2-Chloro-N-[6-[8-[(2-cyano-phenyl)-methyl]-2,8-diazaspiro[4.5]decane-2-carbonyl]-2,3-dihydro-1H-inden-1-yl]-6-methyl-benzamide

[IND_CC-734] 2-Chloro-N-[6-[8-[(2-chloro-4-fluoro-phenyl)-methyl]-2,8-diazaspiro-[4.5]decane-2-carbonyl]-2,3-dihydro-1H-inden-1-yl]-6-methyl-benzamide

[IND_CC-735] 2-Chloro-N-[6-[8-[(2-chloro-6-fluoro-phenyl)-methyl]-2,8-diazaspiro[4.5]-decane-2-carbonyl]-2,3-dihydro-1H-inden-1-yl]-6-methyl-benzamide

[IND_CC-736] 2-Chloro-6-fluoro-N-[6-[8-[(2-methyl-1H-imidazol-4-yl)-methyl]-2,8-diazaspiro[4.5]decane-2-carbonyl]-2,3-dihydro-1H-inden-1-yl]-benzamide

[IND_CC-737] 2-Chloro-N-[6-[8-[(1,5-dimethyl-1H-pyrazol-4-yl)-methyl]-2,8-diazaspiro-[4.5]decane-2-carbonyl]-2,3-dihydro-1H-inden-1-yl]-6-fluoro-benzamide

[IND_CC-738] 2-Chloro-N-[6-[8-[(3,5-dimethyl-isoxazol-4-yl)-methyl]-2,8-diazaspiro-[4.5]decane-2-carbonyl]-2,3-dihydro-1H-inden-1-yl]-6-fluoro-benzamide

[IND_CC-739] 2-Chloro-N-[6-[8-[(4-cyano-phenyl)-methyl]-2,8-diazaspiro[4.5]decane-2-carbonyl]-2,3-dihydro-1H-inden-1-yl]-6-fluoro-benzamide

[IND_CC-740] 2-Chloro-N-[6-[8-[(2-cyano-phenyl)-methyl]-2,8-diazaspiro[4.5]decane-2-carbonyl]-2,3-dihydro-1H-inden-1-yl]-6-fluoro-benzamide

[IND_CC-741] 2-Chloro-N-[6-[8-[(2-chloro-4-fluoro-phenyl)-methyl]-2,8-diazaspiro-[4.5]decane-2-carbonyl]-2,3-dihydro-1H-inden-1-yl]-6-fluoro-benzamide

[IND_CC-742] 2,3-Dichloro-N-[6-[8-[(1-ethyl-3-methyl-1H-pyrazol-4-yl)-methyl]-2,8-diazaspiro[4.5]decane-2-carbonyl]-2,3-dihydro-1H-inden-1-yl]-benzamide

[IND_CC-743] 2,3-Dichloro-N-[6-[8-[(2-dimethylamino-pyrimidin-5-yl)-methyl]-2,8-diazaspiro[4.5]decane-2-carbonyl]-2,3-dihydro-1H-inden-1-yl]-benzamide

[IND_CC-744] 2,3-Dichloro-N-[6-[8-(quinolin-6-yl-methyl)-2,8-diazaspiro[4.5]decane-2-carbonyl]-2,3-dihydro-1H-inden-1-yl]-benzamide

[IND_CC-745] 2,3-Dichloro-N-[6-[8-(quinoxalin-6-yl-methyl)-2,8-diazaspiro[4.5]decane-2-carbonyl]-2,3-dihydro-1H-inden-1-yl]-benzamide

[IND_CC-746] 2,3-Dichloro-N-[6-[8-[(1-methyl-1H-benzotriazol-5-yl)-methyl]-2,8-diazaspiro[4.5]decane-2-carbonyl]-2,3-dihydro-1H-inden-1-yl]-benzamide

[IND_CC-747] 2,3-Dichloro-N-[6-[8-(2-methyl-propyl)-2,8-diazaspiro[4.5]decane-2-carbonyl]-2,3-dihydro-1H-inden-1-yl]-benzamide

[IND_CC-748] 2,3-Dichloro-N-[6-[8-(2-ethyl-butyl)-2,8-diazaspiro[4.5]decane-2-carbonyl]-2,3-dihydro-1H-inden-1-yl]-benzamide

[IND_CC-749] 2,3-Dichloro-N-[6-(8-phenethyl-2,8-diazaspiro[4.5]decane-2-carbonyl)-2,3-dihydro-1H-inden-1-yl]-benzamide

[IND_CC-750] 2,3-Dichloro-N-[6-[8-[3-(3-fluorophenyl)-propyl]-2,8-diazaspiro[4.5]decane-2-carbonyl]-2,3-dihydro-1H-inden-1-yl]-benzamide

[IND_CC-751] 2,3-Dichloro-N-[6-[8-[3-(4-fluorophenyl)-propyl]-2,8-diazaspiro[4.5]decane-2-carbonyl]-2,3-dihydro-1H-inden-1-yl]-benzamide

[IND_CC-752] 2,3-Dichloro-N-[6-[9-[(1-ethyl-3-methyl-1H-pyrazol-4-yl)-methyl]-3,9-diazaspiro[5.5]undecane-3-carbonyl]-2,3-dihydro-1H-inden-1-yl]-benzamide

[IND_CC-753] 2,3-Dichloro-N-[6-[9-[(2-dimethylamino-pyrimidin-5-yl)-methyl]-3,9-diazaspiro[5.5]undecane-3-carbonyl]-2,3-dihydro-1H-inden-1-yl]-benzamide

[IND_CC-754] 2,3-Dichloro-N-[6-[9-(quinolin-6-yl-methyl)-3,9-diazaspiro[5.5]undecane-3-carbonyl]-2,3-dihydro-1H-inden-1-yl]-benzamide

[IND_CC-755] 2,3-Dichloro-N-[6-[9-(quinoxalin-6-yl-methyl)-3,9-diazaspiro[5.5]undecane-3-carbonyl]-2,3-dihydro-1H-inden-1-yl]-benzamide

[IND_CC-756] 2,3-Dichloro-N-[6-[9-[(1-methyl-1H-benzotriazol-5-yl)-methyl]-3,9-diazaspiro[5.5]undecane-3-carbonyl]-2,3-dihydro-1H-inden-1-yl]-benzamide

[IND_CC-757] 2,3-Dichloro-N-[6-[9-(2-methyl-propyl)-3,9-diazaspiro[5.5]undecane-3-carbonyl]-2,3-dihydro-1H-inden-1-yl]-benzamide

[IND_CC-758] 2,3-Dichloro-N-[6-(9-phenethyl-3,9-diazaspiro[5.5]undecane-3-carbonyl)-2,3-dihydro-1H-inden-1-yl]-benzamide

[IND_CC-759] 2,3-Dichloro-N-[6-[9-[3-(3-fluorophenyl)-propyl]-3,9-diazaspiro[5.5]undecane-3-carbonyl]-2,3-dihydro-1H-inden-1-yl]-benzamide

[IND_CC-760] 2,3-Dichloro-N-[6-[9-[3-(4-fluorophenyl)-propyl]-3,9-diazaspiro[5.5]undecane-3-carbonyl]-2,3-dihydro-1H-inden-1-yl]-benzamide

[IND_CC-761] 2-Chloro-6-methyl-N-[6-[8-[(1,3,5-trimethyl-1H-pyrazol-4-yl)-methyl]-2,8-diazaspiro[4.5]decane-2-carbonyl]-2,3-dihydro-1H-inden-1-yl]-benzamide

[IND_CC-762] 2-Chloro-N-[6-[8-[(1-ethyl-3-methyl-1H-pyrazol-4-yl)-methyl]-2,8-diazaspiro[4.5]decane-2-carbonyl]-2,3-dihydro-1H-inden-1-yl]-6-methyl-benzamide

[IND_CC-763] 2-Chloro-N-[6-[8-[(2-dimethylamino-pyrimidin-5-yl)-methyl]-2,8-diazaspiro[4.5]decane-2-carbonyl]-2,3-dihydro-1H-inden-1-yl]-6-methyl-benzamide

[IND_CC-764] 2-Chloro-6-methyl-N-[6-[8-(quinolin-6-yl-methyl)-2,8-diazaspiro[4.5]decane-2-carbonyl]-2,3-dihydro-1H-inden-1-yl]-benzamide

[IND_CC-765] 2-Chloro-6-methyl-N-[6-[8-(quinoxalin-6-yl-methyl)-2,8-diazaspiro[4.5]decane-2-carbonyl]-2,3-dihydro-1H-inden-1-yl]-benzamide

[IND_CC-766] 2-Chloro-6-methyl-N-[6-[8-[(1-methyl-1H-benzotriazol-5-yl)-methyl]-2,8-diazaspiro[4.5]decane-2-carbonyl]-2,3-dihydro-1H-inden-1-yl]-benzamide

[IND_CC-767] 2-Chloro-6-methyl-N-[6-[8-(2-methyl-propyl)-2,8-diazaspiro[4.5]decane-2-carbonyl]-2,3-dihydro-1H-inden-1-yl]-benzamide

[IND_CC-768] 2-Chloro-N-[6-[8-(2-ethyl-butyl)-2,8-diazaspiro[4.5]decane-2-carbonyl]-2,3-dihydro-1H-inden-1-yl]-6-methyl-benzamide

[IND_CC-769] 2-Chloro-6-methyl-N-[6-(8-phenethyl-2,8-diazaspiro[4.5]decane-2-carbonyl)-2,3-dihydro-1H-inden-1-yl]-benzamide

[IND_CC-770] 2-Chloro-N-[6-[8-[3-(3-fluorophenyl)-propyl]-2,8-diazaspiro[4.5]decane-2-carbonyl]-2,3-dihydro-1H-inden-1-yl]-6-methyl-benzamide

[IND_CC-771] 2-Chloro-N-[6-[8-[3-(4-fluorophenyl)-propyl]-2,8-diazaspiro[4.5]decane-2-carbonyl]-2,3-dihydro-1H-inden-1-yl]-6-methyl-benzamide

[IND_CC-772] 2-Chloro-N-[6-[8-[(1-ethyl-3-methyl-1H-pyrazol-4-yl)-methyl]-2,8-diazaspiro[4.5]decane-2-carbonyl]-2,3-dihydro-1H-inden-1-yl]-6-fluoro-benzamide

[IND_CC-773] 2-Chloro-N-[6-[8-[(2-dimethylamino-pyrimidin-5-yl)-methyl]-2,8-diazaspiro[4.5]decane-2-carbonyl]-2,3-dihydro-1H-inden-1-yl]-6-fluoro-benzamide

[IND_CC-774] 2-Chloro-6-fluoro-N-[6-[8-(quinolin-6-yl-methyl)-2,8-diazaspiro[4.5]decane-2-carbonyl]-2,3-dihydro-1H-inden-1-yl]-benzamide

[IND_CC-775] 2-Chloro-6-fluoro-N-[6-[8-(quinoxalin-6-yl-methyl)-2,8-diazaspiro[4.5]decane-2-carbonyl]-2,3-dihydro-1H-inden-1-yl]-benzamide

[IND_CC-776] 2-Chloro-6-fluoro-N-[6-[8-[(1-methyl-1H-benzotriazol-5-yl)-methyl]-2,8-diazaspiro[4.5]decane-2-carbonyl]-2,3-dihydro-1H-inden-1-yl]-benzamide

[IND_CC-777] 2-Chloro-6-fluoro-N-[6-[8-(2-methyl-propyl)-2,8-diazaspiro[4.5]decane-2-carbonyl]-2,3-dihydro-1H-inden-1-yl]-benzamide

[IND_CC-778] 2-Chloro-N-[6-[8-(2-ethyl-butyl)-2,8-diazaspiro[4.5]decane-2-carbonyl]-2,3-dihydro-1H-inden-1-yl]-6-fluoro-benzamide

[IND_CC-779] 2-Chloro-N-[6-[8-(cyclohexyl-methyl)-2,8-diazaspiro[4.5]decane-2-carbonyl]-2,3-dihydro-1H-inden-1-yl]-6-fluoro-benzamide

[IND_CC-780] 2-Chloro-6-fluoro-N-[6-(8-phenethyl-2,8-diazaspiro[4.5]decane-2-carbonyl)-2,3-dihydro-1H-inden-1-yl]-benzamide

[IND_CC-781] 2-Chloro-6-fluoro-N-[6-[8-[3-(3-fluorophenyl)-propyl]-2,8-diazaspiro[4.5]decane-2-carbonyl]-2,3-dihydro-1H-inden-1-yl]-benzamide

[IND_CC-782] 2-Chloro-6-fluoro-N-[6-[8-[3-(4-fluorophenyl)-propyl]-2,8-diazaspiro[4.5]decane-2-carbonyl]-2,3-dihydro-1H-inden-1-yl]-benzamide

[IND_CC-783] 2-Chloro-6-fluoro-N-[6-[9-(1H-pyrrol-2-yl-methyl)-3,9-diazaspiro[5.5]undecane-3-carbonyl]-2,3-dihydro-1H-inden-1-yl]-benzamide

[IND_CC-784] 2-Chloro-6-fluoro-N-[6-[9-(pyridin-2-yl-methyl)-3,9-diazaspiro[5.5]undecane-3-carbonyl]-2,3-dihydro-1H-inden-1-yl]-benzamide

[IND_CC-785] 2-Chloro-6-fluoro-N-[6-[9-(pyridin-4-yl-methyl)-3,9-diazaspiro[5.5]undecane-3-carbonyl]-2,3-dihydro-1H-inden-1-yl]-benzamide

[IND_CC-786] 2-Chloro-6-fluoro-N-[6-[9-(pyridin-3-yl-methyl)-3,9-diazaspiro[5.5]undecane-3-carbonyl]-2,3-dihydro-1H-inden-1-yl]-benzamide

[IND_CC-787] 2-Chloro-6-fluoro-N-[6-[9-[(1-methyl-1H-pyrrol-2-yl)-methyl]-3,9-diazaspiro[5.5]undecane-3-carbonyl]-2,3-dihydro-1H-inden-1-yl]-benzamide

[IND_CC-788] 2-Chloro-N-[6-[9-[(2,6-difluoro-phenyl)-methyl]-3,9-diazaspiro[5.5]undecane-3-carbonyl]-2,3-dihydro-1H-inden-1-yl]-6-fluoro-benzamide

[IND_CC-789] 2-Chloro-N-[6-[9-[(3,4-difluoro-phenyl)-methyl]-3,9-diazaspiro[5.5]undecane-3-carbonyl]-2,3-dihydro-1H-inden-1-yl]-6-fluoro-benzamide

[IND_CC-790] 2-Chloro-N-[6-[9-[(2,5-difluoro-phenyl)-methyl]-3,9-diazaspiro[5.5]undecane-3-carbonyl]-2,3-dihydro-1H-inden-1-yl]-6-fluoro-benzamide

[IND_CC-791] 2-Chloro-N-[6-[9-[(2,4-difluoro-phenyl)-methyl]-3,9-diazaspiro[5.5]undecane-3-carbonyl]-2,3-dihydro-1H-inden-1-yl]-6-fluoro-benzamide

[IND_CC-792] 2-Chloro-6-fluoro-N-[6-[9-[(3-fluoro-4-methoxy-phenyl)-methyl]-3,9-diazaspiro[5.5]undecane-3-carbonyl]-2,3-dihydro-1H-inden-1-yl]-benzamide

[IND_CC-793] 2-Chloro-6-fluoro-N-[6-[9-[(2-fluoro-6-methoxy-phenyl)-methyl]-3,9-diazaspiro[5.5]undecane-3-carbonyl]-2,3-dihydro-1H-inden-1-yl]-benzamide

[IND_CC-794] 8-Chloro-2-[6-[8-[(3-fluoro-4-methoxy-phenyl)-methyl]-2,8-diazaspiro[4.5]decane-2-carbonyl]-2,3-dihydro-1H-inden-1-yl]-4-methyl-3,4-dihydro-2H-pyrrolo[3,4-b]indol-1-one

[IND_CC-795] 8-Chloro-2-[6-[8-[(2-fluoro-6-methoxy-phenyl)-methyl]-2,8-diazaspiro[4.5]decane-2-carbonyl]-2,3-dihydro-1H-inden-1-yl]-4-methyl-3,4-dihydro-2H-pyrrolo[3,4-b]indol-1-one

[IND_CC-796] 2-Chloro-6-fluoro-N-[6-[9-[(3-methyl-3H-imidazol-4-yl)-methyl]-3,9-diazaspiro[5.5]undecane-3-carbonyl]-2,3-dihydro-1H-inden-1-yl]-benzamide

[IND_CC-797] 2-Chloro-6-fluoro-N-[6-[9-([1,2,3]thiadiazol-4-yl-methyl)-3,9-diazaspiro[5.5]undecane-3-carbonyl]-2,3-dihydro-1H-inden-1-yl]-benzamide

[IND_CC-798] 2-Chloro-N-[6-[9-[(1,5-dimethyl-1H-pyrazol-4-yl)-methyl]-3,9-diazaspiro-[5.5]undecane-3-carbonyl]-2,3-dihydro-1H-inden-1-yl]-6-fluoro-benzamide

[IND_CC-799] 2-Chloro-N-[6-[9-[(3,5-dimethyl-isoxazol-4-yl)-methyl]-3,9-diazaspiro-[5.5]undecane-3-carbonyl]-2,3-dihydro-1H-inden-1-yl]-6-fluoro-benzamide

[IND_CC-800] 2-Chloro-N-[6-[9-[(3-cyano-phenyl)-methyl]-3,9-diazaspiro[5.5]undecane-3-carbonyl]-2,3-dihydro-1H-inden-1-yl]-6-fluoro-benzamide

[IND_CC-801] 2-Chloro-N-[6-[9-[(2-cyano-phenyl)-methyl]-3,9-diazaspiro[5.5]undecane-3-carbonyl]-2,3-dihydro-1H-inden-1-yl]-6-fluoro-benzamide

[IND_CC-802] 2-Chloro-N-[6-[9-[(2-chloro-4-fluoro-phenyl)-methyl]-3,9-diazaspiro-[5.5]undecane-3-carbonyl]-2,3-dihydro-1H-inden-1-yl]-6-fluoro-benzamide

[IND_CC-803] 2-Chloro-N-[6-[9-[(2-chloro-6-fluoro-phenyl)-methyl]-3,9-diazaspiro-[5.5]undecane-3-carbonyl]-2,3-dihydro-1H-inden-1-yl]-6-fluoro-benzamide

[IND_CC-804] 2-Chloro-N-[6-[2-oxo-2-[8-(quinolin-6-yl-methyl)-3,8-diazaspiro[4.5]decan-3-yl]-ethyl]-2,3-dihydro-1H-inden-1-yl]-benzamide

[IND_CC-805] 2-Chloro-N-[6-[2-oxo-2-[8-(quinoxalin-6-yl-methyl)-3,8-diazaspiro[4.5]decan-3-yl]-ethyl]-2,3-dihydro-1H-inden-1-yl]-benzamide

[IND_CC-806] 2-Chloro-N-[6-[2-[8-(2-ethyl-butyl)-3,8-diazaspiro[4.5]decan-3-yl]-2-oxo-ethyl]-2,3-dihydro-1H-inden-1-yl]-benzamide

[IND_CC-807] 2-Chloro-N-[6-[2-[8-(cyclohexyl-methyl)-3,8-diazaspiro[4.5]decan-3-yl]-2-oxo-ethyl]-2,3-dihydro-1H-inden-1-yl]-benzamide and physiologically acceptable salts of any of the foregoing.

13. A pharmaceutical composition comprising a compound as claimed in claim 1 and at least one pharmaceutically acceptable carrier or auxiliary.

* * * * *